US011307203B2

(12) United States Patent
Chinnaiyan et al.

(10) Patent No.: US 11,307,203 B2
(45) Date of Patent: Apr. 19, 2022

(54) USING PHAGE EPITOPES TO PROFILE THE IMMUNE RESPONSE

(71) Applicants: The Regents of the University of Michigan, Ann Arbor, MI (US); Exact Sciences Development Company, LLC, Madison, WI (US)

(72) Inventors: Arul M. Chinnaiyan, Plymouth, MI (US); Xiaoju Wang, Ann Arbor, MI (US); Alex Tsodikov, Ann Arbor, MI (US); Jeanne Ohrnberger, Northville, MI (US)

(73) Assignees: The Regents of the University of Michigan, Ann Arbor, MI (US); Exact Sciences Development Company, LLC, Madison, WI (US)

(*) Notice: Subject to any disclaimer, the term of this patent is extended or adjusted under 35 U.S.C. 154(b) by 976 days.

(21) Appl. No.: 15/933,574

(22) Filed: Mar. 23, 2018

(65) Prior Publication Data

US 2018/0224455 A1 Aug. 9, 2018

Related U.S. Application Data

(63) Continuation of application No. 13/050,544, filed on Mar. 17, 2011.

(60) Provisional application No. 61/314,750, filed on Mar. 17, 2010.

(51) Int. Cl.
*G01N 33/574* (2006.01)
*C07K 16/00* (2006.01)

(52) U.S. Cl.
CPC ....... *G01N 33/57434* (2013.01); *C07K 16/00* (2013.01); *C07K 16/005* (2013.01); *G01N 33/57415* (2013.01); *G01N 33/57419* (2013.01); *G01N 33/57423* (2013.01); *G01N 33/57488* (2013.01); *G01N 2333/4703* (2013.01); *G01N 2333/4704* (2013.01); *G01N 2333/705* (2013.01); *G01N 2333/912* (2013.01)

(58) Field of Classification Search
None
See application file for complete search history.

(56) References Cited

U.S. PATENT DOCUMENTS

| | | | |
|---|---|---|---|
| 4,109,496 | A | 8/1978 | Allemann et al. |
| 4,323,546 | A | 4/1982 | Crockford et al. |
| 4,657,760 | A | 4/1987 | Kung et al. |
| 4,873,191 | A | 10/1989 | Wagner et al. |
| 4,968,103 | A | 11/1990 | McNab et al. |
| 4,981,785 | A | 1/1991 | Nayak |
| 5,034,506 | A | 7/1991 | Summerton et al. |
| 5,206,344 | A | 4/1993 | Katre et al. |
| 5,223,409 | A | 6/1993 | Ladner et al. |
| 5,225,212 | A | 7/1993 | Martin et al. |
| 5,283,317 | A | 2/1994 | Saifer et al. |
| 5,358,691 | A | 10/1994 | Clark et al. |
| 5,489,677 | A | 2/1996 | Sanghvi et al. |
| 5,539,082 | A | 7/1996 | Nielsen et al. |
| 5,599,677 | A | 2/1997 | Dowell et al. |
| 5,602,240 | A | 2/1997 | De Mesmaeker et al. |
| 5,614,396 | A | 3/1997 | Bradley et al. |
| 5,631,169 | A | 5/1997 | Lackowicz et al. |
| 5,672,480 | A | 9/1997 | Dowell et al. |
| 5,674,486 | A | 10/1997 | Sobol et al. |
| 5,714,331 | A | 2/1998 | Buchardt et al. |
| 5,719,262 | A | 2/1998 | Buchardt et al. |
| 5,824,544 | A | 10/1998 | Armentano et al. |
| 5,830,730 | A | 11/1998 | German et al. |
| 5,872,154 | A | 2/1999 | Wilson et al. |
| 5,885,530 | A | 3/1999 | Babson et al. |
| 5,885,808 | A | 3/1999 | Spooner et al. |
| 5,904,920 | A | 5/1999 | Dranoff et al. |
| 5,972,334 | A | 10/1999 | Denney, Jr. |
| 5,981,225 | A | 11/1999 | Kochanek et al. |
| 5,994,069 | A | 11/1999 | Hall et al. |
| 5,994,106 | A | 11/1999 | Kovesdi et al. |
| 5,994,128 | A | 11/1999 | Fallaux et al. |
| 5,994,132 | A | 11/1999 | Chamberlin et al. |
| 5,994,523 | A | 11/1999 | Kawakami et al. |
| 6,001,557 | A | 12/1999 | Wilson et al. |
| 6,019,978 | A | 2/2000 | Ertl et al. |
| 6,033,908 | A | 3/2000 | Bout et al. |
| 6,051,230 | A | 4/2000 | Thorpe et al. |
| 6,080,912 | A | 6/2000 | Bremel et al. |

(Continued)

FOREIGN PATENT DOCUMENTS

| | | | |
|---|---|---|---|
| EP | 1270724 | A3 | 5/2003 |
| EP | 1074617 | A3 | 4/2004 |

(Continued)

OTHER PUBLICATIONS

Wang et al. (New England Journal of Medicine 353:1224-35 supplementary appendix) (Year: 2005).*

(Continued)

*Primary Examiner* — Christopher M Gross

(74) *Attorney, Agent, or Firm* — Casimir Jones, S.C.; Tanya A. Arenson

(57) ABSTRACT

The present disclosure provides compositions and methods for using one or more polypeptide probes to profile an immune response. The polypeptide probe can be used to detect one or more antibodies from a sample. Furthermore, the present disclosure provides methods and compositions for characterizing a cancer based on the detection of one or more antibodies, such as autoantibodies.

7 Claims, 130 Drawing Sheets

Specification includes a Sequence Listing.

(56) References Cited

U.S. PATENT DOCUMENTS

| | | | |
|---|---|---|---|
| 6,159,750 | A | 12/2000 | Edmonds |
| 6,180,357 | B1 | 1/2001 | Young et al. |
| 6,207,147 | B1 | 3/2001 | Hiserodt et al. |
| 6,506,559 | B1 | 1/2003 | Fire et al. |
| 6,573,361 | B1 | 6/2003 | Bunkers et al. |
| 6,610,508 | B1 | 8/2003 | Hentze |
| 6,686,147 | B1 | 2/2004 | Scanlan |
| 6,783,961 | B1 | 8/2004 | Edwards |
| 6,943,241 | B2 | 7/2005 | Bernarding |
| 7,067,258 | B2 | 6/2006 | Esser et al. |
| 7,115,416 | B1 | 10/2006 | Edwards |
| 7,205,117 | B1 | 4/2007 | Robertson et al. |
| 7,214,498 | B2 | 4/2007 | Nelson |
| 7,368,527 | B2 | 5/2008 | Fu |
| 7,402,403 | B1 | 7/2008 | Robertson et al. |
| 7,541,150 | B2 | 6/2009 | Miller et al. |
| 7,597,890 | B2 | 10/2009 | Chinnaiyan et al. |
| 7,858,323 | B2 | 12/2010 | Chinnaiyan et al. |
| 8,574,848 | B2 | 11/2013 | Robertson et al. |
| 8,592,169 | B2 | 11/2013 | Robertson et al. |
| 8,617,547 | B2 | 12/2013 | Chinnaiyan et al. |
| 8,722,339 | B2 | 5/2014 | Robertson et al. |
| 9,267,133 | B2 | 2/2016 | Chinnaiyan et al. |
| 2003/0028981 | A1 | 2/2003 | Chandler et al. |
| 2003/0092009 | A1 | 5/2003 | Palm |
| 2003/0138860 | A1 | 7/2003 | Robertson et al. |
| 2003/0175736 | A1 | 9/2003 | Chinnaiyan et al. |
| 2003/0219676 | A1 | 11/2003 | Gordon |
| 2004/0044181 | A1 | 3/2004 | Tang et al. |
| 2005/0032065 | A1 | 2/2005 | Afar |
| 2005/0147961 | A1 | 7/2005 | Esser et al. |
| 2006/0014138 | A1 | 1/2006 | Ghosh |
| 2006/0024692 | A1 | 2/2006 | Nakamura et al. |
| 2007/0037143 | A1 | 2/2007 | Jost et al. |
| 2007/0054353 | A1 | 3/2007 | White et al. |
| 2007/0082330 | A1 | 4/2007 | Barrett et al. |
| 2007/0269798 | A1 | 11/2007 | Dower et al. |
| 2008/0153113 | A1 | 6/2008 | Robertson et al. |
| 2008/0213791 | A1 | 9/2008 | Freije et al. |
| 2008/0213921 | A1 | 9/2008 | Robertson et al. |
| 2008/0280844 | A1 | 11/2008 | Lessnick |
| 2009/0176319 | A1 | 7/2009 | Robertson et al. |
| 2009/0246781 | A1 | 10/2009 | Klem et al. |
| 2010/0009382 | A1 | 1/2010 | Chinnaiyan et al. |
| 2011/0070652 | A1 | 3/2011 | Chinnaiyan et al. |
| 2011/0086061 | A1 | 4/2011 | Robertson et al. |
| 2011/0236903 | A1 | 9/2011 | Mcclelland et al. |
| 2011/0237457 | A1 | 9/2011 | Ohrnberger et al. |
| 2013/0130355 | A1 | 5/2013 | Ohmberger et al. |

FOREIGN PATENT DOCUMENTS

| | | | |
|---|---|---|---|
| EP | 1464709 | A1 | 10/2004 |
| EP | 2130926 | | 5/2016 |
| WO | 90/08832 | A1 | 8/1990 |
| WO | 94/10300 | A1 | 5/1994 |
| WO | 99/02685 | A1 | 1/1999 |
| WO | 00/09675 | A1 | 2/2000 |
| WO | 00/12738 | A1 | 3/2000 |
| WO | 01/98537 | A1 | 12/2001 |
| WO | 2002040716 | A2 | 5/2002 |
| WO | 2002018424 | | 5/2003 |
| WO | 2003010199 | | 2/2004 |
| WO | 2003064593 | | 2/2004 |
| WO | 2005/123993 | A2 | 12/2005 |
| WO | 2005123993 | | 12/2005 |
| WO | 2006100156 | A2 | 9/2006 |
| WO | 2009120561 | A2 | 10/2009 |
| WO | 93/03367 | A1 | 12/2009 |
| WO | 2009/149166 | A2 | 12/2009 |
| WO | 2009149166 | | 12/2009 |
| WO | 2011/120015 | A2 | 9/2011 |

OTHER PUBLICATIONS

Epitope Mapping Protocols, Glenn Morris, Ed. Methods in Molecular Biology vol. 66 (Year: 1996).*

European Search Report of related EP Application No. 18187917.2, dated Mar. 25, 2019, 9 pages.

European Search Report dated Sep. 26, 2017, EP Application 16156268.1, 6 pages.

Abate-Shen et al. Molecular genetics of prostate cancer. Genes Dev. Oct. 1, 2000; 14(19): 2410-34.

Zuckermann et al. Discovery of nanomolar ligands for 7-transmembrane G-protein-coupled receptors from a diverse N-(substituted)glycine peptoid library. J Med Chern. Aug. 1, 19949; 37(17): 2678-85.

Bartel et al. Elimination of false positives that arise in using the two-hybrid system. Biotechniques. Jun. 1993; 14(6): 920-4.

Bradley et al. Formation of germ-line chimaeras from embryo-derived teratocarcinoma cell lines. Nature. May 17-23, 1984; 309(5965): 255-6.

Brinster et al. Factors affecting the efficiency of introducing foreign DNA into mice by microinjecting eggs. Proc Natl Acad Sci U S A. Jul. 1985; 82(13): 4438-42.

Brummelkamp et al. A system for stable expression of short interfering RNAs in mammalian cells. Science. Apr. 19, 2002; 296(5567): 550-3. Epub Mar. 21, 2002.

Caplen et al. Specific inhibition of gene expression by small double-stranded RNAs in invertebrate and vertebrate systems. Proc Natl Acad Sci U S A. Aug. 14, 2001; 98(17): 9742-7 Epub Jul. 31, 2001.

Carrell et al. A novel procedure for the synthesis of libraries containing small orgainic molecules. Angew. Chem. Int. Ed. Engl. 1994; 33: 2059-2061.

Carrell et al. A solution phase screening procedure for the isolation of active compounds from a library of molecules. Angew. Chem. Int. Ed. Engl. 1994; 33: 2061-2064.

Chamberlin et al. New RNA polymerase from *Escherichia coli* infected with bacteriophage T7. Nature. Oct. 17, 1970; 228(5268): 227-31.

Cho et al. An unnatural biopolymer. Science. Sep. 3, 1993; 261(5126): 1303-5.

Cull et al. Screening for receptor ligands using large libraries of peptides linked to the C terminus of the lac repressor. Proc Natl Acad Sci U S A. Mar. 1, 1992; 89(5): 1865-9.

Cwirla et al. Peptides on phage: a vast library of peptides for identifying ligands. Proc Natl Acad Sci U S A. Aug. 1990; 87(16): 6378-82.

Devlin et al. Random peptide libraries: a source of specific protein binding molecules. Science. Jul. 27, 1990; 249 (4967): 404-6.

Dewitt et al. "Diversomers": an approach to nonpeptide nonoligomeric chemical diversity. Proc Natl Acad Sci U S A. Aug. 1, 1993; 90(15): 6909-13.

Dhanasekaran et al. Delineation of prognostic biomarkers in prostate cancer. Nature. Aug. 23, 2001; 412(6849): 822-6.

Elbashir et al. Duplexes of 21-nucleotide RNAs mediate RNA interference in cultured mammalian cells. Nature. May 24, 2001; 411(6836): 494-8.

Elbashir et al. Functional anatomy of siRNAs for mediating efficient RNAi in *Drosophila melanogaster* embryo lysate. EMBO J. Dec. 3, 2001; 20(23): 6877-88.

Elbashir et al. RNA interference is mediated by 21- and 22-nucleotide RNAs. Genes Dev. Jan. 15, 2001; 15(2): 188-200.

Epstein et al. The pathological interpretation and significance of prostate needle biopsy findings: implications and current controversies. J Urol. Aug. 2001; 166(2): 402-10.

Erb et al. Recursive deconvolution of combinatorial chemical libraries. Proc Natl Acad Sci U S A. Nov. 22, 1994; 91 (24): 11422-6.

Eizioni et al. Cancer surveillance series: interpreting trends in prostate cancer—part III: Quantifying the link between population prostate-specific antigen testing and recent declines in prostate cancer mortality. J Natl Cancer Inst. Jun. 16, 1999; 91(12): 1033-9.

Evans et al. Establishment in culture of pluripotential cells from mouse embryos. Nature. Jul. 9, 1981; 292(5819): 154-6.

(56) References Cited

OTHER PUBLICATIONS

Felici et al. Selection of antibody ligands from a large library of oligopeptides expressed on a multivalent exposition vector. J Mol Biol. Nov. 20, 1991; 222(2): 301-10.
Fodor et al. Multiplexed biochemical assays with biological chips. Nature. Aug. 5, 1993; 364(6437): 555-6.
Gallop et al. Applications of combinatorial technologies to drug discovery. 1. Background and peptide combinatorial libraries. J Med Chem. Apr. 29, 1994; 37(9): 1233-51.
Ghose et al. Preparation of antibody-linked cytotoxic agents. Methods Enzymol. 1983; 93:280-333.
Golub et al. Molecular classification of cancer: class discovery and class prediction by gene expression monitoring. Science. Oct. 15, 1999; 286(5439): 531-7.
Graham et al. A new technique for the assay of infectivity of human adenovirus 5 DNA. Virology. Apr. 1973; 52(2): 456-67.
Griffin et al. Initial clinical study of indium-111-labeled clone 110 anticarcinoembryonic antigen antibody in patients with colorectal cancer. J Clin Oncol Apr. 1991; 9(4): 631-40.
Grossler et al. Transgenesis by means of blastocyst-derived embryonic stem cell lines. Proc Natl Acad Sci U S A. Dec. 1986; 83(23): 9065-9.
Hage et al. Recent advances in chromatographic and electrophoretic methods for the study of drug-protein interactions. J Chromatogr B Biomed Sci Appl. Oct. 10, 1997;699(1-2):499-525.
Haskell et al. Efficient production of transgenic cattle by retroviral infection of early embryos. Mol Reprod Dev. Mar. 1995; 40(3): 386-90.
Heegaard NH. Capillary electrophoresis for the study of affinity interactions. J Mol Recognit. 1998 Winter; 11(1-6): 141-8.
Hnatowich et al. The preparation and labeling of DTPA-coupled albumin. Int J Appl Radiat Isot. May 1982; 33(5): 327-32.
Hogan et al. Manipulating the mouse embryo: a laboratory manual. vol. 34. Cold Spring Harbor NY: Cold spring harbor laboratory 1986.
Holen et al. Positional effects of short interfering RNAs targeting the human coagulation trigger Tissue Factor. Nucleic Acids Res. Apr. 15, 2002; 30(8): 1757-66.
Houghten et al. The use of synthetic peptide combinatorial libraries for the identification of bioactive peptides. Biotechniques. Sep. 1992; 13(3): 412-21.
International search report and written opinion dated Mar. 22, 2013 for PCT Application No. PCT/US2012/058100.
Iwabuchi et al. Use of the two-hybrid system to identify the domain of p53 involved in oligomerization. Oncogene. Jun. 1993; 8(6): 1693-6.
Jacobsen et al. Incidence of prostate cancer diagnosis in the eras before and after serum prostate-specific antigen testing. JAMA. Nov. 8, 1995; 274(18): 1445-9.
Jaenich R. Germ line integration and Mendelian transmission of the exogenous Moloney leukemia virus. Proc Natl Acad Sci U S A. Apr. 1976; 73(4): 1260-4.
Jaenich R. Transgenic animals. Science. Jun. 10, 1988; 240(4858): 1468-74.
Jahner et al. De novo methylation and expression of retroviral genomes during mouse embryogenesis. Nature. Aug. 12, 1982; 298(5875): 623-8.
Jahner et al. Insertion of the bacterial gpt gene into the germ line of mice by retroviral infection. Proc Natl Acad Sci U S A. Oct. 1985; 82(20): 6927-31.
Kacian et al. A replicating RNA molecule suitable for a detailed analysis of extracellular evolution and replication. Proc Natl Acad Sci U S A Oct. 1972; 69(10): 3038-42.
Khaw et al. Myocardial infarct imaging of antibodies to canine cardiac myosin with indium-111-diethylenetriamine pentaacetic acid Science. Jul. 11, 1980; 209(4453): 295-7.
Kohler et al. Continuous cultures of fused cells secreting antibody of predefined specificity. Nature. Aug. 7, 1975; 256 (5517): 495-7.
Lam et al. A new type of synthetic peptide library for identifying ligand-binding activity. Nature. Nov. 7, 1991; 354(6348): 82-4.
Lauffer RB. Targeted relaxation enhancement agents for MRI. Magn Reson Med. Dec. 1991; 22(2): 339-42; discussion 343-6.
Extended European Search Report dated May 30, 2016, EP Application 16156268.1, 7 pages.
Obata et al., "Identification of cancer antigens in breast cancer by the SEREX expression cloning method" Breast Cancer, Oct. 1999, vol. 6, Issue 4, pp. 305-311.
Qiu et al., "Development of Natural Protein Microarrays for Diagnosing Cancer Based on an Antibody Response to Tumor Antigens" Journal of Proteome Research, 2004, 3 (2), pp. 261-267.
Zhang Jian-Ying et al., "Enhancement of Antibody Detection in Cancer Using Panel of Recombinant Tumor-associated Antigens" Cancer Epidemiol Biomarkers Prev Feb. 12, 2003; 136-143.
Maattanen, et al. European randomized study of prostate cancer screening: first-year results of the Finnish trial. Br J Cancer. Mar. 1999; 79(7-8): 1210-4.
Madura, et al. N-recognin/Ubc2 interactions in the N-end rule pathway. J Biol Chem. Jun. 5, 1993; 268(16): 12046-54.
Martin, et al. New access to 2'-O-alkylated ribonucleosides and properties of 2'-O-alkylated oligoribonucleotides. Helv. Chim. Acta. 1995; 78: 486.
McConnell, et al. The cytosensor microphysiometer: biological applications of silicon technology. Science. Sep. 25, 1992; 257(5078): 1906-12.
Nielsen, et al. Sequence-selective recognition of DNA by strand displacement with a thymine-substituted polyamide. Science. Dec. 6, 1991; 254(5037): 1497-500.
Office action dated Jan. 2, 2014 for U.S. Appl. No. 13/072,542.
Office action dated Mar. 21, 2013 for U.S. Appl. No. 13/072,542.
Office action dated May 16, 2014 for U.S. Appl. No. 12/914,465.
Office action dated Jul. 11, 2013 for U.S. Appl. No. 12/914,465.
Office action dated Nov. 7, 2012 for U.S. Appl. No. 12/556,831.
PCR Technology: Applications and Principles of DNA Amplification, H Erlich (ed). New York, Stockton Press, 1989.
Rivas, et al. New developments in the study of biomolecular associations via sedimentation equilibrium. Trends Biochem Sci Aug. 1993; 18(8): 284-7.
Robertson, et al. Germ-line transmission of genes introduced into cultured pluripotential cells by retroviral vector. Nature. Oct. 2-8, 1986; 323(6087): 445-8.
Ruijter, et al. Molecular genetics and epidemiology of prostate carcinoma. Endocr Rev. Feb. 1999; 20(1): 22-45.
Sambrook, et al. Molecular cloning: A laboratory manual+ Cold Spring Harbor. 1989: 16.9-16.15.
Sambrook, et al. Molecular cloning: A laboratory manual+ Cold Spring Harbor. 1989: 7.39-7.52.
Sambrook, et al. Molecular cloning: A laboratory manual+ Cold Spring Harbor. 1989: 9.31-9.58.
Scheinberg, et al. Tumor imaging with radioactive metal chelates conjugated to monoclonal antibodies. Science. Mar. 19, 1982; 215(4539): 1511-3.
Schroder, et al. Evaluation of the digital rectal examination as a screening test for prostate cancer. Rotterdam section of the European Randomized Study of Screening for Prostate Cancer. J Natl Cancer Inst. Dec. 2, 1998; 90(23): 1817-23.
Scott, et al. Searching for peptide ligands with an epitope library. Science. Jul. 27, 1990; 249(4967): 386-90.
Sjolander, et al. Integrated fluid handling system for biomolecular interaction analysis. Anal Chem. Oct. 15, 1991; 63 (20): 2338-45.
Stewart, et al. Expression of retroviral vectors in transgenic mice obtained by embryo infection. EMBO J. Feb. 1987; 6(2): 383-8.
Sumerdon, et al. An optimized antibody-chelator conjugate for imaging of carcinoembryonic antigen with indium-111. Int J Rad Appl Instrum B. 1990; 17(2): 247-54.
Szabo, et al. Surface plasmon resonance and its use in biomolecular interaction analysis (BIA). Curr Opin Struct Biol. Oct. 1995; 5(5): 699-705.
Thorpe, et al. Improved antitumor effects of immunotoxins prepared with deglycosylated ricin A-chain and hindered disulfide linkages. Cancer Res Nov. 15, 1988; 48(22): 6396-403.
Tuschl, et al. Small interfering RNAs: a revolutionary tool for the analysis of gene function and gene therapy. Mol Interv. Jun. 2002; 2(3): 158-67.

(56) References Cited

OTHER PUBLICATIONS

Wergeland, et al. Monoclonal antibodies evoked by the free oligopeptide (Gly)5 reacting specifically with peptidoglycan from staphylococci. J Immunol Methods. Nov. 23, 1987;104(1-2):57-63.
Wong, et al. A rapid chemical method of labeling human plasma proteins with 99mTc-pertechnetate at pH 7.4. Int J Appl Radiat Isot. May 1978; 29(4-5): 251-3.
Wong, et al. Imaging endocarditis with Tc-99m-labeled antibody—an experimental study: concise communication. J Nucl Med. Mar. 1982; 23(3): 229-34.
Wu, et al. The ligation amplification reaction (LAR)—amplification of specific DNA sequences using sequential rounds of template-dependent ligation. Genomics. May 1989; 4(4): 560-9.
Zervos, et al. Mxi1, a protein that specifically interacts with Max to bind Myc-Max recognition sites. Cell. Jan. 29, 1993; 72(2): 223-32.
Gingras et al. "Regulation of translation initiation by FRAP/mTOR." Genes & Development. vol. 15, pp. 807-826 (2001).
Morino et al. "Eukaryotic Translation Initiation Factor 4E (elF4E) Binding Site and the Middle One-Third of elF4GI Constitute the Core Domain for Cap-Dependent Translation, and the C-Terminal One-Third Functions as a Modulatory Region." Molecular and Cellular Biology. vol. 20, pp. 468-477 (2000).
Cromer et al. "Identification of genes associate with tumorigenesis and metastatic potential of hypopharyngeal cancer by microarray analysis." Oncogene. vol. 23, pp. 2484-2498 (2004).
Park et al. "Bmi-1 is required for maintenance of adult self-renewing haematopoietic stem cells." Nature. vol. 15, No. 423 (6937), pp. 302-305 (2003).
Brass et al. "Translation initiation factor elF-4gamma is encoded by an amplified gene and induces an immune response in squamous cell lung carcinoma." Human Molecular Genetics. vol. 6, pp. 33-39 (1997).
Bauer et al. "Translation Initiation Factor elF-4G Is Immunogenic, Overexposed, and Amplified in Patients with Squamous Cell Lung Carcinoma." Cancer vol. 92, pp. 822-829 (2001).
Bauer, C. et al. "Overexpression of the Eukaryotic Translation Initiation Factor 4G (ElF4G-1) in Squamous Cell Lung Carcinoma." International Journal of Cancer. vol. 98, pp. 181-185 (2002).
Fukuchi-Shimogori et al. "Malignant Transformation by Overproduction of Translation Initiation Factor elF4G." Cancer Research. vol. 57, pp. 5041-5044 (1997).
Mazumder et al. "Regulated Release of L13a from the 60S Ribosomal Subunit as A Mechanism of Transcript-Specific Translational Control." Cell vol. 115, pp. 187-198 (2003).
Miura et al. "Laser Capture Microdissection and Microarray Expression Analysis of Lung Adenocarcinoma Reveals Tobacco Smoking- and Prognosis-related Molecular Profiles." Cancer Research. vol. 62, pp. 3244-3250 (2002).
Racz et al. "Expression Analysis of Genes at 3q26-q27 Involved in Frequent Amplification in Squamous Cell Lung Carcinoma." European Journal of Cancer. vol. 35, pp. 641-646 (1999).
Molofsky et al. "Bmi-1 dependence distinguishes neural stem cell self-renewal from progenitor proliferation." Nature. vol. 425, pp. 962-967 (2003).
Singh and Figg. "Upregulation of the Androgen Receptor During Prostate Cancer Progression." Cancer Biology and Therapy. vol. 3 pp. 284-285 (2004).
Taplin et al. "Androgen Receptor: A Key Molecule in the Progression of Prostate Cancer to Hormone Independence." Journal of Cellular Biochemistry. vol. 91, pp. 483-490 (2004).
Liao and Witte. "Autoimmune anti-androgen-receptor antibodies in human serum." Proceedings of the National Academy of Sciences USA. vol. 82, pp. 8345-8348 (1985).
Latulippe et al. "Comprehensive Gene Expression Analysis of Prostate Cancer Reveals Distinct Transcriptional Programs Associated with Metastatic Disease." Cancer Research vol. 62, pp. 4499-4506 (2002).
Luo et al. "Gene Expression Analysis of Prostate Cancers." Molecular Carcinogenesis. vol. 33, pp. 25-35 (2002).
Luo et al. "Human Prostate Cancer and Benign Prostatic Hyperplasia: Molecular Dissection by Gene Expression Profiling." Cancer Research. vol. 61, pp. 4683-4688 (2001).
Singh et al. "Gene expression correlates of clinical prostate cancer behavior." Cancer Cell. vol. 1, pp. 203-209 (2002).
Welsh et al. "Analysis of Gene Expression Indentifies Candidate Markers and Pharmacological Targets in Prostate Cancer." Cancer Research. vol. 61, pp. 5974-5978 (2001).
Bolstad et al. "A comparison of normalization methods for high density oligonucleotide array data based on variance and bias." Bioinformatics. vol. 19, pp. 185-193 (2003).
Bo et al. "New Feature subset selection procedures for classification of expression profiles." Genome Biology. vol. 3, No. 4, research0017.1-0017.11 (2002).
Rhodes et al. "Large-scale meta-analysis of cancer microarray data identifies common transcriptional profiles of neoplastic transformation and progression." Proceedings of the National Academy of Sciences USA. vol. 101, No. 25, pp. 9309-9314 (2004).
Rhodes et al. "ONCOMINE: A Cancer Microarray Database and Integrated Data-Mining Platform." Neoplasia. vol. 6, No. 1, pp. 1-6 (2004).
Radmacher et al. "A Paradigm for Class Prediction Using Gene Expression Profiles." Journal of Computational Biology. vol. 9, No. 3, pp. 505-511 (2002).
Tukey et al. "Tightening the Clinical Trial." Controlled Clinical Trials. vol. 14, No. 4, pp. 266-285 (1993).
Kleijnen et al. "The hPLIC Proteins May Provide a Link between the Ubiquitination Machinery and the Proteasome." Molecular Cell. vol. 6. No. 2, pp. 409-419 (2000).
Mah et al. "Identification of Ubiquitin, a Novel Presenilin Interactor That Increases Presenilin Protein Accumulation." Journal of Cell Biology. vol. 151, No. 4, pp. 847-862 (2000).
Hiltunen et al. "Ubiquitin 1 Modulates Amyloid Precursor Protein Trafficking and Aβ Secretion." Journal of Biological Chemistry. vol. 281, No. 43, pp. 32240-32253 (2006).
Thomas et al. "Interaction between Presenilin 1 and Ubiquilin 1 as Detected by Fluorescence Lifetime Imaging Microscopy and a High-throughput Fluorescent Plate Reader." Journal of Biological Chemistry. vol. 281, No. 36, pp. 26400-26407 (2006).
Slifer et al. "The Ubiquilin 1 Gene and Alzheimer's Disease." New England Journal of Medicine. vol. 352, No. 26, pp. 2752-2753 (2005).
Garber et al. "Diversity of gene expression in adenocarcinoma of the lung." Proceedings of the National Academy of Sciences USA. vol. 98, No. 24, pp. 13784-13789 (2001).
Chen et al. "Protein profiles associated with survival in lung adenocarcinoma." Proceedings of the National Academy of Sciences USA. vol. 100, No. 23, pp. 13537-13542 (2003).
Zhong 2003 "Antibodies to HSP70 and HSP90 in serum in non-small cell lung cancer patients" Cancer Detection and Prevention, vol. 27, pp. 285-290.
Zhong 2004 "Identification of circulating antibodies to tumor-associated proteins for combined use as markers of non-small cell lung cancer" PROTEOMICS, vol. 4, Apr. 4, 2004 pp. 1216-1225.
Koziol et al. "Recursive Partitioning as an Approach to Selection of Immune Markers for Tumor Diagnosis." Clinical Cancer Research. vol. 9, No. 14, pp. 5120-5126 (2003).
Rossi et al. "Review: The role of the ubiquitination-proteasome pathway in breast cancer Use of mouse models for analyzing ubiquitination processes." Breast Cancer Research. vol. 5, No. 1, pp. 16-22 (2003).
Huebener et al. "AACR Special Conference in cancer research: ubiquitination in normal and cancer cells." Expert Opin. Biol. Ther. vol 3, No. 1, pp. 187-192 (2003).
Abe et al., "Plasma Levels of Heat Shock Protein 70 inPatients with Prostate Cancer: A Potential Biomarker for Prostate Cancer" Clin Prostate Cancer, Jun. 2004; 3(1): 49-53.
Brass et al., Blood, "Role of Amplified Genes in the Production of Autoantibodies" vol. 93(7) Apr. 1, 1999:2158-2166.
Sjöblom et al., "The consensus coding sequences of human breast and colorectal cancers." Science, (2006) 314 (5797):268-274.
Sivasubramaniam et al., Genes & Dev. (2008); 22(5):687-600.

(56) References Cited

OTHER PUBLICATIONS

Soulet et al., "Fibroblast growth factor-2 interacts with free ribosomal protein S19." Biochem. Biophys. Res. Commun. 2001, 289(2):591-6.
Zucchi et al., "Gene expression profiles of epithelial cells microscopically isolated from a breast-invasive ductal carcinoma and a nodal metastasis." Proc. Nat'l Acad. Sci (2004); 101(52):18147-52.
Gu et al., "A novel fusion of RBM6 to CSF1R in acute megakaryoblastic leukemia." Blood (2007), 110(1):323-33.
Berx & Van Roy, "Involvement of the members of the cadherin superfamily in cancer." Cold Spring Harbor Perspectives in Biology 2009.
Burger et al., "Expression analysis of δ-catenin and prostate-specific membrane antigen: their potential as diagnostic markers for prostate cancer" Int. J. Cancer 2002, 100:228-237.
Ole et al., "A switch from E-cadherein to N-cadherin expression indicates ephithelial to mesenchymal transition and is of strong and independent importance for the progress of prostate cancer." Clin. Cancer Res. 2007, 7003-7011.
Rhodes et al., "Multiplex biomarker approach for determining risk of prostate-specific antigen-defined recurrenc of prostate cancer." Journal of the National Cancer Institute 2003, 95(9):661-668.
Fossa Alexander et al, "Serological Cloning of Cancer/Test is Antigens Expressed in Prostate Cancer Using CDNA Phage Surface Display," Cancer Immunology, Immunotherapy: CII, May 2004, vol. 53, pp. 431-438.
Soussi Thierry, "P53 Antibodies in the Sera of Patients With Various Types of Cancer: A Review," Cancer Research, (Apr. 2000) vol. 60, pp. 1777-1788.
Sreekumar A. et al, "Humoral Immune Response to Alpha-Methylacyl-COA Racemase and Prostate Cancer," JNCI Cancer Spectrum (Jun. 2004) vol. 96, pp. 834-843.
Beer D. G. et al, "Gene-Expression Profiles Predict Survival of Patients With Lung Adenocarcinoma," Nature Medicine (Aug. 2002) vol. 8, pp. 816-824.
Wang X., et al "Prostate Cancer Detection By Epitomic Profiling of the Humoral Immune Response," Prostate Cancer Symposium (2005) XP002558315.
Canevari et al, "1975-1995 Revised Anti-Cancer Serological Respons: Biological Significance and Clinical Implications," Annals of Oncology (1996) vol. 7, pp. 227-232.
Karanikas et al, "Antibody and T Cell Responses of Patients With Adenocarcinoma Immunized With MANNAN-MUC1 Fusion Protein," J. Clin Invest (1997) vol. 100, pp. 2783-2792.
Moingeon, "Strategies for Designing Vaccines Eliciting TH1 Responses in Humans," Journal of Biotechnology (2002) vol. 98, pp. 189-198.
Scanlan et al, "Characterization of Human Colon Cancer Antigens Recognized By Autologous Antibodies," Int. J. Cancer (1998) vol. 76, pp. 652-658.
Zisman et al, "Autoantibodies to Prostate Specific Antigen in Patients With Benign Prostatic Hyperlasia," Journal of Urology (19995) vol. 154, pp. 1052-1055.
Kawahara et al, "Use of Four Monoclonal Antibodies to Detect Tumor Markers," Cancer (1986) vol. 58, pp. 2008-2012.
Carney et al, "Potential Clinical Utility of Serum HER-2/NEU Oncoprotein Concentrations in Patients With Breast Cancer," Clin Chem 2003, 49(10) 1579-98.
Luderer et al, "Measurement of the Proportion of Free to Total Prostate-Specific Antigen Improves Diagnostic Perfomrance of Prostate-Specific Antigen in the Diagnostic Gray Zone of Total Prostate-Specific Antigen," Urology 1995, 46(2) 187-94.
Marley et al, Free and Complexed Prostate-Specific Antigen Serum Ratios to Predict Probability of Primary Prostate Cancer and Benign Prostatic Hyperplasia, Urology 1996, 48(6A Suppl) 16-22.
Nicolini et al, "Biomolecular Markers of Breast Cancer," Front Biosci 2006, 1; 11, 1818-43.
Van Cangh et al, Free To Total Prostate-Specific Antigen (PSA) Ratio Improves the Discrimination Between Prostate Cancer and Benign Prostatic Hyperplasia (BPH) in the Diagnostic Gray Zone of 1.8 Top 10NG/ML Total PSA, Urology, 1996 48(6A Suppl) 67-70.
CAS Entery 142: 2133341 (Database Entry) 2005.
Autoantibodies in Prostate Cancer (Letters To the Editor 2005 New England Journal of Medicine 353: 2815-2817).
Wang 2005 "Autoantibody signatures in prostate cancer" The New England Journal of Medicine, Sep. 22, 2005, vol. 353, pp. 1224-1235.
Somers, Veerle A., et al.; "A Panel of Candidate Tumor Antigens in Colorectal Cancer Revealed by the Serological 2 Selection of a Phage Displayed cDNA Expression Library"; The Journal of Immunology, Sep. 1, 2002; vol. 169 0 p. 2772-2780; Baltimore, MD.
Sioud, M., et al.; "Profiling the immune responses in patient sera with peptide and cDNA display libraries (Review)" International Journal of Molecular Medicine, Jan. 1, 2000; vol. 2, No. 6 p. 123-128; Spandidos, Athens, GR.
Beghetto, Elisa, et al.; "Identification of a human immunodominant B-cell epitope within the GRA1 antigen of 4 Toxoplasma gondii by phage display of cDNA libraries"; International Journal of Parasitology, Dec. 1, 2001; vol. 31, No. 14 p. 1659-1668; Pergamon Press, GB.
Hansen, Mona H., et al.; "Antigen-Specific IgG Antibodies in State IV Long-Time Survival Breast Cancer Patients" Molecular Medicine, Blackwell Science, Jan. 1, 2001; vol. 7, No. 4 p. 230-239; Cambridge, MA.
Sioud, Mouldy, et al.; "Profiling the immune response in patients with breast cancer by phage-displayed Cdna 6 libraries"; European Journal of Immunology, Mar. 1, 2001; Wiley-V C H Verlag GMBH & Co.; vol. 31, No. 3 p. 716-725; Kgaa, DE.
Minenkova, Olga, et al.; "Identification of Tumor-Associated Antigens by Screening Phage-Displayed Human cDNA 1 Libraries With Sera From Tumor Patients"; Publication of the International Union Against Cancer; 106, p. 534-544 (2003); 2003 Wiley-Liss, Inc.
Chen Guoan et al, "Autoantibody profiles reveal uniguilin 1 as a humoral immune response target in lung adenocarcinoma," Research Article, Cancer Res. 2007; 67 (7) Apr. 1, 2007 p. 3461-3467 www.aacrjournals.org.
Erkanli, Al, et al.; "Application of Bayesian Modeling of Autologous Antibody Responses against Ovarian Tumor-3 Associates Antigens to Cancer Detection"; Research Article, Cancer Res 2006; 66: (3). Feb. 1, 2006; p. 1792-1798; www.aacrjournals.org.
Mintz, Paul J., et al.; "Fingerprinting the Circulating Repertoire of Antibodies from Cancer Patients"; Research Article,4 Published online Dec. 23, 2002; doi:1 0.1038/nbt 774; www.nature.com/naturebiotechnology; Jan. 2003 vol. 21 p. 57-63.
Vaarala, Markku H., et al.; "Several Genes Encoding Ribosomal Proteins are Over-Expressed in Prostate-Cancer 5 Cell Lines: Confirmation of L7a and L37 Over-Expression in Prostate-Cancer Tissue Samples"; Publication of the International Union Against Cancer; 78, p. 27-32 (1998); 1998 Wiley-Liss, Inc.
Sure, Ali 0., et al.; "Human Lung Cancer Antigens Recognized by Autologous Antibodies: Definition of a Novel 6 cDNA Derived from the Tumor Suppressor Gene Locus on Chromosome 3p21.3"; Ludwig Institute for Cancer Research; Cancer Research 58, p. 1034-1041; Mar. 1, 1998.
Elek D "Microarray-Based Expression Profiling in Prostate Tumors" Center for Molecular Biology and Biotechnology and Department of Biology, Boca Raton, FL invivo 14: p. 173-182, 2000.
Tureci, Ozlem; "Serological Analysis of Human Tumor Antigens: Molecular Definition and Implications"; Molecular Medicine Today, Aug. 1997 p. 342-349; Elsevier Science Ltd.
Albertus Daniel L. "AZGP1 Antibody Predicts Survival and Histone Deacetylase Inhibitoes Increase Expression in Lung Adenocarcinoma," journal of Thoracic Oncology vol. 3 No. 11 p. 1236-1244, No. 2008.
Walker, Michael G., et al.; Prediction of Gene Function by Genome-Scale Expression Analysis: Prostate Cancer-1 Associated Genes; Genome Res. 19979: p. 1198-1203; Access the most recent version at doi: 10.11 01/gr.9.12.11 98; 1999 Cold Spring Harbor Laboratory Press ISSN1054-9803/99.
Mudenda B, "The Relationship Between Serum p53 Autoantibodies and Characteristics of Human Breast Cancer" Br. J. Cancer (1994) 69 p. 1115-1119; MacMillan Press Ltd. 1994.
Stockert, Elisabeth, et al.; "A Survey of the Humoral Immune Response of Cancer Patients to a Panel of Human Tumor Antigens";

(56) References Cited

OTHER PUBLICATIONS

J. Ep. Med. The Rockefeller University Press; 0022-1007/98/04/1349/06; vol. 187, No. 8 Apr. 20, 1998 p. 1349-1354; http://www.jem.org.
Old, Lloyd J., et al.; "New Paths in Human Cancer Serology"; Ludwig Institute for Cancer Research; J. Exp. Med. The Rockefeller University Press 0022-1007/98/04/1163/05; vol. 187, No. 8, Apr. 20, 1998 p. 1163-1167; http://vww.jem.org.
Kuriyama, M., et al.; "Multipile Marker Evaluation in Human Prostate Cancer With the Use of Tissue-Specific Antigens"; JNCI, vol. 68, No. Jan. 1, 1982 p. 99-105.
Mercer Donald, "Use of Multiple Markers to Enhance Clinical Utility," Immunodiagnosis of Cancer, Immunology Series, 53, pp. 39-54, 1990.
Hale et al, "Zin a-2-Glycoprotein is Expressed by Malignant Prostatic Epithelium and May Serve as a Potential Serum Marker for Prostate Cancer" Clinical Cancer Research, Apr. 7, 2001,(4) 846-53.
Zhong, et al. "Efficient Identification and User of Tumor-Associated Antibodies as Markers of Non-small Cell Lung Cancer" CHEST 2004, vol. 125, pp. 105-106.
Hufton 'Serological antigen selection of phage displayed colorectal tumour cDNA libraries' Biochemical Society Transactions vol. 26,1998, p. S5.
Miller et al.: 'Antibody microarray profiling of human prostate cancer sera:Antibody screening and identification of potential biomarkers' PROTEOMICS vol. 3, 2003, pp. 56-63.
Eisen "Cluster analysis and display of genome-wide expression patterns," 1998 vol. 95, pp. 14863-14868.
Li "Gene Assessment and Sample Classification for Gene Expression Data Using a Genetic Algorithm/k-nearest Neighbor Method," 2001, vol. 4, pp. 727-739.
Goloub "Molecular Classification of Cancer: Class Discovery and Class Prediction by Gene Expression Monitoring," Science, 1999, vol. 286 pp. 531-537.
Crescenzi "The main biological determinants of tumor line taxonomy elucidated by a principal component analysis of microarray data," 2001, vol. 507 pp. 114-118.
Denis and Green. "A novel, mitogen-activated nuclear kinase is related to a *Drosophila* developmental regulator." Senes & Development. vol. 10, pp. 261-271 (1996).
Denis et al. "RING3 Kinase Transactivates Promoters of Cell Cycle Regulatory Genes through E2F." Cell Growth & Differentiation. vol. 11, pp. 471-424 (2000).
Kanno et al. "Selective Recognition of Acetylated Histones by Bromodomain Proteins Visualized in Living Cells." Molecular Cell vol. 13, pp. 33-43 (2004).
Acession NM_015021 data, http://www.ncbi.nlm.nih.gov/nuccore/NM_015021, retrieved Dec. 18, 2011.
European office action dated Jun. 27, 2012 for EP Application No. 09006617.6.
International search report dated Jan. 2, 2012 for PCT/US2011/030091.
NCBI reference sequence for hypothetical protein XP_373908 (current status) http://www.ncbi.nlm.nih.gov/protein/XP_373908.5?report=girevhist Retrieved Dec. 21, 2011.
NCBI reference sequence for hypothetical protein XP_373908 http://www.ncbi.nlm.nih.gov/protein/XP_373908 5?report=genpept. Retrieved Dec. 21, 2011.
Office action dated Jan. 5, 2009 for U.S. Appl. No. 11/145,861.
Office action dated Jan. 16, 2009 for U.S. Appl. No. 11/715,642.
Office action dated Jan. 18, 2012 for U.S. Appl. No. 12/556,831.
Office action dated Feb. 3, 2010 for U.S. Appl. No. 11/145,861.
Office action dated Jul. 8, 2008 for U.S. Appl. No. 11/715,642.
Office action dated Jul. 16, 2012 for U.S. Appl. No. 12/556,831.
Office action dated Aug. 19, 2009 for U.S. Appl. No. 11/145,861.
Stone, et al. Serologic analysis of ovarian tumor antigens reveals a bias toward antigens encoded on 17q. Int J Cancer. Mar. 10, 2003;104(1):73-84.
European Search Report dated Dec. 18, 2009, Application No. 09006617.6, Filed Jun. 8, 2005, 6 pages.
Gravdal, et al. A switch from E-cadherin to N-cadherin expression indicates epithelial to mesenchymal transition and is of strong and independent importance for the progress of prostate cancer. Clin Cancer Res. Dec. 1, 2007; 13 (23):7003-11.
International Search Report dated Feb. 8, 2012 PCT/US2011/028845.
International Search Report dated Feb. 8, 2012 of related PCT/US2011/028845. 6 pages.
Notice of allowance dated May 29, 2009 for U.S. Appl. No. 11/715,642.
Notice of allowance dated Aug. 23, 2013 for U.S. Appl. No. 12/556,831.
Notice of allowance dated Sep. 23, 2010 for U.S. Appl. No. 11/145,861.
Abeam Anti-methionine antibody product ab6456 downloaded from the internet Feb. 8, 2017.
Lenionen et al. (2002 Clinical Chemistry 48:2208-16).

* cited by examiner

FIG. 2

Homo sapiens DCHS1 gene for protocadherin-16 precursor, complete cds, without stop codon, AB384634.1

```
   1 gcgatcgcca tgcagaagga gctgggcatt gtgccttcct gccctggcat gaagagcccc
  61 aggcccccacc tcctgctacc attgctgctg ctgctgctgc tgctgctggg ggctggggtg
 121 ccaggtgcct ggggtcaggc tgggagcctg gacttgcaga ttgatgagga gcagccagcg
 181 ggtacactga ttggcgacat cagtgcgggg cttccggcag gcacggcagc tcctctcatg
 241 tacttcatct ctgcccaaga gggcagcggc gtgggcacag acctggccat tgacgaacac
 301 agtggggtcg tccgtacagc ccgtgtcttg gaccgtgagc agcgggaccg ctaccgcttc
 361 actgcagtca ctcctgatgg tgccaccgta gaagttacag tgcgagtggc tgacatcaac
 421 gaccatgctc cagccttccc acaggctcgg gctgccctgc aggtacctga gcatacagct
 481 tttggcaccc gctacccact ggagcctgct cgtgatgcag atgctgggcg tctgggaacc
 541 cagggctatg cgctatctgg tgatggggct ggagagacct tccggctgga gacacgcccc
 601 ggtccagatg ggactccagt acctgagctg gtagttactg ggaactgga ccgagagaac
 661 cgctcacact atatgctaca gctggaggcc tatgatggtg gttcaccccc ccggagggcc
 721 caggccctgc tggacgtgac actgctggac atcaatgacc atgccccggc tttcaatcag
 781 agccgctacc atgctgtggt gtctgagagc ctggcccctg gcagtcctgt cttgcaggtg
 841 ttcgcatctg atgccgatgc tggtgtcaat ggggctgtga cttacgagat caaccggagg
 901 cagagcgagg gtgatggacc cttctccatc gacgcacaca cggggctgct gcagttagag
 961 cggccactgg actttgagca gcggcgggtc catgaactgg tggtgcaagc acgagatggt
1021 ggggctcacc ctgagctggg ctcggccttt gtgactgtgc atgtgcgaga tgccaatgac
1081 aatcagccct ccatgactgt catctttctc agtgcagatg gctcccccca agtgtctgag
1141 gccgccccac ctggacagct cgttgctcgc atctctgtgt cagacccaga tgatggtgac
1201 tttgcccatg tcaatgtgtc cctggaaggt ggagagggcc actttgccct aagcacccaa
1261 gacagcgtca tctatctggt gtgtgtggct cggcggctgg atcgagagga gagggatgcc
1321 tataacttga gggttacagc cacagactca ggctcacctc cactgcgggc tgaggctgcc
1381 tttgtgctgc acgtcactga tgtcaacgac aatgcacctg cctttgaccg ccagctctac
1441 cgacctgagc ccctgcctga ggttgcgctg cctggcagct ttgtagtgcg ggtgactgct
1501 cgggatcctg accaaggcac caatggtcag gtcacttata gcctagcccc tggcgcccac
1561 acccactggt tctccattga ccccacctca ggcattatca ctacggctgc ctcactggac
1621 tatgagttgg aacctcagcc acagctgatt gtggtggcca cagatggtgg cctgccccct
1681 ctagcctcct ctgccacagt tagcgtggcc ctgcaagatg tgaatgataa tgagccccaa
1741 ttccagagga ctttctacaa tgcctcactg cctgagggca cccagcctgg aacttgcttc
1801 ctgcaggtga cagccacaga cgcggatagt ggcccatttg gcctcctctc ctattccttg
1861 ggtgctggac ttgggtcctc cggatctccc ccattccgca ttgatgccca tagcggtgat
1921 gtgtgcacaa cccggaccct ggaccgtgac caggggccct caagctttga cttcacagtg
1981 acagctgtgg atgggggagg cctcaagtcc atggtatatg tgaaggtgtt tctgtcagac
2041 gagaatgaca accctcctca gttttatcca cgggagtatg ctgccagtat aagtgcccag
2101 agtccaccag gcacagctgt gctgaggttg cgtgcccatg accctgacca gggatcccat
2161 gggcgactct cctaccatat cctggctggc aacagccccc cactttttac cttggatgag
2221 caatcagggc tgttgacagt agcctggccc ttggccagac gggccaattc tgtggtgcag
2281 ctggagatcg gggctgagga cggaggtggc ctacaggcag aacccagtgc ccgagtggac
2341 atcagcattg tgcctggaac ccccacacca cccatatttg agcaactaca gtatgttttt
2401 tctgtgccag aggatgtggc accaggcacc agtgtgggca tagtccaggc acacaaccca
2461 ccaggtcgct tggcacctgt gaccctttcc ctatcaggtg gggatccccg aggactcttc
2521 tccctagatg cggtatcagg actgttgcaa acacttcgcc ctctggaccg ggagctactg
2581 ggaccagtgt tggagctgga ggtgcgagca ggcagtggag tgcccccagc tttcgctgta
2641 gctcgggtgc gtgtgctgct ggatgatgtg aatgacaact cccctgcctt tcctgcacct
2701 gaagacacgg tattgctacc accaaacact gccccaggga ctcccatcta tacactgcgg
2761 gctcttgacc ccgactcagg tgttaacagt cgagtcacct ttaccctgct tgctgggggt
2821 ggtggagcct tcaccgtgga ccccaccaca ggccatgtac ggcttatgag gcctctgggg
```

FIG. 2 (cont'd)

```
2881 ccctcaggag ggccagccca tgagctggag ctggaggccc gggatggggg ctccccacca
2941 cgcaccagcc actttcgact acgggtggtg gtacaggatg tgggaacccg tgggctggct
3001 ccccgattca acagccctac ctaccgtgtg gacctgccct caggcaccac tgctggaact
3061 caggtcctgc aagtgcaggc ccaagcacca gatgggggcc ctatcaccta tcaccttgca
3121 gcagagggag caagtagccc ctttggcctg gagccacaga gtgggtggct atgggtgcgg
3181 gcagcactag accgtgaggc ccaggaattg tacatactga aggtaatggc agtgtctggg
3241 tccaaagctg agttggggca gcagacaggc acagccaccg tgagggtcag catcctcaac
3301 cagaatgaac acagtccccg cttgtctgag gatcccacct tcctggctgt ggctgagaac
3361 cagcccccag ggaccagcgt gggccgagtc tttgccactg accgagactc aggacccaat
3421 ggacgtctga cctacagcct gcaacagctg tctgaagaca gcaaggcctt ccgcatccac
3481 ccccagactg gagaagtgac cacactccaa accctggacc gtgagcagca gagcagctat
3541 cagctcctgg tgcaggtgca ggatggaggg agcccacccc gcagcaccac aggcactgtg
3601 catgttgcag tgcttgacct caacgacaac agccccacgt tcctgcaggc ttcaggagct
3661 gctggtgggg gcctccctat acaggtacca gaccgcgtgc ctccaggaac actggtgacg
3721 actctgcagg cgaaggatcc agatgagggg gagaatggga ccatcttgta cacgctaact
3781 ggtcctggct cagagctttt ctctctgcac cctcactcag gggagctgct cactgcagct
3841 cccctgatcc gagcagagcg gccccactat gtgctgacac tgagtgctca tgaccaaggc
3901 agccctcctc gaagtgccag cctccagctg ctggtgcagg tgcttccctc agctcgcttg
3961 gccgagccgc ccccagatct cgcagagcgg gacccagcgg caccagtgcc tgtcgtgctg
4021 acggtgacag cagctgaggg actgcggccc ggctctctgt tgggctcggt ggcagcgcca
4081 gagcccgcgg gtgtgggtgc actcacctac acactggtgg gcggtgccga tcccgagggc
4141 accttcgcgc tggatgcggc ctcagggcgc ttgtacctgg cgcggcccct ggacttcgaa
4201 gctggcccgc cgtggcgcgc gctcacggta cgcgctgagg ggccgggagg cgcgggcgcg
4261 cggctgctgc gagtgcaggt gcaagtgcag gacgagaatg agcatgcgcc cgcctttgcg
4321 cgcgacccgc tggcgctggc gctgccagag aacccggagc ccggcgcagc gctgtacact
4381 ttccgcgcgt cggacgccga cggccccggc cccaatagcg acgtgcgcta ccgcctgctg
4441 cgccaggagc cgcccgtgcc ggcgcttcgc ctggacgcgc gcaccggggc gctcagcgct
4501 ccgcgcggcc tggaccgaga gaccactccc gcgctgctgc tgctggtgga agccaccgac
4561 cggcccgcca acgccagccg ccgtcgtgca gcgcgcgttt cagcgcgcgt cttcgtcacg
4621 gatgagaatg acaacgcgcc tgtcttcgcc tcgccgtcac gcgtgcgcct cccagaggac
4681 cagccgcctg ggcccgcggc cctgcacgtg gtagcccggg acccggatct gggcgaggct
4741 gcacgcgtgt cctatcggct ggcatctggc ggggacggcc acttccggct gcactcaagc
4801 actggagcgc tgtccgtggt gcggccgttg gaccgcgaac aacgagctga gcacgtactg
4861 acagtggtgg cctcagacca cggctccccg ccgcgctcgg ccacgcaggt cctgaccgtc
4921 agtgtcgctg acgtcaacga cgaggcgcct actttccagc agcaggagta cagcgtcctc
4981 ttgcgtgaga acaaccctcc tggcacatct ctgctcaccc tgcgagcaac cgaccccgac
5041 gtgggggcca acgggcaagt gacttatgga ggcgtctcta gcgaaagctt ttctctggat
5101 cctgacactg gtgttctcac gactcttcgg gccctggatc gagaggaaca ggaggagatc
5161 aacctgacag tgtatgccca ggacaggggc tcacctcctc agttaacgca tgtcactgtt
5221 cgagtggctg tggaggatga gaatgaccat gcaccaacct ttgggagtgc ccatctctct
5281 ctggaggtgc ctgagggcca ggacccccag acccttacca tgcttcgggc ctctgatcca
5341 gatgtgggag ccaatgggca gttgcagtac cgcatcctag atggggaccc atcaggagcc
5401 tttgtcctag accttgcttc tggagagttt ggcaccatgc ggccactaga cagagaagtg
5461 gagccagctt tccagctgag gatagaggcc cgggatggag gccagccagc tctcagtgcc
5521 acgctgcttt tgacagtgac agtgctggat gccaatgacc atgctccagc ctttcctgtg
5581 cctgcctact cggtggaggt gccggaggat gtgcctgcag ggaccctgct gctgcagcta
5641 caggctcatg accctgatgc tggagctaat ggccatgtga cctactacct gggcgccggt
5701 acagcaggag ccttcctgct ggagcccagc tctggagaac tgcgcacagc tgcagccttg
5761 gacagagaac agtgtcccag ctacaccttt tctgtgagtg cagtggatgg tgcagctgct
5821 gggcccctaa gcaccacagt gtctgtcacc atcacggtgc gcgatgtcaa tgaccatgca
```

FIG. 2 (cont'd)

5881 cccaccttcc ccaccagtcc tctgcgccta cgtctgcccc gcccaggccc cagcttcagt
5941 accccaaccc tggctctggc cacactgaga gctgaagatc gtgatgctgg tgccaatgct
6001 tccattctgt accggctggc aggcacacca cctcctggca ctactgtgga ctcttacact
6061 ggtgaaatcc gcgtggcccg ctctcctgta gctctaggcc cccgagatcg tgtcctcttc
6121 attgtggcca ctgatcttgg ccgtccagct cgctctgcca ctggtgtgat cattgttgga
6181 ctgcaggggg aagctgagcg tggaccccgc tttccccggg ctagcagtga ggctacgatt
6241 cgtgagaatg cgcccccagg gactcctatt gtctccccca gggccgtcca tgcaggaggc
6301 acaaatggac ccatcaccta cagcattctc agtgggaatg agaaagggac attctccatc
6361 cagcctagta caggtgccat cacagttcgc tcagcagagg ggctagactt cgaggtgagt
6421 ccacggctgc gactggtgct gcaggcagag agtggaggag cctttgcctt cactgtgctg
6481 accctgaccc tgcaagatgc caacgacaat gctccccgtt tcctgcggcc ccattatgtg
6541 gccttccttc ctgagtcccg gcccttggag gggcccctgc tgcaggtgga ggcggatgac
6601 ctggatcaag gctctggagg acagatttcc tacagtctgg ctgcatccca gccggcacgt
6661 ggattgttcc acgtagaccc aaccacaggc actatcacta ccacagccat cctggaccgt
6721 gagatctggg ctgaaacacg gttggtgctg atggccacag acagagggag cccagccctg
6781 gtgggctcag ctaccttgac ggtgatggtc atcgacacca atgacaatcg ccccaccatc
6841 ccccaaccct gggagctccg agtgtcagaa gatgcgttat tgggctcaga gattgcacag
6901 gtaacaggga atgatgtgga ctcaggaccc gtgctgtggt atgtgctaag cccatctggg
6961 ccccaggatc ccttcagtgt tggccgctat ggaggccgtg tctccctcac ggggcccctg
7021 gactttgagc agtgtgaccg ctaccagctg cagctgctgg cacatgatgg gcctcatgag
7081 ggccgtgcca acctcacagt gcttgtggag gatgtcaatg acaatgcacc tgccttctca
7141 cagagcctct accaggtaat gctgcttgag cacacacccc caggcagtgc cattctctcc
7201 gtctctgcca ctgatcggga ctcaggtgcc aacggtcaca tttcctacca cctggcttcc
7261 cctgccgatg gcttcagtgt tgaccccaac aatgggaccc tgttcacaat agtgggaaca
7321 gtggccttgg gccatgacgg gtcaggagca gtggatgtgg tgctggaagc acgagaccac
7381 ggggctccag gccgggcagc acgagccaca gtgcacgtgc agctgcagga ccagaacgac
7441 cacgccccga gcttcacatt gtcacactac cgtgtggctg tgactgaaga cctgccccct
7501 ggctccactc tgctcaccct ggaggctaca gatgctgatg gaagccgcag ccatgccgct
7561 gtggactaca gcatcatcag tggcaactgg ggccgagtct tccagctgga acccaggctg
7621 gctgaggctg ggagagtgc tggaccaggc ccccgggcac tgggctgcct ggtgttgctt
7681 gaacctctag actttgaaag cctgacacag tacaatctaa cagtggctgc agctgaccgt
7741 gggcagccac cccaaagctc agtcgtgcca gtcactgtca ctgtactaga tgtcaatgac
7801 aacccacctg tctttacccg agcatcctac cgtgtgacag tacctgagga cacacctgtt
7861 ggagctgagc tgctgcatgt agaggcctct gacgctgacc ctggccctca tggcctcgtg
7921 cgtttcactg tcagctcagg cgacccatca gggctctttg agctggatga gagctcaggc
7981 accttgcgac tggcccatgc cctggactgt gagacccagg ctcgacatca gcttgtagta
8041 caggctgctg accctgctgg tgcacacttt gctttggcac cagtgacaat tgaggtccag
8101 gatgtgaatg atcatggccc agccttccca ctgaacttac tcagcaccag cgtggccgag
8161 aatcagcctc caggcactct cgtgaccact ctgcatgcaa tcgacgggga tgctggggct
8221 tttgggaggc tccgttacag cctgttggag gctgggccag gacctgaggg ccgtgaggca
8281 tttgcactga acagctcaac aggggagttg cgtgcgcgag tgccctttga ctatgagcac
8341 acagaaagct tccggctgct ggtgggtgct gctgatgctg ggaatctctc agcctctgtc
8401 actgtgtcgg tgctagtgac tggagaggat gagtatgacc ctgtatttct ggcaccagct
8461 ttccacttcc aagtgcccga aggtgcccgg cgtggccaca gcttgggtca cgtgcaggcc
8521 acagatgagg atgggggtgc cgatggcctg gttctgtatt cccttgccac ctcttccccc
8581 tattttggta ttaaccagac tacaggagcc ctgtacctgc gggtggacag tcgggcacca
8641 ggcagcggaa cagccacctc tgggggtggg ggccggaccc ggcgggaagc accacgggag
8701 ctgaggctgg aggtgatagc acgggggcct ctgcctggtt cccggagtgc cacagtgcct
8761 gtgaccgtgg atatcaccca caccgcactg ggcctggcac ctgacctcaa cctgctatta
8821 gtaggggccg tggcagcctc cttgggagtt gtggtggtgc ttgcactggc agccctggtc

FIG. 2 (cont'd)

```
8881 ctaggacttg ttcgggcccg tagccgcaag gctgaggcag cccctggccc aatgtcacag
8941 gcagcacccc tagccagtga ctcactgcag aaactgggcc gggagccacc tagtccacca
9001 ccctctgagc acctctatca ccagactctt cccagctatg gtgggccagg agctggagga
9061 ccctaccccc gtggtggctc cttggaccct tcacattcaa gtggccgagg atcagcagag
9121 gctgcagagg atgatgagat ccgcatgatc aatgagttcc cccgtgtggc cagtgtggcc
9181 tcctctctgg ctgcccgtgg ccctgactca ggcatccagc aggatgcaga tggtctgagt
9241 gacacatcct gcgaaccacc tgcccctgac acctggtata agggccgaaa ggcagggctg
9301 ctgctgccag gtgcaggagc cactctctac agagaggagg ggcccccagc cactgccaca
9361 gccttcctgg ggggctgtgg cctgagccct gcacccactg gggactatgg cttcccagca
9421 gatggcaagc catgtgtggc aggtgcgctg acagccattg tggccggcga ggaggagctc
9481 cgtggcagct ataactggga ctacctgctg agctggtgcc ctcagttcca accactggcc
9541 agtgtcttca cagagatcgc tcggctcaag gatgaagctc ggccatgtcc cccagctccc
9601 cgtatcgacc caccacccct catcactgcc gtggcccacc caggagccaa gtctgtgccc
9661 cccaagccag caaacacagc tgcagcccgg gccatcttcc caccagcttc tcaccgctcc
9721 cccatcagcc atgaaggctc cctgtcctca gctgccatgt cccccagctt ctcaccctct
9781 ctgtctcctc tggctgctcg ctcacccgtt gtctcaccat ttggggtggc ccagggtccc
9841 tcagcctcag cactcagcgc agagtctggc ctggagccac ctgatgacac ggagctgcac
9901 atcgtttaaa c
```

FIG. 3

Homo sapiens centrosomal protein 164kDa (CEP164), mRNA, NM_014956.4

```
   1 ttgcgcgctg cagggcaaca ccccggcgtc cctggaagct gggggagcgg gagaaataac
  61 tttatttgga ctgagagctg gagaatgaga ataggacctg agagtatatt gggctaagga
 121 ggagaggtgt ttgagcccag atgagtcatg gctggacgac ccctccgcat aggagatcag
 181 ctggttctgg aagaagatta tgatgagacc tacattccta gtgagcaaga aattcttgaa
 241 tttgcccggg agattggtat tgatcccatc aaggaaccag aactgatgtg gctggcgcga
 301 gagggcatcg tggcccccact gcctggagag tggaaaccat gccaggacat cacaggtgac
 361 atttactatt tcaacttcgc caacgggcag tctatgtggg accatccatg tgacgaacac
 421 tatcggagct tggtgatcca agagcgggca aagctgtcaa cttctggggc cattaagaag
 481 aagaaaaaaa aaaaggaaaa gaaagacaag aaggacagag accccccccaa aagttcgctg
 541 gccttgggtt cctcattagc cccagttcat gttcctcttg gggcctggc tcctttacga
 601 ggtcttgtgg ataccccacc ctctgctctt cgtggatctc aaagcgtgag cctggggagc
 661 tcagtggagt ctggacgtca gcttggagaa ctcatgctgc cttcacaggg tctcaagacc
 721 tctgcttata caaagggtct cttgggctcc atatatgagg acaagactgc tctcagcctc
 781 ttgggtttag gagaagaaac caatgaggag gatgaggagg aaagtgacaa ccagagtgtc
 841 cacagctcaa gtgagcctct taggaaccta cacctggaca ttggggcact gggggggtgac
 901 tttgagtatg aggagtctct gagaacaagc cagccagagg agaagaagga tgtttctctg
 961 gattcagatg ctgccggtcc ccctactccc tgcaagccct ccagcccagg tgcagacagc
1021 agtctgagca gtgctgttgg caaagggcga cagggaagtg gagcaagacc tggtcttcca
1081 gaaaaagagg aaaatgagaa gagtgaacct aagatttgca ggaatctggt gacccccaag
1141 gcagacccta caggcagtga gcctgccaaa gcctctgaaa aggaagcacc agaggacaca
1201 gtagatgcag gagaggaggg ttccaggagg gaagaggcag ccaaggagcc aaagaagaag
1261 gcttctgctc tggaagaggg cagttcagac gccagccaag aactggaaat tagtgaacac
1321 atgaaggaac cacagctctc agactccata gcttctgacc ccaagtcctt ccatggcctg
1381 gacttcggtt ttcgcagccg gatctcggag cacctgctgg atgttgatgt gctttcccca
1441 gtcctgggtg gagcttgtcg gcaggcccag caaccactgg gaatagaaga caaggatgac
1501 agccagtcca gccaagatga gctgcagagc aagcagtcca aaggcctgga ggagaggtta
1561 tctcctccac ttccacacga ggagcgggcc cagagtcccc ctcgcagcct ggccactgaa
1621 gaagagcctc cccagggccc cgaggggcag cccgagtgga aggaggcaga ggagcttggg
1681 gaggactctg cagccagcct cagcctgcag ctgtccctcc agagggagca ggccccaagc
1741 ccacctgctg cctgtgagaa gggcaaggag cagcattccc aggccgagga gctgggccct
1801 gggcaggaag aggcagagga tcctgaggag aaggtggcgg tcagccccac cccgccagtc
1861 tctccagagg tgcgatccac agagcctgtg gctcccccag agcagctctc agaggctgca
1921 ctaaaggcca tggaagaggc agtggcccaa gtactcgagc aagaccagag gcacctgctg
1981 gaatccaagc aagagaagat gcagcaactg cgggagaagc tgtgccaaga ggaggaagag
2041 gagatcctcc ggcttcacca gcagaaagag caatctctca gttccttgag ggagcggctg
2101 cagaaagcca ttgaggagga ggaggcccgg atgagagagg aggaaagcca gaggctatcc
2161 tggctccgag ctcaggtcca gtccagcaca caagcagatg aggaccaaat cagggctgag
2221 caagaggctt ccctgcagaa actgagagaa gagttggagt ctcaacagaa ggctgagagg
2281 gccagcttgg aacagaaaaa taggcaaatg ctggagcagc tcaaggaaga gatagaggct
2341 tcggagaaga gcgagcaggc tgccctgaat gctgcaaagg agaaggctct gcagcagctg
2401 agggagcagc tggaagggga gaggaaagaa gctgtggcaa cgctggagaa ggagcacagt
2461 gctgagctgg agcggctctg ctcctcattg gaggccaagc accgggaggt ggtctccagc
2521 ctccagaaga agatacagga agctcaacag aaagaggagg cccagctgca gaagtgcctt
2581 gggcaagtgg agcacagagt tcaccagaag tcttatcacg tggctgggta tgagcacgag
2641 ctcagcagtc tcctgcgaga gaagcgccag gaagtggaag gggagcatga gaggaggttg
2701 gacaagatga aggaggagca ccagcaagtg atggctaagg ccagagagca gtatgaagct
2761 gaggagagga agcagcgggc tgagcttctg ggcacctga ccggagagct ggagcgcctg
2821 cagagggccc atgaacgaga actggagact gtgaggcagg agcaacacaa gcgtcttgag
```

FIG. 3 (cont'd)

```
2881 gacttgcggc gccggcacag ggagcaggaa aggaagctcc aggatttaga gttggacctt
2941 gaaaccagag ctaaagatgt caaggccaga ttggctctgc tggaggtcca ggaggagacc
3001 gcccggaggg agaagcagca gctgcttgat gtgcagaggc aggttgctct gaagagtgag
3061 gaagccacag ccacccatca gcagctggag gaggcacaga aggagcacac ccacctgttg
3121 cagtcaaacc agcagctccg agaaattctt gatgagctgc aggcccgcaa gctgaagctg
3181 gagtcccaag tggatctgct gcaggctcag agccagcaac tgcagaaaca cttcagcagc
3241 ctggaggctg aagctcaaaa gaagcagcac ctgttgagag aagtgacagt tgaggaaaat
3301 aatgcttccc cacattttga gccagatctc catattgagg acctgaggaa atcccttgga
3361 acaaaccaga ccaaagaggt gtcttcttct ctctcccaga gcaaggagga cttatacttg
3421 gacagcctgt cctcccacaa tgtctggcac ctcctctctg ctgagggggt agccctccgt
3481 agtgccaagg agttccttgt gcagcagaca cgctccatgc ggaggcggca gacagctctg
3541 aaagctgccc agcagcattg gcgccatgag ctggccagtg cgcaggaggt ggccaaagac
3601 ccaccaggca tcaaggccct ggaagatatg cgcaagaacc tggagaagga gaccaggcac
3661 ctggatgaga tgaagtcggc catgcggaaa ggccacaacc tgctgaagaa gaaagaggag
3721 aagctgaatc agttggagtc ctctctttgg gaagaggcct cagatgaggg cactctggga
3781 ggatccccca ccaagaaggc agtaaccttc gacctcagtg acatggacag cctgagcagt
3841 gaaagttctg aatctttttc cccgcctcac cgtgagtggt ggcggcagca gaggatcgac
3901 tcaaccccga gtctcacctc ccgcaagatc cacgggctta gccactccct ccggcagatc
3961 agcagccagc tgagcagtgt cctcagcatc ctggacagcc tcaaccctca gtcgccgccg
4021 ccgctcctcg cctccatgcc agcccagctc cctccccggg accctaagag cacccccacc
4081 cccacctact atggctccct ggccaggttc tcagccttat catctgctac acccacgtcc
4141 acccaatggg cctgggattc agggcagggg cccaggctcc cctcctctgt ggctcaaacg
4201 gtggacgact tcctgttgga gaagtggcgc aagtattttc catctggcat cccgctgctc
4261 agcaacagcc ccacccccgct ggagagcagg ctgggttaca tgtctgccag tgagcagctc
4321 cggctcctac agcactccca ttcgcaagtc cctgaggcgg gcagcaccac ctttcagggc
4381 ataattgagg ccaaccggag gtggctggaa cgtgtcaaga atgaccccag gttacctctc
4441 ttctcgtcaa cacccaagcc aaaagctact ttgagcctcc tgcagctggg ccttgatgag
4501 cacaacagag tgaaggtgta tcgcttctga ggccctgagc aggggcttgg ggcagcccag
4561 cctctcctcc acccagacca agtgcctgag gagctgcctg ccttcttcca tctgagaaag
4621 caccctcctt ccccctttga cttgcaggag ccaccaggga ccaggggggtt gagtggaaca
4681 gtaaagccac acattctgtg actatataac ctatctcagg ctaaaatgtg tggactcgta
4741 cgagctcttg tcattgacat ggcaagctga tggcgtgcgg tggctgcggg gtatcagggc
4801 cgggagccct ttgggaggaa gggaggcgtt agaggagctg ccttcggagg ctcagggagt
4861 ccctttggag ctggttgttt ccttggccct gcagcgcact gctcggggct cccaaggagg
4921 ttgtgtgtat ggttcttaat tcatcaggac aaagaccccc agcatgtgtg taccctggga
4981 cccgatttct ctgggcccac atctatctcc aatacctcag cctcagatca gaccctttct
5041 tttttgtctt tcttctctta atttttaaat gcctcttttc ttgagcattc catctctctt
5101 tttgaccctc tcaggactgg gcttagctgt ccagagccct gccggagggt gctgggggct
5161 gtccctctgc aggcactgtg ttttcctcag gggctgtcct cagaacaccc ctcctgctcc
5221 ctggggctcc tcagggagcc atttcagctg gagtctcagg tctcaaaaac aacttctcca
5281 ggaggccaaa aaaagactgg gttggcttct ggtcctcatg atggctttta tcctcctggg
5341 acactttggg tatattcatg ggcattgttt ccatctgtct tttctacctg tgccacccct
5401 gccctgattc cacggctgcc tcaggcaggc aggcaaggag ctaggccggt gcccggccct
5461 ggcagcaagg ggtctttgtg cagttggaga tgctgccgtt gtggcagagc gtcctgcagc
5521 cccgcttcca tcagcaggct ctggggtggg ggctttgcag gggatgctct ctgatgtttg
5581 ttccgttgtt taaataaaat gcacttattt ttgttttttt ttttgcaaaa aaaa
```

FIG. 4

Homo sapiens kelch repeat and BTB (POZ) domain containing 6 (KBTBD6), mRNA 1 cattgtcgcc cacgctgcag tagcggcttc tgcggctcca agccagcggg tcctgtgaag
61 gcgagcagac gcggagaaag gacgcgggag tgagagaggg tgagtcagcc actgtctaaa
121 cgataacggg aggcggctct gcggggtagg gttgaattca gtaaatgggc tcgtgctgct
181 gtctcttcgg agacgctgct atcttagcgt cagcgaggga aggttgagga ggagccagag
241 ccgggtcctg cagcgtttct cgccatcagc gcccgtcgcc atctccacca tgcagtcccg
301 ggaagacgcc ccgcgctctc gccgcctagc cagtccccgt ggtgggaagc ggcccaagaa
361 gattcacaaa cccacagttt cggccttttt cacgggtcca gaggaattaa aggacacggc
421 ccattctgca gccctgctgg cacagctcaa gtccttctac gatgcgcggc tgctgtgtga
481 tgtgaccatc gaggtggtga cgcctggcag cgggcctggc acgggtcgcc tgttcccctg
541 caaccgcaat gtgctggccg cggcatgtcc ctacttcaag agcatgttca caggtggcat
601 gtacgagagc cagcaggcca gcgtgaccat gcacgatgtg gacgccgagt ccttcgaggt
661 gttggtcgac tactgctaca cgggtcgtgt gtctctcagt gaggccaacg tggagcgcct
721 gtacgcggcc tccgacatgc tacagctgga atatgtgcgg gaagcctgtg cctccttctt
781 agcccgacgt cttgacctga ccaactgcac cgccatcctc aagtttgcag atgcctttgg
841 ccatcgcaag ctgcgatccc aggcccagtc ctatatagct cagaacttca agcaactcag
901 ccacatgggt tcaattcggg aggagactct agcagatctg accctggccc agctgctggc
961 tgtcctgcgc ttggatagtc tggacgtgga gagtgagcag acagtgtgcc atgtggcagt
1021 gcagtggctg gaggctgctc ccaaagagcg gggtcccagt gctgcagaag tcttcaagtg
1081 cgtgcgctgg atgcacttca ctgaagaaga tcaggactac ttagaagggc tgctgaccaa
1141 gcccatcgtg aagaagtact gcctggacgt tattgaaggg gccctgcaga tgcgctatgg
1201 tgacctgttg tacaagtctc tggtgccagt gccaaacagc agcagcagca gtagcagcag
1261 caactctctt gtatctgcag cagaaaatcc accccagaga ctgggtatgt gtgccaagga
1321 gatggtgatc ttctttggac accccagaga tccctttctc tgctgtgatc catactcggg
1381 ggacctttac aaagtgccgt cacctttgac ctgtctggct cacactagga ctgtcaccac
1441 tctagctgtc tgtatctctc ctgaccatga catctatcta gctgctcagc ccaggacaga
1501 cctctgggtg tataaaccag ctcagaatag ttggcagcaa cttgcagatc gcttgctgtg
1561 tcgtgagggc atggatgtgg catatctcaa tggctatatc tacatttttgg gggggcgaga
1621 ccctattact ggagttaagt tgaaggaagt ggaatgctac aatgttaaga gaaaccagtg
1681 ggcattggtg gctccactgc cccattcttt tttatccttt gacctaatgg taattcgaga
1741 ctatctctat gctctcaaca gtaagcgcat gttctgttat gatcctagcc acaatatgtg
1801 gctgaagtgc gtttctctga agcgcaatga ctttcaggaa gcctgcgtct tcaatgagga
1861 gatctattgt atctgtgata tcccagtcat gaaggtctac aacccagtta gggcagaatg
1921 gaggcaaatg aataatattc ccttggtctc agagaccaac aactacagaa ttatcaagca
1981 tggccaaaaa ttgttgctca tcacctctcg caccccacag tggaaaaaga accgggtgac
2041 tgtgtatgaa tatgatatta ggggagacca atggattaat ataggtacca cattaggcct
2101 cttgcagttt gattctaact ttttttgcct ctctgctcgt gtttatcctt cctgccttga
2161 acctggtcag agtttcctca ctgaagaaga agaaatacca agtgagtcta gcactgaatg
2221 ggacttaggt ggattcagtg agccagactc tgagtcagga agttcaagtt ctctttctga
2281 tgatgatttt tgggtgcgtg tagcgcctca gtgaaatgca caggatcaac agggtttgtt
2341 gtaactagat tgaaacacta agttgttttt actgttttgg aaaatatctt aaatatcctt
2401 tttgttccta aaggagagga aaagttgatt aacttctggt ttggtttaga aaaagtaatg
2461 tttgaaatac gaaggtaatt taatgttaca aattttaaca ctcaaatcaa cctttttaata
2521 attttctgtg ctaagggtcc agtatttatt tgattattta gtatgtttat gtttcatgac
2581 actaatttag tcttttgata cattttacat tctgtttact gccacaagca ctgtggcaat
2641 aacttttgaa ttttaatttt tataatagaa aaatgattag gaattgctag atagtgtttt
2701 gaaagcatat ctttttcttc agaacaatgt agacttccaa aatggttaac ctaaggggtc
2761 tttacaaaat gtgttataag ttaaacataa tttgggaagt tttacttttg ttttcttcta
2821 tgaagaaaaa aatgcaggct gggcgcggtg gctcacgcct gtaatcctag cactttggga
2881 ggccgaggca ggtggatcac ctgaggtcag ttcaagacca gcctggccaa catggtgaaa

FIG. 4 (cont'd)

```
2941 ccccgtctct actaaaaata caaaaattag ctgggcgtgg tggcatgcgc ctgtaatccc
3001 agctacccag gaggctgagg caggagaatt gctgaaaccc gggagtcaga ggctgcagag
3061 agccgagact gggccactgc actccagcct ggatgacaga gtgagactcc gtctcaaaaa
3121 aaaaaaaaaa aaaaaaagga aaaaaaaaaa agaaaaaaaa ccatatgtgt attagggtga
3181 ctgagtggtg acttcattta taataataca gagaatagct ataagctcat tgacagtaaa
3241 aacaacaaac caggattcta ctgtttgaaa agaagtttcg ttttaatttt ggaatttaga
3301 atgtgtattt gcaaagtcac caattttcat ctaaaaggtt atattctagt tgtgtcacca
3361 aatcatcaaa aaaccttaaa aaagaagtaa cttgctttgt aggtttgtat tgttgatcta
3421 aacctgatac atgcttcatt taatcaggaa taatcctttt ttttctgctg gacatgtata
3481 aatttcactg gattgtataa atttttatct attgccttaa acatttacat gattctcaat
3541 atgttttagc tgtacagttt tggtgttcat cttagaggat tcttcagcag aagtgatatt
3601 tctttactgt tttgtgaggt aatactgatt ttgaaaatat atataagcta aaaacagtat
3661 ttcgttgata tcagtagtca ttgtgttaac tataaagtca agtgccagca aagaacttta
3721 aaactgtaaa gctgtgtata gaactgtttt gtgtagcatg gaaatattct gtcagctttt
3781 taaagtcact aaatgttctt gattatcagc ttgaaggtat ttttgtatta caagttgaca
3841 gttgctgggt gtagtggctc atgcctgtaa tcctagcaac tcggggctga ggtgggagga
3901 ttgcttcagc ccaggagttt gagaccagcc tgggcaacat agcaaaaccc catctctaca
3961 aaaataaaaa atatgtctgg gcatggtggc ccaagtctga gtcccagtta cttgggagga
4021 tcacttgaat gtaggatcac ttgagtctag gagttcgggg ctgcagctat catctgcagc
4081 tataatcata gctcactgca gctatgatca tgtctcagca ctccagcttt ggcaacagaa
4141 cgagatccca tctcttagaa aaacaaagtt gatagttaaa gaacataagt ggatgatggc
4201 atttgaggcc actagtgaaa gtatgtttc tctaaaatat ttctctaata gtgatataaa
4261 tggctatttt attatgatgt ttgtatgtgt tttgtatttc tctgtaaacc atgctccagt
4321 ctttgttttt ctgttaccat aatgtaagag aaggtcctgg aacagagact aaatcccacg
4381 aaactgacat tgttaaacac actaaaacag aagtacttac ctcttgaaga tttaatatat
4441 aatggttgac atgatacatg tacatgatga atgaccagat gcttatggtc tacattttcc
4501 tttatcctgt tagtattacc ttccttaatc tttgttcatt aacatgctaa ttcctcttca
4561 gtgtttattt tctagtgaca gaatgctaac atttcttaca ccctggcaga agggagagaa
4621 atgtgttttg gggtgggtaa ctaaattttt gagtgaaata tcataagatg agaatggaaa
4681 gagggagaca caaagagtta taacaaaaaa acaatggttt ttttagccat ttgactggct
4741 ctttaaatag tctacaagac attcacgttt aacatcactt ttagtgaaat aaaatgtgcc
4801 atactagtat gtgcttcaaa agggcaaatg tgctttagtg ccctaaggct aaattttggt
4861 catttgacat cagagatgtt gtaagtattg cacttaatac gcacctattt ctcaatagtg
4921 ttattttttg gctagcattt tctttaccac tatcttgttg atagcttttt gttctctaag
4981 gttgaaacat gacagtgctt atctcaaaca gattacccat ctgcagaact aaggaaagca
5041 atttatgtat gaaagaaatt cttgaattcg tcattctcaa cctttgaatt aaagcttaga
5101 ctaaatagta atatatcgtg ggaaggattt tggttttgtg atatttctgt gaattaagga
5161 atagatgtta accattattt tgtagaaaag tgatttgtat gtggttaatt ataaataaaa
5221 ctggtacc
```

FIG. 5

Homo sapiens ribosomal protein S19 (RPS19), mRNA, NM_001022.3

```
  1 gtactttcgc catcatagta ttctccacca ctgttccttc cagccacgaa cgacgcaaac
 61 gaagccaagt tcccccagct ccgaacagga gctctctatc ctctctctat tacactccgg
121 gagaaggaaa cgcgggagga aacccaggcc tccacgcgcg acccccttggc cctccccttt
181 acctctccac ccctcactag acaccctccc ctctaggcgg ggacgaactt tcgccctgag
241 agaggcggag cctcagcgtc taccctcgct ctcgcgagct ttcggaactc tcgcgagacc
301 ctacgcccga cttgtgcgcc cgggaaaccc cgtcgttccc tttcccctgg ctggcagcgc
361 ggaggccgca cgatgcctgg agttactgta aaagacgtga accagcagga gttcgtcaga
421 gctctggcag ccttcctcaa aaagtccggg aagctgaaag tccccgaatg ggtggatacc
481 gtcaagctgg ccaagcacaa agagcttgct ccctacgatg agaactggtt ctacacgcga
541 gctgcttcca cagcgcggca cctgtacctc cggggtggcg ctggggttgg ctccatgacc
601 aagatctatg gggacgtca gagaaacggc gtcatgccca gccacttcag ccgaggctcc
661 aagagtgtgg cccgccgggt cctccaagcc ctggaggggc tgaaaatggt ggaaaaggac
721 caagatggcg gccgcaaact gacacctcag ggacaaagag atctggacag aatcgccgga
781 caggtggcag ctgccaacaa gaagcattag aacaaaccat gctgggttaa taaattgcct
841 cattcgtaaa aaaaaaaaaa aaaaaaaaaa aa
```

FIG. 6

Homo sapiens ribosomal protein L34 (RPL34), transcript variant 2, mRNA

```
  1 gtctgcaggt atggatgttg ttctcttttc cctgtcttta tttccttacc aatcggctgc
 61 catccgagga gctgaggaag cctagagctc tcagaagcag tcctttgagc tggtgtaggg
121 gcactcagaa tggtccagcg tttgacatac cgacgtaggc tttcctacaa tacagcctct
181 aacaaaacta ggctgtcccg aacccctggt aatagaattg tttaccttta taccaagaag
241 gttgggaaag caccaaaatc tgcatgtggt gtgtgcccag gcagacttcg aggggttcgt
301 gctgtaagac ctaaagttct tatgagattg tccaaaacaa agaaacatgt cagcagggcc
361 tatggtggtt ccatgtgtgc taaatgtgtt cgtgacagga tcaagcgtgc tttccttatc
421 gaggagcaga aaatcgttgt gaaagtgttg aaggcacaag cacagagtca gaaagctaaa
481 taaaaaaatg aaactttttt gagtaataaa aatgaaaaga cgctgtccaa tagaaaaagt
541 tggtgtgctg gagctacctc acctcagctt gagagagcca gttgtgtgca tctctttcca
601 gttttgcatc cagtgacgtc tgcttggcat cttgagattg ttatggtgag agtatttaca
661 cctcagcaaa tgctgcaaaa tcctgttttc ccccagagag ctggaggtta aatactacca
721 gcacatccct agatactact caagttacag tatatgatca ctaatatagt atgctcttgg
781 taccaggagc tctgatatat atctggtaca tgtttgataa tgacttgatt gttattataa
841 gtacttatta atacttcgat tctgtaaaga gtttagggtt tgattttata aaatccaaaa
901 tgagcctttt attgaatcca gttctctatg tgaccagttc tctgtatgaa tggaagggaa
961 aagaattaaa aatcttgcaa aggggaaaaa aaaaaaaaaa aaa
```

FIG. 7

Homo sapiens HemK methyltransferase family member 1 (HEMK1), mRNA

```
   1 gcgtccgagg gagcgcgcga cgggccacgc acgtccgggc gtccagttcg gggcagcttc
  61 tccggctggt gggtgggtgg ggcagccttt caggcagggt ggcaaccaac tatatctgag
 121 gaccagagcc attttggggc accagagctt gtgacctctc catctccacc cagctgggtc
 181 caggggccac tctcagcact cacctcagca gctgacatca taaagcagac ttgggaacct
 241 ggaagcactc tggagaacct ttccctgaga catggagctt tggggccgaa tgctgtgggc
 301 cctcctgtct ggcccaggga ggaggggaag tacccggggc tgggccttca gctcatggca
 361 accccaacca cctctggctg ggttatccag tgccatagaa ctggtcagcc actggactgg
 421 ggtctttgag aagaggggta tccctgaggc ccgggaatcc agtgagtaca tcgtggctca
 481 tgtccttgga gccaaaacat ttcagagcct gaggccggca ctttggaccc agcccttgac
 541 ctctcagcaa ctacagtgta tccgggagct gagtagccgt cgattgcaga ggatgccggt
 601 gcagtacatc cttggagagt gggacttcca ggggctcagc ctaaggatgg tgcccccagt
 661 gtttattcct cggccagaaa cagaggaact ggttgagtgg gtgctggaag aggtggccca
 721 gaggtcccat gctgtgggat ccccaggcag ccccctcatt ctggaggtgg gctgcggatc
 781 aggagccatc tccctcagcc tgctgagcca gctcccccag agccgagtca ttgctgtgga
 841 taagcgggaa gctgctatct ctctgaccca tgagaatgct cagaggcttc ggttgcagga
 901 caggatttgg atcatccacc tcgacatgac ctcagaaagg agctggacac acctgccctg
 961 gggccccatg gacctgattg tcagcaaccc tccctacgtc ttccaccagg acatggagca
1021 gctggcccct gagatccgca gctatgaaga ccccgcggcc ctggatggtg gggaggaggg
1081 catggacatc attacccaca ttctggcctt ggcaccccgg ctcctgaaag actctggtag
1141 tatcttctta gaagtggacc caaggcaccc ggagcttgtc agcagctggc ttcagagccg
1201 gcctgacctg taccttaatc ttgtggctgt gcgcagggac ttctgtggga ggccccggtt
1261 cctgcatatc cggaggtctg ggccatagca tggctgccct gtggatgcct tgtcagtgcc
1321 gccagcctga ccagagggga ggtggatggc actttccaga gcccaggttc ttatggcatt
1381 tcccagggtt ctgtgatttc cccatgctct gcatttctag gatatttcta ggacacctgg
1441 attggctcca tcacatcaga gtggctgagg gcagttgctc tgtgttggtg aaattgctgt
1501 gggggtatcg gggatatgg ccagtaaagt attgagagac taacaaatgg tgacctaatg
1561 ttttgtccat gacttgcagg tcccctgacc cccttactcc caggtagcac tggggcaagg
1621 gtttccttct gccccagcag ggctggccgt cagtcccctg cttggtagtg gtgtgggggt
1681 gcagtgtgga ggaaggcacg tgagtcctca ctcctggcct tggataccat gggtcctggc
1741 atagagcagc tcactcccag ggattgatta gtcctccact gccctgggtg catgcgtaca
1801 caattccctg gccaagcctg gctcgagcac aggaagctca tctgcgtttt ggctcaagga
1861 tgactgcctg ctttctggag gggagggtct ggaggtcttt gctgcacagt tcctgggtcg
1921 cacatccacg ttcatttaac tgaaggcttg agccagtgag ggtgtttcc tttttatccc
1981 catagctttt agctaaaaca tccctcccga gttgaccccc tggggtttca aataacccat
2041 gtgtccctgg ttggggctgg ggagagtgag aagctgagat actgggcaca gggttgtggc
2101 ctccacccca gctctggtct gtgcagactc atggccacca ggaggcctgc agatccagcc
2161 ttcctgtcaa cagcgacagg aaatctctag gttggtgagt gctggtgatg tgagcctaca
2221 tcagggtggg tcctaagaaa catggcaaac caggctgtct cattccacta gactgccccc
2281 tgccaccctg gcacttccca gggcctggca gtatggtctg atgggcagta tggtccaata
2341 ggcagcatcc tctgctgcag ctgggagagc tgagttccag ggctgtgtcc tgcagtggga
2401 ccttgggcaa ctcctttccc tatgagaagc tggctcttct gagtccaggg ccaacgccaa
2461 ctggcaacct ctttactctt agtcaagtgg aatgtgcatg ctggcatctg aatgtccatt
2521 cgccaggcat ggagagcaag agaaggtatg tactgcctga ggtcacatga cagtgaccaa
2581 gtggagacag taagttagat ccctcccttt ggggagccta tattgctgga gtcataccca
2641 gcctaagtgt tgccctgcac tatggctgga ggacacattt ggtagaggtc acactgcagc
2701 tcccagtgcc ccagtgtcct gccctgtgcc cagccccagc tgcatggact ctgagctgcc
2761 cctggcttcc tttaaggagg ctgctccaga aggaacctgg gtggggaggg cgaagggggt
2821 gcacaaccag ggcaaggctc cccacttcct tagtccccca tgctcacaga cctttgcctg
2881 ctaaggtcct caccagtatt gccctttctg tctttctcct tgtgcccttt ggctcttgct
```

FIG. 7 (cont'd)

2941 gtcttcagca gcatctcagg gtagctgccc tgacctcgga gcagtctgtc gcccccctac
3001 acctcagcca gtcctggctt ccctgatggt ctctccctcc tggcctcagg cccattcctg
3061 aggaagggcc ttggcgagct tgtggatgtt gcaccagaag agagtgcagt gttggagagt
3121 gacactgtcg gggcagctgg ggccacaagc aggagccggc ctcgggcaca actttctgcc
3181 cagaaaaatg tgcagcttga ctctgctgag gaaaaggtcc aagccaagag gactggcagg
3241 cggggcctca agcctgcagc cactggcttg attgggccct ggacgttgag cccagatgtt
3301 ggagccacac cagcctggat ttcaatccca gaatctgccc ctcaccagga tgtgaccttg
3361 ggcagatgac ttcacctcac tcagccttgg cttctaaggc tgagaaatgg gacttaatgc
3421 tttattttat aggatgcatg tgaggagccc atggaatgtg cctggcttgg cacattgtgg
3481 catttttcct tgccttcctc ggagggcaga cacagggagg aaggacccag tgccctcagg
3541 cgtccatctg atgcatggga ccaacataag gcaggcaggg atacaaggca gtctggaaag
3601 aagggaaggc aggagtttca gtcttgggct cttgactcct cactgttgtc tagagatgga
3661 gccagcaggc tggtagcctg gcagcctaca tctcccctca gcctctcctc actatggccc
3721 cagtgccttg aggcccaggc cagggcagcc agtggctcta gctcagggaa agccaggccc
3781 acctgcccta tcccctccct tgctcctgag gccaaagcca gagactcgaa cagcctcccc
3841 accaccacca gcatatgtca aggagcactt gcaggcagaa tgggaggagg acatggagct
3901 gatggagtcc aggctgtgca agcccctgag gtcttgagag atgtgcccac tgcccgtgca
3961 gcctccttca gccagagccc agagcataga caggagtgta ggagtccctg tttgatgtac
4021 tctgggagag taattctatc tcctcttctg atagttgggg aaactgaggc cttgtctcac
4081 agttggatgc ttttcccagt tgtcagtggg tttctccatg ggtctcatac agctgcctta
4141 ttgaaatagg ccccgaaccc cctaaatgca aaaaatactc ttttttgctc ctttacccc
4201 acctggaccc tgggctattg gctgctccca atccttgccc caaacactta gctggctccc
4261 catgacttaa gtgtgttctc ttgtgtccta tggaatccag ttctgaagag gtgggggagg
4321 acaactgtgg gaaaagccct gggggcccct cccaaggccc catcagtgct ctgagtaggc
4381 tgtcatcaga acaaagggct ccactgctga caaggtttga gaactgctgg cttgaggtga
4441 gaaccccttt aacctctgcg ggacagcatg tctttcccta tccaccttcg attcttttct
4501 ctttttttc ttcattggct ccttcttagt ggattctctt ctctactgcc ctgggcttca
4561 gcctttgtgc agtactctcg atgccctgaa cacacacctt ccctttgccc aggcggtgca
4621 aacaatccac ttcttcaagc tccaacacaa atgctgcctc ctttaggatg cctgctctgt
4681 gctctccctg cctcccctag cccatacctc tgctggcacc ttctgtacca tgccttcaga
4741 aaccttctta tccccctcat ctctggggcc ccctgtggat ctggcatacc caagttcagt
4801 aaatgtctat cagtaagctg atggtacatg cattttctag aatagagctg ggacttccca
4861 tgtggcccac atctgacctg gcagcccatg tattccggtc attagggatg ggaagccatg
4921 aggacctggc cttctgcccg acccaggcag ccattcaagt tgagcaatgg ccacttcgaa
4981 gactcaagtg cacctgatcc ctgcgcaaca gccacaccag gagaacaggc tgtccttggc
5041 ggcagtagga gcaggcgcca ggtttcctgg agctcttggc ttcagccagc cccagccag
5101 agtcctggct aggacagtga cctgatctcc tcctcatgac cttctgccct ggacaagccc
5161 cctgaactgg atttgggact gtcaaagcaa ctctacccct gctctggtag gctgaacagt
5221 gacccccaa aatggcagtg tcttaatcac ctaaacctta acatgtgact atattacctt
5281 cacatagcaa aatggacttt gcagatgtga ttaaggatct tgagatggaa ggagtatcct
5341 ggatttttca ggtaaactga gtataatcac aagggcctct gtaaaggagg caggagtgtc
5401 agagtgacgg aagaaaatgt atgtaacaat ggaagcagag gtcagagtga tgcaattgct
5461 ggaggaagag ccatgagccg aggaatgcag acagcctctt ctcctctggg gcctcaagaa
5521 gaatgcagtc ctgccaatac cttgatttta agccctgtga aactgatttc agattgctga
5581 cctccagaac agtaagatca taaatttgtg ttgttttcac atgtgtgaaa acacatgtgt
5641 gataatttgt tacagcagcc acgggaaacg aatatagatt gtggtgccca aattagagtg
5701 ctgctgtaac acacgcctac tgattgaagt ggctttggaa ttgcaacgtg gaaatgggca
5761 gaggctggaa gaattttgag agtcatgata aattgcctta accacctctc ttctgatagg
5821 tgatgtggcc aggggaactc ttcctcaacc ttcagaccta aa

FIG. 8

Homo sapiens eukaryotic translation initiation factor 4 gamma, 1 (EIF4G1), transcript variant 1, mRNA

```
   1 tcctcgacgg ccgccgcccg cctggccttt tagggcctga ctcccgccct tcctggccta
  61 cactcctggg cggcggcagg cctagcttct ggcccagtgc gggttccccg gcggcaggcg
 121 tatcctgtgt gcccctgggc caggcccgaa cccggtgtcc ccgggtgggg ggtggggacg
 181 ccacggccga agcagctagc tccgttcgtg atccgggagc ctggtgccag cgagacctgg
 241 aatttccggt ctggttggtc tggggccccg cggagccagg ttgataccct cacctcccaa
 301 ccccaggccc tcggatgccc agaacctgta ggccgcaccg tggacttgtt cttaatcgag
 361 ggggtgctgg ggggaccctg atgtggcacc aaatgaaatg aacaaagctc cacagtccac
 421 aggcccccca cccgccccat cccccggact cccacagcca gcgtttcccc cggggcagac
 481 agcgccggtg gtgttcagta cgccacaagc gacacaaatg aacacgcctt ctcagccccg
 541 ccagcacttc taccctagcc gggcccagcc cccgagcagt gcagcctccc gagtgcagag
 601 tgcagcccct gcccgccctg gcccagctgc ccatgtctac cctgctggat cccaagtaat
 661 gatgatccct tcccagatct cctacccagc ctcccagggg gcctactaca tccctggaca
 721 ggggcgttcc acatacgttg tcccgacaca gcagtaccct gtgcagccag gagccccagg
 781 cttctatcca ggtgcaagcc ctacagaatt tgggacctac gctggcgcct actatccagc
 841 ccaaggggtg cagcagtttc ccactggcgt ggcccccgcc ccagtttga tgaaccagcc
 901 accccagatt gctcccaaga gggagcgtaa gacgatccga attcgagatc caaaccaagg
 961 aggaaaggat atcacagagg agatcatgtc tggggcccgc actgcctcca cacccacccc
1021 tccccagacg ggaggcggtc tggagcctca agctaatggg gagacgcccc aggttgctgt
1081 cattgtccgg ccagatgacc ggtcacaggg agcaatcatt gctgaccggc cagggctgcc
1141 tggcccagag catagccctt cagaatccca gccttcgtcg ccttctccga ccccatcacc
1201 atccccagtc ttggaaccgg ggtctgagcc taatctcgca gtcctctcta ttcctgggga
1261 cactatgaca actatacaaa tgtctgtaga agaatcaacc cccatctccc gtgaaactgg
1321 ggagccatat cgcctctctc cagaacccac tcctctcgcc gaacccatac tggaagtaga
1381 agtgacactt agcaaaccgg ttccagaatc tgagttttct tccagtcctc tccaggctcc
1441 cacccctttg gcatctcaca cagtggaaat tcatgagcct aatggcatgg tcccatctga
1501 agatctggaa ccagaggtgg agtcaagccc agagcttgct cctcccccag cttgcccctc
1561 cgaatcccct gtgcccattg ctccaactgc ccaacctgag gaactgctca acggagcccc
1621 ctcgccacca gctgtggact taagcccagt cagtgagcca gaggagcagg ccaaggaggt
1681 gacagcatca atggcgcccc ccaccatccc ctctgctact ccagctacgg ctccttcagc
1741 tacttcccca gctcaggagg aggaaatgga agaagaagaa gaagaggaag aaggagaagc
1801 aggagaagca ggagaagctg agagtgagaa aggaggagag gaactgctcc ccccagagag
1861 tacccctatt ccagccaact tgtctcagaa tttggaggca gcagcagcca ctcaagtggc
1921 agtatctgtg ccaaagagga gacggaaaat taaggagcta aataagaagg aggctgttgg
1981 agaccttctg gatgccttca aggaggcgaa cccggcagta ccagaggtgg aaaatcagcc
2041 tcctgcaggc agcaatccag gcccagagtc tgagggcagt ggtgtgcccc cacgtcctga
2101 ggaagcagat gagacctggg actcaaagga agacaaaatt cacaatgctg agaacatcca
2161 gcccggggaa cagaagtatg aatataagtc agatcagtgg aagcctctaa acctagagga
2221 gaaaaaacgt tacgaccgtg agttcctgct tggttttcag ttcatctttg ccagtatgca
2281 gaagccagag ggattgccac atatcagtga cgtggtgctg gacaaggcca ataaaacacc
2341 actgcggcca ctggatccca ctagactaca aggcataaat tgtggcccag acttcactcc
2401 atcctttgcc aaccttggcc ggacaaccct tagcacccgt gggcccccaa ggggtgggcc
2461 aggtggggag ctgccccgtg ggccggctgg cctgggaccc cggcgctctc agcagggacc
2521 ccgaaaagaa ccacgcaaga tcattgccac agtgttaatg accgaagata taaaactgaa
2581 caaagcagag aaagcctgga aacccagcag caagcggacg gcggctgata aggatcgagg
2641 ggaagaagat gctgatggca gcaaaaccca ggacctattc cgcagggtgc gctccatcct
2701 gaataaactg acaccccaga tgttccagca gctgatgaag caagtgacgc agctggccat
2761 cgacaccgag gaacgcctca aaggggtcat tgacctcatt tttgagaagg ccatttcaga
2821 gcccaacttc tctgtggcct atgccaacat gtgccgctgc ctcatggcgc tgaaagtgcc
2881 cactacggaa aagccaacag tgactgtgaa cttccgaaag ctgttgttga atcgatgtca
2941 gaaggagttt gagaaagaca aagatgatga tgaggttttt gagaagaagc aaaaagagat
```

FIG. 8 (cont'd)

```
3001 ggatgaagct gctacggcag aggaacgagg acgcctgaag gaagagctgg aagaggctcg
3061 ggacatagcc cggcggcgct ctttagggaa tatcaagttt attggagagt tgttcaaact
3121 gaagatgtta acagaggcaa taatgcatga ctgtgtggtc aaactgctta agaaccatga
3181 tgaagagtcc cttgagtgcc tttgtcgtct gctcaccacc attggcaaag acctggactt
3241 tgaaaaagcc aagccccgaa tggatcagta tttcaaccag atggaaaaaa tcattaaaga
3301 aaagaagacg tcatcccgca tccgctttat gctgcaggac gtgctggatc tgcgagggag
3361 caattgggtg ccacgccgag gggatcaggg tcccaagacc attgaccaga tccataagga
3421 ggctgagatg gaagaacatc gagagcacat caaagtgcag cagctcatgg ccaagggcag
3481 tgacaagcgt cggggcggtc ctccaggccc tcccatcagc cgtggacttc cccttgtgga
3541 tgatggtggc tggaacacag ttcccatcag caaaggtagc cgccccattg acacctcacg
3601 actcaccaag atcaccaagc ctggctccat cgattctaac aaccagctct ttgcacctgg
3661 agggcgactg agctggggca agggcagcag cggaggctca ggagccaagc cctcagacgc
3721 agcatcagaa gctgctcgcc cagctactag tactttgaat cgcttctcag cccttcaaca
3781 agcggtaccc acagaaagca cagataatag acgtgtggtg cagaggagta gcttgagccg
3841 agaacgaggc gagaaagctg gagaccgagg agaccgccta gagcggagtg aacggggagg
3901 ggaccgtggg gaccggcttg atcgtgcgcg gacacctgct accaagcgga gcttcagcaa
3961 ggaagtggag gagcggagta gagaacggcc ctcccagcct gaggggctgc gcaaggcagc
4021 tagcctcacg gaggatcggg accgtgggcg ggatgccgtg aagcgagaag ctgccctacc
4081 cccagtgagc cccctgaagg cggctctctc tgaggaggag ttagagaaga aatccaaggc
4141 tatcattgag gaatatctcc atctcaatga catgaaagag gcagtccagt gcgtgcagga
4201 gctggcctca ccctccttgc tcttcatctt tgtacggcat ggtgtcgagt ctacgctgga
4261 gcgcagtgcc attgctcgtg agcatatggg gcagctgctg caccagctgc tctgtgctgg
4321 gcatctgtct actgctcagt actaccaagg gttgtatgaa atcttggaat tggctgagga
4381 catggaaatt gacatccccc acgtgtggct ctacctagcg gaactggtaa cacccattct
4441 gcaggaaggt ggggtgccca tgggggagct gttcagggag attacaaagc ctctgagacc
4501 gttgggcaaa gctgcttccc tgttgctgga gatcctgggc ctcctgtgca aaagcatggg
4561 tcctaaaaag gtggggacgc tgtggcgaga agccgggctt agctggaagg aatttctacc
4621 tgaaggccag gacattggtg cattcgtcgc tgaacagaag gtggagtata ccctgggaga
4681 ggagtcggaa gcccctggcc agagggcact cccctccgag gagctgaaca ggcagctgga
4741 gaagctgctg aaggagggca gcagtaacca gcgggtgttc gactggatag aggccaacct
4801 gagtgagcag cagatagtat ccaacacgtt agttcgagcc ctcatgacgg ctgtctgcta
4861 ttctgcaatt atttttgaga ctcccctccg agtggacgtt gcagtgctga aagcgcgagc
4921 gaagctgctg cagaaatacc tgtgtgacga gcagaaggag ctacaggcgc tctacgccct
4981 ccaggccctt gtagtgacct tagaacagcc tcccaacctg ctgcggatgt tctttgacgc
5041 actgtatgac gaggacgtgg tgaaggagga tgccttctac agttgggaga gtagcaagga
5101 ccccgctgag cagcagggca agggtgtggc ccttaaatct gtcacagcct tcttcaagtg
5161 gctccgtgaa gcagaggagg agtctgacca caactgaggg ctggtggggc cggggacctg
5221 gagccccatg gacacacaga tggcccggct agccgcctgg actgcagggg ggcggcagca
5281 gcggcggtgg cagtgggtgc ctgtagtgtg atgtgtctga actaataaag tggctgaaga
5341 ggcaggatgg cttggggctg cctgggcccc cctccaggat gccgccaggt gtccctctcc
5401 tccccctggg gcacagagat atattatata taaagtcttg aaatttggtg tgtcttgggg
5461 tggggagggg caccaacgcc tgcccctggg gtcctttttt ttattttctg aaaatcactc
5521 tcgggactgc cgtcctcgct gctgggggca tatgccccag cccctgtacc acccctgctg
5581 ttgcctgggc agggggaagg gggggcacgg tgcctgtaat tattaaacat gaattcaatt
5641 aagctcaaaa aaaaaaaaaa aa
```

FIG. 9

Homo sapiens BMI1 polycomb ring finger oncogene, mRNA (cDNA clone MGC:12685 IMAGE:4138748), complete cds

```
   1 cagcaactat gaaataatcg tagtatgaga ggcagagatc ggggcgagac aatggggatg
  61 tgggcgcggg agccccgttc cggcttagca gcacctccca gccccgcaga ataaaaccga
 121 tcgcgccccc tccgcgcgcg ccctcccccg agtgcggagc gggaggaggc ggcggcggcc
 181 gaggaggagg aggaggaggc cccggaggag gaggcgttgg aggtcgaggc ggaggcggag
 241 gaggaggagg ccgaggcgcc ggaggaggcc gaggcgccgg agcaggagga ggccggccgg
 301 aggcggcatg agacgagcgt ggcggccgcg gctgctcggg gccgcgctgg ttgcccattg
 361 acagcggcgt ctgcagctcg cttcaagatg gccgcttggc tcgcattcat tttctgctga
 421 acgactttta actttcattg tcttttccgc ccgcttcgat cgcctcgcgc cggctgctct
 481 ttccgggatt ttttatcaag cagaaatgca tcgaacaacg agaatcaaga tcactgagct
 541 aaatccccac ctgatgtgtg tgctttgtgg agggtacttc attgatgcca caaccataat
 601 agaatgtcta cattccttct gtaaaacgtg tattgttcgt tacctggaga ccagcaagta
 661 ttgtcctatt tgtgatgtcc aagttcacaa gaccagacca ctactgaata taaggtcaga
 721 taaaactctc caagatattg tatacaaatt agttccaggg cttttcaaaa atgaaatgaa
 781 gagaagaagg gatttttatg cagctcatcc ttctgctgat gctgccaatg gctctaatga
 841 agatagagga gaggttgcag atgaagataa gagaattata actgatgatg agataataag
 901 cttatccatt gaattctttg accagaacag attggatcgg aaagtaaaca aagacaaaga
 961 gaaatctaag gaggaggtga atgataaaag atacttacga tgcccagcag caatgactgt
1021 gatgcactta agaaagtttc tcagaagtaa aatggacata cctaatactt tccagattga
1081 tgtcatgtat gaggaggaac ctttaaagga ttattataca ctaatggata ttgcctacat
1141 ttatacctgg agaaggaatg gtccacttcc attgaaatac agagttcgac ctacttgtaa
1201 aagaatgaag atcagtcacc agagagatgg actgacaaat gctggagaac tggaaagtga
1261 ctctgggagt gacaaggcca acagcccagc aggaggtatt ccctccacct cttcttgttt
1321 gcctagcccc agtactccag tgcagtctcc tcatccacag tttcctcaca tttccagtac
1381 tatgaatgga accagcaaca gccccagcgg taaccaccaa tcttcttttg ccaatagacc
1441 tcgaaaatca tcagtaaatg ggtcatcagc aacttcttct ggttgatacc tgagactgtt
1501 aaggaaaaaa attttaaacc cctgatttat atagatatct tcatgccatt acagctttct
1561 agatgctaat acatgtgact atcgtccaat ttgctttctt ttgtagtgac attaaatttg
1621 gctataaaag atggactaca tgtgatactc ctatggacgt taattgaaaa gaaagattgt
1681 tgttataaag aattggtttc ttggaaagca ggcaagactt tttctctgtg ttaggaaaga
1741 tgggaaatgg tttctgtaac cattgtttgg atttggaagt actctgcagt ggacataagc
1801 attgggccat agtttgttaa tctcaactaa cgcctacatt acattctcct tgatcgttct
1861 tgttattacg ctgttttgtg aacctgtaga aaacaagtgc tttttatctt gaaattcaac
1921 caacggaaag aatatgcata gaataatgca ttctatgtag ccatgtcact gtgaataacg
1981 atttcttgca tatttagcca ttttgattcc tgtttgattt atacttctct gttgctacgc
2041 aaaaccgatc aaagaaaagt gaacttcagt tttacaatct gtatgcctaa aagcgggtac
2101 taccgtttat tttactgact tgtttaaatg attcgctttt gtaagaatca gatggcatta
2161 tgcttgttgt acaatgccat attggtatat gacataacag gaaacagtat tgtatgatat
2221 atttataaat gctataaaga aatattgtgt ttcatgcatt cagaaatgat tgttaaaatt
2281 ctcccaactg gttcgacctt tgcagatacc cataacctat gttgagcctt gcttaccagc
2341 aaagaatatt tttaatgtgg atatctaatt ctaaagtctg ttccattaga agcaattggc
2401 acatctttct atactttata tacttttctc cagtaataca tgtttacttt aaaaattgtt
2461 gcagtgaaga aaaaccttta actgagaaat atggaaaccg tcttaatttt ccattggcta
2521 tgatggaatt aatattgtat tttaaaaatg catattgatc actataattc taaaacaatt
2581 ttttaaataa accagcaggt tgctaaaaga aggcatttta tctaaagtta ttttaatagg
2641 tggtatagca gtaattttaa atttaagagt tgcttttaca gttaacaatg gaatatgcct
2701 tctctgctat gtctgaaaat agaagctatt tattatgagc ttctacaggt atttttaaat
2761 agagcaagca tgttgaattt aaaatatgaa taaccccacc caacaatttt cagtttattt
2821 tttgctttgg tcgaacttgg tgtgtgttca tcacccatca gttatttgtg agggtgttta
2881 ttctatatga atattgtttc atgtttgtat gggaaaattg tagctaaaca tttcattgtc
```

FIG. 9 (cont'd)

```
2941 cccagtctgc aaaagaagca caattctatt gctttgtctt gcttatagtc attaaatcat
3001 tacttttaca tatattgctg ttacttctgc tttctttaaa aatatagtaa aggatgtttt
3061 atgaagtcac aagatacata tatttttatt ttgacctaaa tttgtacagt cccattgtaa
3121 gtgttgtttc taattataga tgtaaaatga aatttcattt gtaattggaa aaaatccaat
3181 aaaaaggata ttcatttaga aaaaaaaaaa aaaaaaaaaa aaaaaaaaaa aaaaaaaaaa
3241 aaaaaaaaaa a
```

FIG. 10

Human DNA sequence from clone DAMA-147C13 on chromosome 6, complete sequence

```
   1 accatatcct cctacactct gagcaatctc acggggtaga ccgcaggtta acacctctca
  61 gactccttga aaaatagctg gtgacgggtc agtgcccaga gctcacctgc ctttcgccaa
 121 actctaaaca cccctgtgtg tttcccctac tataccctgt tccctggggg caggtccctg
 181 cattatgaag ccactaggaa aatgagataa agctttccta cttttcttcc cctgaaaaga
 241 cagattttgt tttttatttt ttgagaatac caagtaagat tttatttttt atttatttta
 301 aattatttta acctttgttt taggttcaag ggtacacatg caggtttgtt atataggtaa
 361 attgtgtgtc atcgggattt ggcgtaaaaa tttatttcat cacccaggta ataagtatag
 421 tatctgatag gtagtgtttt gatcctctcc ctcctcccat cctccaccct caagtagggc
 481 ccagtgtcta ttattccctt ttttgtgtcc atgtgtactc aatgtttagc tcccacttat
 541 aaaagtgaga acatgcagta tttcattttc tgctcctgtg ttagtttgcc taggataaca
 601 gcccccagct ccatccatga tgctgcaaaa gacgtgatct cgtccttttt tgtctgtgga
 661 gtattccatg gtgtatatgt accacatttt ctttatacag tctactgttg gtgggcattt
 721 aggctgattc catgtctttg ctattatgaa tactgctgca gtgagcattc atgtgcatgt
 781 gtccttatgg tagaacaatg tatactcctt tgggtatatg cctaataatg ggattcctgg
 841 gacgaatggt agctctgttt taaggttctt gagaaattgc caaactgctt tcctcaatgg
 901 ctgaactaat ttatgttccc accagcagtg tataagcctt ccgttttctc tgcaacctct
 961 ccaacatttg ttattttttg actttttaat aatagccatt ctgactggtg tgagacggta
1021 tctcattatg attttgattt gcatttttct aatcattagt aatgttgaac attgtttcat
1081 atgcttcttg gtcacgtgtg tgtcttgaaa aggcagattt tatgtatttg cgtatttatt
1141 tttttcacag gttttttttt tgaaagtctc actctgtcgc ctaggctgga gtacagtggg
1201 ataatctcgg ctcactgcaa tcttcgcctc ctgggttcaa atgactctca tgcctcagcc
1261 acttgagtag ctggggttac agtcatgtgc caccactcct ggttagtttt tgtctttttt
1321 ttttttttgg tagagacagg gtttcatcat gttggccagg ctgttcttga actcctgacc
1381 tcaagtgatc cacccacctc agcctcctaa agtgctagga ttacaggcat gagccatcgt
1441 gcctggcctg aaaaagcaga ttttaaacgg caattcattc ttctatccca ttgtgaacta
1501 tacagttgat ggattttcca tcactaactt gaaactctaa attggcttcc ttctgctccc
1561 cagtaggttt cagggctgcc tcttcacatc ttagtttctg agaactcttg gattttatta
1621 aatagtgagc taaacaaaac aggattgtgg aaggggcccc ttgacaccac acttacctgc
1681 cctccctcaa agtccctgat ctcaggaaaa tctaacacct atgaagaaaa tggggataaa
1741 aaatgcatac aaagattatt accaaaaacg aaagattcgt tgtgtaacta attgagatta
1801 actgaagctc tgccatagct cccagccact gcccccactc accttgctta tatactctaa
1861 ctctgctaac gaactgtcaa gtgtgttgga atgggcagaa tatggggtgg ggagtgcata
1921 atctgtagag cttctacaga tacagtgcta ggtaggtcct ttctataata tctcatctca
1981 tcttaaaaga cttgttggcc gggcatggtg gctcacgctt gtaatcccag cactttggga
2041 ggctgaggaa ggcatatcac ctgaggtcag gagtttgaga ccagcctggc aaacatggtg
2101 aaaccccgtc tctacaaaaa atacaaaaat tagctgggtg tggtggcgcg tgcctgtaat
2161 cccagctact ctggaggctg aggcaggaga atcgattgaa cctgggaggt ggaggttgca
2221 gtgagccgag atcgtgccac tgcactccag cctgggtgac agaatgagac tgtctcaaaa
2281 aaaaaaaaaa aaaaaaaaaa cttgttaatt gtcctcattt cccaggttgg aaaacaggtc
2341 caaagattca cacccaaggt ctaaaggctg taactcctct tcttatacag ctgttacaca
2401 tgcacgtgtg tacacacaca cacacataca cactctcttg agcatgccca cacactcact
2461 acatcttgga actgggatgg ctcaaataaa gggagttagt gaggcctccg ctgagaaaga
2521 gagaaagaga agagtcacaa tccataaccc aattcaccca agtcttatct ttcctgtcct
2581 cagagttcct tctgctctga gaaccaccgt cccttccact ttctcttttg acaagtttca
2641 aaactgaatt ttcccccaca cccccccaat acatttcccc ctcacattcc tccccatcct
2701 gcccaggtaa gctgttagcc taaccttata ggaaccaagt cctgggatcc ttttcaatgt
2761 ctacaaagcc tagccctggc aagggagcac tggctgtgtg gtcctgtgcc agcactgaac
2821 atggccctag ccagtaacag tggggctgaa tgtagttccc tcttatgtct agatctctgc
2881 tccggcagtc aaaggagatg tgaaaccttc tgtgaggcca caacaggaaa tggtaggaga
2941 ggatttcact tctctattaa ttcaaacact gagggagctt tttagaataa agaaggacag
```

FIG. 10 (cont'd)

```
3001 aaaacccaga cacctgtgct cagcagtgtt ttccttcctc tcctcctccc aacccttcca
3061 tttttacaga tatagctctg tctttccacc tctagccaat tcaaaataac atttcagttg
3121 ctctgtccat tgttacttat ttgttaatta ttgatatagc accgggaccg aagaggtatg
3181 gagccccaac caggttccca catgttgcct ttcttttatt gcctctacac aaccacccaa
3241 agagtgagtc ctctcctttc ccattgcctc tgcccttagc ctgaccacca catgcctgca
3301 gtaaactagt cccagggttt gtgtgcaaag cattactggg aaaatacaga gtgagaagat
3361 atggattctg cccccatatc gctttgcttg tacgtcaatt ggggagtgag aacaaacact
3421 ttaaatagtt tatattaaag taagtaagca ataaggccag tggtcttaaa agagaagaga
3481 gaaatcacca tggacatggt agacagggag tactctcagt cgagagggcc tggaatgagc
3541 cttgaatact gggctggatt tgtgttggag aggaggaagg cagttggcat tgtaggtctg
3601 gtgtatagct ccacaagctt gacaatgctg tgaggtgcca tcagggagga ggtgtcctac
3661 gagagcctgg gttagctaaa acaaagacaa gctacaataa cgtcactggc actgcacgtt
3721 ggaggaagtc acaaatgtga tttcttgttt ttttctgaga gtatggccat aataataaat
3781 ctcttctagg cacttcctaa agttgctcca tgtcagttcg caggttcttg ggcagacgg
3841 ttttaactga agtctccatt ttataaacac aaaattgctc aaccagttaa tcacgcctca
3901 tagcataaga ccacattcgt gacttcagtg tcttttcaaa actacacaca cctacatcct
3961 gccaagatta tattacttgc ccaatctgtc caatccccac cccacccctg ccatctaccc
4021 cttacctcac ctccgcccac acacacaccc tcctaccctg tcaggattca ctgctctaga
4081 ccctgacctt tggattatag tttctgtagt cagttcacca tccttccaac ctacagtcaa
4141 attatttgaa ctactaggga tagtctatct gatttgccac aactattttt cctttttttaa
4201 ttttattttt tgccaccaca actattgaag aatgctatct tcatcttacc cacgagaaaa
4261 tggaggcaga gggaggttaa gtggttgccc agatttaccc agatactaag taataaaacc
4321 attacttgaa ctcaggattt attactttaa atcctgtatt gccaataatc aattggaaaa
4381 taactgaaaa ttgcctacta tttataataa caataaaaac catagcatat ttatgaatta
4441 acatatcaaa tataagaatt ttaagaaaaa agaaaacttt attgaagtgc acaaagacct
4501 gagaggtgta gagatatacc atattcatgg ataggccatg ctaacataat gacaacctct
4561 ccccacatct ctaacctaaa tgctacccca attaaagtaa cagtaggatt tcaggagaat
4621 ttaacaaact gattatagaa tgtacatgga aataaagtcc aagagtatct tagaatattt
4681 tgataaagaa aaggaaaata aattttttgg gaaggtggtg aaggaatgga gactagttct
4741 actaaatagt aacacatatt aaaaagccaa aataatcaaa caatatgata ctgattagta
4801 atgagagaaa agcaaattaa aacaacaaaa taccactcta cacccaccat gttgccaaca
4861 tttgaaagtc aaataattac aagcattagt gagcataaag ggaaatgtga actatcttgc
4921 tttgttgatg ggagtgtaaa ctgtttatga tccctgaatt atagaaatta taaactagtt
4981 gggcgaaaaa attaacatag gaaataaagc ggcatatccc aatccttagg ttgagtgctt
5041 taagtcttgg aagatttcaa taaagagaaa ttaggggcag gttcatggaa taagttgaac
5101 tggagttgga cctatggagt gggttaagac aggaacaaga tgagcagaat aaagaaagca
5161 ttcttgtgag aggaaagagc ctgggcaaat gccctaaacc aaaatcagat ataatacctc
5221 aaggaagagt gaggaaaaaa gatttattca agaatagcat tcctgctggg aatagtgagt
5281 aatatttttt attagaaaag gggcaccaga ctagagagga tactgagtgc ttctagagta
5341 cttaagtaac agtatcatag aaggtttcat cagagagcat ctaatctaag cccatcattt
5401 tacagatgaa gactttgagg cccagagagg ggaagtgact tgtctaaagt cacacagcat
5461 aataaagcac ttttaagtct tgcctgacag gaaatatcta gataagttgg aaaacagaga
5521 gacagagaaa ttaggaagaa ctagaaagca ccacatctag aattactaac atgagaataa
5581 aaagaaaaac atctaaaatg gagaaaatac aatacttgaa gctagtattg aggtatattt
5641 cagaaaagag aaagaagtct acgaggcaac taagttctcc tctgaagatc aagaccaata
5701 atgataaggt taggttattc agcacatttt ctatgtgcca aacactattt taagcattct
5761 gtaggtatta acttatttaa gcttcacagc atgaggatat gctgccttat ttcctatatt
5821 aactttttca ctcaactagt tcataatttc tgtaattcgg gcatcataaa cagtttacat
5881 tcccaccaac agaccaagat attacagttc acattttcct ttatcctcgc taatacttat
5941 ttgactttca aatgttggca acatggtggg tgtagagtgg taaggggggac accattgtta
6001 tcatcatcct tttacagaaa atgacaccaa agcacaagtt aagtaacttg cccaagggct
```

FIG. 10 (cont'd)

6061 cacagctaaa cgctgacagt tacgattgaa tccccagcag tcaggttcca gagcccatgc
6121 ttcttaaccg gtacacatga tgctgttaga aatgagatgg ttcagagaca gtgcaacttc
6181 tcttagggag aatttaatat ttcttttag attagactct agtacaatgc caagaacaga
6241 aactccctca ccaaataatt gccctctcaa ctttattgcc accctgtcat ccaaagcaac
6301 tcccagaccc taaggaatgc aagaaagaaa gcatatgcaa agcaatttac caccagtggt
6361 catgtgctgc cacctttcgt tatcttccca ggacagcacc tgtgcagttc tccttggaca
6421 gttcactcag gccaaggaac agattgtcag gaaagacatg tgaattcttt gcccttccag
6481 gctgttttca cttcatgtta ggggcttcat gatactgttt tcccagaact gacataactg
6541 attggtatag cacttgggag cttattcttc ccatccctga gcttctgttt ctcagttacg
6601 gtgagggttg aagggagtta tatgttcctc agggcagcct atacgagaca taaacatttt
6661 cacaaacagt aaaatacaca acacacacac acacgcacaa aacacacaag cagcttcctt
6721 aaccattttg taagcagatt attagaaaat aactctgcct tcgtttctca catattttgc
6781 acaaaccgat agatggaaaa acatcatgta ccgccaagac cagggaataa gagctcagct
6841 ggcaaattag ggttttccc tatttccctc cctaacgagg tcaagctgtg ttcaggttaa
6901 ggcatgctga atttgaaacg acaacccact caagttgaga tatccagaaa caaataccat
6961 gagttaagaa agaagccaca ctgatataaa gaaatgagat ttattgcctt gtgggggaa
7021 gggatgtggt tgtgataggc aggccactct gggatccctg ggatgcaagc ccagggacag
7081 cagagtcccc aggtgggaaa tctacacaca caccccaggg atgtcccaga gacttcttct
7141 accctaagag gagatcctgg gcaggatgtg agaaatctga gcatcctctg tttggatggc
7201 cgaagctgct ggcatcaaac tctggtctgg aagaatcagt ctgggggaga gacagggatg
7261 gaggaaaggc atcaggggat ccatcctcct cctccttctc ctcctcctcc tcccccacaa
7321 aggccttgct cgccctgcct gcaccacacc ctgcagaagt tgatctctcc ttgttcccaa
7381 atcatctcca agcacccttc ctacagcacc ccatgattcc tttttcact caaagcaatt
7441 cttgtgaccc ataactgtgt gtgtgtaact gggtccccaa ctgggaagat gtgcccccat
7501 ggtgctggat acaggccccc acacccaagg gcctgaggat cgctatatgt ccccccatgc
7561 cacaaaataa tcctgacaca tgcacgcatg caccactgta tctggctccc acaggctcac
7621 ccgcccccctc cagatgacat accacctgag caaggcttcc ggaagtagat gatgagaaca
7681 atgcccacga tgatgcccag cacacccagg ccaaaggcca cgccacacag cacattctcc
7741 agcagatctg agggcagtgc gttccggggt actggaggaa atgagtggct cagcctgggg
7801 acctagttag ggagcctccc acccagggaa atgacgtggg tgtctgggat gacatgggag
7861 actgggatgg gcttagggta ggaatggact aaacaaggta ccagtggaga aagaagcctc
7921 ctcccatgga tctatccctt tttgcccccca aaaggaccag aattccaggg agaaagcctc
7981 accccaatag gcaattgctg tgtagcggtc aatttcgtga gtcacaatgc aggagaaaat
8041 gtcagaaggt tctggtgtga agtttaagta agaaaaggcc tggaagctga gtccatcgac
8101 agctgagaca aaagtaggcc caaatccttc cacagggacg gaatgatgct gccagttcac
8161 tgtcagcatg ggtgggaaga gattactgac aaaacagacc aaagtgttgg gcttgccaaa
8221 ctccaggggc ttcagcgtga acacttcagc gataggaaac cctggtgggg ggattgaagt
8281 gtagggggaa aaagagacta gtttagatgg tatctctgtg tttggagggg ccatggcata
8341 tggaggggag ggcagagaag aacacagtgg gtcaggcttt gggagacaga gatgagcgag
8401 gagctgggct ctgaagggag gtcttcttcc aggcaaggac tgcagctaga cgtagaagca
8461 gagccagatc caggctactc tggacccctc caccatgact tccttcagca cttcctgtct
8521 agagctcaca ttgatgtcta accatgcact gtcttctcac taagacatag tcacgtcatc
8581 agatatttcc actcttccca tccatcttgc tgggcatagt agcacaagtg ttaatattca
8641 gtaggtatca gttggtacct gttgaattca tcacattcaa tacatagttc tgaatgccta
8701 ctacatgcta ggtacttcgg cccaccaaaa gaacacaggg tgcagaccaa ggctggtgga
8761 aaaattaagg tgatgaagag aaccagaaag tatttgagat ggggagctgg tatcaagggg
8821 aattattcag tgtacagatc aatgaggtta atgcagccct cctcccttca ctccccagaa
8881 aactcctgac ctctggacac cgggatttc ccatcaagtt ttggccctat ttgctggatc
8941 atccactcgc agaactcttt gtcaaataaa atggcaggag catctccctg ttcctgagcc
9001 cagtcagcaa attcgggcag gcgaggcacc cgagtgttct gggaaaagtc gaagaagaaa
9061 agctggtcct cgtcgtaggc ctcagagagt cccacactgg gactcccatc ctggcagtac

FIG. 10 (cont'd)

```
 9121 actgtgtgca ggaatgtgtg gttttgcagg tcatctggcc acattggagt aggagctgca
 9181 aaggacacag ggtgaggttc agggaggtgg gagccttctc ctccaactta aaaaacagca
 9241 aggtggggct aggcgcagtg gctcatgcct gtaatcccag cactttggga ggccaaggtg
 9301 ggtggatcat gaggtcagga gtttgagacc agcctggcca gcatggtgaa actccatctc
 9361 tactaaaaat acaaaaaagt agctgggcat gttggcatgc gcctgtagct actcgggagg
 9421 ctgagggagg agaattgctt gaaccaggga ggcagaggtt gccgggagct aagattaagc
 9481 cactgcactc cagcctgggt gacagagtga gactctgtct caaaacaaaa caacaaaaac
 9541 aagcaaggcc tgcttaagga gcgtgggctg aggtgagacc ctttcctgtg tctgttattt
 9601 agactccccc tcccaaaggg ggtgaagaac aaattatggc atctctccaa gcttcccctg
 9661 cctataaaaa ggccagttgg caaaagtaaa gagttctact ttctaaagtg acagattcag
 9721 gccaggcatg gtggctcatg cctgtaatcc cagcactttg ggaggctgag gcaggcagat
 9781 tgcttgagcc caggagttca agaccaacct gggcaacaca gcgagaccgt ctctacaaaa
 9841 aatacaaaaa cttagccagg tgtggtggca aacacctgtg gtctcagcta ctctggaggc
 9901 tgaggcagga ggattgcttg tgcctaggaa gttggggctg cagtgagcca tgattgtgcc
 9961 actggactcc agcccaggtg acagaatgag cccgtctcaa aaaatatata tataaaggcc
10021 gggcgcggtg gctcaagctt gtaatcccag cactttggga ggccaaggcg ggtggatcac
10081 ctgaggtcag gagtttgaga ccagcctggc aaacataatg aaaccccatc tctactaaaa
10141 atacaaaaat cagctgggtg tggtggcatg cgcctgtaat cccagctact tgggaggctg
10201 aggcaggaga gtctcttgaa ccccagaggc aggggttgca gggagccgag atcacgtcac
10261 tgcactctag cctgggtgac agagcgagat gccgtgtcaa aaaaaataaa ttaaatcaaa
10321 taaaaaattt aaaaatgtat atatataaaa taaagtgaca gattcagagt cactgttcat
10381 tgtgtgtttg gggctgcac aaagacacct agccaaagaa gcaagtgaaa gcctgcattc
10441 tgctcaccat gccatacatc ctggcatagg gctgtatcct cccaaagggg attcctttgt
10501 ctaattcata ccaggccact gtattgacta gagaaggcca tggatgggtt tctcactctt
10561 agaagggaaa gaggaggaat ggctacagcc tccccaagcc atagatggga ctgcctccca
10621 ctatccccag acacaaatgg taaattggaa aacctgtatc cagacatttc ttcagccact
10681 tcattggcac caagcgtctc tcaaaatgtc ttctgttcct taacctacca ggcctcccaa
10741 agacagcaat gggagaagtg accccataac tgcataaaat aatccctctt ctttgaagct
10801 cttggcagga atcgctcagc cagcaggaaa cctttaaccc aatacccaga aaaacagaca
10861 tttggaggaa gagggatctt ccagattatt cttccattct gccccatcct ctacagagaa
10921 ggaaactaag acacttttca agaatcacaa gataagttaa tgatagaaag cagagtagaa
10981 tcttgagtgg aggagtgaaa ataacattca ctttgttcaa atcccagctc taccactttc
11041 caatggtgtg aacttgcaca aataactctg agtctcattt tcttcatttg taaaatggag
11101 agaacaatct ccgcttcaag agattgtctt aaatggaaca tgcaaagcat cactgatatc
11161 gtttaccaac cacacatagc agctgtcttt ccccactccc ctgttgtttc cactgcctca
11221 taagacttcc caccactcac aaagcacagc gcttttcctc acaaagctga gtgggctccc
11281 taggttcagg atggaagtaa ataggagtac catcttacct tcagggacgg cccaggagtg
11341 gggtagcagc cacagaagtg gtaacatctg tagcagcgca gctccttggt tctgttcatg
11401 acccatacct tcttgccaca cagtaggtag gagctaccaa cccagccaac ccagcttccc
11461 caactccctc cccgagaggg tggccttaga tcatgttttg ccagatcatt tccaataggt
11521 gcccttgtca ttttgtctaa accaatcaga gaagcgtagg gtttaacatc atcagtcact
11581 ggggagacgc ctggggccag taacctcctg aagacttggc tgtttgacca gggcagagta
11641 tggcatgtaa ctgggctggg aagcccagtg gaggaatgtt gcttcctggt ggagttccct
11701 ctttggtttc aagctgtcag cctcagtctg taagcgacca gctggctctt cagagcagtg
11761 ccacctcctg gcagaatgct gcaatgggga accgcatctt ccccaagtaa acccccaggg
11821 ctcttcggac cctgccttct cctccctcct ggctcttcct ctttctcaaa aaaacttatt
11881 ctccttcagg cattagctct aattcatttg gcagacatat attgaaaata caagaaattc
11941 tgggtgttgg gcccagggct agaaatacaa agatgaatag gcatagtctg ccttcaaaga
12001 gcttagagtc tagtgctggg ggagggggcc aagggataat tacacaacaa tgtaatgtat
12061 tcaaataaga atgtgccaag tgttttggaa gtcgcagtaa ttttatgagg atgcggaata
12121 ggaggaacat aatcaggcag gctcctaaga cttgaaggaa aaacaatttg gccagcagaa
```

FIG. 10 (cont'd)

12181 catgaaggaa gagaaaaaca cgccagggca aagggtaggc agaagtacaa agatcacagg
12241 catccagagg tcctctttgg agaccctgtg tactagttga tatgaatgtt gtgaaggtcg
12301 cttgggtgtt cctgtataat aggaggtaat gggggtaga aggatgttgt gataagctac
12361 aaattcgggc aagggccaga tcacgtgggc cctgctacgc cacaaggagg agcttgcttt
12421 tacttagcag atgatagaga tattaaaact ggggaatgac aatcatttta gcattttgga
12481 aaaaatgttc tgattgatat ttcaaacaat gaactggagc ttttaaagaa ttgaggcaaa
12541 actgctgggc aagagtctat agcataccaa gatgaacagt tgcacatata cacaccactc
12601 ctgtagcaat acagcaataa tttaaatgac agataataag agcctgaatt aagtcataat
12661 tagaggaggc agaggagata gaatatcaag ataattagga agtagaatct aaagggtttg
12721 gctactgatt agctgtggga gtgggaaggt ggaggagtca aagatatctc agatttccag
12781 catgggtggc tgggtgggtg gtcagggatg gactgaattg aagcagaaaa gaatgccatg
12841 ggagcaggtt tacagagaga aagagcttga ttttgtacat gttgaatttg aaatgccagt
12901 ggaacagcca gctgaaactg catgggagcg cagtgaggcg tgtgggtatg gaccccaggt
12961 atggtctgaa gaccctgatt tgagagtcat cagcacaaat gtcgaagcag aggccatgaa
13021 taagatcacc caagtaaact gtgcagaagg agtgggaagt gaaacaagga caaaagcatg
13081 catgggctca aaccccaaac ctcataccag ttatccagga tccagtcagg agcatttaac
13141 tactttatgt gcttcagact gaaagaattt aatatagaga attggttaca aaggtgttaa
13201 aagggcaaga agtacaaaaa aaaaaaaaaa ggagagtcct agaaatgtac attttaaaaa
13261 aagattgcta tctggaaatc agaagctgcc atcatccctg agctggaatc tgtaaatcta
13321 ctcattgcct tgtgagagac actgtcatag tcagttccaa tctactagaa aggtgccacc
13381 tccttcaagg ctagaatcct tgagaaggta cttctgctca ggaggctgga gtcctgagtc
13441 tcccattctt cctgctgcta cagctacagc caatagctac cagctattgc cagccaccgc
13501 cactgtttag aggctgaagc aggatgcttc tcagtttctc ttgccttctg atctcccatc
13561 agtgcctcct actggcagaa tcaaaaagga agccagatgt ccaggaaggc tgggaaatac
13621 acacctggct gactcctaag ctaagcagtt caaaacacag tagaggaggg tgtgtgtgtc
13681 actgagacaa agataataac gagtacactg aaataccctg gtttgtaaga atctggtggc
13741 acgaggacca tccagagcac taagaaaaga ccaaggtaga agcagatcag agaaataaaa
13801 aagaggtgtg ccatgaagga gggcaaggtc agcattttta aatgctactc aaaagtcaag
13861 aaaggattga aaagtgtcct tagatttggt gattatgaga tggctgacaa atttattgag
13921 agcagtttca gtgttgtagt gggagtcaac tccagattgt ggtgggctga gaagtaagtg
13981 ggaggtgagg aagaaactgt cagtgtacat gcttcaagtt tgttagacaa aagaaagaga
14041 aagacagaag gggtggggga agaggcagtg agaaagctct aatgtggcaa tcaagtaatc
14101 tgagaaatta atatatgtga atattgtcca acagtgtttc tgaggctttc aaaattcata
14161 ccttccacct tttttttttt ttttttaag acaaagtttc ccctgttgcc cagactggag
14221 tgcagtggct acttacaggt gcaatcataa ctcactccag tcttgaaccc ccgagttcaa
14281 gcgatcctcc cgcctcagta gctggggact ataggcacat gccactgtgc ctggcttcat
14341 atcctctttt gataaacaag taatagcagc agtaatagcc aaaaacaaaa acaactctat
14401 gacctcctag atattctgga acagcaatgt gtatatatgt gtgtgtgtct gtgtggtgga
14461 ggcagggtgc cagggaagga ctagggtttg gaaatcatgg taaccctcca gaaaacaaaa
14521 gaacatttcc cagtatccca acatttatgc actaacccat cagcggttct ggcagtgggg
14581 agattcaggc ccctggacag tagaaaagaa gtttatgaga ctaccagtgg ggagacatat
14641 gggacacagc cacctagagt cctaaaccag gggttagcaa actttttctg taaagggcca
14701 gatggcaaat attttagaca ttgtgggcta tcagatctct gtcatgagta ctcaactgtg
14761 gcacgaaagc ctccatgcac aatatgtaaa tgaaggagag tggctgtgtt cctagtttcc
14821 tcctagcttt tcctcccact tcttgagcat ctccttctca gtctccttca tagactcctt
14881 cctttcagct actctttaaa tactggtgtt ccctggagtt tttgtcctca accctctttt
14941 tatttatgga cactaaaatt caaatttcat gtaattttca tgtgtcacga aatattcttc
15001 atttgctttt tttttcccta accatttaaa aatgtgaaga ccattcttag cttttaggcc
15061 atttaaaaac aggtggtagg caagattgtg ctcacagccc atagtgtgct gaatgatgct
15121 ctacacgtgg tcagaattgg tacgaaagcc ccaaattaaa cccacccttc aaagaggaac
15181 ctcagtcccc ttattattgg attggcaatc agttaacaaa cactttgtgc cagttacacc

FIG. 10 (cont'd)

```
15241 agtctatttg gaaggagatc tggggaagaa caggagaaac tagactgggt ggaagggcat
15301 aggaataggt acagcagaca ctgcaatttc tctgggtgag aggaacaagg cagaggggtc
15361 caagttctcc atagggagca cagtgtagac aagaccaagg tgaggacaaa cataaccatc
15421 cctcaccaag actgtggtga ggggtggtta actccattct ccccttctat aatctcagtt
15481 taaatggtaa caagttcaaa cacttataac tactcttccc tccatgtaat ccttccccac
15541 caggacctcc caactacctc catcataagt atctcaggaa tagtctctca tcagtttgga
15601 aagtaataat tgtgggcaag agatgagcaa ggcagccagt tctgctttgc agtagttcac
15661 tgtctacttt gtcattagct atgaatgcct ctgaaaataa tggcacagca ccggtaaatc
15721 caggaggctc tggctttcta acactcagct ctgccatccc tttctagcat ttaaaaatgg
15781 actctatttg gccaggcgca gtgattcacg cctgtaatcc cagcactttg ggaggccgag
15841 gggggtggat cacgaggtca ggagatcaag gccatcctgg ttaatggtaa aatcccatct
15901 ctactaaaaa tacaaaaaaa aaaaaaaatt agccaggcgt gatggcgggt gcctgtaatc
15961 caagctactc aggaggctga ggcaggagaa tcacttgaat tcgggaggtg gaggttgcag
16021 tgagctgaga tcgtgccatt gcactccagc ctgggtgaca gagcaagact ccatctcaaa
16081 aaataaataa ataaatatat aaaaaggact ctattttttt tcccctagca gagtcagatt
16141 tcttggaaaa gtcatgggca actgtggccc cgctcccatt cttaccattt aatcttttaa
16201 ctctcaacaa tgcaattgtt caccaatact tttgtgttgc caaatcaaat gaactagtct
16261 ctgcaacatc tgacactgtt ggccataccc tatctcctaa attggtcaaa tttctggcat
16321 ccctgatggc actctctcct agttttccct cctacttttc tggcgtcccc ttttcagtcc
16381 ctttgggact cctttctttc agcaacccct taagtattgg tgttccctgg agttttgtcc
16441 tcaaccttta ctcttcttag actatacact tgccctggat ggtcctctca tttactccca
16501 catgccttct gttaccaccc atttgctaat gtcttccaag cttacctctt cagctcagat
16561 cttgctctga gttccacact acccatatct gaaccacttc tggtcaaatc cacttggatg
16621 ctatgcaata gcagtttttt gtttttgttt ttttttaaa tatggaacgc ttcatgaatt
16681 tgcatgttct taaactgtat tcttcacaat agcgttcctc aagaaataaa aaaagtaagt
16741 ttgatgatag caatcattta tttttgaatt tatttccaca tagacataat gcaacatcaa
16801 acacatttat ataatatttt ttattatgta acaatttatt atatttaata agtctattta
16861 ttgcaagcaa tagaaaccaa ttctggctaa cttacatttt aaaaatgagg atttattgga
16921 aagatactga tctaactcat gaaatgaaag taatagttga ataagctagc ctcaggtaga
16981 atagccacag ggaccttaga agcaggggtt gagttgccat taatatgctc acctgcaaag
17041 gcctcctgcc tctttatctt tcaagttttg ctttgctggg agagcctctc tcactggctc
17101 agcttgtatt aggtgtgtac cactggattc attggttgtg gccaggtaca gtattacctc
17161 tatggattag agctattcct agagaaggga gaatcatatg aaaagtaacc acctcaatac
17221 agctattttc aacatatggc atctcagaca attgtatgag atcatctgag gcataaacat
17281 aaggttaaat ctgtgtatta atgctcaaac agcatttcct aactactcag gtgacatatg
17341 tcatctgctt gatgatctct ggtcggtcac ttgtcttatc acatattcaa attacattta
17401 tcatgtgatt caatattgat ttattaattt aaaattatat attccacgaa tttcctttga
17461 atctctgact aaaaaggttt ttttaatttt actttgaaaa gctccaagca cacacagaag
17521 agaagaatct aataaactcc aatgtactct catgaatgtc aacaattttc aacatttaac
17581 attcttccat tcttgtttca tctattgttc tgcatttttt ggagtatttt aaacaaattc
17641 tgtcattaca tttcaccagt aaatactttt aggcatatct ataatagata ataacctttc
17701 ccttaacata actataatgc catcaccaca accaacaaaa ttaaaaatta cttaacttca
17761 tttgacccaa tctgttcatt tctcctagtt atctcaaaaa tgtgtaagag aatgaagttt
17821 taaatgaaaa gcagtgtctt ataattttca aaccgtgcca ttagtttaaa aaaattggtg
17881 agttttctat tttatgtttc ataagctatt gatggttcaa taatgaattc taattaggta
17941 ttccataggc aaataaagtt agcaattgtt actctgaatg tatctccatc tcaagattac
18001 aagagtacac tcatcacttt cccttcccaa tatattccaa ctcctctctt atatttaaga
18061 cttcagtgaa taacaagatg tccacccgag ctacaaatgt gggtcatcgt tgatgacccc
18121 atcttcctca aaccttccca ttcaattgtc ctaacaattc tacctttcta atagctcttg
18181 aatcttcctt tcttttcctt ccattcctac tggtccaggc cttcaatggt tggttttcac
18241 tgattattgc aactttcttt ataattggtc tctctctctc caatcttatt attttccaca
```

FIG. 10 (cont'd)

```
18301 gtgctgccag aaggatattt ttattatgct tagttgatca tattatactt ctgcatgaaa
18361 accttccatg attgttaatg atctactttc cttgtcatga cccataatga cctgaagtct
18421 acttacctac ttctatatgt cttttcaggt gaaatctcac tcctctcagg aagccttcct
18481 tgaacccaga gttgagatta atagcctctt cagtacgttt ccaaagcacc ctgtgttggc
18541 cattatcact gttttaattg tattattctc ttccatttat atgtctgttt catagtcacc
18601 tcatctctac tgcaaggtcc ttaggggagg gtgtactata tatatatata tctccaccaa
18661 gaggcccact aagtgacctt tcactcgatg aacaaatggg ctaccagtct ctgaaggtgc
18721 tgaactgaga atggaagagc cttcaggtat tagatgatga tggattgtcc cttctaacag
18781 atgtttcaaa ggtaaatctt atcaggttta tctataagcc attctttttt tttttttttt
18841 gagatggagt ttcactctgt tgccaaggct ggagtgcagt ggtacggtgt ccgctcactg
18901 caacctccac ctcccaggtt caagtgattc tcctgcctca gcctctggag tatctgggac
18961 tacgggcacg tgccaccata cccggctaat tttttttttt tttttttgta tttttagtag
19021 agatggggtt tcactgtgtt agccaggata atcttgatct cctgacctcg tgatccacct
19081 ggctcggcct ccctaagtgc tttgattaca ggcatgagca accacaccca gtctctatga
19141 gccattttac acctccacag ccttccctat atactctact acccttccaa ttccattcta
19201 ggcccttccc aagctccttg ccaactacca ttttcttcct actccctgcc acctcctgtt
19261 tcagagagca aacctagcca tccagctccc acatttactc ttatttctac ctcagtacat
19321 ttctccatac ccatattcat cctccctttt agtgacatta ctatgatgca gcaatcctta
19381 caactactct acaaggttat aatttattat ccccattata taaacaagaa aactgggact
19441 cagaaaggtt catttattta gcaaatattt attggccacc ttctgtgtct agcagtatgc
19501 tctgtatcag atacctgcca tcatcacact taaagtctaa tgaaaataaa gagacattaa
19561 acaagaaaac atacaaattt ataaactaaa aggtccacac acacacacac acaaaatctc
19621 ttagaattga taaattcagt acagttgcag gatacaaaat tatcatataa aaattaatgg
19681 tgcttctgga tacaaacagt aaactagtgg gaaaagaaat caaagaaagt aatcccattt
19741 acaatagcta caacccctcc ccccaccaaa aaaacaaaat agaataccta gaataaacca
19801 aggaggtgaa agatctctac aaggaaaact atgagacact gaggaaaaaa actgaagagg
19861 tcacaaaaaa atagaaagac atcctatgtc ttcggaagaa ttcgtatcgt gaaaatgact
19921 gtactaccaa aagcaatcta cagatttgtt gcaattccta tcaaaataca aagatattcc
19981 ttgcagaaac agaaaaaaca aacctaaaat taatatggaa ccacagaaaa cacaaatagt
20041 caaggtaatt ctgaacaaaa agaacaaagc tgtagacatc ataccaccca acttcaaaat
20101 atactacaaa gctacagtaa ctaaaagagc acggtactgg cataaaaaca gatacacaga
20161 ccaatagaac cgaataaagg acccagaaat aatagatcca catcttaaca gccaactgat
20221 tttcaacaaa ggtaccaaga tattcaatgg gaaaaggaca cactcttcat taaatggtgc
20281 tgggaacact gaataacaat atgcagaaaa atacaactac accccccatct ctcatcaaat
20341 acaaaaatta aatcaaaatg gattaaaaac ttaaatgtaa gacctgaaac tataaaagtt
20401 actgtaagaa aatactgggg aaatgctcaa gactttgagc aaacattttt tggtttaaga
20461 cttcaaaagg agaggcaatg aaagcaaaaa tacacaaatg ggattacatc aagctaaaag
20521 gcttctgcca cagcaaagga aacaatcaac agagtgaaga gacaaccttc agaatgggaa
20581 aaaatatgtg caaactatcc atctgataag ggattaataa ccagaatata taaggaactc
20641 aaactcaaca gcaaaaatcc tccaaataat cccatttgaa aatgggcaaa tgatctgaat
20701 agacatttct caaaagacat acaaatggcc aacaggcata tgaaaaaatt ctcaacgtta
20761 ctaaccatca gggatatgca aatcaaaacc acaatgagat atcatctgaa tctaattaaa
20821 atggctatta tcaaaaagac acagataaga gatactggtg aggatgcaaa gaaaggggaa
20881 tgctcatata ctgatggtag aaatgtaaat taacatagcc actatggaaa acagcataaa
20941 ggttcctcaa acaactaaaa atagatctac tagatgattc agcaatccca ctgctgggta
21001 tatatccaaa agaaaggaaa tcagtgtatc aaagagatgt gtacatgccc atgtttattt
21061 cagcactacc cacagtagcc aagacatgga atcaatctaa gtgtctatca agtgactgga
21121 taaagaaaat gtggtgtata tatatacaat ggatactagt cagccataaa aaagaatgaa
21181 atcctgtcat ttccagcaac atggatggaa ctggaagtca ttatgttaat gaaataagtc
21241 agacacagaa aaaaaaatat cacgttctca taagtgggag ctaaaaaagt tgatcttatg
21301 gaggtagagg gtagaatgat ggttaccaga gactgggaaa gggagggggt ggaggggga
```

FIG. 10 (cont'd)

```
21361 tgaagagaga ttcattaatg gttacaaaaa tatagttaaa ttgaaggaat aaattctata
21421 gtgtttgata gcacagctgg gtgactacag ttaacattaa tttactgtat attccaaaat
21481 agctagtaga tttgaagtgc tcccaacaga aggaaataat aaatgtttga ggtgatggat
21541 atcctaatta tcctgatttg atcattacac atcgtatgca tgtatcaaaa tatcatatgt
21601 accccataaa tatgtacaat tattatgtat caataaaaaa taaaaaaaaa caattcagaa
21661 gtccataaac ttggatggaa taaaaaaaag tcaactttat tttcaaaaaa ctctcactga
21721 aatctaattt tatgaatgta gaaaataaat ctttgtagta ccagccagca gctgtaacac
21781 tgtcatcaat agaaaacacc atcaattaat attttcatat cacattatag ttgttacaga
21841 catcttaaaa tatcacttac aattatggga gctgttaaac ttgccaaaaa atcatgcttt
21901 ttaatgtatt agtaaagaaa cactgtattg tattaataca gaaacacata ctactagatc
21961 atcacacgtt tctttgaata tagtagtgtc ccccacacag caccaaatgt gattatacag
22021 tttattccta tccatagata tacctatgat aaagtttaat ttataaattt gcacaggaag
22081 agattaacaa caaaatagga caattatatt gtaataaaag ttatgtgaat atggtccttc
22141 tgtctcatac acaaagtatc ttattgtact tattttcaga ccaggttgac cttgggtaac
22201 tgaaatcaca gaaattgaaa ctgcagttaa gggggaccca ctgtattttg ataactatag
22261 tttatatttt attttatgca tttacaaata ttatcagaca agatccaaag gcttcaccaa
22321 actgccaaaa aagctaatgg cacataaaaa gcttaaggag tcctgattta atcagtcatt
22381 caatgaacat gacatccttc ctggaaccat ctcctgttct agcttcctca cattatgttg
22441 ctctgcttct ccttgagatc ttccattggt tccacttcct attcttgctt cctgtatgaa
22501 gatgtaaccc aaagctcaat ccttcaccct aaattgtttt tataccccct cttttacaaa
22561 cctcagctac cttcgtggct gattcaaaca tcacctcaaa ggtgactctc aaatctgctt
22621 ttcctaatct tttttctcta acttcaatct tggatcttaa actccctgct gtgcctagta
22681 aacagaataa tatgccaccc agagtcagct gggttcaaat cccagttctg ctacttacta
22741 aaggtgtgac attaggtaaa tattacctgc tatggtttga atctctcctc caaaactctt
22801 gttgaaaata attgccattt tgacagtttt aagaagtggg acctttaaga gttaattagg
22861 tcatgagggc tctgctctca tgaatggatt aatgctacta atgtaggtat gggttcccat
22921 ttaaaagggg acattctgag gccgggcaca gtggctcaca cctgtaatcc cagcactttg
22981 ggaggccgag gcaggtggat catgaggtca ggagatggag accatcctgg ctaacacggt
23041 gaaaccccgt ccctactaaa aatacaaaaa attagccagg cttggtggcg ggcacctgta
23101 gtcctagcta cttgggaggc tgaggcagga gaatggtgtg aacccgggag gaggagcttg
23161 cagtgagtca agattgcact actgcactcc agtctgggcg acagagcgag actccgcctc
23221 aaaacaaaca aacaaacaaa caaacaaagg gtacattctg gcctctattc tctctccatc
23281 tcatgtgctt gtttgccttt ctgccgtggg atgatgcagc acaaggctct caccagatgc
23341 caatgccatg ctcttggact tccaagcaac tggaactgag ccaaataaac tactgtttat
23401 aaattaccca gtctgtggta ttctgtgata gcatcagaaa acagactaag acgtcctttg
23461 cttctgttgt ttcatttgaa aactgagggt gataatatta gtattgactt tatagggtta
23521 taaggattaa aagagttact acatgtactc attgcagtac ctgacacatt ttaactactc
23581 aataaatgtt ttgtatcacc aatcacatct ccttccaacc ccgacatttt aatttgatgt
23641 ttattaacat ggacggtgcc agccactgga agacagagtt tctatctaac aacataattc
23701 tgatcaagtc attagtcaaa aaatttcagt ggttccccac tgattccaaa cttaacagca
23761 ctggaaacct tctataatgt gttctctaat ataaatttac ctcccatttt ctcttctcct
23821 gctctacttc ttgtagctta tgttctggcc agactggact agactactct ctgtgacaat
23881 aacctgtgct gttctatgtc tgtctttcct cacataattc taatgtctca ggtttgaagg
23941 caataatttt gtctatgatt attcccctat acatggcacc ccataaaaca tacacatttc
24001 aatcttacct aagtcacata cttacttaca catcaattca cctccatatt tgctcaattt
24061 gtgagaacct aatattggcc agatactgtg ctaggaccta gggatattaa aaaaaaaaaa
24121 aaagcaaagc aagaaaaaga atgcataatg gccctgctct caaaatcaag gtctagtact
24181 agagagaaac atgtaatcac ataaatgcca ttcactgtgg aaagtaaaat cataagggga
24241 agggacacca aagaatgagc agttagctca acttgaacag taacattaag cttttcagag
24301 atgttatttg ggcgtacata gattggggaa aagtctactc catatagaaa gtgcacatgt
24361 gtaaaacaca gaggcatgaa acaaaatgat gtgtctggga aacagttcaa tacagctgga
```

FIG. 10 (cont'd)

```
24421 atatagggcc caagaggaag tggttagaca tgaggctgga aagctaggca gactgttttg
24481 gcaaacatag gaatttggac tttatcacat agccaataag gaataacaca gagttttaaa
24541 aagagctatg gccagggcta tattttggaa agctctctcc tggcagtatt gtggcagagg
24601 cagagaggaa agtctaaagc agcactgtcc aacagaactt cttgtaatga ggccgcgcgc
24661 agtggctcac gcctgtaatc ccagcacttt gggaggctga ggcgggcgga tcacgaggtc
24721 aggaattcga gactaatttg gccaacatgg tgaaaccccg tgtctactaa aaatacagac
24781 actagccggg tgtggtggca ggcgcctgta atcccagcta ctcgggaggc tgaggcagaa
24841 ttgcttgaac ccgggaggca gaggttgcag taagccaaga ctgcgccact gcactccatc
24901 ctaggccaca gagcaagact ccgtatcagg gaaagaaaaa aacaacttct tgcaatgaca
24961 caaatgttca ataatctgtg ctttcccata tgacagccac tagtcacatg tggctattga
25021 gaacttaaaa tgtggctagt gtattgaggc actaaattta aaattgtatt aatttaaatc
25081 caaatagcca tgtgtctagc aaataattta ggagactgtt ggtatagctc aggtgataga
25141 attaggacag aagggtgagt tgatggatag ttaagaggca aaattatgag tctgtaaggg
25201 tgtgagaaaa ggaaatcaag aacaggctcc cagattacag actttgtggt taaacagcca
25261 ccattactca ggacaacaga agagaaagag caggtctaga gtgtatagtg atttcatcaa
25321 ttttgaacat actggtgtct gagagttatc ccagtgggaa tatttagtag aaagtttagc
25381 ttagagagct gtctgaacta aagattcaga cttcagaggc tttgagccat ggagtcagat
25441 tacctagaga agttgaacaa aattagaagc aaacaagaat cacagcaaat atcaacacat
25501 aaaaaggggc taaggaagaa aaatctactg agactggaga ggaacagtta cacaaatagg
25561 aaaagaaaca agtgagagtg gtatagaagt caagggtaga gagaatgtca ggaaggaaac
25621 atgatcaaat gtcgaatgcc tcagaggtca aataaagtga gaactgtaaa gtgcttcctg
25681 actttgccag ttaggaggtt cttggtgaca tctgccagaa aagttttggt ggtagcagcc
25741 tgacagaggt agcttgaaga gtggggatgg ggaaagagaa tgtgaccaag aattgagata
25801 gtaaggataa tttcaatttc aggtcttggc tgtgcaagga agccgagaga catgagtctc
25861 taagagggca cgatattgag agggttgtta tctttctgtc agcggggaaa ccaagagaaa
25921 agtttaaaaa ggtcaaaagg gggagaaggg aagacagctt ccgggtaaca gagaaggttg
25981 accaggtcaa tagtaaagga tttcctcaaa ccgaagggag gacctctagt gaaatgagaa
26041 aggaatacac aattgaccca gtttgcaggt gggaaatggg aagccagttc tgcaaattgg
26101 cctttctgtt ctgtgaagtg ccatctgtcg gtgaggagag attagggtct gcagcgtgaa
26161 aatctggacc atactctggg taatcaaggg agaggttatc ggctaatgac aaattaaagg
26221 cttacttttt agctggcaac tgaatcacca taacatttta tgttaccagt tccaaaattt
26281 tggggggaat tcactcaagc ttgggagagg agagatcata actttaagag tataagaggt
26341 ttaaacggtc cactacgaaa taaatagaga aggaaaagtt atcagctggt aaatatcgta
26401 gaaggtagag cggtccaggg actcacaggt ctcactaaag aaaagtctag cgtaggttca
26461 cggcacggag agattttaag gctgcctaag actaaagcca aatacgaagt ccacatctgc
26521 ggtccgcacc ttatctctcc gcgcggcagg cgcgacgagg gcgagaaact ccctctccag
26581 tggtcgcacc acacgacacc agggaagggg cccctctctc cagaccctca tatctccagg
26641 tccaggcccc attttcctcc gctgacagct cagcagcgtg cgcttccgct ggattcaggc
26701 caggaccagc gaagccgcac cttacaccca ccgaggagga aacaagcctg gccacccgag
26761 gctaccccgc taggccgcgg gtagtggggg agggggcgct gaggcaggag gtcagcaccc
26821 gggcgcgggc tcccgcccca cgaaatgcgc gcgctccaag ccccgccgcc ggagatgcgg
26881 ttccggtccg gacgcctgcg cactacggct ctccccgcag cctctggccc tccttccccc
26941 tccccccagtc agggcgcacc cttgcgcctg cgctgtgtgt gttcctggtc tgcggcagcc
27001 atgctgaact cgtatggaga ggcgagtggg ggggacagag tccaggactg cgggatagga
27061 agctggggat atggacaagc agcagcgtta tagcgctctg ggtttcggga catagcctg
27121 ggccatgcgg ccccccttggc cccttggcgc gacccccagg aacgttcgga aagctggtcc
27181 tcgtggctgg gggaaaggcg gggggtgggg gggaagcggg cacgtgaccc cggtcagcca
27241 atctgggtgc tgctgacgtg gccgcgcggc cccgatgctc tccccacccc cccagcccgt
27301 tcgggaaggg aggggctggg ggctacgccc cctcccccag cacggcttcg ttttctgggg
27361 gggggttgac accccggatt acatacccccg taccaagccg agggcaactt tggaggcccc
27421 ctggaaggct ttaggatcca ggtgagaagg ggcccttgtg gggcggagat gtcagtcaag
```

FIG. 10 (cont'd)

27481 tgcttaacca atggtgggga gtccgggagg gggattcttg gggttcagga aagaatcctg
27541 agagtgggaa gatttgtcct tcaaaccttt tacagccaat gggagcgtgg aggggggcg
27601 agcgggagag ggccatgggg ggggagggga atggccagcc tcatgcctcc gtacccattg
27661 gagggcaaag gggttagggg gcggtgtggc ccccctatt ccattcgtcc cctgggggta
27721 cagcagccgg gagccaggtg agaagggatc catcggcggc cgagggaggg gtgacctggc
27781 ggtgggctga ggagtggtgg ctgtggcccc tacccgtgga tgtgaatgct ttaggagttg
27841 gccacccatg ttgtgaactg aggttgttcc caggcgccaa cttcctttct ccccagagcc
27901 tctggaggga gcattgctgt gcgccctttg tgtccgcggt aggggagctc cagtcgtcac
27961 accgcaggct ggaggttacg cttcgagtcg cttaccgaat ttgtgtgcat tcacgtggac
28021 acggcctgtg gggccttttg cccctgtagg gtctttactg agcacgtgtc tactccaggc
28081 tggggtgctt acaagctgaa agcttgaggt ctgcttagga acagaaacca ggcccaaggt
28141 gggtgctggc agtagggggt ctagacagca tggtctgaga tgcgagggag gctcgggacc
28201 tggaatgatt tcacagctcc caaggtttcg ggtttctcca gggtggcctc ttccatcgcc
28261 tccctcatcc cctcccccag tcctgaacag ttctctcctt gtgtactgcg gggagggaa
28321 cggaaaggag gaaagagtta ctttcccaaa ttactgagta gcagtagcct ccctggtgac
28381 tcatgtgggg gaagggagga tagaggatcg ggaggcagtg attttccgga atgcagggaa
28441 taaacgagag caatgtctgg ctgccctttt cctaaggcct agtattttct cagcctccta
28501 agtttttact ccatggccgg ccccctgatg ggcctctgtc ctggcctgca gagccccggt
28561 ggagaaaagc agatttggga ggttgggccg ctagggggag gggaaaaggc ctctgcaaag
28621 ttgctgtgtc attgccctcc atgctgcagc cacccaaacg ggccgcttg tacttttggg
28681 ggccagggcc tgatccctgg ctggggaag gggactctgc tctcctgacg ctcattttcc
28741 cccgccctcc cggggtttgc cctactcggg gggtcagaag acaggagatt ggcggccatt
28801 ttagacgcag taaccgaggt tggagttgaa gggctactgc agaggaggga gggtggcgtg
28861 gttgcagctc aaggacctag gcccttacga gcccttcccg ggcgaggggg aatcttaccg
28921 tatatttgtt cacctacgtt gattattttt cccagatacg tacacaagtt tgttttctcc
28981 ctggtagcga agaaagggga aacgggggag gggacgcccc accaaagccc aggttttctc
29041 gggtggggga gatcctttca ctctcttgta agggggcggg gacggcccca gagatgctct
29101 ggagatcctg actctgggct ctggttgatt cacagagtct gcacccttat ttagataacc
29161 aagttaggag gaagacttaa gagtaagttg gggggagggg gcgaaactga gctcccaaaa
29221 tggctcctgc ccctcctcgg aggcggacgg ccggggggag gggaggaggg gaggaggggg
29281 agggctagtc tgagccgcag ccgccgcctc ctccgctcgc cctcctccct ggcgctgacc
29341 gatggaccag ccgctccgtg ggaggactc cggaccctgg tgggggggcg gggggttct
29401 ttcgcccccg tggcggaggg cccctgagag gcggatacgg gtgtgccttt ggggtgatg
29461 tggcgtgtgg ggggaaaggt ccgagctcgc ctggaggggg agggtttttc ccttaagtca
29521 tccctcccag gacttgcttt ttctgctctg agccggacgc cggaatggag tttgaggaag
29581 aggtgaggtg tgttgcattg tatagggtag atggatgcgt ttggagattt taatcccact
29641 tttagggttg ccgaggattt ttcgaacgag cagaaatgta ttggtaactg taggtgtgag
29701 tggggaggga ttagaaaggt gcttggacgt gcaaatttgg gagacgtatt ttagcttttg
29761 tggtctttgg gactaaacag tagtaaataa tgttttgctc gtctttccat cgtttggctt
29821 gagggaggga gtggagtatt ataagactct ggcaacactg ttttagactg tggggcatgg
29881 gaacgttaga tcccctcatc gccgttctga agcccgtagc tgttcgccat agaggagcag
29941 gccgcggctt ctaagatggc gtctttttcc tcgtttcaga ttcttcgctg ctgctgcctt
30001 accgccgaga accaccaccc gccaggcgtc ttgcggccac acccctggcg ggttcaggca
30061 ggctacgccc acgcgacccc tcccgtttcc ctgctttggc caatggagga gctacgaatg
30121 gcacgacctg ctcgagcttg gcagtctcca gttgggctgt gcatggaagc ttgggaagac
30181 tttgttggaa ggggaggcgg ggagagagtg ctggaggctc tggggcgatg gcttccgcac
30241 ctcttccaac caccctcttt ccctggagtc ggcggaccac agctcagcca attggcttgg
30301 agatgtggcg ggttgccact tccctgtggg tctctgcggc actcttctgc ctggtgactg
30361 acaccttgga aatgaagttt atgacgtcat cgttgcggct ggccaataga aaaagctccc
30421 gcggagaggt gttccttccc cttcgactca gcttcttcac ccgcgtgagc gagcgcgcgc
30481 gcgcggaggg ggtggggaaa atctcaagca gggtggcgcg catgagcggc gaagctcctc

FIG. 10 (cont'd)

30541 ctccccgcct atatataaag ggctggcgcg gggctcggcg gcgccatttc gtgctggagt
30601 ggagcagcct ctagaacgag ctggaggatt ctgcctaccg atacagagcc ttcgagtcgt
30661 ccggggccgc cattacaatc cacctccatc cgcttggaaa tggccttcgt cccggcctat
30721 gactggtccc agcgggcagt acagaccccc tagaagcccc tggagctccc ctttttcggg
30781 ccccgcccaa tcctcggagt ctgtccaccc cctctactcc gccctcaaga ggatttcaaa
30841 gatggaggcg gcggctccct aaaccacttt tcgtgttcat ccgcctccat ccgagatcga
30901 aacgggacct cgtcggcccc gtaggggccc gacaagaaga gggaatccct gcagaccaac
30961 agcgggctat attgacgacg gtgtctgaga tcggggaccg tcttttgaag agtcagtccc
31021 tccttagttg cccgcctcag ctgaggccgc cgccattttc ttgctgtccg ccgtctgcag
31081 agcgcgccaa gctgcccgga gctctccgag aggccccaaa gagactgctt tcgtgccggc
31141 caggcagggg gtttgtcgcc tggaggccca agaggaacgg cctccccccca acttagcggg
31201 ttatgctgga ccgggcggtg aggggaaccg aggccacccg gactttccgc ggctgagggc
31261 agcgccggtt ccttgcggtc aagatgctgc aaaacgtgac tccccacaat aagtacgttt
31321 ccgcgagccg cgtgtgggaa ggggatgttg caggggcggcg gcacaggggt gtggggcgcc
31381 gtgttgggag tactgagcgg ccccggcgcg ctgctgttgc ggcgcagctg tcgactcggt
31441 cgcgcggagg gaattgagcg acggttttgg aacggtggtg gcggctcggc tactgctcgt
31501 ggaggggaat acaggttgtc aatttatacg ctattaatgc cgccgtggcc cagtcttaac
31561 cgagtcaggc agagctagtt tgacggtgga gtggagtgag gttgaacagc aggtttggcg
31621 tttggtgggt ctggtatcta gcggcggtct gttagccttt taggggggat tcacggacac
31681 ctctagcgcc ctgtagggtt gccatggtga cggagcgctt aagggactgg caacggggat
31741 tcccagagaa gggtaaaggg atcactctcc cgtgtgtgca ggttcctaat gcccagggca
31801 tgtcattaaa tcttttgctt tctttgggtg ggtgggttgt gtgtggtgtt tgttggtgca
31861 gggattgttt tttcctaaca ttaaaagttt gattcagggc aggagggtag agctaaggtt
31921 cctagttcag ctctgcgatg taaacaatga gattcccata tgatgtttta attcttaggt
31981 ggtaggaaag actgatcgga ggagcaccag agggactgta aatgaaccac tgttagcgtt
32041 tggtgtccgg agttggtgct acagggggaa ctggtagtgg aatcgtgttg tgtagtgggt
32101 gggtggaagg gggctatcac ttggtgacct tgactgtttt gtacggcttt ttgacttcct
32161 tggagtgagg agactctgat ttggtgcgaa taattttgag ggcctggaag ttacgggctg
32221 tgaagtctga caaattcttc cttgtctgaa tttgttttta agttgatatg gttcttcctc
32281 tgggtttcta gtctatgttc tgttgtggcg tgaactaccc agaccttgtg gaagatggtg
32341 ctctctcttc tatctaggtg gattattctg tgtcttatca gcattttatg gaatttttta
32401 tagccataat ttgttctttt cctccttacc ggcgctcaac caccatggca accaccaaac
32461 ccctagtgag gaggaagctt ggggtttgag tttcttaact ccacccattt tgcttaatcc
32521 ccatccccat agggctgtag ttctgagatg tcgtgccttg tcagaaacaa tttgggagtt
32581 ttttaaaata tgaaaaagaa cagatagagc ctatcagact taagaaggtg ggatctagat
32641 agtatactaa aaatattaat aaaaggaagg cggggccagc aataaaagct ccacagattg
32701 tttggatatt gtttctgctt aagaagcact tggcataagc ttaaccacct cactagggcc
32761 agcacctgga ttcatcagac tattgtgcag atgcactttt tcctcatttg gacgatattg
32821 ccctaatttt gttcccatct ttacaggctc cctggggaag ggaatgcagg gttgctgggg
32881 ctgggcccag aagcagcagc accagggaaa aggattcgaa aaccctctct cttgtatgag
32941 ggctttgaga gccccacaat ggcttcggtg cctgctttgc aacttacccc tgccaaccca
33001 ccacccccgg aggtgtccaa tcccaaaaag ccaggacgag ttaccaacca gctgcaatac
33061 ctacacaagg tagtgatgaa ggctctgtgg aaacatcagt tcgcatggcc attccggcag
33121 cctgtggatg ctgtcaaact gggtctaccg gtgagtagag acattggagc cggggaggtg
33181 tgggatgagc aagaatgcgt gtgaatgggg gtggtctgcc tagtgtagat gctgcggccc
33241 ctagggagtt cccatttctc ccctgtaggg cagttagcta ccagatttct gggtatcttg
33301 gtcctttgtg attgatccga ccgcttgctg taactatctt ggcatctttc cttgtgccct
33361 ccatgtgtcc ttccttaact tttgtgccct ggctccattt tacagattcc cacctcgggt
33421 tgggagagga ccacggtggc caaaattctt agcttcttcc tttccctcat gcagcccatg
33481 gatagccagc cccagaggta atgtcacagg atgggaagtt tccagagtgg gtgggaggtg
33541 ggtggttaga gaaaggcagc aggggcctcc ctgtggatgt caagaatctt ttttatttat

FIG. 10 (cont'd)

33601 ttatttattt tgtcccacag tttaattggg gccgcagttt aactgttcct ttgatgcata
33661 gggggtgtgt gtgtgtgtgt gtgtgtgtgt gagagtcggg gatcggtagt ctccctataa
33721 gcatttattt ttctgtggtt ctgacctaac atttctttat ttaggattat cacaaaatta
33781 taaaacagcc tatggacatg ggtactatta agaggagact tgaaaacaat tattattggg
33841 ctgcttcaga gtgtatgcaa gattttaata ccatgttcac caactgttac atttacaaca
33901 aggtgagttt ttctgtgtgt tcatttagta ggtggggaga aacagtaatt tctattattg
33961 ctggatatgt tgtctacata aagtttaaat cctttgctac tgaaggtgtt atccaggtag
34021 ggtagtcgga gtcttaaaaa cctgactcta gatggtacta ttgaacacag tgatgtgact
34081 tcagagctct agttgaaggt tatttagaac acttcatact tggggggtggt ggtcctgttt
34141 cttagaaatc accagagacc tgagtagacc agggatctgt tttcttgtca gctctcaagt
34201 tttttcttct ttcgaatttt gggagacagt taggagaaag tggaaattag tagtggcctg
34261 gagtagaaat tttctttaag atttgatgac aagatgactg gtgggggtat ggtaatggcc
34321 tagggcctga atgcctctga gaaagatggt gtgtatctat cttctgttgg catttttttaa
34381 ctttctttat tgctgtctgt gttctcatag cccactgatg atattgtcct aatggcacaa
34441 acgctggaaa agatattcct acagaaggtt gcatcaatgc cacaagaaga acaagagctg
34501 gtagtgacca tccctaagaa cagccacaag aaggggggcca agttggcagg taggaagagt
34561 gggagttttg caaatggaca acttaaagat ggggaagaga atcaaactac actttttttcc
34621 ttttttctag cgctccaggg cagtgttacc agtgcccatc aggtgcctgc cgtctcttct
34681 gtgtcacaca cagccctgta tactcctcca cctgagatac ctaccactgt cttcaacatt
34741 ccccacccat cagtcatttc ctctccactt ctcaagtcct tgcactctgc tggacccccg
34801 ctccttgctg ttactgcagc tcctccagcc cagccccttg ccaaggtatg atctgtggat
34861 ttcctctggg cagcagggag gcaagggtct taagtaaagt gggcttggag tgacaggttc
34921 cctatcttgt ttctttctgc agaaaaaagg cgtaaagcgg aaagcagata ctaccacccc
34981 tacacctaca gccatcttgg ctcctggttc tccagctagc cctcctggga gtcttgagcc
35041 taaggcagca cggcttcccc ctatgcgtag agagagtggt cgccccatca agccccccacg
35101 caaagacttg cctgactctc agcaacaaca ccagagctct aagaaaggaa agctttcaga
35161 acagttaaaa cattgcaatg gcattttgaa ggagttactc tctaagaagc atgctgccta
35221 tgcttggcct ttctataaac cagtggatgc ttctgcactt ggcctgcatg actaccatga
35281 catcattaag caccccatgg acctcagcac tgtcaaggta cccactgcat ggggcagatg
35341 ggatgctcaa gcagtgatgg gagcctaggt gcaaaacaat aagtctcctt atgtgggcac
35401 acagcagtct ttggttcttg gcattttact tttataaaat aatagtggaa cagaaggtct
35461 ggtgttttga gaatttgtat ttcttggagt ttgaaacagt agggtggggt ttctttgtct
35521 tgagaaaaat actgtctata attaagtact aatgtggcag tgttgggtta aggaagttat
35581 agggtggaaa gacaggcata ggccacctct ctgtcactta gaaatgattt ctttttctag
35641 acataaatat ttcttcaacc cacccaaatt cctttgactt caaacttgaa ccccagggca
35701 cagatcctta aggtcatccc cactgtgctc tcaagagagg gctcttcttg tggtgtctgg
35761 ggttggcagg gaaaggtgag tcttcctgcc tgtgcagctt ctgatgctgc ctccttctgc
35821 agcggaagat ggagaaccgt gattaccggg atgcacagga gtttgctgct gatgtacggc
35881 ttatgttctc caactgctat aagtacaatc ccccagatca cgatgttgtg gcaatggcac
35941 gaaagctaca ggtgagtgga aaggttggag tttgaaaaat aaatggtatg gggagttatt
36001 ttgtcatgtg tgctgcatag cctcaacgtg agggtctcac tgttctgtac agttgtaaat
36061 tggagctata tcacttggtg gctgggtatg tagggcactg tttatcagca tagttttgag
36121 tttgtgcctc tttctaggat gtatttgagt tccgttatgc caagatgcca gatgaaccac
36181 tagaaccagg gcctttacca gtctctactg ccatgccccc tggcttggcc

FIG. 11

Homo sapiens nucleolin (NCL), mRNA

```
   1 ctttcgcctc agtctcgagc tctcgctggc cttcgggtgt acgtgctccg ggatcttcag
  61 cacccgcggc cgccatcgcc gtcgcttggc ttcttctgga ctcatctgcg ccacttgtcc
 121 gcttcacact ccgccgccat catggtgaag ctcgcgaagg caggtaaaaa tcaaggtgac
 181 cccaagaaaa tggctcctcc tccaaaggag gtagaagaag atagtgaaga tgaggaaatg
 241 tcagaagatg aagaagatga tagcagtgga gaagaggtcg tcatacctca gaagaaaggc
 301 aagaaggctg ctgcaacctc agcaaagaag gtggtcgttt ccccaacaaa aaaggttgca
 361 gttgccacac cagccaagaa agcagctgtc actccaggca aaaaggcagc agcaacacct
 421 gccaagaaga cagttacacc agccaaagca gttaccacac ctggcaagaa gggagccaca
 481 ccaggcaaag cattggtagc aactcctggt aagaagggtg ctgccatccc agccaagggg
 541 gcaaagaatg gcaagaatgc caagaaggaa gacagtgatg aagaggagga tgatgacagt
 601 gaggaggatg aggaggatga cgaggacgag gatgaggatg aagatgaaat tgaaccagca
 661 gcgatgaaag cagcagctgc tgcccctgcc tcagaggatg aggacgatga ggatgacgaa
 721 gatgatgagg atgacgatga cgatgaggaa gatgactctg aagaagaagc tatggagact
 781 acaccagcca aaggaaagaa agctgcaaaa gttgttcctg tgaaagccaa gaacgtggct
 841 gaggatgaag atgaagaaga ggatgatgag gacgaggatg acgacgacga cgaagatgat
 901 gaagatgatg atgatgaaga tgatgaggag gaggaagaag aggaggagga agagcctgtc
 961 aaagaagcac ctggaaaacg aaagaaggaa atggccaaac agaaagcagc tcctgaagcc
1021 aagaaacaga aagtggaagg cacagaaccg actacggctt tcaatctctt tgttggaaac
1081 ctaaacttta acaaatctgc tcctgaatta aaaactggta tcagcgatgt ttttgctaaa
1141 aatgatcttg ctgttgtgga tgtcagaatt ggtatgacta ggaaatttgg ttatgtggat
1201 tttgaatctg ctgaagacct ggagaaagcg ttggaactca ctggtttgaa agtctttggc
1261 aatgaaatta aactagagaa accaaaagga aaagacagta agaaagagcg agatgcgaga
1321 acacttttgg ctaaaaatct cccttacaaa gtcactcagg atgaattgaa agaagtgttt
1381 gaagatgctg cggagatcag attagtcagc aaggatggga aaagtaaagg gattgcttat
1441 attgaattta agacagaagc tgatgcagag aaaacctttg aagaaaagca gggaacagag
1501 atcgatgggc gatctatttc cctgtactat actggagaga aaggtcaaaa tcaagactat
1561 agaggtggaa agaatagcac ttggagtggt gaatcaaaaa ctctggtttt aagcaacctc
1621 tcctacagtg caacagaaga aactcttcag gaagtatttg agaaagcaac ttttatcaaa
1681 gtaccccaga accaaaatgg caaatctaaa gggtatgcat ttatagagtt tgcttcattc
1741 gaagacgcta aagaagcttt aaattcctgt aataaaaggg aaattgaggg cagagcaatc
1801 aggctggagt tgcaaggacc caggggatca cctaatgcca gaagccagcc atccaaaact
1861 ctgtttgtca aaggcctgtc tgaggatacc actgaagaga cattaaagga gtcatttgac
1921 ggctccgttc gggcaaggat agttactgac cgggaaactg ggtcctccaa agggtttggt
1981 tttgtagact tcaacagtga ggaggatgcc aaagctgcca aggaggccat ggaagacggt
2041 gaaattgatg gaaataaagt taccttggac tgggccaaac ctaagggtga aggtggcttc
2101 gggggtcgtg gtggaggcag aggcggcttt ggaggacgag gtggtggtag aggaggccga
2161 ggaggatttg gtggcagagg ccggggaggc tttggagggc gaggaggctt ccgaggaggc
2221 agaggaggag gaggtgacca caagccacaa ggaaagaaga cgaagtttga atagcttctg
2281 tccctctgct ttcccttttc catttgaaag aaaggactct ggggttttta ctgttacctg
2341 atcaatgaca gagccttctg aggacattcc aagacagtat acagtcctgt ggtctccttg
2401 gaaatccgtc tagttaacat ttcaagggca ataccgtgtt ggttttgact ggatattcat
2461 ataaactttt taaagagttg agtgatagag ctaaccctta tctgtaagtt ttgaatttat
2521 attgtttcat cccatgtaca aaaccatttt ttcctacaaa tagtttgggt tttgttgttg
2581 tttctttttt ttgttttgtt tttgtttttt tttttttgc gttcgtgggg ttgtaaaaga
2641 aaagaaagca gaatgtttta tcatggtttt tgcttcagcg gctttaggac aaattaaaag
2701 tcaactctgg tgccagaaaa aaaaaaaaaa aa
```

FIG. 12

Homo sapiens splicing factor, arginine/serine-rich 14 (SFRS14), transcript variant 1, mRNA

```
   1 ggcggcttgc gcctgcgcgg cgcggcgctg cggagaccgt tggttcattt gcatgtcccc
  61 gcctcgcgcg gcggcggcgg cgggtgagga gcctgaggcg gcggcggggg tggctccgcg
 121 cgcggtggtc tcgggggcaa aataacatgg cagccagacg aattacacag gagacttttg
 181 atgctgtatt acaagaaaaa gccaaacgat atcacatgga tgccagtggt gaggctgtaa
 241 gcgaaactct tcagtttaaa gctcaagatc tcttaagggc agtcccaaga tccagagcag
 301 agatgtatga tgacgtccac agcgatggca gatactccct cagtggatct gtagctcact
 361 ctagagatgc cggaagagaa ggcctgagaa gtgacgtatt tccagggcct tccttcagat
 421 caagcaaccc ttccatcagt gatgacagct actttcgcaa agaatgtggc cgggatctgg
 481 aattttctca ctctgattct cgggaccagg tcattggcca ccggaaattg ggcatttcc
 541 gttctcagga ctggaaattt gcgctccgtg gttcttggga acaagacttt ggccatccag
 601 tttctcaaga gtcctcttgg tcacaggagt atagttttgg tccctctgca gttttggggg
 661 actttggatc ttccaggctg attgagaaag agtgtttgga gaaggagagt cgggattatg
 721 acgtggacca tcctggggag gctgactctg tgcttagggg cggcagtcaa gtccaggcca
 781 gaggtcgagc tctaaacatc gttgaccagg aaggttccct cctaggaaag ggggagactc
 841 agggcctgct cacagctaag gggggtgttg ggaaacttgt cacattgaga aatgtgagca
 901 caaaaaaaat acccaccgtg aatcgtatta ctcccaaaac tcagggcact aaccaaatcc
 961 agaaaaacac tccaagtcct gatgtgaccc tggggacaaa cccagggaca gaagatatcc
1021 agttccccat tcagaagatc cctctggggc tggatctgaa gaatcttcgg ctccccagaa
1081 gaaagatgag ctttgacatc atagataagt ctgatgtttt ttcaagattt gggatagaaa
1141 taatcaaatg ggcaggattc cacaccataa aagatgatat taaattttcc caacttttcc
1201 agactctctt tgaacttgaa acagaaacct gtgctaaaat gcttgcctca ttcaaatgtt
1261 ccttaaaacc agagcacaga gatttttgct tttttactat caaatttta aagcactctg
1321 ctttgaaaac acccagagtt gataatgagt tttaaacat gcttttagac aaaggtgctg
1381 tgaagaccaa aaattgcttt tttgaaatca taaagccttt tgacaagtac ataatgagac
1441 ttcaagaccg gcttctgaag agtgtcacac ctttgcttat ggcctgcaat gcctacgagc
1501 taagtgtcaa gatgaagacc ctcagtaacc ccctggactt ggctcttgcc ctagaaacca
1561 ccaactctct ctgccggaag tctttggccc ttttgggaca gacattttcc ttggcctctt
1621 ctttccggca ggagaaaatc ttagaagctg tcggcctgca agatatagct ccctcacctg
1681 ctgcgtttcc aaacttcgaa gactccactt tgtttgggcg agagtacata gaccacctga
1741 aggcctggct agtcagcagc ggatgtcccc tccaggttaa gaaagccgaa ccagagccga
1801 tgcgagagga ggagaaaatg attcctccta cgaaacctga aattcaggcc aaggctccaa
1861 gtagtctgag tgatgctgtc ccccagcgag cagatcacag ggtagtgggc accatcgacc
1921 agcttgtgaa acgtgtcatc gaaggcagcc tgtctcccaa agagagaact cttctcaaag
1981 aggaccctgc ttactggttt ttgtctgatg aaaatagtct ggagtataaa tattacaagc
2041 tgaagttggc agaaatgcag cggatgagcg agaacttgcg aggagccgac cagaagccga
2101 cctcagcaga ctgtgcagtg agggccatgc tgtactcccg ggctgtccgc aacctcaaga
2161 agaaactcct tccgtggcag cggcgggggc tcctccgtgc tcaagggctc cggggctgga
2221 aggcgaggag agcgaccacc gggacccaga ccctcctatc ctcaggcacc aggctgaaac
2281 accacggccg gcaggctcca ggcctctcac aggcaaaacc atccctgcca gacagaaatg
2341 atgctgccaa ggactgcccg ccagacccag ttggaccttc tcctcaggac cccagcttag
2401 aagcctcagg cccatccccc aagccagcag gagtggacat ctctgaagca cctcagacct
2461 cttctccctg cccatctgct gacattgaca tgaagacaat ggagactgca gagaaactgg
2521 ctagatttgt tgctcaggtg ggaccagaga tcgaacaatt cagcatagaa aacagcaccg
2581 ataaccctga cctgtggttt ctacatgacc aaaatagttc tgctttcaaa ttctatcgaa
2641 agaaagtgtt tgaactatgt ccatcaattt gtttcacgtc atctccgcac aaccttcaca
2701 ctggtggtgg tgacaccacg ggttctcagg agagccccgt ggacctcatg gaaggggaag
2761 cagagtttga agacgagccc cctccgcggg aggctgagct ggagagccca gaggtgatgc
2821 ctgaggagga ggacgaggac gatgaggatg gggagagga ggcccccgct cctggagggg
2881 cgggcaagtc tgagggcagc acccctgccg acggccttcc cggcgaggct gccgaggacg
2941 acctggctgg agcacctgcc ttgtcacagg cctcctcagg tacctgcttc cctcggaaga
```

FIG. 12 (cont'd)

```
3001 ggatcagcag caagtcattg aaggttggca tgattccagc tcccaagaga gtgtgtctca
3061 tccaggagcc aaaagtccat gaaccagttc gaattgccta tgacaggcct cggggtcgtc
3121 ccatgtccaa aaagaagaaa cccaaggact tggacttcgc ccagcagaag ctgaccgata
3181 agaacctggg cttccagatg ctgcagaaga tgggctggaa ggagggccat ggcctgggct
3241 ccctcggaaa gggcatcagg gagccggtca gcgtgggaac cccctcggaa ggggaagggt
3301 tgggtgctga cgggcaggag cacaaagaag acacattcga tgtgttccga cagaggatga
3361 tgcagatgta cagacacaag cgggccaaca aatagatcaa aaccactgat gtgaaagata
3421 agccttgaag cagcaattgc ccttaaaaca tcatccctgc cctggatcgg cctggagcca
3481 gtgcccaagt acggtttggt gtgtacatga aaacaaacgt ctctgcagtc tctggggcgg
3541 aggtttcgct ggcttttctt tctctcaaag aaaaaaacat gcaccatttt caatgtgctt
3601 ttgcctctcc tctctgttca catgctttta gcagcaagtc ccctccaaat ctgtcttggt
3661 tccccttcag aaggtggcgc tgcccccgaa aggcacctca gcctgtgagt gctgaggaac
3721 cagctcctct ggctgatttt ccagttggac tggccattgc tctccagaag tgctctgtta
3781 gcaaacgtga tgtggaaacg atcacagatg gtgttttctc gttgttcgcc agaatttata
3841 cgggggagac aaattcccgg taattaccaa gtctgcactc gggtaccaaa gctctgaagc
3901 tctctgaaca gttgccatac ttgagttgat gaatgtgtta ttcatggtgt ctcatctcat
3961 caatgcatct tgagagactt aatgaaattt tagcaacagt atagaatagc tctatcgggt
4021 ggggagtaat cattaaacag atgaaatcgg ccccagattt acatgtctct ttagaatcca
4081 cagtgtaagc aaactacagt tacaaaggga tgggggttgt aaaccctctg agactctgca
4141 cttttcgcac gtatggcatc gtcaagtgct gtcttattac agcctttgta aggagaggca
4201 ggctcctcct ggggtgggct ctgcagctgc tctatttcca ggcatgtgat cgcccccgct
4261 ctccagattc cccagcactc tgctgcgtgt aactccactc aattctccac tcatccttcc
4321 ttgtgaagca ggatcgttga agttttaagt atgggcaaaa atctggaaaa cttaggatcc
4381 ctctgacacc ccaggattag gggacacagc agtggctagg gcatcagcca cagaactgag
4441 cgggaaatgc cacttgtatt ggctgtaaag aaatcctggc tttgggccag gcacagtggc
4501 tcaagcctgt aatcccagca ctttaggagg ttgaggcgga tggatcacct gaggtcagga
4561 gtttgagacc agcctggcca acatggtgta accccgtctc tactaaaaat acaaaaaaat
4621 tagccaggcg tggtagcggg cacctgtaat cccagctact caggaggctg aggcaggaga
4681 atcacttgaa ccggggaggc agaggttgca gtgagctgag atcatgccac tccactccag
4741 cctgggcgac agagcaagac tccatctc
```

FIG. 13

Homo sapiens cDNA clone IMAGE:40127577

```
  1 ctgcgagaat cgaggcactc gctggcgtac ccatgtatcg aaatgagttc acggcctggt
 61 accggcggat gtcggtggtc tacgggatcg gcacctggtc tgtgttgggc tcactgcttt
121 actatagccg gacaatggcg aagtcgtcag tagaccaaaa ggatggctca gcaagtgaag
181 tacccagtga actctctgaa cgcccaaaag gattttatgt ggaaacagtt gtcacatata
241 aagaagattt tgttccaaat acagaaaaga tcctcaacta ttggaaatca tggactggtg
301 gccctggtac agaaccatga ctggctgctg aattctgaaa accaggactt ggttcaacat
361 ttaaatttga tagttgccct gattcccatt ttggt
```

FIG. 14

Homo sapiens chromosome 3 genomic contig, GRCh37 reference primary assembly, Region: 49917591..50054681

1 cgcggcgctg ggtcggtggc ggaggctgag gagaaggagg agcgggccgt ggaggcttcg
61 ccgcctaggt aagggcccgg gactggaggg gaggcgtgcc agagcctgcc agggaatagc
121 cagcagacag gcccgctcta gacatcgcag gcccgcgcag cctgaaagct gtggcttcag
181 tgtcgcgggg cggctgcggc ctcgctcggg aagaagacca agcaacggtg agatgaggga
241 ggcgccgccc gtggcaggaa cgccccggaa ccgtcgcggg cctggggcgg ggcccggcgc
301 ggcagtagat taccggtccc gccgcggagc ggccagctgt gaggctgggg ccggcgcgtg
361 gttgcggctc tgtgctccta ctcttcggag ctgtaagcgg gctgttcttg cggttttcct
421 gtttcagatc caattctgtg gcatcactag gaagggagct cttgtgctta gcacgtagcc
481 tcgtcctcag acttggacag acacaaggga ggctccgctg gaccggaggg cacaagagct
541 ccgagcccgg tcgtcggggc ggtagaacct ggaagcggga gagtggtctg gtgggttctg
601 cgcccgttag gcaatgaagg agaaggatgt tttatcgtat tcacgcttta gattccatta
661 gcggtgtaaa tagatgtttt tctctttatt ttagaattga cgttaggcga atgggttcaa
721 ctttgggaat gccttttttt tttttttttt tttgaaggaa gggccctgtt tcgtagggta
781 cataaaccgt gagcgtaatt gtatttttttg catattccag gtttgcttgt gaaggtcaga
841 gtagccggat ttaagtgaag gagttcagta gacatgcaga catggtcacc tggttcattt
901 tctgaaccct ggattgtgcc ctcggcttgc tagtttccac cttcctattg agaaatgcca
961 ccagcgtgaa tgatttaaat atgtcaccat tactgaattt gtgaggtctc taacgagagg
1021 tgtcaagagc tggtgcgtga tggtaggact ggcagtgaag aaagtaacta aataatatgt
1081 taccattttg gtgaaacaca aaagttgaat ttgaaccttg tctcagaaac tagcatctaa
1141 ctagatacct aacctgcagg acaggtccca ggtctctctg gatagttgta gcacctttcc
1201 ttatagaatt ctattaccag gccgagcctg gtggctcaca cctgtaatcc cagcactttg
1261 ggaggctgag gtggggagtt cgagaccagc ctgactaaca tggagaaacc gcgtctctac
1321 taaaagtaca aaattagccg ggcatggtgg cacatgcctg taatcccagc tacttgggag
1381 gctgaggcag gagaatcgct tgaacctggg aggcggaggt tgcggtgagc tgagattgct
1441 ccattgcact ccagcctggg ccacaagagt gaaactctgt ctcaaaaaaa aaaaaaaaaa
1501 aaaaaaaaaa aaacccgcaa aactcaacaa aaaccaacat agtagaggca gcgtttcgcc
1561 ttatgcccag ctaatttttt gtattttttt agtagaggcg gagtttcgct atgttggcca
1621 ggctggtctt gaactactga cctcaggtga tccacctgcc ttggcctccc aaagtgctgg
1681 gattacaggc gtgagccacc gtgcccggcc ctgttatagt atttctaaaa caaattgtga
1741 gcctgggcaa catcgcaaaa ccctgtctct acaaaaaata caaaaaaaaa aaattagcca
1801 ggcgtggtgg catgctcctg ttagccctaa ctactcagga ggctgagatg gaaaaatcgc
1861 ttgagccggg gaggtagagg ttgtagtaag gggagatagt gccactgcac tccaacctgg
1921 gccacagaac aagactgtct caaaaaaaaa aaaatcaatt aaataaattg tggtaaatat
1981 atatttttat gtatgtttat gtatatttta acaaaatttg ctctttaaac cattgttaag
2041 tatacaattc agccaggcac ggtggctcac gcctgtaatc ccagcacttt gggacgccga
2101 ggtgggcgga tcacgaggtc aggagatcga gaccatcctg gctaacacgg tgaaacccca
2161 tctctactaa aaatacaaaa aatgagccgt gcgtggtggt gggcgcctgt agtcccaggt
2221 actcaggagg ctgaggcagg agaatggtgt gaacccgaga ggcggagctt gcagtgagcc
2281 gagattgcgc cactgcactc cagcctgggc aacagagcga gactccgaga ctccatctca
2341 aaaaaaaaaa aaaaaagtat acaattcaat ggtattaatt acattcacaa tgtagtacaa
2401 gcaataccac tatttctgaa actttagtat ctcaaacaga aactctgtaa ccagggaggg
2461 catggtggct cacgcctgta atcccagcac tttgggaggt caacgtgggc agatcacttg
2521 agttcaggag ttcaagaaca gcctggccaa catggtgaaa ccccgtatct actaaaaata
2581 caaaaattag ccatgcatgg tggcatgcat ctgtaacacc agctactaag gaggcagagg
2641 ttgcagtgag ctgaggtcat gccattgcac ttcagcctgg gctgcacagc cagactccat
2701 ctcaaaaaaa aagaaaaaaa gaaactgtaa ccattaaaca agttaacttc ccatttcctc
2761 ctcttaatct ctaatctact ttgtgtctgt ctgtgagtgt gcttgttcta ggtactgcaa
2821 atactaaatg gaatcataca gtattgtcct tttttgtgtc tggtttattt cacttagtgt
2881 aatggtttca aggttgatcc atgttgtact gtgtatcaga atttcattcc tttttaaggc

FIG. 14 (cont'd)

2941 ttaatccgtt gtgtgtgtac actacatttt gtttattaat tcatttgtag cagacacttg
3001 ggttgcttct gccttttgac tattgtaaat aatgatgctg tgatcattgg tgtacaaata
3061 tctctttgag tccctgcttt gaattctttt gggtatatac ccagaaggga aattgctata
3121 tggtaattat tattattatt aattatttta tttatttttt tttgagacag ggtcttgctc
3181 tgttgcccag gctggagttc agtggcacag tcatggctca ctgcagcctc gaactcgagc
3241 tcaagcagtc atcccgcctc agcttcctga gtagctggga ctacaggcat gggctgccac
3301 aaccagctaa tttttttgtt taatttttat tttttgtgat gaagtcttgc cttgttgtct
3361 agggtggtct cgaactcctg agttcaagtg atcctcctgt cttggcctcc cgaagtgctg
3421 gcattacagg catgagccac cacatctggc ccataatttt tttattttaa tttttttgtg
3481 gagacagggt ctccctatgt tgcctatgct ggtctcaaac tcctggcctc aagccatttt
3541 ccctccttgg cctctcaagg tactggtatt acaggcatga gccactgcac ccagttgata
3601 cttggttatt atatgtttag ctttttgagg acccaccata ctgttttcct caatggctgc
3661 atcgttttac attcccacca gtaatacaca agggttccaa ttttcccaca tcctccccaa
3721 cacttatttt ctgtttttcc tttttgata aatttgtgtg tgtatatgtg gtttttttatt
3781 tgtgtgtttt gatgatagcc accctaatgg gtgtgaagtg gtatctcgtt gtgttttctt
3841 ggtttttgct tgtttgtacc tttttaccca tttttaagtg tgctacttag tagtagtaag
3901 tacattcttc tttttgtgca accataataa aaatccagct tcagaacttt tttcatcttc
3961 ccaaactgag tttctgtacc cattgaatag taactcccta ttctctcctc ccctgacaat
4021 caccattctg ctttctgtct ctatgaattt gactactcta ggtatctcat gtaagtggaa
4081 tcatataata tttgatcttt tgtgtatggc ttattttact tagcataata tcttcaggat
4141 tcatccatct tgtagtatgt atcagaattt tattcctttt taaggctgag taatattcca
4201 ttatacatat ataccacatt ttgtttatcc atttatctat tgatggacat ttgggttgtt
4261 tccacctttt tgctcttgtg aatataatgg tgctatgaat atcagtgtac aaatatcttt
4321 tttttttttt tttttgtgag acagtatcgc tcttgtcacc caggctggag tgcagtggcg
4381 cgaccttggc tcactgcaac ctctgcctcc tgggttcaag gcattctcct gcctcagcct
4441 cccgagtagc tgggattaca gatgtgcgcc accatgccta gctaattttt ttatttttag
4501 tagagaagga gtttcgccat gttgggcagg ctggtcttga acttctgacc tcaggtgatc
4561 aacctgcctc ggcctcccaa agtggtggaa ttacaggtgt cagccaccgc gcccagccac
4621 aaatatcaag tctttacttt catttctttt gggaatatat atactcagaa atggaatcga
4681 caattgacag agcaaatggt aattctatgt gtaatttttt tttaaatttt tttttttgag
4741 acggattctt gctctgtcgc ccaggctgga gtgcagtggc gtgatctcgg ctcactccaa
4801 gctccgcctc ctgggttctt gccattctcc tgcctcagcc tcccgagtag ctgggactac
4861 agcatccgcc accacgcccg gctaattttt tgtattttta gtagagacgg ggtttcaccg
4921 tgttagccag gatagtctcc atctcctgac ctcatgatct gcccgccttg gcctcccaaa
4981 gtgctgggat tacaggcgtg agccaccgcg cccggccaat tttttttttt ttttttttta
5041 gacagggtct tgctctgttg tccaggctgg agtgcagtgg tgcagtcaca gttctctgca
5101 gccctgacct tctcagttca agctatcctc tcacctcacc ctcttaagta gctgagacta
5161 caggtgcatg ccaccatgcc taactaattt ttttattttt ttgtagctgt gggatttcgc
5221 taggttgccc aggctttatg tatcattttt tgaggaactg ccttactgtt ttccacactg
5281 gttgcaccat tttacattct gttagcagtg tacaaaggtt ttgttataga ctgaattgtg
5341 tccccctgaa aattcacgtg ttgaagccct aagccccagt gtgactgtat ttggaaatag
5401 gacctttaca gagaaattaa aaagttagaa gatatcataa ggggctgggc gcgggtggct
5461 catgcctgta atcccagcac tttgggaggc tgaggcaggc ggatcacaag gtcaggagat
5521 cgagaccatc ctggccaaca cggtgaaacc ccgtctctac taaaaataca aaacattaac
5581 cgggcgtggc ggcatgcacc tgtagtccca gctgctgggg aggctggggc aggagaatgg
5641 cgtgaacccg ggaggcacag cttgcagtga gccaaaatcg cgccactgca ctccagcctg
5701 ggcgacagag cgagactcca tctcaaaaaa aaaaaaaaaa aaaaaaaaag aagatataag
5761 gatgagacct taatccagca ggactgctgt cttcgtaaga aaaggactgg ataccaggag
5821 tgcgtgtaca gagagaaaaa gctgcatgag gacagaggta gaagggggct gcctgcaagc
5881 caaggagaga gacctcacct aaaacaaacc ttgctgacac cttgatcttg gactcccagc
5941 ctccagagct gtgagaataa tttctgtggc ttaagccttc cactccatgg tattttgtta

FIG. 14 (cont'd)

6001 tggcagtcct agcatactgt gtaatatagg tttcaattca gtttctctgc atcctccaca
6061 tcctggccaa cacttgttat tttctttctt tttttttttt ggagacagat tctcgctctg
6121 tcacgcaggc tggagtgcag tggcacaatc ttggctcact gcaacctcca cctcccgggt
6181 tcaagcgatt ctcctgcctc agcctcccga gtaactggga ttacaggcag ccgccaccgt
6241 gcccagctaa tttttgcatt ttagttgaga tggtgtttct ccatgttggc caggctggtc
6301 ttgaactcct gacgtcaggt gacccgccag ccttggcctc ccaaagtgtt gggattataa
6361 gcatgagcca ccgcgcctgg cattttcttt tttttgaga cagagtctca ctctgttgcc
6421 caggccggag tgaagtggca tgatctcggc tcactgcaac ctctgcctcc cagattgaag
6481 caattcttgt gcctcagcct cccgggtagc tgggattaca ggcgtgtgcc accacgcctg
6541 gctaattttt gtattttagt agagacaggg tttcaccata ttagccaggc tggtcttgaa
6601 ctcctgacct caagtgatct gtccaccttg gcctcccaag gtgctgggat tacaggtgtg
6661 agccatctca cccggcctat tttctgtttc gttttttttt ttttcattag tagctatcct
6721 agtggatgtg aagtggtatc ttattgtggt ttctgatttg catttccctg atgataagtg
6781 atgttgagcg tctgttcatg ttcttattgg ctatttgcat attctctttt ggagaagtat
6841 ctattcatgt cttttgttga ccattttaaa atggggtttt tcatcctggc taacacggtg
6901 aaaccctgtc tctactaaaa atacaaaaaa aaaaaaaaaa aaaaattagc cgggcgcagt
6961 ggcaggcgcc tgtagtccca gctactcggg aggctgaggc agaaggatgg tgtgaacctg
7021 ggaggcagag ctcgcagtga gcagagattg agccactgca ctccagcctg ggcgacagag
7081 cgagactccg tctcaaaaaa aaaaaggggg gggggggggg ttttgagctg ggtgtgcagg
7141 tgcacacctg tattcccagc tgctcaggag gctgaggtag gtggatctct tgagcccagg
7201 tgtttgaggg tgcagtgagc tgtgattgca ccactggact ctaccctggg tgacagagtg
7261 gcccagtctc taaaaataaa ataaaattag gtttttgtct gtgttgttga gttttaggag
7321 tcctttatac actctagata ttaattcctt gtcagatatt tgacttacaa atattttctc
7381 tctgtggttg tctttatact ctgttgatag tgtcttttga tgcacagagg ttttcatttt
7441 gatgaagtcc aatttatctt cttttttaa aatctgtgcc tcatctgcaa atattaccaa
7501 tcgaaagtca tgaaattttt cccctaagat tttatagttt tagcgcttac gtttgggtct
7561 ttgatccaat ttgagttaat tttttatata tttttgttgt gtaagagtcc cactttattg
7621 ttatgcatgt ggatattcag ttttcggagt accattttcc atttgggaaa aagattgtac
7681 tttccccatt ggatggtctt gacacctttg ttgaaaatca gttgactaaa gttcaagact
7741 agccttgcca acatggcaat atcccgtctg tactaaaaat accacaatta gctgggcatg
7801 gtggtgcctg gctgtaatcc cagctactcg ggaggctgag gcaggagaat cgcttgaact
7861 gggaggtgga ggctgcagtg agctgagatt gcgccactgc cctccagcct gggcgacaga
7921 gcgagacatg agaatctgtc ttaaaaaaaa aagaaaattg accatatatg tgaggattta
7981 tttctggtct ctccattcag ttgattggtc tttatgtcta tctttatgtc cttactgcac
8041 tgttgtgatg gctgtagcta aatggtacac ttaaaaatgg ttaaaatagg ccaggcacgg
8101 tggctcacgc ctataatctt agcactttag gaggctgagg tgggcagatt gcctgtgctc
8161 aggggttcga gaccagccta ggcaacatag tgaaaccccg attttactaa aatacaaaaa
8221 ttagctgggt gtggtgtgtg cctgtaattc cagctactca ggaggctaag gcacaagaat
8281 tgcttgaggc ctggtgctgt ggctcacgcc tgtaatccca gcactttggg aggccgaggc
8341 aggtcaagag atcgagacca tcctggccaa tgtcatgaaa cctagtctct actaaaaata
8401 caaaaaatta gctgggtgtg gtggcgcgca cctagtccca gctacttggg aggctgaggc
8461 aggaggatca cttgaaccca ggaggtggag gttgcagtga gccaagattg cgccactgca
8521 ctctagattg gcagcagagt gagactctgt ctcaaaaaag aaaaaaaaaa aaaagaattg
8581 cttgaaccca ggaggtagag gttgcagtga gctgagattg caccctgcac tccagcctgg
8641 gcaacagagt gagactattt acatacccaa tttttttttt tttttttttt tgggatggtg
8701 tcttgcactg tcgcccaggc tggagtgctg tggcgtgatc ttggctcact gcaacctctg
8761 cctcctgggt tcaagcaatt ctcctgcctc aggctctcaa gtagctgggt tacaggtacc
8821 tgccaccacg cctggctaat ttcttgtatt tttagtagag atggagtttc actatattgg
8881 ccaggctggt ctcaaatttc tgaccttgtg atccgctggc ctcagcctcc caaagtgctg
8941 ggactacagg tgtgagccac cacgcctggt catacccaaa tattttacca taattataca
9001 agaatttatt atttttattt ttttcttttt aaattcttta atcttcttca tttgttaatg

FIG. 14 (cont'd)

```
 9061 ctttgctgaa tcataaaaaa ttatgaaata aaaagaatag gtcttgttga ttcttctttt
 9121 tacttacctc cccctactta ccccctctta ctttatcaaa gaaaacactt catttgaaac
 9181 ttaacggaag tacattctcc cagagaggaa aatccttcag gacaacattt ttttttgttt
 9241 gcttgttttt tttgagacgg agtctcactc tgtccccgag gctggagtgc agtggtgtga
 9301 tcgcagctca ttgcaacctc tgcctcccgg gttcaagcga ttctcctgcc tcagcctccc
 9361 gagtagctgg gactacaggc gcctgtcacc atgccctgct aatttctgta tttttagtag
 9421 aaacagttgg ccaggatggt ttcaatctta tgactttgtg atctgaccac tttggcctcc
 9481 caaagtgctg ggaatacagg cgtgagccac agtgctcagc caatttttttg tatttttagt
 9541 ggagaaaagg tttcaccgtc tttgccagga tggtcttgat ctcctgacct cgtgatccgc
 9601 ccgcctccca aagtgctggg attacaggcc tgagctacca cgcccagcct ttttattttt
 9661 ttattttatt tattttattc tcagccttct gggtaactgg gactacaggt gtataccacc
 9721 acgctcagct aatttatgta tttttagtag aaatggggtt tcgccatatt ggccaggctg
 9781 gttttgaatt cctggtctca agtgatctgc ctgcctccgc ctcctaaagt gctgagatta
 9841 caggcatgag ccactggccc agactacact taaaatttc aaatcgagat attttggggg
 9901 gcaagggtgc ttctagcagc cactaattcc agttcttgag tgcatattaa agttgctact
 9961 gtttaaaagc ttgtagttgg atccagggag tgggtaggcg gtcagagtaa cccttgcttc
10021 ttggtgtctc cttgatgctc ttagctgaat gtcctgtgta gcccacaaca tttactttgg
10081 gaaaaaatta agagtgttta aagcaggatc aagctgctgc ataccacagc taaaactact
10141 agaataagac ccctggttct gtttcattgt tttttggagc taaagtcatg attaagaagg
10201 atggcctggg atattggtac tgtgctgcta gaggtgcaat tcctggttct ttgcaagata
10261 gaccagagtg aaagcatttg ttaggaatgt ttttattaat caagagtgaa aggcaaggcc
10321 aggcgtggtg actcaggctt gtaatcccag cactttggga ggccaaggtg tgggatcatt
10381 tgaggtcagg agttcaagac cagcctggcc aacatggtga aaccccgtct ctactaaaaa
10441 tacaaaaatt ggctgggtgt ggtggtgcat gcctgtaatc ccagctactc gggagactga
10501 ggcaggagaa tcgcttgaat ccgggagacg gaggttgcag taagctgaga tcatgtcact
10561 gtggtacagt ctgggtgaca gagggagact gtttcaaaaa aaaaaaacag aaagaatgaa
10621 aggcaaaaca ttaaaaatag aattaccatg tgatctaaca attttacttc tggatatata
10681 tccaaaataa ttgaaaacaa agaaaaagaa aaacagagtc tcgatgagat atttgtaccc
10741 atgttcataa cagcgttatt cacattagct aaaatgtgga agcaacccaa ctattcattg
10801 atggatgaat agataaggaa aatgtggtat gtacatataa ctgaaaaatt attcagtgtt
10861 aggaaggaag gtaattctga catatgctac aacatggatg aaccttgagg atattatgct
10921 aagtgaaata agccagtcat gtaaaagaca aataccatat aatttcactt agacactttg
10981 agtagtgaaa atcatagaaa cagaaaatag ttgtcaggga tggtgtgagg gatgaatcag
11041 cagttactat ttctttttgt ttgtttgttt tttgagatgg ggtcttgctc tgttgcccag
11101 gctggagtac agtggtgtga tcttggctca ctgcaacctc tgcctcccag gcacaagcca
11161 tcttcccacc tcagcgtcct cagtagctgg gactacagat gtgttccacc ttgtccggct
11221 gatttgtgtg tgtgtatatg tgtgtgtgtg tgtggagaca aggttttgcc atgttgccca
11281 ggctggtctc gaactcctga gctcaagcat caagcaatct accttttca gctttccaaa
11341 gtgctggcat tacagacaag ggccactgtg cctggccttt actatatttt attttattta
11401 ttatttattt atttatttat ttatgtattt tgagatgaag tctcactctg ttgcccaggc
11461 tggagtgcag tggcacgatc ttggctcact gcatcctctg cctcccaagt tcaagtgatt
11521 ctcctgcctc agcctccagt tattattatt attattatta ttttttgtt gttctgtttt
11581 tttgaggtgg agtctcgccc tgtcgcccag gctggagtgc agtggcacaa actcggctca
11641 ctgcaacctc catctcccag gttcaagtga ttcttctgcc tcaacctccc aagtagctgg
11701 gaatacaggt gcccgccacc acgcctggct aatttttgta tttttagtag agacggggtt
11761 tcaccacatt ggtcaggctg gtcttgatct cctgatcttg tggtccacct gcctcggcct
11821 cccaaagtgc tgggattata ggtgtgagcc cccatgccct gccttgttat tattattatt
11881 tttatttttt tgtctgagac ggagtcttgc tctgtcaccc aggctagaat gcagtggcac
11941 gatcttggct tagtacaacc tctgcctccc gagttcaagt gattctcctg cctcagcctc
12001 ccgagtatat aggactacag gtgtgtgcca ccatggctaa tttttgtatt tttagtagag
12061 atggggtttc accatgttgg tcaggatggt ctagatctct tgacctcgtg atctacccgc
```

FIG. 14 (cont'd)

```
12121 cttggcctcc caaagtgctg ggattacagg catgagccac tgcgcctggc cccagttttt
12181 gtatttttaa tagagacagg gttttggcat gttggccagg ctggtctcag actcctgacc
12241 tcaagtgatc tgcccacttc agccttctga agtgctggga ttaaagacat gagcactgtg
12301 cccagccact tttactatat tttaaattag gttacttatc ctttgttttt tttttttttt
12361 gagacgaagt tttgctcttg ttgcccaggc tggtgtgcaa tggtgcatct cgactcaacg
12421 caacctctgt ctcccgggtt caagtgattc tcctgcctca gcctcccgag tagctgggat
12481 tacaggcatg catcaccacg ccagctaatt ttgtattttt agtagagaca gggtttctcc
12541 atgttggtca ggctggtctc aaactcccga cctcaggtga tccacctgcc ttggcctccc
12601 aaagtgttgg gattacaggc gtgtgccact gctcctggct tatttttctt tttgttactg
12661 agttgaaatc atttttttata tattttagat acaagtcact taccaaatat gtaatttgca
12721 caaattttct cccattctgt gggatgtctt ttcatttaaa ccaaaaaatt gtagagatgg
12781 gggttttgct gtgttgccca ggttggtctt gaactcctgg tcttaagtga tcctctgacc
12841 ttggcctcaa aaagtgctgc gattataggc atgagccaat gtgcgcagct tacctttttct
12901 tcttttcttt tttttgagg cagggtcttg ctctgttgcc caggctggag tgcagtggtg
12961 caatcatggc ttactgcagg ctgaaactcc catgctcaag tgatcctccc actttagcct
13021 cctaggtaac tgggacctta ggggcgtgcc atcacacctt gctaattttt tttttttttt
13081 gagatggagt cttgccctgt cgcccaggtt ggagtgcagt ggagcgatct tggctcactg
13141 caaattccac ctcccggatt caagtgattc tcctccctca gcctcctgag tagctgggac
13201 tacaggcgtg tgccaccacg cccagctaat tttgtattc tgagtagaga cgggatttca
13261 ccacattggc caggctggtc tcgatctctt gacctcgtga tctgcccgcc ttggcctccc
13321 aaagtgctgg gattacaggt gtgagtgtga gccaccgaac ctggcctttt tttttttttt
13381 tgagaccgtc tctgtcaccc aggctggagt gcagtaacat gacacaatct ccgctcactg
13441 caacctctgc cttctgggtt caagtgatcc ttctgccaca gcctcctgag tagctgggat
13501 tgcaggcatg tgctaccacg cctggctaat tttgtattt ttagtagaga cggggtttca
13561 ccatgttggc ctacctggtc ttgaattcct gacctcagat gatctgcccg catcagcctc
13621 ccaaagtgct ggggttacaa gcgtgagcca ccacgcctag ctggacctga ctaattaaaa
13681 aaaaaatttt gtaggctggg cagggtggct cacacctgta atcccagtac tttgagaggt
13741 ggaggcgggg taatcgcctg aatcaggagt ttgagaccag cccgggcaac ataacgaaac
13801 cctaggtcta ccagaaatac acaaaaaaat tagccgagca tggtagtgca catttgtagt
13861 cccagctact caggaggctg aggtgggagg atggctggag ccagggaagc agtggttaca
13921 gtgagccgag aatgtgccac tgcactcccg cttgggtgac agagtgagat aaggtctcag
13981 aaaaaaaaaa aaaatttata ggccgggcgc aatggctcac gcctgtaatc ccagcacttt
14041 gggaggacca ggcgggcgga tcacaaggtc aggagatcga gaccaccctg gccaacatgg
14101 tgaaaccccg tctccactaa aaaaatacaa aaattagctg ggcgtggtgg cacgtgcctg
14161 tagtcccagc tacttggcag gctgaggcag aagaattgct tgaaccctgg aggcggaggt
14221 tgcagtgagc cgagattgca ccattgcact ccagcctggg cgacagagcg agactccatc
14281 tcaaaaaaaa aaaaaaaaaa aatttgtgaa gacaaggtct caatatttgc ccaggatggt
14341 ctgaaacttc tgggctcaag ccatccttct gcctcagcct cccaaagtat tggaattaca
14401 ggtgtgagcc actgtgtctg gcctatttat agactcttaa ttctgtttcc ttggtctgta
14461 tgtctatact atgtcagtgc cacactgtct tgattactgt agctttgtgg tgagttttgg
14521 aattgggaag tgtcagtcct ctaactttgt tgtatatatt cttttctgtt ttgcacagat
14581 atcaggttac aaatatttg cacactttt ttttttttg aaatggagtc ttactctgtc
14641 acccaggctg gagtgcagtg gcgcgatctc agcccactgc aagctccgcc tcccaggttc
14701 acaccattct cctgcctcag cctccccagc agctgggact gcaggcgcac actgccatgc
14761 ccagctaatt tttttgtatt ttaagtagag acagggtttc actgtgttag ccaggatggc
14821 ctcgatctcc tgacctcgtg atccgcctgc ctaggcctcc caaagtgctg ggattacagg
14881 cgtgagccac cgcacccggc cttgcacatg tttttaaaac ttaatacata atagcttatc
14941 ctgtatcaat taacatagct actttattta ttcttagggc cgcatagtat tttttttttct
15001 ttctttttt ttttttttt tttttttgag actgagtctc gctctgttgc ccaggctgga
15061 gtgcagtggt gtgatcttgg cttaagcaac ctctgcctcc tgggatcaag cctcgggatc
15121 ctcctacctc aacctctgca gtatttggga ctacagacac ctgctaccac acccagttaa
```

FIG. 14 (cont'd)

```
15181 ttttcgtatt tttttgtaga gatagggtct ctattgatgt gcatttaggc tttataatat
15241 ttatatatat attttttgaa acaaagtttt gctcttgttg cccaggctgg agtgcagtgg
15301 catgatcttg gctcactgca accttcgcct cccaggttca agtgattctc ctgccttaga
15361 ctcccgagta gctgggatta cagtttttaa aaaatgtatc ctaggctggg cgcagtggct
15421 cacgcctgta atcccagccc tttgggaggc tgaggcgggt ggatcacctg aggtttggag
15481 tttgagacca gcctggccaa catggtgaaa cctcgtctgt actaaaaata caaaaattag
15541 ctgggtgtac tggcgggcac ctgtaatctc agcttcttgg gaggctgaga caggagaatc
15601 tcttgaactt gagaggcggt ggttgcagtg agccattgca ctccagcctg ggtgtcaagc
15661 aaaactctgt ctctctctct ctctgtgtct ctctctctct ctctgtgtgt gtgtgtgtgt
15721 gtgtgtgtat atgtatatat attctgccaa tattttgtga ttagagagtt taaagtattt
15781 acatttaaag taattactga taaggacttt tgccattttg ctactacttt tatgtttagc
15841 tgattttttt tttttggta gtgaaaaaaa attttttttt tttgagagca tgagactgtt
15901 gcctaggctt tggtgagcaa aatagtgcag tgccacaatc tcagctcact gcaactttgg
15961 gctcaagtga tcctcctgtc ccagtctcct gagtagctgg tagtataggt gtgccaccac
16021 catgcctggc taatttttgt atttttgtta gagatagggt tttgccatgt tgcccaggct
16081 ggtctcaaac tgggttcaaa caatctacct gccttagcct tccaaagtgt tgggattaca
16141 ggcattagcc actttctgcc ccctcccccg cttttttttt tttttttttt tttttgagac
16201 ggagtttcac tcttgttgcc caggctggag tgcagtggca tgatttcagc tcactgcaac
16261 ctccgcctcc cgggttcagg cattttcctg cctctgcctc ccaagtagct gggattacag
16321 gcttgccacc atgcctggct aattttgtat ttttaataga gatggggttt ctctatgttg
16381 gtcaggctgg tctcgaactc ctgacctcag gtgatcctcc tgccttggct tcccaaagtg
16441 ctgggattat aggcgtaagc catcacgcct ggcccacgct ttattttttt atttttattt
16501 tttattattt atttatttat tttttgagac ggagtttcgt tcttgttgcc caggctggag
16561 tgcaatggca taatctcagc tcaccgcagc ctccgcctcc tgggttcaag tgattctcct
16621 gcctcagcct cctgagtagc tgaatttaca ggcatgcgcc accatgccca gctaattttg
16681 tatttttagt agagacgggg tttctccatg ttggtcaggc tggtctcgaa ctccagacct
16741 caggtgatcc tcccgcctcg gcctcccaaa gtgctgggat tacaggcgta agccaccagg
16801 cctggcctgc ttttttaatt ttttatttat tttttctttt taagagggag ggtcttgctg
16861 tgttgtccag attggagaac agtgatgaga tcatagctca ctgcagactt ggattcctgg
16921 actcaagcaa tcctcccgct tcattctttg caagtaactg gaagtgcaga catgtgccac
16981 ctgccttttt tgttttttaa atttttcata gagatggggt cttgctatat tgcctaggct
17041 ggtctcaaac tcctggcctc aagcaatcgg cttcctgaag tgctgggatt acagatgtta
17101 gccactggcc tgttgtgaaa atgttttgac tttcttctca ttttctttct ttcttttttt
17161 tttttttga agtagagaga gtctcactat atggccaatg gtggtttcaa accccctgagc
17221 ccaaggaatc ctcctgcctc agcctcccag tgcttgtcgt gctaggacaa caagcatgag
17281 ccactgtgcc tagccccttc tcattttctt tttctttcta gtgcataagc aggcaacctt
17341 attttcttat gtgtatattc taaagatatg ttctttgcag ttaccatggg aattacactt
17401 aacatctcac agttataatc taatttgaat ttatactaac ttaagttcca tagtatacaa
17461 atctctgctc ctatccagct cctttctctt ccccttttctg ttaagtcatg gattacatct
17521 ttgtaaatcg tatctcagga acctagatta ataatttttt atgcatctgt cttttagatc
17581 acattgaaag tgaaaagtag gagttacaaa gcaaaattgc aataatgcta gtttttacag
17641 ttgcccctgt atttgccttt accagagatc tttctttctt tttttttttt ttgggatgga
17701 gtctcgctct ttcgcccagg ctggagtgca atggcgcaat ctcagctgac tgtaacctct
17761 gcctcccggg ttcaaaagat tttcttgcct caggctcctg agtagctggg actgtagttg
17821 tacgccacca cacgtggctg atttttgtat ttttagtaga gatggggttt tgccatgttg
17881 gccaggctgg tcttgaactc ctgacctcag gtgtgagcca ccgcacctgg ccgagatctt
17941 tatttcttca catggcttca cgtctagctt ttaaaaattc attctgggcc gggcgcagtg
18001 gctcacgcct gtaatcccga cactttggga ggctaaggcg ggcggatcac gaggtcagga
18061 gatcgagacc atcctggtta acacagtgaa accccgtctc tactaaaaac acaaaaggcc
18121 gggtgcggtg gctcacgcct gtaatcccag cactttggga ggctgaggtg ggtggatcac
18181 gaggtcagga gatcgagacc atcctggcta acatggtgaa accccgtctc cactaaaaat
```

FIG. 14 (cont'd)

```
18241 acaaaaaaca aaacaaaaca aaaaaaacta ttagctggca ttgcggtggg cacctgtagt
18301 cccagctact cgggaggctg aggcaggaga atggcgtcaa cccaggaggc ggagcttgca
18361 gtgagccaag atcacgccac tgcactccag cctgggagac agcaagactc tgtctcaaaa
18421 acaaaaaaca aaaaaccaca aaaattagcc gggcgtggtg gcgggcgcct gtagtcccag
18481 ttactcggga agctgaggca ggagaatggc atgaacccag gaggtggagc ttgcagtgag
18541 ccgagatcgc tcaactgcat tccagccttg gcaacagagc gagactccat ttcaaaaaaa
18601 aaaaaaattc attctgaaga attccttttt tttttttttt ttttgtaaaa atggagtctc
18661 actctgttgc cctggctgga gtgctgagtg ccatggcatg atctcagctc actgcaacca
18721 acccccactc caagttgaag cgatactcct gcctcagcct cctgactagc tgggattagg
18781 ggtgcctgct actgcacctg gctaattttt gtatttttag tagagacggg tttcaccatc
18841 ttggccaggc tggtgtcgaa ctcctgacct cgtgaccaac ccacttcggc ctcccaaagt
18901 gctgggatta caggcgtgag ccactgtgcc cggactgaag aattcccttt tagcatttct
18961 tacaaggtct gtatagtggt aatgagcctc cctcagcttt tgtttatctg agaatgtctt
19021 gatttttttc cttttttttt tttttttttg agatggagtc tcgctctgtc gcccaggctg
19081 gagtgcagtg gcgtgatctc agctcactgc aagctccgcc tcctgggttc acaccattct
19141 cctgcctcag cctcgtgagt agctgggact acaggtgccc gccaccacgc ctggctaatt
19201 tttttttttt tttttgtatt tttagtagag acggggtttc actgtgttag ccaggatggt
19261 ctcaatctcc tgaccttgtg atccgcccgc ctcggcctcc caaagtgctg ggattacagg
19321 tgtgagccgc ctcgcccggc caatgttttt ccctattttt tgaaagacag tgttgccatt
19381 tacagaattc ttggttggca atttatattt agggtttttt tttttttttt tgagacagag
19441 tcttgctctg ttgcccaggc tggagtgcag tggtgtgacc tcggctcact gcaacctccg
19501 cctccagggt tcaagtcatt ctcctgcctc agcctcccaa gtagctggga ctacaggtgc
19561 ccgccactac gcctggctaa tttttgtat ttttagtaga gacggggtgt caccatgttg
19621 gccaggctgg tctcgaactc ctgacctcaa gtgatccaca cgcctcagcc tcccaaagtg
19681 cagggattac agacatgagc ccccacgccc ggcctaggtc ttgtatgatc atacattttg
19741 ccttggcatt catatggctt tctaaatttc accatataca tgttgctttg gaatgtccta
19801 atttgccaaa gagtttcacc tcaacttctg tgggcatcta tctgtaatct cttgccccaa
19861 gtgcctgtta gtctgtagtc tgctttgcag ctttcattag caatacctgc tgctttctct
19921 gcctgagttt tgtattaggt tgaaatagaa acatgcacct tatgtctgtc cttcaaatac
19981 ccccgcagac agggtagaac agatatgtac gataatttgc aaataaggtc tgctttgctc
20041 tttgagggag ggagctggga attgggcttc tactgcttta agacaaaaaa cactgccatg
20101 ctggagaggg ggtagggcaa ggttgagtaa aacaccacag aactttcctt ctgttttgaa
20161 gatggctttt tcttcattgg atatttgctt gtaaaccttt gactcttttc taaaactgtc
20221 aaatttggtt cagacagtta ctacttgttt ttctgatgtt tctatgaagg aatgagacct
20281 tgaaacttcc tagtctgcca ttttgatgac ctatgggctg tctttgtact ctcttgatag
20341 tgtcctttga tacacagaag tttttaattt tggtgaagtc cctttatcta ctttttcttt
20401 taaagttcct tgtgctgtag gggtcatatt taagaaatca ttgccaaatc caaggtcatg
20461 aagatttgcc tctttttcag tagctataac aaaggtcctg gaaataactt cttatcttga
20521 cttgagttac atgtctgtct tcaaagcaat gactgtggtg agggtaatag attattccga
20581 ttgctcatgc tggatggtgt ccgatcaggt ctgagacagt ggggttgata ctacagtgct
20641 gtttccaaaa aggaagggct agtgagcgct agaaaaatca gtaaatactt acttcatgta
20701 gtaaatgtga agcattcata gcacattgaa aagtttatgg tgcccagagt accttttttt
20761 tttttttttt ttgagacagc ctcactctgt ttcctgaact ggaatgcagt ggtgcgatct
20821 tggctcactg cagcctcaac ctcctgggtt caagcgatcc tcccccactt cagccttcca
20881 agaagctgag actacacata gtcatcatgc ctgactaatt tttgtatata tattttttaa
20941 gatggagtct cgctctgtca cccaggctgg agtgcagtgg catgatcttg gctgactgta
21001 gcctccgcct cccggtttca agcgtttctc ctgcctcagc ctcctgcata gctgggatta
21061 caggtgcctg ccaccacacc tggctaattt ttgtattttt agtagagatg agatttcacc
21121 atgttgccta ggctggtctc gaactcctga cctcaggtga tccacctgcc tagcctccca
21181 aagttctggt aatttttgta tttttgtag agatggcatt ttgctatgtt gcccaggctg
21241 gtctcaaact ccttggctca agcggtctgc ctgccttggc ctcccaaagt gttgaggtta
```

FIG. 14 (cont'd)

```
21301 caggtatgag ccaccgtgcc cgaccccaga gtacacattt taattaaaaa cttatttttc
21361 tggccgggca cggtggctca cgcctgtaat cccagcactt tgggaggccg aggtgggtgg
21421 atcacaatgt taggagttcg agaccagcct ggccaatatg gtgaaacccc atctctacta
21481 aaaatacaaa aattagccgg gcatggtgac gcgtgcctgt agtcccagct actcgggagg
21541 ctgaggcaga agaatcgctc gaaccgggga ggcagaggtt gtggtgggct gagatagtgc
21601 cactggactc cagcctgggc gacagagaga gattctgtct ttaaaaaaaa aaaaaaagta
21661 tttttcttat tataaattta atatgtaagt gatgtaagtg tttgaaagtg acttccagct
21721 ggatgcggtg gctcatgcct gtaatcctag cactttggga ggccgaggcg ggcggactgc
21781 ttgagctcag gagtttgaga ccagcctggg taacacagtg aaaacccgtc tctactaaaa
21841 tacaaaaaaa ttagctgggc ggccggcgtg cgcctgtagt tctagctact tgggaggctg
21901 aggcaggaga attgcttgaa cccggaggtt gcagtgggct gagatcgtgc ctttgcactt
21961 cagcctgggc aacaaagcaa gactccatct cttaaaaaaa aaaaaaaaaa agaaggccgg
22021 gtgcagtggc tcacgcctgt aatctcacac tttgggaggc ctaggtgggc ggatcatgag
22081 gtcaggagat ctagaccaca gtaaaccccg tctctactaa aaatacaaaa aattagctag
22141 gcgtggtggc gggcgcctgt agtcctagct actcgggagg ctgaggcagg agaattgctt
22201 gaacccggag gttgcaatgg gctgagatca tgcctttgca ctccagcctg ggcgacagag
22261 cgagactcca tctcaaaaaa aaaaaagaaa agaaagaaaa gaaagacctt caaaattatt
22321 gctgctgatg tggtccctca taaaccaagc agtgggaaac tggtttagct tttagttcac
22381 attctaaagt actaattttt gtggtttatt ttgtacaggt actgctataa ccagaatttg
22441 gtagaaaaag gatttacttg ttggggccct cttgataaaa agagatgtgg ggggattctc
22501 gacctgctaa cagaactgga ccttttcggt aagttctcaa atttgaatat tgaaattgcc
22561 agtattttaa ttataaatgt gtaacatttt cgcctactat aaatgaagat attttctctg
22621 tggagaaata gtttctgatt ttttaaaaat agaaatttgg ctgggcgcgg tggctcacgc
22681 ctgtaatccc agcactttgg gaggctgagg cgggcagatc atgaggtcag gagatcgaga
22741 ccatcctggc tatcacggtg aaaccccgtc tctactaaaa aatacaaaaa aaactagccg
22801 ggcgtggtgg cggctgcctg tagtcccagc tactcgggag gctgaagcag gagaatggtg
22861 tgaacctggg aggcggagct tgcagtgagc cgagatcgtg ccactgcact ccagcttggg
22921 cgacagagga agactctgtc tcaaaaacaa aaacaaaaaa aaaaaaagaa aaaaaaagaa
22981 aaatagaaac tcaatttgga aaataatttc gaaaatgatt gtgagcctga atacccagca
23041 tgccaaatgt tttgtcacat agcattttaa aattttattt atttgtttgt tttttgagac
23101 aagtctctct ctgtctccca ggctggagtg cagtggtgcg atcttgactt actgcaacat
23161 ccgcctcccg tgttcaagtg attctcctgc ctcagccttc tgagtagctg ggattacagg
23221 cgcgtgccac tatgcctggc taatttcatt attttaatat taaaaaatac ccaaatattt
23281 tatttctttt tgtctcttag cgaaggaata catatttggc tagtaaggaa agctagcaaa
23341 atttacataa atgtttataa aagttgtatt gagttcacta atttatgtct agaattcaga
23401 gctgtgcctt gtctgtggca tgttgacgca gtttgctaag ccacctctca attttagggg
23461 ttacttggta ccaagaagag tggagaaagt ggtagcattt agttgtaaat agattgtatt
23521 ttaaatttgt agggaattaa tttttttata gctagtatca tacacactgt attttaacta
23581 gtatttaaac atttttcgta ttgtgtttac aattaatgag atgctatatg aatgtgactt
23641 ttttggtttt acttggtaca tagcaaataa atctgacctt taaatgtatg cattcataag
23701 tattgttgct ccagttgaaa cttctattaa ctagtacatt ttcctttttt tacctttttt
23761 caaaatggag tctcactctg ttgcccatgc tggagtgcag gggtatgatc tcagctcact
23821 gcagcctttg cctcctaggt tcaagtgatt ctcctccctt agcctcctga gtagctggga
23881 ctacaggtgt atgccaccat gcctggctaa ttattgtatt ttttttttta gtagagatgg
23941 cgtttcacca tgttggccag gctgatctca aactcctgac ctcaagtgat ccacctacct
24001 cagcctccca aagtgctggg actataagtg tgagccaccg cacctgccat ttggattggc
24061 aatctgcaag attttattac ttaaatgcaa cagatgttct cattcattgt tctgaagctt
24121 ggagttccaa tgaaaaattt aggtggagaa ctgagtttag aaaatccata taatgtttag
24181 taaaactagt atttcataaa tgctgaatga cagagattgg tctttaaatt aaaacaacag
24241 tgtgatgttg ggtatttttt ttctttcaaa atactaagga ttagatcagt ggtcagcaaa
24301 ctacagctga tagcctgttt ttgtaaataa agttttactg gaaaacagcc actcttactc
```

FIG. 14 (cont'd)

```
24361 atttgcagat tgtgtatggc tgctttcatg ctatgatggc agagttgaat agttgtaaca
24421 gagattgtat aacccacaaa atccgatatg tttacgaact ggctcttcat ggaaaaagtt
24481 tcctgacctc tcatctagat caatggggtt gtacgttacc atttaaaaat atttaggttg
24541 taatctatcc tcttattact tgtatttatg ggtaactatt ttgtaagtaa ggctgtttcg
24601 tatagaatta acgtggttta ggtaagcatt cagaaatgtt aggttaattt agctttattg
24661 tctaactttt ttcaaattta gaacatttgt ctttgactcg tttaaactta tttaaaatta
24721 tattttccca ccttaatttt agtttaaatg taagtcatta tatgctgttt tttaacatct
24781 ttgactagga gggagacagt ttttgggaac taatttgaac caaaacagat ataggaaaat
24841 gattttgtta catttccttt gaacttttct tttaaaattt gtttttattt ggttgaaaat
24901 aattttcata actactgata ttttatatta gtagaatggt ttcttgattc gtctgtataa
24961 aatacaaatc taagaacccct gctacagtaa gttactctaa atctatttga tcttaattta
25021 gaagagtaag ataatcttta ggccatgttg gatgtgttct ggtcagaaaa catgtagatt
25081 tcatacctca gtcctcatcc catgagtgtc tgatgaagct taaatcttcc tgcaagaaag
25141 acttgaatga ttttaaacat gagagacact gtatttagtg gtaacatctt aattttagtg
25201 ttaaattgta ttgcctaaga agaacatcta gggcgggcgt ggcggctcac gcctgtaatc
25261 ccagcacttt gggaggccga ggcgggtgga tcacgaggtc aggagatcaa gaccatcctg
25321 gctaacacgg tgaaaccccg cctctacaaa aaatacaaaa aaattagctg ggcgtggtag
25381 cgggcgcctg tagtcccagc cccttgggaa gctgaggcag gagaatggcg tgaacccggg
25441 aggcggagct tgcagtgagc caatatcgcg ccactgcact ccagcctggg cgacagagcg
25501 agactccgtc tcaaaaaaaa aaaaaagaag aacatctaaa cttgctcctc ttatgatgaa
25561 ccacatagac ataactagtg ttaatggggg tcagtggaag tcatcatgtt ctgaaaatcc
25621 attaaatgta catcattcta gtgtttaggt taatgctgtt aaattcctgt tactttaaga
25681 aagggttggc cgggcatggt ggctcacgcc tgtaacccta accttgggga gacagagatg
25741 ggtggctcac ctgaggtcaa gagttcaaga ccagcctggg cagcatggta aaaccccatc
25801 tctgctaaaa ataaaaaaat tagctgggca tggtggcgca tgcctgtaat cccagctact
25861 ctggaggctg aggcatgaga attgcttgaa cccaggaggc agaggctgca gtgaaccgag
25921 atcatgccat tgcactccag cctgggcaac agagcgagac tccgtctcaa aaaaaaagaa
25981 aaagagaaag aaaaggtttg gcattgcaac tatttctctt gaactgagtg acccagaatc
26041 agttgtcctt tgaattttag tatagtagca tagtctgagc tcagaagggc cttatgatag
26101 accctgtatg ttctgggagg caagaattga gttggtatta atatcttaat gcttttgttt
26161 tactgctgaa taacagatga cccttcaggt cttttcatgt tttccttttt catgtctccc
26221 tgcctaggat cctaggtgcc taattgccta cttaaactag tttagggaat cttggactga
26281 agccaaaaca tgtaaaatgc cctgaaggtt aggcaaaggg aagaagttgg gtagtatgaa
26341 agattaggtc acatcttgtt tatctcttga gttctataaa ttgagaatgt aaatttaata
26401 ctatgtctat ttttaaaatg tattttattg ccatgaaaaa gtagcatgag acattggaat
26461 atggaatatc agcttcttca tttgggtcat ggggatcatg cttgaagacc taatgctctc
26521 tctaggtcta tctcagcatt gagcccctgg atgctgttgc gtggcttaga tgacttatac
26581 atgctttgtg gcatgattca tactaccttc taccttctgt gatacccttg ggtagttata
26641 ataggaccca ggttagagtg cttcttggtg gagccactgt agaactggga tttagatgca
26701 gccagggctg atgctcagct ggtgaacact ggtgtgcttg ttcctactgg tgatttacaa
26761 ccagtgtttc ttctttttgg gcctgcatcc attttgattg ggtggtgtcc atgctgtatc
26821 tgtaataaaa tatttttgaa tgttaccgct ggatgcagcg tgagaaagat acctcctgaa
26881 acttactgta agaaatttac agtgcattga tttttctgat atataggaat cgtcatgttg
26941 accttggaat tcttaagttc cctggctgta ggaaatggaa atttttgtag tatgtcacca
27001 ttgttagctt atttggtatt gcggattttc cctgttgcag gactgggtga aagctttttc
27061 tgcagcagtc atgttgaaaa ccttgtgttg actttcctcg tgttctgaaa tgggagcata
27121 aaagtttact ccgccacttc gtcttaaaat agcaaaactt tgctgttttc tgcagatcta
27181 ggaccttgtt acagaactct gccaaaaaaa aaatgtttac agaagaatgt gctgtgatta
27241 gagaagaata tgctggtgtg tagatttcaa actctctgga caatatgaat aacactgtct
27301 ttgtttctac agtgggagcc aagaagaaag gtttgctccc gggtggaaca gggattatcc
27361 tcctcctccc cttaagagtc atgctcaaga gagacactct ggcaactttc ctggcagaga
```

FIG. 14 (cont'd)

```
27421 ttcacttccc tttgatttcc aggggcattc ggggcctcct tttgcaaatg tagaggagca
27481 ttctttcagc tatggagcta gagacggacc gcatggtgac tatcgaggag gggagggacc
27541 tggacatgat ttcagggggg gagatttttc gtcttctgat ttccagagca gagattcatc
27601 acagttggac ttcaggggta gggacataca ttctggggat tttcgggata gagaaggacc
27661 acctatggac tatagggtg gagatggtac ttctatggat tatagaggta gggaggcacc
27721 tcatatgaac tacagagaca gggatgctca cgctgttgac ttcagaggta gggatgctcc
27781 tccatctgac ttcaggggcc ggggcactta tgatttagat tttagaggcc gggatggatc
27841 ccatgcagat tttaggggaa gggatttatc agatttggat tttagggcca gagaacagtc
27901 ccgttctgat tttaggaata gagatgtatc tgatttggac tttagagaca aagacggaac
27961 acaagtagac tttagaggcc gaggttcagg tactactgat ctagacttta gggacaggga
28021 tacgccacat tcagatttca gaggtagaca ccgatctagg actgatcagg attttagggg
28081 cagagagatg ggatcttgta tggaatttaa agatagggag atgcccccctg tggatccaaa
28141 tattttggat tacattcagc cctctacaca agatagagaa cattctggta tgaatgtgaa
28201 caggagagaa gaatccacac atgaccatac gatagaaagg cctgcttttg gcattcagaa
28261 gggagaattt gagcattcag aaacaagaga aggagaaaca caaggtgtag cctttgaaca
28321 tgagtctcca gcagactttc agaacagcca aagtccagtt caagaccaag ataagtcaca
28381 gctttctgga cgtgaagagc agagttcaga tgctggtctg tttaaagaag aaggcggtct
28441 ggactttctt gggcggcaag acaccgatta cagaagcatg gagtaccgtg atgtggatca
28501 taggctgcca ggaagccaga tgtttggcta tggccagagc aagtcttttc cagagggcaa
28561 aactgcccga gatgcccaac gggaccttca ggtatgttga tggggtggat tgcttttttt
28621 tttttttttt tttttttttt tgagacggag tctcgctctg ttgcccagcc tggagtgcag
28681 tggtgcgatc tctgctcatg caagctccgc ctcctgggtt catgccattc tcctgcctca
28741 gcctcctgag tagctgggac tgactacagg cgcccaccac cacgcctggt gtgagccacc
28801 gcgcccggcc tgcttttttt ttttttcttt aaataagact tttgtgaagg atgacattta
28861 tttatttatt tatttattta tttttgaaac ggagtcttgc tctgtcaccc aggctagagt
28921 gcagtgacat aatctcagct cactgcaacc tccgcctccc agggtcaagc aattttcctg
28981 cctcaacctc ctgagtagca gggattgcag gcatgtgcca ccatgcccag ttaatttttg
29041 tatttttagt gcagatgggg tttcaccatg ttggccaggc tggtctcgaa ctcctgacct
29101 cgtgatccgc ccacctcggc ctcccaaagt gctggaatta caggcatgag ccaccgtgcc
29161 tggccagttt tttttttttt ttttcatttt atttttatct ttgcataacc attagaaagc
29221 aaaatttgta ttcaggagtg gaatgtagga atgtaaatct ctagagaaaa ggtcctcagc
29281 tcagatcata tatatgtgtg tgtgtgtgta tatatatata tgaatatata tgtatatata
29341 tgaatatata tttatatata tatatttctt ttttctttta ttcttttctt cctgcttcac
29401 tttccatttg tgtatatatg tgtgtgtata tatgaaggaa ctatatatat atatatttga
29461 gacacggtct tgctctgtca ctcgggctga agtgcggtgg tgtaattatg gctccttgca
29521 gccttgacct cccaggctca agcgatcctc ccacctcagc cttctgagta gctggaacta
29581 cagatgtgcg ccagccacta tgcctggcta gttttttttt ttttcctttg agaatgagtc
29641 ttgctctgtc gctcaggctg aagtgcagtt gtgcgatctc agctcactgc aacctctacc
29701 tcctgggttc aaggggttcc cccgcctcag ccttccagga agctgggact acaggtatat
29761 ttcaccattc ctagttagtt gtgttttttt ttttcttttt tgagatggag cctcaccgtg
29821 ttgcctaggc tggagtgcag tggcacgatc ttggctcaca gcaacctccg cctcccgtgt
29881 tcaagcagtc ttcctgcctc agcctcctga gtagttggga ctgtagttgt gcaccaccaa
29941 atctgactaa tttttgtatt ttttgtagag atgaagttta ggcatgttac ctaggctggg
30001 ctggaacccc tgatctcaaa tgatccaccc ttctcagctt cccaaagagc tgggatttca
30061 ggcatgcacc accatgcctg gccagcaatt tttgtatttt tttgtagaca gaaggttgca
30121 acatatttcc caggctggtt tcaaattcct gggttcaagc agtcccccca ccttagcttc
30181 ccaaagtgct gggattacag caatgagcca ctgcccctac ccttttgatg tgtgtttatt
30241 cattattttg ttttatgatg ctgatttaca tgccttggga taatttagtt tgaaagtata
30301 tgtctttggg agttgactct tgcaactctc gcttagttag acctgtgatt gtttagggat
30361 cattttctta tttaaattca ttgagagaat acttaggagt ctccctagtt gtgaagagct
30421 gatattaatg ttgcaactat cctcttgcag ctaacgtaat taacttaaat gttaaacttc
```

FIG. 14 (cont'd)

```
30481 ttgaatatat gatttaagca aggagggtta tatttgtaat tttacaatga aggtattctc
30541 ttttaaagta gatttggctg ggtacagtgg cctatgcttg taatttcagt gctttaggag
30601 gctgaggtgg gaggatcact tgaggccagg aacttgagac cagtgtggtg caacctcagg
30661 agagaatgtg agggtgggga agaaaaataa ggccaggcac agtggctcat gcctgtaatc
30721 ccaacacttt gggaggcaaa ggtgggcaga tcatttgagg tcaggatttc aagaccagcc
30781 tggtcaacat ggtgaaaccc catctctact aaaaataaca aaaattaggc caggcgtggt
30841 ggttcttgcc tgtaatccca acactttggg aagctgaggc aggtggatca tttgaggtcg
30901 tgggtttgag accagcctga ccaacacgga gaaaccccat ttctactaaa aatacaaaat
30961 tagctgggcg tagtgatgca tgtgtgtaat cccagctact cgggaggctg aggcaggaga
31021 atcccttgaa cctgggaggc agaggttgcg gggaggcaga ggttgcacta ttacactcca
31081 gcctgggcag caagagcgaa actccatctg aaaaaaaaaa aaaaaacgaa aaccaaaacc
31141 agccaggtgt ggaggtgggc gcctgtaatc ccaactactt gggaggctga ggcaggagaa
31201 ttgcttgaac ctgggggggcg gaggctgcag tgggctgaga ttgtgccact gcactccagc
31261 ctgggcgaca gagcgacact ctgtctcaaa aaaaaaaaga cattatctag tcatcttctc
31321 tcaccagagg tatgaagtac tgctagttta cagcccattc tccagctctc agaccaggga
31381 aatttttctt ttttttgag acggggtct cgctctgtca cccaggctgg agtgcagtgg
31441 cacaatcttg gctcactgaa acctctgcct cccaggttca agtgattctt ccgcctcagc
31501 ctcctgagta gctgggacca caggcgtgca cagcacagtt ggctaatttt tgtattttta
31561 gtagagacgg ttttaccatg ttggctaggc tgagaaaatt actgttttga gactatgtta
31621 gtgtgtcttt ctggttatta aagtcttact cagtcttgtc tctcgtaatg ttttgcttta
31681 ctttgaagac tctttcagtg agacttggtc ttagcacatt tacattctta tgatttgaag
31741 tcacattctg gcactcagaa caatagagaa aattgtaatt ttttatatct tcacgtgaca
31801 tgtcattatc atttttgatc ctgagtggct aaatttcatg ttgatttgtg ttttgtgcag
31861 taaagtatat ttgtgaaata atttttcatt ctcaatttaa ggatcaagat tataggaccg
31921 gcccaagtga ggagaaaccc agcaggctta ttcgattaag tggggtacct gaagatgcca
31981 caaaagaaga ggtaaggcat gtcttctctc ctgtttctct gtgtcaatta aaaattaaaa
32041 aaacctttta atttgaaaaa ttgtagattc acaagaaggt gcaaagaaat gcacagagaa
32101 gtcttgtgta tttttttccc atcttccctc agtgttaata ttttgcacaa ctgtggtata
32161 gtatctaaac caggaaattg accctggtat aatacataaa gtttattcag atttcaccat
32221 ttatacatgc actcactgag gtgaggttaa aaaaaattat gacaaatgat tgctctcttt
32281 agacctgatc acatccttta gagcatatta tttctggagt atgtacataa ggatgcagtt
32341 tatttacaat agtaaaaact agaaactgcc taactgccct gtatcaaagg attggctgac
32401 taaattaagt ctgaacttat ggcagtgctc gctctgtgcc aggcattgtg tgatacttac
32461 aagcattagt tcatttaatt atcacatatt taatataatc actctaaata ttaagcatta
32521 ctgtatgtaa ttgttctaga tactgagtga cacagcagtg tatattatca agtcactgcc
32581 tccatggata atgaaaaagc aagcaaaagg attacacaat tttagtcagc aaataaatac
32641 tctgaagaaa actaaagtac aggcggggca tggtagctcg gcctgtaact cggagacaga
32701 gtcttgcttt gtcgcccagg ctggagtgtg tggcgcgacc ttggtgcact gcaacctcca
32761 cctccccagt tcaagcagtt ctcctgccgc agcctcccga gtagctggga ctacaggcac
32821 acaccaccac gcccagctaa tttttgtact tttagtagag acggagtttc accacattgg
32881 tcaggctggt cttgaactcc tgacctcagg ttatctccct gcttctgcct cccaaagtac
32941 tgccattaca ggcatgagcc accaagccca gcccattttt gatttttttg aggcagcgtc
33001 tcactttgtt gcccaggctg gagtgcagtg gcacaatcac ggctcactgc agcttctacc
33061 tcttgggctc aatcgatcct accacctcag cctcctgagt agctgggacc acgggcatgc
33121 atgctaatgg ggctgttttt tgtattgtgt agttagggag acatcactga ggaagaggca
33181 ttcgagccca ggcttgaatg ccgtgagaga acagtttata tgaatatggg gaaatgaact
33241 gcccaggcag ttcatgctga ggaagtgctg tggccctgga ctgtaatgaa cccagtacat
33301 cattttatat ttaacacatg agaaactgga cactaaaagg ttacacagca agtgagcaga
33361 gagcttggaa tgcacacagt atgatttcag agcttaagcc tttgaaggtt atgctcttct
33421 gcttttcttt tttttttttt tttttgaga cagagtctca ctctgtcacc caggctggag
33481 tgcagtggcg cgatctcggc tcactgcaac ctctgccgcc agggttcaag agattctcct
```

FIG. 14 (cont'd)

```
33541 gcctcagcct cccaagtagc tgggattaca agcacctgcc actgcaccca gctgattttt
33601 gtatttttag tagagatggg gtttcaccat cttggtcagg ctgatcttga actcctgacc
33661 tcaagtgatc cacccgcctc ggcctctcaa agtgctgaga ttacacgcat gagccaccgc
33721 gcccagcatt ttgtttgttt gtttgtttgt ttgtttttga gacagagtct tgctctgtca
33781 cccaggctgg agtgcagtgg cacaatcttg ggtcactgca acctccgcct ctcgggttca
33841 aatggttctc ctgcctcagc ctcctgagta gctgggacta caggcatgtg ccaccacgcc
33901 cggctaagtt tttgtatttt tagtagagac ggggtttcac cgtgttagct aggatggtct
33961 cgatcccctg acgtcatgat ccgcctgtct cggcctccca aagtgctagg attacagatg
34021 tgagccaccg cttctggccc tgcttttcct atgtacctga gaatttttaa atatttattt
34081 atttattttt gagacagggt actccagact ggagtgcaat ggcccaatca aggctcacta
34141 cagcctcaaa ctcctgggct caaactatcc tcccgagtag ctgggattat aggtgtgagc
34201 cagtactcct ggctaatttt tttttttttt ttgagatgga gtctcgctct gttgcccagg
34261 ctggaatgca gtggtgcgat cttggctcac tgcaagctcc ttctcccggg ttcacgccat
34321 tcttctgcct cagcctccca agtagctggg actacaggtg cccgccacca cgcctggcta
34381 atttcttgta tttttagta gaaacggggt tttaccgtgt tagccaggat ggtctcaatc
34441 tcctgacctt gtgatctgcc cacctcggcc tcccaaagtg ctgggattac aggcgtgagc
34501 caccgtgccc ggccaatttt tttttttttt tttttttttt tttttaaag atagtgtctc
34561 gctctgttgc ccaggctgga gtgcagtgtc atgatctcag ctcactgcag cctcagcctt
34621 ccaggttcaa gtgattctcc tgcctcagcc ttccaagtag ctgggattac aggtgtgtgc
34681 caccacacca ggctaatttt tgtattttta gtagaaatgg ggtttcacca tgttagccag
34741 gctggtctcg aactcctgac ctcaggttat ccacccgcct tggattccca aagtgctggg
34801 attacatgtg tgagccacca cgcccggtct ctcctggcta attaagaatt tttttttttt
34861 ttttagagat agggtctcac tatgttgccc aggcttgtct caaacatgtg gctttaagca
34921 atcctctcac cttggcctcc caaagtgctg ggattatagg caggagccac tgcatcccac
34981 caatttttga ataattatgt tctactcatt caatatgtga atgccttgag tgttcatagt
35041 ttaactttgc ttttccaaag taatcatggc tttaaattat gtatgataaa aactgttagg
35101 gaaaatctga tattcagtgt ttgattatga tttgtatcat ttgtataaat gccatatttt
35161 tgcagattct taatgctttt cggactcctg atggcatgcc tgtaaagaac ttgcagttga
35221 aggagtataa cacaggtgag tttcttgact tgcatatggc cttgggttag gaagggtctt
35281 tgtcagatct ctgcatcatg tgctacttaa aatttgtttc aagaaaccac aattaaaatt
35341 tccagaagcc tcccgttggt gcctccaaat aacaaccagc tttagtttta gctgtggttc
35401 tttgtggatg tttgtccaca catgggtgat gaggatgcat gttccagttc ttctgaatgc
35461 ctgtgatata tagagtgttg cagcaattgc cttgaatata ttttatataa ttattaaact
35521 tgctatgcat gttcttcatg gtggtggaat gtttatgctt gagcctaata ggatttaata
35581 agcttgttgt atgtaaaatt ttacattcat tgcttcagta aaatttatga cttcccagag
35641 aaattgtaca aattagtggt ttaattttca gttttgcttt gagaatggag tcctgttaca
35701 gttattttgt tgaaatccat gaatagaccc agaagagctt tccctttgac atctgttctg
35761 tggtctgaat ggtagattaa acttttcaga atatcctcct agttgtattt cacagtacca
35821 atttcagtca tttcctttaa atcttactac agtaaaagta ggcaaaggtg aaatgccaag
35881 aactcaaggt ttttgaccaa tatttttaga actatgtata ataataagtt tatttattta
35941 aaaataaagg taatctttag gtgacctatt ttgcagaatt ttaaatggaa gggaatagag
36001 catgagtctt cacagaactt agaatttcag taattcagtt aaagacatct tcaagtaaga
36061 acatgtcata ttttgaggat ataatttact attagcagtt tatcatggga taaaaatttt
36121 gcattaacta gataacttct tcagaatgct tctgcagagg aaaattatcc acaaaataaa
36181 ttttggtgct tgaaagaata tggtgttaag ttcagaaata atttgttctg taatttgaga
36241 acaagctcag aagtattatt tctcagagag ccaattattt atttgtttta aaaacatcaa
36301 ccctgaattt gtggaagcat gagtaagagt agatatatta ttattcttgg tatctcactt
36361 atgttggtta tatttatttt ttgcatatgc cttatacatg ctttctttgg gaactcaagg
36421 tagaatttac aggctggaga tgctttttaa ctctcaggat aataacctca gtctggtttc
36481 atgaactgtg ctttcattaa gtattgatat gtttaggaaa ggagatgtct taatatttaa
36541 atagcagttc aaactccagt ttctttagta ttcattgact ttctaattgt caaatttgtc
```

FIG. 14 (cont'd)

```
36601 aggacagtaa aaattgtatt aacatatagt gtctagagag gaagttctta aatttgccga
36661 ttgtggtagc tgttagaatt ggcagactga agacattgat acacatggga aatcattcag
36721 ggcagtgctt aaaaataaaa cgaaaaatac ctttcagcaa atacaatctt ttcttggcat
36781 tctgttaagt tgtgtttttt atttttgttt tttagtgaaa gaattggatt gctagtttca
36841 tgttatttat attacatctc tatgtgacaa ataggatgaa cttttgacaa tatcagccag
36901 atcatgttac tcccatgtct aaaaccctct tagggccttc atcttcactt ggaagaaatt
36961 cccagcttct tcttttgtct tacaaaccca tgcgtgagct gacccttggc tgtttgatct
37021 cattcagtac tgccctccac ctaccctatt ttgctgtagc cacactgagc ttttctcttg
37081 tctttgacca atacaaactt ctttctgtgt cagggtcttt gcactactct tctctctgat
37141 ctttacttgt cttctggggt ttagttcttg gcttcagttt cacgtctctg aggccttgtg
37201 tcactctcaa atctaaaatc atcgggcagt tgttttccat catatccttg tttggatcta
37261 tcactgattg gatatttcta tcactggtat ttttcagttg gatctatcac tgatctatca
37321 ctggtcactg attggattga atctgtcagt ggtattggat ctatcactga tatttttctc
37381 cgtggttttg tgtatcttat ttctctcact agagaggaat gtcagcagga gccttattcc
37441 ttcttgtttc caccagtgct tgacactcgg taggttccct atatgcatgg aatagattat
37501 tatttatggt gtatgtgaag agcagctgtg atttcccctc aggtgaggaa cataaaaggg
37561 tagtgtaggt ttcacagcag tgcagcttag gtcttacata tctgttgaag aatatgtctt
37621 ggaacaatca gatgttctaa gaactatagt gtttactgtt aaaagatcat atgtggtagt
37681 caggcatggt gttgcacacc tgtagtccta gctacttggg agtctgagat gggagaattt
37741 tttgagcctg agaatttgag atcagcctga gcaacatagc aagaccttgt ctcttaaaaa
37801 gaaaaagaaa aaaaaatgtg aatcttagta gtaacagtga cttaaaaatt ttttttata
37861 agagaaaggg tcttactctg ttgcccaggt tggagtgcat tggtacgatc atagcttact
37921 gtaacctcaa acccctcggc tcaagtgatc cttctgtctc aacctccaga gtatttggga
37981 ctacaggtgc gtaccaccat ggcaggctaa tttttaaact ttttgtagag gcgcggtctc
38041 actatgtttc ccaggctggt cttgaactcc tgggttcaag tgattctcct gcctcatcct
38101 cccacagtgc tgggattaca gatgtgaacc agtatgcaca gacaaaaagg tgacattcat
38161 aggtgaaaac tggtaataaa tattttaggc tgagtgatga cctgcagaga ccatgcagga
38221 tggatattgc tcataagagg ggaattgtgg agtacagtct gtcctgttag ttgatgtaat
38281 ggagggctga tctataacac aggagagaag attaacgcct cttcgttgac tctagtaatg
38341 tattagtgta atttttgtct cctctagagc tgtataagta cagggtcaca attttatcta
38401 gaacctgtga ggttaaatga gcttatgaat ttttcaagtt atagaaatgt agtttacata
38461 gatcatatgg gaattatatc tcccagggga atgtgtactc agacataata cttacgctgc
38521 aaaattatta atattctcac taacaggagt aaataaagtc tcacagtata ggccaggatt
38581 tgcctcaaaa tgagtttgtt gaattttacc aaaaaacttg acatttatgg gattttggaa
38641 ttgtagataa gagattttgg acctatatat gttgtgtata tttgaatttt tcatttgcca
38701 tttacaaata cattataacc ccatgaattg taaattatct tgaattatat gattatttct
38761 ggaaaaagta ccaggagtaa aatgtctttt ggtgactaga caaactctag tatatatata
38821 aaatggaata cttctcagca atgaagaaga aactactcat gcacctaaca acatggatga
38881 atctcaatgg caatatgctg agtgaaagaa actagactca taaggatata tacactacca
38941 taaggaggaa tgaaatactg atgtatgcta caagttggat gaaccttgaa aacattataa
39001 aagaagccag acacaaaaga ccaaatattg tgcaattcag tttatatgaa atatctagag
39061 aaggcacacc cgtagagata gaaagcagat tggtggttgc caggggctaa gcgggaatgg
39121 ggaacgactc cctaatggtt atggtacttc ttttgggctg atagaagtgt tctggaacta
39181 ggtagtagtg atggttgcat gacattgtga atgtacttaa tgctcctgaa ttgtacactt
39241 taaaatgatg catttatttt gatgtgtatt tgcttacttt gttttttttt ttttttttg
39301 agatgaaatc ttgctcccgt tgtgtaggca ggagtgcagt ggcatgacct cggctcactg
39361 caacctccat ctcccgggtt caaacgattc tccttcctca gcctcccaag taactgggat
39421 tacaggtgtg tgccaccaca cctggctaat tttttgtatt tttagtagag acggggtttc
39481 gccatgttgg ccaggctggt cttgaactcc cgacctcagg ttatctacct gcctgggcct
39541 cccaaagagc tagcattaca ggagtgagcc actgtgccca gccagcttac aatttttttaa
39601 aaaggctaca tactatatgt gtatgtgtga tttcacttat gtgacattct ggaagggaca
```

FIG. 14 (cont'd)

39661 aaattttagg gattggaaat agtggtggcc agggtattgg gggaggagtt aactataaag
39721 cggaagcatg agggaatttt tgggtataat ggaattgttc tatatcttga ttgtggtgat
39781 gatgtatcaa tgttaaattc cccgagttga taactactgt ggttatgtta gagaacatct
39841 tttttctttt cttttttttt ttaaacggag tctcgtttgg tcacccaagc tggagcgtaa
39901 tggcgcgatc tcagcttact gcaacctctg cctcctggat tcaagcaatt ctgcctgcct
39961 taacttcctg agtagctggg attacaggcg cctgcccta ctcctagcta atttttgtat
40021 ttttttagt agcgacaggg ttgcgccatg ttgaccaggc tggtcttgaa cacctgacct
40081 caggtgatct gcccaccttg gcctcccaaa gtgctggaat tacagacgtg agccaccatg
40141 cccggctgag agtatcttta ttcttagaaa atacataatg aagtttttag aagtaaagta
40201 ctgtgatgta tgcagctttc tctcatggtt tcgaaaataa tacttgctat aaatggagaa
40261 ggaaggaaga gagtattgat aaagtagatg gatcacaatg ttattaatag ttgaatctgg
40321 ggccacacgc ggtggctcac gcctgtaatc ccagcacttt gggaggccaa ggcaggtaga
40381 tcatctgagg tcaggagttt gagaccagcc tggccaacat ggcgaacgaa acctgtctac
40441 taaaaaatac aaaaattagc cgggcgtggt ggcgggtgcc tgtaatccca gctactcggg
40501 aggctaaggc aggagaatca cttgaactcg ggaggcggag gttgcagtga gccaagatca
40561 cgccattgca ctccagcctg ggcgacagag caagaattca tcttaaaaaa aaaaaaaaaa
40621 aaagttgaac ctgggtaaag catatatgaa tcttttccct gtactattat tattgcaatt
40681 tttttgtaac ttggaaatta tttccaataa aaagttgaaa aactgacaaa actgatttat
40741 tttattttat tttttatttt tttgagacgg agtcttgcac tgtcaccagt gctggagtgc
40801 agtggcgcga tatcggctca ctgcaacctc cgcctcctgg gttcaagcga ttctcctgcc
40861 tcagccatcg gagtagctgg gattataggc gcctgccacc atgcccagct aatttttgt
40921 atttttagt agagacgggg tttcaccatg ttggccagcc tggtctcaaa ctgacctcat
40981 gattcgtcca cctctgcctc ccaaagtgct gggattacag gcatgagcca ctgcgtccgg
41041 cctatatttt atctttaaat gatcagcaga aaccttgtaa gctgaagact gcaatcaaca
41101 gcttatgtca agtaaactat agagcagtgg ttctcagagt ggatcctgga ccatcatcat
41161 ctctttaccc cttgggaact tgttggaatc caaattctta agccccatcc taaacctact
41221 gaatcagaaa ctctggggtg gggcccagta gcctgtgctt ttaagaagtc ctccagatat
41281 ttttaatgta ccctgaggac cactggcagt agataaagtg tttgtttaga ttctttattc
41341 tagaactttt gtatagttta aaagtgactt aataataagc aagtggacct tttgtaagta
41401 gacaaagcta atgcttatgt gctttaggag ccagtgctga tcacatgcct tgcctaccta
41461 atatcagttc tcctgctctg catagcagga gaaggagctg gagtagtgtt ggtactatct
41521 tatgacttta gttatatgta actaaggaca tataacttag ttgtttttc tgtttatata
41581 tagtatactt cctccagaga tcttggaatg gttgtagatc ttctcattca cacagtgttt
41641 ctgtgacata tgaatgcagg cagaattgct tttgattttt aggtttgttt gcatactacg
41701 tagtatataa gcttgctgtg atatttttcc aaaagggatt tatatcattt aagcaaaaat
41761 gatacagctt ctggattatg tttcctaata aggctcaaac atagaaagta attatagtaa
41821 ctgaagtgct acagaattac tttagtactg gtttattaac taatgtcaca aagttagagg
41881 attactaagg tggtgttagt aggaagaagc aatatcttgc tttagcccgt cagtgttcat
41941 gtggtgaatg gacagtctct gtattcttgg gaaggaaaat tcttcttgga aagtgagtat
42001 ttgcaatgac taggtcagtc acttggtctg ttgcctggca ttttgggtct actgaaagtg
42061 acgttgtagc aaaggccctg taccttctgc atttcttttc ttttcttttt tttttttttt
42121 tttttttttt tttggtagaa acaaggtctt gctttgttgc ccaggctgcc cttgacctcc
42181 tgtcaagcag tcctcccacc ttagcttcct gagtagctgg gactacaggc gtgtgccacc
42241 atgcctggtt aatgtaaatt tgtttggttt ttttgagaca gagtttcact cttgttgccc
42301 aggttggagt gcagtgacgt gatctcagct cactacagtc tctgcctcct gggttcaagc
42361 gattctcctg cctcagtctc ccaagtagct gggcttacag gcacccgcca ccacgcccag
42421 ctaatttttt gtattttttt agtagagacg gggtttcatc atgttggcca ggctggtctt
42481 gaactcccga gctcaggtga tccacccacc tcggcctccc aaagtgctgg gattacaggt
42541 gtgagccacc gtgtctggcc tatttttaaa tttttttga gacagagtct ctctcagtca
42601 cccaggctgg agtgcagtgg tgcaatctca gctcactgca gtctctgcct cctgagttca
42661 attctcctgc ctcagcctcc ctagtagctg ggattacagg cctgccatcg tgcccagcta

FIG. 14 (cont'd)

```
42721 atttttgtat ttttagtaga gacagggttt caccatgttg gccaggctgg tttcaatctc
42781 ctgacttcaa gcaatccacc tgcctcggcc tcccaaagtg ctgggattac aggcatgaac
42841 caccacgcct ggcctaaatt ttttttttgt agagacaggg tctcacgctg ttgctcaggc
42901 tggtcttaca ctccaaggct caagcaatcc tcctgccttg gactcccaaa atgctgagat
42961 tacaagtgta agacactgag gccagctgcc ctttacattt cttaagggta acaggctcat
43021 gtcctttcat tattcacaat ttaaatattt tgagtcttta cttctgtgtc aatataacag
43081 aagtaacttc cttacgaaga aaattccaga gggaatcttt caatgtaggg atagaaatcc
43141 attgtgaaac tcgagaattg acactgatga tataaaacat gcacagtagc cgagtgtggt
43201 gatgtgtgcg tgtagtctta gctactcaac agtccgagac atgagctcag gagtttgtga
43261 ccagcatggg caatatagtg agactctgtc tcaaaaaaag gaaaaaaaaa agtgcatagt
43321 ttatggtatc ccaactggag gagctaaaga cagaatagct taacatcatt tagaaaaaaa
43381 attataattg aaaagtgcaa atacacattt tgcagtgttt ttggcattta caaaatatgt
43441 aaacactttt agtttcttag ggaaaagatg acgataggct gattgaaaaa tatcattttt
43501 acttgtcaca tctctaaaac agcagaagtt cttgttttta accaggagtc ctatcaggtt
43561 tgatacaacc ttcggggagg atgtggcagt tgaaatttaa ggaaacttag tttccttaag
43621 gtggctgagc ttaaaaaatc aaaatgttta ggaaggcagg agacactaat agggctgggc
43681 tagtcttgtg gaggcagtgg atggacgctt tggctggcct agggaagaat ctgtgattca
43741 gtgctgcagg gatcaggtga tcctggtgag agaggtcctg gaacaagggt taatttggtc
43801 atttttggaa tgacctggga tttggcttat ttattttatt tttaaaattt cccgctgggc
43861 acagtggctc aaacctgtaa ttccagcact ttggaacgcc aaggccagtg gatcactcga
43921 gctcaggagt tcgagaccac cctgggcaac atggtgaaac tctatctctc caaaaaaaat
43981 acaaaaaaaa ttagctggat gtggtggtgc atgcttgtag tcccagctac ttaggaggct
44041 aaagcaggaa gatcacttga gctagggagg tgagggtgga ggttgcagtg agccaagatc
44101 atgccactgc actccagcat gggcaacaga gagagacctt gtctcaaaaa aataaaatgg
44161 tgaatgtaaa ataaaatggt agctcacgcc tataatcctg gtactttggg aggccgagat
44221 gggtggatca cttgaggcca ggagttacag accagcctgg tcaatatggc aaaactccca
44281 tctctactaa aaatacaaaa actagctggg ctggtggtgt atgcctataa tcccagttac
44341 tcaggaggct gaggcagagg tcacagtgag ctgagatcac accactgcac tccaggctgg
44401 atgacagagt gagaccctgt ctaacgtgac atcacatcac atcacatcac atcacatcgc
44461 atcgcatcgc atcgcatcgc atcgcatcgc atcgcatcgc atcgcattgc atcacatcac
44521 atcacaacat aacataaatt ttcaaggcag aaatcttgta gtcagcctta ctgtttgttg
44581 acaaggacac ggccctgagc acagaaatct cggcagttga taaagccaag aagaaggata
44641 ctaattaaag aaattttcag attttgcatc ttctggcatc tcagctaaat agctctgagg
44701 aggaggatgc cacttaccag ttttgagaca caggcaggtt atattatttt cctgaaaacc
44761 atttagctga gatggaattt gcctctctga ggttggggaa ggtgtttgaa ctctgtttac
44821 agccctctgt cagttccact gccttgctga gttccctcac ccttctttag atagaattgc
44881 tgttggcttc tatagtcctc acttacctct tttgccaaat gctcaggtag ccttggctga
44941 gtcttccagg tttgataagg ctgtatgggg cttcctatgc cttttggtag ttagaagtca
45001 ctgaagaggt acttctgcta cagtgacaag aagaaaaggg cattactcag cttgtatagt
45061 gcaagggctg cttgactccc agcttcagtc taggcagggg aatttattta tacaattacc
45121 ttaaatgagc accagataga ggccatctat aaaaactgtt tacaggattt aaaaatacgt
45181 tgacattggc ttcttccttt aactttctgc ttgcaacaga acatctgatg cgacctatgc
45241 tgctcactgt ttctaggtta cattctctac ccttgcagtg taaattaatt tttgcctggt
45301 tccatgtttc ttgcttaggt tatctcttag gtcttttgtc tgatttaaat ataagccttc
45361 ttaggactag atagtggtga tggttgcact actttgtcaa tataccactg aattgtatgt
45421 attcactctt ttaagaatga gtttattttt atttttattt ttattttgag atagagcctc
45481 actctgtcgc ccaggctgga gtgcagtggc gtgatctcag ctcactgcaa cctccacctc
45541 ccgggttcac gccattctcc tgcctcagcc tcccgagtag ctgggactac aggcgcctgc
45601 caccacgccc ggctaatttt ttgtattttt agcagagacg gggtttcact gtgttagcca
45661 ggatggtctc gatctcctga ccttgtgatc cgcccacctc ggcctcccaa agtgctgggt
45721 ttacaggcgt gagccaccat gcctggcctt aagaatgagt tgattgttct tagtctcagt
```

FIG. 14 (cont'd)

45781 tgagtacatt gtgttatgta tagaaaatgt tatattttca tttttaaaaa ttattattat
45841 tattttgaga tggggtctca ctttgtcacc caggctggag tgcagtggca cggtcttggt
45901 tcactggcaa cctccacctc ccaggtacaa gtgattcttc tgcatcagcc tcctgaatag
45961 cgggaattac aggcgcctgc caccaagcct aagtaatttt tgtatttttt ttttttagta
46021 gagacggggt ttcaccatgt tagccaggct gatcttaaac tcctgacctc aagtgatcca
46081 ttcgtctcag actcccaaag tgctgggatt acagatgtga gccattgcgc ccagcccatt
46141 ttaaaaaatt aaactggcct ggtgcggtgg ctcacgcgtg tgatcccagc actttgggag
46201 gccgaggcaa gcggatcatg aggtcaggag attgagacca tcctggctaa catggtgaaa
46261 ccccatctgt actaaaaaat acaaaaaatt agccgggcat ggtggcgggc tcctgtagtc
46321 ccagctaatt gggaggctga gacaggagaa tggcatgaac ccgggaggca gagcttgcag
46381 tgagccgaga tagcgccaat gcactccagc ctgggcaaca gagcaagact ccgtctcaaa
46441 aaaaaaaaaa aacaaaacaa aaaaaaacca aaacattaaa ccatactctc taactgtgaa
46501 gaagttgtga tttattcttt agtgttacct gccattcttt ttgtctcttt ctctctcttc
46561 tcttctcctc tcttctcttc tctcttcttc cctcccttcc cctcccctcc cctccccttc
46621 tcttttcttc tcttctcttt tcttttcttt cagagttttg ctctgttgcc caggatggag
46681 tgcattggca tgctcacggc tcactgcagt gtcaacctcc caggttcaag ctgtcctcct
46741 acctcaccct ccctagtagc tgggactata gacatgcacc accatgccta attattttgt
46801 atttttgta gagacgaggt tttgccatgt tgcccaggct ggtcttgaac tcctgagctc
46861 aagtgagcta cctgcctcag cctcccaaaa tgctgtgatt acaggtgtga gccttatttt
46921 attatttttt tttgggacag agtctctctc tgtcctccag gctggagtgc agtggcacga
46981 tcttggctca ctgcaacctc tgcttctcgg gttcaagcaa ttctcctgcc tcagcctccc
47041 aagtagcctc ccaaagtgct gggattacag gcatgagcca ccatgccagg cctctgatgc
47101 atatattttt taaaaatagt attttccacc ttacagtgta tttaagagtt tgtaaatttc
47161 ctttttttgtt ttctttttgg aacagtgttg ctctgttgcc caggctggag tgcagtgaca
47221 tgatcttggc tcattgcaac ctccacctcc cagattcaag tgattctcct gcctcagctt
47281 cccgagtagc tgggattaca ggtgcccgcc actacgccca gctaaatttt ttgtaatttt
47341 agtagagaca ggtttcacca tgttggccag gcaggtcttg atctcctgac ctcaagtgat
47401 ccgcccacct cgacctccca aagtcctggg attacggaca taagatactg tgcctggctg
47461 agtttgtaaa tttctttctt tctttttctt tttttttttg agacagagtc ttactctgtc
47521 acctgggcta gaatgcaata atgcgatctc tgctcactgc aacctctgcc tcctgggttc
47581 aaacaattcc cctgcctcag cctcctgagt agctgggatt acagccgcct gccactatgc
47641 ccagctaatt tttgtatttt ttgtagagat ggggttttgc cgtgtaggcc aggctggtct
47701 agaactcctg acttcaggtg atccacccac cttggcctcc caagcgtggg gattacaggt
47761 atgagccacc acgcccggtc atcaaagata atgtttttaa tgatcaggag cactttgaga
47821 tgtttagaac aatctgaaac ctgatttcca agccatctca aaatatactt tggtaatcaa
47881 gacagggaaa tgatggtgtt atatcatttg tgggactcaa ctgattttgt tgagtattga
47941 ttttgctgtg ggattccttg ttctcttggt tgtgttgggc ctactgcttt ttaaaaaagt
48001 attttgagac agggtcttac tctgttgctc aggctggagt gtagtggcgc agtctcttgt
48061 ctctgcaacc tcaatctcct gggctcaagg gatcctccca cctcagcctc ccaagtagct
48121 gggaccacag gtacccacca tcacacctgg ctaatttttg tatttttgt agacatgggg
48181 gtcactgtct tgcccaggca ggtcttgaac tcctaagctc aaacaaccgt cctgccttgc
48241 cctcccaaat tgctggaatt acaggtgtga gccagtgcgc ctggccttct tttttttttt
48301 taaccactat tttttagaac tagatttggc ctggaaagag aaaaaagata ttcctcgact
48361 tgatctatat attttatggt tcattcattt gctttagagg tagaaggagc aggaaaaagt
48421 acaacaaaac aaaatcttac ctttggtgtt taatttgaat gcccacagat gcttttgcat
48481 ttattagtag tgagttttca taattatcaa atatgtagta gaaaaatctg gctgtgcatg
48541 gtggctaatg cctgtaaatc cctatatgct gggaggctga ggcaggtgga ttttctgagc
48601 tcaggagttc aagaccagcc tgggcaacat ggcaaaaccc catctctgcc aaaaataagc
48661 tgggtgtggt ggcacacgcc tgtggtacca ggtactccgg aggctgagct gagaagattg
48721 tggaggtttc agtgagccaa gattgcacca ctgcactcca acctgggtga cagagtgaga
48781 ctccatctca aaaaaaagaa aaaaaaatct ccttgtccag gagctgtgtt gagtgggctg

FIG. 14 (cont'd)

```
48841 tggactagca ggaattcata gctctggtga aagatgacta gataatgtca tttttttttt
48901 aaaagtccct gaatgattgt gacagggtag gaaaatcatc acatagcaaa atcttcatta
48961 gattttccct aatgacttat caactgggtt tgtgcaccaa acgaaacaac ttcctgcctt
49021 tgtttgtctg aaagtcaaag aaaatattat tcaggtatat tatattgtac tccatgctac
49081 agaagtttct ggcagcaata taggttatat gccaatcggt taaataatat ttgtgggcca
49141 ggcccggtgg ctcatgcctg taatgccagc actttgggag gccgaggcgg gtggatcact
49201 tgaggtcagg agttcaagac cagccagggc aacatggtga aaccccatct ctactaataa
49261 aacaaaaatt agcctagtgt ggtggcacac gcctgtaatc ccagctactc aggaggctga
49321 ggtaggagaa tcgcttgaac ccggaaggtg gaggttgcag ctgagattgt gccattgcac
49381 tctagcctgg ggccacaaga gtgaaactgt ctcaaaataa ataaataaat aaataaaata
49441 ataataatat ttgtgtaagt acagggatat gtttcttcaa ctccaaagta tgagttaatg
49501 tgcatatgcc aactctagaa ataaagtatt aagtcaaaac tcccaagaaa atttccccaa
49561 aaagttgcta acagacgtta ttttatttta tttatttatt ttgatacaga gtctctccca
49621 ctgtcaccca ggctggagtg gtgcagtggc atcatctcga ttcactgtag cctccgcctc
49681 ccagattcaa gccattctcg tgcctcagcc tcccttgtag ctgggattac agttgcccac
49741 caccacgcct ggctgatttt tgtattttta gtagagatga ggtttcacca tgttggccac
49801 gctggtctcg aactcctgac ctcaagtgat ctgcccgcct tggcttccca aagtgctggg
49861 attacagttg tgagccactg cacctggcct ttaattttaa tttctaaaac tatggagtaa
49921 tactacattg agggaacaga attttctatt ccttcatttg tattattatt aaatacagtc
49981 atgcattgca taatgacagg aatacatttt gagaaatgga tcaagtgatt ttttcattgt
50041 gtaaacatca tagggtatat ttacacaaac tagatgttat agcctactat acagctaggc
50101 tatattgtat agcctgttac tcttcggcca caaaactgta cagtgtgtta ctgtattgaa
50161 caccataggc aattgagaca caacggcatt tgtgtatcta aatatagaaa aggtaatgca
50221 ttgtgccacc aaatcaacaa cagctatgat gtcactgggt gataggaatt tttcagtgcc
50281 attataatct tatggaacca ttgtttcata tgcatgcagt ttgctgttga tcaaaatgta
50341 gttaagcagc acatggctgt aattaaaaca ctattgtttg ttataataga aaataaaatt
50401 tttcttttta gcctctgtat taataaagag cactagaaag tactttgttt atcagataat
50461 gaatatgttt gacagatgta catacgtatt tatcaaatga atcttttttt gtgggggaaa
50521 ccttaactaa gaataggcct gtgttttaaa atggctgcct ggaggacaag tgctataagg
50581 aaatttcagt ggtatttgct tgacctggca ttaagtgggg ggaaaaacaa gccccaggtg
50641 aattgataga tggatgtctg aacatgttca ggaatgatgt tttgaacaat gtttgcctcc
50701 tgtgtcatgt aggcagagag atgataaaag tttttttccc ctcttgatac caggtaattc
50761 tgataccgac taccagaagt tagcttcaga ctccgcaggt tgaagggctt tgtcccataa
50821 gaccattctt acttcagaca ccaattgcaa tgatcagtta tcaggtccca aggttaccta
50881 cacttatgtc tgatttggct acaaaattgg aggttcccac agtctacccc ttcagatttg
50941 ataactttct aatatggctg caaaaaactc agagaaatac ttatgtttat cagtttttta
51001 taaaggatac aattagccag atgaggagat agataggca aagtccagga gggtcctgag
51061 tgttgagtgt aggagtctct gtcctgtgga atatgccacc gtcccagcat gtagatgtat
51121 tcaccaatca ggaagctctc tgagcccttt tgtgtagttg tttttatgga ggtctcatta
51181 tgtaggcagg attgattaaa tcattgacag tgggtgattt gctcaagccc ctctcccctc
51241 atcagaagtt ggtgggtggt actgaaagtt ctgaacttct ggtcaaggct ttgtctttct
51301 aggtagccct catcctgaag ctatctaggg gctttccaag agttgtctta ttagaacaaa
51361 gaacactcct atcaccctta tcactcagga aattccaagg gttttaggag ctgtatgcca
51421 ggaacctggg acagaccaag tatctttctg tgataccaca gaatgggacc ccaaaagcca
51481 gctccagctg gtgtctagtg cctttagttg ggcactggat atcggttaca gggcataagt
51541 ggcccagtgg ggttgccgtt taacccatct ctgctgtatt aacctcatgt accttagctc
51601 atggctaggt cgtttcaagt ctcacctaat gtcagttgtt tcatccttct ctggatgcat
51661 gttcacttct ggaataggtg aatatctggg ccactatgtt tgctgtcatc ctgagcaaac
51721 ttccagctta gaaaccagct ttatggaatc atcccagagc ctttatttta ttttatttta
51781 ttttatttta tttatttatt tatttatttt ttgaggcaga gtcttgctct gtagcccagg
51841 ctgaaatgca gtggcaaagt catggctcac tgcagcttca acctcccagg ctcaagcaat
```

FIG. 14 (cont'd)

51901 ccttccgttt cagcctccca agtagctgag attacaggtg tgtaccacga cacctggctg
51961 atttaaaacc ttttgtagag atagtgtccc agtgtgtttg cccaggctgg tctcagactc
52021 ctggggttaa gcgatcctct tgcctcagcc tcccaaaatg ttgggattac gggcgtgagc
52081 cactgaactt ggtcccagag ccttttagaa cagtgttgag ttgcccttta tttgcaccag
52141 ggctaaggca gtagaaaaaa aatgtttatg ggccatgttt ttcttcctag tcaaaataaa
52201 aatagccatg taatctatgg aggcagcaga tatgttgtta gtatacacta gaagtcagga
52261 aattcgtact gcctttcagc tgctaaagta ctgggacata tttgagaagc agtaatgcag
52321 aggcagctgt ctgatctttg atctctgata atgcttattt cattgcatcc ctgaaaccac
52381 cctgcaaagg atttatcatc tttgctgctt tgcatatgga atagcatagg cccagagaga
52441 cgtagcttga ctgcaatcac atggtgagtt agttgtagct tctgcaaatg tacagaacta
52501 agaagctact tttcttgtgt gttattctag tgatgatggt cattataatt gatgtacctg
52561 atattatgct aggtttaggg atacagaaat gaaagaagat cacagtccct catctgggac
52621 ctctgttttt ttggtgtcac ctctctgcat agacagttct gcagtattga tgctgctgtt
52681 ctggttgatc cttctgtcat gcctgcacca tcttttctgc cagactgaag tgttcttgct
52741 tggggaaaag cagatttgca aaggttctct ttttcctgat tgttgctttg cagattgagt
52801 atatttgttt gtttgttttt aagtgaacaa aagttgaatg agattgatta ctggctcttt
52861 aaagaataat tactccccct tttgacttat gtagcatctt gaggtgatct atgaccgttt
52921 gtacttgtca tgacttccat tagattaaac tctggggcaa agacgttgct cttcattgtg
52981 ctcatatgac accattactg ccagtggaat tgaaataaat tgagtaaggg cgagtgtttc
53041 ctaacaaatg ttatcctggg cctgaggaac catcatcaag atggagtggc cctgcgatta
53101 attttggact taaagcaaaa aacaaacaaa ttttttttctt taaataacca gttggcacag
53161 atacagaata aaataagata gatccacgtg tagtttttga aaatttaggt caggtggctc
53221 actcctataa tcccagcact ttgggaggcc aaggcgtgtg gataactcga ggttaggagt
53281 ttaagaccag tctggccatc atgatgaaac cccatctcta ctaaaagtac aaaaattagc
53341 tgggcatggt ggcgcatgcc tgtaaaccta gctactcagg aggctaaggc aggagaattg
53401 cttgaacctg gtaggcggta gttgcaatga gccgagattg cgccactgca ctccagcctg
53461 ggtgacagag tgagactctg tctcaaaaga aaaaaaaatt taagaaataa tcatcagtgt
53521 atatcttcct tttttcattt ttctttaaaa aaaaaaacaa cccttgtatg catagctgaa
53581 ggagaaataa ttgaaagtgt ttataagatt tcaaggtgat gggctggaca cagttgctca
53641 tgcctaataa tctgcacgcc tgtaatccca gctattcggg agcctgaggc aggagaatca
53701 cttgaaccca ggaggcagag gttgcagtgg gccgagatag tgccattgca ctctagcctg
53761 ggcgacaaag gtgaaactcc atctcaaata aaaaaaaaga tttcaaggtg atgggtttca
53821 tgtggaccaa ttttatcctt ccctgatgat aatttgacat atgagtcaga tattttccta
53881 attttcgtaa ttcgagtggg attgtgtgtt tgtttgtttg ttttgagaca gggtctcact
53941 ctgttgttca ggctggagtg cagtaggcca gtcatggctc actgtagcct tggcttctca
54001 ggctcaagtg agcctcccac ctcagcctct taagtagctg ggactatagg tgcgtgctcc
54061 cacacctggc taattttttc tgtttttttt tgtagagaca aggtctcatt atattgccga
54121 ggctgggact cctgagctca agtaatcctc ctaccttggt ctcctaaagt gctgggatta
54181 tatccacgag ccaccacacc cagcctcgca tgagatttta acagagcaaa gtacctgttg
54241 gaaatcttgc gcacaaagcc tcctttattc tgttattccc actgacagga attcagatac
54301 ctggatcaat tctgtttcgg ttttgctaaa atctctaact tgatatttta cttttctaaa
54361 aacctgtatt atcaatgaaa tggaattagg aaaacaggac ctatagaagt taagacctct
54421 tcaatctatt gatgtttcat ggtgcctttt atattcaaaa tgctttgttc tcacaaaaat
54481 aatacttttt gtttggagaa aaaggctgtg gggtgtgtgt gtgtgtgtgt gtgtgtgttt
54541 tcctctcaaa gatagcagta aaataaactc cttctgacaa aggcttctta aaagaaagga
54601 gaaaaaaaaa ccttcctgct aattgtgttc tttaaaatcc tgattccccg ttttactttc
54661 tggatgtgta ttctgggctt tttcaatgtc aaccaatact ctcttgatgg gaaattcagc
54721 tggatttggg tatgttcatt gggttttcct agaacagttt gaagatccat ctcatttacc
54781 taaacaaata ttccttataa ttattatgaa aattgggcct gttatagact aataattgac
54841 ttaaaccata cagggttatg tttgtcagta tctcgtgagt cagcttttct aggggcagag
54901 attgaagagt tagttctgag attgaatact atttatcagg gttttgtttt gtgtacctta

FIG. 14 (cont'd)

54961 ttctcctgta accacctggt tggcttttat catagataca tttttgggaa acaggcaacc
55021 acatggttaa tgaagataga gaagacgtga aatttgttac ctttatagat tttttcccct
55081 tgccctgttc tcattcttct catttgccta aaaaaaaata taaggaggcc gggtgcggtg
55141 gctcacgcct gtaatcccag cactgaggca ggcagatcac ctgagctcag gagttcgaga
55201 ccagcctggc caacgtggcg aaactccgtc tctactgaaa atacaaaaat tagccgggcg
55261 tggtagtccc agctactgca ggtacctgag gcaggagaat tgcttgagcc tgagaggcag
55321 aggttgcaat gagccgagat tgtgtgccat tgcattccag cctgggtgac aaagcaagac
55381 tctgtctcaa aaaaaaaaaa aaaagtataa ggagtattca catttctatg agatctgtaa
55441 atttaggtta gaaaatttag ttaactgtgt tttgtaatag tcatataaat aagcacaaag
55501 accctccaga cttcttccca gcatgtgaca gtggaagaaa ggggtaataa agtagatttt
55561 tttgttactc tcattggtaa aaataagtct gtccatggga aggttaacac tgagtttacc
55621 atcttgatga ttccatatgg ttcctagcaa ttctaatctc aaagttggtt ggcagaatgt
55681 ttaggtcttt gggtagaata tcttctgtgc cttttctgtg aattgtaaaa ttacatttgg
55741 gaaataaaga aaaaaatccc tgattatccc actatagcaa tacaaccact gtaaacattt
55801 tggtatacag ttgtgttgca ttatatgcat tttctgattt ttgtatgtcc acctgtgctt
55861 atttgaactg tatccccctc cccacttccc acaccctgtt ttctcactcc tggagtgagc
55921 atgggcagtg gggatgagac tcgcctgtgg cttcagtttg tctcctttc taagtttctc
55981 tgagtgggca ttcactgtgc tggctgtgat tctgttattt aaagcaatat attttcatac
56041 cttatggccc ttaaatgcaa gccaacctct tcatctggtg tcaaccaaag gaaaagtgat
56101 ctgttgcagc gctggaggaa aaactggcaa tgttggactt acctaaattg aaagatggta
56161 tgttgttctt caccttgggg tcttcaagta tgatttttga cagtgcatgg tttttatctt
56221 acatgctgac ttttgtctct aacccttgag ttagatgcaa tttaattcca gcccttttc
56281 cctatataca ttttacataa ttatccataa gggtatattc atttttaagg ctcttaaaat
56341 atactatatc aagtatcttt ccatattgct atacaatttt tgtagctgtc atttataata
56401 agacatttta gttttcgtct tttcagaaga attttgggag ctagtataat cagctcctta
56461 gaatgctttc taatttgcat actcaggtct actcacaata gttctgccat agatatttaa
56521 aatagaagca actgttatgc tgctaaattg aatatttctt aactaggctt atttcttaac
56581 aggggcatag atgtatgttt tcaggcatat gggacccttt ctgtaactag gcttctagag
56641 tttagaatta agattattta aattggtcta tgatcttatt gaagagtgag aggctagagt
56701 gtagtggtta aaaacatcaa cttgaatctg gactgcttgc atttaaagct cagtattggt
56761 acttacttgg ttactttgat cagtttacct atcctttctt tgccgccttc tacatggcta
56821 aaatcaggtt aataatattt acctcttaag atagtattgt gaatattaaa tcagtatata
56881 caaagtattt agaataaaat cttgaaccaa caagttttat gtaaatatta cttactttca
56941 taggctagtt tgctaattgc tgaaaatcct tatggcacaa ccatgagtct tgaacacaca
57001 gaataccttt ttttttttta acgttttagg cagtatagtt aaaccttaaa tttctgttct
57061 tgtttgatag ctaaagtttc agtcagaata aatttagtgt tgggcttgtg aatataatat
57121 taaatctgaa gtatgttgtc aacatatagt attgcagggt tgatgtctag aaatgctata
57181 ttagatgctc ataatgtttt ctgtatcttt ttcttcccaa tgtctacttg tcctttagca
57241 aagtatgaac gttgtcatga atcttttctc tctgtccaca gattctgtgt gctcctctgg
57301 gccacagtag ttacttcttt aagcacagaa aggaaactta gggctttgcc agttttagta
57361 ttagttctct atgtttttca tccgggcagc tatggagagg gttgctttcc acacacctgg
57421 gtactccatt gatatgttct gtagaggtaa tcaacacact agagagtaca cctgtttgtt
57481 ccatggctaa ccctttctga ttgtagacat gcatttgagt gtttgcagtg gatatttggt
57541 gctaacaggt gtcttagttc cttctgttat tctgtaatgt ttcccaagaa tattcagagc
57601 tgtttataaa atgcagagtg atttatgtat taggtgttca atgagtttga tcaagaagat
57661 tcacttgaaa ggaattaact aacaaagcag tttccattgt taataggata tgcatgctgt
57721 ttctctaaag tatttttatt tcttcaaaga gttattaagc agaggagact gattttgtgg
57781 taagtttgga ggggttagtt ttaatccacg ttggtcaaaa ctaaaagtag attagaaaat
57841 ctatttctca tcctacagta gtgctgaggt ttctagtaga ttgtttttct tcttcctagt
57901 cattttctga aactcaaaac aagaatcaac ctataccatt gtaatgtttc acagttaact
57961 tggagtattt aacaagtcta aaatcaaagt ttattgttat tagtaaaaca ttttgaagcc

FIG. 14 (cont'd)

```
58021 attcatttca tgtgacaagg aatcttattt caccaaatgt ggtatgtttt taaacttata
58081 ctttctattg ttctagtttt gttgatcttt gatattgatg cagtgatatc agtttcctat
58141 tgttatatat actttgtggt caaaattatc atagggtttt gtgtttttct ttgcctgagt
58201 tttgcttctc atctgaacat cacatctttt tcttgcggtt ccatttacac agtgtgattc
58261 ctagagatga gcttctttat cctctgaggc agtggaggaa gcatggaagc cacttgggga
58321 gcactgcatt gacaagtgta tttttgtagt cacatggtgg cagtgtcagg gaaattatag
58381 gactggttag attctagttc agcaacctat aaatcccagg acttcccagt ctcgtgagtc
58441 atacaactct caggcctgtg ctgcaaatga cacttgctta ggagtaaggt gaagggtatt
58501 ttatagctct aatggtttgt acagttctta aacatgtatt gattgctaac aactgctgtc
58561 tttctcccag cttgccccac caccagtctt tgtgcataag cacaattttg gacatagtta
58621 tttgtactta tttatgcttt tacaccttct tccttttata aagattttag ctggtttatg
58681 acttgagttg aaacaaggaa aaaaagagga gacctgaaat ggtctgtccc ctgccaacca
58741 gaagcctcct gtggtatcca aacagaatag ttgcctcagt ctgtcagcac ttctgtcttt
58801 gaaggtggtt tctgcttgaa aagtggtgac tattagcata gcctggggat aattgctttt
58861 ttttcttctc tcgggatacc tttttttttt ttttttccca gatactttct tgctcttgtc
58921 gactttgttt ttccagaaga tttagcctgt ggttaaaatg tttcgggtcc ccacgtgaac
58981 tctctgtggg attacccaat tctggggtac cttcaccaga tcaccagtgc taaagagggc
59041 aaaggatctt cttggttaat agaaaaggct gttttggaat gaatctcaaa gtccagaaac
59101 atcgagactt ttcttcaata ctttttttcta tttggggtag caactttacc tagtgtaggg
59161 gagggagggg ttagttggga gggcttgtgt ttaaggggtt cagaaacagg ggatttaagt
59221 gtgtcttttg tgtttgcaag gcactaacac cactcccgtc tgtatttaaa tgctgtcccc
59281 aggttacgac tatggctatg tctgcgtgga gttttcactc ttggaagatg ccatcggatg
59341 catggaggcc aaccaggttg ctttatactt cggtcaaatg atgctggaag gatatatttt
59401 tttatatatg gggagggagg gtttcaaatg attttacttt ggaaaggtac aagaagtcta
59461 tctgtggagc atactgtatt ccaaccatcg gttgtgagga aaatctttaa aaaggctgga
59521 aagctttctc tacaaaactt aatgggcaca gagtgcattt taaaagctag agcccagttg
59581 cttttggact agattccaaa gacaatagtt ggaaaaaaaa aaaaaagaca catctggagt
59641 gtttcctttt ggagtgtgac tgagatggta atcctgatgc aaagaatgat ccttgattgt
59701 ctgtgacccc aaggatctgc ctagcacaga aattctaggt caatagttac acccagacct
59761 agggtgaaga cctctgatgg tgacttctgt ggcatcagat cctgcctgca ggggctactt
59821 ccaaaagaga gctatcaggg aagagagagg agtggattgt tggtgtctat tgcattcatc
59881 attgtttttt gccaattgga gttgcatact caagtccttg gctgcgtata gtcagagctg
59941 gtgaatcaga atctgtactc accttacgtt tgaactatct ggagttactc agcttgccac
60001 ctagattttt catctatgtc tttaatagaa ccctacctgg tagttttgag aggaattaat
60061 aaataggtag aatccttctt gttatggtgc ttccttgggg aaagttgttt tctttgggtt
60121 gtttcagttc ctccatctgt aaagtaggaa aagaaactta ggaatatagt ttgatgtgtt
60181 tttttttct tttttttttt ttttaatgta cccactgcct atacttaaca gtgtgaatac
60241 agtgggccca gaatctttct ttctttcttt tttttttttt gagacggagt tttgctcttg
60301 ttgcccaggc tggattgcaa tggtgcgatc tcggctcact gctacctcca cctccctggt
60361 tcaagcgatt ctcctgtctc agcccccctga gtagctggga ttacaggcat gcgccaccac
60421 gccggctaat tttgtatttt tagtagagat ggggtttctc catgttggtc aggctgctct
60481 cgaactccag acctcaggtg atctgcctgc ctcggcctcc caaagtcctg ggattacagg
60541 catgagccac cgtgcccagc caggcccaga atcttaaaag aaggctctgc cagagaagag
60601 tagttattag atgagaactc ttcttcttct gtagcctgat gctttgttca gctttgttta
60661 actcagtgtg gctcattata cgtacttttc tcttcttggc caagttctcc tcttatgggt
60721 atggagatga catgctctaa atgctttggg agcaagcact cattagagaa gacttttgat
60781 gtatccttat cttgttagta gtttaagctt gtcagatcct taaagaatga caggcttagg
60841 accatatccc ctagacttaa gaggattctc attgaccatt tgttcagtgt ccatcactga
60901 atcacttacc aaatacagtt gacactctgt atccacaggt tccacaccca tagattcaac
60961 caaatgctga ttggacatat tcaggaaaaa aatgcattaa cactgcaaca ataaaaaata
61021 atacaggcca ggagtggtgg cttactctgt aatcccaaca ttttgggagg cccgggtggg
```

FIG. 14 (cont'd)

61081 aggattgctt gaggccagga gtttgagacc agcctgggca acacagggag accccatctc
61141 tacaaaaaat aaaagtgaaa aaattagcca agtgtggtgg ctatcaactt gggaggctaa
61201 gatgagagga ttacttgagt ctggattgag actgcagtga gctgtgatca ctctgctgca
61261 ctctagcctg gggtgacaga gtgagacccc gtctcaaaaa acaaaaaagt acagttaact
61321 atttatatag tctttattag gtattagata taagtaatct agagatggtt taaagtatgt
61381 tggaggatgt gtgtaggttg tatgcaaata ccatgtgatt ttatataagg gacttgagca
61441 tcctgagatt tttgtgtcct tgtgggtcct ggaaccaatc ccctgtggac accaagggac
61501 aactgtacta accatgtgtc agaaactgct acatgccaat tttggagaga agaaaaaagc
61561 ttccaatctg tgtgctttcg gtggatccta ttctgacagt ctgtccaatt ttgagaacac
61621 tcattaattc ataagcagtg aatgtgatta agtcgttcgc ctctgtgcta aatactcaat
61681 gtaatagctg atagctgagt gctataaaga aaatgaagca gggtattggg agaatgcatc
61741 atggtggcaa ttttagaggg gtggtcaggg aaacttcttg aggagtgaca tacatttaag
61801 ttgtgactct tggcgaataa tgtatccaga acacttacta tagtacctag cacttggtag
61861 catttgaatt aatttgaaat tcagtgtcct tctttctctc tcttaccctc ctccacatgt
61921 caagtaattt ccaattataa attttgtgtg tgtgtgtgag acggagtcca gccaggctgg
61981 agtgcagtgg cgtaatcttg gctcactgca acctccgcca cccgggttcc agagatcctc
62041 ctgtctcagc ctcccaggta gctgggacta cagatatgcg ccaccatgct tgggtaaatt
62101 tttttctttt tttttttttt ttgagatgga gtctcgctct gttgcccagg ctggagtgcg
62161 gtggcacgat ctcagctcat tgcaacctct acctcctggg ttcaagtgat tctcctgcct
62221 cagcctccca aatagctggg attacaggtg cccgccacca cacctggcta atttttgtat
62281 ttttagtaga gatggggttt caccatgttt gccaggctgg tctggaactc ctgacctcag
62341 gtgatccgac tgccttggcc tcccaaagtg ctgggactgc aggcgtgagc caccatgtcc
62401 tgccaatttt tgtattatta gtagagatgg ggtttcacta tgttggccag gctggtcttg
62461 aactgcagac cttaggtgat ctgcccacct tggcctccca aagtgctggg atgacacgca
62521 cgagtcaccg tgcctggcct tcaattataa ttataagaaa ataaatttat ttttatatct
62581 gaagtttaat aaaactaatt ctttaaggaa atggatgtgg attaaactcc ttatgacata
62641 gtaaacaatc ttatgagaga cataagaatg tgagggaaga agtcctgtct cctcagggtg
62701 aataaagtaa atattttggg aggctgaggc gagcggatca tgaggtcagg agagcaagac
62761 catcctgacc aacaaggtga aaccccgtct ctactaaaat acaaaaaaat tagccaggtg
62821 tggtggcgca cgcctgtagt cccagctact tgggaggctg ggcaggata attgcttgaa
62881 cccaggaggt ggaggttgca gtgagccaag attgcaccac tgcactccag cctgctgaca
62941 gagcaagact ctgtctcaag aaaacaataa aattgaataa ataaataaat aaataaaata
63001 aatatttgtg gaagataaaa tgtgtttgta ggccgggcac tatggctcaa gcttataatc
63061 ccaccacttt gggagaccaa ggctggagga tcacttgagc ccaggagttt gaaatgagca
63121 tggggtaaat agtgagaccc tgtctaaatt taaaaaaaaa aaaaaaaaaa aaaaagtctt
63181 tgtctatcct ttcccccagt tttacttaca gaccaaattg gtatggattc tgagtcacca
63241 cgatctgctt ggcaactctt agtagagcct gagtgtgtgt gtgcctctga gaaggttact
63301 ccgaagtact ttgagttttt ttgtaactct ttgctattcc gactcttgat gtgaaatgtc
63361 ttttatttat cattggctgg tacttgtagg cctaggggat ggaaataaag gaattttctg
63421 ctagcttgct ttgtcaaata ttgttgggta tgtgtgcctt cgtgaagttg ctcaagatga
63481 taaccaaggt ccctctagcc ttttcctggt gcctagatca agctgttaaa cagtaggatg
63541 ctctgcagca gtactgagct ttgtggctgt ggtgaccgat cagggtatca cttaggcagc
63601 agctgtctat ctggagaaat aatttccaac aggtatgaag gtatgaatct gttagtctgt
63661 accatcacca tttctgtcta ggagaagggg gcagccagca agcactgtca ggcagagcct
63721 ttcgttccac ccttcctgca aagtgtattt ctagccctgt catatgccct tggctttctt
63781 tgttgtcaag tctctgggag attgagggta catattattt ccttctgctt tgtgtgccct
63841 tgcactggga cttggggagg ggagtaagaa gtattgtgtt aaaatgttaa tccctttcat
63901 tggttgccca gttgtgagta ctagccctct cagactgttg gcatttggta tgcagggatt
63961 agcattttat gttctcaagt atgctggtgt gatgcttatt gtctattatt tggccaaatt
64021 agtcactaaa gtgcccttat agaagataac tctgggagag gtatttattt ctctgaaatt
64081 tttattctcc tttccccttt cctttccttt cctttttctt tttctttttt tctttccttt

FIG. 14 (cont'd)

```
64141 ttctcccctc cccccccctcc cctctcctct tattggagac aaggtctccc tctgtcacct
64201 acgctggagt gtagtggtac aatcatggct cactgcggcc tcgatctctt gtgccgaagt
64261 gatcctccca actcagttct ctttagtagc tggaactacc accaccacag ctggctattt
64321 tttttttttt tttttgtag aggcagggtt ttgcaacatt ccccaggctg gtcttgaact
64381 cctggactca agcaatttac ctatctcggc ctcccaaagc actgggattc caggtgtgag
64441 ccactatgcc tggcctattt ttaaattttt atttttttga gacttagggt tctgttctgt
64501 tgctcaggct ggagtacagt ggtacgatga gagctcattg cagctttgaa ctcctgggct
64561 taagcaatcc tctcacctca gccttctgag tagctggact acaggcacct gccaccatgt
64621 tcggctaatt aaaaaaataa caaactctgt tcgtaaagat ggggtcttgc tgtgttgctc
64681 aggctgctct tgaactcctt gcctcaagtg agcctcccac ctggacctgc caaattgctg
64741 ggattataag catgagccac tgcgcccagc cttactcacc tttttgtatg acactatcag
64801 tctttctaaa gtgcaaagaa aaagggttct gttatcatct gatgtgaaaa ttcctttaaa
64861 cattgacttt ttctggtgtg aggaatgaaa gctgtggaat acgtgaagtt ttatgaaata
64921 gtgttttttt gtgtgtgtgt caacaaaatt aagagagttt gggttattga agatacaaga
64981 gtgtttttga aggtatatat aggaaaccaa atctcaaatg tggtctgtcc ttgtgattaa
65041 aattagagca atagggaagc caggtgtgat ggctcacacc tgtaattcca gcacttttgc
65101 aggctgtgac aggaggatca cttgagccca ggagttgagt ccagcctggg taacatagca
65161 agacctcatc tctacaaaac attgttaaaa attagctggg tgtagtggca catgcctatt
65221 gtcccagcta tttggaaggc taaagtggga ggattgcttg agcctgggag gtcaaagcta
65281 cagtgagccg tgattgtgcc actgcactgc aacctgggcg acagagagat cctgcctcaa
65341 aaaaaaaaaa aaaagcaaca gagaaagctt atgtttttag tgatgagaat gctatttgtg
65401 aggccatgat ggaaaaaatt gaagaaccta gtttgttgga aacttaaatt ggtagtaaag
65461 acataatact atctgaaaca ctttagtact taaattgtgt gcattccaag caacaaaacc
65521 aataatctgt aggttgaagg ttgtagtgtt acctaaacaa ctatcacccc aaaaacactt
65581 cattgaggag tatccagcat cctagccaga gctcaactgt ataacttatg gctggaatca
65641 tgccattctt gctggaaact tcaatttcag tactttttcc ttatcaccct cagaagggta
65701 gtagtagaaa catggggaac tgcattctaa aatgagtgta taggttcata acctagctag
65761 aaaaaaaaat taaaacaatt aatgagtaca aaccaagggt tattgaagag tctcgctctc
65821 aagagagttg ggtattcaa gaaaattgaa agtgagttta aggatcgatg acttgattac
65881 acattttggc tatttatcca ctgattgaga cttttttttt tgagatggag tctcactggt
65941 tcgcccaggc tgtagcgcag ggtgcgattt tatccactga ttgagacttt tttttttttt
66001 tttttcagat ggagtctcgc tgtgtcgccc aggctgtagc acagaggtgc tcactgcaac
66061 ctccgcctcc tgggttcaag tgattctcct gccttagcct cccgagtaac tgggattaca
66121 agcatgtgcc accacgcctg gctaattttt gtattttcag tagaaatggg gtttcaccat
66181 gttggccagg ctggtcttga actcctcacc tcaggtgatc cgcccgcctc ggcctcccag
66241 agtgctggga ttacacatgt gagccactgt gcccagccca gtgattgaga ctcgactgga
66301 catgaagcag tataatgtag cagtataaca tagtattctg gaagcagact accgggggtt
66361 gcatttcggc tccatcactt tctaaggtgt acttgaacaa gtggcttaac ctctctgtgt
66421 tttaacgtac tctcacacac atctagggat taaataagtt aatgcatgta aggtgattag
66481 aactggggct ggtggccggg tgcggtggct catgcctgta atcctagcaa gttgggaggc
66541 caagacgggc ggatcacgag gtcaggagat ggagaccatc ctggctaaca tggtgaaacc
66601 ccgtctctac taaaaataca aaaaaattag ctgggcgtgg tggcgggcgc ctgtagtccc
66661 agctacttgg gaggctgagg caggagaatg gcgtgaactg ggaggcggag cttgcagtga
66721 gccgagatcg caccactgca ctccagcctg ggcgacagag tgagactcca tctcaaaaaa
66781 aaaaaaaaag aactggggct ggcacaaagt gaatgttgag tgcatctttg ttgttttcac
66841 acaacttctc atctgaaaca aagtcttaag ttacagcagc tctggtcttg gcttaatgga
66901 gtatatggca aaaagaggat ttggtggcag tgcctaggag gatttttttt tttcccatca
66961 acaatacttc tcatttagcc tgttgattga tacggattat caggggactc cttccagctt
67021 ccctagttgg agtttttttt tttttttttc ctttttgag acagggtctc attctgtctc
67081 ctaggctgga gtgcagtggt gcgatctcgg ctcactgcaa cctccgtttt tggggctcaa
67141 gccactctca tgcctcagcc tcccaagtag ctgtggctac agacacgtgc ctggctaatt
```

FIG. 14 (cont'd)

67201 ttgtattttt gtagagacgg ggttttgcca tattgcccag gctgatctcg aactcctgag
67261 gtcaaagcga tctgcctacc tcagcctccc aaagtgctgg attacaggag tgagctacca
67321 tgtccggccc ttagtaggag tttctgctgc cttagccttc aagagagaat cttaaatttt
67381 cttttttttt tttgagacag agtctggctc tgtcgcccag gttggagtgc ggtggcgtga
67441 tctcggctca ctgcatgctc cgcctcccgg gttcacacca ttctctcgcc tcagcctcct
67501 gagtagctgg gactacaggc gcctgccacc acacccggct aatttttttg tatttttagt
67561 agagacgggg tttcaccatg ttagccagga tggtctcgat ctcctgacct cgtgatccac
67621 ccgcctcggc ctcccaaagt gctgggatta caggcgtgag ccacctctcc cggccataag
67681 aatcttaaat tttctaaaga gaaagagcag gagacagaca gtaccacatg gagtatgttt
67741 aggccatgta ggaaatctag cctgtggctt taaaaccgta agttctaaat tagctgggta
67801 tggtggtgca cacctgtagt cctagctact ctggaggctg aggtaggagg atcacttgtg
67861 cccaggagtt caaggttgca gtgagctgtg atggtgtcac cgcactccag cctgggcaac
67921 agaatgagat gctgtctctc aaagcaaaac accctaagct ctgataacca gcccattatt
67981 tgccacatct caggctcttt aattatgaga ggtgctctaa acgactcatt ttaattctct
68041 cgaatttgaa aaataaacat ttatcatttg gcagttttaa gggaaccttc tgatatgtgt
68101 cctacaatgg gtttataatt atttttgtca caaatcatgg tttatttcta tggattaaag
68161 tagtttagtt cttaatttgt tctaaattgg aaatatacct atatgtttta acctcgtgct
68221 tcagtgttgt cacatctcat tagttcaggg gtcgtacaaa ggcatagttc agttagccat
68281 cttgattata actttggttt atgaccttat gtatgttcag atggtatagg gttcgtagca
68341 cagaaagatt tagaattcca gcttcattac ctcctggctc ttttgtaact tttttttttt
68401 tttttttttt tttttgagac ggatcttgct ctgttgtcca agctggagtg cagtggtgtg
68461 atctgggctc aatgcaacct ccacctcccg ggttaaagcg attctcctgc cttggcctcc
68521 cgagtagctg ggattacggg catacaccac cacgcccagc taatgtttat tttagtagag
68581 atggggtttc accatgttgg ccaggctgga cttgaactcc tgacctcagg tgatccaccc
68641 accttggcct ttcaaagtgt tgggattata ggcgtgagcc accgtgcctg gcctctcttt
68701 tgtaacttct gaacctcagt tttctcatct gtaaaatgag aggatgatca taataccacc
68761 catagtgcag ttgtgaggtt agagtatgta gtatatgtaa agtgatcagc atgataactg
68821 gcatgtggta agtgctctgt agtaaagggt gattcataac actggactct gcttggttgt
68881 accaacttct cattttccct ggctccttat ccacctcttg ggattcagag ttggctgaaa
68941 gtggcaggca gtgctgcttt gggtggcagc ttgattttag acagccagtt cacatagtgc
69001 ttttgttcag gacctctcgg gatttctaga cagacagcaa gagagttggg ctaacacctg
69061 tcatgaagtg tctaaggaat gagtgcacaa gcattcaggc atgtgagggc agaagaccat
69121 gaccatacct gccttcctac agtaaacagc ctgttgtttc tgcaggtagc attgcaggta
69181 gttcttttat cagaaaattc ttgtaggctg caggtgacat tgagtgttat taggtatctt
69241 cttcattcaa gttgaacttg gaggttacag tatatcttta tgtcccccctc tccacaggtg
69301 tttaagtgtt gtcattcatc ctctagtgca tagattatgt gtgcacattt cttgttaagg
69361 atattgatga actgatagtt tatctagaat aatgtttatt ttatatttta ttttattgag
69421 acagggtctt gctctatcac ccaagctgga gtgcagcggc atgatcatgg ctcactgcag
69481 cctcaacctc ctgggttcaa gccatcctcc ctacctcagc cttctgaata gttgggacta
69541 caggtgtgcg ccaccacacc tggctaattt tgaggggggta gaggggaggt acagatgaga
69601 tctcactgtg ttgtccaggc tggccttttg ctcctggact caagcagtcc tgcctcagac
69661 tcacaaagtt ctggaattac agatgtgagc cactgtaccc agcctagaat aattattatt
69721 tatttttatt tttatttatt tattttttga gacagagttt tgctcttgtt acccaggctg
69781 gagtgcgatg gcacagtctt ggctcactgc aacctctgcc tcccgggttc cagtgattct
69841 cctgcctcag cctcccatgt agctggaatt acaggcacac caccacacct ggctaatttt
69901 tgtattttta gtagagacag ggtttcacca tgttggccag gctgctctcg aactcctgac
69961 ctcaggcaat ccacccgtct cggcctccca aagtgctggg attacaggcg tgagtgatgg
70021 cacccagcca gaataattag ttttaatctc acagggtgag atttgtgagg ttaattttgt
70081 atattaatga tgtatatatt accaaaatct gtggtcaagt gaaatttgtg cttaatcttt
70141 gcaaatgcta tttccaaagg aaaatatgta ggagaaaagg tggtgtatca caggatgtag
70201 agtagtggtt actgggcaca agggtggccg gggagtcggg gggtggcagg agaggataga

FIG. 14 (cont'd)

70261 gaatgataac tgattgatac agggtctctt ttttgggatg aggaaaatat tttagaatta
70321 aatagtgagg atggttgacc aagcttgtgc atgtactaaa agccattaaa ttgtatatac
70381 tttaaaacag tggattttat ggtatgtgaa ttttatctca attttaaaaa aagtctttaa
70441 atgtagtatg aaactttttt taaggccagg cagggtggct cacacctgta atcccagcac
70501 tttgggaggc tgaggcgggc agatcacctg aggtcaggag ttctagacta gcctggccaa
70561 catgatgaaa ccctgtctct accaaaaata cgaaaattag cccagcatgg tggtgtgttc
70621 ctgtagtccc agctactcgg gaggctgagg caggagaatt gcttgaactc aggaggcaga
70681 ggttgcagtg agctgagatt gtaccactgc actccagcct gggcgacaga gcaagactgt
70741 ctcaaaaaaa aaaaaaaaaa aaaaaaagtt tttttagggt tccagcacaa tgggaatgag
70801 tccagatcta aaataaagta cagattcatt taccaccctc caccctaccc caacccccca
70861 aaaagattgt ctatcagttt gtcaggaagt tagagtaaaa tggtcttaaa atgcatcaag
70921 agggctgggc acagtggctg atgcctgtag tttcagctac tcaggaggct gagataggag
70981 gatcacttga gcccaggaat tcgagtgagc catgattaga tcactgcact ctagcctgaa
71041 tgacagagca ataccttgtc tcttaaaaaa aaaaaggcat gaagaatttt tttgctaatg
71101 gtatctactt accacagagg aacatttaag ctaaacatct gaaagattat ggatggagtt
71161 ggtaacaggc tccatttgaa ctggttatgt agtttatgct cagtaaggtt gaacggactt
71221 tctgctttga gttattcaca gttaaaaata aaggactatt ttgaagtaga ccgaaaatga
71281 aaataacatt aagaaatcct tggactaatt tttaggggag attcctgtaa tcggatggtt
71341 tgtagttgtc aatgtagacc tttcctggtt tcctgaaatt gctaatcaaa gctcaaagcc
71401 atgggaaaag actggattgc agctagaatg tgtgctctcc acatatgtct ttcttagagg
71461 cctctttcaa gcagcattga cactatggct atcatctttg accctcttag tatacagaga
71521 gttgtaggtt ttcttttttt aagggggaaa acattattga cataaattat atatcataaa
71581 agtcactcat tttaactgta caattcaatg atttttagt aaatttacca agttgtaaca
71641 tttattatta taattagttt tacaacattt ttctttctt tcttttttt tttttctttt
71701 tctttttttc tgggacacag gatcttgctc tgttgcccaa gctgagtgca gtggcatgac
71761 catggctcac tgcagcctcc acctcccggg ctcaagcaat tctcccacct caacctcctg
71821 agtagctgga actataagtt ggaaccatcg tgcccagcta atttttatt ttttgtagag
71881 agaaggtctt gctatattgt ccaggttggt cttgaacttc taaactcaag caatccttcc
71941 tgcctcacct tcccaaagtg ctgggattac aggtgtgaac catcatgcct ggtctagaac
72001 attttcatta cctcaatcgg atccccgttt ggggatacat ttacattttt aattttttaa
72061 tttttatttt ttttagagac gaggtctcaa tctattgcca aggtggtctt gaactcctgg
72121 tttcaagtga tcctcccacc ttggtttccc gaagtgctgg gattacaggc atgaaccacc
72181 atgcccagtc cattccaatt ttttttttct tttttttga gatagagcct cactctgtcg
72241 cccaggctgg agtgcagtgg cgtgatctca gctcactgca acctccacct cccgggttca
72301 cgccattctc ctgcctcagc ctcccgagta gctgggacta caggtgcctg ccaccacgcc
72361 cggctaagtt tttgtatttg tagtagagac ggggtttcac cgtgttagcc aggatggtct
72421 caatctcctg accctgtgat ccgcccgtct cagcctccca aagtgctgag attacaggcg
72481 tgagccaccg tgcctggccc attccaattt tttacaaaag tgatttcaga cttataaaaa
72541 agctgcaaaa attcctgtgt tcttttcacc tagattctac cttttttttt tttttttttt
72601 ttgaggcgga gttttgctct tgtttcccag gctggagtgc aatggcgcaa tctcggctca
72661 ccacaacctc cccgtcccgg gttcaagcaa ttctcctgcc tcagcctccc aagtaattgg
72721 gattacagcc atgcgccacc acgcctggct aattttatat tttttagtgg agaccaggtt
72781 cctccatgtt ggtcaggctg gtattgaact cccgacctca ggtgatctga ccacctgggc
72841 ctcctaaagt gctgggatta caggcgtgag ccaccgtgcc aggcccaccc agattcttct
72901 tagcacattt gaatgcagat ttttgaatag ttatgatcta ttctcattga aaaagggaca
72961 tcatttgact tgacctccca ccagactctt cctttgaggt tggatggagg tgcttaatgg
73021 atgctgtgga tggtgtgtga atttccattg ggttgagtgg atgatgtatg tggaaggcga
73081 ttgggattta ctttgtcggt gtctccaaga ggtcccccac tgggctttgt caggtgctgg
73141 ggttggaggt caagaagtag ggcaacatct aaagcttcta ctcctgggca ctgtgaggtt
73201 tttataggtc ttttaaaaaa aacagtgaat aggccgaacg cggtggctca cacctgtaat
73261 cccagcactt tcagaggccg agggaggcgg atcacgaggt caagagatca agaccatcct

FIG. 14 (cont'd)

73321 ggcctcgtgg tgaaacccca tctctactaa aaatacaaaa attagctggg catggtggca
73381 catgtctgta gtcccagcta ctcgggaggc tggagcagga taatcgcttg aaccctggag
73441 gtggaggttg cagtgagccc agatttcacc actgcactcc agcctggcga cagcgaggct
73501 ctgtctcaaa aatatgttct tccatgagac agcgggcatt tggatgcctg atacaaaaag
73561 aggagggact atgtgctagt cagctttaga ctgagaagca gcagcaacca tggcaaaggg
73621 gaagcaaact ttcctgagtg gccttaataa tgttattcgt caggcagtgg ctcttaaaca
73681 ggggcttcaa gcagtgattt ttgacatgct cttctcctcc ccaaccactg gacatttggc
73741 aatgtctgga gacatttttg gttgtcacca ctgggagagg gtgctactgg tatctagtga
73801 atagagccag ggatgctgct aaacatccta cagtgcaaag ggcagctctc cacacaaaga
73861 atcatctggc ccaaaaatct ctattgctga ggttgaaaaa tactggtgta aggagacaag
73921 agttgtggtt agtcagaaag gatgacctgg cttgccgtgg attgtcttat aataatcagt
73981 tatctctttc cttgccttat tcctggtccc aacagagtga ggattggcaa ggggggtttgg
74041 gaatatagtg ggaatgctgt gtagtgagag tgcaggcacg gcactccaga ctaccagtca
74101 cgagcttagc ctgtgtcctt ggggtaggag ctgtagaata agacctattt tgatatgtgg
74161 accagaataa gttctttaaa taatcaaagg taataaacat tcttaaaata tactatcact
74221 aaggtagtct gtcatccagc agaatgaggg agtagtcaga agattacaca tatttggcag
74281 caattactag aaaaaacaaa caagttgaga gttttcaaaa tagatgttac ttcatatttc
74341 agatagtttt ccagggaata ttgaaaatgc aagtgcagat tttcacatcc ttctttatac
74401 tgattaaaac atttgaatct attggatcat cttttcatta ggctttactt cacagggcca
74461 tctactggat cctgtatgct gatatagtta aggggactga cctcaaagta aaagatgcat
74521 atattttatc ttaatacaat atcactttgc tgtgaagggg agctgctgtg tatatagaat
74581 gctgtgtaat agtgattggg ctgttgggaa tcacattgga aatatcagta agcaactcat
74641 tttaactttt gttaacacag ttaagtgctg agcacctctt gtgtttgaag ctctgtgcta
74701 ggtaatatgt gttcattaat gaatgaaaaa acaatacaaa aattagccag gcatggtggc
74761 gtacacctgc agtcccagct actcaggagg ctgaggcaca agaattgctt gaacccagaa
74821 ggtggaggtt gcggtgagcc gagatcacgc cactgtactc cagcctggcc aacagagtga
74881 gactgtctca aaaaaaaaaa aaaaaaaaaa aaaagttttt tatttttaaa tttttgttt
74941 tatttctttt ttactttttt ttcttttgag acagagtcac gctctgtcac ccaagctgga
75001 gtgcagtagc accatcttgg ctcactgcaa cccccgcct gccaggttca agtggttgtc
75061 ctgcttcagc ctcccaagta gctgggacta caggtaccca ccaccacgcc cggctaattt
75121 ttgtattttt agcagaggcg gggtttcacc atattggcca ggctggtctc aaactcctga
75181 ccttatggtc tgcccgcctc agcctcccaa agtgctggga ttacaagcat gagccactgt
75241 gcctggcaaa atttttattt tattattatt attatttttt tttttttttt tgagatggag
75301 cctcgctctg ttgcccaggc tggagtgcag tggcgcgatc tcggatcact gcaagctccg
75361 cctcctgggt tcatgccatt ctcctgcctc agcctcctga gtagctggga ctacaggcgc
75421 gtgccaccac gcccggctaa tttttgaat tttttagta gaggcggggt ttcaccatgt
75481 tagccaggat ggtctccatc tcctgacctc gtgatccacc tgcctcagcc tcccaaagtg
75541 ctgggattac aggcgtgagc caccgctccc ggccaatttt tattttattt ttaattgata
75601 attgtacatg tttatggagt acccatgtta tgatacatgt gcacattgta gaataatttt
75661 taattgataa ttgtatacgt ttatggagta cccacgttat gatacatgtg tacattgtag
75721 aatgattgaa tcagactagt taacatatcc atcacctcat gtagttattt ctttgtagtg
75781 agaacattta aaatctcttt tagcaatttt gaaatagata caatacattg ttattaacta
75841 tagtcaccat gctgtgcaat agataactaa aacttcttcc tcctgtctga ctgaaacttt
75901 atactctttg actaacattc tcccgttctc ctccacccgc cttctccacc cacggcctct
75961 ggtaaaccac cattctgctc tctacttctg tctgaatatt tgattttttt agattgcaca
76021 tgtgagatca tgcagtattt gtctttctgt acctagttta taatacactt agctaagtgt
76081 ccttcatgtt tttccacatg tcgcaaatgg cagaatttcc ttcttttta aggccaaata
76141 gtatttcatt gtgcttacat accacatttt cattatccat tcattcattg atgggcaatg
76201 gatgaatgga tatcatggct attgtgaata gtactgcagt gaacatggga atgcaggtat
76261 ctctcagaca taatgatttc agtttcattg gatatatact gtacccaaaa gtgggactgc
76321 tagatcatat ggtgattctc gttttagttt tttttttttt aagaacctcc atacagtttc

FIG. 14 (cont'd)

```
76381 caaaatatct gtactaattt acattcccac agtgtaaagg gttccctttt ctccatatcc
76441 tcactaacac ttgttaccgt tcatcttttt tatagtaacc atgctaacaa gtatgaggtg
76501 acatctcatt atggttttgt ttgtttgttt gagacagtgt cttgctgcat cacacaggct
76561 ggagttcagt ggcgtgatcc cagctcattt gcagccttaa cttcctgcac tcaagcagtc
76621 ctcccacctc agcctcccag gtagctggtg tgtcaccatg cctagcgttt tttttttttt
76681 tttttgaga cagagtctcg ctgtgttgcc caggctggag tgcagtggta tgacctcggc
76741 ttactgcaat ctctgcctcc cgggttcaag taattctcat gcctcagcct cctgagtagt
76801 tgagattaca ggcatgtgcc accacaccca gttaactttt gtatttttag tagagatgag
76861 gtttcattat gttgtccggg ctggtcttga actcctaggc tcaagtgatc ctcccacctt
76921 ggtttctgaa agtgctggga ttaccagcat gaaccactat gcccagctcc ttatggtttt
76981 aatttgtaat tctctgataa ttattgatgt tgaacatttt gtcatatatt ttttggcaat
77041 ttttttctt cttttaaaaa ttttgttttt agccataagg ccaggaatgc acgtatgtct
77101 tctttcaaga aatgtctggg ctgggcacag tggctcacgc ctgtaatccc aacactttgg
77161 gaggccgagg cgggtggatc acgaggtcag gagatcgaga ccatcctggc taacatggtg
77221 aaaccccgtt tctactaaaa atacaaaaaa attagctggg tgtggtggtg ggcgcctgaa
77281 gtcccagcta tgtgggaggc tgaggcagga gaatggcgtg aacccaggag gtggagcgtg
77341 cagtgagcca agatcgcgcc actgcactcc agcctgggcg acagagcaag actctgtctc
77401 aaaaaaaaaa aaaagaaaaa gaaaaaaaaa tgtctattca ggtcctttgc ccattttta
77461 atagggttat ttgttttcat tattgagtag tttgagttct ttgtacattt tggatattag
77521 ccctttatca gatggaagat ttgtaagtat tttctctcaa tctgtgcatt gtttcttcac
77581 tttgttaatt gtttccttgc tttgcagaag ctttttagtt tgacgcaatt ccatttgtct
77641 gtttttgctt ttgttgcctg gcctttgggg gtcatgcaca agaaatcatt gcctagacca
77701 gtgttgtgga gctttccaac tatagtttct tctagtagtt ttacaatttc tgttcttaca
77761 tgaagctatg aacagttcct gtatagttat ccctgccacc cttctcccaa cattacatac
77821 acagcctccc caactatcag catcctgcag tgtagtgtat atgttacaat cagtgaagca
77881 acattgatac atcattatca agggttcact ctgggtgttg taccttctat gggtttccac
77941 aaatgtatgt catatatcca ccattatagt atcatacaga atagtttcat tgccctagaa
78001 accctctttt ctccacctgt ttgttctttc ctcttgcaaa cccctgcaac cactgaactt
78061 tttattgtcc gtgtagtttt gccttttgca gaattttata tagttggaat tggacaatat
78121 gtagcctttt cagattggct tctttcattt agtagtacat ttctctatgt agtctcattc
78181 ctctatgtct ttttgtggtt tgatagctca tttcttttta gcactgaata atatcccatt
78241 gtatggatat atcacagttt attcattcac ctactaaatg acattttggt tgcttccatg
78301 ttttgacagt tacgaataaa gctgcaataa atatccatat gcatgttttt gtacggacat
78361 acgttttcaa ctagtttggg taaatacaag ggcatgatt actggatcgt atggtaggag
78421 tgtgtttttt tttttttttt tttttttttt ttttgacacg gagccttgct ctgtcaccag
78481 ctggagtgca gtggtgcgat ctcggttcat tgcaacctct gcctcccagg ttcaagtgat
78541 tcttctgcct cagcctccca agtagctggg actacaggtg catgaccatg cccagctaat
78601 tttttgtatt tttagtagag acagggtttc aacatgttgg ccaggatggt cttgatcttg
78661 tgacctcgtg attcgtccac ctcggcctcc caaagtgttg ggattacagg cgtaagccac
78721 tgcacccagc ctgtagagta tgtttaattt tgtaagaaac tgtcaaacag tttttccaaa
78781 gtagcgatta caatttgcat tgctaccagc aatgaattag agttctgttg ctctgtatcc
78841 ttgccagcat ttggatggta gccattttta tttttattta tttatttttt tttttgaga
78901 caaggtcttg ctctttcacc caggctggag tacagttgga cgatctcagc tcactgcagc
78961 ctccgcctcc caggttcaag ttattctcct gcctcagcgt tctgcatagc tgggattaca
79021 ggcacgcacc accacaccca gctaattttt gtatttttag tttcaccatg ttggctaaga
79081 tggtcttgaa ctcctgacct taggtgatct gccccgcctt ggcctcctga attgctggga
79141 ttacaggcat gagccaccat gcctggcctc ctttgggtat ttctattgga cagtcatgtc
79201 attcatgaat aaagacaatt ttatttcttc ctttctaatc catatacctt ttatgtcctt
79261 ttcttggctt attgcactag ctaggatttc tagtacaatg ctgaaaggag ctgtctttct
79321 cttcttttct ctcctttcct tgccttttcc ttttcttctt tttctttctt ttcttcctat
79381 agagataggg tctcgctatg ttgccaaaac tggtctccag ctcttgggcc caggtgatcc
```

FIG. 14 (cont'd)

```
79441 tcccacctca gcctcccaaa gtgctgggat tacaggtgtg agccaccaca cctagctgaa
79501 aaggagctgt tgagaataca tccttgtctt gttcctgatg ttagtgggaa gaaagcatct
79561 agtctctcac cataagtgtg atgttagcta taggtttatc aagttgagga ggttcccctc
79621 tgttcctagt ttgctgagag gttttttttt ttaaatcatg aaaggggatt ggatttttgt
79681 caaatgattt ttctgcatct attggtatgt tcatgttaat ttcttcttca gcatgtcgat
79741 gtgatggatt acattaattg attttttttt tttttttag atgcagggtc tcactctgtt
79801 gcccaggcta gagtgcagtg gcacaatcac agctcactat aacctcaagt tcctcagctc
79861 aagcaacttt cccatctcag ctttccaagt agctaggact acaggcacat accaccatac
79921 ccatctagtt ttttaaaaca ttatttgtaa agatgaagtc tctctatttt gtccaggctg
79981 gtctggaact cctgggcggg ctcaagcagt cttcaccttg gcctcccaat ttgtttggat
80041 tacaggtgtg agccactatg cccagcctca tttttgttat tagtaatttg tatcttcttt
80101 cttttttctt tagactggtt aaatgtttat caattttatt gatcttttca aagaaccaac
80161 ttttggtttc actgatttat ctctattgat ttactgtttt caatttcatt gacttcagct
80221 ctaattttta ttattttctt ctgcttactt ttgatttaat ttgctctttt actggtttcc
80281 taaagtggaa gctcagatta ttgattttta gatttttctt ctcttttaat atatgcattc
80341 agtgctataa atttccctct cagcactgct ttttgtgtat cgcacaaatt ttgataagtt
80401 gtgtttttca ttatcgttta cagttgtgtg ttaatcccca tacagttaat gatggggata
80461 aattctgaga aatgcactct taggcaattt tgtctttgtg caaataccat ggagtgtaca
80521 tacacaaacc taaatggtat agcctgctac ccacctaggc tatatcattt agcctattgc
80581 tccttaactg caaacctgta caacttgtta ccatattgta tatgataggc agttgtgaca
80641 cagtagtatc taaagataga aacggtacag tgaaaataca gtatttcagt attttgggac
80701 caccatcata tatgcaagcc cattgttgac tgagatgtca ttatacagca tctgaccata
80761 attcggaata tttttaaatt cctcttgaga tttcttcttt agcttgtgtg ttatttagaa
80821 gtatgttttt aaatctccat atactttggg atttttacaa ctatattact gttactgact
80881 tctagtttaa ttctattgtg atctgagagc atatattatt ttttctgtca ttttaaactg
80941 gaaaaggtat gttttatggc ccataatgtg ctgcgtgagc ttgaagagaa tatgtagttc
81001 gctgttgctg gatgaaatag tctacaaatg ttgattagat tgctgctgtt attttgatgc
81061 gtatccttcc agatttttct atgcatgtat catctatctg tgtatctatc tgtaggatag
81121 gagagtcttg tacaaatggt tttataactc tttaacttca aatattgtgg acttacttcc
81181 ttgtcattaa atacatttaa ggctgggtgc agtggctcat acctgtaatc ctagcacttt
81241 gggaggccga aacaggcaga tcacctgagg tcaggagttt gagaccagcc tagccaacat
81301 gttgaaaccc cgtctctact aaaaatacaa aaattagctg ggtgtggtgg cacacgcctg
81361 taatcccagc tgctcaagag gctgaggcac gaaaatcggt tgaacccaag gaggcggagg
81421 ttgcggtgaa ccaagattgc gccagtgcac tccagcctgg gtgacagagc aaaactttgt
81481 ctctaaataa ataaataaac aaataaaata catacctatg tacatacata cattttaaga
81541 atcattttga tatattcatc tccatactga ggaatttaag tgcttttttt tttttttttt
81601 tttttttttt tttgagacag agtctcactt tgttgcccag gctggagtgt ggcggcacga
81661 tcttggctca ctgcaacctc tctacctcct gggttcagga aattctcctg cctagccggg
81721 tgagatttcc tctttagctt gtgtgttatt tagaagcatg tttttgtacc tatcgtagct
81781 tctctagaga agggaggtag gagaatcgct tgagcccggg aggtcaaggc tgcagtgact
81841 gacccatgac catgccactg cactgtagcc tgggtgacag agtgagcccc tgtctcaaaa
81901 aggaaaaaaa agaaatcagc atattttatg acttaataaa tgtattcaaa ttccatccag
81961 atatttccta atttattatt ttactaacag tgtttgagag cacttgtctc ccctgccttc
82021 caaccagtgt caagtgtatt ttaacaaaat acttgtattg ggtagtagta catggttggt
82081 tgttactctc taatcgcctg ttgtgtttga aatatttaat aatttttta atgttgctag
82141 tgtagtgaag aagataatga tttagttttt cttctttctt tttttttttt gagatggagt
82201 ttcacccttg ttgcccaggc tagagtgcaa tggtgcgatc tcagctcacc aaaacctctg
82261 cctcccgggt tcaagtgatt ctcctgcctc agcttcccga gtagctggga ttataggctc
82321 atgtcaccac gcctggctaa ttttgtattt ttagtagaga cagggtttct ccatgttggt
82381 caggctggtc gcgaactccc gatcttaggt gatctgccta ctttggcctc ccaaagtgct
82441 gggattacag gcgtgagcca ccgcacctga caaatgatgt agtttttctc ccttaggtta
```

FIG. 14 (cont'd)

82501 ttagtaggca gaatagtttt acatttgatt attagttatt catatttctt ttgtgacttg
82561 ttggttctta atatatctat tcagccaaaa atgaaaaata ggatatctta gcctgtctag
82621 tcttaaggta aatatatgtg ggatataagg gagtttgggg gctgggcgca gtgactcaca
82681 cctgtaatcc cagcacgttg ggaagctgag gtgggctgat cacttgagcc caggagttca
82741 agaccagcct gggcaatgta gcaaaacccc atctctacca aaagtacaaa aattagccag
82801 gtacagtggc acatacctgt attcccagct actagggagg ctgagatgga aggatagctt
82861 gagcccaaga ggttgaggct gcagtgagct ataagcatgc cccactacat tccagcctgg
82921 gtgacagagc gagaccctgt ctcaaaaaaa agattttttt gaaaagttga aaatgagtat
82981 attcgctgaa tacgagatga gttttcccaa gaatttatcc ctcagaatct ttcacgttct
83041 tcctcctcct tctcctcctc ctgctttctt cttcttcttt cttcttttc tgtttcttct
83101 tcttgctttt ataaagtctt agctcctgtg gagttttctc tcagttactt cttatttatt
83161 tatttgagac agagtttcac tcttgttgcc caggctggag tacagtggcg cgatctcggc
83221 tgactgcaac ctccgcctcc tgggttcaag ctattctcct gtttcagcat cccaagtagc
83281 tgggattaca ggtgcctgcc accacacctg actaatttct gttacttctt ttgagccaca
83341 aagtatttga aaaagatgca ttaagtagtg accgcagtcc gtgctagtat tgggtgctta
83401 cagaggtcta gtagaatacc gtgttttaaa aggaggtgaa tttaataatt gctgtgatta
83461 ctctggcatt atacgctcac aaataaaatg tttggtgatt tttttttttt tttttttgg
83521 agacagattc ttgctctgtc acccaggctg tgcaatgatg tgatctcagc ttactgcaac
83581 ctccgagttc aagtgattct cgtgcctcag cctctcgagt agctgggatt acaggcaccc
83641 gccatcatgc ctggctaatt tttgtatttt tgtagagatg gggtttcacc atgttggcca
83701 ggctggtctt gaactcctga cttcaggtga tccacccatc tcagcctccc aaagtgctgg
83761 gattacaggt gtgagccact gctcccagcc gggtgtgata tttttaataa aacaagtatt
83821 caaattcact tacaggacca atgaaagaat cgtttgtcgt aattttatgc caaagggtac
83881 ttgtggctta agataaactt cccataatga cattatccac agattcaaaa agtagtttat
83941 cttaaacaac ttctgtgaca ttttaaaatg atgtggctta gaaaattgct aggttatcta
84001 aaatggctct attgatgatg taaatgtagc acatgaagag cttgaataaa atagactttt
84061 gaagtgtgca aatggaaaga acagtccttc taaataatta tttcccctcc cttttattga
84121 cgtatacata cagaaaagat atcatgtcgt aagtgtattg cttagtgaat tactccaaag
84181 ttggatatac ctggttaacc accacctgaa tgaaaaaaac agaacactgc ttcatatgga
84241 gaagcccctc ctgcccctcc tggtcattgt ccttttcatc cctcccacag gtagtcactg
84301 agttctaata ccacagagtc ttttgacttt cttttgagcc ttatgtaatt agaatcacaa
84361 aagatgtatt cttttgcctg acttttatac ttagtattgt ttttgaaatt catcttgtgt
84421 gtaactgcga tttgttcatt ttcattgctt agtgaattat tccaaagttg gatatacctg
84481 gttaaccacc acccgaatga aaaaaacagt ttttggccgg gcacgatggc tcacgcctgt
84541 tatcccagca ctttgggagg ctgaagcgtg cagattacga ggtcaggaga tcaagaccat
84601 cctggctaac acggtgaaac cccgtctcta ctaaaaatac aaaaaattag ctgggcgtgg
84661 tgacgggccc ctgtagtccc agctactcag gaggctgagg caggacacct gtaatcccag
84721 ctacttgaga tgctgaaaca ggagagtggc gtgaacttgg gagatggagc ttgcagtgag
84781 ccgagattgc gccactgcac tccagcctgg gcgacagagc aagactccgt ctcaaaaaac
84841 aaaaaacaaa aaacaagaaa acagtttcc agtctaagaa tgtattacaa tttattcaaa
84901 ttccactcta gatggactgt gggttttttt ttttccccca tttggagcta tggcaaatga
84961 tgtttttca aagttgttat ttctcagcca ggcgcggtgg ctcacgcctg taatcccagt
85021 actttgggag actgaggtgg gcagatcacc tgaggtcaga agcaagacca gcctggctaa
85081 catggcgaaa ccccgtcttt tctaaaaata caaaaattag ccaggtgtgg tgatgggcac
85141 ctgtaatccc agctacacag gaggctgagg caggataatc acttgaaccc aggaggtaga
85201 ggttgcagtg agctgagatc acaccactgc actccagcct gggtgacaga gcgagactct
85261 atctcaaaaa agaaaacaaa acaccacgga attgttattt ctcttggcga ataggtagat
85321 gcacttattc ctgttaatat atacctacct gtgaatgtgc ttgttggatt ttctatgtat
85381 cttctgtctg ccacctagaa atttaacctt ttatatatat acaactttaa tttttttttt
85441 tttttttta agagacaggg tgtcactatg ttgcccaggc tggttgggaa ctcctggcct
85501 taagccgtcc tcctgcttca gtctcccaaa gtgttgggaa tataggcgtg agccactgtg

FIG. 14 (cont'd)

```
85561 ccccactgtt caagttttca ttgattgctg cctacatata gttgttcaac agctattgat
85621 tccccctgct ctgtatatat gtctcctagt gtaggtatca gggttacagc agtaattaag
85681 accacattat ttcattttat catttaaata tataagacta attgataaat taagtataga
85741 actttgacca acatggtgaa accccatctc tactagaaat acaaaaatta gctgggtgtg
85801 gtggcagacg cctgtaatcc cagctactca ggaggccgag gcagaactgc ttggagatgg
85861 aggttgcagt gaaccaatat cagaccacta tactccagct tggatgacag agggagactt
85921 tgtctctttt tttttttctt tttttttgag acggaatctc gccgtcttcc aggctggagt
85981 gcagtggcac gatctcggct cactgcagcc tccgcctccc gggttcaagc gattcttcta
86041 cctcagcctt ccgagtagct gggattacag gcacccacca ccatgcccgg ctaatttttg
86101 tatttttagt agacagggtt tcaccatgtt ggccaggctg gtctcaaacc cctgacctca
86161 agggatcaac ctgctttggt ctcccaaagt gctaggatta taggcgtgag ccactgtgcc
86221 cggccctttt tttttttttt ggagacagaa tttcgcccag ttgccagact ggagtgcagt
86281 ggcacgatct cagctcactg caacctctgc ttcatgggtt caagccattt tcctgcctca
86341 gcctcccaaa tagctgggac tacaggcatg caccaccacg tctggctaat tttttgtatt
86401 tttagtaaag ccagagtccc aaagtgctgg gactaggcag gcgtgaacca ccacgcctgg
86461 ccaagactct gtctctcaaa aaaaaaaaaa agaaaaaaaa atataggact ttgggaggcc
86521 gaggcaggca gatcacctga ggtcaaaagt ttgagaccag cctgactaac atggtgaatc
86581 cccatatcta ccaaaaaata caaaaattag gcaggtgtgg tggcgtgcac ctgtagtccc
86641 agctattggg gaagccgagg tgggagattg tacctgggag gcagtgagca gagatcgcac
86701 cactgcactc cagcctgggt gacagagtga gaccttgtct caccaaaaaa aaaaaaaaaa
86761 aaaaaatagc ataggtaggc atttgatgat ttgatgattt cattcgcatc cctaaaagtt
86821 tatttgttcc tgggtcgtca gatagctttt tggccatctt cctgttgaga aaattgatgt
86881 acccttctgg agtcctccaa ttttccatta taatatggta agtgggagct agagctttgg
86941 gtaagaattg ggatgtgata aggaggatga gttttgcagt ggtgtgcatg gttaggagga
87001 gaaaaagctg gaggcagagt gttcacttag aggcttgggg taggaggggt aggtttaagt
87061 ggtgctcatc tgggccagaa tagggcaaaa agggaagaat gaaataacca gatgtctttg
87121 ctttgtcagt agtcttgcag ccctgaaagc ttttttttgtt gtgttatatt tgttgtaatt
87181 gaggtataat ccacataaca taaaacttac ctctttcaag tgtacaattt agtagttttt
87241 agtatattca taaaattgtg caactatcac cactgatacc agaacatttc tgggaacaaa
87301 aagaaactat atatccatta agagtcactc tccattttct cctacttcct tctctacccc
87361 cagtcatctg ctagtcggct ttctgtctct atagatttgc ctgctctgga tatttcatat
87421 aaatggaatc atataccata tggtcttttg tgactggctt cttttactta gcctaatgtt
87481 tttaaggttc atccatgtta tatgaatcag tacttaaatc atttataggg ttgaataata
87541 ttccatcata tggatatacc acattgtctt tatctgctca ttaattggta gacatttagg
87601 ttgtttccac ttttgtttat tatgaataat actattcaca ttcatgtaca aggttttgtg
87661 tggacacatt ttcagttctc ttcgatatat accaaagagc cacaatgcta aaacttccag
87721 ctttttacca gctatcccca gatgcgtagc ctagtaagcc ccatgttgga gtggtgtagt
87781 gttgaaaaca tggcatactc atacattaga taaccaggtt tcaattctgg tttggaagcc
87841 tttggatatt tgcattaccc atttgaattc tctcttgggc tgtgtttggt ttggggtttt
87901 gtacttgttt tttttttttt aactagatgt tttgaggcac ttggtactgt ggacatgtgt
87961 cagtcttaaa tatttgggtt ttgagcatat caagggcttg gtttgcagtt gacagttgaa
88021 tagcagtctt cttccttcca ttccttacag attctcctgt tcagagtcaa ccattgaata
88081 gcatatttat tgtttctgcc tgtgtgtctg ttagtgctca tatggtctag ttcctgagtt
88141 aagaagtata gggtagtggt catctttttt ctttgacttg attcctgcgt actgtgaatg
88201 cagagcaatg caggatatgt tgggttttct acaaacagag catcagccca gagacatgtt
88261 tgcatttgtt tctgtcaggt ttcctggctc aactggcacc ctttaaggcc agagaacgtt
88321 agtttaggca cttttcctag taaaatactt cttgtggctc ttcctgtgta cttggaataa
88381 aggaggcatt ccattgttag acatgcttgg gtagttcagg gtaatcttag agtcatgaga
88441 gatatgatat aaaggaataa ctagctaaac cagaaaaaat gcctgggtaa tgactagcaa
88501 ataggtggtc aacagatgtc ctcattagat tgaaaggtcc atgaaagcag ggactatttc
88561 ttttctttac tgcttaaaaa ggttagaact ggacctggca acatatgatg agctaaataa
```

FIG. 14 (cont'd)

```
88621 atacatattt gtgaattggg ttaacacata ttgcataaag tggttttggc tctgttttat
88681 tcttcataag ccctagtgat ctttttaatt tctgtaaaat gtggtcttga cccccccaac
88741 ccaagtgacc tccttatttg ctaggctctg atatttctgt taggtttcta ctgtattttc
88801 tgagatagca attagtagat actatttctc ctttgatgga gctagccata tattcttgtt
88861 tgttcatttt agctttcaaa tttctgtctg attcttgttc ttttactctg gaatgtagtg
88921 aatggaatga cttggaaggt acaaggtagg tcagtttagg ttgtctaggg ccttgcattt
88981 aaaagtttaa tttgatgaca tggtggatta caagaatgta acagtatcaa aatgatacta
89041 tcttcttgtg gtggtatgta gacttaaaaa gagaaactgc agagaaaagg gtcccttagg
89101 atgtagagca gcagttgata tgtgagaagt tgatgccttg cattagggat taggagtaga
89161 tgtggaagga agagatcagg tttgaaagag tttaaacaaa gaatctctag gatttgataa
89221 cactggatat cagaggggaa ggtacaagag agagggcaga atcaaaggcc actcagaggt
89281 taaaggaatc ataccggttt ggcatggtgg ctcacgcctg tcatcccagc actttgggag
89341 gctgaggcgg gcagatcacg aggtcaggag ttcgagacca gcctagccaa tatggcgaaa
89401 ccccgtctct actaaaaata caaaaattag ctgggcgtgg tggcgtgtac ctgtaggccc
89461 agctactcag gagactgagg cagaagaatc acttgaaccc aggaggcaga ggttgcagtg
89521 agccgagatc gtgccactgc actccagcca gggcgacaga gcgagactct gtctcaaaaa
89581 ataataataa taataaataa ataaaggagt aattccaaca cttgggaggc cgaggcagga
89641 ggattgcttg agcccaggag ttcaagacca gcctgggcaa catagtaaaa cctcatcgct
89701 ataaaaattt tttaaaaaga aatttagcca ggcatggtgg tgtgcccctg tagttcccat
89761 tactagagag gttgaggtgg aaggatctct tgaacccaag aggtcgagag tacagtgagc
89821 catgatgcac cagggcactc cagcatgggc aacagagtga gactttggga ggccatggca
89881 gaaggattgc ttgagcccag gagttcgaga ccagcctggg caatgtagtg ggaccttgtc
89941 tctataaaaa ttttacaaat atatataaaa gctgggcatg gggcacgtg cctgtagtcc
90001 cagtgactgg tgggtggggc gggggtgagg tgggagaatc acttgggccc aggaagtcga
90061 gattgcagtg agccatgatc atgccactgc tctctagcct gggtgacaga gtgagactct
90121 ttttgtctta aaaaaaaaaa aaaaaaaaaa aaaaaatggt tgtaccttga acagatacaa
90181 agcatgtaga agaggaaagc atttgggagg gagaataatt ggttggatac attaagtgtc
90241 aagtgacagt aggacctcta gaaatacaca aacagagctc cacaggtttt ttcattgtca
90301 tttcttatac cttttgttcc actacctact tttttcctac aactttctgt ttattttata
90361 gtttatgaat tttaagcaaa atacttcctt ctgcctctta ccagtaattt tcaaaagcgt
90421 ctgtattggt taggattaga tttggctggg aatgacagaa aactaaaaat aaaagcagtt
90481 taaacaagtt tatttctctc taatgcaaat gaagtttgag ctgtccaggc tttcttatgg
90541 tggtttggtc atgatcaggg acccaggttc tttcaaccat gtagccccat cttaacatgt
90601 gatttctatc ttattgttca agatggctat ttgagtgtca gttatcagtt ttatttagca
90661 accaatggga aggaaggggg atgaaaatgg gccctgtctt taaggatact tcctggacat
90721 agtgagtaga aggatggtta ccagagtatg ggaagggtag ttaggggggct gggggaaggg
90781 tgggaatggt aaaggggtat aaaaaaggta gaatgagtaa gaccatcaga gaaatgcaaa
90841 tcaaaaccac aatgatatag gtggctcacg cctatatgta tctcacacca gttagaatag
90901 tgatcagtaa aaagccagga aacaacaggt gctggagagg atgtggagaa acaggaacac
90961 ttttacactg ttggtgggac tgtaaactag ttcagccatt gtggaagaca gtgtggcgat
91021 tcctcaagga tctagaacta gaaataccat ttgacccagc catcccatta ctgggtatat
91081 acccaaagga ttataaatca tgctgctata aagacacatg cacatgtatg tttattgcgg
91141 cactattcac aatagcaaag acttggaacc aatccaaatg tccatcaatg atagactgga
91201 ttaagaaaat gtggcacata tacaccatgg aatactatgc agcaataaaa aaggatgagt
91261 tcatgtcctt tgtagggaca tggatgaagc tgtaaaccat cattctgagc aaactatcta
91321 agggcagaaa accggacacc acatgttctc acttatacgt gggaattgaa caatgagaac
91381 acttggacac agagcgggga acatcacaca ctggggcctg tcgtggggtg ggggaggggg
91441 gagtgatagc attaggagat atacttaatg taaatgacga gttaatgggt gcagcacacc
91501 aacatggcac atgtatacat gtgtaacaaa cctgcacatt gtgcaccatg taccctagaa
91561 cttaaagtat aaaaaaaaag acctactatt tgataccaca atagggtgag tatagtcaat
91621 aatgacttaa ttgtacattt taaaataaca taaaaagaaa aaaataaaat aatgcagagt
```

FIG. 14 (cont'd)

```
91681 ataatttgat tggttgtaac tcaaaagata aatgcatgag gggatggata ctctattccc
91741 catgatatgc ttatttcaca ttgcatgcct gtatcaaaac atctcctgta ctccataaat
91801 aaatacacct actatgtatc cacaaaaatt tcttaaaaaa ggatactttt gagcgtttca
91861 agcattactt ctagttatgt tcagttgatc agaatttagt catagccaca cttcagcttc
91921 aaggagggct gcagaacgtc tttattttag gcagctatgt gcccagttaa aaagcagatt
91981 ttctcccaag gtaaagagag cagataggca ttaggagact actagtagtc ttttaatttt
92041 ccaggccggg cacggtggct cacacctgta atcccagcac tttgggaggt cgaggcaggc
92101 ggatcatgag atcaagagat ggagaccatc ctggccaaca tggtgaaacc ccatctctac
92161 taaaaaaaat acaaaaatta gctgggcgtg gtggtgcgtg cctgtagtcc aagctactca
92221 ggaggctgag gcaggagaat tggttgaacc caggaggtgg aggttgcagt gagcgaaggt
92281 cgtgccattg cgctccagcc tggcaacagg gcgagactcc atctcaaaaa aaaaaaaaaa
92341 aaagcaggga tttgctccca aggtaagaga gcaaatagac attgggagac tattagtagt
92401 ctcttaattt cccagaatga gaaccagatt ctttccggtt acagaactcg tttctccaaa
92461 cattaattat tcttataata attttaaaaa atactaaata tataattatc accagccaaa
92521 tgcttctttt aagaaataga gacagggggc cgggcacggt ggctcacgcc tataatccca
92581 gcactttggg aggccgaggc aggtggatca cctaaggtca gagttcgaga ctagcctggc
92641 caacatgggg aaaccctgtc tctactaaaa atacaaaatt agccgggcat ggtggtgcat
92701 gcctgtaatt ccagctattc gggaggctga ggcaggagaa ccgcttgaaa caaggaggca
92761 gaggttgcag tgagccgaga tcgtgccatt gcactccaac ctgggcaaca agagcaaaac
92821 tccatctcaa aaaaaaaaga aaaagaaata gagaagagac agggaagcca agctcatgcc
92881 tgtaatcaca gcacttcggg aggccaaggt gggcagatca cctgaggtca ggagtttgag
92941 accagcctgg ccaacatgga gaaacccagt ctctactaaa aatacaaaaa ttagctgggc
93001 atggtggtgc ataccggtaa tcccagctac tcaggaggct cagacaggag aagtgcttga
93061 acccgggagg cagaggttgc agtgagccaa gactgtgcca ctgcactcca gcctgggtga
93121 cagagtgaga ctctgtctcg aaaagaaaaa aaagaaaaag agacggggcc tcacatatgt
93181 acagtggtat gatccgtagt tcactataat cttgagctcc tgaaacctga tgctttaaaa
93241 caaaacagta caaaactact aaatttataa ttaaatatat aaataaaata taataaaaat
93301 gttcacttct gtttttatat tctttaaaat gacccatagg ctggtgatta gtaactaaag
93361 catatgctgt ggaacatcca gcactgatgt aagtatatga agtttgaatg ccaggtcagt
93421 agattcagaa gctaagttac tgtatggtaa agaccatgtt ttgcctgagc agctttggat
93481 atggtttttt cttttttttc ttttttgag atggagtctc gctctgtcac caggtggagt
93541 gcagtggcgt aatctcagct cactgcaagc tctgcctccc aggttcaagt aattctgcct
93601 cagcctcccg agtagctggg gctacaggtg cataccacca cgcccagcta atttttgtat
93661 ttttagtaga gatggggttt taccatgtag gccaggatgg tctcaatctc ccgacctcgt
93721 gatccccctg ccttggcctc ccaaagtggt aggattacag gactgagcca cagcacttgg
93781 ccggatatag tttttctatg tgtgtttttc ctaaacctta ttatacataa acatacaagg
93841 acagagatca aatgcccccct gtctagaaac accatttctg ccaggcccat cttaataaga
93901 ctatgtcttc tttttatttg tttctatact tcctttttttt tttttttttt tctgagacag
93961 ggtttcactc ttgttgccac cacactcagc taatttttgt gtttttagta gagacaaggt
94021 ttcatcatgt tagccaggct ggtctggaac tcctgacctg aagtgatccc cccacctcgg
94081 catcccgaag tgctgggatt acaagcgtga gccatcacgc tcagcctaga cttcttagtg
94141 tggtgtttca ttttcttttc tctggttccc atccagcttt gttcattgta catgctcacg
94201 gtgcacttta tatgacctgt tggcatattt tctcactctc tttttgtctc tcttcacttc
94261 cagcagtgtt aaataactct ttccattctg cagttttcct gataagaatt tcagatggtg
94321 gtggccaggt gcggtggctc acgcctgtaa tcccagcact ttgggaggcc aaggcggcag
94381 atcacttgag gtcaggagtt tgagaccagc ctggccaaca tggcgaaacc ccatctctac
94441 taaaaataca aaagctagcc gggtgtagta gcgcatgctt gtaatcccag ctactaggga
94501 ggctgagtca ggagaattgc ttgaacccgg gaggcggaag ttgcagtgag ccgagatcac
94561 aacactgcac tccagcctgg gcgacagagc gagactccgt ctccaaaaaa aaaggcaatg
94621 aataattgga caaggaacca aaactttat tctgaaaaga gaaaattcca gtctatagca
94681 agggcagttt tccttctaag gaacagtact gatatatcat ggctaaagaa gcaggctcag
```

FIG. 14 (cont'd)

```
94741 cttctttgtc cctttcacta atttgctatg gcttctaaca taggctagga aaagaaaaaa
94801 atctgtttct ctttctcctc tcctctcctc tcctcttccc tctcctctcc tctcctctca
94861 tcttccctcc cctcccctcc cctctcctcc cctactcccc tctcctcccc tcccctctct
94921 ttatctgtct atctgctaag ggcagcaaat ctgtatccat acaggtctgc agcaacttca
94981 attcttgcct cctcagaaga aacaatttga ctgagggtca taaggcagaa ggagagacca
95041 aggcaagttt tacaacagga gagagtttat ttaaaagctt tagaacagga atgaaaggaa
95101 ggaaagtaca cttggaagag ggccaagcag gtgacctgaa agacaagtgc accaacacat
95161 agcctttcaa caggatagag agcagttaaa actgccctgg aaaagccaga cttacaggct
95221 actctgtata atagaaactt caggacaggg tgcggtggct cacacctgta atctcagcac
95281 tttgggaggc cgaggtgggc ggatcacgag gtcagaagat cgagaccatc ctggctaata
95341 cggtgaaacc ccgtctctac taaaaataca aaaaattagc cgggcatggt ggcgggtgcc
95401 tgtagtccca gctacttggg aggctgaggc aggagaatgg tgtgaacctg ggaagcggag
95461 cttgcagtga gctgagatca tgccattgca ctccagcctg gtcgacagag ccagactccg
95521 tctcaaaaaa aaataaataa aaaagaaact tcagcatgct tcctaatact gttcaaaggt
95581 ctcccttttt atgattttat ttaaaaaaat tttttttttt tgagacagag tctcactctg
95641 ttgcccaggc tggaacgcag tggcgtgatt tcggctcact gcaacctccc ctcccaggtt
95701 caagcaattc tcgtgcctca gcctcctgag tagctgggat tacaggtgcc caccaccatg
95761 tctggctaat ttttttgtat ttttaataga gacagggttt caccatcttg gccaggctag
95821 tcttgaactc cacaccttgt gatccaccca ccttggcctc ccaaagtgct gggattacag
95881 acgtgagcca ctgcgcccag ctcaattttt atatttttgg tacagaccag gtttcactat
95941 attggccagg ctgttctcaa actcctgacc tcagttgatt cgcccacctc agctcccaaa
96001 gtgctgggat tacaggcatg agccactgcg cccagcaggg tctccctttt taaacgtatt
96061 ttctttttat agcctacaaa ctacaagaga tgccttttaa taaactggat ggtatgtctt
96121 aacgtctgat ggagtttaaa ggcatccaag ggttacgtct gtgatagatt gccaaggcat
96181 acaggtctga tcaggagagt ttcttgatga ctagctatgg gctatgcctt tgtagcacat
96241 gatcccaact ccagcaggga tatagttagt gacatgctgg ctttgtcttc tccctaactc
96301 ctggattact acaaatttct tcttcgtgca ggaatcattc cctcactcta tacatatctg
96361 ctgttaaaaa aaaaaaagtt aagatattat agccattata ttgtagcagc catgatatta
96421 tagctcagta aatgctgctt tccaaatatt ggctaattta accatagcat gtcttcaatg
96481 ttagaagcca gccctcattt ttatcaaggg ctgaagtttg ataattcttt gtgttatttg
96541 cttgtgaaaa taagtagaac aaaaaggatt agggacctaa ccttgtatcc catgtatccc
96601 agtgaacctt ttctgactta aagcttcctt tctttttttt tggagatggg agtcttgctc
96661 tgtcgcgagg ctagagtgca gtggcgcgat cttggctcac tgcagcctcc gcctcctggg
96721 ttcaagtgat tctcctgcct cagcctccca agtaattggg actacaggct catgccacca
96781 tgcccagcta attttttttt taatttttag tagagacggg gcttcaccat gttggccagt
96841 atggtctcga tctcttgacc tcgtgatcca tccaccttgg cctcccaaaa agcttccatt
96901 cttagtcttg gtacttctaa gtggcattgg gtcaatagct ttctgcctaa gaagagaatt
96961 ggctgggcat gatggctaac acctgtaatt ccagcccttt gggaggctgt ggcaggagga
97021 tcatttgagc ccaggagttc aagaccagcc ggggcatcat aggaagaccc catgtctgca
97081 taaaataaaa taaattagcc agacttggtg acatgcacgt attgtcccag cttgtcagga
97141 agctgaggtg ggatgattgc ttgagctcag gagatcaagg ctacaatgag ctatgatcat
97201 acaacaccag tgcactctag cctgagtgac agagcaagac cctgtctcaa aaaaagcagg
97261 ggggcatagt cacctcccta aaatattagt tgaacagtat gtattcagaa gtccagaggc
97321 tctgtatttt attaatattt tcaaggcact atttctgcag aaatcaagtc agcaagactc
97381 tttgaggacg ttacaggcag aggggctaaa gatacctttg aggaagctca agtacttggg
97441 tgggaggtga tagataaagg gtcagtagaa ataatgtctc tttttatttt ttttcccatt
97501 aaaaaatttt gttttaatag caatggagat ggggtctcac tgtgttccct gagctggtct
97561 ggtctcgagc tcctgggttc aagcagttct cccaccttga ccttctaaag tgtagggatt
97621 atagacatga gccaccatgc gtggcaaatt tcttttcttt cctttttttt tttttttttt
97681 tgagacagag ttttgctctt gttgcccagg ctggagtgtg gtggcacgat cttggttcac
97741 tgcaccctcc acctcccagg ttcaggtgat tctcttgcct cagcctcctg agtagctggg
```

FIG. 14 (cont'd)

```
 97801 attacaggcg cccgccacca tgcccgggta atttttgtat ttttagtaga gatgggattt
 97861 caccatgttg gccaggctgg tcttgaactc ctgacctcag gtgatccacc cgcctcagcc
 97921 tcccaaagtg ctgggattac aggtgtgagc caccgctgcc ggttccaatg tctcttttgg
 97981 atggtggatc ctgaagaata gctgctggtt ctttggggat gcctggggaa tactgtgcag
 98041 gctttgtgat gggctcagca gtgaggcctg tacagtatct taggtcttgt gggcctcagt
 98101 ctgctctctt ggctgttctc taccacctcc tgccattaag tttttaagaa aaaggaatag
 98161 ttttattata ttctttggta aacaaagcaa attaagaagc tttatatttt ccacatttat
 98221 ttaccaaact ccctatttgt ttttctctat agtgattcag tttagagacc tattcaatga
 98281 agcatgcctt gatgttgaat ttagagtcta ctttttccag aagaaaagag ccagggagct
 98341 ccaatagtag tcatctcaga atataaaagt gttatagaaa tgatgtaaat caggccgggt
 98401 acaggggctc acgcctgtaa tcccagcact ttgggaggcc gaggcgggcg gatcatgagg
 98461 tccggagatc gagaacatcc tggctaacag ggtgaaaccc cgtctctact aaaaatacaa
 98521 aaaaaatcag ccaggtgtgg tggccggcac ctgtagtccc aactactcag gaggctgaga
 98581 caggagaatg gcgtgaaccc aggaggaaga gcttgcagtg agccgagatc gcgccactgc
 98641 actccagcct aggcaacaga gcaagactcc gtccccaaaa aaagaagaaa aagaagaaaa
 98701 gaaatgatgt aaatcagctg cccttcactc tgtgttgagg tggggatgt ccctaattgc
 98761 agtaggagag agcctctctt ttatctggga ctaaaagccc ttgccctaca tacctcataa
 98821 ttattttagg gttaactgat tcaattgtca gaaaagaaca agctgtatct tgtttctgta
 98881 catattctac tttgtgagta tttttatttc attgctatgt gattggaatc aactcaggaa
 98941 agaggaaaaa aataagatag aggttataga attctgaatt ctgaagggaa ttctgagaat
 99001 tatcagtaaa atatgtcaaa atgtgatatt ttacttccac caagaattag gccatatctt
 99061 tgtgtgaaaa taaattatta ttatttattt atttattttg agatggagtc tcgctctttt
 99121 cacccaggct ggagtgcaat cacacaatct cggctcgctg caacctccac ctcccaggtt
 99181 caagcgatgc tcctgcctca gcctcccgag tagctgggat tagaagcgcc cattaccaca
 99241 cccagctaat tttgtacttg tagtagagac agggtttcac catgttggcc aggctggtct
 99301 cgaactcctg acctcaggtg atccaccccc cccccccca cccttggtct cccaaagtgc
 99361 tgggattaca ggcatgggcc accgcaccca gcatacggaa ataaattatt aaccagagaa
 99421 attttgacta aggtttttat aaatgttagg tgaaccattg ctctaaaaga tacaaaatta
 99481 taacaagctg aaaagttttt taaaaatctg cattttagtg gttcagtttt tcagttgttc
 99541 tgagtgctaa tagttggagt ttataaattg taagaagcaa tctacggaga ttctgtgatg
 99601 aaggaatttg ttgaatgccc tgtctgcctc acagtctcag tctttatgat agagtcttgt
 99661 cttctcacaa ggagagaaaa gatttgaggc tcttttgatt acttacttac ttgcttattt
 99721 atatattttg cctctttgtt tttgccgcaa atacaaatgt aatggaacct tagaatagga
 99781 gagacgtgtg gatcccctgg taggcactgt tctttctatg ttcctggagc caagttcatg
 99841 gaattacctc caagactacg gatccctggt tttctttcat catgatagga ggcattttct
 99901 agaacctgaa tcttacttta aaatgcatgt aagacctgca aggagtggta gtgaagtggg
 99961 tggaatatat tcttagcacc agacaccttt aaaatattta agttctcggc cgggtgccct
100021 ggctcacgcc tgtaatccca acactttggg aggccgaggt gggcagctca cgaggtcagg
100081 agaccgagac catcctggct aacacggtga aaccccatct ctactaaaaa tacaaaaaat
100141 tagccaggcg tggtgatggg tgcctgtagt cccagctact cgggaggctg aggcaggaaa
100201 attgcatgaa cccgggaggc agagcttgca gtgagctgag atcgcaccac tgcactccag
100261 cctgggtgac agagcaaggc tccttctcaa aaaaaaaaaa aaaaaaaaaa aaaaatatat
100321 atatatatat atatatacac acacacacac acacacacac gtgtgtatat atatacacac
100381 acacatgcat atatatatac acacacatgt atatctatag atatatacat atatatgtgt
100441 atatttacat tttcttatgt cagggtctgg cttggagtgt attgtgttcc cagagcagaa
100501 ttcttttttt tttttttgag attgggtctt actttgtcac ccaggctgga atgcaatggc
100561 gtgagcttgg ctcactgcag cctcgacctc acaggttcaa gcaaccctcc cacctcagcc
100621 cctggagtag ttaggataac aggcgcacac taccattttg tattttttgt agaggcgggg
100681 ttttatcaca ttgcccaggc tggtctcgaa ctcctgagct caagcaatcc acctgccttg
100741 acctccccaa atgctggggt tacaggcgtg agccactgtg cccagccgca gagttcatct
100801 tgagaccctg acttctgcca gctctgatcc tagtgggtgg ggctctgggg ctcagtgaaa
```

FIG. 14 (cont'd)

```
100861 cagtcagccg ttttgcttca gagaacacaa ataagatttt ggcttgatgc tggttgttgc
100921 tggcgtcata tagtctaaaa cgtttgctgt caagaacatt ttagtaaaag tttttgttgt
100981 gctttcatct agtcaagaaa agataggaag tggcagctga cagggcagtg tcttcatgcc
101041 cctcaacctt acattggaca ctgaagtagg attgtgtttt cactggaagt cccagtgggg
101101 ccttatctcc tggatgctca aagtgcagct cagatcctgt tgggtaaaaa gtctagtcaa
101161 aatggaggac atggagaagg ccaacaggca gagctataga gctgacatag ggcattcttt
101221 gtacttccct tagccactgt actttctttc ttcctccatc tcctccttcc ctcttctatc
101281 tcattttggt ttggcctttg ggaatagtgg gttttaaaaa atatttgaac tataacatat
101341 ccttgtacca taaagaatga gcctgactgc tttacaaagg atttctataa aaagtaatct
101401 tttatactaa gagaaatgac acatctgttt taaacctgtt acttttcttc cccgggcttt
101461 gctctttctg caggtccgtt tgacatggtt cttgaaactc ctggtagcag ccatttacta
101521 gtagcactct ttatcttaga cacagcacct aaagcaattg taggtgtttt aagaacagaa
101581 agcccatctt aagcagacca gtttgaggga ttggcagtgc tgtcaagaaa caagggcttt
101641 gtggcagtct ctctaaaaac tccctatgag tccatttctt gcaaacttct ttagactcta
101701 ctgtatcttt tcatcagaag ctacctcttt gatgtgggaa gtgtcatgaa tggactgact
101761 ctctggaatt taaaaacaaa gacaatatgg caaaaagaaa acctgacttt tagtactgta
101821 tgtgttgcta attagctctg tattcttggg cagactactc catgtatccc agccatccat
101881 atgccctatt tgtaaggatc taatgagatg atattgtgaa gaatgccttt gtaaactgta
101941 aattgctttg tgaataaaga tactatctct gataaacagt accagttctc agccaccaat
102001 aacctgatac tcccatactg tgtttggaag aaacacaaaa caatgaagag taattgtgac
102061 ttttcaatgt gagttgtatt cacaaagctc atatactttt tccctgcctt ttgatactgt
102121 ttatcgcttt ctgtgttgta atgggaagat cacacagcaa tcattttctc agtacaaagt
102181 ataactacaa ctgagcttgc attgaagatc tttaacaaag atgcaaagct gctgtccaga
102241 aatgttttct ttccatttc tcttgtacct cccagtattt taagaatcct tgaggctggg
102301 caccataact cacgcctgta atctcaacac tttgggaagc tgaggcagga ggatcacttg
102361 ggcccaggag tttgagacca gcctgggcaa catagtgaga cccccatctc tacaaaaaaa
102421 tttaaaaatt agctgggcat ggtggtgtgc acctgtggtc tcagctactt agggaggctg
102481 aggtaggagg attgcttgag cctgggaggt caaggctgca gtcagtcatg attgcaccac
102541 tgtgctctat ctagcctcca acctgggcaa cagaagcgag accctgtctt ttttttaaaa
102601 aaaaaagact atccttgatg attggttttg agccaacgga atgggagcat atggtagagt
102661 ttcaacactc tgaccctagt ccttctgaca ggcagtcaca aaatgagatc atgaagtctc
102721 taagagcagc tgatgaaaaa ggaaatggga atgtagatgt tcaatcagca gccctccaga
102781 cccagagttt gctcctctgt ggtgtctcta ggtggagaat aaggacttga tttgccattc
102841 tggagtgcaa atatctagct ttttgcagct tcatattaag atttcttgaa atgtacttag
102901 taatatccat gtgtgacttt gccaagtgat ggctttgggc tggaaaggat tttagcaggt
102961 tttagtctaa tttaagccta atctaacact gctgagaaag gaggagatgt ctttggtttt
103021 actttctaat atatggtacc tcttagccgg gtgcagtggc tcatgcctgt aatcccagca
103081 cttcgggagg ccgaggcagg cgatcacttt aggccaggag ttcaagacca gcctggccaa
103141 catggtgaaa ccccatctct actaaaaata caaaaattat cccggtgtag tggcgcacac
103201 ctgtaatccc agctacttgg gaggcagaaa caggagaatc gcttgaacct gggaggcaga
103261 ggttgcagtg tgccaagatc atgccactgc atgccactcc agcctgggca acagagcaag
103321 accctgtctc aaaaaaaaaa aagagagatc tatctctctt ctttttatat acatatacat
103381 atacatacat acatacatat atgtatgtac acacatatat atatatggcc cctctttttt
103441 tatttgagtc ggaatctggc tctcttgcca ggctagagtg cagtggcatg atcttggctc
103501 actgcaacct ctgacttcct ggttcaaacg gttctcctgc ctcagcctcc cgagtagctg
103561 ggattacaag catgtgccac cacacccagc tcacttttgt atttttagta gagacgggat
103621 ttcaccatgt tggcagggat ggtcttgatc tcctgacctt gtgatcctcc cacctcagcc
103681 tcccaaagtg ctgggattac aggcatgggc caccgtgccc agcctttttt tttttttttt
103741 taaagagacg gagtctcact ctgtcaccca ggctggagtg cagtggcgtg atcttggctc
103801 agtgcaacct ccacctcccg ggttctagca attctgcctc agtcttccga ctggctggga
103861 ctgcaggtgt atatcaccgc aaccagctaa ttttttgtat tttagtagag acagggtttc
```

FIG. 14 (cont'd)

```
103921 actgtgttgc ccaggctggt ctcgaactga gctcaggcag tccacccgcc tcggcctccc
103981 aaagtgctag gattacaggc gtgagccacc gtgcctggcc tatatggtac ctctttagga
104041 gccagacctg gttaatcaga cacatggctt tcatgactcc tttgcttgag tagcttaata
104101 actcaataaa tcaaaagatg aataaatatt ctaatgtgtg aagatactct aatagataat
104161 aggcaattaa gaatggacat ccacggctgg gcgctggggc tcatgcctgt aatcccagca
104221 ctttgggagg ctgaggcggg tggatcatga ggtcaggagg tagagcccat cctggccaac
104281 atggtgaaac cccatctctg ctaaaataca agctactcga gaggccgagg caggagaatt
104341 gctcgaactt gggaggcgga ggttgcagtg agccaaaatc gcatcactgc actccagcct
104401 ggcgacagag cgagactccg tctcaaaaaa aaaaaaaaag aatggacatc tactgaaggt
104461 gattgcatca tcctacccat tcattaatct aactccctac aggatacttt cctaggagac
104521 actgacaggt ctgttttctg aaatccagag aaaggcagca atggggaggg gtgcagtgta
104581 tgtatgtcat acctgtgctt ggtatatctg agttgcctgt gtatgatagc agctggggaa
104641 tcaaatcata gataaattgt tctcatacag gtttgtccta tgactaccta ttcttattaa
104701 acaattggct atattgaccc tttttggttt tggaaaaata ataataattt ttttaagaga
104761 gaaaaagaaa caattggcta cccttcaaca gtgatgttaa aaccatttca cattctttag
104821 cagtggtcac tgtcctatgt ctaactatgt gcaggttgag aaaaaggact gcccgagtta
104881 tagatgattc tgtgagaata agaaatcatt gcttttgtaa cacatgaggt aaaagtaatc
104941 tcaaagttga catgctgatg gggactcctg gcaaggggag ttccctgccc tcaacaaaag
105001 gtcatccaca gctactggaa catttttgtt gtctgagaag tataaagtgc cttagaaata
105061 cctgaatcca ttaatgcctc cagttggtga aatcagaatt tgcaggtgac tgaaattgac
105121 agtagtgcct tgttcttact cactgttcaa atgacaaccc acatgtttta tggattgggt
105181 atacagatgt atgctctaac agcagtatct ccctccagag ccactgtgta ccaagcacca
105241 ggtcctccag ggatagttgg ctctattcag tctttgattc attcaacaag agcttactaa
105301 gctccttttt ggtaccagat actctttgtt gctgaaaata aataaaaggc cagcaagatt
105361 aagtagactg tgagatctgg accagtaatt tgacaacaca aagtactgtc gtaaagatac
105421 agtttctgat gtgtagtgac cattccgtat gaaagcttag tctttcagga gattaaaatg
105481 ggtggtggaa tattcctacc tagcaagcaa gcaaggtgaa atgagtggct gtttgactcc
105541 cacctgctga tgctggtctt ttttggttcc tagggcttat aatgatcaac atttcttgag
105601 ccctcactat attctatgct aagctcttta catgtatgaa tttacttaat cttcacaacc
105661 accctaagaa ataggtactg ttgtccttac tttacagatg aggaaatgga agcacaaaga
105721 agttaaggac cttgctgaag gtcatggagt agaggcagga ttcaaattta gggaactcag
105781 cctacagtcc atgctcttaa agatgttata tcctgtctct gggcttagaa ggggttcatc
105841 ttaggccgga cacagtggct cacgtctgta atcccagcac tttgggaggc caaagcgggc
105901 agatcacgag gtcaggagtt cgagaccagc ctgaccaaca tagtgaaacc ccatctctac
105961 taaaaataca aaaattagcc aggcatggtg gtgtgcgcct gtagtcccag ctactcggga
106021 ggctgaggca ggagaattgc ttgaacctgg gaggcggagg ttgtggtgag ccgagatcgt
106081 gccactgtac ttgagagtga gtgacagagc aagactctgt ctcaaaaaaa aaaaaaagac
106141 ggccaggcgc agtggcttac gcctgtaatc ccagcacttt gggaggccga ggtgggcgga
106201 ttacctaagg ttgggaattc gagaccagcc tgaccaacgt ggagaaaccc cgtctctact
106261 aaaaatacaa aattagccaa gcgtggtggc atatatctat aatcccagct actcgggagg
106321 ctgaggcagg agactcgctt gaacctggga ggcggaggtt gcagtgagcc gagatcacgc
106381 catagcactc cagcctgggc aacaagagcg aaactctgtc tcagggaaaa aaaaaaaaaa
106441 aaaaggaggg ggcgcttcat cttgactaac ttcctgcatt ggtggagctt gatagagtgg
106501 tccttcccag atccttccct gcatacagag cctgtctctt ttctgattgg tccctaaggc
106561 cagattacct gtccctaata ctgagcagaa gctggtgaat gaaacaggag atccctcagt
106621 caaaacaaaa ggaaaaagaa aaatgaaaca ggagatccct tctctacagc ccagatgtaa
106681 gtccagctgt gcccttcacc acctgggtga ccccacctct gtgaacatag gtcctcatct
106741 gtaaagtgta gataatgtta tttcatcgga tcatttaggg gattaaataa gataatgtac
106801 ttcgtggttt ctggctctta gtaagtgctt aataaatgtt agcgattttt attatcattg
106861 tccttagcct tgagaacaag ccagggaata gtgtctcaga ccagatgcta agacctaggt
106921 agatgggcaa ttttccttgg ttttgacaag acaataattt tatcctgtgt atttctcttg
```

FIG. 14 (cont'd)

```
106981 acttttttga tgtgaaaagc agagaggtaa agcattattt gacagatgta tggattcaag
107041 caagaaactg aggtccaatt gcaaagaaat ggcttgtata actcagagcc ctgtctgagg
107101 aaacacagag gaccctagag ggcggagaat gaacacagcg caggggctag ttccagagtc
107161 gcattctcgg ttagttcact ttcaagtgtg ggtgagggtc ccttgtcagt aggcagagaa
107221 tttttttccc ctgcaccaac acatacctgc tgcctagtgt ttattaaaca aaactttatt
107281 ttaatgtgaa atagaattca tgacttgtcc aaaatggaga ggcaagggag ctctttaaca
107341 ggcttgttga gcccctttc ccacctgttc ctgtgccaga ctttcccaaa ggcttacttg
107401 ccaatggttg ctcctcagat ctcagggcta gctcactcta taggctccaa gccagagtga
107461 taccgccgcc gccgctgttg ctcccaccag ccaatcagtt tcctgctgta aggatgtaac
107521 ttgctgtgaa gctttcacct tcctcctttc ttcctgtctt caatgttgta tgtctttgtc
107581 ctggtgcttt tgccatacag ccagtgtttc aaagaaaatt ttcaggcact aaagttatag
107641 cccttactac ctttccaagg agatgtgaga tagctgtgga aaagaagagg gctcctctgc
107701 ctctgtgcag aaggaacagt ttacttcttg atagtgtgct agctcctgag ctaggtgggg
107761 gacttgctgg gattcaagag agtgcattac ctgacctctg gacaagtaga ctgggcatag
107821 cctgcccaag gacagcaccc taacctgcag gaaccaaggc cgaagactga tttcaccttc
107881 tcgtactccc ctttcctaag ctaaagcttg ctctgtaaca ctgcccccagg tctgtggctt
107941 aaaacagcca tttcctttca ccagtgaatt aagctcactc tttataaaat gtttcagctt
108001 ggggattgga aaggctctct gtgcctttct gtctctgtct gtttctccaa gggttgatgt
108061 tgatggcttc tgtctttgtc tttacaggga actctaatga tccaggacaa agaagttacc
108121 ctggagtatg tatcaagcct ggatttttgg tactgcaaac gagtaagtac caagaatccc
108181 tttctttaga agtaagtatc tggaataaca gctcctccat atctctagga aggctgcctg
108241 ctaacatgca ttcccaagga caaagctctt cttcctcagg tcacttcagt tgaacaggag
108301 gaggtcaaga caaggtcatt cataatttct ccttcccagc tgctacatgt ggccatagag
108361 agttctggac ctgcaattgg agacactttc ccaaggacat gtgccattat ttctatcagt
108421 tataaaaata acagttcctt gacatataat atcttctcac ctctcctggg ggtggtcata
108481 aaggaattct tggttggaaa agtaggtttg gagagactag ttctttggga gtcgtacatt
108541 ttttggatat tcttgggttt ccaagggtat agaacttcag acaccatggc atttacctc
108601 tattaaactc catattctct tagagtggga tatttaaaat tttaggctat actctttttt
108661 tttgaaacgg aatctcattc tgttgcccag gctagagtgc aatggcgtga tttccactca
108721 ctacaacctc tggctcctgg gttccagtga ttctgctgcc tcagcctccc gagtagctgg
108781 gattacaggc acttgccacc tcacctgcct gatttttgta tttttagtag agatggggtt
108841 tcaccatgtt ggccaggctg gtcttgaact ccgacctcaa gtgatccacc tgcctcagcc
108901 tcccaaagtg ctgggattat aggcatgagc caccgcgctg gcctgtttat ttatttattt
108961 atttattttg agacagagtc ttgctctgtc gcccaggctg gagtgcagtg gcgcgatctc
109021 agctcactac aacctctgcc acccgggttc aaacgattct cctgccccag cctcccgagt
109081 agctaggatt acagttgtgt gccaccatgc tcagctaatt tttttgtagt tttagtaga
109141 gatggggttt caccatcttg gccaggctgg tcttgaactc ctgacctcat tatccaccca
109201 cctcggcctc ccaaagtatt gagattacag gcttgagcca cggcacccag ccggctatac
109261 tctttaaagg tccagtttga ttgcagtgag catgaaaata taatttgttt tcattgctac
109321 tacttagtat caaaaataat tatgaaaaat atataaagtt tctgagcccc gacacactaa
109381 aaatgttaca gtacttgaaa aaatttagta aagactttag cttgacattt gttagtctcg
109441 gtagaattga cattgtgtta gtctcggtag aatacaactt gaagagctat gattgttatt
109501 agccaaagta ctcatatttc atggatatac tcccttatgg tgtcatttta ggaagatatt
109561 tcgtttcctt ttattgagat aaaatacatg taacattaca tttgccattt taaccatttt
109621 gaagcattaa ttcagtgaca ttaagtacct tcacaatgtt gtgcagctat caacactact
109681 tcctagaact tctttttttt ttttttttaa ataagagatg ggatctcact atgttgccca
109741 ggctggtctc acagtccctg gctcaagtca tcctctcacc tcaacctccc aaatagctgg
109801 gactataggt gccatcatgt ccaggttagt tccagaaatt tttttttct gtcttttttt
109861 tgagacagga tctcactctt gtttctcaag ctggagtaca gtgatgtgat catggctcac
109921 tgtacccttg acctcctgtg ctcaagcgat cctctcacct tggcctcccg aagttctggg
109981 attacaggtg tgagctgcca tatctagcct cagatctttt ttaaaccctc aaaaggaaac
```

FIG. 14 (cont'd)

110041 ctcttatcat taatcagtaa cttcccactt cttcttcccc cagtccccag aaaccattaa
110101 tcttttttct atctccatgg atttgcctat tccggatatt tcatataaat ggaatcaaaa
110161 tatgtaaact tttctgttgg cctttcacct agcatgtttt cagagttcat gtatgttgca
110221 gtatttatca gtacctcatt tctttttgtg gctaaataat atgaatatat cacattttgt
110281 tcatccattc ctcaattgat ggacatttgg gttgtttcta ccctgacttt ggtgaataat
110341 agaacctttg tgtgctagtt tttgtttgaa cagctgtttt cagttatttg gggtatgta
110401 tccaggagtg gaattgctga gtcatatggt aattttatat ttaactcttt gaggaaccat
110461 caaactgtat ttcttttatt ttattagcaa acctttttcat agaccacagc tgtaccattt
110521 tatattccag caatatgtaa gggcttcatt tctccacctg cttgccaaca tttgttcttt
110581 tccctttatt tgataatagc catcctaatg ggtatgaaat aatatctcat tgtggttttg
110641 atttgcattt tcctaatgac tttgagggtt ttttttcatg tgtttgttgg ccatttgtat
110701 acctcctttg gagaaatgtt caaccaagtc ctctgccctt tggaattgat ttgcatgtat
110761 ttttgttgtt gagttataag agtactttat attttctgga tattaatccc ttatcagata
110821 tatgatttat aaatattttc tatgtgttat ctttcacttt cttgagagta tcctttctaa
110881 agaaaaaaaa agagagagag agagataagg tgtggctcat ggctgtaatc ccaacacttt
110941 gggaggctaa agtgggcaga tcacttgagc ccaggagttc gagaccagcc tgggcaacat
111001 ggcaaaaccc catctctaca aaaaatacaa aatttaactg ggtgtggtgg tgcatgccta
111061 tgatcgcggc tactaagcag gctgaggtgg gaggatcacc tgagcccagg aggtcgaggc
111121 atcagtgagc tatgatagtg ccactgtact tcagtactcc atcctgggtg acagagcaag
111181 accttgtctc aaaatttttt ttagctgggt gtggtggctc acgcctataa tcccagcact
111241 ttgggaggcc gaggcaggcg gatcatctga ggtcgggagt tggagatcag cctgaccaac
111301 atggagaaac cccatctcta ttaaaaatac aaagttagct gggcatggtg gcacatgcct
111361 gtaatcccag ctacttggga ggccgaggca ggagaatcac ttgaacctgg gaggcagagg
111421 ttgcggtgag ctgaaattgc actattgcac tccagcctgg acatcaagag tgaaactcca
111481 tctcaaaaac aaaaaagaaa aattttaagt ttattatgta cctattaaaa ttttttttgta
111541 attaaaacaa atgctaatgg cggtattatt cataatagcc aaaaaatgga aataaccaaa
111601 atgtccattg gctgatggat ggatgaacaa gttggcatat ccatacaatg aaatgctatt
111661 tgacaatgaa aaggaatgaa gtactgatgc atgttacaac ctagatgaac cttgaaaata
111721 ctatgccaga cacagaagac catacattgc acaattccat gtccctaggg gtaagaatgg
111781 gggaggtaac tccactagat ttcttttggg gtgatgaaaa tgtttcagaa ttagattatg
111841 gtgatggttg cactatacat ttactaaaaa tcattgaatt gtacacataa aataggtaaa
111901 ctttatgggg tttgttttttg tttttaagag agagtcttgg tttgtcaccc aggctggatt
111961 gcagtggcac aatctcggct cacgacaacc tccacctccc aggttcaagt gattctcgtg
112021 cctcagcctc ccaagtagct gggattacag gcgtgtgcca ccatccccag ctaatttttg
112081 tatttttaat agagatgagg tttctccatg ttggctaggc tggtcttgaa ctcctggccc
112141 gaaatgatcc aacttcctcg gcctcccaaa gtactgggat tactggcatg agccatcatg
112201 ccaggcctgt tttatgctat ttaaattata cctactaagg ttaggatcct aactgccact
112261 cactaactga agtgtcacat actttattcg ttggcatgta tatactcagt tgtcccagca
112321 ccatttgttg aagagactat tctttcccca ttggcacttt ccccattgtt agaaatcagt
112381 tgaccataat ctataggttt attcctagat tctcagtttt attctgttga tctatatgtt
112441 tacaaatagc accagttacc acagcagctc tcctgtagta acaactctcc aatcccagta
112501 gcttaaaaca gcaagcatat tcttcactca cattacatgt cagggactat gggttgtttg
112561 ctacagttct gttccacgtg gcttctcatc ccaggaccca ggcggaagaa acagtctcaa
112621 tatggggcag tgtccctctg gctaagggag agagaggttc attcacgcaa gcagtggctc
112681 ctaaggcttc tcttagacct agtgtaggtc atgttcactc atgttttatt ggtgaaagca
112741 aggaaggcac atggccaagg ctgacaatgg agagaggaag tatactcacc ctgtgggaag
112801 gcataacagc catttggcag tgggcagggg tgtgtgtgtg tgtgtgtgtg tgtgtgtgtg
112861 tgtgtgtgtg tgtgtgtgtt tataatctgt ttatagggaa gggaacaatg aaataactga
112921 ctgtagtgat cttcctcaag tgagttaacc tctctaggcc tcagtttcct catctacaaa
112981 atgaggagat aagagtaccc atttcatgaa gtttattggg gttgtcagga tcaataagtg
113041 atgacatata cagtaggcca aatacatggt atgtactatt taagaattag ccggctgggc

FIG. 14 (cont'd)

```
113101 gcagtgactc acacctataa tcccagcaat ttgggaggcc gaggcgggca gatcacctga
113161 ggtcgggagt tcgagaccag cctgaccaac atggagaaac cctgcctcta ctaaaaatac
113221 aaaattagcc aggtgtagtg gcacatgcct gtaatcccgg ctactcggga ggctgaggca
113281 ggagaatcgc ttgaacccgg gaggtggagg ttgtggtaag ccgagatcat gccgttgcac
113341 tccagcctgg gcaacaagag tgaaactccg tctcaaaaga aaaaaaaaaa aagaattagc
113401 cactgctact attgttattg ttttctcctc aactccatct ggcagacctt tactcgccct
113461 ataaggccct cctcaaatac catcctcttt atagttctta ctcttttatt tcctgccaac
113521 caagtttctg cccccatggc atttggaagc tcagtggcaa aagttcaggg atttcggggt
113581 tgggcagtgt gcttgacttt ttgttcacat gttcagacaa aaataattac attcacatta
113641 aaaatgtctc ttaccttatt ctgggctagt gaatgttccc tttcaatgtc ttttagatag
113701 ctgccagaga cactatctgt atctcttcct cctaccttgt acctcattat cagtgtttga
113761 gaaaggagtt gataactgaa ttctcagttc tagccaaatg tgaatgggga tctcatagtc
113821 agttcaggcc caagttttgg gtgcagactg taaatggctt tgggacaata atattctata
113881 aaccatgtaa cagtagtttt ctaggcatat ttcctatagg aatctttatc cagggcaaag
113941 gcatttgggc tgcaccaaag tcccagatgc cttgttataa ggtagctctc aaacagtagc
114001 tcatcagatc ccatctgcca gctctaatca gtggggaata tcagattctt tttttaagct
114061 ttgaggggat ctgggatatg gcttgtttct ttcatttttg gggggtttca ctttgttaga
114121 tatacataag atttttaaaa atgttttcag tcaaattgat ttccttcttc cttacagtgt
114181 aaggcaaaca ttggtgggca ccgatcttcc tgttcattct gcaagaaccc aagagaaggt
114241 gagtggcgaa agtggtagca gtttttatct cgtgcattga gcaaaacaaa tttcatgttt
114301 tccttggctt tgaagaatta tcatccctaa atccaagttg atctacaaac cttttttttt
114361 tttttttgaga tggagtctcg ctgtgttgcc caggctggag tgcagtggca ccatcttggc
114421 tcactgcaac ctccagctcc caggttcaag cgattcccct gccctagcct cctgattagc
114481 tgggattcca ggcatgtgcc accacgccct gtagcccggc taattttttt gtatttttag
114541 tagagacggg gtttcaccat gttggtcagg ctggccttga actcctgacc ttgtgacccg
114601 acccaccttg gcctcccata gtgctgggat tacaggtgtg aatcactgca caaggcctgc
114661 aaacctttat ttatttattt atttttgaga cagagtctcg tactcaccca ggctggagtg
114721 cagtggcgca atctcggatc actgcaagct ccgcctccca ggttcacgct gttctcctgc
114781 ctcagcctct ctagtagctg ggactatagg cgcccaccac catgcccagc taattatttg
114841 tattttagta gagacggagt ttcaccgtgt tagccaggat ggtctcgatc tcctgacctc
114901 gtgatctgtc tgcctcagcc tcccaaagtg ctgcgattac aggcgtgaac caccacgacc
114961 ggcccaaacc tttcaaaagt gcaatttgag ctaggcatgg tggctaacgc ttgtaatccc
115021 agcactttgg gaggccaagg caggtggatc acctgtggtc aggagttcaa gaccagcctg
115081 accaacatgc cgaaaccctg tctctactaa aattacaaaa attagccaca ggtgtggtgg
115141 cacatgcttg gaatcccagc tccttgggag gctgagacac tagaatcgct tgaacccagg
115201 agtcagaggt tgcagtgagc tgagatctcg ccactgcact ccagcctagg caacagagtg
115261 agaaaaaaaa aattgcagtt tggtgcccaa cttaacgtaa cctgttagta aatgatttca
115321 gatcttattt tcaccagagg aaagagatag ggttgtgggc tcctaggcta aagtggctaa
115381 gtgggcagct gagcagaggt cagtatattg ttatttggaa tacatttaag gattaaggat
115441 gttaggttga aaaagagtct ttatgacatc agtctgtgtg gcaaaccttt ctcccactcc
115501 tacttctttg aagttattgg gaatcatttg ctctattgtt ttctctttta cattctgtaa
115561 gcatttcagg attttcaaga gaaaaacatt tgttaaaata acagtaaaaa cataaatagg
115621 agaaaataat caggatgtgg ggaacatttt attattttag aggaataaaa ctaccagctt
115681 ctcaagcact tatctttaat gtaaatttct ttagagaaat ttcaggtagg caacttcgaa
115741 gagtcagaca catgcatcca taacaacagt cctgtagtca tcccttaagg aaagccacag
115801 catgaccata aaatatagtt cagtgcaggg attcaggtag ccttctgttt gttgcaaggt
115861 tagagtttaa tgtgcctaca aggagtttct taggtgggct tttgtcctct tgtggagatt
115921 ttactctggt gaagactgaa aggcaggtgt tctgaaaatc tttaggggaa ggctgtgtat
115981 gttctagaaa ccaaaccaaa atgtgggaag gaggatgaac aactgagatt tttgcttgtt
116041 aggtcacttc aggttaggca aagttgtgtt tttttccccc cacaagaaac actttttttc
116101 aaagctattc cagcaaatga atagatagtt ttttgttttt tttcttttt tttttgagac
```

FIG. 14 (cont'd)

```
116161 ggagtcttgc tctgtcaccc aggctgaagt gcagtggcgc aatctcggct cactgcaagc
116221 tctgcctccc aggttcacgc cattctcctg cctcagcctc ccaagtagct gggattacag
116281 gcacccgcca ccgtgcccag ctaatttttt gtattttcag tagagacagg gtttcactgt
116341 gttagccagg atggtctcga tctcctgacc tcgtgatctg cccgcctcag tctcccaatg
116401 tgctgggatt acaggcgtga gccaccgctc ccggccatga atagatagtg tatgaaaacc
116461 actgggcacc ataccactaa gatgagacag ctttaatctg gaaacctgtc actgctatta
116521 tgtaatctct atattgctct catataatac ctctttttga gccacatgga ttccagtgaa
116581 ccctccaaga atgaattagt tacaagaatg tgcccctaat tataaaacaa actataaaga
116641 caaattatcc tgctgtagta ggacatttga aataaatcat ttatattttg aaggacgtct
116701 gcccattatg tttatttgca tataaaggag ctacgtgcag atagggtctg ttcctagctt
116761 cactggagga gggcctgtgg tcttacagga tatgagtagc tgtttgagca ctgtaacact
116821 ggaagaagca aggcttctag atgtgtgttt gggatatgtg tttctactaa accttaagta
116881 agggccatat cttcggtaat tttgtcccca gatgtgttgt tatcattgat tatgatagtc
116941 aggttcaagg tgtcatgaag gatttgttat atttaaatgt ttagtaggtg atatagagat
117001 ttcataagat tacatttttt aaatgcttgg atagtttctt ctgtgaacta tttcatgtcc
117061 tgtctcagct tcacttaaaa tattttgtca ggaactgtca gaggactttt tattagatat
117121 ttctgagata atattaaaag cattccaggc cgggcgtgtt tgctcacacc tgtaatccca
117181 gcactctggg aggccgaggc aagtggatca cctgaggtca ggagttcgag accagcctgg
117241 ccaacatggt gaaacctcgt ttctactaaa aatacaaaaa attacctggg cgtggtggtg
117301 ggcacctgtg atcccagcta ctctgaaggc tgaggcagga gaatcgcttg aacccgggag
117361 gcagaggttg cagtgagcca agatcatgcc attgcacttc agctgggcaa caagagcaaa
117421 actccgtctc aaaaaaaaaa aaaaaaaaaa aaggcattcc agtatgagta tttgctggca
117481 ggtaaggaga aattacagta gcagtgtttt ttcttttttt tttttttga taaagctttc
117541 tagagattct ctttgtttct gttccactag tgacagaggc caagcaagaa ttaataacct
117601 accctcagcc tcagaaaaca tccataccag caccattgga aaaacagccc aaccagcccc
117661 taagaccagc tgataaggaa cctgaaccca ggaagaggga agaaggccaa gagtcacgct
117721 taggacatca aaagagagaa gcagaaaggt atctgcctcc ttctcgaagg gaagggccaa
117781 ctttccgaag agaccgagag agggagtcat ggtctggaga gacacgccag gatggagaga
117841 gcaaaagtaa gtagtttgtc agggcacata ccagactgtg atcatcacaa tggagcatag
117901 atggccaatg ttatgtccgg gagctatctg ctttccagta ccctgagaga tctgtgcatg
117961 acctgatgac agaggccatt gctgtctgtg gaccttcctg tactgcttaa aggaatctat
118021 gcccttcaaa tagtaaattg ctatatgaat gcagtaaggc atgattttag atttctaagt
118081 attggtgaag aaaagtatgc agtatttatt tgtttagcat tttttacag aaccagcctt
118141 gctagtagca tctatagtaa aaaatgacag tcagattctt gggacttcaa aaatttatct
118201 ttctctccct tgtgttgccc ttctcccatt tatggttgat tcagctatca tgctaaagcg
118261 tatctatcgt tccacaccac ctgaggtgat agtggaagtg ctggagccct atgtccgcct
118321 tactactgcc aacgtccgta tcatcaagaa cagaacaggc cctatggggc atacctatgg
118381 ctttattgac ctcgactccc atgcggtgag tttcctccac cttggattgg cctagagaca
118441 gatggctaaa gaaccttcaa gaaggtttga ctgggggccg ggcctggtgg cttacgcctg
118501 taatcccagc actttgggag gccgaggtgg gtggatcacg aggtcaggaa atcaagacca
118561 tcctggctaa cacggtgaaa ccctgtctct actaaaaaat acagaaaaat tagctgggcg
118621 tggtggcagg cgcctgtagt cgcagctact cgggaggctg aggcaggaga atggcgtgaa
118681 ctccggaggc ggagcttgca gtgagccgag atcgcgccac tgcacttcag cctgggtgac
118741 agagcgagac tctgtctcaa aaaaaaaaaa aaaaaatttg agggacttct tgatcatttg
118801 aattcttgtg tgctacctga tatcataatc cctcttgctc tctcctttgg gtttattgtt
118861 cattcaggtc aggtgacagc cctcaaaagt taggatcccg tctggttttc taggttcatt
118921 tttttcttgt gtcatttact gtttccaact tactcgcttg tgaagaatct gagtactgaa
118981 tccttcatga ttttagtgaa ctttctgatt tattttgtcc agccacagat ggttttatat
119041 ttgatgataa aacatttcct ctttttcctc aaagtattta tagattcctg tggcttaaat
119101 ttttagttgc ggggcctttt tctatggaag taaggtgaag ataatgaaag tcattggtat
119161 ttcttagatt tttcatgctc aaaagtcaca agggactttg taaactgaat ctgattgatg
```

FIG. 14 (cont'd)

```
119221 ataattgcaa cctaaaagaa gaggatttga atttctgaag tttatgccag aactgacatc
119281 tattctgatt cctgttccaa tcagtccttc attaaaagtt gcctgtttct gccagtatgc
119341 tcttactgtt aaaattttga cagaatataa tgtagtaaat ttatcctctg agaaggaaaa
119401 tccacgttca cttctctttc aaaggagaat ttttctgtct ttgggttctg gcattttctg
119461 tctctgggtt caagtgtgtc tggttctata ggaagctctt cgtgtggtga agatcttaca
119521 gaaccttgat ccgccattta gcattgatgg gaagatggta gctgtaaacc tggccactgg
119581 aaaacgaagg taaggcagaa gggtgaggat ctcttgtgct gccccccactt gtgtttttga
119641 gaggaaactc cttttcctgg ctggaaaaac agtaaagcat gatgttttcc taacatggac
119701 tgcttcagat aggtgtttat tacagtttct ttctgaagcc tgacttgtcc tgactctcga
119761 attgttttct ttcttgaata atactaggta cttttgtcct ttcccttttg actgtctggt
119821 atctttgggt cccaaatggc ctggcgtggt agcacatatc tctattccaa gctactaaag
119881 aggctgaggc gagatgggga gcgggttaca tgagcccagg agttctaggc catagtgtgc
119941 aatgaagatg cctgtgaata accactgtac tctaccctgg gcaacacagc aagaccctat
120001 ctcttaacaa aaaaatgatg gtacagtttt ggatgtgcag acacatgtca atacattctt
120061 gccccttgca atcctaggaa aatgctgtcc tggcttttcc ttcccctgac cttgtgcata
120121 tttccatagc actgggaaat ctaatttctc tttcctcctt cactcatctt gacccaggag
120181 tggtaacttg gaaatggcca tgtcagagaa acaggcttac caatatgggg catatcttgc
120241 tctagcaccc tccacttaat ggctgttttg ctccaccact tggctttgta agagtcttac
120301 tgctcattgg gcaggcgtgg tggctcacgc ctgtaatctc agcacctggg gaggccgagg
120361 cgggcagatc atgaggtcag gagattgaga tcatcctggc taacacggta aaaccccgtc
120421 tctactaaaa atacaaaaaa aaaaaaatta gctgggcgtg gtggtgggca cctgtagtcc
120481 cagctacttg ggaggctgag gcaggagaat ggtgtgaacc caggaggcgg agcttgcagt
120541 gagctgagat cacgccaccg cactccagcc tgggcgacag agcaagactc cgtctcaaaa
120601 aaaaaaaaaa aaaaaaaaag agtcttactg ctcattcttt caggagtgtc tggaccaccc
120661 aacctgcttg ctgtctaggt tggttccttt ccctgcaaaa tgaggaacag aggatttctc
120721 gataggaact gtaggattaa gtactcgtca aatgccactt ggtagcagcc ttaagaattg
120781 ttgtgttatc tgttgcagaa atgattctgg ggaccattct gaccacatgc attactatca
120841 ggtaggctgt aacaggtggg gagtgctcta ttaaaatcct caggtgacta taagggtgat
120901 cttgaatttt ctttagtggg tgactgttaa ggtgaatgac cattggatag ttctgtaatt
120961 ttaacttgcc tttctgtgat agggtaaaaa atatttccga gataggaggg gaggtggcag
121021 aaattcagac tggtcttcag atacaaatcg acaaggacaa cagtgtaagt aacctttgtt
121081 ttatttctgt tgctcttttt tgcttgactt gctactcatt acttgacatc tgtgtgatca
121141 cagttggcaa gatacactgt tgactgaggg tgctcatcca gagagaggca tctgtagatg
121201 cacctatttg tgttggtcac cctaattctt gggttcttga tgagtctcca gtaagggctt
121261 cattggacag agactaacat tggctctgat cttgttacct ttagcatcat ctgactgcta
121321 catatatgat tctgctactg gctactatta tgaccccttg gcaggaactt attatgaccc
121381 caatacccag gtgagtttgg ggcttttttt tttttttttt tttttttacc tctgtcaatg
121441 attcttttga gaaaagcacc cataatttgc tacttgagga ttttattccc tggattctct
121501 ggatgctcat tgcatgaaaa gtggaaaagt ttagatctat ggaaacagaa ctgttgccta
121561 tatggaaaat cagtgccttg tggcaataca ggtaagaaca gtgttgctct tgaaaaagtg
121621 gacagtgggt ggtctgaatg tgtcctggtc cctggagtgg gtttttagat tgatgtggac
121681 tcttcttaga cttgtaagta aaaaagttgt ttcttcccct aaaagggaac tgtgcgcctt
121741 agacctggaa ttgctgggaa actgaaacat tctgtagact tacttgtttc caactgtatc
121801 gcagcaagaa gtctatgtgc cccaggatcc tggattacct gaggaagaag agatcaagga
121861 aaaaaaaccc accagtcaag gaaagtcaag tagcaagaag gaaatgtcta aaagagatgg
121921 caaggagaaa aaagacagag gagtgacgag ggtaagagga attgttaatt tgctgtcttt
121981 tgccacatag ttattaaaat gttggaggta cgaacagagg atatctatgt ttgcaagtgt
122041 aaagtaactt taaaaatact ctgtcagccg ggcgtggtgg ctaacgcctg taatcccagc
122101 actttgggag gccaaggcgg gcggatcatg aggtcaggag atcgagacca tcctggccaa
122161 catggtgaaa cccctgtctc tactaaaaat acaaaaatta gctgcgtgtg gtggtacacg
122221 cctgtagtcc cagctactca ggaggctgag gcaggagaat tgcttgaacc ctggaggcag
```

FIG. 14 (cont'd)

```
122281 aggttgcagt gagccgagat cgcgccacta cactccagcc tggcaacaga gcaagactct
122341 gtatcaaaaa aaaaaaaaaa acctctgtta atgagtattt ttacctggtg taggcaattc
122401 cctcacctct tatatcccaa ctctctcttt tacaaatggg aaaactatgg atggtagaac
122461 aaagtggccc agctcaaatc ccaacacctc agctccatac attttcactt ttctacattc
122521 ctttttagt gtttgacttt atacacattt ctctagttgt aattatagca ggagatactg
122581 tttagtcact ttttatccta agtatttttt ccatgtttct atatactcta ttatttttaa
122641 tgcccacatg gtaaaaattc acggtataac tgtaccttca ttttcttcat ctctcctaca
122701 ttatttgtct tctctttcta atcttttctt tttccttttt tttttttttt ttctgagaca
122761 aagtcttcct ctgtctccca ggttggagtg cagtggcatg atcatagctc acttctacgt
122821 caaacccatg ggcttaagca gtcctcccac ctcagcctcc caagtagcgg ggactacagg
122881 catgagccac catgaccagc taatttttgc ttttttgtag agacaggatc ttgctagatt
122941 gaccaggctg atctcgaact tctggcctca agtaagcttc ctgtctcagt ctcccaaagt
123001 gcttcagtta caggcaagac ccaccttgct cgcctctttc taatcttata ctgtcataat
123061 atataacatt tagcatttg tttcttcttt taaattactc cctatgacac attttcagaa
123121 tcagagatga tgaacatttt tacatctaat acaaaatcaa attattaggc agggtgcagt
123181 ggctcacacc tgtaatccca gcacgttggg aggccaagac aggtggatgc ctgagtttag
123241 gagtttgaca ccagcaacat ggtgaaactc catctctacc aaaaatacaa aaaaaattag
123301 cctactgtgg tgatgcatgc ctgtagtcca agctacttgg gagactgagt taagaggatc
123361 gcttgagccc aggagattgc agtgagctgt gattgcgcca ctgcactcca gcatggacaa
123421 cagagccaga cttgtctcaa aaaaaaaaaa aaaagaaaat ctgccgggca tggtggctca
123481 tgcctgtaat cccagcactt tgagaggcca aggcaggcgg attactttag gtcaggagtt
123541 tgagaccgcc tagccaatat ggtgaaaccc ccatctctac taaaaagaca aaaattagct
123601 ggacgtggtg gcgcaagcct gtagtcccag ctactcagga ggctgaggca ggagaatctc
123661 ttgaacctga gaggcagagg ttgcagtgag ccaagatcac acctaccttg atatcagtta
123721 tgcattagtg aaaatggatg aatttgcttg tgattcaatt cataacacct tttttccct
123781 tttttttctt ttgagacgga gccgctctgt cgcccaggct ggagtgcagt ggcgtgatct
123841 atctcggctc actgcaacct ccgccttcca ggctcaaggg attctcctgc ctcagcctcc
123901 tgagtagctg ggatatcagg cgctgccaca acgcccagct aatttttgta tttttagtag
123961 agacgcggtt tcaccatgtt ggtcaagctg gtctcgaact cctgaccttg tgatccgccc
124021 acctcagcct accaaagtgc tgggattaca ggcatgagcc actgcgccca gccttttttt
124081 ccccttctaa cactgttagt tgtttagaga tacagaaaag aggagagaga gtgtgtgtgt
124141 gtgtttaaaa acttagagtc atactgattt aatatttgga ctctgcttca gccacttaat
124201 ctgtcaaact atattcccaa tcatttgtaa aattaagata gtaaagctta cataggagga
124261 tcatagtaaa gtctgaagaa gacaatgttt atatatacat gcctcatctg gtctgacata
124321 cagtaatcat gcaatatata ctaacgtttt attttatttt attttatttt ttgagacaga
124381 gtctctctct gtcacccagg ctggaatgga gtggcacgat ctcggctcac tgcaacctct
124441 gcctcccagg ttccagcagt tcttctacct cagcctccca agtagctggg attacaggcc
124501 aaaaccacca cacccagcta atttttgtat ttttactaga gacggggttt caccatgttg
124561 gccaggctgg agcacagtgg cacaatcttg gctcactgca agctccgcct ctcgggttca
124621 ttctcctgcc tcagcctccc tactaactgg gactacaggt gcccgccacc acgcccagct
124681 aatttttgt atttttagta gagatggagt ttcactgcat tagccagggt ggtctcgatc
124741 tcctgacgtt gtgatccacc tgccttgacc tcccagagtg ctgggattat aggcgtgagc
124801 caccgcaccc agcccagcct ttatcagtta ttatgagtga atatcatgtg agagttacct
124861 ctggtttgat cagtttcagg aaaatgccag tgaagggaag gcccctgcag aagacgtctt
124921 taagaagccc ctgcctccta ctgtgaagaa ggaagagagt ccccctccag taagaccaac
124981 attgatcccc tggacctagg gctggggctg gggatggttc cgagtagaag aggaagcgca
125041 aaggctgatg ccttcctctg gtgttggtct tttacctcac tatgtctccc gaataaggat
125101 tcccatttct tttgagtaca agcatgagat aaagttttct gtctgctaat gggggtatta
125161 ctggagaacc agaggcagtt atctggactc tttctctctg ccctgtgcca ttcttaccag
125221 acgagatgcc tagccctttt tatcatcttg ttcttgtcag ttctctaaat caccaaggaa
125281 acccgttttc tcagcctcaa tctttcctgc cttttggcat cacacaagaa tctcttagat
```

FIG. 14 (cont'd)

```
125341 atggagtgca tgcgtggtca ttttttata gtttctgcct gttcagagtg aatgatgcta
125401 atattggtgc ccattttta gatgccttca agcagtagtc tcaacctaat caccagtgat
125461 tctgattgaa tgcaggtata taacaatagt gaccatgcat tatttattta ttttgagtga
125521 tcatagacca atgattatgc atcattattt aacagttctt ataaggtacc cttttcctgc
125581 tccgcattat taattcagct cattgtggca tctgtcttaa ccatgctttg cctttacctt
125641 acatgtgagc tggatctgtc tacccaagtg cctattaatg cagttgcttt tagtttactt
125701 cctaaatcct ctttgctaga gtcttaatga aagtcatctt ttcttccctc catgagttac
125761 agtaatttgg aggtatttat ctcttcctct ttgtaatttg taacctttta ctattttcta
125821 tgtttatttt cctttctctt ccttctcctc acattctgtt gctagagtca cttctaaagg
125881 aatctttctt gtttattctt aatgaacaag gagcaaagcc aagctctggc catgttgctt
125941 tcatctggga aatgagcagc atggctagtg agtttatttt gaacccaatt caatgaaatg
126001 agatgcccat atcagaatat caaaaaaaat ggaccccaaa atataggttg aatttggtat
126061 tgatccctgg ccttctcctt ccagcctaaa gtggtaaacc cactgatcgg cctcttgggt
126121 gaatatggag gagacagtga ctatgaggag gaagaagagg aggaacagac ccctccccca
126181 cagccccgca cagcacagcc ccagaagcga gaggagcaaa ccaagaagga gaatgaagaa
126241 gacaaactca ctgactggaa taaactggct tgtctgcttt gcagaaggca gtttcccaat
126301 aaagaagttc tgatcaaaca ccagcagctg tcagacctgc acaaggtatt aggggaagga
126361 gctatgccct ttcaaactgt tgactcttgg ccgggctttg tggctcatgc ctgtaatcct
126421 agcactttgg gaggccgagg cgggtggatt gcctgggctc agaagtacaa gaccagtctg
126481 ggcaacatgg tgaaaccccc tttgtactaa aatacaaaaa attagccagg tgtggtgttg
126541 tgtgcctgta gtcccagcca ctcgggaggc tgaggcagga gaattgctag aacctgggag
126601 gcagaggttg cagtgagccg agatcgtgcc actgcactcc agcctgggta acagagcaag
126661 actccatctc ttaaaaaaca aaacaaaaca aaactgttga ctcatattat tgatggggat
126721 tatggggaat aaaaaagatt atttaggccg ggcctagtgg tttacacctg taatcccagc
126781 actttgggag gccaaggcac ctaggtagat cacttgagat caggagtttg agaccagctt
126841 ggccaacatg gtgaaactgt ctctactaaa aatacaaaaa ttacctggat gtggtggcgc
126901 atgcctgtaa tcccaactac ttgggaggtt gaggcaggag aatcgcttga acctgggagg
126961 caaaggttgc agtgaaccga gatcacacca ctgcactcca gcctgggtga cagaccaaga
127021 ctctatctca aaaaaaaaaa aaaaaaaaaa aaaaagccgc agcagcttat acaatccttc
127081 ctcagtgtat atcagcccca gttcctatca ttaaaacagt ccaattcaag aatgaattgc
127141 tctggattaa ggttatgcct accctcaaag aacttccatg tataggccga agccaagcat
127201 tatgactgtg gctagggtgc caaatatgga ggatgggtag gaagagaaag ggttgtggaa
127261 taggacatta cttgctgggt ttctcatctt agctgtgtca ttaacgttac agttggacct
127321 cagataagcc ccttttcttc tttggtcctt gtaacttcat ctgattctat ccagctctga
127381 cagtgtgcag ttttcaccat aggtgagtca aattctgcca tttcttcatg tagtgaatat
127441 tgttatgagc cacagcacaa catctatact tgggatgtta aaccgacata cattggtctt
127501 cccctgtagt attcccattt atatgaactg accaaggatc caaattatgg acaaataaag
127561 tccctaaatg gactcacatt ctcagagcaa tttgtttcac accccttctc tagtagatgt
127621 tgcaagagca ggtgatggaa ctagattcag actttctctg aatacagagc tcaaagtttt
127681 atttagctaa aagctgagaa gttctgcttt tggtaatagg tacactactt ttcccagcca
127741 tctctgtgga ggctttgcaa agataggact ctgaaaagct cctgataatc cctggaacag
127801 actacctccc atgtcctttg acctgaagtt gtgagttgtc agactgacac attgaaattt
127861 cacccatctg atgtaaatac taataaatgg ctaaagagat aaaaagtaat cgtcaggaaa
127921 gaggagccac aggtctggtg aattcacaaa ctgaactggt cataggacag tggaaagtag
127981 actgtagtac ttttcctttc cttaaggtcg tctgctacaa agaaccacca cttcatgtaa
128041 gagctgcttt ggactcctta agtttcatac atatgtctga gggcttgtgt agtagagcca
128101 tgcgtgagga atttgcaact ctcagagcag tctcttggaa ccctggggct cctttccatg
128161 tttctctggg ggctgaaaga gtgactcatg tctgggaatg gtatgtatgg cagagtatgt
128221 gggcatttgg ttttcttcac tggtgtgccc acatcctctg tcccatgatt ttcaacttag
128281 ataaagagat agatatttgt ttcccacatc ttggagataa gtaaaatgat attcctctta
128341 tgccatacca cataactaat ctgcatgaca agaccagtta gggattgttg gttgcaggat
```

FIG. 14 (cont'd)

```
128401 acagtgatca tttagtagat ctgatcaatc aaaagagcta caatccaaaa gcaactattg
128461 ggaaaggcct agaagcatct ctaggaccat tgtttcttag acctatactc atagaattgc
128521 ctctcttctc agcaaaacct ggaaatccac cggaagataa aacagtctga gcaggagcta
128581 gcctatctgg aaaggagaga acgagaggta aactttggtg acctattact cccttgacct
128641 cagctctttt tgctttctga tatagacttc ataggctgtg ctgatccctc cttataagaa
128701 gatggagaac aaaagcagcc tcaaaagata gtgcatacat ttgccaaatt atataataca
128761 atcaaaatag gtgcttttta ttatttgtaa gtttatactt caatgaagtt gatatctttt
128821 ttaaaaggtg gtgttagggt ctctaggtag ataacactcc tctttcctgc ttagctttta
128881 aattagttga gttaatgaac aagtgttgaa tagcgctgct gaaatagcat cttttactat
128941 taaaggctaa gctggaggaa gtagcttagt gtcagagtca aatggacttg ctacctcaac
129001 cacacagtta gggtgaatta cccagtcata ggcttcactg gcctctctca tgatggttaa
129061 gaacccacct atgggtcagg cacggtggct cacgcctata atcccagtac tttgggaggc
129121 tgagacgggc ggatcacttg agctcacaag tttgaaacca gcctgggcga catggcgaaa
129181 tcctatctct acaaaaaata taaaaattag gtggacatgg ggtgtgtgcc tgtagtccca
129241 gctacttgag aggctgaggg aggatcgcat gagctgggag gcagaggttg cagtgagctg
129301 agtttgtgcc actgcgctcc agcctgggtc atagagccag accttgtctc aaaaaaaaaa
129361 aaaaaaaagg aagccacctg tggagagcca ggcacagtgg cacatgcatg taatcccagc
129421 agtttaggag gctgaggtgg gagaattgct tgagcccaag agttccaggc tgcagtgagc
129481 tatgatcaca gccctgtact ccagcctggg tcacagagta agtccctgtc tcaaaaccaa
129541 acaaaagaat ccacctatgg aggactgtta gagatagtga attcacaaac tgaactggcc
129601 ataggacagt ggaaagtaga ttgtagtatt tttcctttcc ttagagttgt ctactacaaa
129661 gaaccacctc tccatgtaag agctgctttg gactccttaa gttttatatt atatgcccga
129721 gggcttgtat agtggagggc ttgtgtactt tcccctgctt ctcagaaggg gaaaagacag
129781 cggaaccaag cgtgccaact tattctttcc aaatgtttaa gttaggaagt cactgctttc
129841 tctagaagaa cgtgtaaagg agtgagagat tccaggagtt accaagtgag ctactttcac
129901 tttaaaagaa ataacaaggc cgggtgcggt ggctcacacc tgtaatccca gcactttggg
129961 aggccgaggc tggtggatca tgaggtcagg agttcgagac tagcctgact aacatagtga
130021 aaccccgtct ctactaaaaa tagaaaaatt agctgggcat tgtggcactc acctgtagtc
130081 ccagctactt gggaggctga ggcaggagaa tcgcttgaac ctgggaggcg gaggttgcag
130141 tgagctgaga tcacgccagt gtactccagc ctgggcaaca gagtgagact ctgtctcaag
130201 aaaaaaataa taataataac agcaatgggg tagaatttcc ccactcccca attccctcag
130261 gtggcaatct caggtctgct cttctgctta ccaacaggga aagtttaaag gaagaggaaa
130321 tgatcgcagg gaaaagctcc agtcttttga ctctccagaa aggaaacgga ttaagtactc
130381 cagggaaact gacaggtaag ccaggaactc ttcattcagc ctaggcctca agcctaatga
130441 taaaaccacc tcctccttca actgtactgc tgttttctgt ctcagggaga tgatattatg
130501 agtagattct gtctgaactg ctaaaacatg aggtctatgc cagccttttt actatctgtc
130561 tttatacggg gagtgtacat ggaaggttgg ctggcagctt cgccttccca aagccagggc
130621 tggagtagcc atgatcggga accctttctg tcttcatcag taatactgca ccctctttac
130681 gggcctgata agaatgtcac actcttgggc tttttctcta gggaacctcc attctcacac
130741 ataggtgcta aataaatggt tggctgctga tggagatgta tgatatctag cttcctatac
130801 ttgttttcag tcagctagtt cccaagttgt aagcccagag ttatatagaa tttgttgata
130861 acccactgtt tacaggtgtc aagtgcaaga aatactcagg tggacaagac atagattatc
130921 cttgactgaa cacagaatag acaagactta ggtgatggtg cgtctcatag ggcagacaca
130981 gaaatcagtg gggaagggaa gggcatttca gggaatttca tataccaggg atataagagc
131041 ttatgatgtg tttgaggagt tgcaaatagt ttgatggtcc tgaacactgc aggtatattg
131101 ttgagtgaca gtagataagc ctggtccaaa agatgcaggc cagttcatga agtttaaaca
131161 ccttgaacac cttgctaagg ctttatctta aaggcagtgg acggtcatgg aataatttta
131221 agcagggtat tgacttagct ttgcattttg gagagattac taatcatgtg gaagatgagt
131281 ttgtagagag actaatgcat tatgcaaatt ctatagtaat tcaagtgaaa gatcatgatt
131341 gcctgagtga aggtgatgag tctagaaagg agagtggcct ataatcccaa cacagagagg
131401 ctgaggaagg aggatctctt gagcctagga gttccaggcc agcctaggca acatagggag
```

FIG. 14 (cont'd)

131461 aagggagacc ctgcctctat ttaaaaaaag aaaagaaaag gagtgtggct tagagagagg
131521 tgtcagatct gccagtcttt gtgatcacct ggggaaaggg agaagtcact gatggtgttc
131581 aggtctctgg tctctggata gctaggagga gaagggacag taaagtcctt gaaaaggaaa
131641 aatgggggcc aggcgtggtg gcttacgcct gtaatcccag cactttggga ggccgaggcg
131701 ggtggatcac aaggtcagga gttcgagacc agcctggcca agatggtgaa acccccttctc
131761 tactaaaaat ataacaatta gctgggcgct gtggcaggcg cctgtaatcc cagctactca
131821 ggaggctggg gcagaagaat cgctcaaacc tgggaggcag aggttgcagt gagctgagat
131881 catgccactg cactctagcc tgggtgacag agcaagactc tgtctcaaaa aaaaaaaaaa
131941 aaaaaaaaga aaaggaaagg aaaaatgggg ccaggtgtgg tggctcacac ctgtaatccc
132001 agcactttgg gaggctgagg caggtggatc acttaaggtc aggagttcga gaccagcctg
132061 gccaacatgg tgaaaccctg tctctaccaa aaatataaaa aaattagcca ggcgtggtgg
132121 tgggtacctg taatcccagc tactcgggag actggggcag gagaatcgct tgaacatggg
132181 aggtggaggt tgcagtgagc caagattgca ccactgtact ctagcctggg taatagagcg
132241 agactccaaa tcaaaaaaaa aaaagaaaag aaaagaaaag gaaaagtggg taacaagtgg
132301 atgcatgagc agaaggaaag ggagataatt gacagagcaa ggcccttgag gaggctggac
132361 aggttttggg gctctggcat tccagcttat ttgatccaac ccacaataag agaagtattt
132421 ttgtatcatg gcccaataat aaagtgtgtg tgtgcacaac tgaaaaagtt ttcatctaaa
132481 atactttctt accaggtaca gtgaaccctg atatttttat tcaagtctag tctctcttca
132541 tttttatgag ttgttacagt gggaccattt agtgtgacat tccattgggt cattctctgc
132601 aatttgaaat acagtggatt aggactaggt gaaggagtca gccatcagga ggaaggacac
132661 cttggccttg agtcttctgg gacaaggctt aggtggggtg cggaaagaga cccttcttta
132721 ttctcagcac cctttatacc acattctcct ggctcttctc ctttccagtc accttttctg
132781 ctcctcttcc ttttctggat aaatccaggt gttctctagg actcttctct cagtgcttct
132841 ttggtcttgc tgctctaccc tcttgacctg ggctttctaa ggtacccatg gcctcaacca
132901 ccaccacagt ctaacaagtc caaatctcct gtattattat ttcagagtag cagcatcata
132961 gcatcactgt ctacatggtc tgatccatcc tcctccttta tcccctgtgt ccaattagtg
133021 accaaatccc taattaagtc ttgccccctg tcttagtctg ttttatgata ccataactga
133081 ataccacaga ctgggtaatt tataatgaac agaaatttat ttggctcatg cttctggagg
133141 ctgggaggtc caagattgag gagctgcatc tggtgagggc cttcttgctg tgtcacctca
133201 tggtggaaag taaaagaaca agagagctta ggcaaaagag ggggttggga gaaagaaacc
133261 agactaatca ttttatcagg agaacccact cctgcaataa cagcattaat ccatttgtga
133321 gggcagagct ctcatgacct aatcacttcc tgaagtttca cctctcaata ctgttgcatt
133381 ggggattatg tttccaacat atgtactttg agggacacat ttaaaccaca gcatctccca
133441 ttctattcca cctccacact ggactcctac tcccagtctt tgctcccact gttcttcagt
133501 ccattctcta ccctgccacc aaaatgactt ttgtaaagag aaatctactc ttataacttg
133561 tctttttaca aaccgtatac cttgcctaca gggaggcctg agctccaact tttgccagaa
133621 ggatgaggtt cagagacatg atttagctta ataagttcaa ggttttttac agtctgaccc
133681 catgcagcct tttttttttt tccttttgtt ttgagacagt ctcattctgt cgcccaggct
133741 ggagtgcaat ggcacgatct tggctcactg caacctccgc ctcccaggtt caagcgattc
133801 tcctgcctca gcctccccag tagctgggac tatgggctaa tgtttgtatt tttagtagag
133861 aggggtttca cctgttggtc agggtggtct cgaactcctg acctcaggtg atccacccgc
133921 cttggcctcc caaagtgctg ggattacagg cgtgagtcac tgcacccggc caccaagcag
133981 ccttaccttt gtcagtttct actactactc tcttggacaa attgtctttt gtgtctcctt
134041 gcttgtgtcc tccttttctc ttacacaaac tccttatttc gagatccaat tcagatgtat
134101 cttcctgttg aaattcctgt catttttggt gatgcccctt cagagttttc gttccttcta
134161 ctgcatttct tttttttttt tgaaacagag tttcactctt gttgcccagg ctggagtgca
134221 atggcgcgat atcagctaac cacaacctcc acctcctggg ttcaagcgat tctcctgcct
134281 cagcctcccg agtagctagg attacaggca tgcgccacca cacccggcta attttgtatt
134341 tttagtagag acagggtttc tccatgttgg tcaggctggt cacgaactcc caacctcagg
134401 tgatctgccc acctcagcct cccaaagtga ttccttctac tgtatttcta tagcagacat
134461 ctactgttgc tacatccatg gttgagctct cttcaatgtt ctataagcat ctcttgacat
134521 aatgtttgag acctttcttg tgaacagggc catatcttag tagtctgtgt acccagcaac
134581 aaaacatagc tatcaggcac tcagaggtac tgttaaatat acttacttaa taagaggcag

FIG. 14 (cont'd)

```
134641 atatgaatca agaggacaga gattttatat taggcttata agcaggtctt catcaaaatg
134701 atggtgtcag gttgggcatg gtggctcatg cctgtaatcc agcactttgg gaggccaagg
134761 catgcggatt acctgaggtc aggagtttga gagcagcctg gccaacacag tgaaactctg
134821 tctctactga aaaaaaaaaa aattaaaaat tagccaggtg tggtggcggg cacctgcaat
134881 cccagctaat cgggaggctg aggcaggaga atcgcctgaa cccaggaggc agaggttgca
134941 gtaagctgag ttcgagccat tgcactccag cctgggcaaa aagagtgaaa ctccgtctca
135001 aaaaaaaaaa aaaaggaagt gatggtgtct gcttcttttg cagtgatcgt aaacttgttg
135061 ataaagaaga tatcgacact agcagcaaag gaggctgtgt ccaacaggct actggctgga
135121 ggaaagggac aggcctggga tatggccatc ctggattggc ttcatcagag gaggtaaaat
135181 ggtttccatc ttttgggggg tgacatgaac ctggaatgta attaactttc actttctggc
135241 ctagagtgat gtctttgcca ttttgctggg ctttctctac tgctgggata ggacatgaga
135301 gttgaacact ttagccttga atactgggtt atagcttggc aggctgggcc ctttgcagtt
135361 tggagttagg aagagaagga aggagttgga atggatttca tcatactttt acatggagta
135421 aatagtagag cagtatctga ggcagtttga gactgaagaa tcatttgggc aaaagaacca
135481 gggaatcagc aatgaaaggt acagaggcat ctctgagagg gactgtcagc ggaagtcttt
135541 ggtggctaaa atttaaggag catgttgttc tggttcccat gaaggacttt gcccctcata
135601 tttcaagagc ctctagaaaa ggtgataaga ggaaacatta cccattttgt gttggcttgc
135661 ttctcctctg aaaatgccaa ccataagaga ttggcttatt tctctcctac cgagtttctc
135721 atatctctgg tattaaagcc tgtatcttgc aatcatagca tcaccaccca ccttaattca
135781 tcttgggtat ttgtttaata atgaaagatt cttttctttt tttttttttg agacagagtc
135841 ttgctctgtc gcccaggctg gaatgcagtg gtgcgatctc agctcactgc aacctcctcc
135901 tcccaggttc aagcaattct cccaccccaa cctcctgagt agctgggatt acaggtgcat
135961 accaccatac ccagctaatt tttgtgtttt tagtagagac agagttttgc catgttggcc
136021 aggctggtct cgaactcctg gcctcaagtg atccgcccac ctcagcctcc caaagtgttg
136081 ggattacagg cgtgagccac tgtgcccggc caaaagattc tttaaaaaaa ttatcctgcc
136141 agggtccggg cgcagtggct tatgcttgta atcccagcac tttgggaggc cgaggtgggt
136201 ggatcacaag gtcaggagtt cgagaccagc ctgaccaata tgatgaaacc cctgtctcta
136261 ctaaaaatac aaaaattagc tgggtgcagt ggcgcgcgcc tgtaatcaca gctactcagg
136321 aggctgaggc agaagaatcg cttgtaccgg ggaggcagag gttgcagtga gccaagatct
136381 tgatcgtgcc actgcactcc agcctgggtg acagagcgag actctgtctc aaaaaaaaaa
136441 ttattctgcc aggtgtggtg gctcacatct gtaatcccaa cactttggga ggccaaggtg
136501 ggcggatcac ttgaggccag gagttcgaga ccagcctggc caacatggcg aaaccctgtc
136561 tctactaaaa atacaaaaat tagccgggcg tggtggcagg cgcctgtagt cccagctact
136621 cagaggctga ggcacaagaa ttgcttgaac cggggaggca gacttgcagt gagcccagat
136681 cgcaccactg cactctagcc cgggcgacag agcatgactc catctaaaaa aaaaaaaaaa
136741 attatcctat atactgcttc ttactagtcc agaaatgcct gtggtcaaag accagcgctg
136801 aggctaatta atctataggg cccacttcat agtttgtctt tgttttacag gctgaaggcc
136861 ggatgagggg ccccagtgtt ggagcctcag gaagaaccag caaaagacag tccaacgaga
136921 cttaccgaga tgctgttcga agagtcatgt ttgctcgata taaagaactc gattaagaaa
136981 ggagacaagt tccatgggat acaacctccc tcttgttttg tttgtctctc cttttctttt
137041 gttactgttc ttgctgctag aactttttta aataaacttt ttttcaatgt g
```

FIG. 15

Homo sapiens breast cancer metastasis-suppressor 1-like (BRMS1L), mRNA

```
   1 ggggaggagc caaggggcg agcaagctcg gtggctgggt gggttggggc gttccgcgcg
  61 cccttcattg aagcggcggt ggccgggctg ggcgccggta gtggaaagcg acggcgcggc
 121 tggaaaatgc cagtccattc ccgaggggat aagaaggaga ccaaccatca cgatgagatg
 181 gaggtggact acgccgaaaa tgaggggagc agctccgagg acgaggacac tgagagctcg
 241 tcggtctccg aggatggaga tagctcagaa atggatgatg aagactgtga aagaagaaga
 301 atggaatgtt tggatgaaat gtccaatctt gaaaaacagt ttaccgatct caaagatcaa
 361 ctttataaag aacgattaag tcaggtggat gcaaaactac aagaagtcat agctggaaaa
 421 gcaccagaat acttggaacc gctggcaact ttacaggaaa atatgcaaat tcgtacaaag
 481 gtagcaggaa tctatagaga gctctgctta gaatctgtaa agaacaaata tgaatgtgaa
 541 attcaagctt ctcgccagca ttgtgagagc gaaaagctgt tgctatatga tacagtccag
 601 agtgaactag aggagaagat aagaaggctt gaagaggata ggcacagcat tgatattacc
 661 tcagagctgt ggaatgatga gcttcagtca agaaaaaaga ggaaggatcc tttcagtcct
 721 gacaaaaaga agccagttgt tgtttcaggt ccatatatag tttatatgct acaagatctt
 781 gatattcttg aagactggac aacaattagg aaggcaatgg ctacattggg gccacacaga
 841 gtgaaaacgg aaccacctgt gaaactggaa aaacatctgc acagtgctag atctgaagag
 901 ggaagactat attatgatgg tgaatggtat atacgtggac aaacaatatg tattgataaa
 961 aaagatgaat gtcctacaag tgctgtaatt acaacaatta accatgatga agtttggttt
1021 aagaggcctg atggaagcaa atctaagctt tacatttcac agctacagaa aggaaaatat
1081 tcaattaaac attcataatc atgatttaag tgttatctaa atttacctta ttagtgttac
1141 caaatgtaag tgccatgaga gtaaaaaaat gtattcaata acttaatatt ctcactgaat
1201 catgagagaa tgtgtatttg taggtagtac tctaaataga tctcattgat atgttattaa
1261 aagaaacagt aataaaaatt ttatcacgat ccttacgttg atttgcctct taggtccgat
1321 gaccaatagg tattctgtat atggtagggg tttctttcta aacatttttc tttggtttta
1381 aaaaaagtta tgcaaatttg tcttatcttt agtaaactat gactacattt atctgcaatt
1441 tttaaaattt tccatatctt tgtcattcat tgtgtgtttg taaataaggc cgatagaatg
1501 tttcctataa atggtttgta ctagtacatt agtgttaaac cagaactgaa atttaaacat
1561 atatatatat gaggatgtat atatggcatc atcagcttat ttagaactga tggccatacc
1621 ttacaatctt gttttaccca aaattaagct attggggttg aaagctaaaa ggagcacttt
1681 tgtagaatag caacttttct tttcctcttt cttgattgta tggtggggtg gtgacctatt
1741 tttacaaatt atacctaatg agtaaaatta gtgtaaagtg ataacatgct tctacctgta
1801 tttctagtga ccctttagcg gcaggtattt atacctggta tttatgatgc agtatataag
1861 tggtgaacaa taactgacag tattgtgctt gctgtacatg tctggtcttt tgaaacagat
1921 tttagtaagc attttccaga ggtaaaactg tgtccttatt ctaattttat tcctagggca
1981 aagtagacag ggattatttc cttgaatcta tttccaaatt aatatttttt tctttggtat
2041 ttctacactt taaggccatt tggtgcaatt tagaaagtgt tggcctccct tccgctagcc
2101 acattcaaaa ttaacttcca aaacctcagg aacagtacaa agaattgaaa ccctcaatat
2161 ggcagcacag ccggctgtag tgtatattta gggtacacca aatcaggtat tcctggtggt
2221 cttgtgcact ttaatttctg ttacaatgag ttaagaggat gaggaagaaa tctacttatt
2281 aacacttact gcagaaatgt ctgcattatt ccgtttgttt tcttattatt ttacctctcc
2341 aaacatcttc ctgtgcagat cactacttca tagttgccaa attttaaaac acttaactgc
2401 tgaaattcag tgtcagcaaa gtgatattac gttgttctgt ttctaattaa ccttagcaaa
2461 tgtacataat gtcaaaaccc aatagtattt gacagtactt atgtatacaa tgtttgataa
2521 gcatttttaa taagatttgt atttttaaat ttagtatata ataaaaagat gtgtttcagt
2581 gtgaaaaaaa aaaaaaaaaa aaaa
```

FIG. 16

Homo sapiens NK3 homeobox 1 (NKX3-1), mRNA.

```
   1 gcggtgcggg ccgggcgggt gcattcaggc caaggcgggg ccgccgggat gctcagggtt
  61 ccggagccgc ggcccgggga ggcgaaagcg gagggggccg cgccgccgac cccgtccaag
 121 ccgctcacgt ccttcctcat ccaggacatc ctgcgggacg gcgcgcagcg gcaaggcggc
 181 cgcacgagca gccagagaca gcgcgacccg gagccggagc cagagccaga gccagaggga
 241 ggacgcagcc gcgccggggc gcagaacgac cagctgagca ccgggccccg cgccgcgccg
 301 gaggaggccg agacgctggc agagaccgag ccagaaaggc acttggggtc ttatctgttg
 361 gactctgaaa acacttcagg cgcccttcca aggcttcccc aaacccctaa gcagccgcag
 421 aagcgctccc gagctgcctt ctcccacact caggtgatcg agttggagag gaagttcagc
 481 catcagaagt acctgtcggc ccctgaacgg gcccacctgg ccaagaacct caagctcacg
 541 gagacccaag tgaagatatg gttccagaac agacgctata agactaagcg aaagcagctc
 601 tcctcggagc tgggagactt ggagaagcac tcctctttgc cggccctgaa agaggaggcc
 661 ttctcccggg cctccctggt ctccgtgtat aacagctatc cttactaccc atacctgtac
 721 tgcgtgggca gctggagccc agctttttgg taatgccagc tcaggtgaca accattatga
 781 tcaaaaactg ccttccccag ggtgtctcta tgaaaagcac aaggggccaa ggtcagggag
 841 caagaggtgt gcacaccaaa gctattggag atttgcgtgg aaatctcaga ttcttcactg
 901 gtgagacaat gaaacaacag agacagtgaa agttttaata cctaagtcat tcctccagtg
 961 catactgtag gtcatttttt ttgcttctgg ctacctgttt gaaggggaga gagggaaaat
1021 caagtggtat tttccagcac tttgtatgat tttggatgag ttgtacaccc aaggattctg
1081 ttctgcaact ccatcctcct gtgtcactga atatcaactc tgaaagagca aacctaacag
1141 gagaaaggac aaccaggatg aggatgtcac caactgaatt aaacttaagt ccagaagcct
1201 cctgttggcc ttggaatatg gccaaggctc tctctgtccc tgtaaaagag aggggcaaat
1261 agagagtctc caagagaacg ccctcatgct cagcacatat ttgcatggga gggggagatg
1321 ggtgggagga gatgaaaata tcagcttttc ttattccttt ttattccttt taaaatggta
1381 tgccaactta agtatttaca gggtggccca aatagaacaa gatgcactcg ctgtgatttt
1441 aagacaagct gtataaacag aactccactg caagaggggg ggccgggcca ggagaatctc
1501 cgcttgtcca agacaggggc ctaaggaggg tctccacact gctgctaggg gctgttgcat
1561 tttttatta gtagaaagtg gaaaggcctc ttctcaactt ttttcccttg ggctggagaa
1621 tttagaatca gaagtttcct ggagttttca ggctatcata tatactgtat cctgaaaggc
1681 aacataattc ttccttccct ccttttaaaa ttttgtgttc ctttttgcag caattactca
1741 ctaaagggct tcattttagt ccagattttt agtctggctg cacctaactt atgcctcgct
1801 tatttagccc gagatctggt cttttttttt tttttttttt tttttttccc gtctccccaa
1861 agctttatct gtcttgactt tttaaaaaag tttgggggca gattctgaat tggctaaaag
1921 acatgcattt ttaaaactag caactcttat ttctttcctt taaaaataca tagcattaaa
1981 tcccaaatcc tatttaaaga cctgacagct tgagaaggtc actactgcat ttataggacc
2041 ttctggtggt tctgctgtta cgtttgaagt ctgacaatcc ttgagaatct ttgcatgcag
2101 aggaggtaag aggtattgga ttttcacaga ggaagaacac agcgcagaat gaagggccag
2161 gcttactgag ctgtccagtg gagggctcat gggtgggaca tggaaaagaa ggcagcctag
2221 gccctgggga gcccagtcca ctgagcaagc aagggactga gtgagccttt tgcaggaaaa
2281 ggctaagaaa aaggaaaacc attctaaaac acaacaagaa actgtccaaa tgctttggga
2341 actgtgttta ttgcctataa tgggtcccca aaatgggtaa cctagacttc agagagaatg
2401 agcagagagc aaaggagaaa tctggctgtc cttccatttt cattctgtta tctcaggtga
2461 gctggtagag gggagacatt agaaaaaaat gaaacaacaa aacaattact aatgaggtac
2521 gctgaggcct gggagtctct tgactccact acttaattcc gtttagtgag aaacctttca
2581 attttctttt attagaaggg ccagcttact gttggtggca aaattgccaa cataagttaa
2641 tagaaagttg gccaatttca ccccattttc tgtggtttgg gctccacatt gcaatgttca
2701 atgccacgtg ctgctgacac cgaccggagt actagccagc acaaaaggca gggtagcctg
2761 aattgctttc tgctctttac atttctttta aaataagcat ttagtgctca gtccctactg
2821 agtactcttt ctctcccctc ctctgaattt aattctttca acttgcaatt tgcaaggatt
2881 acacatttca ctgtgatgta tattgtgttg caaaaaaaaa aaaaaagtgt ctttgtttaa
2941 aattacttgg tttgtgaatc catcttgctt tttccccatt ggaactagtc attaacccat
3001 ctctgaactg gtagaaaaac atctgaagag ctagtctatc agcatctgac aggtgaattg
3061 gatggttctc agaaccattt cacccagaca gcctgtttct atcctgttta ataaattagt
3121 ttgggttctc tacatgcata acaaaccctg ctccaatctg tcacataaaa gtctgtgact
```

FIG. 16 (cont'd)

```
3181 tgaagtttag tcagcacccc caccaaactt tatttttcta tgtgtttttt gcaacatatg
3241 agtgttttga aaataaagta cccatgtctt tattagattt a
```

FIG. 17

Homo sapiens ribosomal protein SA (RPSA), transcript variant 1, mRNA.

```
   1 cgcctgtctt ttccgtgcta cctgcagagg ggtccatacg gcgttgttct ggattcccgt
  61 cgtaacttaa agggaaattt tcacaatgtc cggagccctt gatgtcctgc aaatgaagga
 121 ggaggatgtc cttaagttcc ttgcagcagg aacccactta ggtggcacca atcttgactt
 181 ccagatggaa cagtacatct ataaaaggaa aagtgatggc atctatatca taaatctcaa
 241 gaggacctgg gagaagcttc tgctggcagc tcgtgcaatt gttgccattg aaaaccctgc
 301 tgatgtcagt gttatatcct ccaggaatac tggccagagg gctgtgctga agtttgctgc
 361 tgccactgga gccactccaa ttgctggccg cttcactcct ggaaccttca ctaaccagat
 421 ccaggcagcc ttccgggagc cacggcttct tgtggttact gaccccaggg ctgaccacca
 481 gcctctcacg gaggcatctt atgttaacct acctaccatt gcgctgtgta acacagattc
 541 tcctctgcgc tatgtggaca ttgccatccc atgcaacaac aagggagctc actcagtggg
 601 tttgatgtgg tggatgctgg ctcgggaagt tctgcgcatg cgtggcacca tttcccgtga
 661 acacccatgg gaggtcatgc ctgatctgta cttctacaga gatcctgaag agattgaaaa
 721 agaagagcag gctgctgctg agaaggcagt gaccaaggag gaatttcagg gtgaatggac
 781 tgctcccgct cctgagttca ctgctactca gcctgaggtt gcagactggt ctgaaggtgt
 841 acaggtgccc tctgtgccta ttcagcaatt ccctactgaa gactggagcg ctcagcctgc
 901 cacggaagac tggtctgcag ctcccactgc tcaggccact gaatgggtag gagcaaccac
 961 tgactggtct taagctgttc ttgcataggc tcttaagcag catggaaaaa tggttgatgg
1021 aaaataaaca tcagtttcta aaagttgtct tcatttagtt tgctttttac tccagatcag
1081 aatacctggg attgcatatc aaagcataat aataaataca tgtctcgaca tgagttgtac
1141 ttctaaaaaa aaaaa
```

FIG. 18

Homo sapiens cytochrome c oxidase subunit Va (COX5A), nuclear gene encoding mitochondrial protein, mRNA.

```
  1 gcccacgcgc cagagtcgca gtgggcgggc ctacgtgctc cgcccgctgt gagcctgtcc
 61 ggcccccgcc cgctccggag caacccgcga gcttacaccg gcttctctct gtcctcagcc
121 cgcgcgccgc catcgccgtc atgctgggcg ccgctctccg ccgctgcgct gtggccgcaa
181 ccacccgggc cgaccctcga ggcctcctgc actccgcccg gacccccggc cccgccgtgg
241 ctatccagtc agttcgctgc tattcccatg ggtcacagga gacagatgag gagtttgatg
301 ctcgctgggt aacatacttc aacaagccag atatagatgc ctgggaattg cgtaaaggga
361 taaacacact tgttacctat gatatggttc cagagcccaa aatcattgat gctgctttgc
421 gggcatgcag acggttaaat gattttgcta gtacagttcg tatcctagag gttgttaagg
481 acaaagcagg acctcataag gaaatctacc cctatgtcat ccaggaactt agaccaactt
541 taaatgaact gggaatctcc actccggagg aactgggcct tgacaaagtg taaaccgcat
601 ggatgggctt ccccaaggat ttattgacat tgctacttga gtgtgaacag ttacctggaa
661 atactgatga taacatatta ccttatttga acaagttttc ctttattgag taccaagcca
721 tgtaatggta acttggactt taataaaagg gaaatgagtt tgaactgaaa aaaaaaaaaa
781 aaaa
```

FIG. 19

Homo sapiens family with sequence similarity 53, member B (FAM53B), mRNA.

```
   1 cgccgccgcc gcacgccgcc tgcctcctgc acgccgccgc cgcgcctagc gcccgggccc
  61 gcgacaccgc ccgctaagcg ccgggccgag ttcacgcagc cgcggtctgg cggctccgcg
 121 gcggcggcgg gtgcgggcgg cctggccggt gccggttaaa gggacgagtt gcaaacactt
 181 caggaagtga caagtcgatt tcctcctccc cgggagtcgc tcgtacaaag cgctcggcgc
 241 cggcaggcga gcgtgcgcgc ggcggacgcg cggcgggcac cccggacgac ttggcgagcg
 301 ctggcggtga cggcgcgggg tccgcgcccg gagcgccccg ccgcgcacag gagttgacca
 361 catttggcca tttcccagaa gggccccacc ccaagggtga gtggccaatg gggagctgtt
 421 tctgctgaca tcaattcccc aggaggtact caccccaagt ctgcccaagt gaagatggct
 481 gatacccacc ctgggatgga gcccagcgcc tgaggccctt atcatggtga tggtcctaag
 541 tgaaagcctc agcacccggg gagctgactc cattgcatgt gggaccttca gccgtgaact
 601 gcacacgcca aagaagatga gtcaaggacc tacacttttc tcttgtggaa ttatggaaaa
 661 tgacagatgg cgagacctgg acaggaaatg ccctcttcag attgaccaac cgagcaccag
 721 catctgggaa tgcctgcctg aaaaggacag ctcactatgg caccgggagg cagtgaccgc
 781 ctgcgctgtg accagtctga tcaaagacct cagcatcagc gaccacaacg ggaacccctc
 841 agcacccccct agcaagcgcc agtgccgctc actgtccttc tccgatgaga tgtccagttg
 901 ccggacatca tggaggccct tgggctccaa agtctggact cccgtggaaa agagacgctg
 961 ctacagcggg ggcagcgtcc agcgctattc caacggcttc agcaccatgc agaggagttc
1021 cagcttcagc ctcccttccc gggccaacgt gctctcctca ccctgcgacc aggcaggact
1081 ccaccaccga tttggagggc agccctgcca aggggtgcca ggctcagccc cgtgtggaca
1141 ggcaggtgac acctggagcc ctgacctgca ccccgtggga ggaggccggc tggacctgca
1201 gcggtccctc tcttgctcac atgagcagtt ttcctttgtg gaatactgtc ctccctcagc
1261 caacagcaca cctgcctcaa caccagagct ggcgagacgc tccagcggcc tttcccgcag
1321 ccgctcccag ccgtgtgtcc ttaacgacaa gaaggtcggt gttaaaaggc ggcgccctga
1381 agaagtgcaa gagcagaggc cttctctaga ccttgccaag atggcacaga actgtcagac
1441 cttcagcagc ctcagctgcc tgagcgcagg gacagaggac tgcggtcccc agagcccctt
1501 cgcccgccac gtcagcaaca ccagggcctg gaccgccctg ctctcagcct ccggcccagg
1561 gggcaggacc cccgctggga ccccggtccc tgagcctctt ccccctccct tcgacgacca
1621 cctcgcctgc caggaggacc tgtcctgtga ggagtcagac agctgcgccc tggacgagga
1681 ttgtggcagg agagcggagc cggctgcagc ctggcgggac cgcggggccc ctgggaacag
1741 cctctgctcc ctggacggcg agttggacat tgagcagata gagaagaact gaggggggtgt
1801 gggcccaggc agggctgggg tgtgctggca tcgacagccc ccactctggg cactaggtgg
1861 gcccttgaag gggagcccaa ctcgtgggcc tgatgaaagc ttcctgagtg gtgtcgggtc
1921 ccagagaggg agcccacctg ctgcctgggg gagagcctgg cctggccgcg tcatacagcg
1981 ggtgtgtcag cctctcaccg gctccccgag cgtggcagcc accaggtcca cagaactact
2041 gcagcccaga ggacagcttt gaagtttgcg tcttttctgc ctctttccct gtgggatgtt
2101 gggcagtctc tgttgtcccc ggcagagctg ggcaccgctc tgtatccccc tggtggtggg
2161 ggctgtcagg gagggcctgg ggtgggggcc aggggccatc tgctatgtca gggcccttct
2221 tggcctcact caggttcact tctggggagt cggccccgca gcttctttca ctcagtttta
2281 ctccgtgcct tctctcccag gtctccctgc ttcaggcttg ggaaggttcg ggagatgctt
2341 ccttctgtaa caccagaacc atttggcctt aattccaatg tgagagacag aatccctggg
2401 gtgctggact ggccctccag agggtaagcc atgtccggag tctcgggccc aaggaacgat
2461 ttggagggtg cttgttaggg cctcccgtgt tgggtagaaa tttggtggat ctgttggctg
2521 aaaagacgga cttgcttgcc tctcctacag catggagagg ctgaccccat ggctctgcca
2581 ccgttggggc agggttagca gatggcagcc cttctctgtg gctgacaggt cactgagtga
2641 taagcatggt tggttccggt gagtgtaggg atggcacgat accagggcag cctcttgaaa
2701 acggcctcgg gagacgggag ctgcgagcag gtgggcagat gagggcccta tgcgcactca
2761 ggggtgaagg gcgtccgctg gccactctgc aggggcccct gcaggattcc aggcacctcc
2821 cgtttgtcct tgaggactgc tggctgtaac cagggcacat cacccacctc aagacaagcc
2881 cacgcccttg tcagcttagg gggagcccag tcctgagggc tgcatctctg ttgtaggccc
2941 agccaccggc acaaagctgg attcatgctc cctgccccta ccccaccctg gctcctcacc
3001 ctggggcatc cgaggagcct agccccctga gggtttgctc tcctctcaag gtttgtagct
3061 cctctccggc tgccttgcag acaccaccac atgggctctg ctctatggga atctggcttt
```

FIG. 19 (cont'd)

```
3121 tagcgaatgt ggcgtcttct gcaaacaata gcaattgggc tggcttagga gcaagtggct
3181 cattttccca taaggctaaa aataactggt gcgctccctt gtgttggctg acacgcgcgt
3241 tcaaagcact tttgtagtca ctttgctttt gctcgtcttc atggacgagt gaacgcctcg
3301 cttctgcagg ttgagtccag atgcttctca ccttctttct cctcaagaaa gatgcttttt
3361 gggaaacgtt gtttaaatct tatttttta ctacatcaaa aggatggtgg ttcaagttcc
3421 caatatgtgg gtggcacttc ttaaaaatca gctttaagga gctggcagaa agcccccagc
3481 cccacagccc tgagagatgg tgttgctagc tcaggtggct gacacatggg gtatgccggg
3541 cactgggcag gtcccagagc cggggaacca gctcacctct ggttgctgta gctcctgccg
3601 gaggcatgtc tacttgtgat cccggacagc cgaacccaag agctggtggc tctgagcaga
3661 cagagacatc ttggcctgtc cctgcctggg ggtcatggag accatgtctt cttagagcaa
3721 atgtggaggc ggccagggca gttgttgggt gaatgtggag agcacatggc catgtcttgc
3781 ccccggagta ccactgggcg tggggggtcc tggcaccaca tgcccggtgt ggccgagggc
3841 acacagcctc tatagcaggc cttcctgtgg aaggcagagg cagtgaggga ggtggacggt
3901 gccagctgag gctgaggcat gcagcagccc ccagctacct ttgcttaggg ctggggtggg
3961 aggcacatgg tgacaggtat atgtcgtggg actggggtgt gggtgacctg ccctcaaacc
4021 ttgcctgcca cctccccatt caggcctggt ggcaggaagg gacaagctgt ggagctggct
4081 gagtcacagc cacctcccca cctccccgca agctggtccc atcgaccagc aagcccagcc
4141 ccagggcgct tagggagaaa tgacccagcc tcctcagacc ccgcctgcct gtcctgtgcc
4201 caccacgcag cagtcagggg agaaaatggt ggctatccct tctgcttaga gaaagaaatg
4261 gcctttagct ggtttcatgt ttgtgttttg actggaggga gtagacccta tctataaggt
4321 gccaccccat catccaagct gccacactgc ccggagcagc ctgttcctgc actccacccct
4381 gctggcccca ggacttctga tctcagtcct ctgggaggga ggttcgccta ggaggtgccc
4441 cccacattgg tgtccccatg ggcagcaggc agacagctca cccccaccag catgatggcc
4501 ccagctgggg gcagtggcag gagccttact tttgtcacag ccttgcccac aaaccctgcc
4561 tctgagggga gactgaggaa gggcagagcc agaagcaagc cgtgccaggc catctgcctg
4621 ctcatggggt cctaaagcgc gggctaagcc tgcaggaaag ccggggcggt gggggggct
4681 tagtgccaca tgcaccccac tcattccaaa gccaccaaac tgccaggggc tgccgtccac
4741 ccgtggggcc caggggctgg ggccacagcc ttgccatttt cgttgccata ccctcttgcc
4801 ttactcgcgg tggaggccgg atttgcacgg gcagacgtgc acctgggccc gtggggagct
4861 tgttctgacc agacgtacag attttcattc tcagaaagcc ttacttttca accaaatttt
4921 tgtagccagt tttgtgaatt tgtacactga aagaaaattt aaataaaggg gaagtccaca
4981 ttaaaaagaa aacaaaacaa accctaacta acttccaaat gggtctcctg gtgcgggggc
5041 gtgagtggcc gtgccctggg tgtgctgcct gtctgagcaa gcttccctag ctgtggaacc
5101 ccgggccccc tgctgcgggc tctgccttgg tgtcatgcct gctgcacccc cgtttccact
5161 gacgtgccgt ctgtggctat gggggtggtc actggaatga cggtcactcc agacgtcagc
5221 cggcagggat gcagcaggct ggccgcgcac cggggctcgg gcaccctctg gccccacact
5281 ggcaatgatg ccacaccttg ccatgtccac gctgttggtc aaacccctct gtcatgcctc
5341 tttaaagaga aaagaagaga aagatttttt ttttttttaa tggcagaccg aagtggagat
5401 cttgtagcct agataggata gtctgacctt ctagcatagt ctttttggca aatgatttgt
5461 gttttcagtg tgtggggaag ctgtcctggg ggctggggcg acagatagca cataggctgt
5521 ttctggggct gcaggggctt ccctgagctg gatgttgtgg gtgttgccgt gcttcaggaa
5581 gtgtggcgac cagaaagcgt agacccgggg cccagggtct gcccgcccct gcagcctggc
5641 ctccccgcac aggctgtggc ttgcactcca gccgctctag tctctcagga atttgcttgt
5701 tacttgtact gtgtaaataa agcttcctgg ttcaataccc
```

FIG. 20

Homo sapiens genomic DNA, chromosome 11 clone: CTD-2579L12, NTs 149521-151500.

```
149521 gcaatggaca agtcttggtt aaatgtgctt tggaggaact tcctgaaatg gggaagagga
149581 tcatctgaaa atgagataga gatccacatc tgatttgtaa ttttgaacct aatagtttat
149641 tatttatatt tgagagtatc ctaaatctgc tattagcagc caaaaatgaa tacaagaaag
149701 tacaatcgtt atttaaaaga agcaagttat agttgacaaa gattaaaatg ttaaaagttg
149761 tttgaagttt aggcaactga caataacaga acaacttatt aataacagta atgaagttaa
149821 aaattataga gcatttgcta taacctaagt atgtccgttt aaacttcacc actttcttag
149881 attaggaagc tgaccttcag ataagtaaaa ttatatcgga aaggtcctct taattcacag
149941 tgccaaatcc agattttccc tgacttcccc aaatgccact tataagataa tttaattatt
150001 attcatcccc tgatgactgc aggaaaacct ctgtgggtaa gtagagataa atgtgaagag
150061 cagaagcaaa gaaaagagct agcagtagtg aatgttgaac ttcatgtgct aattggtgtg
150121 tgtccatttc tgatacagcc actttgagac aagggctata tcatccatga attggatctt
150181 aatgtccatt gctgtatttt tacttctcta gtttttaaga aatttaggct gtggttcaca
150241 ttgtgtattc gaaagataga atacctcgct aactagacaa acaaaagctt tgttctaaaa
150301 atgtactttc cttaaagcag aagtaacctg cagagaagca ggatgcctga agagagatgg
150361 atctctgctt actgtgtctt tagaacagaa atagtggttt tcaacttcac aactctgcat
150421 tgagccctcc tttcacatct tccctgtatc attgcagaat tgatctgaat aattctcatt
150481 ttatcttaga caatttttttg tgtggcttga aaaaataaat ttgcaataga ggtgaaatgg
150541 aaaaaattat ccttcatttc ctactccaaa ctgaggataa acaattattc ttggaaattc
150601 caccatagaa ttgaattcat tgtacgtgtg aattgcacct tttaagcttt taaatgatgt
150661 ggcattttta tttagcagca ttccaaaagg gaccacgaaa taaatgagct ccctggtttt
150721 gcagcatttt ataattccaa tatgaaagtt ttagcattat tactaactga agaatcagaa
150781 aggaaattca tagactatca cttctgggtt ttcaagtatt tttaatccat gcaactcttc
150841 ctccaaactt tttcttcaac ttctcatgag aaagtcagca tataaagttc ttaaaagctg
150901 tgctcccctg accgaaatgg agatgagtac catggtggga gaatgcatct ttccccctcg
150961 agagtcctct agcacctgcg gtggtctctg gaagaactca gcagaactcc caagtgccaa
151021 ggaacacata ttacagaaca acggactgca gaaattcaga tagatgaaaa ctatagatca
151081 ttctaggtac tttgttccca gacttataat actcccaata gcttctctaa tgtatgatca
151141 agtggctgtc tgctgtaata ttttcagagc tataatgttt atatctaacc tcttatattt
151201 atgtccaaat cagctggtat attttggctt attctgagca gtagctgcta gatctatctt
151261 gtggtacaca ttaagcctat tccttcttcc acagttcttc ttgacattat gctacttaaa
151321 aagtcatccc ttatcaaaat caaatttcat tattttagtt atatcacatc caatatttaa
151381 ttgtgtaaac cactctttac tctagctatt cgtcctcaga attgcttctg ttataaatgc
151441 tctttttgaa cagacttcct agagtagaag agaaagctcc agatatgatc tgatgggggt
```

FIG. 21

Homo sapiens mitogen-activated protein kinase kinase kinase 9(MAP3K9), mRNA.

```
   1 atggagccct ccagagcgct tctcggctgc ctagcgagcg ccgccgctgc cgccccgccg
  61 ggggaggatg gagcaggggc cggggccgag gaggaggagg aggaggagga ggaggcggcg
 121 gcggcggtgg gccccgggga gctgggctgc gacgcgccgc tgccctactg gacggccgtg
 181 ttcgagtacg aggcggcggg cgaggacgag ctgaccctgc ggctgggcga cgtggtggag
 241 gtgctgtcca aggactcgca ggtgtccggc gacgagggct ggtggaccgg gcagctgaac
 301 cagcgggtgg gcatcttccc cagcaactac gtgaccccgc gcagcgcctt ctccagccgc
 361 tgccagcccg gcggcgagga ccccagttgc tacccgccca ttcagttgtt agaaattgat
 421 tttgcggagc tcaccttgga agagattatt ggcatcgggg gctttgggaa ggtctatcgt
 481 gctttctgga taggggatga ggttgctgtg aaagcagctc gccacgaccc tgatgaggac
 541 atcagccaga ccatagagaa tgttcgccaa gaggccaagc tcttcgccat gctgaagcac
 601 cccaacatca ttgccctaag aggggtatgt ctgaaggagc ccaacctctg cttggtcatg
 661 gagtttgctc gtggaggacc tttgaataga gtgttatctg ggaaaaggat tcccccagac
 721 atcctggtga attgggctgt gcagattgcc agagggatga actacttaca tgatgaggca
 781 attgttccca tcatccaccg cgaccttaag tccagcaaca tattgatcct ccagaaggtg
 841 gagaatggag acctgagcaa caagattctg aagatcactg attttggcct ggctcgggaa
 901 tggcaccgaa ccaccaagat gagtgcggca gggacgtatg cttggatggc acccgaagtc
 961 atccgggcct ccatgttttc caaaggcagt gatgtgtgga gctatggggt gctactttgg
1021 gagttgctga ctggtgaggt gccctttcga ggcattgatg gcttagcagt cgcttatgga
1081 gtggccatga acaaactcgc ccttcctatt ccttctacgt gcccagaacc ttttgccaaa
1141 ctcatggaag actgctggaa tcctgatccc cactcacgac catctttcac gaatatcctg
1201 gaccagctaa ccaccataga ggagtctggt ttctttgaaa tgcccaagga ctccttccac
1261 tgcctgcagg acaactggaa acacgagatt caggagatgt ttgaccaact cagggccaaa
1321 gaaaaggaac ttcgcacctg ggaggaggag ctgacgcggg ctgcactgca gcagaagaac
1381 caggaggaac tgctgcggcg tcgggagcag gagctggccg agcgggagat tgacatcctg
1441 gaacgggagc tcaacatcat catccaccag ctgtgccagg agaagccccg ggtgaagaaa
1501 cgcaagggca agttcaggaa gagccggctg aagctcaagg atggcaaccg catcagcctc
1561 ccttctgatt tccagcacaa gttcacggtg caggcctccc ctaccatgga taaaaggaag
1621 agtcttatca acagccgctc cagtcctcct gcaagcccca ccatcattcc tcgccttcga
1681 gccatccagt tgacaccagg tgaaagcagc aaaacctggg gcaggagctc agtcgtccca
1741 aaggaggaag gggaggagga ggagaagagg gccccaaaga agaagggacg gacgtggggg
1801 ccagggacgc ttggtcagaa ggagcttgcc tcgggagatg aaggatcccc tcagagacgt
1861 gagaaagcta atggtttaag taccccatca gaatctccac atttccactt gggcctcaag
1921 tccctggtag atggatataa gcagtggtcg tccagtgccc ccaacctggt gaagggccca
1981 aggagtagcc cggccctgcc agggttcacc agccttatgg agatggcctt gctggcagcc
2041 agttgggtgg tgcccatcga cattgaagag gatgaggaca gtgaaggccc agggagtgga
2101 gagagtcgcc tacagcattc acccagccag tcctacctct gtatcccatt ccctcgtgga
2161 gaggatggcg atggcccctc cagtgatgga atccatgagg agcccacccc agtcaactcg
2221 gccacgagta cccctcagct gacgccaacc aacagcctca agcggggcgg tgcccaccac
2281 cgccgctgcg aggtggctct gctcggctgt ggggctgttc tggcagccac aggcctaggg
2341 tttgacttgc tggaagctgg caagtgccag ctgcttcccc tggaggagcc tgagccacca
2401 gcccgggagg agaagaaaag acgggagggt ctttttcaga ggtccagccg tcctcgtcgg
2461 agcaccagcc ccccatcccg aaagcttttc aagaaggagg agcccatgct gttgctagga
2521 gacccctctg cctccctgac gctgctctcc ctctcctcca tctccgagtg caactccaca
2581 cgctccctgc tgcgctccga cagcgatgaa attgtcgtgt atgagatgcc agtcagccca
2641 gtcgaggccc ctcccctgag tccatgtacc cacaaccccc tggtcaatgt ccgagtagag
2701 cgcttcaaac gagatcctaa ccaatctctg actcccaccc atgtcaccct caccaccccc
2761 tcgcagccca gcagtcaccg gcggactcct tctgatgggg cccttaagcc agagactctc
2821 ctagccagca ggagcccctc cagcaatggg ttgagcccca gtcctggagc aggaatgttg
2881 aaaaccccca gtcccagccg agacccaggt gaattccccc gtctccctga ccccaatgtg
2941 gtcttccccc caaccccaag gcgctggaac actcagcagg actctacctt ggagagaccc
3001 aagactctgg agtttctgcc tcggccgcgt ccttctgcca accggcaacg gctggaccct
3061 tggtggtttg tgtcccccag ccatgcccgc agcacctccc cagccaacag ctccagcaca
```

FIG. 21 (cont'd)

```
3121 gagacgccca gcaacctgga ctcctgcttt gctagcagta gcagcactgt agaggagcgg
3181 cctggacttc cagccctgct cccgttccag gcagggccgc tgcccccgac tgagcggacg
3241 ctcctggacc tggatgcaga ggggcagagt caggacagca ccgtgccgct gtgcagagcg
3301 gaactgaaca cacacaggcc tgccccttat gagatccagc aggagttctg gtcttagcac
3361 gaaaaggatt ggggcgggca agggggacag ccagcggaga tgaggggagc tggcgggcac
3421 agccctttct cagggttgga ccccctgaga tccagcccta cttcttgcac tgataatgca
3481 ctttgaagat ggaagggatg gaaacagggc cacttcagag ggtctcctgc cctgcagggc
3541 ctttctaccc gtgtccactg gaggggctgt ggccatcagc tctggctgtg taggggagga
3601 aggggtgcat gcatgtcccc caccctccac agtcttcctt gcctttagag tgaccctgca
3661 gagtcactca gccaaatctg tctgctgctc cctctcctca gccagttggg tgtgcgcaga
3721 gctgtcatag ggtccctttg tcagccccga gttcagcttc ccaaacacca gtgttggata
3781 ttctgtgatt gattttggtc ctcctccgct gtcccccaac acccaggaat gggaatctgg
3841 cttggttcga gataggagct tttctgtgtc ctaagccctt tcatgctagc aggaagactg
3901 aaagcaaggt ggcccagtgt ggggtcatag ggcttgatag acctggcact gcctatctgc
3961 acttccaggt gccccaccta tttatctgag cccacaggtg gaaaggggaa ctgcctcagt
4021 gagaacgggg ggacggggat gttaggaaaa atacagtaaa gttgcaatga agaggttcat
4081 gaagtatgtc cttgttcttt ttggaaactc tcggcaaagg gcaaaccagc aagtattgag
4141 ggtacccatc tagctacttg gggtcaggac ctcgtcagac caggttcgga tacaatcatc
4201 tgctcatccc aggaatagtt tcttgggga ctcactcact ggtgccagtt ctaagtcaga
4261 gacaaaattc cactgtctgt tccttttgct gtctgaactt tatgtgttac tcccttcctt
4321 tggtcttcac tctaatccct ggagtttgtg ggcttttggt tatgtttggt tagtagatat
4381 caccgcaatg ccctagaaca gctatgaagc agaataccat atggccacct ggacattggg
4441 acttgggaat tcactctcaa ctgggccatc catgttgtga tgcccttgaa gtaaaatgga
4501 gccagcagga gtaccttctg taaatgcatg tggcaaagtg ctatttatag ggtgcccagg
4561 gagccgctga tgtacaataa ccttgaggtc ccccatactg aaaactgacc aaggcctgtg
4621 cacaggtagc ccctcatgct gggctctgga ccatgagctg agtaggaagg atagcagagg
4681 ccaaccctga ccttcctgga agttgtttcc ttaacttgaa tgttgagctt cctctaaagc
4741 tttctcgtgt atgtcttctc catgccacta ctctgaggcc tcctgtgtta tgtgtgaaca
4801 gttgtcttta tgtgggaatg acgacttgat tgggagtaga gtctcaaggt cattcccctc
4861 ttccctcaag actctctgaa tgctgctcca ctgtcttttg tcttggaggt cactcagcag
4921 gttccttgca tttgctgcct ggatgtgcag ctggcaacag tgatgaattg gtcactgctc
4981 tttctctata actgggatag atgtcctgcc ttggggtcac taaaggggtg accttgttcc
5041 ttgctttatg agcccattag cactttggtt caaggggccc accaagtctt ggacgggaag
5101 gcgctactgg ttttattgcc caaggttttg ttattgcttc tcttctgtgt ccttctcttt
5161 gttcagtgaa gccaatatgt aagatactgt ttttgtcccc attcccctac tcctgagcta
5221 ggaggaaaaa atgtgaatct taccagcagt tccagccaac caagtgattc ttcttcattc
5281 ttgatgggga gaagtacata caaagtttgt tctgacaggg cgcggtggct cacgcctgta
5341 atcccagcgc tttgggaggc agaggcaggt ggatcacctg aggtcgggag ttcgagacca
5401 gcctgaccaa catggagata tcctgtctct actaaaaata caaaaaaatt agccaggcat
5461 ggtggcacgt gcctgtaatc ccagctactc gcaaggctga ggcaggagaa tcgcttgaac
5521 ctgggaggcg gaggttgcag tgagccaaga ttgcgccatt gcactccagc ctgggcaaca
5581 agagagaaac tctgtctcaa aa
```

FIG. 22

PREDICTED: Homo sapiens hypothetical LOC643783, transcript variant 2 (LOC643783), partial miscRNA.

```
  1 ccgggccccg ccgcgccgcc tccttcccag ctcgcccgcc caggcctggc ctcctgcttt
 61 tccatttgat tccctgcctc tttctattcg gactggaatg ccgggccagg ctccggggcg
121 cgccgctgcg gcagccgcac ctcgcaggtc ccccggccga ccccgacgcg gaagcggcgg
181 ccctcctcgc cgtcggggag ccagggagcc ggggacgatc agtcacataa ggcttagagg
241 atcaaggatc ctgcccagat gacttaccga aatgttacag attaagttgg tgtggtaacc
301 tgggctgagc actctgggag aggaagagaa gagagaagac aggaaacaac tgaactatga
361 ccaatcccag cacggaggcc cagaaaactt taagatttga gtattaatgt ctcaaggtca
421 ggagcaacct caaggctaaa actcagatct caggactcaa tttcacagaa gttccactat
481 aaaggcaata atctaaagct ttaaatgata tgaaaatttt gtaataagag ttcagtattt
541 ctgccaacat tggcgcatgg attgcaaagt tcacaggatt gaaaacacca tcgacataat
601 ggaaattgaa cagcatctga ttactgagtg ctatatcagc aagttaaaag gatcttttgc
661 ataccttttta atggtatata tcctaaaact gaagtgttca atatagacat ccagattgaa
721 actcaggcag tgaattacat acacaacaaa tcagttgaac atggcagagc ttgtcagact
781 tatgaaagat taaatacatt ttacatttcc acaagtgtgg tatt
```

FIG. 23

Human prostate specific antigen gene, complete cds.

```
   1 gaattccaca ttgtttgctg cacgttggat tttgaaatgc tagggaactt tgggagactc
  61 atatttctgg gctagaggat ctgtggacca caagatcttt ttatgatgac agtagcaatg
 121 tatctgtgga gctggattct gggttgggag tgcaaggaaa agaatgtact aaatgccaag
 181 acatctattt caggagcatg aggaataaaa gttctagttt ctggtctcag agtggtgcag
 241 ggatcaggga gtctcacaat ctcctgagtg ctggtgtctt agggcacact gggtcttgga
 301 gtgcaaagga tctaggcacg tgaggctttg tatgaagaat cggggatcgt acccaccccc
 361 tgtttctgtt tcatcctggg catgtctcct ctgcctttgt cccctagatg aagtctccat
 421 gagctacaag ggcctggtgc atccagggtg atctagtaat tgcagaacag caagtgctag
 481 ctctccctcc ccttccacag ctctgggtgt gggagggggt tgtccagcct ccagcagcat
 541 ggggagggcc ttggtcagcc tctgggtgcc agcagggcag ggcggagtc ctggggaatg
 601 aaggttttat agggctcctg ggggaggctc cccagcccca agcttaccac ctgcacccgg
 661 agagctgtgt caccatgtgg gtcccggttg tcttcctcac cctgtccgtg acgtggattg
 721 gtgagagggg ccatggttgg ggggatgcag gagagggagc cagccctgac tgtcaagctg
 781 aggctctttc ccccccaacc cagcacccca gcccagacag ggagctgggc tcttttctgt
 841 ctctcccagc ccacttcaa gcccataccc ccagcccctc catattgcaa cagtcctcac
 901 tcccacacca ggtccccgct ccctcccact taccccagaa ctttctcccc attgcccagc
 961 cagctccctg ctcccagctg ctttactaaa ggggaagttc ctgggcatct ccgtgtttct
1021 ctttgtgggg ctcaaaacct ccaaggacct ctctcaatgc cattggttcc ttggaccgta
1081 tcactggtcc atctcctgag cccctcaatc ctatcacagt ctactgactt ttcccattca
1141 gctgtgagtg tccaacccta tcccagagac cttgatgctt ggcctcccaa tcttgcccta
1201 ggatacccag atgccaacca gacacctcct tcttcctagc caggctatct ggcctgagac
1261 aacaaatggg tccctcagtc tggcaatggg actctgagaa ctcctcattc cctgactctt
1321 agccccagac tcttcattca gtggcccaca ttttccttag gaaaaacatg agcatcccca
1381 gccacaactg ccagctctct gattccccaa atctgcatcc ttttcaaaac ctaaaaacaa
1441 aaagaaaaac aaataaaaca aaaccaactc agaccagaac tgttttctca acctgggact
1501 tcctaaactt tccaaaacct tcctcttcca gcaactgaac ctggccataa ggcacttatc
1561 cctggttcct agcacccctt atcccctcag aatccacaac ttgtaccaag tttcccttct
1621 cccagtccaa gaccccaaat caccacaaag gacccaatcc ccagactcaa gatatggtct
1681 gggcgctgtc ttgtgtctcc taccctgatc cctgggttca actctgctcc cagagcatga
1741 agcctctcca ccagcaccag ccaccaacct gcaaacctag ggaagattga cagaattccc
1801 agcctttccc agctcccccct gcccatgtcc caggactccc agccttggtt ctctgccccc
1861 gtgtcttttc aaacccacat cctaaatcca tctcctatcc gagtccccca gttcccctg
1921 tcaaccctga ttcccctgat ctagcacccc ctctgcaggc gctgcgcccc tcatcctgtc
1981 tcggattgtg ggaggctggg agtgcgagaa gcattcccaa ccctggcagg tgcttgtggc
2041 ctctcgtggc agggcagtct gcggcggtgt tctggtgcac ccccagtggg tcctcacagc
2101 tgcccactgc atcaggaagt gagtaggggc ctggggtctg gggagcaggt gtctgtgtcc
2161 cagaggaata acagctgggc attttcccca ggataacctc taaggccagc cttgggactg
2221 ggggagagag ggaaagttct ggttcaggtc acatggggag gcagggttgg ggctggacca
2281 ccctccccat ggctgcctgg gtctccatct gtgtccctct atgtctcttt gtgtcgcttt
2341 cattatgtct cttggtaact ggcttcggtt gtgtctctcc gtgtgactat tttgttctct
2401 ctctccctct cttctctgtc ttcagtctcc atatctcccc ctctctctgt ccttctctgg
2461 tccctctcta gccagtgtgt ctcaccctgt atctctctgc caggctctgt ctctcggtct
2521 ctgtctcacc tgtgccttct ccctactgaa cacacgcacg ggatgggcct gggggaccc
2581 tgagaaaagg aagggctttg gctgggcgcg gtggctcaca cctgtaatcc cagcactttg
2641 ggaggccaag gcaggtagat cacctgaggt caggagttcg agaccagcct ggccaactgg
2701 tgaaacccca tctctactaa aaatacaaaa aattagccag gcgtggtggc gcatgcctgt
2761 agtcccagct actcaggagg ctgagggagg agaattgctt gaacctggga ggttgaggtt
2821 gcagtgagcc gagaccgtgc cactgcactc cagcctgggt gacagagtga gactccgcct
2881 caaaaaaaaa aaaaaaaaaa aaaaaaaaaa agaaaagaaa agaaaagaaa aggaatcttt
2941 tatccctgat gtgtgtgggt atgagggtat gagagggccc ctctcactcc attccttctc
3001 caggacatcc ctccactctt gggagacaca gagaagggct ggttccagct ggagctggga
3061 ggggcaattg agggaggagg aaggagaagg gggaaggaaa acagggtatg ggggaaagga
```

FIG. 23 (cont'd)

3121 ccctggggag cgaagtggag gatacaacct tggcctgca ggccaggcta cctacccact
3181 tggaaaccca cgccaaagcc gcatctacag ctgagccact ctgaggcctc ccctccccgg
3241 cggtccccac tcagctccaa agtctctctc cctttctct cccacacttt atcatccccc
3301 ggattcctct ctacttggtt ctcattcttc ctttgacttc ctgcttccct ttctcattca
3361 tctgtttctc actttctgcc tggttttgtt cttctctctc tctttctctg gcccatgtct
3421 gtttctctat gtttctgtct tttctttctc atcctgtgta ttttcggctc accttgtttg
3481 tcactgttct cccctctgcc ctttcattct ctctgtcctt ttaccctctt cctttttccc
3541 ttggtttctc tcagtttctg tatctgccct tcaccctctc acactgctgt ttcccaactc
3601 gttgtctgta tttttggcct gaactgtgtc ttccccaacc ctgtgttttt ctcactgttt
3661 ctttttctct tttggagcct cctccttgct cctctgtccc ttctctcttt ccttatcatc
3721 ctcgctcctc attcctgcgt ctgcttcctc cccagcaaaa gcgtgatctt gctgggtcgg
3781 cacagcctgt ttcatcctga agacacaggc caggtatttc aggtcagcca cagcttccca
3841 cacccgctct acgatatgag cctcctgaag aatcgattcc tcaggccagg tgatgactcc
3901 agccacgacc tcatgctgct ccgcctgtca gagcctgccg agctcacgga tgctgtgaag
3961 gtcatggacc tgcccaccca ggagccagca ctggggacca cctgctacgc ctcaggctgg
4021 ggcagcattg aaccagagga gtgtacgcct gggccagatg gtgcagccgg gagcccagat
4081 gcctgggtct gagggaggag gggacaggac tcctgggtct gagggaggag ggccaaggaa
4141 ccaggtgggg tccagcccac aacagtgttt ttgcctggcc cgtagtcttg accccaaaga
4201 aacttcagtg tgtggacctc catgttattt ccaatgacgt gtgtgcgcaa gttcaccctc
4261 agaaggtgac caagttcatg ctgtgtgctg gacgctggac agggggcaaa agcacctgct
4321 cggtgagtca tccctactcc caagatcttg aggggaaagg tgagtgggga ccttaattct
4381 gggctggggt ctagaagcca acaaggcgtc tgcctcccct gctccccagc tgtagccatg
4441 ccacctcccc gtgtctcatc tcattccctc cttccctctt ctttgactcc ctcaaggcaa
4501 taggttattc ttacagcaca actcatctgt tcctgcgttc agcacacggt tactaggcac
4561 ctgctatgca cccagcactg ccctagagcc tgggacatag cagtgaacag acagagagca
4621 gcccctccct tctgtagccc ccaagccagt gaggggcaca ggcaggaaca gggaccacaa
4681 cacagaaaag ctggagggtg tcaggaggtg atcaggctct cggggaggga gaaggggtgg
4741 ggagtgtgac tgggaggaga catcctgcag aaggtgggag tgagcaaaca cctgccgcag
4801 gggaggggag ggccctgcgg cacctggggg agcagaggga acagcatctg gccaggcctg
4861 ggaggagggg cctagagggc gtcaggagca gagaggaggt tgcctggctg gagtgaagga
4921 tcggggcagg gtgcgagagg gaagaaagga cccctcctgc agggcctcac ctgggccaca
4981 ggaggacact gcttttcctc tgaggagtca ggaactgtgg atggtgctgg acagaagcag
5041 gacagggcct ggctcaggtg tccagaggct gccgctggcc tccctatggg atcagactgc
5101 agggagggag ggcagcaggg atgtggaggg agtgatgatg gggctgacct gggggtggct
5161 ccaggcattg tccccacctg ggcccttacc cagcctccct cacaggctcc tggccctcag
5221 tctctcccct ccactccatt ctccacctac ccacagtggg tcattctgat caccgaactg
5281 accatgccag ccctgccgat ggtcctccat ggctccctag tgccctggag aggaggtgtc
5341 tagtcagaga gtagtcctgg aaggtggcct ctgtgaggag ccacggggac agcatcctgc
5401 agatggtcct ggcccttgtc ccaccgacct gtctacaagg actgtcctcg tggaccctcc
5461 cctctgcaca ggagctggac cctgaagtcc cttccctacc ggccaggact ggagcccta
5521 cccctctgtt ggaatccctg cccaccttct tctggaagtc ggctctggag acatttctct
5581 cttcttccaa agctgggaac tgctatctgt tatctgcctg tccaggtctg aaagatagga
5641 ttgcccaggc agaaactggg actgacctat ctcactctct ccctgctttt acccttaggg
5701 tgattctggg ggcccacttg tctgtaatgg tgtgcttcaa ggtatcacgt catggggcag
5761 tgaaccatgt gccctgcccg aaaggccttc cctgtacacc aaggtggtgc attaccggaa
5821 gtggatcaag gacaccatcg tggccaaccc ctgagcaccc ctatcaactc cctattgtag
5881 taaacttgga accttggaaa tgaccaggcc aagactcaag cctccccagt tctactgacc
5941 tttgtcctta ggtgtgaggt ccagggttgc taggaaaaga aatcagcaga cacaggtgta
6001 gaccagagtg tttcttaaat ggtgtaattt tgtcctctct gtgtcctggg gaatactggc
6061 catgcctgga gacatatcac tcaatttctc tgaggacaca gataggatgg ggtgtctgtg
6121 ttatttgtgg gatacagaga tgaaagaggg gtgggatcca cactgagaga gtggagagtg
6181 acatgtgctg gacactgtcc atgaagcact gagcagaagc tggaggcaca acgcaccaga
6241 cactcacagc aaggatggag ctgaaaacat aacccactct gtcctggagg cactgggaag
6301 cctagagaag gctgtgagcc aaggagggag ggtcttcctt tggcatggga tggggatgaa

FIG. 23 (cont'd)

```
6361 gtaaggagag ggactggacc ccctggaagc tgattcacta tggggggagg tgtattgaag
6421 tcctccagac aaccctcaga tttgatgatt tcctagtaga actcacagaa ataaagagct
6481 cttatactgt ggtttattct ggtttgttac attgacagga gacacactga aatcagcaaa
6541 ggaaacaggc atctaagtgg ggatgtgaag aaaacaggga aaatctttca gttgttttct
6601 cccagtgggg tgttgtggac agcacttaaa tcacacagaa gtgatgtgtg accttgtgta
6661 tgaagtattt ccaactaagg aagctcacct gagccttagt gtccagagtt cttattgggg
6721 gtctgtagga taggcatggg gtactggaat agctgacctt aacttctcag acctgaggtt
6781 cccaagagtt caagcagata cagcatggcc tagagcctca gatgtacaaa aacaggcatt
6841 catcatgaat cgcactgtta gcatgaatca tctggcacgg cccaaggccc caggtatacc
6901 aaggcacttg ggccgaatgt tccaagggat taaatgtcat ctcccaggag ttattcaagg
6961 gtgagccctg tacttggaac gttcaggctt tgagcagtgc agggctgctg agtcaacctt
7021 ttactgtaca gggggtgag ggaaagggag aagatgagga aaccgcctag ggatctggtt
7081 ctgtcttgtg gccgagtgga ccatggggct atcccaagaa ggaggaattc
```

FIG. 24

Homo sapiens histone cluster 2, H2aa4 (HIST2H2AA4), mRNA.

```
  1 cgactttccc gatcgccagg caggagtttc tctcggtgac tactatcgct gtcatgtctg
 61 gtcgtggcaa gcaaggaggc aaggcccgcg ccaaggccaa gtcgcgctcg tcccgcgctg
121 gccttcagtt cccggtaggg cgagtgcatc gcttgctgcg caaaggcaac tacgcggagc
181 gagtgggggc cggcgcgccc gtctacatgg ctgcggtcct cgagtatctg accgccgaga
241 tcctggagct ggcgggcaac gcggctcggg acaacaagaa gacgcgcatc atccctcgtc
301 acctccagct ggccatccgc aacgacgagg aactgaacaa gctgctgggc aaagtcacca
361 tcgcccaggg cggcgtcttg cctaacatcc aggccgtact gctccctaag aagacggaga
421 gtcaccacaa ggcaaagggc aagtgaggct gacgtccggc ccaagtgggc ccagcccggc
481 ccgcgtctcg aaggggcacc tgtgaactca aaaggctctt ttcagagcca ccca
```

FIG. 25

Homo sapiens ubiquitin-conjugating enzyme E2I (UBC9 homolog, yeast)(UBE2I), transcript variant 2, mRNA.

```
   1 gggtcctcgg agctgctctg gctgcgcgcg gagcgggctc cggagggaag tcccgagaca
  61 aagggaagcg ccgccgccgc cgccccgctc ggtcctccac ctgtccgcta cgctcgccgg
 121 ggctgcggcc gcccgaggct gccctgagga tctgtgtttg gtgaaaagga gccaaattca
 181 cctgcagggc aggcggctct agcagcttca gaagcctggt gccctggcga cactggacct
 241 gccttggctt ctttgatccc aaccccaccc ccgatttctg ctctgctgac tggggaagtc
 301 atcgtgccac ccagaacctg agtgcgggcc tctcagagct ccttcgtccg tgggtctgcc
 361 ggggactggg ccttgtctcc ctaacgagtg ccagggactt tgaacatgtc ggggatcgcc
 421 ctcagcagac tcgcccagga gaggaaagca tggaggaaag accacccatt tggtttcgtg
 481 gctgtcccaa caaaaaatcc cgatggcacg atgaacctca tgaactggga gtgcgccatt
 541 ccaggaaaga aagggactcc gtgggaagga ggcttgttta aactacggat gcttttcaaa
 601 gatgattatc catcttcgcc accaaaatgt aaattcgaac caccattatt tcacccgaat
 661 gtgtaccctt cggggacagt gtgcctgtcc atcttagagg aggacaagga ctggaggcca
 721 gccatcacaa tcaaacagat cctattagga atacaggaac ttctaaatga accaaatatc
 781 caagacccag ctcaagcaga ggcctacacg atttactgcc aaaacagagt ggagtacgag
 841 aaaagggtcc gagcacaagc caagaagttt gcgccctcat aagcagcgac cttgtggcat
 901 cgtcaaaagg aagggattgg tttggcaaga acttgtttac aacatttttg caaatctaaa
 961 gttgctccat acaatgacta gtcacctggg ggggttgggc gggcgccatc ttccattgcc
1021 gccgcgggtg tgcggtctcg attcgctgaa ttgcccgttt ccatacaggg tctcttcctt
1081 cggtcttttg tatttttgat tgttatgtaa aactcgcttt tattttaata ttgatgtcag
1141 tatttcaact gctgtaaaat tataaacttt tatacttggg taagtccccc aggggcgagt
1201 tcctcgctct gggatgcagg catgcttctc accgtgcaga gctgcacttg gcctcagctg
1261 gctgtatgga aatgcaccct ccctcctgcc gctcctctct agaaccttct agaacctggg
1321 ctgtgctgct tttgagcctc agaccccagg tcagcatctc ggttctgcgc cacttccttt
1381 gtgtttatat ggcgttttgt ctgtgttgct gtttagagta aataaactgt ttatataaag
1441 gttttggttg cattattatc attgaaagtg agaggagg
```

FIG. 26

Homo sapiens TIMP metallopeptidase inhibitor 2 (TIMP2), mRNA.

```
   1 cgcagcaaac acatccgtag aaggcagcgc ggccgccgag aaccgcagcg ccgctcgccc
  61 gccgcccccc accccgccgc cccgcccggc gaattgcgcc ccgcgcccct cccctcgcgc
 121 ccccgagaca aagaggagag aaagtttgcg cggccgagcg gggcaggtga ggagggtgag
 181 ccgcgcggga ggggcccgcc tcggccccgg ctcagccccc gcccgcgccc ccagcccgcc
 241 gccgcgagca gcgcccggac cccccagcgg cggcccccgc ccgcccagcc ccccggcccg
 301 ccatgggcgc cgcggcccgc accctgcggc tggcgctcgg cctcctgctg ctggcgacgc
 361 tgcttcgccc ggccgacgcc tgcagctgct ccccggtgca cccgcaacag gcgttttgca
 421 atgcagatgt agtgatcagg gccaaagcgg tcagtgagaa ggaagtggac tctggaaacg
 481 acatttatgg caaccctatc aagaggatcc agtatgagat caagcagata aagatgttca
 541 aagggcctga gaaggatata gagtttatct acacggcccc ctcctcggca gtgtgtgggg
 601 tctcgctgga cgttggagga aagaaggaat atctcattgc aggaaaggcc gaggggggacg
 661 gcaagatgca catcaccctc tgtgacttca tcgtgccctg ggacaccctg agcaccaccc
 721 agaagaagag cctgaaccac aggtaccaga tgggctgcga gtgcaagatc acgcgctgcc
 781 ccatgatccc gtgctacatc tcctccccgg acgagtgcct ctggatggac tgggtcacag
 841 agaagaacat caacgggcac caggccaagt tcttcgcctg catcaagaga agtgacggct
 901 cctgtgcgtg gtaccgcggc gcggcgcccc ccaagcagga gtttctcgac atcgaggacc
 961 cataagcagg cctccaacgc ccctgtggcc aactgcaaaa aaagcctcca agggtttcga
1021 ctggtccagc tctgacatcc cttcctggaa acagcatgaa taaaacactc atcccatggg
1081 tccaaattaa tatgattctg ctcccccctt ctccttttag acatggttgt gggtctggag
1141 ggagacgtgg gtccaaggtc ctcatcccat cctccctctg ccaggcacta tgtgtctggg
1201 gcttcgatcc ttgggtgcag gcagggctgg gacacgcggc ttccctccca gtccctgcct
1261 tggcaccgtc acagatgcca agcaggcagc acttagggat ctcccagctg ggttagggca
1321 gggcctggaa atgtgcattt tgcagaaact tttgagggtc gttgcaagac tgtgtagcag
1381 gcctaccagg tccctttcat cttgagaggg acatggccct tgttttctgc agcttccacg
1441 cctctgcact ccctgcccct ggcaagtgct cccatcgccc cggtgcccac catgagctcc
1501 cagcacctga ctccccccac atccaagggc agcctggaac cagtggctag ttcttgaagg
1561 agccccatca atcctattaa tcctcagaat tccagtggga gcctccctct gagccttgta
1621 gaaatgggag cgagaaaccc cagctgagct gcgttccagc ctcagctgag tctttttggt
1681 ctgcacccac ccccccaccc cccccccccc gcccacatgc tccccagctt gcaggaggaa
1741 tcggtgaggt cctgtcctga ggctgctgtc cggggccggt ggctgccctc aaggtccctt
1801 ccctagctgc tgcggttgcc attgcttctt gcctgttctg gcatcaggca cctggattga
1861 gttgcacagc tttgctttat ccgggcttgt gtgcagggcc cggctgggct ccccatctgc
1921 acatcctgag gacagaaaaa gctgggtctt gctgtgccct cccaggctta gtgttccctc
1981 cctcaaagac tgacagccat cgttctgcac ggggctttct gcatgtgacg ccagctaagc
2041 atagtaagaa gtccagccta ggaagggaag gattttggag gtaggtggct ttggtgacac
2101 actcacttct ttctcagcct ccaggacact atggcctgtt ttaagagaca tcttattttt
2161 ctaaaggtga attctcagat gataggtgaa cctgagttgc agatatacca acttctgctt
2221 gtatttctta aatgacaaag attacctagc taagaaactt cctagggaac tagggaacct
2281 atgtgttccc tcagtgtggt ttcctgaagc cagtgatatg gggttagga taggaagaac
2341 tttctcggta atgataagga gaatctcttg tttcctccca cctgtgttgt aaagataaac
2401 tgacgatata caggcacatt atgtaaacat acacacgcaa tgaaaccgaa gcttggcggc
2461 ctgggcgtgg tcttgcaaaa tgcttccaaa gccaccttag cctgttctat tcagcggcaa
2521 ccccaaagca cctgttaaga ctcctgaccc ccaagtggca tgcagccccc atgcccaccg
2581 ggacctggtc agcacagatc ttgatgactt ccctttctag ggcagactgg gagggtatcc
2641 aggaatcggc ccctgcccca cgggcgtttt catgctgtac agtgacctaa agttggtaag
2701 atgtcataat ggaccagtcc atgtgatttc agtatataca actccaccag acccctccaa
2761 cccatataac accccacccc tgttcgcttc ctgtatggtg atatcatatg taacatttac
2821 tcctgtttct gctgattgtt tttttaatgt tttggtttgt tttgacatc agctgtaatc
2881 attcctgtgc tgtgtttttt attacccttg gtaggtatta gacttgcact tttttaaaaa
2941 aaggtttctg catcgtggaa gcatttgacc cagagtggaa cgcgtggcct atgcaggtgg
3001 attccttcag gtctttcctt tggttctttg agcatctttg ctttcattcg tctcccgtct
3061 ttggttctcc agttcaaatt attgcaaagt aaaggatctt tgagtaggtt cggtctgaaa
```

FIG. 26 (cont'd)

3121 ggtgtggcct ttatatttga tccacacacg ttggtctttt aaccgtgctg agcagaaaac
3181 aaaacaggtt aagaagagcc gggtggcagc tgacagagga agccgctcaa ataccttcac
3241 aataaatagt ggcaatatat atatagttta agaaggctct ccatttggca tcgtttaatt
3301 tatatgttat gttctaagca cagctctctt ctcctatttt catcctgcaa gcaactcaaa
3361 atatttaaaa taaagtttac attgtagtta ttttcaaatc tttgcttgat aagtattaag
3421 aaatattgga cttgctgccg taatttaaag ctctgttgat tttgtttccg tttggatttt
3481 tgggggaggg gagcactgtg tttatgctgg aatatgaagt ctgagacctt ccggtgctgg
3541 gaacacacaa gagttgttga aagttgacaa gcagactgcg catgtctctg atgctttgta
3601 tcattcttga gcaatcgctc ggtccgtgga caataaacag tattatcaaa gagaaaaaaa
3661 aaaaaaaaaa

FIG. 27

Homo sapiens WD repeat domain 77 (WDR77), mRNA.

```
   1 cgtccagttt gagtctaggt tggagttgga accgtggaga tgcggaagga aaccccaccc
  61 cccctagtgc ccccggcggc ccgggagtgg aatcttcccc caaatgcgcc cgcctgcatg
 121 gaacggcagt tggaggctgc gcggtaccgg tccgatgggg cgcttctcct cggggcctcc
 181 agcctgagtg ggcgctgctg ggccggctcc ctctggcttt ttaaggaccc ctgtgccgcc
 241 cccaacgaag gcttctgctc cgccggagtc caaacggagg ctggagtggc tgacctcact
 301 tgggttgggg agagaggtat tctagtggcc tccgattcag gtgctgttga attgtgggaa
 361 ctagatgaga atgagacact tattgtcagc aagttctgca agtatgagca tgatgacatt
 421 gtgtctacag tcagtgtctt gagctctggc acacaagctg tcagtggtag caaagacatc
 481 tgcatcaagg tttgggacct tgctcagcag gtggtactga gttcataccg agctcatgct
 541 gctcaggtca cttgtgttgc tgcctctcct cacaaggact ctgtgtttct ttcatgcagc
 601 gaggacaata gaattttact ctgggatacc cgctgtccca agccagcatc acagattggc
 661 tgcagtgcgc ctggctacct tcctacctcg ctggcttggc atcctcagca aagtgaagtc
 721 tttgtctttg gtgatgagaa tgggacagtc tcccttgtgg acaccaagag tacaagctgt
 781 gtcctgagct cagctgtaca ctcccagtgt gtcactgggc tggtgttctc cccacacagt
 841 gttcccttcc tggcctctct cagtgaagac tgctcacttg ctgtgctgga ctcaagcctt
 901 tctgagttgt ttagaagcca agcccacaga gactttgtga gagatgcgac ttggtccccg
 961 ctcaatcact ccctgcttac cacagtgggc tgggaccatc aggtcgtcca ccacgttgtg
1021 cccacagaac ctctcccagc ccctggacct gcaagtgtta ctgagtagat tggatttaag
1081 acaaaaagca agtcccccat gagtgtccac ttctttgccc tgccctctca gcttgtgaga
1141 caacacagga gccttctata gtatgttgat atgctagatc tgtgccgtta ataggcatcg
1201 tctctcagcc tgagggaggc tggattctgg gttcctgtag tcacagggag gaaaagcttt
1261 cttaaaaatg gacatgtatg tgcgtgtgag tgtgtgtgta gatttatagt ttttggtagt
1321 ggcaggaata aaaaaaatcc atcctacatc ttccctaagc actgcctctc tctcaccccc
1381 caaaacaagt tgacgaaagg gttttatgta gctgtctatg aggaattggc cgtgtctggg
1441 tgggttatgg gatgtgggca tccctgggtt cttggaagca gctcttatgc tactcataga
1501 gatgggattg actttatttt tttatagtgc ttaattcacc attatgagaa atgcttccag
1561 tcacaaaaat gcagcccagc tcactctgag gaagaagcag gacttggtac ggttttacac
1621 aactccttac cattaaactg aatcagaaat ccatttctg gctgaataaa aagtttggct
1681 tgcctgtgta atgcccactc ccttcccct ggctccctag tgatgggaca tatatgagag
1741 agaagtgttt ttctatcata gacaccatag gggaaagttt ggggatgaag gagagcttaa
1801 aggtgtttca attaagttag aaaactgaca caggctgttg agaattcttt gccacttttc
1861 ccaccccaaa acagcatggg gcctgacatc ttctgccctg gtccccttc tcttgatgtg
1921 gaaagtctga atgcagtatt tatagacttc taaggtttta aaatccagta tcaagaagaa
1981 aatcagaaat actggttggt gaaataaaga gtttaggcat tgttggcctg tcttttttga
2041 agcatgtgtg ttatgtgtag ttagatatat ttcacttatg tgagtcatca tggtgttggt
2101 cttgtagccc attatttttc ctgtgcttcc ccagcttccc aaagtagcta gttagaactt
2161 aaggtaaata tttattcttg ggttggtgga gtggatattg ccagttagga gtcatggatc
2221 aattactgat tatattgaaa gtaaatataa tcaattatgt acttttgagc tttgcaggtt
2281 caatttaggt aaaaatcaca ttatgaaact gggaaagtct gaaggaatat gggcaaaata
2341 tttctcagta aagcttccat gcttcaccct tgacatgatt acccttgagt aaaacatggg
2401 aatttgtaaa aaaaaaaaaa aaaaaaaa
```

FIG. 28

Human DNA sequence from clone RP1-20N2 on chromosome 6q24 Contains the gene for a novel protein similar to yeast and bacterial cytosine deaminase, NTs 48121-50100.

```
48121 ttcgattttg gtgctgtgaa aagaatagaa aagaaaaaga aaatgaagag gtaagctcat
48181 agcagattct ctttgtatgg atttaaggga aggacattat ccacaacaga aaactgacca
48241 tttggatttt cttgtttgta gaaggtcttt aacatttcca ctgcttcctc agcccgatat
48301 ccagggatac actgatggaa tgagaaagtt gagaataaac ataggcctat gaaaatgtgt
48361 gctgtatccc ataaaaacaa catatatata catgattatg taaacagatt tcagatgtta
48421 ataaactttg gggatattag taacatgggt aaggaggtac acttccaaaa gatgtttgat
48481 atatcatctt tttcattact cccaatcaac tgttattagg catcactccc aatcaactgt
48541 tattcatcca ttaactatta tagaagttac cagctttgtg atcttgggtt aggcacttaa
48601 actctccatg ccttatttat acaatgctgg caataatagc acttacttca ggggattttg
48661 tgaggattaa gtgagataat acctgttaaa taccaggcac atcataagtg ctcattaagc
48721 attagttatt tttatctgct cctatttact agtggtccat taagcattcc atgctataga
48781 gctagggttg gcaaattata cttggtggac caaatctgtt ccatagctga gaactgtgag
48841 ctaagaatgg tttttatatc ttaaaagctt tgttaaagaa aaaaaaagac taggtgacag
48901 agatgtaagc ggctcacaaa gggtgaaata tttactagtt aacccctttgc agaaaaagtt
48961 tatcaaccct tgctacagag gattttaaaa aataaaatac agcttgttct atctttagca
49021 tctaactggg gaaaagaaat cataacatgt gaaagaataa ataagaaatt gtgctaacag
49081 taaggagtgt tatatgaaat attacctgaa gaacatgaaa cttgaacttg ccttagagat
49141 agagaatatt taaagaggct aagcagagca tttcagggaa agggcaagaa gaagcctggg
49201 ttgtgtgtga ggaaatcagc tgacagagga ggagactatt aaggaagcat aaggaaagaa
49261 agacaaaaaa ttggggtaaa aatatgtacg gctttgaaag cttgtcagaa gagtttggac
49321 ttaaaaccaa gcacccttct gaagtgcatg aagtgacaca atgagcatct ggaaggaagg
49381 agccagaaag cataggcaca gaggacagga ggaccagcta ctgtgagatg ctgttcagaa
49441 cgaacctccc attctcctgt gtcttcagtc tgcccttgcc tgggcctccg acacctgcat
49501 aaaccttcgc cataacaaat aaccttccat ccaccctgtc ccgtcaaagg ctgacaccct
49561 gctcctgcct tcactcctca gtggcctcat cttcactggc ttgagttccc agcacttcac
49621 tgagtctgcc ctctcagaaa tccccaggtc cctactgacc aaaacacttg cctcctttca
49681 gattcctcaa ctctgcagtc ctggaggcaa ctggccacac ctgctctgtc tgaccgctct
49741 tgcctccctt ggcttctcag cattttacca tcctaaccac tgccagccag tcccgtcaca
49801 gctgccccct gcttcctgct gtgttaagtg ctggagctcc ccagaggtcc ccctccactc
49861 cactcgcaca ctcagagccc tctcctctta cgtgggatga gagcagtggt tctcaaccat
49921 tgctgctcag gagaaccagt tggaactctc tggaaacaca gcactgttgg ccccctgcct
49981 tctgattcag atggtctggg gcagggactg agcagagtca ggcacagaag cctccaggtg
50041 attctaacgg gcagtccggg atgagaactg ctgagttaca ggcctcgaag gaaactgcac
```

FIG. 29

Homo sapiens lamin A/C, mRNA (cDNA clone MGC:23638 IMAGE:4863480), complete cds.

```
   1 gagcgccgca cctacaccag ccaacccaga tcccgaggtc cgacagcgcc cggcccagat
  61 ccccacgcct gccaggagca agccgagagc cagccggccg gcgcactccg actccgagca
 121 gtctctgtcc ttcgacccga gccccgcgcc ctttccggga cccctgcccc gcgggcagcg
 181 ctgccaacct gccggccatg gagaccccgt cccagcggcg cgccacccgc agcggggcgc
 241 aggccagctc cactccgctg tcgcccaccc gcatcacccg gctgcaggag aaggaggacc
 301 tgcaggagct caatgatcgc ttggcggtct acatcgaccg tgtgcgctcg ctggaaacgg
 361 agaacgcagg gctgcgcctt cgcatcaccg agtctgaaga ggtggtcagc cgcgaggtgt
 421 ccggcatcaa ggccgcctac gaggccgagc tcggggatgc ccgcaagacc cttgactcag
 481 tagccaagga gcgcgcccgc ctgcagctgg agctgagcaa agtgcgtgag gagtttaagg
 541 agctgaaagc gcgcaatacc aagaaggagg gtgacctgat agctgctcag gctcggctga
 601 aggacctgga ggctctgctg aactccaagg aggccgcact gagcactgct ctcagtgaga
 661 agcgcacgct ggagggcgag ctgcatgatc tgcggggcca ggtggccaag cttgaggcag
 721 ccctaggtga ggccaagaag caacttcagg atgagatgct gcggcgggtg gatgctgaga
 781 acaggctgca gaccatgaag gaggaactgg acttccagaa gaacatctac agtgaggagc
 841 tgcgtgagac caagcgccgt catgagaccc gactggtgga gattgacaat gggaagcagc
 901 gtgagtttga gagccggctg gcggatgcgc tgcaggaact gcgggcccag catgaggacc
 961 aggtggagca gtataagaag gagctggaga agacttattc tgccaagctg gacaatgcca
1021 ggcagtctgc tgagaggaac agcaacctgg tgggggctgc ccacgaggag ctgcagcagt
1081 cgcgcatccg catcgacagc ctctctgccc agctcagcca gctccagaag cagctggcag
1141 ccaaggaggc gaagcttcga gacctggagg actcactggc ccgtgagcgg gacaccagcc
1201 ggcggctgct ggcggaaaag gagcgggaga tggccgagat gcgggcaagg atgcagcagc
1261 agctggacga gtaccaggag cttctggaca tcaagctggc cctggacatg gagatccacg
1321 cctaccgcaa gctcttggag ggcgaggagg agaggctacg cctgtccccc agccctacct
1381 cgcagcgcag ccgtggccgt gcttcctctc actcatccca gacacagggt gggggcagcg
1441 tcaccaaaaa gcgcaaactg gagtccactg agagccgcag cagcttctca cagcacgcac
1501 gcactagcgg gcgcgtggcc gtggaggagg tggatgagga gggcaagttt gtccggctgc
1561 gcaacaagtc caatgaggac cagtccatgg gcaattggca gatcaagcgc cagaatggag
1621 atgatccctt gctgacttac cggttcccac caaagttcac cctgaaggct gggcaggtgg
1681 tgacgatctg ggctgcagga gctggggcca cccacagccc ccctaccgac ctggtgtgga
1741 aggcacagaa cacctggggc tgcgggaaca gcctgcgtac ggctctcatc aactccactg
1801 gggaagaagt ggccatgcgc aagctggtgc gctcagtgac tgtggttgag gacgacgagg
1861 atgaggatgg agatgacctg ctccatcacc accacggctc ccactgcagc agctcggggg
1921 accccgctga gtacaacctg cgctcgcgca ccgtgctgtg cgggacctgc gggcagcctg
1981 ccgacaaggc atctgccagc ggctcaggag cccaggtggg cggacccatc tcctctggct
2041 cttctgcctc cagtgtcacg gtcactcgca gctaccgcag tgtgggggc agtgggggtg
2101 gcagcttcgg ggacaatctg gtcacccgct cctacctcct gggcaactcc agcccccgaa
2161 cccagagccc ccagaactgc agcatcatgt aatctgggac ctgccaggca ggggtggggg
2221 tggaggcttc ctgcgtcctc ctcacctcat gcccaccccc tgccctgcac gtcatgggag
2281 ggggcttgaa gccaaagaaa aataaccctt tggttttttt cttctgtatt tttttttcta
2341 agagaagtta ttttctacag tggttttata ctgaaggaaa aacacaagca aaaaaaaaaa
2401 aaaaaaa
```

FIG. 30

Homo sapiens mRNA for Lsm3 protein.

```
  1 gcgcagggtt tgaaacatgg cggacgacgt agaccagcaa caaactacca acactgtaga
 61 ggagcccctg gatcttatca ggctcagcct agatgagcga atttatgtga aaatgagaaa
121 tgaccgagag cttcgaggca gattacatgc ttatgatcaa catttaaata tgatcttggg
181 agatgtggaa gaaactgtga ctactataga aattgatgaa gaaacatatg aagagatata
241 taaatcaacg aaacggaata ttccaatgct ctttgtccgg ggagatggcg ttgtcctggt
301 tgcccctcca ctgagagttg gctgaaacaa agaatttgtc ctgtatggaa aacgggagac
361 tttgtacagt ggcctctcta aaagtacaaa acattcataa gagaaacctg catacatttt
421 gatattaaga aataattccg gggattcttc cactcctgaa atgagttgat ttgcagataa
481 ctcacaactt cttaagctaa atggtatttt catttttctc aagctctcca ataaatatga
541 ccaccaagaa aaaaaaaaaa aaaaaaa
```

FIG. 31

Homo sapiens chromosome 19 clone CTB-25B13, NTs 20521-22500.

```
20521 tttaagggtg tacaagctct aattgttttt tttttttttt tgagatggag tttcactctg
20581 tagcccaggc tggagtgcag tggcgcaatc gcggctcact gcaagctccg cctcctgggt
20641 tcacaccatt ctcctgcctc agtctcccga gtagctggga ctacaggcgc tcgccaccac
20701 gcccggctaa tttttttgta tttttagtag agacggggtt tcaccatgtt agccagggtg
20761 gtctcgatct cctgaccttg tgatccgcct gcctcggcct cccaaagtgc tgggattaca
20821 ggcgtgagtg actgcgccca gcctcacagg ctctaattct tgactaattt tcctgtacac
20881 gtcacttgta attgaaaagc tgagtgtaag atcagccgac acacccagag ttttatttta
20941 ttttatttat ttatttatgg tttttttttg agatggagtc tcactctgtc gcccaggcta
21001 gagtgcagtg gcgccatctc ggcttactgc aagctccacc tcctgggttc acgccattct
21061 cctacctcag tctcctgagt agctgggact acaggcgccc accaccacgc ctggctaatt
21121 tttttgtatt tttagtagag acagggtttc accgtgttag gcaggatggt ctcgatctcc
21181 tgacctcgtg attcgcccgc ctcggcctcc caaagcgctg ggattagaag cgtgagccac
21241 cgcgcccgga ctattttatt tattttttttg agatggagtt tcactttgt tgcccaggat
21301 tgagtgcagt gccccgatct tggctcacta caacctctgc ctcctgggtt caagcgactc
21361 tcctgcctca gtgtcctgag tagctgggat tacaggcgtc tgccaccacg cccggctaat
21421 tttgtatttt tagtagagaa caggtttcac tatgttggtc aggctggtct tgaactcctg
21481 acctcagcgc atccagaatt ttagacgggg cccccagggt gaggtcttgg caccctccag
21541 tagagaagaa gggacatggg ccatacgtgg ggtgtccttt ctgggagcct tgcgtccctt
21601 acctgcctag ccagggattg cacctcacag cacgcagcca gcaggaacgg caccgtgatc
21661 tgatttcacc tgcgggccct gggccctggg ggtgtttgac aattggggca tatcacagtg
21721 tgagctagtc ccgtctcggg ggtttggagg ctccacgtgg ccgtggtaca ggagcaggca
21781 gttccatcct ctggcctgga tcaggctctg cacacggagg cctgtgggcc agatgactga
21841 caggaggggga gttgggtgga acctcggcct gcctgatatc cagcaacaga gggcaagggc
21901 ggcagcacct ccagcatgac agtcccttcc aagcacgtca ggatgctccc ttgcctgtgc
21961 tggcagcttc ctaaacatgg ggactgggca tggtggcagg tttttgtcct tctgaaagag
22021 caattttgct gtgaggttac ttgctccttg agttcttgtc tgaggcccac ctggcggctg
22081 ctccgtgagg aacgaggtgg ccctgctgca gctcagcatc ccgccacgct cccaggagtg
22141 tgtgtttcct gggggagcg gcccgggacc gtggctctgt ggtccattct gtggatgtcc
22201 acaaggcctg ggcgttctgt gggtttgggt ggcagtcccg tctgggcagc tcctgctggg
22261 ctgggtgtgg gtctcctgct ggtctgcccc cagctgcaca acgtgtcttg tgccttgccc
22321 tcttgtacct ctgcaggttt tggctacggg cctccacctc caccgccaga tcagtttgcc
22381 cctccggggg ttcctcctcc accagccact cccggggcag cacctctggc tttcccaccg
22441 cctccgtctc aggctgcccc ggacatgagc aagcccccga cagctcagcc agacttcccc
```

FIG. 32

Homo sapiens ADAM metallopeptidase domain 9 (ADAM9), transcript variant 2, non-coding RNA.

```
   1 cggcagggtt ggaaaatgat ggaagaggcg gaggtggagg cgaccgagtg ctgagaggaa
  61 cctgcggaat cggccgagat ggggtctggc gcgcgctttc cctcggggac ccttcgtgtc
 121 cggtggttgc tgttgcttgg cctggtgggc ccagtcctcg gtgcggcgcg gccaggcttt
 181 caacagacct cacatctttc ttcttatgaa attataactc cttggagatt aactagagaa
 241 agaagagaag cccctaggcc ctattcaaaa caagtatctt atgttattca ggctgaagga
 301 aaagagcata ttattcactt ggaaaggaac aaagaccttt tgcctgaaga ttttgtggtt
 361 tatacttaca acaaggaagg gactttaatc actgaccatc ccaatataca gaatcattgt
 421 cattatcggg gctatgtgga gggagttcat aattcatcca ttgctcttag cgactgtttt
 481 ggactcagag gattgctgca tttagagaat gcgagttatg ggattgaacc cctgcagaac
 541 agctctcatt ttgagcacat catttatcga atggatgatg tctacaaaga gcctctgaaa
 601 tgtggagttt ccaacaagga tatagagaaa gaaactgcaa aggatgaaga ggaagagcct
 661 cccagcatga ctcagctact tcgaagaaga agagctgtct tgccacagac ccggtatgtg
 721 gagctgttca ttgtcgtaga caaggaaagg tatgacatga tgggaagaaa tcagactgct
 781 gtgagagaag agatgattct cctggcaaac tacttggata gtatgtatat tatgttaaat
 841 attcgaattg tgctagttgg actggagatt tggaccaatg gaaacctgat caacatagtt
 901 gggggtgctg gtgatgtgct ggggaacttc gtgcagtggc gggaaaagtt tcttatcaca
 961 cgtcggagac atgacagtgc acagctagtt ctaaagaaag gttttggtgg aactgcagga
1021 atggcatttg tgggaacagt gtgttcaagg agccacgcag gcgggattaa tgtgtttgga
1081 caaatcactg tggagacatt tgcttccatt gttgctcatg aattgggtca taatcttgga
1141 atgaatcacg atgatgggag agattgttcc tgtggagcaa agagctgcat catgaattca
1201 ggagcatcgg gttccagaaa ctttagcagt tgcagtgcag aggactttga gaagttaact
1261 ttaaataaag gaggaaactg ccttcttaat attccaaagc ctgatgaagc ctatagtgct
1321 ccctcctgtg gtaataagtt ggtggacgct ggggaagagt gtgactgtgg tactccaaag
1381 gaatgtgaat tggacccttg ctgcgaagga agtacctgta agcttaaatc atttgctgag
1441 tgtgcatatg gtgactgttg taaagactgt cggttccttc caggaggtac tttatgccga
1501 ggaaaaacca gtgagtgtga tgttccagag tactgcaatg gttcttctca gttctgtcag
1561 ccagatgttt ttattcagaa tggatatcct tgccagaata acaaagccta ttgctacaac
1621 ggcatgtgcc agtattatga tgctcaatgt caagtcatct ttggctcaaa agccaaggct
1681 gcccccaaag attgtttcat tgaagtgaat tctaaaggtg acagatttgg caattgtggt
1741 ttctctggca atgaatacaa gaagtgtgcc actgggaatg ctttgtgtgg aaagcttcag
1801 tgtgagaatg tacaagagat acctgtattt ggaattgtgc ctgctattat tcaaacgcct
1861 agtcgaggca ccaaatgttg ggtgtggat ttccagctag gatcagatgt tccagatcct
1921 gggatggtta acgaaggcac aaaatgtggt gctggaaaga tctgtagaaa cttccagtgt
1981 gtagatgctt ctgttctgaa ttatgactgt gatgttcaga aaaagtgtca tggacatggg
2041 aaatgaatac tgcattgagg gacggacttc tggtcttctt cttcctaatt gttcccctta
2101 ttgtctgtgc tatttttatc ttcatcaaga gggatcaact gtggagaagc tacttcagaa
2161 agaagagatc acaaacatat gagtcagatg gcaaaaatca agcaaaccct tctagacagc
2221 cggggagtgt tcctcgacat gtttctccag tgacacctcc cagagaagtt cctatatatg
2281 caaacagatt tgcagtacca acctatgcag ccaagcaacc tcagcagttc ccatcaaggc
2341 cacctccacc acaaccgaaa gtatcatctc agggaaactt aattcctgcc cgtcctgctc
2401 ctgcacctcc tttatatagt tccctcactt gatttttta accttctttt tgcaaatgtc
2461 ttcagggaac tgagctaata cttttttttt ttcttgatgt tttcttgaaa agcctttctg
2521 ttgcaactat gaatgaaaac aaaacaccac aaaacagact tcactaacac agaaaaacag
2581 aaactgagtg tgagagttgt gaaatacaag gaaatgcagt aaagccaggg aatttacaat
2641 aacatttccg tttccatcat tgaataagtc ttattcagtc atcggtgagg ttaatgcact
2701 aatcatggat tttttgaaca tgttattgca gtgattctca aattaactgt attggtgtaa
2761 gatttttgtc attaagtgtt taagtgttat tctgaatttt ctaccttagt tatcattaat
2821 gtagttcctc attgaacatg tgataatcta atacctgtga aaactgacta atcagctgcc
2881 aataatatct aatattttc atcatgcacg aattaataat catcatactc tagaatcttg
2941 tctgtcactc actacatgaa taagcaaata ttgtcttcaa aagaatgcac aagaaccaca
3001 attaagatgt catattattt tgaaagtaca aaatatacta aaagagtgtg tgtgtattca
```

FIG. 32 (cont'd)

```
3061 cgcagttact cgcttccatt tttatgacct ttcaactata ggtaataact cttagagaaa
3121 ttaatttaat attagaattt ctattatgaa tcatgtgaaa gcatgacatt cgttcacaat
3181 agcactattt taaataaatt ataagcttta aggtacgaag tatttaatag atctaatcaa
3241 atatgttgat tcatggctat aataaagcag gagcaattat aaaatcttca atcaattgaa
3301 cttttacaaa accacttgag aatttcatga gcactttaaa atctgaactt tcaaagcttg
3361 ctattaaatc atttagaatg tttacattta ctaaggtgtg ctgggtcatg taaaatatta
3421 gacactaata ttttcataga aattaggctg gagaaagaag gaagaaatgg ttttcttaaa
3481 tacctacaaa aaagttactg tggtatctat gagttatcat cttagctgtg ttaaaaatga
3541 atttttacta tggcagatat ggtatggatc gtaaaatttt aagcactaaa aattttttca
3601 taacctttca taataaagtt taataatagg tttattaact gaatttcatt agtttttttaa
3661 aagtgttttt ggtttgtgta tatatacata tacaaataca acatttacaa taaataaaat
3721 acttgaaatt ctcttttgtg tctcctagta gcttcctact caactattta taatctcatt
3781 aattaaaaag ttataatttt agataaaaat tctagtcaaa tttttacaga tattatctca
3841 ctaattttca gacttttgcc aaagtgtgca caatggcttt ttgttaataa agaacagatt
3901 agttttgaag aaggcaaaaa tttcagtttt ctgaagacag catgttattt taacaatcaa
3961 gtatacatat taaaaattgt gagcaatctc aaaaaaaaaa aaaaa
```

FIG. 33

Homo sapiens alpha-2-glycoprotein 1, zinc-binding (AZGP1), mRNA.

```
   1 ccattggcct gtagattcac ctcccctggg cagggcccca ggacccagga taatatctgt
  61 gcctcctgcc cagaaccctc caagcagaca caatggtaag aatggtgcct gtcctgctgt
 121 ctctgctgct gcttctgggt cctgctgtcc cccaggagaa ccaagatggt cgttactctc
 181 tgacctatat ctacactggg ctgtccaagc atgttgaaga cgtccccgcg tttcaggccc
 241 ttggctcact caatgacctc cagttcttta gatacaacag taaagacagg aagtctcagc
 301 ccatgggact ctggagacag gtggaaggaa tggaggattg gaagcaggac agccaacttc
 361 agaaggccag ggaggacatc tttatggaga ccctgaaaga catcgtggag tattacaacg
 421 acagtaacgg gtctcacgta ttgcagggaa ggtttggttg tgagatcgag aataacagaa
 481 gcagcggagc attctggaaa tattactatg atggaaagga ctacattgaa ttcaacaaag
 541 aaatcccagc ctgggtcccc ttcgacccag cagcccagat aaccaagcag aagtgggagg
 601 cagaaccagt ctacgtgcag cgggccaagg cttacctgga ggaggagtgc cctgcgactc
 661 tgcggaaata cctgaaatac agcaaaaata tcctggaccg gcaagatcct ccctctgtgg
 721 tggtcaccag ccaccaggcc ccaggagaaa agaagaaact gaagtgcctg gcctacgact
 781 tctacccagg gaaaattgat gtgcactgga ctcgggccgg cgaggtgcag gagcctgagt
 841 tacggggaga tgttcttcac aatggaaatg gcacttacca gtcctgggtg gtggtggcag
 901 tgccccccgca ggacacagcc ccctactcct gccacgtgca gcacagcagc ctggcccagc
 961 ccctcgtggt gccctgggag gccagctagg aagcaagggt tggaggcaat gtgggatctc
1021 agacccagta gctgcccttc ctgcctgatg tgggagctga accacagaaa tcacagtcaa
1081 tggatccaca aggcctgagg agcagtgtgg ggggacagac aggaggtgga tttggagacc
1141 gaagactggg atgcctgtct tgagtagact tggacccaaa aaatcatctc accttgagcc
1201 cacccccacc ccattgtcta atctgtagaa gctaataaat aatcatccct ccttgcctag
1261 cataaaaaaa aaaaaaaa
```

FIG. 34

Homo sapiens desmocollin 3 (DSC3), RefSeqGene on chromosome 18. NTs 46261-48240.

```
46261 tcatttcaaa atttaggagt taatttatat ttttaattga atcagatttc ataggcatag
46321 atattgtctg tcaatattca tatgtttata tagtggtaat ttattaaact tcttaatcca
46381 gatgtattat tttagttatc ttttttccac tctagtgtca tagtttaaac ttgttctttg
46441 atgttgagta tttattataa caatagtttt ttttgcctgc actctacaat gtatatttcc
46501 agatataatt tgtttatgta acttgttgac catttataat ggggaaaaaa gcttgctaaa
46561 agttctcaag atagctagga aaatatcaat gagatatatc taaaagaaag ggagaggggt
46621 ttggaagatt actgccactc tctttcctta tatatttctt aggacttctg aggtgctttt
46681 atgcttcttg ttttgtgtaa agtatatata tatatatata tatatacaca cacacaaagt
46741 atatataaac acaaagtata tatatacaca cacatataca caaagtatat atatatacac
46801 acaaagtata tatatatgta cacaaaatat atatatatac acaaaagtac ttacaaggca
46861 tgttcttacc tcaaaaagat gccaacttat ttatgagaaa tagatcctac tttatggaaa
46921 agcaaaatag gaacatgaca ataaaccaat atgataaagc actgtcagag ttcaaaaaca
46981 cctatgatac ctaaatgtac tcatgtagtt tggatcaacc agaaaggctg gtgacaagag
47041 gtacagctta cttggtaact taaagaataa gaagggtttg aaagtgaaga gacggtgaga
47101 atagctaaag aagaggaaaa cagcatagcc tacaagacag gagatgataa agtttagggg
47161 ctatttagca aataataaat aaattgattt agaatagaag aaatcatgtg ttggaaaaga
47221 ggcttgaaac aagttcggtg ttagagaaga gaatattaag aaacaagtgg gagataggac
47281 ttctaaatgc tgcactaagg atttcggatt tattctcatg gtaaaggaga gccagccaag
47341 gcttttctac aggagagagg tataatcaag cagcgtgaag ctgagtcagt agggggatca
47401 gtgagaatag gaagacatca gggttgggga agatgaaagc ttagtttaag catgagttaa
47461 ttctaccagg atgatggtaa ttgttatatt aagataggga tgaataagaa atatttcaaa
47521 ggtataaagg ataagcttgt tgactgactg aacttaagga acaaagtaaa aagcagagtc
47581 aaagtggcag aggctatagc cagggacaac gactacatat ccagcctttt ctatgtctcg
47641 gggtgaagat gcctttctta ttcactattt ctctcttcaa ctcctccaca ccaccatgca
47701 aaatcatagc ccatctatgc ttgacgtgcc tacatgtaga aacctgtgat gatctctcca
47761 gcgagaaagc aggtttaatc ccttgacagt ccttgactca tagtaagttc ttattttatt
47821 tttaagaccg gcatggatga ctttacttta atatctgttc tttgccattt aatgctagag
47881 ctgatgatat tgagtggcca tttcacaata tgtacctgtt ctgtgttagg aacacttcta
47941 aaaggggctt ggaattatta atttatacaa aaacataaaa tttcatcttg aatctataaa
48001 cttgctttaa tacaatgagt aaaagtgatc attttagctt tggatctgaa tttcacttga
48061 aggcatgcac atgggattag gagttgggtg aataatcagg actggaaaag taaacctaga
48121 aattattgac atggataaag agttgttgat accctgtgag aaggaacttt gggaaatgtg
48181 gatggaggag gacagaaagg agcagagaat aaaagtatga aagctagccc tgtaggctca
```

FIG. 35

Homo sapiens PERP, TP53 apoptosis effector (PERP), mRNA.

```
   1 ctctgagtca ccggaatcta ggtggggccg cccggagcgg cgtcctcggg agccgcctcc
  61 ccgcggcctc ttcgcttttg tggcggcgcc cgcgctcgca ggccactctc tgctgtcgcc
 121 cgtcccgcgc gctcctccga cccgctccgc tccgctccgc tcggccccgc gccgcccgtc
 181 aacatgatcc gctgcggcct ggcctgcgag cgctgccgct ggatcctgcc cctgctccta
 241 ctcagcgcca tcgccttcga catcatcgcg ctggccggcc gcggctggtt gcagtctagc
 301 gaccacggcc agacgtcctc gctgtggtgg aaatgctccc aagagggcgg cggcagcggg
 361 tcctacgagg agggctgtca gagcctcatg gagtacgcgt ggggtagagc agcggctgcc
 421 atgctcttct gtggcttcat catcctggtg atctgtttca tcctctcctt cttcgccctc
 481 tgtggacccc agatgcttgt cttcctgaga gtgattggag gtctccttgc cttggctgct
 541 gtgttccaga tcatctccct ggtaatttac cccgtgaagt acacccagac cttcaccctt
 601 catgccaacc ctgctgtcac ttacatctat aactgggcct acggctttgg gtgggcagcc
 661 acgattatcc tgattggctg tgccttcttc ttctgctgcc tccccaacta cgaagatgac
 721 cttctgggca atgccaagcc caggtacttc tacacatctg cctaacttgg gaatgaatgt
 781 gggagaaaat cgctgctgct gagatggact ccagaagaag aaactgtttc tccaggcgac
 841 tttgaaccca tttttggca gtgttcatat tattaaacta gtcaaaaatg ctaaaataat
 901 ttgggagaaa atattttta agtagtgtta tagtttcatg tttatctttt attatgtttt
 961 gtgaagttgt gtcttttcac taattaccta tactatgcca atatttcctt atatctatcc
1021 ataacattta tactacattt gtaagagaat atgcacgtga aacttaacac tttataaggt
1081 aaaaatgagg tttccaagat ttaataatct gatcaagttc ttgttatttc caaatagaat
1141 ggactcggtc tgttaagggc taaggagaag aggaagataa ggttaaaagt tgttaatgac
1201 caaacattct aaaagaaatg caaaaaaaaa gtttattttc aagccttcga actatttaag
1261 gaaagcaaaa tcatttccta aatgcatatc atttgtgaga atttctcatt aatatcctga
1321 atcattcatt ttagctaagg cttcatgttg actcgatatg tcatctagga aagtactatt
1381 tcatggtcca aacctgttgc catagttggt aaggctttcc tttaagtgtg aaatatttag
1441 atgaaatttt ctcttttaaa gttctttata gggttagggt gtgggaaaat gctatattaa
1501 taaatctgta gtgttttgtg tttatatgtt cagaaccaga gtagactgga ttgaaagatg
1561 gactgggtct aatttatcat gactgataga tctggttaag ttgtgtagta aagcattagg
1621 agggtcattc ttgtcacaaa agtgccacta aaacagcctc aggagaataa atgacttgct
1681 tttctaaatc tcaggtttat ctgggctcta tcatatagac aggcttctga tagtttgcaa
1741 ctgtaagcag aaacctacat atagttaaaa tcctggtctt tcttggtaaa cagattttaa
1801 atgtctgata taaaacatgc cacaggagaa ttcggggatt tgagtttctc tgaatagcat
1861 atatatgatg catcggatag gtcattatga ttttttacca tttcgactta cataatgaaa
1921 accaattcat tttaaatatc agattattat tttgtaagtt gtggaaaaag ctaattgtag
1981 ttttcattat gaagttttcc caataaacca ggtattctaa acttgtttcc agtttgtagt
2041 ttttccattt ttcaaatctg ggaaaggaa ttaaaaaaaa aatgggtaat aagaacatgg
2101 gatataatga aaagtggttt ttgtttgttt ttttgtttga agttttaagg gccttgctca
2161 ttttaggtgt ccaaaaccaa tttttgagtg gagattaatg aattctaata gtctattccc
2221 tgaacttttc ctcaatgaac aataccctag acacacatta aacaatttct ctgcagtgct
2281 atcaaccaga ggaaaatgga ctaagagatt tctggcaggt tcagacaccc gggggacatg
2341 tgtgcagtgt agctgaagcc tcctccttgt gctggggtcc ccttccattc aggtggtggg
2401 gtagcagtct ctctattttc cccttgccct ccttcccatt ttatcatttg ttattttttt
2461 tcccaccata agtcatatgt tacttccact atggtgtatg tcattgtgag gatgggtgca
2521 gagaggctgg gtgggagaac ggaaatatat ctccctaggg ctactgttgg ccagctagtc
2581 cttggcagtg aatttttcta tgcttttcaa aatgcgaggt gaatgtttct catagagaaa
2641 tgtaatctgg gtgattatac caaaattgaa aagaaaaacc cacacaacta tgccgtggct
2701 ggtggagaat ttgaagtggt cattaaaaat gttaaaaatc ccatctttta aagtgatacc
2761 acagctcatt caagaagata ctggatatct agagattaag aaacgtggtc tcctgttaaa
2821 catgaaaatg actccgttta taagcttctc taccacatgc acttgtcttt gcatgatttc
2881 ccatccagcc ttcttcccct cctcaatcac acaatacctt aacggcgcac atttaggaaa
2941 aatgcaacct cctgggacca acgagcctga tataatagaa ccatgtcaac ctaaagtatt
3001 tatgacaaag ataaactctt attttgcaga aatggtctgc ttccttcagc cttgttctag
3061 tatagagatc tgccattcct tgttgatcca gattcaccaa gacagatacc tttatgtcat
```

FIG. 35 (cont'd)

```
3121 aacagaaggg aagttccaga ggattctgga gagtaatgaa gaattgggct gagaaaccac
3181 ctgaaggcta acagtgcatt gcatgagatt tcccacagta aagctgaggt gctttttggt
3241 tcagtaatta aatattgagt tcccaccctt taaataagca gttctaggtt cctaagcaat
3301 tatttcactc tgtaagtagc cagacatgct aagtggcact tactgctgat tgtaacaaag
3361 aagtaatata tcaaggtctt tccatgttca cacaaggtag cttgtgtgta ataacttagc
3421 ttcaaaacca tagactgcag aactcacaag ttcaacagcc tttccttttt taaggaaatg
3481 aaaacaatgg aaaatatagt catcataact taattcggtt tatttttttt ttctgtaaac
3541 tccccctgaa agacattcct attaatacag taaatgtgaa cactgacttg tttttataag
3601 cacatctgaa agggcatatt tgagtctcat cccaactttg gtccttgcta tctgtgcagg
3661 cttgggcagg tcatctccct gctggtctca atatcctcac ctgtaaaatg attgtaaatg
3721 atccccctac cttcaagatt ctctgattga tagaattttt tctttaatta aaaaatttta
3781 aatattcctt gagttggaag cactgatcaa taagtggatt gcttagggag gttggaacga
3841 atagattcag tcccaacttc ctcttttaaa ttccctcttc ctcactcttc ctgcaacact
3901 tatttttaca gttgagtttt aaaaataagt aatatataaa ataatttctg tagtgtggtt
3961 tcagatttaa aaattcctgc agacaggctg ggcttgcaac cccatcagtc gatggtcaga
4021 gccctttgct ttttgagacc atttttaggt gagcttggct tgcctggata cagtgtgcag
4081 tgcattcttc ctgaattttg caattctggt atctgggtgt attttctagg tgtgtcaggg
4141 tgagtgtaat ccacctaggg tgtggaaaaa gccaagaaag ggaaattaaa agaggttcct
4201 atccagtcat gttaatgatc ttccacttgt actatcctgt gcttcgttgt taacctcgaa
4261 aacatacttt gttggctgca aaaataaaca aagggaaact caaaaaaaaa aaaaaaaaa
```

FIG. 36

Homo sapiens 3 BAC RP11-783D3 (Roswell Park Cancer Institute Human BAC Library) NTs 178621-180600.

```
178621 ggcaccgtgg gagtttgcag ctctggttgc tccaagagca caaatattaa tgtagcacag
178681 atattaatat tattaattag cacagacatt aatgtagtca cagaaagaaa aagagatgaa
178741 aaagagacag gttcttcact gcatgagagg ctccgtttgg gatctctcag aaatgtggaa
178801 gcagaggcta cagcacaagc ctgggttatt gctagtagca agacagaaaa taaggcttgg
178861 gtaagctgta gttatagtta caatggaaat gactggccca agagagtgct acagattaca
178921 tagcagctac taagaaaaag gacaggcaga aggggtaggc aagacatgtt ctctggctgt
178981 tgcagccacc aaaaagccag gatacaaagg cagggagtta tctgaactgc cttcctggag
179041 ggtcatgcat ttaggatccg actcattgac tcttttcctt aattttgctc tgtacatttc
179101 tctaagaggg ctaaccagtg tcaaggtttg ataatatctg aaatggtatt ctggtgccaa
179161 agtatcatct cacaaattat ttagaaattg caaagagaaa atatatttta taatccagat
179221 atctggcagt taaccacatg accaaattta gcatcactaa cagtaggaca actagatatt
179281 atatacctct tgctgtgata tactatgaag tacacatcat caactatgaa gtattatttt
179341 tttttctttt gagatagggt catgctctgt cgcccaattt agagtgcagc gatgcaatca
179401 tagctcactg cagctttgac ctcccagtct caagtgatcc tcccacctca gcctccctag
179461 tagctgggac tacagatgtg ttccaccaca cctggctaat ttttatatat tttttgtagt
179521 gatggggttt caccatgttg cacaggctgg tcttgaactc ctgggcttaa gcaatctgcc
179581 tgaaagttct gggattatag gcatgagcca ctgtgtccag actatgaagt attcttgcca
179641 aaactgatca acctaaatct aatcaagctt ctgggccaga actgtccaat agcaatgtaa
179701 tgtcagctac atgtaattta aaattttcta gttgccacca aaagcacaga aaagaaaaaa
179761 tagataaatt gtgctacatc aagattaaat acttctttgc atcaaaggac ataatcaaca
179821 cagagaaaag gcaaaccact gaatgggaga aaatatttgc aaattgatat tcataatatg
179881 taaagaatct ttacaactca acacccacaa aataaaaaaa aagattaaaa aatggggaaa
179941 ggacttgaat agacatttct ccaaagaaga tgtacaactt gccaataagc acaagaaaag
180001 actaattatg agggaaatgc aaattaaaac cacaatgaga tcaaacacat tatgttggct
180061 atcataaaaa gaaagtgcca ggcgcaatga tcacagctac tcaacaggct gggtggaaga
180121 atcccttgag accaggagtt agaggctgca gtgtgttatg atcatgcctg tgaatagcca
180181 ctgcactcca acataggtaa catagcaagc cccatccata aaataaaata aaataaaata
180241 aaataaaggc aacaaaaaat aacaagtatt ggtaaggatg tggagaaatt ggaaccctcg
180301 tgcattgctg gtgggtgtgt aaaaaggtat ggctgctgtg aaaaatggga tggctattct
180361 tcaaaaaatt aaccacagaa ttactatatg atccagcaat cccacttctg catacacatc
180421 caaaagaagt ggactcaagg actcagacag atatttgtac ccccctgttc atagcagcat
180481 tatttacaat agccaaaaag tagaagcaac cacagattca tcaatgtatg aatggataaa
180541 caaaatgtgg catatacaca tagtgggata tcattcagct ttaaaaaggg aggaaattct
```

FIG. 37

Homo sapiens cytochrome c oxidase subunit Va (COX5A), nuclear gene encoding mitochondrial protein, mRNA.

```
  1 gcccacgcgc cagagtcgca gtgggcgggc ctacgtgctc cgccccgctgt gagcctgtcc
 61 ggccccccgcc cgctccggag caacccgcga gcttacaccg gcttctctct gtcctcagcc
121 cgcgcgccgc catcgccgtc atgctgggcg ccgctctccg ccgctgcgct gtggccgcaa
181 ccacccgggc cgaccctcga ggcctcctgc actccgcccg gacccccggc cccgccgtgg
241 ctatccagtc agttcgctgc tattcccatg ggtcacagga gacagatgag gagtttgatg
301 ctcgctgggt aacatacttc aacaagccag atatagatgc ctgggaattg cgtaaaggga
361 taaacacact tgttacctat gatatggttc cagagcccaa aatcattgat gctgctttgc
421 gggcatgcag acggttaaat gattttgcta gtacagttcg tatcctagag gttgttaagg
481 acaaagcagg acctcataag gaaatctacc cctatgtcat ccaggaactt agaccaactt
541 taaatgaact gggaatctcc actccggagg aactgggcct tgacaaagtg taaaccgcat
601 ggatgggctt ccccaaggat ttattgacat tgctacttga gtgtgaacag ttacctggaa
661 atactgatga taacatatta ccttatttga acaagttttc ctttattgag taccaagcca
721 tgtaatggta acttggactt taataaaagg gaaatgagtt tgaactgaaa aaaaaaaaaa
781 aaaa
```

FIG. 38

Homo sapiens isolate PD047 mitochondrion, NTs 4801-6780.

```
4801 ttcacttctg agtcccagag gttacccaag gcacccctct gacatccggc ctgcttcttc
4861 tcacatgaca aaaactagcc cccatctcaa tcatatacca aatctctccc tcactaaacg
4921 taagccttct cctcactctc tcaatcttat ccatcatagc aggcagttga ggtggattaa
4981 accaaaccca gctacgcaaa atcttagcat actcctcaat tacccacata ggatgaataa
5041 tagcagttct accgtacaac cctaacataa ccattcttaa tttaactatt tatattatcc
5101 taactactac cgcattccta ctactcaact taaactccag caccacgacc ctactactat
5161 ctcgcacctg aaacaagcta acatgactaa cacccttaat tccatccacc ctcctctccc
5221 taggaggcct gcccccgcta accggctttt tgcccaaatg ggccattatc gaagaattca
5281 caaaaaacaa tagcctcatc atccccacca tcatagccac catcaccctc cttaacctct
5341 acttctacct acgcctaatc tactccacct caatcacact actccccata tctaacaacg
5401 taaaaataaa atgacagttt gaacatacaa aacccacccc attcctcccc acactcatca
5461 cccttaccac gctactccta cctatctccc cttttatact aataatctta tagaaattta
5521 ggttaaatac agaccaagag ccttcaaagc cctcagcaag ttgcaatact taatttctgt
5581 aacagctaag gactgcaaaa ccccactctg catcaactga acgcaaatca gccactttaa
5641 ttaagctaag cccttactag accaatggga cttaaaccca caaacactta gttaacagct
5701 aagcacccta atcaactggc ttcaatctac ttctcccgcc gccgggaaaa aaggcgggag
5761 aagccccggc aggtttgaag ctgcttcttc gaatttgcaa ttcaatatga aaatcacctc
5821 ggagctggta aaaagaggcc tagcccctgt ctttagattt acagtccaat gcttcactca
5881 gccattttac ctcaccccca ctgatgttcg ccgaccgttg actattctct acaaaccaca
5941 aagacattgg aacactatac ctattattcg gcgcatgagc tggagtccta ggcacagctc
6001 taagcctcct tattcgagcc gagctgggcc agccaggcaa ccttctaggt aacgaccaca
6061 tctacaacgt tatcgtcaca gcccatgcat ttgtaataat cttcttcata gtaataccca
6121 tcataatcgg aggctttggc aactgactag ttcccctaat aatcggtgcc cccgatatgg
6181 cgtttccccg cataaacaac ataagcttct gactcttacc tccctctctc ctactcctgc
6241 tcgcatctgc tatagtggag gccggagcag gaacaggttg aacagtctac cctcccttag
6301 cagggaacta ctcccaccct ggagcctccg tagacctaac catcttctcc ttacacctag
6361 caggtgtctc ctctatctta ggggccatca atttcatcac aacaattatc aatataaaac
6421 cccctgccat aacccaatac caaacgcccc tcttcgtctg atccgtccta atcacagcag
6481 tcctacttct cctatctctc ccagtcctag ctgctggcat cactatacta ctaacagacc
6541 gcaacctcaa caccaccttc ttcgaccccg ccggaggagg agaccccatt ctataccaac
6601 acctattctg atttttcggt caccctgaag tttatattct tatcctacca ggcttcggaa
6661 taatctccca tattgtaact tactactccg gaaaaaaaga accatttgga tacataggta
6721 tggtctgagc tatgatatca attggcttcc tagggtttat cgtgtgagca caccatatat
```

FIG. 39

Homo sapiens myosin, heavy chain 9, non-muscle (MYH9), mRNA.

```
   1 gagggcgggg cgggaaggcg gcgaggagcc gagctgggtg cggtgaggcg cgcagatcac
  61 cgcggttcct gggcagggca cggaaggcta agcaaggctg acctgctgca gctcccgcct
 121 cgtgcgctcg ccccacccgg ccgccgcccg agcgctcgag aaagtcctct cgggagaagc
 181 agcgcctgtt cccggggcag atccaggttc aggtcctggc tataagtcac catggcacag
 241 caagctgccg ataagtatct ctatgtggat aaaaacttca tcaacaatcc gctggcccag
 301 gccgactggg ctgccaagaa gctggtatgg gtgccttccg acaagagtgg ctttgagcca
 361 gccagcctca aggaggaggt gggcgaagag gccatcgtgg agctggtgga gaatgggaag
 421 aaggtgaagg tgaacaagga tgacatccag aagatgaacc cgcccaagtt ctccaaggtg
 481 gaggacatgg cagagctcac gtgcctcaac gaagcctcgg tgctgcacaa cctcaaggag
 541 cgttactact cagggctcat ctacacctat tcaggcctgt tctgtgtggt catcaatcct
 601 tacaagaacc tgcccatcta ctctgaagag attgtggaaa tgtacaaggg caagaagagg
 661 cacgagatgc cccctcacat ctatgccatc acagacaccg cctacaggag tatgatgcaa
 721 gaccgagaag atcaatccat cttgtgcact ggtgaatctg gagctggcaa gacggagaac
 781 accaagaagg tcatccagta tctggcgtac gtggcgtcct cgcacaagag caagaaggac
 841 cagggcgagc tggagcggca gctgctgcag gccaacccca tcctggaggc cttcgggaac
 901 gccaagaccg tgaagaatga caactcctcc cgcttcggca aattcattcg catcaacttt
 961 gatgtcaatg gctacattgt tggagccaac attgagactt atcttttgga gaaatctcgt
1021 gctatccgcc aagccaagga agaacggacc ttccacatct tctattatct cctgtctggg
1081 gctggagagc acctgaagac cgatctcctg ttggagccgt acaacaaata ccgcttcctg
1141 tccaatggac acgtcaccat ccccgggcag caggacaagg acatgttcca ggagaccatg
1201 gaggccatga ggattatggg catcccagaa gaggagcaaa tgggcctgct gcgggtcatc
1261 tcaggggttc ttcagctcgg caacatcgtc ttcaagaagg agcggaacac tgaccaggcg
1321 tccatgcccg acaacacagc tgcccaaaag gtgtcccatc tcttgggtat caatgtgacc
1381 gatttcacca gaggaatcct caccccgcgc atcaaggtgg gacgggatta cgtccagaag
1441 gcgcagacta aagagcaggc tgactttgcc atcgaggcct tggccaaggc gacctatgag
1501 cggatgttcc gctggctggt gctgcgcatc aacaaggctc tggacaagac caagaggcag
1561 ggcgcctcct tcatcgggat cctggacatt gccggcttcg agatctttga tctgaactcg
1621 tttgagcagc tgtgcatcaa ttacaccaat gagaagctgc agcagctctt caaccacacc
1681 atgttcatcc tggagcagga ggagtaccag cgcgagggca tcgagtggaa cttcatcgac
1741 tttggcctcg acctgcagcc ctgcatcgac ctcattgaga agccagcagg ccccccgggc
1801 attctggccc tgctggacga ggagtgctgg ttccccaaag ccaccgacaa gagcttcgtg
1861 gagaaggtga tgcaggagca gggcacccac cccaagttcc agaagcccaa gcagctgaag
1921 gacaaagctg atttctgcat tatccactat gccggcaagg tggattacaa agctgacgag
1981 tggctgatga agaacatgga tcccctgaat gacaacatcg ccacactgct ccaccagtcc
2041 tctgacaagt ttgtctcgga gctgtggaag gatgtggacc gcatcatcgg cctggaccag
2101 gtggccggca tgtcggagac cgcactgccc ggggccttca agacgcggaa gggcatgttc
2161 cgcactgtgg ggcagcttta caaggagcag ctggccaagc tgatggctac gctgaggaac
2221 acgaacccca actttgtccg ctgcatcatc cccaaccacg agaagaaggc cggcaagctg
2281 gacccgcatc tcgtgctgga ccagctgcgc tgcaacggtg ttctcgaggg catccgtatc
2341 tgccgccagg gcttccccaa cagggtggtc ttccaggagt ttcggcagag atatgagatc
2401 ctgactccaa actccattcc caagggtttc atggacggga agcaggcgtg cgtgctcatg
2461 ataaaagccc tggagctcga cagcaatctg taccgcattg gccagagcaa agtcttcttc
2521 cgtgccggtg tgctggccca cctggaggag gagcgagacc tgaagatcac cgacgtcatc
2581 atagggttcc aggcctgctg caggggctac ctggccagga aagcatttgc caagcggcag
2641 cagcagctta ccgccatgaa ggtcctccag cggaactgcg ctgcctacct gaagctgcgg
2701 aactggcagt ggtggcggct cttcaccaag gtcaagccgc tgctgcaggt gagccggcag
2761 gaggaggaga tgatggccaa ggaggaggag ctggtgaagg tcagagagaa gcagctggct
2821 gcggagaaca ggctcacgga gatggagacg ctgcagtctc agctcatggc agagaaattg
2881 cagctgcagg agcagctcca ggcagaaacc gagctgtgtg ccgaggctga ggagctccgg
2941 gcccgcctga ccgccaagaa gcaggaatta gaagagatct gccatgacct agaggccagg
3001 gtggaggagg aggaggagcg ctgccagcac ctgcaggcgg agaagaagaa gatgcagcag
3061 aacatccagg agcttgagga gcagctggag gaggaggaga gcgcccggca gaagctgcag
```

FIG. 39 (cont'd)

3121 ctggagaagg tgaccaccga ggcgaagctg aaaaagctgg aggaggagca gatcatcctg
3181 gaggaccaga actgcaagct ggccaaggaa aagaaactgc tggaagacag aatagctgag
3241 ttcaccacca acctcacaga agaggaggag aaatctaaga gcctcgccaa gctcaagaac
3301 aagcatgagg caatgatcac tgacttggaa gagcgcctcc gcagggagga gaagcagcga
3361 caggagctgg agaagacccg ccggaagctg gagggagact ccacagacct cagcgaccag
3421 atcgccgagc tccaggccca gatcgcggag ctcaagatgc agctggccaa gaaagaggag
3481 gagctccagg ccgccctggc cagagtggaa gaggaagctg cccagaagaa catggccctc
3541 aagaagatcc gggagctgga atctcagatc tctgaactcc aggaagacct ggagtctgag
3601 cgtgcttcca ggaataaagc tgagaagcag aaacgggacc ttggggaaga gctagaggct
3661 ctgaaaacag agttggagga cacgctggat tccacagctg cccagcagga gctcaggtca
3721 aaacgtgagc aggaggtgaa catcctgaag aagaccctgg aggaggaggc caagacccac
3781 gaggcccaga tccaggagat gaggcagaag cactcacagg ccgtggagga gctggcggag
3841 cagctggagc agacgaagcg ggtgaaagca aacctcgaga aggcaaagca gactctggag
3901 aacgagcggg gggagctggc caacgaggtg aaggtgctgc tgcagggcaa aggggactcg
3961 gagcacaagc gcaagaaagt ggaggcgcag ctgcaggagc tgcaggtcaa gttcaacgag
4021 ggagagcgcg tgcgcacaga gctggccgac aaggtcacca agctgcaggt ggagctggac
4081 aacgtgaccg ggcttctcag ccagtccgac agcaagtcca gcaagctcac caaggacttc
4141 tccgcgctgg agtcccagct gcaggacact caggagctgc tgcaggagga gaaccggcag
4201 aagctgagcc tgagcaccaa gctcaagcag gtggaggacg agaagaattc cttccgggag
4261 cagctggagg aggaggagga ggccaagcac aacctggaga agcagatcgc caccctccat
4321 gcccaggtgg ccgacatgaa aaagaagatg gaggacagtg tggggtgcct ggaaactgct
4381 gaggaggtga agaggaagct ccagaaggac ctggagggcc tgagccagcg gcacgaggag
4441 aaggtggccg cctacgacaa gctggagaag accaagacgc ggctgcagca ggagctggac
4501 gacctgctgg tggacctgga ccaccagcgc cagagcgcgt gcaacctgga gaagaagcag
4561 aagaagtttg accagctcct ggcggaggag aagaccatct ctgccaagta tgcagaggag
4621 cgcgaccggg ctgaggcgga ggcccgagag aaggagacca aggctctgtc gctggcccgg
4681 gccctggagg aagccatgga gcagaaggcg gagctggagc ggctcaacaa gcagttccgc
4741 acggagatgg aggaccttat gagctccaag gatgatgtgg gcaagagtgt ccacgagctg
4801 gagaagtcca agcgggccct agagcagcag gtggaggaga tgaagacgca gctggaagag
4861 ctggaggacg agctgcaggc caccgaagat gccaagctgc ggttggaggt caacctgcag
4921 gccatgaagg cccagttcga gcgggacctg cagggccggg acgagcagag cgaggagaag
4981 aagaagcagc tggtcagaca ggtgcgggag atggaggcag agctggagga cgagaggaag
5041 cagcgctcga tggcagtggc cgcccggaag aagctggaga tggacctgaa ggacctggag
5101 gcgcacatcg actcggccaa caagaaccgg gacgaagcca tcaaacagct gcggaagctg
5161 caggcccaga tgaaggactg catgcgcgag ctggatgaca cccgcgcctc tcgtgaggag
5221 atcctggccc aggccaaaga gaacgagaag aagctgaaga gcatggaggc cgagatgatc
5281 cagttgcagg aggaactggc agccgcggag cgtgccaagc gccaggccca gcaggagcgg
5341 gatgagctgg ctgacgagat cgccaacagc agcggcaaag gagccctggc gttagaggag
5401 aagcggcgtc tggaggcccg catcgcccag ctggaggagg agctggagga ggagcagggc
5461 aacacggagc tgatcaacga ccggctgaag aaggccaacc tgcagatcga ccagatcaac
5521 accgacctga acctggagcg cagccacgcc cagaagaacg agaatgctcg gcagcagctg
5581 gaacgccaga acaaggagct taaggtcaag ctgcaggaga tggagggcac tgtcaagtcc
5641 aagtacaagg cctccatcac cgccctcgag gccaagattg cacagctgga ggagcagctg
5701 gacaacgaga ccaaggagcg ccaggcagcc tgcaaacagg tgcgtcggac cgagaagaag
5761 ctgaaggatg tgctgctgca ggtggatgac gagcggagga acgccgagca gtacaaggac
5821 caggccgaca aggcatctac ccgcctgaag cagctcaagc ggcagctgga ggaggccgaa
5881 gaggaggccc agcgggccaa cgcctcccgc cggaaactgc agcgcgagct ggaggacgcc
5941 actgagacgg ccgatgccat gaaccgcgaa gtcagctccc taaagaacaa gctcaggcgc
6001 ggggacctgc cgtttgtcgt gccccgccga atggcccgga aaggcgccgg ggatggctcc
6061 gacgaagagg tagatggcaa agcggatggg gctgaggcca aacctgccga ataagcctct
6121 tctcctgcag cctgagatgg atggacagac agacaccaca gcctcccctt cccagacccc
6181 gcagcacgcc tctccccacc ttcttgggac tgctgtgaac atgcctcctc ctgccctccg
6241 ccccgtcccc ccatcccgtt tccctccagg tgttgttgag ggcatttggc ttcctctgct

FIG. 39 (cont'd)

```
6301 gcatcccctt ccagctccct cccctgctca gaatctgata ccaaagagac agggcccggg
6361 cccaggcaga gagcgaccag caggctcctc agccctctct tgccaaaaag cacaagatgt
6421 tgaggcgagc agggcaggcc cccggggagg ggccagagtt ttctatgaat ctatttttct
6481 tcagactgag gccttttggt agtcggagcc cccgcagtcg tcagcctccc tgacgtctgc
6541 caccagcgcc cccactcctc ctcctttctt tgctgtttgc aatcacacgt ggtgacctca
6601 cacacctctg ccccttgggc ctcccactcc catggctctg ggcggtccag aaggagcagg
6661 ccctgggcct ccacctctgt gcagggcaca gaaggctggg gtgggggag gagtggattc
6721 ctccccaccc tgtcccaggc agcgccactg tccgctgtct ccctcctgat tctaaaatgt
6781 ctcaagtgca atgcccccctc ccctccttta ccgaggacag cctgcctctg ccacagcaag
6841 gctgtcgggg tcaagctgga aaggccagca gccttccagt ggcttctccc aacactcttg
6901 gggaccaaat atatttaatg gttaagggac ttgtcccaag tctgacagcc agagcgttag
6961 aggggccagc ggccctccca ggcgatcttg tgtctactct aggactgggc ccgagggtgg
7021 tttacctgca ccgttgactc agtatagttt aaaaatctgc cacctgcaca ggtatttttg
7081 aaagcaaaat aaggttttct tttttcccct ttcttgtaat aaatgataaa attccgagtc
7141 tttctcactg cctttgttta gaagagagta gctcgtcctc actggtctac actggttgcc
7201 gaatttactt gtattcctaa ctgttttgta tatgctgcat tgagacttac ggcaagaagg
7261 catttttttt ttttaaagga aacaaactct caaatcatga agtgatataa aagctgcata
7321 tgcctacaaa gctctgaatt caggtcccag ttgctgtcac aaaggagtga gtgaaactcc
7381 caccctaccc cctttttat ataataaaag tgccttagca tgtgttgcag ctgtcaccac
7441 tacagtaagc tggtttacag atgttttcca ctgagcatca caataaagag aaccatgtgc
7501 tacga
```

FIG. 40

Homo sapiens asparagine synthetase domain containing 1 (ASNSD1), mRNA.

```
   1 gctattggta agactcgcgg gaaaagaaag ggtgagcgcg gctggaagcg cgcatgcgct
  61 gtggctaatg ccgtaggctc cttcagggct gagccatccc gcgtgtcttg cgctcggtgg
 121 aaatgcccag ccgagggacg cgaccagagg acagctctgt gctgatcccc accgacaatt
 181 cgaccccaca caaggaggat ctaagcagca agattaaaga acaaaaaatt gtggtggatg
 241 aactttctaa ccttaagaag aataggaaag tatataggca acaacagaac agcaatatat
 301 tctttcttgc agaccgaaca gaaatgctgt ctgagagcaa gaatatattg gatgaactga
 361 aaaaagaata ccaagaaata gaaaacttag acaagaccaa aatcaagaaa tagtcaacct
 421 gatttcacat aacaatgtgt ggcatttgtt gttctgtaaa cttttctgct gagcatttca
 481 gtcaagattt aaaagaggac ttactatata atcttaaaca gcggggaccc aatagtagta
 541 aacaattgtt aaagtctgat gttaactacc agtgtttatt ttctgctcac gtcctacact
 601 tgaggggtgt tttgactacc cagcctgtgg aagatgaaag aggcaatgtg tttctatgga
 661 atggagaaat ttttagtgga ataaaggttg aagctgaaga gaatgacact caaattttgt
 721 ttaattatct ttcctcctgt aagaatgaat ctgagatttt gtcactcttc tcagaagtac
 781 aaggtccctg gtcatttata tattatcaag catctagtca ttatttatgg tttggtaggg
 841 atttttttgg tcgccgtagc ttgctttggc attttagtaa tttgggcaag agtttctgcc
 901 tctcttcagt tggcacccaa acatctggat tggcaaatca gtggcaagaa gttccagcat
 961 ctggactttt cagaattgat cttaagtcta ctgtcatttc cagatgcatt attttacaac
1021 tgtatccttg gaaatatatt tctagggaga atattattga agaaaatgtt aatagcctga
1081 gtcaaatttc agcagactta ccagcatttg tatcagtggt agcaaatgaa gccaaactgt
1141 atcttgaaaa acctgttgtt cctttaaata tgatgttgcc acaagctgca ttggagactc
1201 attgcagtaa tatttccaat gtgccaccta caagagagat acttcaagtc tttcttactg
1261 atgtacacat gaaggaagta attcagcagt tcattgatgt cctgagtgta gcagtcaaga
1321 aacgtgtctt gtgtttacct agggatgaaa acctgacagc aaatgaagtt ttgaaaacgt
1381 gtgataggaa agcaaatgtt gcaatcctgt tttctggggg cattgattcc atggttattg
1441 caaccccttgc tgaccgtcat attcctttag atgaaccaat tgatcttctt aatgtagctt
1501 tcatagctga agaaaagacc atgccaacta cctttaacag agaagggaat aaacagaaaa
1561 ataaatgtga aataccttca gaagaattct ctaaagatgt tgctgctgct gctgctgaca
1621 gtcctaataa acatgtcagt gtaccagatc gaatcacagg aagggcggga ctaaaggaac
1681 tacaagctgt tagcccttcc cgaatttgga attttgttga aattaatgtt tctatggaag
1741 aactgcagaa attaagaaga actcgaatat gtcacttaat tcggccattg gatacagttt
1801 tggatgatag cattggctgt gcagtctggt ttgcttctag aggaattggt tggttagtgg
1861 cccaggaagg agtgaaatcc tatcagagca atgcaaaggt agttctcact ggaattggtg
1921 cagatgagca acttgcaggt tattctcgtc atcgtgtccg ctttcagtcg catgggctgg
1981 aaggattgaa taaggaaata atgatggaac tgggtcgaat ttcttctaga aatcttggtc
2041 gtgatgacag agttattggt gatcatggaa aagaagcaag atttcctttc ctggatgaaa
2101 atgttgtctc ctttctaaat tctctgccga tttgggaaaa agcaaacttg actttacccc
2161 gaggaattgg tgaaaaatta cttttacgcc ttgcagctgt ggaacttggt cttacagcct
2221 ctgctcttct gcccaaacgg gccatgcagt ttggatcaag aattgcaaaa atggaaaaaa
2281 ttaatgaaaa ggcatctgat aaatgtggac ggctccaaat catgtcctta gaaaatcttt
2341 ctattgaaaa ggagactaaa ttgtaatgtg attcacaatg taacaatata aaaataagtt
2401 tttatataat tatataaaag taagatactc tgctgcttta ctattgtata atatagtagt
2461 tttaaagttc aaaaaaaaaa aaaaaaa
```

FIG. 41

Homo sapiens cathepsin F (CTSF), mRNA.

```
   1 ggaggactca ggccccgctg gccgcgggct cggtacccgg tgggtcggtg gagcgtctgt
  61 tgggtccggg ccgccggctt cgccctcgcc atggcgccct ggctgcagct cctgtcgctg
 121 ctggggctgc tcccgggcgc agtggccgcc cccgcccagc cccgagccgc cagctttcag
 181 gcctgggggc cgccgtcccc ggagctgctg gcgcccaccc gcttcgcgct ggagatgttc
 241 aaccgcggcc gggctgcggg gacgcgggcc gtgctgggcc ttgtgcgcgg ccgcgtccgc
 301 cgggcgggtc aggggtcgct gtactccctg gaggccaccc tggaggagcc accctgcaac
 361 gaccccatgg tgtgccggct ccccgtgtcc aagaaaaccc tgctctgcag cttccaagtc
 421 ctggatgagc tcggaagaca cgtgctgctg cggaaggact gtggcccagt ggacaccaag
 481 gttccaggtg ctggggagcc caagtcagcc ttcactcagg gctcagccat gatttcttct
 541 ctgtcccaaa accatccaga caacagaaac gagactttca gctcagtcat ttccctgttg
 601 aatgaggatc ccctgtccca ggacttgcct gtgaagatgg cttcaatctt caagaacttt
 661 gtcattacct ataaccggac atatgagtca aaggaagaag cccggtggcg cctgtccgtc
 721 tttgtcaata acatggtgcg agcacagaag atccaggccc tggaccgtgg cacagctcag
 781 tatggagtca ccaagttcag tgatctcaca gaggaggagt tccgcactat ctacctgaat
 841 actctcctga ggaaagagcc tggcaacaag atgaagcaag ccaagtctgt gggtgacctc
 901 gccccacctg aatgggactg gaggagtaag ggggctgtca caaaagtcaa agaccagggc
 961 atgtgtggct cctgctgggc cttctcagtc acaggcaatg tggagggcca gtggtttctc
1021 aaccagggga ccctgctctc cctctctgaa caggagctct tggactgtga caagatggac
1081 aaggcctgca tgggcggctt gccctccaat gcctactcgg ccataaagaa tttgggaggg
1141 ctggagacag aggatgacta cagctaccag ggtcacatgc agtcctgcaa cttctcagca
1201 gagaaggcca aggtctacat caatgactcc gtggagctga gccagaacga gcagaagctg
1261 gcagcctggc tggccaagag aggcccaatc tccgtggcca tcaatgcctt tggcatgcag
1321 ttttaccgcc acgggatctc ccgccctctc cggcccctct gcagcccttg gctcattgac
1381 catgcggtgt tgcttgtggg ctacggcaac cgctctgacg ttcccttttg ggccatcaag
1441 aacagctggg gcactgactg ggggtgagaag ggttactact acttgcatcg tgggtccggg
1501 gcctgtggcg tgaacaccat ggccagctcg gcggtggtgg actgaagagg ggcccccagc
1561 tcgggacctg gtgctgatca gagtggctgc tgccccagcc tgacatgtgt ccaggcccct
1621 ccccgggagg tacagctggc agagggaaag gcactgggta cctcagggtg agcagagggc
1681 actgggctgg ggcacagccc ctgcttccct gcaccccatt cccaccctga agttctgcac
1741 ctgcaccttt gttgaattgt ggtagcttag gaggatgtcg gggtgaaggg tggtatcttg
1801 gcagttgaag ctggggcaag aactctgggc ttgggtaatg agcaggaaga aaattttctg
1861 atcttaagcc cagctctgtt ctgcccccgc tttcctctgt ttgatactat aaattttctg
1921 gttcccttgg atttagggat agtgtccctc tccatgtcca ggaaacttgt aaccaccctt
1981 ttctaacagc aataaagagg tgtccttgtc ccgaaaaaaa aaaaaaaaaa aa
```

FIG. 42

Homo sapiens genomic DNA, chromosome 11q clone:RP11-822I2, NTs 157801-159780.

```
157801 ttgagtaata gaaaataaat ctgggtcact tttttgtagc tgtaaatcca gccttagtaa
157861 tcctgacctc cattaacata gctagtattt caaattccac tgtaacagtt gctctgactc
157921 tttgggggct gggaggcaat ccaagtagcc agagaagcaa ttgtttcaca tgcttcaatc
157981 ctgccactcc agaaaaaata taagggggac tagggcaaaa gaaaatctct tatttgtttt
158041 ccatttctca tttctcgtat ctttattgct tctctctcat ccttaacctg tatctccctt
158101 cagctgatgc ctgattacct tctaccatgt tcaacattat gatcagtcac ctactatgtg
158161 ccaggaagtg tgcagtgtgt gaggatacca gaccctacct actgggagct tacagtctag
158221 ctcaacaggc acatcattaa ataagcaatt gcagcaatta tattaagtgc tgggccaagg
158281 gaggtaccag aagtcataag aatccctcct ctgaggggat agaagtgaag acttcagagg
158341 ggaagtaatg attctggatg tgtaggactc agccaggtga agtgtaaaag taaggatgga
158401 ggagagtgtt ctaaaagagg gaacaacata atcaaagttc tggacaggag agagatttga
158461 catatttgag gaagtgaaaa ttttatctag aaacttgcaa tgagtaagta aacaccaggt
158521 caagaggaac tgagagattg gcagacaatg gaaaaccatt gaaaaggatt aaactgggaa
158581 gtgatatgtt ctcttttgca tttaaaaaga tcaccaatgg ggatatggag aatggtctgg
158641 ataggtctta agactagagc caggaagaca tgttagaagg ctatcaattg accctaaaga
158701 cactgcttca atccctttga tgacagtgag tttgctttcc ccagagatag cttattggac
158761 ctcaggactg ctgtgagaaa cagaaaatgc tcctttacgt gttgcctgaa gttaggctca
158821 ccgatttggg gcatgttcta attctaccag ctaggaacac acagaatcgc ttgtcaaaca
158881 ttctgagtca gatatgtcct ccctatgtct tttctgagaa aggcatacag aaattcccag
158941 ctaaacatca ccagttccct catttgttcc tcagatgata tggtccattc aagttttgta
159001 atcatcatgg gggtagatgg agggtcccag tcctcacaac cattctggta atttactctt
159061 gaatttactg gttcacatgt atctattttg tagtgtggct cctgaaactg aaaaacctac
159121 cccaggtatt ctgtgaacag acagagtaga gagtctgtca ctgcccacgg agagatgatt
159181 aggcttccgg gaaaaggtga gaacactggc aaagttccgg aaggaggaac aatatccctt
159241 cttcccttct tcatgagtcg taccatccct tacttttggc tggtcacata accacccaaa
159301 ataagggcta cattttccag ccactctagc agctaggggt gacagagtga ctaagattta
159361 cctggaagta tcgtgtgtga cttctgggaa gggtccttaa agagaggggt agtcctggct
159421 gggtgcggtg gctcacgtct gtaatcccag cactttggga ggccgaggca ggcggatcac
159481 aaggtcagga gttcaagacc agcctggcca agatgctgaa accccatctc taataaaaat
159541 acaaaaaaat tagccgggca tgctggcggg cgcctgtaat cccagctact taggaggctg
159601 agatggagaa ttgcttgaac ttgggaggca gagtttgcag tgggccaaaa tggcgccact
159661 gcactccagc ctgggcaaca gagcaagcct ccgtctcaaa aaaaaaaaaa aaaaaaaaaa
159721 aagagagggg tagtccttgt tgctgttgct gcaggtattt tctccttctt cccagctgga
```

FIG. 43

Homo sapiens casein kinase 2, alpha prime polypeptide (CSNK2A2), mRNA.

```
   1 gcggccgccc gccgccgcgc tcctcctcct cctcctccag cgcccggcgg cccgctgcct
  61 cctccgcccg acgccccgcg tcccccgccg cgccgccgcc gccaccctct gcgccccgcg
 121 ccgccccccg gtcccgcccg ccatgcccgg cccggccgcg ggcagcaggg cccgggtcta
 181 cgccgaggtg aacagtctga ggagccgcga gtactgggac tacgaggctc acgtcccgag
 241 ctggggtaat caagatgatt accaactggt tcgaaaactt ggtcggggaa aatatagtga
 301 agtatttgag gccattaata tcaccaacaa tgagagagtg gttgtaaaaa tcctgaagcc
 361 agtgaagaaa aagaagataa aacgagaggt taagattctg gagaaccttc gtggtggaac
 421 aaatatcatt aagctgattg acactgtaaa ggaccccgtg tcaaagacac cagctttggt
 481 atttgaatat atcaataata cagattttaa gcaactctac cagatcctga cagactttga
 541 tatccggttt tatatgtatg aactacttaa agctctggat tactgccaca gcaagggaat
 601 catgcacagg gatgtgaaac ctcacaatgt catgatagat caccaacaga aaaagctgcg
 661 actgatagat tggggtctgg cagaattcta tcatcctgct caggagtaca atgttcgtgt
 721 agcctcaagg tacttcaagg gaccagagct cctcgtggac tatcagatgt atgattatag
 781 cttggacatg tggagtttgg gctgtatgtt agcaagcatg atctttcgaa gggaaccatt
 841 cttccatgga caggacaact atgaccagct tgttcgcatt gccaaggttc tgggtacaga
 901 agaactgtat gggtatctga agaagtatca catagaccta gatccacact tcaacgatat
 961 cctgggacaa cattcacgga aacgctggga aaactttatc catagtgaga acagacacct
1021 tgtcagccct gaggccctag atcttctgga caaacttctg cgatacgacc atcaacagag
1081 actgactgcc aaagaggcca tggagcaccc atacttctac cctgtggtga aggagcagtc
1141 ccagccttgt gcagacaatg ctgtgctttc cagtggtctc acggcagcac gatgaagact
1201 ggaaagcgac gggtctgttg cggttctccc acttttccat aagcagaaca agaaccaaat
1261 caaacgtctt aacgcgtata gagagatcac gttccgtgag cagacacaaa acggtggcag
1321 gtttggcgag cacgaactag accaagcgaa gggcagccca ccaccgtata tcaaacctca
1381 cttccgaatg taaaaggctc acttgccttt ggcttcctgt tgacttcttc ccgacccaga
1441 aagcatgggg aatgtgaagg gtatgcagaa tgttgttggt tactgttgct ccccgagccc
1501 ctcaactcgt cccgtggccg cctgtttttc cagcaaacca cgctaactag ctgaccacag
1561 actccacagt gggggacgg gcgcagtatg tggcatggcg gcagttacat attattattt
1621 taaaagtata tattattgaa taaaaggttt taaaagaaaa aaaaaaaaaa aaaa
```

FIG. 44

Homo sapiens aurora kinase A interacting protein 1 (AURKAIP1), transcript variant 1, mRNA.

```
   1 cccgcacccc ctgggattgt gggaaatgta gtttttttgcc tccgtaaggg accaggcgga
  61 gctgaggaac cgcgcgagga ctgggaccgt gattccacta accggaaacc gtcgcctttc
 121 gggcccggcg gggcctgagc caatgcagaa tcgggggccg cgaggacgcc agcgggcgct
 181 gtgcgtagga accgccgggt ggccgctgcc gatcggggcc gacttgggga cggaccggaa
 241 gtgcccgagg gcggccgcag aacggtcaat ttgagccgcg tcgagctccc ctgggacctg
 301 tggccgccgc ccacagacca tgctcctggg gcgcctgact tcccagctgt tgagggccgt
 361 tccttgggca ggcggccgcc cgccttggcc cgtctctgga gtgctgggca gccgggtctg
 421 cgggcccctt tacagcacat cgccggccgg cccaggtagg gcggcctctc tccctcgcaa
 481 gggggcccag ctggagctgg aggagatgct ggtccccagg aagatgtccg tcagcccccct
 541 ggagagctgg ctcacggccc gctgcttcct gcccagactg gataccggga ccgcagggac
 601 tgtggctcca ccgcaatcct accagtgtcc gcccagccag atagggggaag gggccgagca
 661 gggggatgaa ggcgtcgcgg atgcgcctca aattcagtgc aaaaacgtgc tgaagatccg
 721 ccggcggaag atgaaccacc acaagtaccg gaagctggtg aagaagacgc ggttcctgcg
 781 gaggaaggtc caggagggac gcctgagacg caagcagatc aagttcgaga aagacctgag
 841 gcgcatctgg ctgaaggcgg ggctaaagga agcccccgaa ggctggcaga cccccaagat
 901 ctacctgcgg ggcaaatgag tctggcgccg cccttcccgc ccgttgctgc tgtgatccgt
 961 agtaataaat tctcagagga ctcagccttt aaaaaaaaaa aaaaaaaaaa aaaaaaaaaa
1021 aaaaaaaaaa aa
```

FIG. 45

Homo sapiens BAC clone RP11-327O17 from 4, NTs 107401-109380.

```
107401 aagaaataag cttattcaag acctgtagga ccaattttag caagaatcct gctaaatcaa
107461 tttatgattt cccccccgct ccacaccctt gaaatctgat caccccttgat atatagctcc
107521 tcatctccca cctttgatct gtaagtcctt ggcctgcctt tagcaagagt cctattaggt
107581 cgggttagca agaatccccc tacacttgat gtctcctctt aataattttc ccctcttagt
107641 gaattttcct ctcccctcac actctgccca ttggctataa atttccagct gtctttgctg
107701 tattcagaat agagccctat ctctgcctcc tactgtaata ctctaatgca atatagtctt
107761 caataaagct ttacttacca tctcaaccag catcagaata atttttcctt taacatatcc
107821 aagcttggtc agaattaggg tgtacctaca cctacctgca ctattaatac tccgcacagc
107881 agggagaaag gaactaccta ccaggtgtca tgggcatgga aggatgtgag gaacgctagc
107941 actggccaaa tacagtggcc tcacaagcca tcttcacctt caggaaaatg aatattgagc
108001 tgccacagac actctgctgc cctcttaatt taccattacc atgaatctac aggatgctct
108061 gttccaaaca cccagtacat tcttatacat cttgtcctga tagatgcctg tgaggtaggc
108121 agggctgaga attatgaatt gttgtctatc aggctgaagt gactttccaa aaattgaagt
108181 tgacagcaat aaggtcaaga atcagctctg tgctgttttg acggagtgag tcattgcctc
108241 cttgaatctg gcacatacca gccaactgtc aaggtttgtt cttccacatg gtctaactgc
108301 taaatacaaa gtatactagg tttgtcagct tagggcatgt ttgcttccac tctgaaaaca
108361 tttcagctgc cctaatatat tgctataaag aattctctta ttattactgt cttcctcctc
108421 atatttagct ctgtcttcca tcacttcaaa agaagcattt gtagcttccc catcctcttt
108481 ctttctagtt gactttgaag actatctata taagtatttc tggcataaaa ctgacaggta
108541 aatgacttca aagctaattt ccgccccccc ccaccccttg ccctttttca gtctcaagat
108601 accatgtcag tcctctattc actctcaaaa atgatggctt aactgcacag tgccgttctg
108661 ggtcaattct taaatatact agaatatact agacatatct ggctcattta agtcattctt
108721 caccaatctt tcttcttatt tacctccttc ctcaacttgg aaattttgcc ttttcacaat
108781 atgtggatag ccatttctgc caagattgtg ccgacaagac tggttataaa tctacctact
108841 ttgtaaaagg ggaatatttt tgtaaccatt gcatatctct attaaaacat gaaagaaaca
108901 ctgaaggcca agtgttcaag tgacacgcag gaaaaaaaaa agctgatatt cagaaagcca
108961 agcatacaga gaaataatga gaggttaatg aagtgagttc tgaatcacaa gtgctgttca
109021 gaaaacaaaa aaagacatct gtgaaggctg accttggaac tagtcactgt tattcagtcc
109081 atatgtatgt atgtttttat taaaataact gttcaaagtt aactttcatc caagttaact
109141 tctgaagaaa taaaaaggca tcacgttaag gtttcaaaaa tttaaccatt ctacctttag
109201 caatggttag tccaccttat tttcacacat ttccatctta atgaaagcaa gtacattaaa
109261 ggatactcag aatagctgca aggcatacca caagatgtac cacaagatta gaaatttctt
109321 taaaagtaat taagatcggc cgagtgcagt ggctgactcc agcaatccca gcattttggg
```

FIG. 46

Homo sapiens ADP-ribosylation factor 6 (ARF6), mRNA.

```
   1 ggtcggcctc tgctgcgcct gcgtggtcgg gaggggaagt gaggcggttt cctcggcgcc
  61 ttttccggca gcggcggcgg cagaactggg aggaggagtt ggaggccgga gggagcccgc
 121 gctcggggcg gcggctggag gcagcgcacc gagttcccgc gaggatccat gacctgacgg
 181 ggccccggag ccgcgctgcc tctcgggtgt cctgggtcgg tggggagccc agtgctcgca
 241 ggccggcggg cgggccggag ggctgcagtc tccctcgcgg tgagaggaag gcggaggagc
 301 gggaaccgcg gcggcgctcg cgcggcgcct gcggggggaa gggcagttcc gggccgggcc
 361 gcgcctcagc agggcggcgg ctcccagcgc agtctcaggg cccgggtggc ggcggcgact
 421 ggagaaatca agttgtgcgg tcggtgatgc ccgagtgagc gggggcctg ggcctctgcc
 481 cttaggaggc aactcccacg caggccgcaa aggcgctctc gcggccgaga ggcttcgttt
 541 cggtttcgcg gcggcggcgg cgttgttggc tgaggggacc cgggacacct gaatgccccc
 601 ggccccggct cctccgacgc gatggggaag gtgctatcca aaatcttcgg gaacaaggaa
 661 atgcggatcc tcatgttggg cctggacgcg gccggcaaga caacaatcct gtacaagttg
 721 aagctgggcc agtcggtgac caccattccc actgtgggtt tcaacgtgga gacggtgact
 781 tacaaaaatg tcaagttcaa cgtatgggat gtgggcggcc aggacaagat ccggccgctc
 841 tggcggcatt actacactgg gacccaaggt ctcatcttcg tagtggactg cgccgaccgc
 901 gaccgcatcg atgaggctcg ccaggagctg caccgcatta tcaatgaccg ggagatgagg
 961 gacgccataa tcctcatctt cgccaacaag caggacctgc ccgatgccat gaaaccccac
1021 gagatccagg agaaactggg cctgacccgg attcgggaca ggaactggta tgtgcagccc
1081 tcctgtgcca cctcagggga cggactctat gaggggctca catggttaac ctctaactac
1141 aaatcttaat gagcattctc cacccatccc ctggaaggag agaaatcaaa aacccattca
1201 taggattatc gccaccatca cctctttcaa ttgccacttt ctcttctttt gaatttgaac
1261 tctggagtta ctgttctaca gtttggcggg gacggggctt ggggtttc tcttttgttt
1321 gtttcccttt ctttttcctt tttttttttt tttttttttt gttggctttg cgttaggatg
1381 ctctgatctg acatttgaca tgaacacaaa gttgctagat gctcttgttg acttccagca
1441 gatgggatgg gggaaacaca gcagttcttg gtaaagtcct ttgtaataat agtttgattt
1501 ttttatttcg agagaatctt tcattttcct atgtatgctt ttttcctttt ttgcccagtt
1561 tccttatcac ttgctgtaga tggcttattt tgcattcatg cagactatgt tgcaagtctg
1621 tttcatctag taaactgaaa attattgctt aatcaaactg ccgtttgtct tttatattta
1681 aggccttccc ccccttcct tatgagttct aacttagtaa tttcaaatgt gacctttat
1741 atctaagacc agtatagtaa acttagccca cagtggcaaa taatgagtaa tattgtaata
1801 tgttccagtt gcacctcagt atgttaaaca ggtaatgtaa gaagttctct gaaatgtcag
1861 caagtaagtt ctgaaacaca tcatgcatga gtaggaataa aacccaagtt ccccataacg
1921 tagataactt aatgctgcat aaaaatatga aagtgtaacc catgaaggac actttttctt
1981 tccactgcaa agttagccac tttgctgttt ttcctctttt ttaaactttg aaaatagact
2041 ctttccagaa attggagcaa taatggtgtt accacacaca gattaaataa tttgtagata
2101 ttttaagtga cttttgggca aaactggaat gtatactttt accttgtttc aaacacctaa
2161 gaccagtaat ttaaaaatta ctaaaaggtt tactttgttc attaataaaa catttaacaa
2221 ttcaaattat atgcaccttt tacctagttg aaaaaaatac acattcctgt tttcacatta
2281 tagcaactga ttaagctgaa gctgtaagtc atttttata gatgagtgat ccgcatctcc
2341 atcaattaga acactggaaa agatgtttta taaaagaggt atttaatttt gtttgtagga
2401 ttaactcatg caaataataa aaaagatatc ctgttggttc aatagtacac tgtctccttt
2461 aaggaaggaa gcgtgatgaa tgaatgatgt gtagacttga gggatgacta ttaaagggga
2521 cgtaggatga agagaaagaa cctacagatg acaatgaatg taaacttatt tttcttcatg
2581 tgtaagcagt gtgctcgctg gtgatatcca gatcctaaca agattacttg gttagctggt
2641 taggaccagt aactggattg cgaccactat gataatattt tgaaccaaat gttaatgctt
2701 gatgcagaat tgtaaagcag catctggttc ctatatagcc ttaaggatta attttagtga
2761 tcctcaagga attaaatagg gaatttcaga aatgtagact gcaaaggcag tatacaggaa
2821 aaggtggagt gggttttgtt tatgagggtg tctgaaaact aaaattgagc gggatatcat
2881 ggtatagttg gacagtattg gtccttcaca ctttggccat attgtataat ggagctttta
2941 ccaaagatgt atgagaagtg taagactata aaaaaatgaa ctattcaaag taaaactctt
3001 aacaaacatt ttacttaaag cagatgcaaa agggtattct catgtaggct cctgttggtg
3061 cagagggatt tttttgattt caggatacaa ctaaagtacg aagttctcag tttcacttta
```

FIG. 46 (cont'd)

```
3121 gtagaaagag ctctagaaat gaggctgata aacacatcta agaacactgg ttgctttcta
3181 aaatttccaa agctccacca taaatgtaat ttttagtgtt tcaaatgatt gcattttaaa
3241 gtatataaat atgggttatc caatatcaat gctatagtaa catcctgaaa caaaacaagc
3301 acaaaggtat aaatgcctaa actggaggaa acttgaaacc ctcatgttaa atcttaaatg
3361 tagtatttct aacttgtgaa gacagattgg taggcagcca tttttttgtg tcttaaaata
3421 actgggggca tagttaaaat tttatacatc aagtgattgc tattattgaa tgttgcaggt
3481 gagatgtggt tatttttagt ttatttgaaa tgtttgactg gaaagggggg agggggaagc
3541 aaatatttga aatttggaaa accctaaacc ttttggtaag aaattgtaat tttcacttaa
3601 aattttcttt aaggatataa gaggtttata attgatgtag ttaaattgaa caataaccat
3661 tggtgactgg agcaggtaat tatagcctgc agaaaaaatt atctaagaat tttaaaaata
3721 agatcctgaa gttgtttaat tgcatccatt tctgtattta tgtgaattta taaactgcag
3781 taagttttga atgaggttaa tcttgtttaa tataagtaaa tgagtctgta gactgtgatc
3841 tccccaaact aaaaagtaca gtacttggaa ttgtgttctt tatggttgta gtgttggtaa
3901 agcactaata tgcagaaaat aaaggaatta cacagtgca
```

FIG. 47

Human DNA sequence from clone RP1-278O22 on chromosome 20 Contains two novel genes, NTs 26161-26140.

```
26161 ttgtcactag aaggaggaag gaatgctgtg tggcaaggaa aggaattaat gtccacttga
26221 gatggatttg agaaggatgt ctgcaagcag aaataaaggg ttaaagggtg cttacattaa
26281 aaattttgat agctactgct ctcaaaattg tatcgcgatt tatattccca gtgccaacag
26341 tgtttgaaga gtctggctct ccagagcctg tagacactgg atattgtcag tgttttaaat
26401 ttcagcagat ctgatatcta aaaatggtat ctcactgttc taaactgttc tagtatggtg
26461 ttctacgtga acaccctttc atgtgtttag ctggcctttg catttctttt tttttttttt
26521 tgaactgcct atgcatatct tttggtcaaa attcaattga attgcccttt tttattgtta
26581 gagctgctac aaacattact gaaaaggcaa ctcagttgtg tgtgtgtgta tgcacacaca
26641 tatatattta taatacatat gttacttagg gtttgtacca gctctatgag ctccttgagg
26701 gtggcacctt gctgtaatac agcctgacac ctaatacgaa gtagaaatca gtgattattt
26761 atcacgcaaa taaagaaaca aataagtgaa cgaatgaatg agtcaatagt gttgactgcc
26821 ttgtattgtc ctaggcccaa gagacagtga aatatccctg ttcttgtata cttttctgta
26881 agtttctgga agtttctctg taaagcatct cagtaagctt ttctataggc tgtgagaaac
26941 gcatgagtca ggctaatagg aggcatataa ttttgaattg cttttcagaa atggccttca
27001 tattccttta cactcactca tcctgttgat aagagcagat ggcctactgc atgtgactca
27061 gactcaaaca cacacctccg ctcccttgaa gtgccagccc tggagctttg ttgaggctcg
27121 catctgccac gggagtcagc tagtacgttg cccagttcaa catccatcca ggatttcata
27181 ggaacttgag aatcattgtt tttggcttga atcctgggtt tgaggtttct tcgtgtagga
27241 atctgaaaaa aggatttgga aacgttgttg tctctaatcc caaagtatgt atctgggagg
27301 ctgccttcgc catcacccac ctaataactc aggctcccgg ggccatttcg ctcaagtgca
27361 ttcattcctt tggtagaatc aaaagaaact gatccaggtg acagagtacc tgggttctaa
27421 tcccagtttt gatgagcaag ttatttaccc cttacagccc cattttccct attctaaaat
27481 gatatggttg caactgacga tctccaagtc tccgtccaac tcaacaattc agagtggaat
27541 tctgaattct gctctgccac caacagcatg tcctcggagc tttgcctatt actcatgaga
27601 atgtcaacgt ctgggtaaat agatattttg gggtcagctc taaaaaaccc agaagtacgt
27661 attgtatgtt gattttggca cacggacaag cctgaacagg gctgtgtcaa gcctttttacc
27721 atgatagctg ccggaagaaa ggccaggcga agcagtctgg gtgagctgct tggaatgaag
27781 aggaccagcc cacatcccat ggcacagatg accttcagga gaagtggagg ggagcagcta
27841 atgtaaagaa atcattagca tctgtgttgg aaatggctta tgacactgtc tcaaagccac
27901 gttctcagac aacagggaaa gctgtaaata gatgcacaca gttatccaag catagcagag
27961 taaaactaaa ggaaagccaa attaaacagg ctcaaccaaa gttttgagtg aaagtgttga
28021 atattgctca tgccttcaga acgggaagct ctgtttagaa tactcacaat ggtgggtcct
28081 cttgaggtga ctacaggctg gtaggtcggt tctatcctcc ccctaggagc catctcagca
```

FIG. 48

Homo sapiens isolate PD047 mitochondrion, NTs 2041-4020.

```
2041 gttcaacttt aaatttgccc acagaaccct ctaaatcccc ttgtaaattt aactgttagt
2101 ccaaagagga acagctcttt ggacactagg aaaaaacctt gtagagagag taaaaaattt
2161 aacacccata gtaggcctaa aagcagccac caattaagaa agcgttcaag ctcaacaccc
2221 actacctaaa aaatcccaaa catataactg aactcctcac acccaattgg accaatctat
2281 caccctatag aagaactaat gttagtataa gtaacatgaa aacattctcc tccgcataag
2341 cctgcgtcag attaaaacac tgaactgaca attaacagcc caatatctac aatcaaccaa
2401 caagtcatta ttaccctcac tgtcaaccca acacaggcat gctcataagg aaaggttaaa
2461 aaaagtaaaa ggaactcggc aaatcttacc ccgcctgttt accaaaaaca tcacctctag
2521 catcaccagt attagaggca ccgcctgccc agtgacacat gtttaacggc cgcggtaccc
2581 taaccgtgca aaggtagcat aatcacttgt tccttaaata gggacctgta tgaatggctc
2641 cacgagggtt cagctgtctc ttacttttaa ccagtgaaat tgacctgccc gtgaagaggc
2701 gggcatgaca cagcaagacg agaagaccct atggagcttt aatttattaa tgcaaacagt
2761 acctaacaaa cccacaggtc ctaaactacc aaacctgcat taaaaatttc ggttggggcg
2821 acctcggagc agaacccaac ctccgagcag tacatgctaa gacttcacca gtcaaagcga
2881 actactatac tcaattgatc caataacttg accaacggaa caagttaccc tagggataac
2941 agcgcaatcc tattctagag tccatatcaa caatagggtt tacgacctcg atgttggatc
3001 aggacatccc gatggtgcag ccgctattaa aggttcgttt gttcaacgat taaagtccta
3061 cgtgatctga gttcagaccg gagtaatcca ggtcggtttc tatctacttc aaattcctcc
3121 ctgtacgaaa ggacaagaga aataaggcct acttcacaaa gcgccttccc ccgtaaatga
3181 tatcatctca acttagtatt atacccacac ccacccaaga acagggtttg ttaagatggc
3241 agagcccggt aatcgcataa aacttaaaac tttacagtca gaggttcaat tcctcttctt
3301 aacaacatac ccatggccaa cctcctactc ctcattgtac ccattctaat cgcaatggca
3361 ttcctaatgc ttaccgaacg aaaaattcta ggctatatac aactacgcaa aggccccaac
3421 gttgtaggcc cctacgggct actacaaccc ttcgctgacg ccataaaact cttcaccaaa
3481 gagcccctaa aacccgccac atctaccatc accctctaca tcaccgcccc gaccttagct
3541 ctcaccatcg ctcttctact atgaaccccc ctccccatac ccaacccccct ggtcaacctc
3601 aacctaggcc tcctatttat tctagccacc tctagcctag ccgtttactc aatcctctga
3661 tcagggtgag catcaaactc aaactacgcc ctgatcggcg cactgcgagc agtagcccaa
3721 acaatctcat atgaagtcac cctagccatc attctactat caacattact aataagtggc
3781 tcctttaacc tctccaccct tatcacaaca caagaacacc tctgattact cctgccatca
3841 tgacccttgg ccataatatg atttatctcc acactagcag agaccaaccg aacccccttc
3901 gaccttgccg aaggggagtc cgaactagtc tcaggcttca acatcgaata cgccgcaggc
3961 cccttcgccc tattcttcat agccgaatac acaaacatta ttataataaa caccctcacc
```

FIG. 49

Human DNA sequence from clone RP1-278O22 on chromosome 20 Contains two novel genes, NTs 25321-27300.

```
25321 ctggagaatc ccttgaaccc aggaggagga ggttgcagtg agcgatcctg ccacggcact
25381 ccagcagggg tgacaagaat gaaactctat ttcaaaataa agaaaaaaaa gaaaaaaaaa
25441 gaaaacccaa cctcaactag cttaagcaaa agcaaattta tgtggtgaaa gggtggatct
25501 ggttttagaa tcagttacca agggctcaag aagtgtcaca gggactgatc cccccacccc
25561 cccgtccccc atgtcgtgtc attctccagg tctttccttt tcattgccag gagctccagg
25621 tttctaccct cagaactcca aggccattgg aaaacagagg gcagttttct tagttgccca
25681 aggaaatgtt cccaaattgt atcaaaagcc cacctctagg ttaattattg tggctggagg
25741 atgtaatcca ttcataggtc agggctggcc aggtgtagtg gctcatgcct gtaatcccag
25801 cactttggga gactgagatg ggtgggtcac ttgaggtcag aagttcgaga ccagcctggc
25861 caacaggatg aaaccccgtc tctactaaaa atacaaaaat tagccaggca tggtggcggg
25921 cgcctgtaat cccagctgct cgggaggctg aggcaggaga atggattgaa cccaggaggt
25981 ggaggttgca gtgagcagag atcacgccac tgcactcaag cccaggcaac gaagcgagac
26041 tccttctcaa aaaaaaaaaa agagagaaac ataggctagg actaggcata tgccatgcct
26101 tgtgacataa actggacatg gggaagggga gtgattcccc agtgttagtt agccttgctc
26161 ttgtcactag aaggaggaag gaatgctgtg tggcaaggaa aggaattaat gtccacttga
26221 gatggatttg agaaggatgt ctgcaagcag aaataaaggg ttaaagggtg cttacattaa
26281 aaattttgat agctactgct ctcaaaattg tatcgcgatt tatattccca gtgccaacag
26341 tgtttgaaga gtctggctct ccagagcctg tagacactgg atattgtcag tgttttaaat
26401 ttcagcagat ctgatatcta aaaatggtat ctcactgttc taaactgttc tagtatggtg
26461 ttctacgtga acaccctttc atgtgtttag ctggcctttg catttctttt tttttttttt
26521 tgaactgcct atgcatatct tttggtcaaa attcaattga attgcccttt tttattgtta
26581 gagctgctac aaacattact gaaaaggcaa ctcagttgtg tgtgtgtgta tgcacacaca
26641 tatatattta taatacatat gttacttagg gtttgtacca gctctatgag ctccttgagg
26701 gtggcacctt gctgtaatac agcctgacac ctaatacgaa gtagaaatca gtgattattt
26761 atcacgcaaa taaagaaaca aataagtgaa cgaatgaatg agtcaatagt gttgactgcc
26821 ttgtattgtc ctaggcccaa gagacagtga aatatccctg ttcttgtata cttttctgta
26881 agtttctgga agtttctctg taaagcatct cagtaagctt ttctataggc tgtgagaaac
26941 gcatgagtca ggctaatagg aggcatataa ttttgaattg cttttcagaa atggccttca
27001 tattccttta cactcactca tcctgttgat aagagcagat ggcctactgc atgtgactca
27061 gactcaaaca cacacctccg ctcccttgaa gtgccagccc tggagctttg ttgaggctcg
27121 catctgccac gggagtcagc tagtacgttg cccagttcaa catccatcca ggatttcata
27181 ggaacttgag aatcattgtt tttggcttga atcctgggtt tgaggtttct tcgtgtagga
27241 atctgaaaaa aggatttgga aacgttgttg tctctaatcc caaagtatgt atctgggagg
```

FIG. 50

Human DNA sequence from clone RP3-523G1 on chromosome 6p22.3-24.1, NTs 34621-36600.

```
34621 attcatctgt gttattggga aatgatgtga acttaatttc tctttccctt ctaaaacttt
34681 gcttactgaa tggaaatgtt cctgagatct gtttatttgg ttctatattt atgtacctcc
34741 cttttaaaat agagaataca tgttaatgtt tctttgatga ctcagtgtgt attatcggta
34801 acagtccatt catgatgttg ccataccaca cagcataatt ttctatctgc ttctgattga
34861 ttcttcattc tcccttgatc tcagtttgtc atttaataca tctaagtttt tcactcaaca
34921 aatcaaatac tgatggagaa tctgctatac accaggcact gtgctgctag gagctgagga
34981 ttgaacgggg agaaacagga agctccctgc tctcatagtg cttcttagtt ggggagaaaa
35041 gacattcatg atataatcac ataaatacct atttttatat gtaaaaaatg ttgtcaaaga
35101 aaagaacggg gtgatgggaa cagttggaag aggtgtaaaa actccagaga agctgtggct
35161 cctagaaaga aggtaggttt taggactaga atggtgatag tgggccggaa gagagagagt
35221 gcattcgaaa gacactgagg agattgcatc agtaggactt ggtgacacat tagatgcaga
35281 ggaagaggga cagaaatgct tcaaggagga cttttaggca tctgtcttgg gtaactagat
35341 gatgccaatg gctgagatgg ggaattcttg ggtagatgag gtttggtggg atggtgattg
35401 ttataacttt gactttgaac gtgctgagtt caggtgacat tgtgataccc caaaggaggt
35461 gcagagtagg tagctggaga cacaggcccg aagatgatga gaggtctggc ctagaaacat
35521 ggatgcagga gtcatggatc catcaaggca ctgtgagttt ggatgagatc atctagcaga
35581 acacttaagt ggagaagcaa agtggtctag agactaagcc atgaggaact ccaacactta
35641 gaggcgtaga aagcaggtag aaagggaaca cctgaagact taggaaggag gggccagaaa
35701 gggatgatgg cacccgaaga cagtggtgtt caggaagcca agggaggaag gtatttagac
35761 aggaggggga gagcagaatt ggcaaagctg tggagaaagt gagatgagaa ctcctattaa
35821 aaacacacaa ctggtccaat gacatgggat ggcatggaaa tcactgatga ccaagcagga
35881 gacaggggtg gaccgcaggg gaaaaagagc aagctgaagc cagctaagga atgtcctcgg
35941 gccatctcct agcggaggcg gtagagccgt ggttgaaggt acaggaagtg gactgttagg
36001 gcccaggttc cccttaacca tgagacctga agcaagttac tttatttctc tagggctcaa
36061 ttttctcacc tgtaaaacaa gagtaacagt gctcacctac taggttgctg tgaggttctt
36121 tttctttttc tttttttttt ggagacagag tctcactctg tcacccaggc tggagtgcag
36181 tggtgcaatc ttggctcact gcaatctcca cctcccgggt tccagctatt ctcctgcctt
36241 agcctcctga gtggctggga ctacaggcgc ctgccaccac aactggctaa tttttgtatt
36301 tttagtagag atggggtttc accacgttgg ccagcctgga ctcaaactcc tgacctcagg
36361 tgatctgcct gcttcagcct cccaaagtgc tgggattaca ggcgtgagcc accacacctg
36421 gccttctgtg aggttcttaa catgtaagcc acttagccca gtggctgact catagtagtt
36481 gctgaataaa tgctaatttt atattaacac cctcataacc cattaaatca atatttattg
36541 agcatccatc tgccaggcac tgtactagat gctgacaaag acaccccaa caacaaataa
```

FIG. 51

Homo sapiens mitogen-activated protein kinase kinase kinase 5(MAP3K5), RefSeqGene on chromosome 6. NTs 222121-224100.

```
222121 tgagcctagg agtttgagat caccccaggc agtgtggcaa aaccgcatct ctacatgaaa
222181 aatacaaaaa taagtcaggc atggcagcat gtgcctgtgg tcctggctac tagggaggct
222241 gaggtgagag gatcaattga gcccaggagg tcaaggccac agtgagctga gattgcacca
222301 ctgcactctg gcctggggga cagagtgaga ccctgtctca aaaaaaaaaa aaaaaaatag
222361 tattgtatca atgttaattt cctggttttg ataatagtgc caaaggtata taaactgtta
222421 aggcaagagc aagtggctga aggctataca ggaactctct gcactatttt tgcaacttct
222481 ctgttatcct aaaattattt caaaataaaa agttaaaaaa aaagtgttta ggccgggcgc
222541 ggtggctcac gcctataatc ccagcacttt gggaggccga ggcgggcgga tcacgaggtc
222601 aggagatcaa gaccatcctg gctaacacag tgaaacccca tctctactaa agatacaaaa
222661 aattagccgg gcgaggtagc gggcgcctgt agtcccagct acgtgggagg ctgaggcagg
222721 agaatggcat gaaccccagg gggtggagcc tgcagtgagc cgagatcgtg ccactgcact
222781 ccagcctggg tgaaagagcg agactccttc tcaaaaaaaa aaaaaaaaaa aaaaagtgtt
222841 taatcttttt tccaaaagga gcacacagaa cagagagtac agtacaagtc ccttaagaat
222901 ttgtttttttc tcagactatt ttctcacttg tcatcaagaa tcagccttta gattattggc
222961 agcattagtc ctctagtaca gtctgcttgt gggtgaccag atggagtaat gctgagcaca
223021 gagactatga tggccgtgct aaggtaagag tattgataat gtaagcatac ttcctctatc
223081 aacaataatt gttaacagct gcttcaagca cttgatatta ccactagttg ttaactgaat
223141 caagcatgtg ctccaagttc acattaatgt gaattgaaca gcattgtgta cgtacgagga
223201 gcttcatgca agtgttatac actgcactca caagtattat gatcttacta agcattagaa
223261 atactctgtg ttaaagaagc ttggtctagg ccaagcgtgg tggctcatgc ctataatctc
223321 agcactttgg gaggccaagg caggcagatc acatgaggcc aggaatttga gaccagcctg
223381 gccaacatgg tgaaacccca tctctactaa aaatacaaat attagccagg tatgatggcg
223441 catgcctata atcctaacta ctcaggaggc cgaagcagaa gaatcacttg aacctgggag
223501 gcggaggttg cagtgagcca agatcatgcc actgcactcc agcctgggtg acagagtgag
223561 actctgtctc aaaaaaaaaa aaaagaaaga aaagaaaaag aaacttggtc tagttatttt
223621 ccttcctctg gggaagtaac catttgggtg ggaatagttt tgttgttgat cccatcttgc
223681 tggtttggaa acaatgcact ggctccactt ttccactcat gggctttaag gccccccttga
223741 gtcccagtct ttctcctgac acatggctgt ctcctgacag tcccctctgc tttacattgt
223801 tctcagaggg tcctgggcca tcgtttgagc ttcattcttt caaatacact tccctctttc
223861 tctatcaagc caaggctccc ctcccccaga actctgcata ggcccttcag cctccatgaa
223921 tcccttagtg agtgagtaaa ctaccactgg attcagtcac tgcaaatgta ctttatttac
223981 cccttagcac tcttactaca tgtatgtgtt agggttcttc aaagaaacag aaccaatagg
224041 atacatagag atatataaga gaagatttat aatgggaatt ggctcatgtg attatggagg
```

FIG. 52

Homo sapiens RAS p21 protein activator (GTPase activating protein) 1, mRNA (cDNA clone IMAGE:4733187), partial cds.

```
   1 agaatacgag gaggaagagg tggccatacc gttgaccgct cctccaacta accagtaagt
  61 taagactgct gttcaggaat ttgggaagct ggccccagaa aagaagtgga aatgaagggg
 121 tggtatcacg gaaaacttga cagaacgata gcagaagaac gcctcaggca ggcagggaag
 181 tctggcagtt atcttataag agagagtgat cggaggccag ggtcctttgt actttcattt
 241 cttagccaga tgaatgttgt caaccatttt aggattattg ctatgtgtgg agattactac
 301 attggtggaa gacgtttttc ttcactgtca gacctaatag gttattacag tcatgtttct
 361 tgtttgctta aaggagaaaa attactttac ccagttgcac caccagagcc agtagaagat
 421 agaaggcgtg tacgagctat tctaccttac acaaaagtac cagacactga tgaaataagt
 481 ttcttaaaag gagatatgtt cattgttcat aatgaattag aagatggatg gatgtgggtt
 541 acaaatttaa gaacagatga acaaggcctt attgttgaag acctagtaga agaggtgggc
 601 cgggaagaag atccacatga aggaaaaata tggttccatg ggaagatttc caaacaggaa
 661 gcttataatt tactaatgac agttggtcaa gtctgcagtt ttcttgtgag gccctcagat
 721 aatactcctg gcgattattc actttatttc cggaccaatg aaaatattca gcgatttaaa
 781 atatgtccaa cgccaaacaa tcagtttatg atgggaggcc ggtattataa cagcattggg
 841 gacatcatag atcactatcg aaaagaacag attgttgaag gatattatct taaggaacct
 901 gtaccaatgc aggatcaaga acaagtactc aatgacacag tggatggcaa ggaaatctat
 961 aataccatcc gtcgtaaaac aaaggatgcc ttttataaaa acattgttaa gaaaggttat
1021 cttctgaaag aggccaaaaa aaaaaaaaaa aaaaaaaaaa aaa
```

FIG. 53

Homo sapiens heat shock 90kDa protein 1 beta (HSPCB) mRNA, complete cds.

```
   1 agctctctcg agtcactccg gcgcagtgtt gggactgtct gggtatcgga aagcaagcct
  61 acgttgctca ctattacgta taatcctttt cttttcaaga tttttatttt agatgcctga
 121 ggaagtgcac catggagagg aggaggtgga gacttttgcc tttcaggcag aaattgccca
 181 actcatgtcc ctcatcatca ataccttcta ttccaacaag gagattttcc ttcgggagtt
 241 gatctctaat gcttctgatg ccttggacaa gattcgctat gagagcctga cagacccttc
 301 gaagttggac agtggtaaag agctgaaaat tgacatcatc cccaaccctc aggaacgtac
 361 cctgactttg gtagacacag gcattggcat gaccaaagct gatctcataa ataatttggg
 421 aaccattgcc aagtctggta ctaaagcatt catggaggct cttcaggctg gtgcagacat
 481 ctccatgatt gggcagtttg gtgttggctt ttattctgcc tacttggtgg cagagaaagt
 541 ggttgtgatc acaaagcaca acgatgatga acagtatgct tgggagtctt ctgctggagg
 601 ttccttcact gtgcgtgctg accatggtga gcccattggc aggggtacca aagtgatcct
 661 ccatcttaaa gaagatcaga cagagtacct agaagagagg cgggtcaaag aagtagtgaa
 721 gaagcattct cagttcatag gctatcccat caccctttat ttggagaagg aacgagagaa
 781 ggaaattagt gatgatgagg cagaggaaga gaaaggtgag aaagaagagg aagataaaga
 841 tgatgaagaa aaacccaaga tcgaagatgt gggttcagat gaggaggatg acagcggtaa
 901 ggataagaag aagaaaacta agaagatcaa agagaaatac attgatcagg aagaactaaa
 961 caagaccaag cctatttgga ccagaaaccc tgatgacatc acccaagagg agtatggaga
1021 attctacaag agcctcacta atgactggga agaccacttg gcagtcaagc acttttctgt
1081 agaaggtcag ttggaattca gggcattgct atttattcct cgtcgggctc cctttgacct
1141 ttttgagaac aagaagaaaa agaacaacat caaactctat gtccgccgtg tgttcatcat
1201 ggacagctgt gatgagttga taccagagta tctcaatttt atccgtggtg tggttgactc
1261 tgaggatctg cccctgaaca tctcccgaga aatgctccag cagagcaaaa tcttgaaagt
1321 cattcgcaaa aacattgtta agaagtgcct tgagctcttc tctgagctgg cagaagacaa
1381 ggagaattac aagaaattct atgaggcatt ctctaaaaat ctcaagcttg gaatccacga
1441 agactccact aaccgccgcc gcctgtctga gctgctgcgc tatcataccT cccagtctgg
1501 agatgagatg acatctctgt cagagtatgt ttctcgcatg aaggagacac agaagtccat
1561 ctattacatc actggtgaga gcaaagagca ggtggccaac tcagcttttg tggagcgagt
1621 gcggaaacgg ggcttcgagg tggtatatat gaccgagccc attgacgagt actgtgtgca
1681 gcagctcaag gaatttgatg ggaagagcct ggtctcagtt accaaggagg gtctggagct
1741 gcctgaggat gaggaggaga agaagaagat ggaagagagc aaggcaaagt ttgagaacct
1801 ctgcaagctc atgaaagaaa tcttagataa gaaggttgag aaggtgacaa tctccaatag
1861 acttgtgtct tcaccttgct gcattgtgac cagcacctac ggctggacag ccaatatgga
1921 gcggatcatg aaagcccagg cacttcggga caactccacc atgggctata tgatggccaa
1981 aaagcacctg gagatcaacc ctgaccaccc cattgtggag acgctgcggc agaaggctga
2041 ggccgacaag aatgataagg cagttaagga cctggtggtg ctgctgtttg aaaccgccct
2101 gctatcttct ggcttttccc ttgaggatcc ccagacccac tccaaccgca tctatcgcat
2161 gatcaagcta ggtctaggta ttgatgaaga tgaagtggca gcagaggaac ccaatgctgc
2221 agttcctgat gagatccccc ctctcgaggg cgatgaggat gcgtctcgca tggaagaagt
2281 cgattaggtt aggagttcat agttggaaaa cttgtgccct tgtatagtgt ccccatgggc
2341 tcccactgca gcctcgagtg cccctgtccc acctggctcc ccctgctggt gtctagtgtt
2401 tttttccctc tcctgtcctt gtgttgaagg cagtaaacta agggtgtcaa gccccattcc
2461 ctctctactc ttgacagcag gattggatgt tgtgtattgt ggtttatttt attttcttca
2521 ttttgttctg aaattaaagt atgcaaaata aagaatatgc cgtttttata cgaaaaaaaa
2581 aaaaaaaaaa aaaaaaaaa
```

FIG. 54

Homo sapiens ribosomal protein S6 (RPS6), mRNA.

```
  1 cctcttttcc gtggcgcctc ggaggcgttc agctgcttca agatgaagct gaacatctcc
 61 ttcccagcca ctggctgcca gaaactcatt gaagtggacg atgaacgcaa acttcgtact
121 ttctatgaga agcgtatggc cacagaagtt gctgctgacg ctctgggtga agaatggaag
181 ggttatgtgg tccgaatcag tggtgggaac gacaaacaag gtttccccat gaagcagggt
241 gtcttgaccc atggccgtgt ccgcctgcta ctgagtaagg ggcattcctg ttacagacca
301 aggagaactg gagaaagaaa gagaaaatca gttcgtggtt gcattgtgga tgcaaatctg
361 agcgttctca acttggttat tgtaaaaaaa ggagagaagg atattcctgg actgactgat
421 actacagtgc ctcgccgcct gggccccaaa agagctagca gaatccgcaa acttttcaat
481 ctctctaaag aagatgatgt ccgccagtat gttgtaagaa agcccttaaa taaagaaggt
541 aagaaaccta ggaccaaagc acccaagatt cagcgtcttg ttactccacg tgtcctgcag
601 cacaaacggc ggcgtattgc tctgaagaag cagcgtacca agaaaaataa agaagaggct
661 gcagaatatg ctaaactttt ggccaagaga atgaaggagg ctaaggagaa gcgccaggaa
721 caaattgcga agagacgcag actttcctct ctgcgagctt ctacttctaa gtctgaatcc
781 agtcagaaat aagatttttt gagtaacaaa taaataagat cagactctg
```

FIG. 55

Homo sapiens 3 BAC RP13-616I3 (Roswell Park Cancer Institute Human BAC Library) NTs 22921-24900.

```
22921 ttgatcttcc tgcctcagcc ttccaagtag ctgggactta aaggcgtgag ccaccacacc
22981 tgactaattt tcgtattttt tgtagagatg gggtttcgcc atgttgcccg ggctgttctc
23041 gaactcctga gctcaagcaa tctgcccacc tcagcctccc aaagcgctgg gattacaggc
23101 atgagccacc atcccagcca aaactataaa acttttagaa aagaacatag aagaaaatct
23161 ttgggtcctg ggggcaaaga gctctgagac ttgacatcaa aagcatgccg cataatagga
23221 aaatactaga ctttatttag gggttaagag tttagactct ggactctctc agccttggtt
23281 tcactagtta gctctatcac taactacatt gggcattgaa aattcctctg ttgtcccacg
23341 tggtgcatgg atgattgtag acgaggacac tgagatcctg aaggcagaag taatttctct
23401 aagcaacgtt gttggttggt ggcagagtct gggttacaac ccctggtttc ctgattccga
23461 gtccaagtga aatacttttg cccctgcagt agaccctgct acagaggata aaaaggcacg
23521 tcataggcta ggagaaaaat tttgcctacc acatatgtaa ccaaggacta gcagctagga
23581 catctgaaga attctcaaca ttcaacgggg tagaagaatg aacgattcaa tagaatatgg
23641 gcaaaagaca tgaagaggca ttttaccaaa catagggtgc tatggtccga atgtttgcat
23701 tctcctcaaa ttcctgtgtt gaaatcctaa cccccaaggt attggtatta ggaggcaggg
23761 gccctgggaa gtgattaggt cataaaggtg gagtcctcat ggatgggatt agtgtcttta
23821 taaaagagac ctttgccatg tgaggttaca gtgagaagac atctgtctat gaagaaagtg
23881 ggccctcacc aaacacagtc tgctggcact ttgcacttca actccccagc ttccagaact
23941 gtaaggaata taagtctgtt gttggtaagc cacccggtct atgatatttt gttatagcag
24001 cccaaacaga ctaagacagg tgacaaataa acatgaaaag atgttcaaca tcattagcca
24061 ttagggaaat gcagattaaa accacagcga aatatcatga tacagttttc agcatggcta
24121 aactagaaaa tagtgacacc accaaatgcc gacaaggctg tggggaaact gggttgttca
24181 gacactgcca ctggggctgt agcgtactat agccactttc ataaacagtt tgtcagtttc
24241 ttaaaaaact aaacctgcaa ctaccatatg acccagcaat tacacccctg ggcacctacc
24301 caagagaaat gaaaactcaa cgtttgcgca aaaacctgtg taggaatgtt caagcagctt
24361 tattcataat atgcccaaac aggaaacaac tcagctgtcc ttcagtaggt aaatagttaa
24421 gcaaattgtc atacccctgt gtcatggagc actacctagc aataacaagg agcaaattat
24481 tgatacataa caatctggat gaatctccag agaattatgt tgaatgaaaa aagccagccc
24541 ctgaaggata catactgtat gatgccattt acataacatt cttgaaattc taaaattaca
24601 gagatgggga acagatttgt ggttaaagat ggagccgggt gggaagaaag taggtgtggc
24661 tataaacggg taacatgaag gatccttgtg gtgatggaaa tttctgtatt tttattgtat
24721 ccgtgtcagt atcctggttg tgatatggta atacagtttt gcaagatact acccttaggg
24781 gaaatgaggt aagacctggc atctctctgt attatttctt aattgcatgt gaatctacaa
24841 ttatttcaaa ataaaaagta tgattgaagt aactctcagg aagcttagcc tactgtggat
```

USING PHAGE EPITOPES TO PROFILE THE IMMUNE RESPONSE

CROSS-REFERENCE

This application is a continuation of U.S. patent application Ser. No. 13/050,544, filed Mar. 17, 2011, which claims the benefit of U.S. provisional application Ser. No. 61/314,750, filed Mar. 17, 2010, which are incorporated herein by reference in their entireties.

BACKGROUND

It is desirable to improve cancer detection, prognostic prediction, monitoring, and therapeutic decisions. For example, when cancer is identified at the earliest stages, the probability of cure is very high and therefore diagnostic screening tests that can detect these early stages are crucial.

One example in which early detection can be beneficial is prostate cancer (PCA). PCA is a leading cause of male cancer-related death, second only to lung cancer (Abate-Shen and Shen, *Genes Dev* 14:2410 (2000); Ruijter et al., *Endocr Rev,* 20:22 (1999)). Prostate cancer is typically diagnosed with a digital rectal exam and/or prostate specific antigen (PSA) screening. An elevated serum PSA level can indicate the presence of PCA. PSA is used as a marker for prostate cancer because it is secreted only by prostate cells. A healthy prostate will produce a stable amount—typically below 4 nanograms per milliliter (ng/ml), or a PSA reading of "4" or less—whereas cancer cells produce escalating amounts that correspond with the severity of the cancer. A level between 4 and 10 ng/ml may raise a doctor's suspicion that a patient has prostate cancer, while amounts above 50 ng/ml may show that the tumor has spread elsewhere in the body.

The advent of prostate specific antigen (PSA) screening has led to earlier detection of PCA and significantly reduced PCA-associated fatalities. However, a major limitation of the serum PSA test is a lack of prostate cancer sensitivity and specificity, especially in the intermediate range of PSA detection (4-10 ng/ml). Elevated serum PSA levels are often detected in patients with non-malignant conditions such as benign prostatic hyperplasia (BPH) and prostatitis, and provide little information about the aggressiveness of the cancer detected. Coincident with increased serum PSA testing, there has been a dramatic increase in the number of prostate needle biopsies performed (Jacobsen et al., *JAMA* 274:1445 (1995)). This has resulted in a surge of equivocal prostate needle biopsies (Epstein and Potter *J. Urol.,* 166: 402 (2001)).

Thus, development of biomarkers to detect cancer, with improved sensitivity and specificity is advantageous.

SUMMARY

Provided herein are methods and compositions for screening for, or characterizing, a cancer in a subject. In one embodiment, an antibody profiling panel comprising: a plurality of polypeptide probes, wherein at least one of the polypeptide probes comprises a full-length or fragment of a protein encoded by a gene listed in Tables 1, 2, 3, or 4; and each of the probes in the plurality of polypeptide probes is capable of being specifically bound by an antibody, is disclosed herein. In another embodiment, an antibody profiling panel comprising: a plurality of polypeptide probes, wherein at least one of the polypeptide probes comprises a sequence listed in Tables 1, 2, 3, or 4 or a sequence encoded by a sequence listed in Tables 1, 2, 3, or 4; and each of the probes in the plurality of polypeptide probes is capable of being specifically bound by an antibody, is disclosed herein. In one embodiment the subject is a human. In one embodiment the antibody is an autoantibody. In another embodiment the antibody is a human autoantibody. In one embodiment the presence of a human autoantibody that binds to a polypeptide probe is indicative of cancer (e.g. an expression level for one or more autoantibodies is indicative of the presence, absence, or stage of the cancer). In another embodiment the quantity or level of a human autoantibody that binds to a polypeptide probe is indicative of cancer. In one embodiment the cancer is a prostate, lung, breast or colon cancer.

In one embodiment, the polypeptide probe comprises a polypeptide sequence selected from SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof. In another embodiment, the polypeptide probe comprises a polypeptide sequence encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof.

In yet another embodiment, the polypeptide probe comprises the full-length or a fragment of a protein that is encoded by DCHS1 (SEQ ID NO: 29), Centrosomal Protein (CEP 164) (SEQ ID NO: 30), KBTBD6 (SEQ ID NO: 31), RPS19 (SEQ ID NO: 32), RPL34 (SEQ ID NO: 33), Hemk1 (SEQ ID NO: 34), eIF4G1 (SEQ ID NO: 35), BMI1 (SEQ ID NO: 36), BRD2 (SEQ ID NO: 37), RP3-323M22 (Nucleolin) (SEQ ID NO: 38), SFRS14 (SEQ ID NO: 39), LOC388789 (SEQ ID NO: 40), RNA binding motif protein 6 (genomic DNA sequence) (SEQ ID NO: 41), BRMSL1 (SEQ ID NO: 42), NKX3-1 (SEQ ID NO: 43), RPSA (SEQ ID NO: 44), Cytochrome C Oxidase 5 subunit (SEQ ID NO: 45), FAM53B (SEQ ID NO: 46), a fragment of the UTR region of chromosome 11 (*Homo sapiens* genomic DNA, chromosome 11 clone: CTD-2579L12, NTs 149521-151500) (SEQ ID NO: 47), MAPKKK9 (SEQ ID NO: 48) cDNA clone XR_113641.1 (*Homo sapiens* hypothetical LOC643783, transcript variant 2 (LOC643783), partial miscRNA) (SEQ ID NO: 49), PSA (SEQ ID NO: 50), H2aa4 (SEQ ID NO: 51). UBE2I (SEQ ID NO: 52), TIMP2 (SEQ ID NO: 53), WDR77 (SEQ ID NO: 54), a fragment of Deaminase Domain Cont 1 (Human DNA sequence from clone RP1-20N2 on chromosome 6q24 Contains the gene for a novel protein similar to yeast and bacterial cytosine deaminase, NTs 48121-50100) (SEQ ID NO: 55), Lamin A/C (SEQ ID NO: 85), Lsm3 (SEQ ID NO: 86), a fragment of cDNA clone Chromosome 19, which encompasses the nucleic acid sequence for DAZ associated protein (*Homo sapiens* chromosome 19 clone CTB-25B13, NTs 20521-22500) (SEQ ID NO: 87), ADAM metallopetidase domain 9 (SEQ ID NO: 88), AZGP1 (SEQ ID NO: 89), Desmocolin 3 (SEQ ID NO: 90), PERP (SEQ ID NO: 91), Chromosome 3 UTR region ropporin/RhoEGF (*Homo sapiens* 3 BAC RP11-783D3 (Roswell Park Cancer Institute Human BAC Library) NTs 178621-180600) (SEQ ID NO: 92), Cox5a (SEQ ID NO: 93), a Mitochondrion sequence (*Homo sapiens* isolate PD047 mitochondrion, NTs 4801-6780) (SEQ ID NO: 94), MYH9 (SEQ ID NO: 95), ASND1 (SEQ ID NO: 96), Cathepsin F (SEQ ID NO: 97), Mastermind-like 2 (*Homo sapiens* genomic DNA, chromosome 11q clone:

RP11-822I2, NTs 157801-159780) (SEQ ID NO: 98), CSNK2A2 (SEQ ID NO: 99), AURKAIP1 (SEQ ID NO: 100), a fragment of Chromosome 4 (*Homo sapiens* BAC clone RP11-327O17 from 4, NTs 107401-109380) (SEQ ID NO: 101), ARF6 (SEQ ID NO: 102), JAG1 (Human DNA sequence from clone RP1-278O22 on chromosome 20 Contains two novel genes, NTs 26161-26140) (SEQ ID NO: 103), a Mitochondrion sequence (*Homo sapiens* isolate PD047 mitochondrion, NTs 2041-4020) (SEQ ID NO: 104), a fragment of Chromosome 20 (Human DNA sequence from clone RP1-278O22 on chromosome 20 Contains two novel genes, NTs 25321-27300) (SEQ ID NO:105), a fragment of Chromosome 6 UTR region (Human DNA sequence from clone RP3-523G1 on chromosome 6p22.3-24.1, NTs 34621-36600) (SEQ ID NO: 106), a fragment of MAPKKK5 (SEQ ID NO: 107), RASA1 (SEQ ID NO: 108), Hsp90b (SEQ ID NO: 109), ribosomal protein S6 (RPS6) (SEQ ID NO: 110), or a fragment of *Homo sapiens* chromosome 3 (*Homo sapiens* 3 BAC RP13-616I3 (Roswell Park Cancer Institute Human BAC Library) NTs 22921-24900) (SEQ ID NO: 111).

In one embodiment, the antibody profiling panel comprises a plurality of polypeptide probes, wherein at least one of the polypeptide probes comprises a full-length or fragment of a protein listed in Table 1, or a polypeptide sequence selected from SEQ ID NO: 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, or 141, and each of said probes in said plurality of polypeptide probes is capable of being specifically bound by an antibody. In one embodiment, one or more of the polypeptide probes can comprise SEQ ID NO: 1, 2, 3, 4, 5, 6, or 7. In another embodiment, one or more of the polypeptide probes can comprise a polypeptide encoded by SEQ ID NO: 15, 16, 17, 18, 19, 20, or 21. In one embodiment, the antibody profiling panel can further comprise a full-length or fragment of a protein listed in Tables 2, 3, or 4. In another embodiment, the antibody profiling panel, one of the polypeptide probes can comprise SEQ ID NO: 8, 9, 10, 11, 12, 13, or 14. In another embodiment, one or more of the polypeptide probes can comprise a polypeptide encoded by SEQ ID NO: 22, 23, 24, 25, 26, 27, or 28. In one embodiment the antibody is an autoantibody. In another embodiment the antibody is a human autoantibody. In one embodiment the presence of a human autoantibody that binds to a polypeptide probe is indicative of cancer (e.g. an expression level for one or more autoantibodies is indicative of the presence, absence, or stage of the cancer). In another embodiment the quantity or level of a human autoantibody that binds to a polypeptide probe is indicative of cancer. In one embodiment the cancer is a prostate, lung, breast or colon cancer.

In one embodiment, the plurality of probes comprise a polypeptide probe comprising a full-length or fragment of a protein encoded by CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, Deaminase Domain, FAM53B, 5'UTR BMI1, RP3-323M22, or LOC388789. In one embodiment, the polypeptide probe comprises SEQ ID NO: 2, 5, 9, 11, 14, 56, 57, 58, 59, 60, 61, 62, 63, 64, 65, 66, 67, 68, 69, or a fragment thereof. In another embodiment, the polypeptide probe comprises a polypeptide sequence encoded by SEQ ID NO: 16, 19, 70, 72, 73, 74, 76, 77, 78, 79, 80, 81, 82, 83, 84, or a fragment thereof.

In one embodiment, the plurality of probes comprise a polypeptide probe comprising a full-length or fragment of a protein encoded by CEP164, RPL34, BRMSL1, NKX31, RPSA, Cytochrome C oxidase 5 Subunit, UTR-region of chromosome 11, MAPKKK9, cDNA clone XR_113641.1, PSA, H2aa4, UBE2I, TIMP2, WDR77, or Deaminase Domain. In one embodiment, the plurality of probes comprise a polypeptide probe comprising a polypeptide sequence selected from SEQ ID NOs. 2, 5, 56, 57, 58, 59, 61, 62, 63, 64, 65, 66, 67, 68, or 69. In one embodiment, the plurality of probes comprises a polypeptide probe comprising a polypeptide sequence encoded by SEQ ID NO: 16, 19, 70, 72, 73, 74, 76, 77, 78, 79, 80, 81, 82, 83, or 84.

In one embodiment, the plurality of probes comprise a polypeptide probe comprising a full-length or fragment of a protein encoded by FAM53B, 5'UTR BMI1, RP3-323M22, or LOC388789. In one embodiment, the plurality of probes comprise a polypeptide probe comprising a polypeptide sequence selected from SEQ ID NO: 9, 11, 14, or 60. In one embodiment, the plurality of probes comprises a polypeptide probe comprising a polypeptide sequence encoded by SEQ ID NO: 23, 25, 28, 71, or 75.

In another embodiment, an antibody profiling panel comprising: a plurality of polypeptide probes, wherein at least one of the polypeptide probes comprises a full-length or fragment of a protein that is DCHS1, CEP164, KBTBD6, RPS19, RPL34, RNA binding protein 6, or Hemk1; and each of the probes in the plurality of polypeptide probes is capable of being specifically bound by an antibody, is disclosed herein. In another embodiment, the plurality of probes further comprise a polypeptide probe comprising a full-length or fragment of a protein encoded by eIF4G1, 5'UTR BMI1, BRD2, RP3-323M22, SFRS14, or LOC388789. In one embodiment, the polypeptide probe comprises a sequence listed in Table 1 or 2, such as SEQ ID NO: 1, 2, 3, 4, 5, 6, 7, 8, 9, 10, 11, 12, 13, 14, or a fragment thereof. In one embodiment the antibody is an autoantibody. In another embodiment the antibody is a human autoantibody. In one embodiment the presence of a human autoantibody that binds to a polypeptide probe is indicative of cancer (e.g. an expression level for one or more autoantibodies is indicative of the presence, absence, or stage of the cancer). In another embodiment the quantity or level of a human autoantibody that binds to a polypeptide probe is indicative of cancer. In one embodiment the cancer is a prostate, lung, breast or colon cancer.

In another embodiment, one or more of the probes is displayed by a phage. In one embodiment, the one or more probes is attached to a substrate, such as attached via a phage. In another embodiment, the substrate is an array. In yet another embodiment, the panel comprises at least 2, 3, 4, 5, 6, 7, 8, 9, or 10 different probes. In one embodiment, the panel characterizes a cancer, such as prostate cancer, with at least 80% sensitivity and specificity. In another embodiment, the panel screens for a cancer, such as prostate cancer, with at least 80% sensitivity and specificity.

Also provided herein is a method of characterizing or screening a subject for a cancer, such as prostate cancer, lung cancer, breast cancer or colon cancer. In one embodiment, the method comprises detecting in a sample obtained from a subject a presence or level of one or more antibodies to one or more polypeptide probes comprising a full-length or a fragment of a protein encoded by DCHS1, CEP164, KBTBD6, RPS19, RPL34, SFRS14, RNA binding protein 6, or Hemk1; and characterizing or identifying, the prostate cancer based on a presence or level of the one or more antibodies. In one embodiment, the method further comprises detecting a presence, absence or level of one or more antibodies to one or more polypeptide probe comprising a full-length or a fragment of a protein encoded by eIF4G1, 5'UTR BMI1, BRD2, RP3-323M22, SFRS14, or LOC388789. In one embodiment the antibody is an autoantibody. In another embodiment the antibody is a human autoantibody.

In another embodiment, the method comprises detecting in a sample obtained from a subject a presence or level of one or more antibodies to one or more polypeptide probes comprising a full-length or a fragment of a protein encoded by CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, or Deaminase Domain; and characterizing the prostate cancer based on a presence or level of the one or more antibodies. In one embodiment, the method further comprises detecting a presence, absence or level of one or more antibodies to one or more polypeptide probe comprising a full-length or a fragment of a protein encoded by FAM53B, 5'UTR BMI1, RP3-323M22, or LOC388789. In one embodiment the subject is a human. In one embodiment the antibody is an autoantibody. In another embodiment the antibody is a human autoantibody. In one embodiment the presence of a human autoantibody that binds to a polypeptide probe is indicative of cancer (e.g. an expression level for one or more autoantibodies is indicative of the presence, absence, or stage of the cancer). In another embodiment the quantity or level of a human autoantibody that binds to a polypeptide probe is indicative of cancer. In one embodiment the cancer is a prostate, lung, breast or colon cancer.

Also provided herein is a method of obtaining a biopsy, wherein a determination of whether a biopsy should be obtained is based on detecting an expression level for an antibody. In one embodiment, a subject suspected of having cancer based on an expression level of an antibody is recommended to have a biopsy obtained. In another embodiment, a biological sample is obtained from a subject with a PSA level of greater than about 2.5 ng/ml, and the sample is contacted with one or more probes for an antibody, and based on the expression level of an antibody, a biopsy is obtained or recommended for the subject. In one embodiment, the subject has a PSA level between about 2.5 ng/mL and about 10 ng/mL. In one embodiment the subject is a human. In one embodiment the antibody is an autoantibody. In another embodiment the antibody is a human autoantibody.

In one embodiment, the method further comprises contacting a biological sample obtained from the subject with one or more probes for a second antibody when the biopsy provides a positive result for a cancer, such as prostate cancer, and based on the expression level of the second antibody, a prognosis or theranosis is provided. In one embodiment the subject is a human. In one embodiment the second antibody is an autoantibody. In another embodiment the second antibody is a human autoantibody.

Also provided herein is a method of characterizing, identifying, or screening for a cancer in a subject. In one embodiment, the method comprises detecting an expression level for one or more antibodies, wherein the expression level of the one or more antibodies is indicative of the presence, absence, or stage of the cancer. In another embodiment, the indication is whether the cancer is aggressive or indolent. In one embodiment, the method of identifying a cancer as aggressive or indolent comprises: obtaining a positive biopsy result for cancer from the subject; contacting a biological sample obtained from the subject with one or more probes for an antibody; detecting an expression level for the antibody; and characterizing or identifying the cancer as aggressive or indolent based on the expression level of the antibody. In one embodiment the subject is a human. In one embodiment the antibody is an autoantibody. In another embodiment the antibody is a human autoantibody. In one embodiment the presence of a human autoantibody that binds to a polypeptide probe is indicative of cancer (e.g. an expression level for one or more autoantibodies is indicative of the presence, absence, or stage of the cancer). In another embodiment the quantity or level of a human autoantibody that binds to a polypeptide probe is indicative of cancer. In one embodiment the cancer is a prostate, lung, breast or colon cancer.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 2 lists the nucleic acid sequence for DCHS1 (SEQ ID NO: 29).

FIG. 3 lists the nucleic acid sequence for Centrosomal Protein (CEP 164) (SEQ ID NO: 30).

FIG. 4 lists the nucleic acid sequence for KBTBD6 (SEQ ID NO: 31).

FIG. 5 lists the nucleic acid sequence for RPS19 (SEQ ID NO: 32).

FIG. 6 lists the nucleic acid sequence for RPL34 (SEQ ID NO: 33).

FIG. 7 lists the nucleic acid sequence for Hemk1 (SEQ ID NO: 34).

FIG. 8 lists the nucleic acid sequence for eIF4G1 (SEQ ID NO: 35).

FIG. 9 lists the nucleic acid sequence for BMI1 (SEQ ID NO: 36).

FIG. 10 lists the nucleic acid sequence for BRD2 (SEQ ID NO: 37).

FIG. 11 lists the nucleic acid sequence for RP3-323M22 (Nucleolin) (SEQ ID NO: 38).

FIG. 12 lists the nucleic acid sequence for SFRS14 (SEQ ID NO: 39).

FIG. 13 lists the nucleic acid sequence for LOC388789 (SEQ ID NO: 40).

FIG. 14 lists the nucleic acid sequence for RNA binding motif protein 6 (genomic DNA sequence) (SEQ ID NO: 41).

FIG. 15 lists the nucleic acid sequence for BRMSL1 (SEQ ID NO: 42).

FIG. 16 lists the nucleic acid sequence for NKX3-1 (SEQ ID NO: 43).

FIG. 17 lists the nucleic acid sequence for RPSA (SEQ ID NO: 44).

FIG. 18 lists the nucleic acid sequence for Cytochrome C Oxidase 5 subunit (SEQ ID NO: 45).

FIG. 19 lists the nucleic acid sequence for FAM53B (SEQ ID NO: 46).

FIG. 20 lists the nucleic acid sequence for a fragment of the UTR region of chromosome 11 (*Homo sapiens* genomic DNA, chromosome 11 clone: CTD-2579L12, NTs 149521-151500) (SEQ ID NO: 47).

FIG. 21 lists the nucleic acid sequence for MAPKKK9 (SEQ ID NO: 48).

FIG. 22 lists the nucleic acid sequence for cDNA clone XR_113641.1 (*Homo sapiens* hypothetical LOC643783, transcript variant 2 (LOC643783), partial miscRNA) (SEQ ID NO: 49).

FIG. 23 lists the nucleic acid sequence for PSA (SEQ ID NO: 50).

FIG. 24 lists the nucleic acid sequence for H2aa4 (SEQ ID NO: 51).

FIG. 25 lists the nucleic acid sequence for UBE2I (SEQ ID NO: 52).

FIG. 26 lists the nucleic acid sequence for TIMP2 (SEQ ID NO: 53).

FIG. 27 lists the nucleic acid sequence for WDR77 (SEQ ID NO: 54).

FIG. 28 lists the nucleic acid sequence for a fragment of Deaminase Domain Cont 1 (Human DNA sequence from clone RP1-20N2 on chromosome 6q24 Contains the gene for a novel protein similar to yeast and bacterial cytosine deaminase, NTs 48121-50100) (SEQ ID NO: 55).

FIG. 29 lists the nucleic acid sequence for Lamin A/C (SEQ ID NO: 85).

FIG. 30 lists the nucleic acid sequence Lsm3 (SEQ ID NO: 86).

FIG. 31 lists the nucleic acid sequence for a fragment of cDNA clone Chromosome 19, which encompasses the nucleic acid sequence for DAZ associated protein (*Homo sapiens* chromosome 19 clone CTB-25B13, NTs 20521-22500) (SEQ ID NO: 87).

FIG. 32 lists the nucleic acid sequence for ADAM metallopetidase domain 9 (SEQ ID NO: 88).

FIG. 33 lists the nucleic acid sequence for AZGP1 (SEQ ID NO: 89).

FIG. 34 lists the nucleic acid sequence for Desmocolin 3 (SEQ ID NO: 90).

FIG. 35 lists the nucleic acid sequence for PERP (SEQ ID NO: 91).

FIG. 36 lists the nucleic acid sequence for Chromosome 3 UTR region ropporin/RhoEGF (*Homo sapiens* 3 BAC RP11-783D3 (Roswell Park Cancer Institute Human BAC Library) NTs 178621-180600) (SEQ ID NO: 92).

FIG. 37 lists the nucleic acid sequence for Cox5a (SEQ ID NO: 93).

FIG. 38 lists the nucleic acid sequence for a Mitochondrion sequence (*Homo sapiens* isolate PD047 mitochondrion, NTs 4801-6780) (SEQ ID NO: 94).

FIG. 39 lists the nucleic acid sequence for MYH9 (SEQ ID NO: 95).

FIG. 40 lists the nucleic acid sequence for ASND1 (SEQ ID NO: 96).

FIG. 41 lists the nucleic acid sequence for Cathepsin F (SEQ ID NO: 97).

FIG. 42 lists the nucleic acid sequence for Mastermind-like 2 (*Homo sapiens* genomic DNA, chromosome 11q clone:RP11-822I2, NTs 157801-159780) (SEQ ID NO: 98).

FIG. 43 lists the nucleic acid sequence for CSNK2A2 (SEQ ID NO: 99).

FIG. 44 lists the nucleic acid sequence for AURKAIP1 (SEQ ID NO: 100).

FIG. 45 lists the nucleic acid sequence for a fragment of Chromosome 4 (*Homo sapiens* BAC clone RP11-327O17 from 4, NTs 107401-109380) (SEQ ID NO: 101).

FIG. 46 lists the nucleic acid sequence for ARF6 (SEQ ID NO: 102).

FIG. 47 lists the nucleic acid sequence for JAG1 (Human DNA sequence from clone RP1-278O22 on chromosome 20 Contains two novel genes, NTs 26161-26140) (SEQ ID NO: 103).

FIG. 48 lists the nucleic acid sequence for a Mitochondrion sequence (*Homo sapiens* isolate PD047 mitochondrion, NTs 2041-4020) (SEQ ID NO: 104).

FIG. 49 lists the nucleic acid sequence for a fragment of Chromosome 20 (Human DNA sequence from clone RP1-278O22 on chromosome 20 Contains two novel genes, NTs 25321-27300) (SEQ ID NO:105).

FIG. 50 lists the nucleic acid sequence for a fragment of Chromosome 6 UTR region (Human DNA sequence from clone RP3-523G1 on chromosome 6p22.3-24.1, NTs 34621-36600) (SEQ ID NO: 106).

FIG. 51 lists the nucleic acid sequence for a fragment of MAPKKK5 (SEQ ID NO: 107).

FIG. 52 lists the nucleic acid sequence for RASA1 (SEQ ID NO: 108).

FIG. 53 lists the nucleic acid sequence for Hsp90b (SEQ ID NO: 109).

FIG. 54 lists the nucleic acid sequence for ribosomal protein S6 (RPS6) (SEQ ID NO: 110).

FIG. 55 lists the nucleic acid sequence for a fragment of *Homo sapiens* chromosome 3 (*Homo sapiens* 3 BAC RP13-616I3 (Roswell Park Cancer Institute Human BAC Library) NTs 22921-24900) (SEQ ID NO: 111).

DETAILED DESCRIPTION

Figure 1:
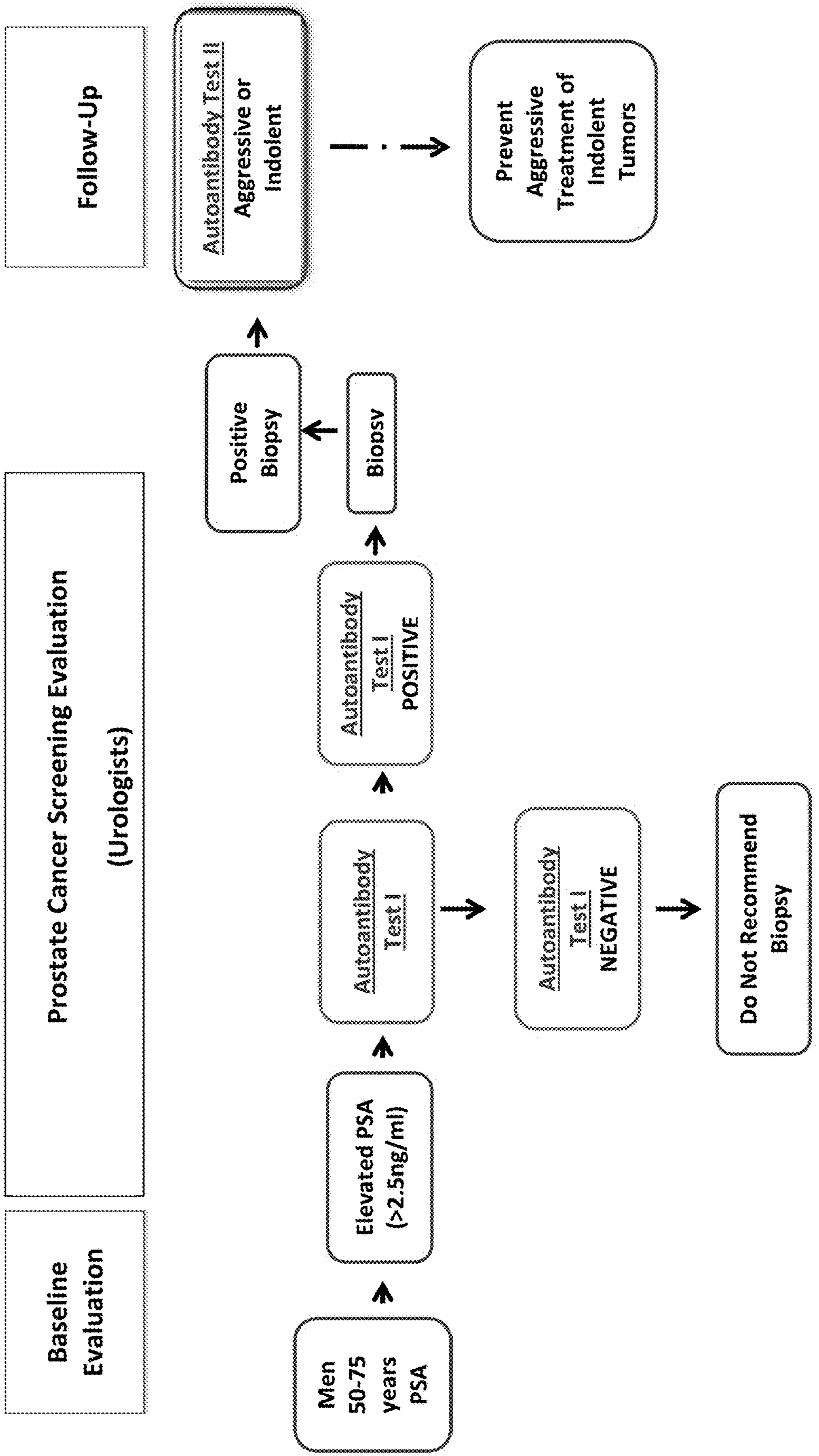
FIG. 1 is a schematic depicting detecting in a sample from a subject with PSA levels greater than 2.5 ng/mL the expression of one or more autoantibodies ("Autoantibody Test I"). If the result of the Autoantibody Test I is negative, a biopsy is not recommended to be obtained from the subject for further analysis. If result of the Autoantibody Test II is positive, then a biopsy is obtained. If the biopsy is positive for prostate cancer, expression of one or more autoantibodies is detected from a sample from the subject to characterize the cancer as aggressive or indolent, and a prognosis or theranosis provided.

The compositions and methods of the present disclosure relate to compositions and methods for characterizing a cancer or screening for a cancer. Provided herein are tests which can be used to analyze a presence or absence of an antibody from a subject, such as a subject being tested or screened for a cancer. In one embodiment, an antibody is an autoantibody. In another embodiment, the test comprises a single antigen, thus detecting only an antibody that binds to that antigen. In another embodiment, a panel of antigens is constructed such that the panel tests for a presence of one or more antibodies which specifically bind to two or more antigens derived from proteins associated with a specific cancer, such as lung cancer, prostate cancer, or ovarian cancer. By detecting an antibody to a protein associated with a disease state, the compositions and methods provided herein allow for the characterization of a cancer.

A cancer is characterized for a subject using a composition or method disclosed herein. In one embodiment, a subject is an individual or patient. In one embodiment, a subject is a human. In another embodiment, a subject is a cancer patient. In one embodiment, a subject exhibits no symptom of cancer, such as no symptoms of prostate cancer. In another embodiment, a subject has no detectable symptom of cancer, such as no detectable symptoms for prostate cancer. In yet another embodiment, a subject exhibits a symptom of cancer, such as a symptom for prostate cancer. In one embodiment, a subject is a human. In another embodiment, a subject is an individual. In yet another embodiment, a subject is a patient, such as a cancer patient.

Characterizing a cancer, or screening for a cancer, can include detecting the cancer (including pre-symptomatic early stage detecting), determining the prognosis, diagnosis, or theranosis of the cancer, or determining the stage or progression of the cancer. In one embodiment, a prognosis is predicting or giving a likelihood of outcome of a disease or condition, such as an extent of malignancy of a cancer, a likelihood of survival, or expected life expectancy, such as in an individual with prostate cancer. In another embodiment, a prognosis is a prediction or likelihood analysis of cancer progression, cancer recurrence, or metastatic spread or relapse.

In one embodiment, the diagnosis is prediction or likelihood an individual or subject has a disease or condition, such as prostate cancer. In one embodiment, the individual is an asymptomatic individual. In another embodiment, the individual is a symptomatic individual.

In one embodiment, a theranosis is a therapy selected based on an outcome of determining a binding of one or more antibodies from a sample from a subject to an antigen or polypeptide probe as described herein. In one embodiment, a theranosis is identifying an appropriate treatment or treatment efficacy for a cancer. In one embodiment, a theranosis is modifying a treatment. In another embodiment, a theranosis is selecting a treatment regimen. In yet another embodiment, a theranosis is discontinuing or not selecting a particular treatment regimen. In one embodiment a treatment regimen or therapeutic agent is selected based on the presence or absence of an autoantibody that binds to polypeptide probes described herein. In one embodiment the autoantibody is a human autoantibody. In one embodiment a treatment regimen or therapeutic agent is excluded based on the presence or absence of an autoantibody that binds to polypeptide probes described herein. In one embodiment the autoantibody is a human autoantibody.

In yet another embodiment, characterizing or screening for a cancer is detecting the cancer, such as pre-symptomatic early stage detecting. In one embodiment, characterizing a cancer is determining the stage or progression of the cancer, such as early-stage, late-stage or advanced stage of cancer. Characterizing or screening for a cancer can also be determining the likelihood or possibility an individual has a cancer. Characterizing or screening for a cancer can also be identification of a cancer, such as determining whether expression of one or more antibodies is indicative of the cancer.

In one embodiment, an antigen panel is used to detect a presence of one or more antibodies to one or more proteins, antigens, mimotopes, or epitopes. In one embodiment, one or more polypeptide probes described herein is a protein or fragment thereof. In another embodiment, one or more polypeptide probes described herein comprises an antigen, mimotope, or epitope. A "mimotope" can mimic the epitope of a protein or peptide. In one embodiment, the mimotope is structurally similar to an antigen or epitope of an expressed protein, but is unrelated or weakly related at the protein sequence level.

In one embodiment, the antigen panel comprises one or more polypeptide probes comprising a polypeptide sequence selected from SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof. In another embodiment, the antigen panel comprises one or more polypeptide probes comprising a sequence encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof. In yet another embodiment, the polypeptide probe comprises the full-length or a fragment of a protein that is encoded by SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

In one embodiment, the antigen panel comprises one or more polypeptide probes derived from one or more proteins encoded by one or more genes selected from: CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, Deaminase Domain, FAM53B, 5'UTR BMI1, RP3-323M22, or LOC388789. In one embodiment, detection of one or more antibodies is used to detect a presence of prostate cancer in a subject.

In one embodiment, the antigen panel comprises one or more polypeptide probes derived from one or more proteins encoded by one or more genes selected from: DCHS1, CEP164, KBTBD6, RPS19, RPL34, RNA binding protein 6, Hemk1, eIF4G1, 5'UTR BMI1, BRD2, RP3-323M22, SFRS14, and LOC388789. In one embodiment, detection of one or more antibodies is used to detect a presence of prostate cancer in a subject.

A cancer can also be characterized by determining a presence or absence, or level, of one or more antibodies in a sample. In one embodiment, a sample is obtained from a subject. The subject can be a mammal, including, but not limited to, humans, non-human primates, rodents, and the like. In another embodiment, a sample is a biological fluid. The biological fluid can be, but not limited to, peripheral blood, sera, or plasma. The sample can be ascites, urine, cerebrospinal fluid (CSF), sputum, saliva, bone marrow, synovial fluid, aqueous humor, amniotic fluid, cerumen, breast milk, bronchioalveolar lavage fluid, semen, prostatic fluid, cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, or bronchopulmonary aspirates.

In one embodiment, the level, presence, or absence of an antibody can be determined by detecting the binding of one or more antibodies to a polypeptide probe. In one embodiment, an antibody is an autoantibody. An autoantibody refers to an antibody produced by a host (with or without immunization) and directed to a host antigen (such as a tumor antigen). Tumor-associated antigens recognized by humoral effectors of the immune system are an attractive target for diagnostic and therapeutic approaches to human cancer.

The binding of an antibody with a polypeptide probe can be specific, such that the interaction of the autoantibody with the polypeptide probe is dependent upon a presence of a particular structure (i.e., the antigenic determinant or epitope) of the polypeptide probe. Antigenic determinates or epitopes can comprise amino acids in linear or non-linear sequence in a polypeptide probe and can also comprise one or more amino acids which are in proximity to each other via protein folding (e.g., conformational epitopes). Thus, a single polypeptide or protein can potentially be bound by multiple antibodies which recognize different epitopes. In some instances, known epitopes of a particular polypeptide can be used as a probe to detect for a presence, absence or level of autoantibodies which bind a particular epitope The polypeptide probe can be an antigen identified through serologic identification of antigens, for example by recombinant expression cloning (SEREX), such as described by Kim et al., *Biotech. Lett.* (2004); 26: 585-588. Generally, in this method, an antigen can be identified by screening expression cDNA libraries from human solid tumors with sera of autologous patients. This type of screening of a cDNA expression library by conventional methods typically requires the preparation of a large number of membrane filters blotted with bacteriophage plaques that are then searched with a specific probe. In the case of the SEREX experiments, the screening is performed using sera from cancer patients, which can be in very limited quantities.

A polypeptide probe for detecting an antibody can also be identified by phage-display technology, which can be based on the insertion of foreign nucleotide sequences into genes encoding for various capsid proteins of T7 phage, resulting in a heterogeneous mixture of phages, each displaying the different peptide sequence encoded by a corresponding insert. A physical link between a displayed fusion protein and DNA encoded for it make this phage target selectable. The phage target can express or display a polypeptide probe, which can be used to detect antibodies that are produced by a subject, or autoantibodies, which can then be used to detect or characterize a cancer. The polypeptide probe can be displayed by a phage and used to detect an antibody from a sample obtained from a subject. In one embodiment, an antibody is an autoantibody.

Polypeptide Probes

Provided herein is a composition and method for detecting one or more antibodies in a sample using one or more polypeptide probes. Polypeptide is used in its broadest sense and can include a sequence of subunit amino acids, amino acid analogs, or peptidomimetics. The subunits can be linked by peptide bonds. The polypeptides can be naturally occurring, processed forms of naturally occurring polypeptides (such as by enzymatic digestion), chemically synthesized or recombinantly expressed. The polypeptides for use in the methods of the present invention can be chemically synthesized using standard techniques. The polypeptides can comprise D-amino acids (which are resistant to L-amino acid-specific proteases), a combination of D- and L-amino acids, β amino acids, or various other designer or non-naturally occurring amino acids (e.g., β-methyl amino acids, Cα-methyl amino acids, and Nα-methyl amino acids, etc.) to convey special properties. Synthetic amino acids can include ornithine for lysine, and norleucine for leucine or isoleucine. In addition, the polypeptides can have peptidomimetic bonds, such as ester bonds, to prepare polypeptides with novel properties. For example, a polypeptide can be generated that incorporates a reduced peptide bond, i.e., $R_1$—$CH_2$—NH—$R_2$, where $R_1$ and $R_2$ are amino acid residues or sequences. A reduced peptide bond can be introduced as a dipeptide subunit. Such a polypeptide can be resistant to protease activity, and can possess an extended half-life in vivo. A polypeptide can also include a peptoid (N-substituted glycines), in which the one or more side chains are appended to nitrogen atoms along the molecule's backbone, rather than to the α-carbons, as in amino acids. Polypeptide and peptide are intended to be used interchangeably throughout this application, i.e. where the term peptide is used, it can also include polypeptide and where the term polypeptides is used, it can also include peptide.

In one embodiment, a polypeptide probe can be a fragment or portion of a larger protein. A fragment can range in size from two amino acid residues to the entire amino acid sequence minus one amino acid. In one embodiment, a polypeptide probe is a fragment of an untranslated region (UTR) of a protein, such as a fragment that is encoded by a nucleic sequence that is a UTR region of a gene, such as the 5' or 3' UTR of a gene.

The fragment can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 amino acids in size. In one embodiment, the fragment is less than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 amino acids in size. A polypeptide probe useful in the compositions and methods herein, regardless of size, is capable of specific interaction with an antibody, such as an autoantibody.

In one embodiment, a polypeptide probe can be a fragment of a protein encoded by a gene, or a region upstream or downstream of a coding sequence, such as a UTR region, of a gene listed in Table 1, Table 2, Table 3 or Table 4. In one embodiment, the polypeptide probe comprises a polypeptide sequence selected from SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof. In another embodiment, the polypeptide probe comprises a polypeptide sequence encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof. In yet another embodiment, the polypeptide probe comprises the full-length or a fragment of a protein that is encoded by SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

In one embodiment, a polypeptide probe is a fragment of a protein encoded by a gene, or a fragment encoded by a sequence of a UTR region of a gene.

In one embodiment, the gene can be CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, or Deaminase Domain. In another embodiment, the gene is FAM53B, 5'UTR BMI1, RP3-323M22, or LOC388789.

In another embodiment, a polypeptide probe comprises SEQ ID NO: 2, 5, 9, 11, 14, 56, 57, 58, 59, 60, 61, 62, 63, 64, 65, 66, 67, 68, 69, or a fragment thereof. In another embodiment, a polypeptide probe comprises a polypeptide encoded by SEQ ID NO: 16, 19, 23, 25, 28, 70, 71, 72, 73, 74, 75, 76, 77, 78, 79, 80, 81, 82, 83, 84, or a fragment thereof.

In one embodiment, the gene can be DCHS1, CEP164, KBTBD6, RPS19, RPL34, RNA binding protein 6, or Hemk1. In another embodiment, the gene is eIF4G1, 5'UTR BMI1, BRD2, RP3-323M22, SFRS14, or LOC388789. A polypeptide probe can comprise a peptide sequence, or fragment thereof, such as those listed in Tables 1, 2, 3 or 4.

In one embodiment, a polypeptide probe comprises SEQ ID NO: 1, 2, 3, 4, 5, 6, 7, 8, 9, 10, 11, 12, 13, 14, or a fragment thereof. In another embodiment, a polypeptide probe comprises a polypeptide encoded by SEQ ID NO: 15, 16, 17, 18, 19, 20, 21, 22, 23, 24, 25, 26, 27, 28, 29, 30, 31, 32, 33, 34, 35, 36, 37, 38, 39, 40, 41, or a fragment thereof.

TABLE 1

| Clone ID | Gene | NCBI Designation | Gene Sequence | Peptide Sequence | Clone DNA Sequence (Encoding Peptide Sequence) |
|---|---|---|---|---|---|
| 2E11 | DCHS 1 (protocadherin-16 precursor) | AB384634.1 | FIG. 2 (SEQ ID NO: 29) | PQTTAPRRARPRRS (SEQ ID NO: 1) | AGCTTTCGCTAGAGACGCCTCCATAAGTCACTTGCCCGTTGGCCCCCACGATCGGGGTCGGTTGCTCGCAGGGCTGAGCAGAGATGTGCCAGGAGGGTTGTTCTCACGCAAGAGGACGCTGTACTCCTGCTGCTGGAAAGTAGGCGCCTCGTCGTTGACGTCAGCGACACTGACGGTCAGGACCTGCGTGGCCGAGCGCGGCGGGGAGCCGTGGTCTGAGG (SEQ ID NO: 15) |
| 1B4A | Centrosomal Protein (CEP 164) (Minus strand) | NM_014956.4 | FIG. 3 (SEQ ID NO: 30) | PVSSSGSYSTPIRKSLRRAAPPFRA (SEQ ID NO: 2) | TGGAGGAGAGGCTGGGCTGCCCCAAGCCCCTGCTCAGGGCCTCAGAAGCCATACACCTTCACTCTGATTGTGCTCATCAAGGCCCAGCATGCAGGAGGCTCAAAGTAGCTTTTGGCTTGGGTGTTGACGAGAAGAGAGGTAACCTGGGGTCATTCTTGACACGTTCCAGCCACCTCCGGTTGGCCTCAATTATGCCCTGAAAGGTGGTGCTGCCCGCCTCAGGGACTTGCGAATGGGAGTGCTGTAGGAGCCGGAGCTGCTCACTG (SEQ ID NO: 16) |
| 37A8 | KBTB D6 | NM_152903.4 | FIG. 4 (SEQ ID NO: 31) | SSFSPLN (SEQ ID NO: 3) | GAATTCGTCATTCTCACCTTTGAATTAAAGCTTAGACTAAATAGTAATATATCGTGGGAAGGATTTTGGTTTTGTGATATTTCTGTGAATTAAGGAATAGATGTTAACCATTATTTTGTAGAAAAGTGATTTGTATGTGGTTAATTATAAATAAAACTGGTACCAGAA (SEQ ID NO: 17) |
| 4H10 | RPS19 | NM_001022.3 | FIG. 5 (SEQ ID NO: 32) | AARRPHDAWSYCKRREPAGVXQSSGSLPQKVREAESPRMGGYRQAGQAQRACSLR (SEQ ID NO: 4) | TTTATTAACCCAGCATGGTTTGTTCTAATGCTTCTTGTTGGCAGCTGCCACCTGTCCGGCGATTCTGTCCAGATCTCTTTGTCCCTGAGGTGTCAGTTTGCGGCCGCCATCTTGGTCCTTTTCCACCATTTTCAGCCCCTCCAGGGCTTGGAGGACCCGGCGGGCCACACTCTTGGAGCCTCGGCTGAAGTGGCTGGGCATGACGCCGTTTCTCTGACGTCCCCCATAGATCTTGGTCATGGAGCCAACCCCAGCGCCACCCCGGAGGTACAGGTGCCGCGCTGTGNAAGCAGCTCGCGTGTAGAACCAGTTCTCATCGTAGGGAGCAAGCTCTTTGTGCTTGGCCAGCTTGACGGTATCCACCCATTCGGGGACTTTCAGCTTCCCGGACTTTTTGAGGAAGGCTGCCAGAGCTCTGACNAACTCCTGCTGGTTCACGTCTTTTACAGTAACTCCAGGCATCGTGCGGCCTCCGCGCTGC (SEQ ID NO: 18) |
| 3D10 | RPL34 | NM_033625.2 | FIG. 6 (SEQ ID NO: 33) | QARLFIFITQKSFIFLFSFLTLCLCLQHFHNDFLLLDKESTLDPVTNTFSTHGTKTLLLTSLFL (SEQ ID NO: 5) | TTCTCGAGTGCGGCCGCAGCTTGGGTATGGAGACATATCATATAAGTAATGCTAGGGTCNGTGGTAGGAAGTTTTTTCATAGGAGGTGTATGAGTTGGTCGTAGCGGAATCGGGGGTATGCTGTTCGAATTCATAAGAACAGGGAGGTTAGAAGTAGGGTCTTGGTTCCATGTGTGCTAAATGTGTTCGTGACAGGATCAAGCGTGCTTTCCTTATCGAGGAGCAGAAAATCGTTGTGAAAGTGTTGAAGGCACAAGCACAGAGTCAGAAAGCTAAATAAAAAAATGAAACTTTTTTGAGTAATAAAAATGAAAAGACGCGCTTGA (SEQ ID NO: 19) |
| 40A3 | RNA binding protein 6 (Minus strand) | NT_022517.18 | FIG. 14 (SEQ ID NO: 41) | LRGITKNDRNFNRKIHLNWISK (SEQ ID NO: 6) | CTCTGAGGGGCATCACCAAAAATGACAGGAATTTCAACAGGAAGATACATCTGAATTGGATCTCGAAATAAGGAGTTTGTGTAAGAGAAAAGGAGGACACAAGCAAGGAGACACAAAAGACAATTTGTCCAAGAGAGTAGTAGTAGAAACTGACAAAGGTAAGGCTGCTTGGTGGCCGGGTGCAGTGACTCACGCCTGTAATCCCAGCACTTTGGGAGGCCAAGGCGGGTGGATCACCTGAGGTCAGG |

TABLE 1-continued

| Clone ID | Gene | NCBI Designation | Gene Sequence | Peptide Sequence | Clone DNA Sequence (Encoding Peptide Sequence) |
|---|---|---|---|---|---|
| | | | | | AGTTCGAGACCACCCTGACCAACAGGTGAAA CCCCTCTCTACTAAAAATACAAACATTAGCC CATAGTCCCAGCTACTGGGGAGGCTGAGGCA GGAGAATCGCTTGAACCTGGGAGGCGGAGGT TGCAGTGAGCCAAGATCGTGCCATTGCACTC CAGCCTGGGCGACAGAATGAGACTGTCTCAA AACAAAAGGAAAAAAAAAA (SEQ ID NO: 20) |
| 25C4 | Hemk1 (minus strand) | NM_016173.3 | FIG. 7 (SEQ ID NO: 34) | RGCCAGIRCT (SEQ ID NO: 7) | CACTTCTTCAAGCTCCAACACAAATGCTGCC TCCTTTAGGATGCCTGCTCTGTGCTCTCCCT GCCTCCCCTAGCCCATACCTCTGCTGGCACC TTCTGTACCATGCCTTCAGAAACCTTCTTAT CCCCCTCATCTCTGGGGCCCCCTGTGGATCT GGCATACCCAAGTTCAGTAAATGTCTATCAG TAAGCTGATGGTACATGCATTTTCTAGAATA GAGCTGGGACTTCCCATGTGGCCCACATCTG ACCTGGCAGCCCATGTATTCCGGTCATTAGG GATGGGAAGCCATGAGGACCTGGCCTTCTGC CCGACCCAGGCAGCCATTCAAGTTGAGCAAT GGCCACTTCGAAGACTCAAGTGCACCTGATC CCTGCGCAACAGCCAC (SEQ ID NO: 21) |

TABLE 2

| Clone | Gene | NCBI Designation | Gene Sequence | Peptide Sequence | Clone DNA Sequence (Encoding Peptide Sequence) |
|---|---|---|---|---|---|
| 24E1 | eIF4G1 | NM_182917.3 | FIG. 8 (SEQ ID NO: 35) | IRDPNQGGKDITEEI MSGARTASTPTPPQT GGGLEPQANGETPQV AVIVRPDDRSQGAII ADRPGLPGPEHSPSE SQPSSPSPTPSPSPV LEPGSEPNLAVLSIP GDTMTTIQMSVEE (SEQ ID NO: 8) | TTCTTCTACAGACATTTGTATAGTTGTCATAGTG TCCCCAGGAATAGAGAGGACTGCGAGATTAGGCT CAGACCCCGGTTCCAAGACTGGGGATGGTGATGG GGTCGGAGAAGGCGACGAAGGCTGGGATTCTGAA GGGCTATGCTCTGGGCCAGGCAGCCCTGGCCGGT CAGCAATGATTGCTCCCTGTGACCGGTCATCTGG CCGGACAATGACAGCAACCTGGGGCGTCTCCCCA TTAGCTTGAGGCTCCAGACCGCCTCCCGTCTGGG GAGGGGTGGGTGTGGAGGCAGTGCGGGCCCCAGA CATGATCTCCTCTGTGATATCCTTTCCTCCTTGG TTTGGATCTCGAATTCGGATC (SEQ ID NO: 22) |
| 3C4 | 5'-UTR BMI1 | BC011652.2 | FIG. 9 (SEQ ID NO: 36) | GGGRGAGGGRGAGAG GGRPEAA (SEQ ID NO: 9) | ATCACAAATAGGACAATACTTGCTGGTCTCCAGG TAACGAACAATACACGTTTTACAGAAGGAATGTA GACATTCTATTATGGTTGTGGCATCAATGAAGTA CCCTCCACAAAGCACACACATCAGGTGGGGATTT AGCTCAGTGATCTTGATTCTCGTTGTTCGATGCA TTTCTGCTTGATAAAAAATCCCGGAAAGAGCAGC CGGCGCGAGGCGATCGAAGCGGGCGGAAAAGACA ATGAAAGTTAAAAGTCGTTCAGCAGAAAATGAAT GCGAGCCAAGCGGCCATCTTGAAGCGAGCTGCAG ACGCCGCTGTCAATGGGCAACCAGCGCGGCCCCG AGCAGCCGCGGCCGCCACGCTCGTCTCATGCCGC CTCCGGCCGGCCTCCTCCTGCTCCGGCGCCTCGG CCTCCTCCGGCGCCTCGGCCTCCTCCTCCTCCGC CTCCGCCTCGACCTCCAACGCCTCCTCCTCCGGG GCCTCCTCCTCCTCCTCCTCGGC (SEQ ID NO: 23) |
| 8A6 | BRD2 | BX908719.9 | FIG. 10, (SEQ ID NO: 37) | ESRPMSYDEKRQLSL DINKLPGEKLGRVVH IIQAREPSLRDSNPE EIEIDFETLKPSTLR ELERYVLSCLRKKPR KPYSTYEMRFISWF (SEQ ID NO: 10) | TGTAGGGCTTCCGGGGTTTCTTACGTAGGCAGGA AAGGACATAGCGCTCAAGCTCTCTAAGTGTGGAT GGCTTGAGTGTTTCAAAATCAATCTCAATCTCTT CTGGGTTTGAATCACGTAAAGAGGGCTCCCTGGC TTGGATTATATGCACAACTCGGCCCAGCTTCTCC CCAGGTAATTTGTTGATGTCCAGGCTCAGCTGCC GCTTCTCATCGTAACTCATGGGCCTGCTCTC (SEQ ID NO: 24) |
| 15F1 | RP3-323M22 (Nucleolin) | NM_005381.2 | FIG. 11 (SEQ ID NO: 38) | LVSILLTKTIY (SEQ ID NO: 11) | TTACTGTTACCTGATCAATGACAGAGCCTTCTGA GGACATTCCAAGACAGTATACAGTCCTGTGGTCT CCTTGGAAATCCGTCTAGTTAACATTTCAAGGGC AATACCGTGTTGGTTTTGACTGGATATTCATATA AACTTTTTAAAGAGTTGAGTGATAGAGCTAACCC TTATCTGTAAGTTTTGAATTTATATTGTTTCATC |

TABLE 2-continued

| Clone | Gene | NCBI Designation | Gene Sequence | Peptide Sequence | Clone DNA Sequence (Encoding Peptide Sequence) |
|---|---|---|---|---|---|
| | | | | | CCATGTACAAAACCATTTTTTCCTACAAATAGTT TGGGTTTTGTTGTTGTTTCTTTTTTTTGTTTTGT TTTTGTTTTTTTTTTTTTTGCGTTCGTGGGGTTG TAAAAGAAAAGAAAGCAGAATGTTTTATCATGGT TTTTGCTTCAGCGGCTTTAGGACAAATTAAAAG (SEQ ID NO: 25) |
| 6E2 | SFRS14 | NM_001017392.3 | FIG. 12 (SEQ ID NO: 39) | KAECFKNLIVKKQKS LCSGFKEHLNEASIL AQVSVSSSKRVWKSW ENLISSFMVWNPAHL IISIPNLEKTSDLSM MSKLAAALE (SEQ ID NO: 12) | AAGCAGAGTGCTTTAAAAATTTGATAGTAAAAAA TCTCTGTGCTCTGGTTTTAAGGAACATTTGAATG AGGCAAGCATTTTAGCACAGGTTTCTGTTTCAAG TTCAAAGAGAGTCTGGAAAAGTTGGGAAAATTTA ATATCATCTTTTATGGTGTGGAATCCTGCCCATT TGATTATTTCTATCCCAAATCTTGAAAAAACATC AGACTTATCTATGATGTCAAAGCT (SEQ ID NO: 26) |
| 12B2 | 5'-UTR BMI1 | BC011652.2 | FIG. 9 (SEQ ID NO: 36) | QRSGRDNGDVGAGAP FRLSSTSQPRRIKPI APPPRAPSPEXGAGG GGGGRGGGGGGPGGG GVGGRGGGGGGGGRG AGGGRGAGAGGGRPE AA (SEQ ID NO: 13) | AAGCTTATTATCTCATCATCAGTTATAATTCTCT TATCTTCATCTGCAACCTCTCCTCTATCTTCATT AGAGCCATTGGCAGCATCAGCAGAAGGATGAGCT GCATAAAAATCCCTTCTTCTCTTCATTTCATTTT TGAAAAGCCCTGGAACTAATTTGTATACAATATC TTGGAGAGTTTTATCTGACCTTATATTCAGTAGT GGTCTGGTCTTGTGAACTTGGACATCACAAATAG GACAATACTTGCTGGTCTCCAGGTAACGAACAAT ACACGTTTTACAGAAGGAATGTAGACATTCTATT ATGGTTGTGGCATCAATGAAGTACCCTCCACAAA GCACACACATCAGGNGGGGATTTAGCTCAGTGAT CTTGATTCTCGTTGTTCGATGCATTTCTGCTTGA TAAAAAATCCCGGAAAGAGCAGCCGGCGCGAGGC GATCGAAGCGGGCGGAAAAGACAATGAAAGTTAA AAGTCGTTCAGCAGAAAATGAATGCGAGCCAAGC GGCCATCTTGAAGCGAGCTGCAGACGCCGCTGTC AATGGNCAACCAGCGCGGCCCCGAGCAGCCGCGG CCGCCACGCTCGTCTCATGCCGCCTCCGGCCGGC CTCCTCCTGCTCCGGCGCCTCGGCCTCCTCCGGC GCCTCGGCCTCCTCCTCCTCCGCCTCCGCCTCGA CCTCCAACGCCTCCTCCTCCGCTTGAATTCGGAT CCCCGAGCATCACACCTGACTGGAATACGAACAG CTCCACATNCNGT (SEQ ID NO: 27) |
| 21D10 | *Homo sapiens* hypothetical LOC388789 (LOC388789) | BC150559.1 | FIG. 13 (SEQ ID NO: 40) | PASASILAGVPMYRN EFTAWYRRMSVVYGI GTWSVLGSLLYYSRT MAKSSVDQKDGSASE VPSELSERPSLRPHS SN (SEQ ID NO: 14) | TTGGGCGTTCAGAGAGTTCACTGGGTACTTCACT TGCTGAGCCATCCTTTTGGTCTACTGACGACTTC GCCATTGTCCGGCTATAGTAAAGCAGTGAGCCCA ACACAGACCAGGTGCCGATCCCGTAGACCACCGA CATCCGCCGGTACCAGGCCGTGAACTCATTTCGA TACATGGGTACGCCAGCGAG (SEQ ID NO: 28) |

TABLE 3

| Clone | Gene | NCBI Designation | Gene Sequence | Peptide Sequence | Clone DNA Sequence (Encoding Peptide Sequence) |
|---|---|---|---|---|---|
| 8E10 | BRMSL1 | NM_032352.3 | FIG. 15 (SEQ ID NO: 42) | APRTRTLRARRSPRM EIAQKWMMKTVKEEE WNVWMKCPILKNSLP ISKINFIKND (SEQ ID NO: 56) | TCGTCGAGGCTCCTGCTCCTGTGACTCTCGAGCAG CCAGAGGCTCCTACCTCTATCGAGTCTTTACCTAC TACTTCTGACACTTTCTTCTTCTTACCTTACAAAC CTACTTTACAGGTTAGAACTTTTTGTCAAATGGCT AGAGTTTCTAGTTGAAATATTTCTTGCTAATTCAG TCCACCTACGTTTTGATGTTCTTCAGTATCGACCT TTTCGTGGTCTTATGAACCTTGGCGACCGTTGAAA TGTCCTTTTATACGTTTAAGCATGTTTCCATCGTC CTTAGATATCTCTCGAGACGAATCTTAGACATTTC TTGTTTATACTTACACTTTAAGTTCGAA (SEQ ID NO: 70) |
| 1D10 | 5'-UTR-BMI1 | NM_005180.5 | FIG. 9 (SEQ ID No: 36) | GGRGGGGGGGGRGAG GGRGAGAGGGRPEAA (SEQ ID NO: 9) | GGAGGTCGAGGCGGAGGCGGAGGAGGAGGAGGCCG AGGCGCCGGAGGAGGCCGAGGCGCCGGAGCAGGAG GAGGCCGGCCGGAGGCGGCATGAGACGAGCGTGGC GGCCGCGGCTGCTCGGGGCCGCGCTGGTTGNCCAT TGACAGCGGCGTCTGCAGCTCGCTTCAAGATGGCC GCTTGGCTCGCATTCATTTTCTGCTGAACGACTTT TAACTTTCATTGTCTTTTCCGCCCGCTTCGATCGC CTCGCGCCGGCTGCTCTTTCCGGGATTTTTATCA |

TABLE 3-continued

| Clone | Gene | NCBI Designation | Gene Sequence | Peptide Sequence | Clone DNA Sequence (Encoding Peptide Sequence) |
|---|---|---|---|---|---|
| | | | | | AGCAGAAATGCATCGAACAACGAGAATCAAGATCA CTGAGCTAAATCCCCNCCTGATGTGTGTGCTTTGT GGAGGGTACTTCATTGATGCCACAACCATAATAGA ATGTCTACATTCCTTCTGTAAAACGTGTATTGTTC GTTACCTGGAGACCAGCAAGTATTGTCCTATTTGT GATGTCCAAGTTCACAAGACCAGACCACTACTGAA TATAAGGTCAGATAAAACTCTCCAAGATATTGTAT ACAAATTAGTTCCAGGGCTTTTCAAAAATGAAATG AAGAGAAGAAGGGATTTTTATGCAGCTCATCCTTC TGCTGATGCTGCCAATGGCTCTAATGAAGATAGAG GAGGACGGTTGCAGATGAAGATAAGAGAATTATAA NCTGATGATGAGATAATAAGGCTTGCGGCCGCACT CGAGAAACAGT (SEQ ID NO: 71) |
| 1H2 | NKX3-1 | NM_0067167.3 | FIG. 16 (SEQ ID NO: 43 | GTNQRREGKSSGIFQ HFV (SEQ ID NO: 57) | GGAGAGAGGGAAAATCAAGTGGTATTTTCCAGCAC TTTGTATGATTTTGGATGAGTTGTACACCCAAGGA TTCTGTTCTGCAACTCCATCCTCCTGTGTCACTGA ATATCAACTCTGAAAGAGCAA (SEQ ID NO: 72) |
| 4H9 | RPSA | NM_002295.4 | FIG. 17 (SEQ ID NO: 44) | GKWCHACAELPEPAS TTSNPLSELPCCCMG WQCPHSAEENLCYTA QW (SEQ ID NO: 58) | CGGGAAATGGTGCCACGCATGCGCAGAACTTCCCG AGCCAGCATCCACCACATCAAACCCACTGAGTGAG CTCCCTTGTTGTTGCATGGGATGGCAATGTCCACA TAGCGCAGAGGAGAATCTGTGTTACACAGCGCAAT GGTAGGTAGGTTAACATAAGATGCCTCCGTGAGAG GCTGGTGGTCAGCCCTGGGGTCAGTAACCACAAGA AGCCGTGGCTCCCGGAAGGCTGCCTGGATCTGGTT AGTGAAGGTTCCAGGAGTGAAGCGGCCAGCAATTG GAGTGGCTCCAGTGGCAGCAGCAAACTTCAGCACA GCCCTCTGGCCAGTATTCCTGGAGGATATAACACT GACATCAGCAGGGTTTTCAATGGCAACAATTGCAC GAGCTGCCAGCAGAAGCTT (SEQ ID NO: 73) |
| 5B1 | Cytochrome C Oxidase 5 Subunit | NM_004255.3 | FIG. 18 (SEQ ID NO: 45) | INTLVTYDNVPEPKI IDAALRACRRLNDFA STVRILEVVKDKAGP HKEIYPYVIQELRPT LNELGISTPEELGLD KV (SEQ ID NO: 59) | GATAAACACACTTGTTACCTATGATATGGTTCCAG AGCCCAAAATCATTGATGCTGCTTTGCGGGCATGC AGACGGTTAAATGATTTTGCTAGTACAGTTCGTAT CCTAGAGGTTGTTAAGGACAAAGCAGGACCTCATA AGGAAATCTACCCCTATGTCATCCAGGAACTTAGA CCAACTTTAAATGAACTGGGAATCTCCACTCCGGA GGAACTGGGCCTTGACAAAGTGTAAACCGCATGGA TGGGCTTCCCCAAGGATTTATTGACATTGCTACTT GAGTGTGAACAGTTACCTGGAAATACTGATGATAA CATATTACCTTATTTGAACAAGTTTTCCTTTATTG AGTACCAAGCCATGTAATGGTAACTTGGACTTTAA TAAAAGGGAAATGAGTTTGAACTGAAA (SEQ ID NO: 74) |
| 17B8 | FAM53B | NM_014661.3 | FIG. 19 (SEQ ID NO: 46) | EVHIKKKTKQTLTNF QMGLLVRGREWPCPG CAACLSKLP (SEQ ID NO: 60) | GGGAAGTCCACATTAAAAAGAAAACAAAACAAACC CTAACTAACTTCCAAATGGGTCTCCTGGTGCGGGG GCGTGAGTGGCCGTGCCCTGGGTGTGCTGCCTGTC TGAGCAAGCTTCCCTAGCTGTGGAACCCCGGGCCC CCTGCTGCGGGCTCTGCCTTGGTGTCATGCCTGCT GCACCCCCGTTTCCACTGACGTGCCGTCTGTGGCT ATGGGGGTGGTCACTGGAATGACGGTCACTCCAGA CGTCAGCCGGCAGGGATGCAGCAGGCTGGCCGCGC A (SEQ ID NO: 75) |
| 3C11 | UTR-Region Chromosome 11 | AP003173.4 | FIG 20 (SEQ ID NO: 47) | DHSMVEFPRIIVYPQ FGVGNEG (SEQ ID NO: 61) | ATTCTATGGTGGAATTTCCAAGAATAATTGTTTAT CCTCAGTTTGGAGTAGGAAATGAAGGATAATTTTT TCCATTTCACCTCTATTGCAAATTTATTTTTTCAA GCCACACAAAAAATTGTCTAAGATAAAATGAGAAT TATTCAGATCAATTCTGCAATGATACAGGGAAGAT GTGAAAGGAGGGCTCAATGCAGAGTTGTGAAGTTG AAAACCACTATTTCTGTTCTAAAGACACAGTAAGC AGAGATCCATCTCTCTTCAGGCATCCTGCTTCTCT GCAGGTTACTTCTGCTTTAAGGAAAGTACATTTTT AGAACAAAGCTT (SEQ ID NO: 76) |
| 3F6 | MAPKKK9 | NM_033141.2 | FIG 21 (SEQ ID NO: 48) | SSGSGESRLQHSPSQ SYLCIPFPRGEDGDG PSSDGIHEEPTPVNS ATSTPQLTPTNSLKR GGAHHRRCEVALLGC | TCAAGCGGGAGTGGAGAGAGTCGCCTACAGCATTC ACCCAGCCAGTCCTACCTCTGTATCCCATTCCCTC GTGGAGAGGATGGCGATGGCCCCTCCAGTGATGGA ATCCATGAGGAGCCCACCCCAGTCAACTCGGCCAC GAGTACCCCTCAGCTGACGCCAACCAACAGCCTCA |

TABLE 3-continued

| Clone | Gene | NCBI Designation | Gene Sequence | Peptide Sequence | Clone DNA Sequence (Encoding Peptide Sequence) |
|---|---|---|---|---|---|
| | | | | GAVLAATGLGFDLLE AGKCQLLPLEEPEPP AREEKKRREGLFQRS SRPRRSTSPPSRKLF KKEEHQACGRTRVTS (SEQ ID NO: 62) | AGCGGGGCGGTGCCCACCACCGCCGCTGCGAGGTG GCTCTGCTCGGCTGTGGGGCTGTTCTGGCAGCCAC AGGCCTAGGGTTTGACTTGCTGGAAGCTGGCAAGT GCCAGCTGCTTCCCCTGGAGGAGCCTGAGCCACCA GCCCGGGAGGAGAAGAAAAGACGGGAGGGTCTTTT TCAGAGGTCCAGCCGTCCTCGTCGGAGCACCAGCC CCCCATCCCGAAAGCTTTTCAAGAAGGAGGAGCAC CAAGCTTGCGGCCGCACTCGAGTAACTAGTTAACC CCTTGGGGCCTCTAAACGGGTCTTGAGGGGGTTAN CTNGTTACTCGNGTGCGGCCGCNNGCTTGGTGCTC NNCNTTN (SEQ ID NO: 77) |
| 21H4 | cDNA clone | XR_113641.1 | FIG 22 (SEQ ID NO: 49) | QKLCQAKEKGMCMKK LRMLWECQKLYLSLG F* (SEQ ID NO: 63) | ATCCCAGCACGGAGGCCCAGAAAACTTTAAGATTT GAGTATTAATGTCTCAAGGTCAGGAGCAACCTCAA GGCTAAAACTCAGATCTCAGGACTCAATTTCACAG AAGTTCCACTATAAAGGCAATAATCTAAAGCTTTA AATGATATGAAAATTTTGTAATAAGAGTTCAGTAT TTCTGCCAACATTGGCGCATGGATTGCAAAGTTCA CAGGATTGAAAACACCATCGACATAATGGAAATTG AACAGCATCTGATTACTGAGTGCTATATCAGCAAG TTAAAAGGATCTTTTGCATACCTTTTAATGGTATA TATCCTAAAACTGAAGTGTTCAATATAGACATCCA GATTGAAA (SEQ ID NO: 78) |
| 4C4 | PSA | M27274.1 | FIG 23 (SEQ ID NO: 50) | S E G R T V T N K V S R K Y T G (SEQ ID NO: 64) | TGTGTGGGTATGAGGGTATGAGAGGGCCCCTCTCA CTCCATTCCTTCTCCAGGACATCCCTCCACTCTTG GGAGACACAGAGAAGGGCTGGTTCCAGCTGGAGCT GGGAGGGGCAATTGAGGGAGGAGGAAGGAGAAGGG GGAAGGAAAACAGGGTATGGGGGAAAGGACCCTGG GGAGCGAAGTGGAGGATACAACCTTGGGCCTGCAG GCCAGGCTACCTACCCACTTGGAAACCCACGCCAA AGCCGCATCTACAGCTGAGCCACTCTGAGGCCTCC CCTCCCCGGCGGTCCCCACTCAGCTCCAAAGTCTC TCTCCCTTTTCTCTCCCACACTCTATCATCCCCCG GATTCCTCTCTACTTGGTTCTCATTCTTCCTTTGA CTTCCTGATCCTGTGTATTTTCGGCTCACCTTGAT TTGTCACTGTTCTCCCCTC (SEQ ID NO: 79) |
| 5A1 | H2aa4 | NM_001040874.1 | FIG 24 (SEQ ID NO: 51) | QRGSGQQEDAHHPSS PPAGHPQRRGTEQAA GQSHHRPGRRLA (SEQ ID NO: 65) | ACGCGGCTCGGGGACAACAAGAAGACGCGCATCAT CCCTCGTCACCTCCAGCTGGCCATCCGCAACGACG AGGAACTGAACAAGCTGCTGGGCAAAGTCACCATC GCCCAGGGCGGCGTCTTGCCTAACATCCAGGCCGT ACTGCTCCCTAAGAAGACGGAGAGTCACCACAAGG CAAAGGGCAAGTGAGGCTGACGTCCGGCCCAAGTG GGCCCAGCCCGGCCCGCGTCTCGAAG (SEQ ID NO: 80) |
| 1B4 | UBE2I | NM_194259.1 | FIG 25 (SEQ ID NO: 52) | ILYPETLLKLLISLR RFWAEMMEFSRYTIM SSENRDNLTSSFPN* (SEQ ID NO: 66) | TGTGGCATCGTCAAAAGGAAGGGATTGGTTTGGCA AGAACTTGTTTACAACATTTTTGCAAATCTAAAGT TGCTCCATACAATGACTAGTCACCTGGGGGGGTTG GGCGGGCGCCATCTTCCATTGCCGCCGCGGGTGTG CGGTCTCGATTCGCTGAATTGCCCGTTTCCATACA GGGTCTCTTCCTTCGGTCTTTTGTATTTTTGATTG TTATGTAAAACTCGCTTTTATTTTAATATTGATGT CAGTATTTCAACTGCTGTAAAATTATAAACTTTTA TACTTGGGTAAGTCCCCCAGGGGCGAGTTCCTCGC TCTGGGATGCAGGCATGCTTCTCACCGTGCAGAGC TGCACTTGGCCTCAGCTGGCTGTATGGAAA (SEQ ID NO: 81) |
| 18D3 | TIMP2 | NM_003255.4 | FIG 26 (SEQ ID NO: 53) | CSKHSSLLLFSSCKQ LKIFKIKFTL (SEQ ID NO: 67) | ATGTTCTAAGCACAGCTCTCTTCTCCTATTTTCAT CCTGCAAGCAACTCAAAATATTTAAAATAAAGTTT ACATTGTAGTTATTTTCAAATCTTTGCTTGATAAG TATTAAGAAATATTGGACTTGCTGCCGTAATTTAA AGCTCTGTTGATTTTGTTTCCGTTTGGATTTTTGG GGGAGGGGAGCACTGTGTTTATGCTGGAATATGAA GTCTGAGACCTTCGGTGCTGGGAACACACAAGAGT TGTTGAAAGTTGACAAGCAGACTGCGCATGTCTCT GATGCTTTGTATCATTCTTGAGCAATCGCTCGGTC CGTGGACAATAAACAGTATTATCAAAGAGAAAAAA AA (SEQ ID NO: 82) |

TABLE 3-continued

| Clone | Gene | NCBI Designation | Gene Sequence | Peptide Sequence | Clone DNA Sequence (Encoding Peptide Sequence) |
|---|---|---|---|---|---|
| 2B10 | WDR77 | NM_024102.2 | FIG 27 (SEQ ID NO: 54) | NSLPLFPPQNSMGPD IFCPGPLSLDVESLN AVFIDF* (SEQ ID NO: 68) | GCCACTTTTCCCACCCCAAAACAGCATGGGGCCTG ACATCTTCTGCCCTGGTCCCCTTTCTCTTGATGTG GAAAGTCTGAATGCAGTATTTATAGACTTCTAAGG TTTTAAAATCCAGTATCAAGAAGAAAATCAGAAAT ACTGGTTGGTGAAATAAAGAGTTTAGGCATTGTTG GCCTGTCTTTTTTGAAGCATGTGTGTTATGTGTAG TTAGATATATTTCACTTATGTGAGTCATCATGGTG TTGGTCTTGTAGCCCATTATTTTTCCTGTGCTTCC CCAGCTTCCCAAAGTAGCTAGTTAGAACTTAAGGT AAATATTTATTCTTGGGTTGGTGGAGTGGATATTG CCAGTTAGGAGTCATGGATCAATTACTGATTATAT TGAAAGTAAATATAATCAATTATGTACTTTTGAGC TTTGCAGGTTCAATTTAGGTAAAAATCACATTATG AAACTGGGAAAGTCTGAAGGAATATGGCAAAATA TTTCTCAGTAAAGCTT (SEQ ID NO: 83) |
| 5F4 | Deaminase Domain Cont 1 | AL031320.1 | FIG 28 (SEQ ID NO: 55) | VSGSQRVKYLLVNPL QKKFINPCYRGF (SEQ ID NO: 69) | GAGATGTAAGCGGCTCACAAAGGGTGAAATATTTA CTAGTTAACCCCCTTGCAGAAAAAGTTATCAACCC TTGCTACAGAGGATTTTAAAAAATAAAATACAGCT TGTTCTATCTTTAGCATCTAACTGGGGAAAAGAAT CATAACATGTGAAAGAATAAATAAGAAATTGTGCT AACAGTAAGGAGTGTTATATGAAATATTACCTGAA GAACATGAAACTTGAACTTGCTAGAGATAGAGAAT ATTTAAAGAGGCTAAGCAGAGCATTTCAGGGAAAG GGCAAGAAGAAGCCTGGGTTGTGTGTGAGGAAATC AGCTGACAGAGGAGGAGACTATTAAGGAAGCATAA GGAAAGAAAGACAAAAAATTGGGGTAAAAATATGT ACGGCTTTGAAAGCTT (SEQ ID NO: 84) |

TABLE 4

| Clone | Gene | NCBI Designation | Gene Sequence | Peptide Sequence | Clone DNA Sequence (Encoding Peptide Sequence) |
|---|---|---|---|---|---|
| 1G7 | Lamin A/C | BC014507.1 | FIG 29 (SEQ ID NO: 85) | SCGPRSMRTRWSSIRR SWRRLILPSWTMPGSL LRGTATWWGLPTRSCS SRASASTASLPSSASS RSSWQPRRRSLRPHSS (SEQ ID NO: 112) | AAGCTTCGCCTCCTTGGCTGCCAGCTGCTTCTGGA GCTGGCTGAGCTGGGCAGAGAGGCTGTCGATGCGG ATGCGCGACTGCTGCAGCTCCTCGTGGGCAGCCCC CACCAGGTTGCTGTTCCTCTCAGCAGACTGCCTGG CATTGTCCAGCTTGGCAGAATAAGTCTTCTCCAGC TCCTTCTTATACTGCTCCACCTGGTCCTCATGCTG GGCCCGCAG (SEQ ID NO: 142) |
| 1B10 | Lsm3 | AJ238095.1 | FIG 30 (SEQ ID NO: 86) | MRNDRAASRQIT (SEQ ID NO: 113) | AATGAGAAATGACCGAGCAGCTTCGAGGCAGATTA CATGACTTATGATCTACATTTAAATATGATCTTGG GAGATGTGGAAGAAACTGTGACTACTATAGAAATT GATGAAGAAACATATGAAGAGATATATAAATCAAC GAAACGGAATATTCCAATGCTCTTTGTCCGGGGAG ATGGCGTTGTCCTGGTTGCCCCTCCACTGAGAGTT GGCTGAAACAAAGAATTTGTCCTGTATGGAAAACG GGAGACTTTGTACAGTGGCCTCTCTAAAAGTACAA AACATTCATAAGAGAAACCTGCATACATTTTGATA TTAAGAAATAATTCCGGGGATTCTCCACTCCTGAA ATGAGTTGATTTGCAGATAACTCTACAACTTCTTA AGCTAAATGGTATTTTCATTTTTCTCAAGCTCTCC AATAAATATGACCACCAA (SEQ ID NO: 143) |
| 2D7 | cDNA clone Chromo 19 | AC027307.5 | FIG 31 (SEQ ID NO: 87) | LAHRPPCAEPDPGQRM ELPAPVPRPRGASKPR DGTSSHCDMPNCQHPQ GPGPAGEIRSRCRSCW LRAVRCNPWLGR (SEQ ID NO: 114) | GGAGTTTCACTTTTGTTGCCCAGGATTGAGTGCAG TGCCCCGATCTTGGCTCACTACAACCTCTGCCTCC TGGGTTCAAGCGACTCTCCTGCCTCAGTGTCCTGA GTAGCTGGGATTACAGGCGTCTGCCACCACGCCCG GCTAATTTTGTATTTTTAGTAGAGAACAGGTTTCA CTATGTTGGTCAGGCTGGTCTTGAACTCCTGACCT CAGCGCATCCAGAATTTTAGACGGGGCCCCCAGGG TGAGGTCTTGGCACCCTCCAGTAGAGAAGAAGGGA CATGGGCCATACGTGGGGTGTCCTTTCTGGGAGCC TTGCGTCCCTTACCTGCCTAGCCAGGGATTGCACC TCACAGCACGCAGCCAGCAGGAACGGCACCGTGAT CTGATTTCACCTGCGGGCCCTGGGCCCTGGGGGTG TTGACAATTGGGCATATCACAGTGTGAGCTAGTCC |

TABLE 4-continued

| Clone | Gene | NCBI Designation | Gene Sequence | Peptide Sequence | Clone DNA Sequence (Encoding Peptide Sequence) |
|---|---|---|---|---|---|
| | | | | | CGTCTCGGGGTTTGGAGGCTCCACGTGGCCGTGGT ACAGGAGCAGGCAGTTCCATCCTCTGGCCTGGATC AGGCTCTGCACACGGAGGCCTGTGGGCCAG (SEQ ID NO: 144) |
| 1H3 | ADAM metallo-peptidase domain 9 | NR_027878.1 | FIG 32 (SEQ ID NO: 88) | NSGASGSRNFSSCSAE DFEK (SEQ ID NO: 115) | TCGGCATAAAGTACCTCCTGGAAGGAACCGACAGT CTTTACAACAGTCACCATATGCACACTCAGCAAAT GATTTAAGCTTACAGGTACTTCCTTCGCAGCAAGG GTCCAATTCACATTCCTTTGGAGTACCACAGTCAC ACTCTTCCCCAGCGTCCACCAACTTATTACCACAG GAGGGAGCACTATAGGCTTCATCAGGCTTTGGAAT ATTAAGAAGGCAGTTTCCTCCTTTATTTAAAGTTA CTTCTCAAAGTCCTCTGCACTGCAACTGCTAAAGT TCTGGAACCCGATGCTCCTGAATTC (SEQ ID NO: 145) |
| 3F5 | alpha-2 glycoprotein 1 (AZGP1) | NM_001185.3 | FIG 33 (SEQ ID NO: 89) | SSVPPQDTAPYSCHVQ HSSLAQPLVVPWEAS (SEQ ID NO: 116) | TCAAGCGTGCCCCCGCAGGACACAGCCCCCTACTC CTGCCACGTGCAGCACAGCAGCCTGGCCCAGCCCC TCGTGGTGCCCTGGGAGGCCAGCTAGGAAGCAAGG GTTGGAGGCAATGTGGGATCTCAGACCCAGTAGCT GCCCTTCCTGCCTGATGTGGGAGCTGAACCACAGA AATCACAGTCAATGGATCCACAAGGCCTGAGGAGC AGTGTGGGGGGACAGACAGGAGGTGGATTTGGAGA CCGAAGACTGGGATGCCTGTCTTGAGTAGACTTGG ACCCAAAAAATCATCTCACCTTGAGCCCACCCCCA CCCCATTGTCTAATCTGTAGAAGCCGGAAGCTTGC GGCCGCACTCGAGTAACTAGTTAACCCCTTGGGGC CTCTAAACGGGTCTTGAGGGGTTANCTNGTTNCTC GNGTGCGGCCGCNNGCTTCCGGCTTCTNCNGNTTN GNCNNTG N (SEQ ID NO: 146) |
| 5F3 | Hemk1 (minus strand) | NM_016173.3 | FIG. 7 (SEQ ID NO: 34) | VAVAQGSGALESSKWP LLNLNGCLGRAEGQVL MASHP (SEQ ID NO: 117) | GTGGCTGTTGCGCAGGGATCAGGTGCACTTGAGTC TTCGAAGTGGCCATTGCTCAACTTGAATGGCTGCC TGGGTCGGGCAGAAGGCCAGGTCCTCATGGCTTCC CATCCCTAATGACCGGAATACATGGGCTGCCAGGT CAGATGTGGGCCACATGGGAAGTCCCAGCTCTATT CTAGAAAATGCATGTACCATCAGCTTACTGATAGA CATTTACTGAACTTGGGTATGCCAGATCCACAGGG GGCCCCAGAGATGAGGGGGATAAGAAGGTTTCTGA AGGCATGGTACAGAAGGTGCCAGCAGAGGTATGGG CTAGGGGAGGCAGGGAGAGCACAGAGCAGGCATCC TAAAGGAGGCAGCATTTGTGTTGGAGCTTGAAGAA GTG (SEQ ID NO: 147) |
| 5F8 | Desmocollin 3 | NG_016782.1 | FIG 34 (SEQ ID NO: 90) | SAFRGYLANNK (SEQ ID NO: 118) | TAAGCTTTCATCTTCCCCAACCCTGATGTCTTCCT ATTCTCACTGATCCCCCTACTGACTCAGCTTCACG CTTCTTGATTATACCTCTCTCCTGTAGAAAAGCCT TGGCTGGCTCTCCTTTAGGATGAGAATAAATCCGA AATCCTTAGTGTAGCATTTAGAAGTCCTATCTCCC ACTTGTTTCTTAATATTCTCTTCTCTAACACCGAA CTTGTTTCAAGCCTCTTTTCCAACACATGATTTCT TCTATTCTAAATCAATTTATTTATTATTTGCTAAA TAGCCCCTAAAC (SEQ ID NO: 148) |
| 1G12 | DAZ Associated protein | AC027307.5 (this is for a chromosome 19 clone, not the specified gene) | FIG 31 (SEQ ID NO: 87) | SLAHRPPCAEPDPGQR MELPAPVPRPRGASKP PRRD (SEQ ID NO: 119) | GGCTAATTTTGTATTTTTAGTAGAGAACAGGTTTC ACTATGTTGGTCAGGCTGGTCTTGAACTCCTGACC TCAGCGCATCCAGAATTTTAGACGGGGCCCCCAGG GTGAGGTCTTGGCACCCTCCAGTAGAGAAGAAGGG ACATGGGCCATACGTGGGGTGTCCTTTCTGGGAGC CTTGCGTCCCTTACCTGCCTAGCCAGGGATTGCAC CTCACAGCACGCAGCCAGCAGGAACGGCACCGTGA TCTGATTTCACCTGCGGGCCCTGGGCCCTGGGGGT GTTTGACAATTGGGGCATATCACAGTGTGAGCTAG TCCCGTCTCGGGGGTTTGGAGGCTCCACGTGGCCG TGGTACAGGAGCAGGCAGTTCCATCCTCTGGCCTG GATCAGGCTCTGCACACGGAGGCCTGTGGGCCAG (SEQ ID NO: 149) |
| 1G5 | RPL34 (Minus strand) | NM_033625.2 | FIG. 6 (SEQ ID NO: 33) | LFIFITQKSFIFLFSF LTLCLCLQHFHNDFLL LDKESTLDPVTNTFST HGT (SEQ ID NO: 120) | GTCTTTTCATTTTTATTACTCAAAAAAGTTTCATT TTTTTATTTAGCTTTCTGACTCTGTGCTTGTGCCT TCAACACTTTCACAACGATTTTCTGCTCCTCGATA AGGAAAGCACGCTTGATCCTGTCACGAACACATTT AGCACACATGGAACCAA (SEQ ID NO: 150) |

TABLE 4-continued

| Clone | Gene | NCBI Designation | Gene Sequence | Peptide Sequence | Clone DNA Sequence (Encoding Peptide Sequence) |
|---|---|---|---|---|---|
| 3C9 | PERP (Minus strand) | NM_022121.4 | FIG 35 (SEQ ID NO: 91) | PYQIYQVMIN (SEQ ID NO: 121) | CTTACCAGATCTATCAGGTCATGATAAATTAGACCCAGTCCATCTTTCAATCCAGTCTACTCTGGTTCTGAACATATAAACACAAAACACTACAGATTTATTAATATAGCATTTTCCCACACCCTAACCCTATAAAGAACTTTAAAAGAGAAAATTTCATCTAAATATTTCACACTTAAAGGAAAGCCTTACCAACTATGGCAACAGGTTTGGACCATGAAATAGTACTTTCCTAGATGACATATCGAGTCAACATGAAGCCTTAGCTGAAATGAATGATTCAGGATATTAATGAGAAATTCTCACAAATGATATGCATTTAGGAAATGATTTTGCTTTCCTTAAATAGTTCGAAGGCTTGAAAATAAACTTTTTTTTGCATTTCTTTTAAAAGTT (SEQ ID NO: 151) |
| 3D11 | Chromosome 3 UTR region ropporin/ RhoEGF | AC117381.5 (*Homo sapiens* BAC RP11-783D3) | FIG 36 (SEQ ID NO: 92) | VSTFLSRVGRVSLLNFLPF (SEQ ID NO: 122) | GTTTCCACATTCTTGTCAAGGGTTGGTAGGGTCAGTCTTTTAAATTTCTTGCCATTTTAGTGACTGTGCATTGGTATTTCATTGTGGTTTATTTGCATGATGACTAATGCTCAACACCAACTAATCATGTTGAGTATTTTTAATGTGCTTATTTGCCACTCATATATCTTCTTTGATGAAGTGTCTCTTCAAATATTTTGCCCATTTAAAAACTGTATTGATTCTTATTATTGAATTGCAATAATTCTTTCTATCCGGATATATATCCTTTGCCAGATATGTGTATTACAAATGTTTTCTCCTAGCCTTCCACCTCAGCCTCCCAAGTAGCTGGGAATGCAGGTGTGCACCACCACTCCAGGGTTTTTTGTTGTTGTTGTTGTTGTTTTTCTGTAGAGACAGGGTCTTGCCATGCTGCCGAGGCTGCTCTCAAACTCCTGGGATCAAGAAATCCTCCTGCCCTCGGCCTCCCAAAGTGCTGACATTACAAGCATGAGCCACTGTGCCTGGCTAACTTTTCATCTTTTAAAGTAGTGTCTTGCAAAGAACAACATTTTAATGAAGTCCATTTATCAACTTTTTGATTCATTGTCCATGCTTTTTGCATAATAAGAAATCTTTGCCTGCCTCAAAATTGCAAAGCTT (SEQ ID NO: 152) |
| 3E4 | Cox5a | NM_004255.3 | FIG 37 (SEQ ID NO: 93) | NTLVTYDMVPEPKIIDAALRACRRLNDFASTVRILEVVKDKAGPHKEIYPYVIQELRPTLNELGISTPEELGLDKV (SEQ ID NO: 123) | AACACACTTGTTACCTATGATATGGTTCCAGAGCCCAAAATCATTGATGCTGCTTTGCGGGCATGCAGACGGTTAAATGATTTTGCTAGTACAGTTCGTATCCTAGAGGTTGTTAAGGACAAAGCAGGACCTCATAAGGAAATCTACCCCTATGTCATCCAGGAACTTAGACCAACTTTAAATGAACTGGGAATCTCCACTCCGGAGGAACTGGGCCTTGACAAAGTGTAACCGCATAATAAAAGGGAAATGAGTTTGAACTG (SEQ ID NO: 153) |
| 4B11 | Mito-chondrion sequence | HQ113226.2 | FIG 38 (SEQ ID NO: 94) | PPSHHIPNLSLTKRKPSPHSLNLIHHSRQLRWIKPNPATQNLSILLNYPHRMNNSSSTVQP (SEQ ID NO: 124) | GCCCCCATCTCATCATATACCAAATCTCTCCCTCACTAAACGTAAGCCTTCTCCTCACTCTCTCAATCTTATCCATCATAGCAGGCAGTTGAGGTGGATTAAACCAAACCCAGCTACGCAAAATCTTAGCATACTCCTCAATTACCCACATAGGATGAATAATAGCAGTTCTACCGTACAACCCTAACATAACCATTCTTAATTTAACTATTTATATTATCCTAACTACTACCGCA (SEQ ID NO: 154) |
| 4B3 | MYH9 (Minus strand) | NM_002473.4 | FIG 39 (SEQ ID NO: 95) | SAGSCSSA (SEQ ID NO: 125) | GGGTTCGTGTTCCTCAGCGTAGCCATCAGGCTTGGCCAGCTGCTCCTTGTAAAGCTGCCCCACAGTGCGGAACATGCCCTTCCGCGTCTTGAAGGCCCCGGGCAGTGCGGTCTCCGACATGCCGGCCACCTGGTCCAGGCCGATGATGCGGTCCACATCCTTCCACAGCTCCGAGACAAACTTGTCAGAGGACTGGTGGAGCAGTGTGGCGATGTTGTCATTCAGGGGATCCATGTTCTTCATCAGCCACTCGTCAGCTTTGTAATCCACCTTGCCGGCATAGTGGATAATGCAGAAATCAGCTTTGTCCTTCAGCTGCTTGGGCTTCTGGA (SEQ ID NO: 155) |
| 4D10 | ASND1 | NM_019048.2 | FIG 40 (SEQ ID NO: 96) | KLLFALQLWNLVLQPLLFCPNGPCSLDQELQKWKKLMKRHLINVDGSKSCP (SEQ ID NO: 126) | AAATTACTTTTCGCCTTGCAGCTGTGGAACTTGGTCTTACAGCCTCTGCTCTTCTGCCCAAACGGGCCATGCAGTTTGGATCAAGAATTGCAAAAATGGAAAAAATTAATGAAAAGGCATCTGATAAATGTGGACGGCTCCAAATCATGTCCTTAGAAAATCTTTCTATTGAAAAGGAGACTAAATTGTAATGTGATTCACAATGTAACAATATAAAAATAAGTTTTATATAATTATATAAAAGTAAGATACTCTGCTGCTTTACTATTGTATAATAT (SEQ ID NO: 156) |

TABLE 4-continued

| Clone | Gene | NCBI Designation | Gene Sequence | Peptide Sequence | Clone DNA Sequence (Encoding Peptide Sequence) |
|---|---|---|---|---|---|
| 4D9 | Cathepsin F | NM_003793.3 | FIG 41 (SEQ ID NO: 97) | EDDYSYQGHMQSCNFS<br>AEKAKVYINDSVELSQ<br>NEQKLAAWLAKRGPIS<br>VAINAFGMQFYRHGIS<br>RPLRPLCSPWLIDHAV<br>LLVGYGNRSDVPFWAI<br>KNSWGTDWGEKGYYYL<br>HRGSGACGVNTMASSA<br>VVD<br>(SEQ ID NO: 127) | CAGAGGATGACTACAGCTACCAGGGTCACATGCAG<br>TCCTGCAACTTCTCAGCAGAGAAGGCCAAGGTCTA<br>CATCAATGACTCCGTGGAGCTGAGCCAGAACGAGC<br>AGAAGCTGGCAGCCTGGCTGGCCAAGAGAGGCCCA<br>ATCTCCGTGGCCATCAATGCCTTTGGCATGCAGTT<br>TTACCGCCACGGGATCTCCCGCCCTCTCCGGCCCC<br>TCTGCAGCCCTTGGCTCATTGACCATGCGGTGTTG<br>CTTGTGGGCTACGGCAACCGCTCTGACGTTCCCTT<br>TTGGGCCATCAAGAACAGCTGGGGCACTGACTGGG<br>GTGAGAAGGGTTACTACTACTTGCATCGCGGGTCC<br>GGGGCCTGTGGCGTGAACACCATGGCCAGCTCGGC<br>GGTGGTGGACTGAAGAGGGGCCCCCAGCTCGGGAC<br>CTGGTGCTGATCAGAGTGGCTGCTGCCCCAGCCTG<br>ACATGTGTCCAGGCCCCTCCCCGGGAGGTACAGCT<br>GGCAGAGGGAAAGGCACTGGTACCTCAGGGTGAGC<br>AGAGGGCACTGGGCTGGGGCACAGCCCCTGCTTCC<br>CTGCACCCCATTCCCACCCTGAAGTTCTGCACCTG<br>CACCTTTGTTGAATTGTGGTAGCTTAGGAGGATGT<br>CAGGGTGAAGGGTGGTATCTTGGCAGTTGAAGCTG<br>GGGCAAGAACTCTGGGCTTGGGTAATGAGCAGGAA<br>GAAAATTTTCTGATCTTAAGCCCAGCTGTGTTCTG<br>CCCCCGCTTTCCTCTGTTTGATACTATAAATTTTC<br>TGGTTCCCTTGGATTTAGGGATAGTGTCCCCCTCC<br>ATGTCCAGGAAACTTGTAACCACCCTTTTCTAACA<br>GCAATAAAGAGGGTCCTTGTCCCGAAAAAAAAAAA<br>AA<br>(SEQ ID NO: 157) |
| 4F1 | Master mind-like 2 | AP000779.4 (*Homo sapiens* genomic DNA, Chromosome 11q) | FIG 42 (SEQ ID NO: 98) | GTNQRQTMENH<br>(SEQ ID NO: 128) | GGCAGACAATGGAAAACCATTGAAAAGGATTAAAC<br>TGGGAAGTGATATGTTCTCTTTTGCATTTAAAAAG<br>ATCACCAATGGGGATATGGAGAATGGTCTGGATAG<br>GTCTTAAGACTAGAGCCAGGAAGACATGTTAGAAG<br>GCTATCAATTGACCCTAAAGACACTGCTTCAATCC<br>CTTTGATGACAGTGAGTTTGCTTTCCCCAGAGATA<br>GCTTATTGGACCTCAGGACTGCTGTGAGAAACAGA<br>AAATGCTCCTTTACGTGTTGCCTGAAGTTAGGCTC<br>ACCGATTTGGGGCATGTTCTAATTCTACCAGCTAG<br>GAACACACAGAATCGCTTGTCAAACATTCTGAGTC<br>AGATATGTCCTCCCTATGTCTTTTCTGAGAAAGGC<br>ATACAGAAATTCCCAGCTAAACATCACCAGTTCCC<br>TCATTTGTTCCTCAGATGATATGGTCCATTCAAGT<br>TTTGTAATCATCATGGGGGTAGATGGAGGGTCCCA<br>GTCCTCACAACCATTCTGGTAATTTACTCTTGAAT<br>TTACTGGTTCACATGTATCTATTTTGTAGTGTGGC<br>TCCAGAAA<br>(SEQ ID NO: 158) |
| 5D11 | CSNK2A2 | NM_001896.2 | FIG 43 (SEQ ID NO: 99) | SSCSEYNVRVASRYFK<br>GPELLVDYQMYDYSLD<br>MWSLGCMLASMIFRRE<br>PFFHGQDNYDQLVRIA<br>KVLGTEELYGYLKKYH<br>IDLDPHFNDILGQHSR<br>KRWENLSIVRTDTLSA<br>LRP<br>(SEQ ID NO: 129) | TCATCCTGCTCGGAGTACAATGTTCGTGTAGCCTC<br>AAGGTACTTCAAGGGACCAGAGCTCCTCGTGGACT<br>ATCAGATGTATGATTATAGCTTGGACATGTGGAGT<br>TTGGGCTGTATGTTAGCAAGCATGATCTTTCGAAG<br>GGAACCATTCTTCCATGGACAGGACAACTATGACC<br>AGCTTGTTCGCATTGCCAAGGTTCTGGGTACAGAA<br>GAACTGTATGGGTATCTGAAGAAGTATCACATAGA<br>CCTAGATCCACACTTCAACGATATCCTGGGACAAC<br>ATTCACGGAAACGCTGGGAAAACTTATCCATAGTG<br>AGAACAGACACCTTGTCAGCCCTGAGGCCCTAGAT<br>CTTCTGGACAAACTTCTGCGATACGACCATCAACA<br>GAGACTGACTGCCAAAGAGGCCATGGAGCACCCAT<br>ACTTCTACCCTGTGGTGAAGGAGCAGTCCCAGCCT<br>TGTGCAGACAATGCTGTGCTTTCCAGTGGTCTCAC<br>GGCAGCACGATGAAGACTGGAAAGCGACGGGT<br>(SEQ ID NO: 159) |
| 7A9 | AURKAIP1 | NM_001127230.1; NM_001127229.1; NM_017900.2 (transcript variants) | FIG 44 (SEQ ID NO: 100) | AARLGPSLECWAAGSA<br>GPFTAHRRPAQVGRPL<br>SLARGPSWSWRRCWSP<br>GRCPSAPWRAGSRPAA<br>SCPDWIPGPQGLWLHR<br>NPTSVRPAR<br>(SEQ ID NO: 130) | CGGCCGCCCGCCTTGGCCCGTCTCTGGAGTGCTGG<br>GCAGCCGGGTCTGCGGGCCCCTTTACAGCACATCG<br>CCGGCCGGCCCAGGTAGGGCGGCCTCTCTCCCTCG<br>CAAGGGGGCCCAGCTGGAGCTGGAGGAGATGCTGG<br>TCCCCAGGAAGATGTCCGTCAGCCCCCTGGAGAGC<br>TGGCTCACGGCCCGCTGCTTCCTGCCCAGACTGGA<br>TACCGGGACCGCAGGGACTGTGGCTCCACCGCAAT<br>CCTACCAGTGTCCGCCCAGCCAGATAGGGGAAGGG<br>GCCGAGCAGGGGGATGAAGGCGTCGCGGATGCGCC<br>TCAAATTCAGTGCAAAAACGTGCTGAAGATCCGCC<br>GGCGGAAGATGAA<br>(SEQ ID NO: 160) |

TABLE 4-continued

| Clone | Gene | NCBI Designation | Gene Sequence | Peptide Sequence | Clone DNA Sequence (Encoding Peptide Sequence) |
|---|---|---|---|---|---|
| 3C1 | Chromosome 4 | AC096741.3 (*Homo sapiens* BAC clone RP11-327017) | FIG 45 (SEQ ID NO: 101) | GKERENIRTNT (SEQ ID NO: 131) | GGCAGGGAAGGGAGAACATTAGGACAAATACCTAA<br>TGCACGCCAGGCCCTANTAATCGTAGATGATGGGT<br>TGATGGGTGTAGCAAACCACCATGGCACATGTATA<br>TCTATGTAACAAACCTGCACATTCTGTACATGTAT<br>CCCAGAACTTCAAGTAAAATTTTAAAAAATTCAAA<br>AAAAGTAATAGGAAAAGGGGAAACATCCACGTGAG<br>CAGTCCAGTTTCCCAATCTGGAACTTGGAGCTGTT<br>CACCTGGTGGGTGTTTGTGACTATTCAGACACAGA<br>CAACAAAGGCTACTCCAGATTGAAGTGCACTGCTT<br>ACTTTCAGTGACCTCATAGAACTACTCAACATTGT<br>TTTTGGTGATTCCTGTGCTATGGTTTGAATGGCTC<br>CGCTCCAAAACTCAGGTGTTGCCAATGNGATGGTA<br>TTAAGAAGTAGGGCATTTAAAAAACAACAACAGGC<br>CTGGCGCGGTGGCCCACGCCTGTAATCCCAGCACT<br>TTGGGAGGCTAAGGCGGGCGGATCACCGGAGGTCA<br>GGAATTCAAAACCAGCCTGGCCAACATGGCGAAAC<br>CCTGTCTCTACTAAAAATACAAAAATTAGCCAGGC<br>ATGGTTGCGGGCGCCTGTAATCCCGGCTACTCGGG<br>AGGCTGAGGCAGGGGAATCCTTGAACCCGGGA<br>(SEQ ID NO: 161) |
| 3C3 | ARF6 | NM_001663.3 | FIG 46 (SEQ ID NO: 102) | PKCRLQRQYTGKGGVG FVYEGV (SEQ ID NO: 132) | GAAATGTAGACTGCAAAGGCAGTATACAGGAAAAG<br>GTGGAGTGGGTTTTGTTTATGAGGGTGTCTGAAAA<br>CTAAAATTGAGCGGGATATCATGGTATAGTTGGAC<br>AGTATTGGTCCTTCACACTTTGGCCATATTGTATA<br>ATGGAGCTTTTACCAAAGATGTATGAGAAGTGTAA<br>GACTATAAAAAAATGAACTATTCAAAGTAAAACTC<br>TTAACAAACATTTTACTTAAAGCAGATGCAAAAGG<br>GTATTCTCATGTAGGCTCCTGTTGGTGCAGAGGGA<br>TTTTTTTGATTTCAGGATACAACTAAAGTACGAAG<br>TTCTCAGTTTCACTTTAGTAGAAAGAGCTCTAGAA<br>ATGAGGCTGATAAACACATCTAAGAACACTGGTTG<br>CTTTCTAAAATTTCCAAAGCTCCACCATAAATGTA<br>ATTTTTAGTGTTTCAAATGATTGCATTTTAAAGTA<br>TATAAATATGGGTTATCCAATATCAATGCTATAGT<br>AACATCCTGAAACAAAACAAGCACAAAGGTATAAA<br>TGCCTAAACTGGAGGAAGCTTG<br>(SEQ ID NO: 162) |
| 3D1 | 3' UTR rgion JAG1 | AL135937.2 2 (Human DNA sequence from clone RP1-278022 on chromosome 20) | FIG 47 (SEQ ID NO: 103) | QTQTHTSAPLKCQPWS FVEARICHQSQLVRCP VQHPSRIS (SEQ ID NO: 133) | CTCAGACTCAAACACACACCTCCGCTCCCTTGAAG<br>TGCCAGCCCTGGAGCTTTGTTGAGGCTCGCATCTG<br>CCACGGGAGTCAGCTAGTACGTTGCCCAGTTCAAC<br>ATCCATCCAGGATTTCATAGGAACTTGAGAATCAT<br>TGTTTTTGGCTTGAATCCTGGGTTTGAGGTTTCTT<br>CGTGTAGGAATCTGAAAAAAGGATTTGGAAACGTT<br>GTTGTCTCTAATCCCAAAGTATGTATCTGGGAGGC<br>TGCCTTCGCCATCACCCACCTAATAACTCAGG<br>(SEQ ID NO: 163) |
| 5A5 | Mitocho-ndrion sequence | HQ113226.2 | FIG 48 (SEQ ID NO: 104) | PRLHQXKANYIYSIDP IT (SEQ ID NO: 134) | AGACTTCACCAGTCAAAGCGAACTACATATACTCA<br>ATTGATCCAATAACTTGACCAACGGAACAAGTTAC<br>CCTAGGGATAACAGCGCAATCCTATTCTAGAGTCC<br>ATATCAACAATAGGGTTTACGACCTCGATGTTGGA<br>TCAGGACATCCCGATGGTGCAGCCGCTATTAAAGG<br>TTCGTTTGTTCAACGATTAAAGTCCTACGTGATCT<br>GAGTTCAGACCGGAGTAATCCAGGTCGGTTTCTAT<br>CTACTTCAAATTCCTCCCTGTACGAAAGGACAAGA<br>GAAATAAGGCCTACTTCACAAAGCGCCTTCCCCCG<br>TAAATGATATCATCTCAAGCTT<br>(SEQ ID NO: 164) |
| 3E1 | Chromosome 20 | AL135937.22 | FIG 49 (SEQ ID NO: 105) | P Q T T A P R R A R P R R S (SEQ ID NO: 135) | CTCGCTCAAACACACACCTCCGCTCCCTTGAAGTG<br>CCAGCCCTGGAGCTTTGTTGAGGCTCGCATCTGCC<br>ACGGGAGTCAGCTAGTACGTTGCCCAGTTCAACAT<br>CCATCCAGGATTTCATAGGAACTTGAGAATCATTG<br>TTTTTGGCTTGAATCCTGGGTTTGAGGTTTCTTCG<br>TGTAGGAATCTGAAAAAAGGATTTGGAAACGTTGT<br>TGTCTCTAATCCCAAAGTATGTATCTGGGAGGCTG<br>CCTTCGCCATCACCCACCTAATAACTCAGGC<br>(SEQ ID NO: 165) |
| 5A9 | Chromosome 6 clone UTR region (Minus strand) | AL034375.23 | FIG 50 (SEQ ID NO: 106) | G T I S I V C C<br>W G C L C Q H L<br>V Q C L A D G C<br>S I N I D L M G<br>Y E G V N I K L<br>A F I Q Q L L | ATTGTTTGTTGTTGGGGGTGTCTTTGTCAGCATCT<br>AGTACAGTGCCTGGCAGATGGATGCTCAATAAATA<br>TTGATTTAATGGGTTATGAGGGTGTTAATATAAAA<br>TTAGCATTTATTCAGCAACTACTATGAGTCAGCCA<br>CTGGGCTAAGTGGCTTACATGTTAAGAACCTCACA<br>GAAGCCAGGTGTGGTGGCTCACGCCTGTAATCCCA |

TABLE 4-continued

| Clone | Gene | NCBI Designation | Gene Sequence | Peptide Sequence | Clone DNA Sequence (Encoding Peptide Sequence) |
|---|---|---|---|---|---|
| | | | | (SEQ ID NO: 136) | GCACTTTGGGAGGCTGAAGCGGGCAGATCACCTGA<br>GGTCAGGAGTTTGAGTCCAGGCTGGCCAACGTGGT<br>GAAACCCCATCTCTACTAAAAATACAAAAATTAGC<br>CAGTTGTGGTGGCAGGCGCCTGTAGTCCCAGCCAC<br>TCAGGAGGCTAAGGCAGGAGAATAGCTGGAACCCG<br>GGAGGTGGAGATTGCAGTGAGCCAAGATTGCACCA<br>CTGCACTCCAGCCTGGGTGACAGAGTGAGACTCTG<br>TCTCCAAAAAAAAAAGAAAAAGAAAAAGAACCTCC<br>AGCAACCTAGTAGGTGAGCCCGGTTACTCTTGTTT<br>TACAGGTGAGAAAATTGAGCCCTAGAGAAATAAAG<br>TAACTTGCTTCAGGTCTCATGGTTAAGGGGAACCT<br>GGGCCCTAACAGTCCACTTCCTGTACCTTCAACCA<br>CGGTTCTACCGCCTCCGCTAGGAAATGGCCCGAGG<br>ACATTCCTTAGCTGGCTTCAGCTTGCTCTTTTTCC<br>CCTGCGGTCCACCCCTG<br>(SEQ ID NO: 166) |
| 5H2 | MAPKKK5 | NG_011965.1 | FIG 51<br>(SEQ ID<br>NO: 107) | G M S H H A W P<br>R P S F F N T E<br>Y F<br>(SEQ ID NO: 137) | AGAGGGAGTATAGGGCTGTGCACAGAGACTATGAT<br>GGCCGTGCTAAGGTAAGAGTATTGATAATGTAAGC<br>ATACTTCCTCTATCAACAATAATTGTTAACAGCTG<br>CTTCAAGCACTTGATATTACCACTAGTTGTTAACT<br>GAATCAAGCATGTGCTCCAAGTTCACATTAATGTG<br>AATTGAACAGCATTGTGTACGTACGAGGAGCTTCA<br>TGCAAGTGTTATACACTGCACTCACAAGTATTATG<br>ATCTTACTAAGCATTAGAAATACTCTGTGTTAAAG<br>AAGCTTGGTCTAGGCCAAGCGTGGTGGCTCATGCC<br>T<br>(SEQ ID NO: 167) |
| 1H5 | RAS<br>p21<br>Protein<br>activator<br>(RASA1) | BC020761.1 | FIG 52<br>(SEQ ID<br>NO: 108) | D R R P G S F V<br>L S F L S Q Met<br>N V V T H F R I<br>I A Met C G D Y<br>Y I G G R R F S<br>S L S D L I G Y<br>Y S H V S C L L<br>K G E K L L Y P<br>V A P P E P V E<br>D R R R V R A I<br>L P Y T K V P D<br>T D E I S F L K<br>G D Met F I V H<br>N E L E D G W<br>Met W V T N L R<br>T D E Q G L I V<br>E D L V E E V G<br>R E E D P H E G<br>K I W F H G K I<br>S K Q E A<br>(SEQ ID NO: 138) | GATCGGAGGCCAGGGTCCTTTGTACTTTCATTTCT<br>TAGCCAGATGAATGTTGTCACCCATTTTAGGATTA<br>TTGCTATGTGTGGAGATTACTACATTGGTGGAAGA<br>CGTTTTTCTTCACTGTCAGACCTAATAGGTTATTA<br>CAGTCATGTTTCTTGTTTGCTTAAAGGAGAAAAAT<br>TACTTTACCCAGTTGCACCACCAGAGCCAGTAGAA<br>GATAGAAGGCGTGTACGAGCTATTCTACCTTACAC<br>AAAAGTACCAGACACTGATGAAATAAGTTTCTTAA<br>AAGGAGATATGTTCATTGTTCATAATGAATTAGAA<br>GATGGATGGATGTGGGTTACAAATTTAAGAACAGA<br>TGAACAAGGCCTTATTGTTGAAGACCTAGTAGAAG<br>AGGTGGGCCGGGAAGAAGATCCACATGAAGGAAAA<br>ATATGGTTCCATGGGAAGATTTCCAAACAGGAAGC<br>TT<br>(SEQ ID NO: 168) |
| 18H9 | Hsp90b | Ay359878.1 | FIG 53<br>(SEQ ID<br>NO: 109) | YFAYLISEQNEENKIN<br>HNTQHPILLSRVREGM<br>GLDTLSLLPSTQGQER<br>EKNTRHQQGEPGGTGA<br>LEAAVGAHGDTIQGHK<br>FSNYELLT<br>(SEQ ID NO: 139) | TGAAGTGGCAGCAGAGGAACCCAATGCTGCAGTTC<br>CTGATGAGATCCCCCCTCTCGAGGGCGATGAGGAT<br>GCGTCTCGCATGGAAGAAGTCGATTAGGTTAGGAG<br>TTCATAGTTGGAAAACTTGTGCCCTTGTATAGTGT<br>CCCCATGGGCTCCCACTGCAGCCTCGAGTGCCCCT<br>GTCCCACCTGGCTCCCCCTGCTGGTGTCTAGTGTT<br>TTTTTCCCTCTCCTGTCCTTGTGTTGAAGGCAGTA<br>AACTAAGGGTGTCAAGCCCCATTCCCTCTCTCACT<br>CTTGACAGCAGGATTGGATGTTGTGTATTGTGGTT<br>TATTTTATTTTCTTCATTTTGTTCTGAAATTAAGT<br>ATGCAAAATAA<br>(SEQ ID NO: 169) |
| 4D7 | ribosomal<br>protein S6<br>(RPS6) | NM_001010.2 | FIG 54<br>(SEQ ID<br>NO: 110) | C I V D A N L S<br>V L N L V I V K<br>K G E K D I P G<br>L T D T T V P R<br>R L G P K R A S<br>R I R K L F N L<br>S K E D D V R Q<br>Y V V R K P L N<br>K E G K K P R T<br>K A P K I Q R L<br>V T P R V L Q H<br>K R R R I A L K<br>K Q R T K K N K | GTTGCATTGTGGATGCAAATCTGAGCGTTCTCAAC<br>TTGGTTATTGTAAAAAAAGGAGAGAAGGATATTCC<br>TGGACTGACTGATACTACAGTGCCTCGCCGCCTGG<br>GCCCCAAAAGAGCTAGCAGAATCCGCAAACTTTTC<br>AATCTCTCTAAAGAAGATGATGTCCGCCAGTATGT<br>TGTAAGAAAGCCCTTAAATAAAGAAGGTAAGAAAC<br>CTAGGACCAAAGCACCCAAGATTCAGCGTCTTGTT<br>ACTCCACGTGTCCTGCAGCACAAACGGCGGCGTAT<br>TGCTCTGAAGAAGCAGCGTACCAAGAAAAATAAAG<br>AAGAGGCTGCAGAATATGCTAAACTTTTGGCCAAG<br>AGAATGAAGGAGGCTAAGGAGAAGCGCCAGGAACA<br>AATTGCGAAGAGACGCAGACTTTCCTCTCTGCGAG<br>CTTCTACTTCTAAGTCTGAATCCAGTCAGAAATAA |

TABLE 4-continued

| Clone | Gene | NCBI Designation | Gene Sequence | Peptide Sequence | Clone DNA Sequence (Encoding Peptide Sequence) |
|---|---|---|---|---|---|
| | | | | E E A A E Y A K<br>L L A K R Met K<br>E A K E K R Q E<br>Q I A K R R R L<br>S S L R A S T S<br>K S E S S Q K<br>(SEQ ID NO: 140) | GATTTTTTGAGTAACAAATAAATAAGATCAGA<br>(SEQ ID NO: 170) |
| 36C4 | Homo sapiens chromosome 3 genomic contig | AC128709 (Homo sapiens 3 BAC RP13-616I3) | FIG 55 (SEQ ID NO: 111) | L I C I S L M A<br>N D V E H L F M<br>F I C H L S<br>(SEQ ID NO: 141) | CCTGGGCAGTGATTAGGTCATAAAGGTGGAGTCCT<br>CATGGATGGGATTAGTGTCTTTATAAAAGAGACCT<br>TTGCCATGTGAGGTTACAGTGAGAAGACATCTGTC<br>TATGAAGAAAGTGGGCCCTCACCAAACACAGTCTG<br>CTGGCACTTTGCACTTCAACTCCCCAGCTTCCAGA<br>ACTGTAAGGAATATAAGTCTGTTGTTGGTAAGCCA<br>CCCGGTCTATGATATTTTGTTATAGCAGCCCAAAC<br>AGACTAAGACAGGTGACAAATAAACATGAAAAGAT<br>GTTCAACATCATTAGCCATTAGGGAAATGCAGATT<br>AAAA<br>(SEQ ID NO: 171) |

An antibody, such as an autoantibody, to one or more of a protein, or a fragment of a protein, encoded by a gene such as listed in Tables 1, 2, 3 or 4, or a polypeptide encoded by a UTR sequence of a gene such as one listed in Tables 1, 2, 3 or 4, can be detected according to one or more methods described herein and used to characterize a cancer, such as prostate cancer. Many of the proteins may have a role in various cancers, including prostate cancer. For example, the human DCHS1 protein (protocadherin-16 precursor) is believed to be a calcium-dependent cell adhesion protein found in the cell membrane of fibroblast cells. Without being bound by theory, DCHS1 is a cadherin, a class of type-1 transmembrane proteins. Cadherins typically play important roles in cellular adhesion, for example, by binding cells expressing similar cadherins to each other. Structurally, DCHS1 is thought to contain 27 cadherin repeats (extracellular calcium ion-binding domains). DCHS1 expression has been associated with certain cancers, potentially playing a role in tumor adherence (see, e.g., Sjoblom, et. al. *Science*, (2006) 314:268-274).

Another of the proteins, CEP164 is believed to be a centrosomal protein which binds chromatin and plays a role in the DNA damage-activated signaling cascade. It is known to interact with ataxia telangiectasia mutated (ATM) and ATM/Rad3-related (ATR) kinases which phosphorylate CEP164 upon replication stress, ultraviolet radiation (UV), and ionizing radiation (IR). CEP164 also plays a role in cell cycle regulation, specifically at the G2/M checkpoint and in nuclear division (see, e.g., Sivasubramaniam et al., *Genes & Dev.* (2008); 22(5):687-600). As CEP164 plays a role in genome stabilization, misregulation or mutation of this gene and/or protein can play a role in certain cancers.

In a further example, the human KBTBD6 (kelch repeat and BTB (POZ) domain containing 6) is a protein expressed in a wide variety of normal tissues. Its expression and/or misregulation has also been noted in multiple cancer types, including prostate, ovarian, kidney and lung tumors. The function of the protein is not currently known, however, the presence of the kelch repeat and BTB domain suggest that the protein is involved in protein-protein interactions and actin filament organization.

Certain ribosomal proteins, such as RPS19 and RPL34 have also been associated with certain cancers. RPS19 (ribosomal protein S19) encodes a ribosomal protein that is a component of the 40S subunit. Located in the cytoplasm as part of the ribosomal complex, mutations in this gene are associated with Diamond-Blackfan anemia, suggesting a non-ribosomal function for the protein in erythropoietic differentiation. RPS19 protein is also known to interact with fibroblast growth factor-2 (see, e.g., Soulet et al., *Biochem. Biophys. Res. Commun.* (2001); 289:591-596). Increased expression of RPS19 has been associated with some cancers, but the role of RPS19 in cancer development is unknown. RPL34 (60S Ribosomal protein L34) is a ribosomal protein that is a component of the 60S subunit and is located in the cytoplasm. Expression of the gene encoding the RPL34 protein is known to be regulated by c-MYC and has been shown to have increased expression in primary invasive and metastatic breast cancer cells and colorectal cancer cells (see, e.g., Zucchi et al., *Proc. Nat'l Acad. Sci.*, (2004); 101:18147-18152; Sjoblom, et. al. *Science*, (2006) 314:268-274).

Certain nucleic acid-binding proteins, such as RMB6 and HEMK1 have also been associated with certain cancers when misregulated and/or mutated. RBM6 (RNA binding protein 6) is a cytosolic protein that binds to poly-G homopolymers in vitro, but its function in vivo is not currently known. The protein thought to be phosphorylated (potentially by ATM or ATR) in its active form. The gene encoding the protein, without being bound by theory, is located in a portion of the genome, modifications of which are associated with cancerous transformation, such as lung carcinomas. Additionally, translocations of the gene which result in aberrant fusion proteins have been reported to be associated with cancer cells (see, e.g., Gu et al., *Blood*, (2007); 110:323-333). The human HEMK1 (HEMK methyltransferase family protein 1) protein is an S-adenosylmethionine-dependent methyltransferase and is also thought to bind nucleic acids. HEMK1 is considered a tumor-suppressor, misregulation of which is associated with various cancers, including prostate cancer, pancreatic cancer and liver cancer (see, e.g., U.S. Pat. App. Pub. No. 2008/0213791).

Thus one or more polypeptide probes, such as a fragment of a protein encoded by a gene, or a polypeptide encoded by a sequence of a UTR region of a gene, such as a gene listed in Tables 1, 2, 3 or 4, can be used to detect one or more antibodies, such as autoantibodies, from a sample from a subject. In one embodiment, the polypeptide probe comprises a polypeptide sequence selected from SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof. In another embodiment, the polypeptide probe comprises a polypeptide sequence encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof. In yet another embodiment, the polypeptide probe comprises the full-length or a fragment of a protein that is encoded by SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

In one embodiment, a polypeptide probe is a fragment of a protein encoded by CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, or Deaminase Domain, or may be a polypeptide encoded by a UTR sequence of the gene, such as the 5' or 3' UTR sequence of CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, or Deaminase Domain. In one embodiment, a polypeptide probe can be a fragment of a protein encoded by FAM53B, 5'UTR BMI1, RP3-323M22, or LOC388789. In one embodiment, a polypeptide probe comprises a peptide sequence, or fragment thereof, such as those listed in Tables 1, 2, 3, and 4. The polypeptide probe can comprise SEQ ID NO: 2, 5, 9, 11, 14, 56, 57, 58, 59, 60, 61, 62, 63, 64, 65, 66, 67, 68, 69, or a fragment thereof, or a fragment thereof. In another embodiment, the polypeptide probe comprises a polypeptide encoded by SEQ ID NO: 16, 19, 23, 25, 28, 70, 71, 72, 73, 74, 75, 76, 77, 78, 79, 80, 81, 82, 83, 84, or a fragment thereof.

In another embodiment, a polypeptide probe is a fragment of a protein encoded by DCHS1, CEP164, KBTBD6, RPS19, RPL34, RNA binding protein 6, or Hemk1, or may be a polypeptide encoded by a UTR sequence of the gene, such as the 5' or 3' UTR sequence of DCHS1, CEP164, KBTBD6, RPS19, RPL34, RNA binding protein 6, or Hemk1. In one embodiment, a polypeptide probe can be a fragment of a protein encoded by eIF4G1, 5'UTR BMI1, BRD2, RP3-323M22, SFRS14, or LOC388789. In one embodiment, a polypeptide probe comprises a peptide sequence, or fragment thereof, such as those listed in Tables 1 and 2. The polypeptide probe can comprise SEQ ID NO: 1, 2, 3, 4, 5, 6, 7, 8, 9, 10, 11, 12, 13 or 14, or a fragment thereof. In another embodiment, the polypeptide probe comprises a polypeptide encoded by SEQ ID NO: 15, 16, 17, 18, 19, 20, 21, 22, 23, 24, 25, 26, 27, 28, 29, 30, 31, 32, 33, 34, 35, 36, 37, 38, 39, 40, 41, or a fragment thereof.

Antibody Profiling Panel

Also provided herein is an antibody profiling panel. A panel as provided herein can be used to analyze one or more antibodies to a plurality of polypeptide probes, such as one or more autoantibodies. A panel allows for the simultaneous analysis of multiple antibodies, such as autoantibodies, to a plurality of polypeptide probes correlating with carcinogenesis and/or metastasis. For example, a panel can include markers identified as correlating with cancerous tissue, metastatic cancer, localized cancer that is likely to metastasize, pre-cancerous tissue that is likely to become cancerous, and pre-cancerous tissue that is not likely to become cancerous. Depending on the subject, panels may be analyzed alone or in combination in order to provide the best possible diagnosis and/or prognosis.

In one embodiment, an antibody profiling panel can comprise a plurality of polypeptide probes, wherein one or more of the probes is capable of binding an antibody. In another embodiment an antibody profiling panel can comprise a plurality of probes, wherein one or more of the probes is capable of binding an antibody that targets a foreign antigen. In another embodiment an antibody profiling panel can comprise a plurality of probes, wherein each of the probes is capable of binding an autoantibody.

In one embodiment, an antibody profiling panel comprises 2-100 probes, 50-200 probes, 100-500 probes 200-750 probes, 200-1000 probes, 2-5,000 probes or 2-10,000 probes. In one embodiment, an antibody profiling panel comprises at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 polypeptide probes. In another embodiment, an antibody profiling panel comprises at least about 50, 100, 150, 200, 250, 500, 750, 1000, 5000, 10,000, 15,000, 20,000, 25,000, 30,000, 40,000, 50,000, 60,000, 70,000, 75,000, or 100,000 polypeptide probes. In one embodiment, the probes are polypeptide probes. In another embodiment, the probes are molecules that mimic an epitope bound by a particular antibody.

An antibody profiling panel can comprise at least 2, 3, 4, 5, 6, 7, 8, 9, 10, 11, 12, 13, or 14 polypeptide probes, wherein the polypeptide probes are a fragment of a protein encoded by a gene, or a fragment encoded by a sequence of a UTR region of a gene, such as genes listed in Tables 1, 2, 3, or 4. In one embodiment, the polypeptide probe comprises a polypeptide sequence selected from SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof. In another embodiment, the polypeptide probe comprises a polypeptide sequence encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof. In yet another embodiment, the polypeptide probe comprises the full-length or a fragment of a protein that is encoded by SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

In one embodiment, an antibody profiling panel comprises a plurality of polypeptide probes, wherein at least a subset of the polypeptide probes is a fragment of a protein encoded by a gene, or a fragment encoded by a sequence of a UTR region of a gene, wherein the gene is CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, or Deaminase Domain. In one embodiment, the polypeptide probe can comprise a fragment of a protein encoded by a gene, or a fragment encoded by a sequence of a UTR region of a gene, wherein the gene is FAM53B, 5'UTR BMI1, RP3-323M22, or LOC388789.

In another embodiment, an antibody profiling panel comprises a plurality of polypeptide probes, wherein at least a subset of the polypeptide probes is a fragment of a protein encoded by a gene, or a fragment encoded by a sequence of a UTR region of a gene, wherein the gene is DCHS1, CEP164, KBTBD6, RPS19, RPL34, RNA binding protein 6, or Hemk1. In one embodiment, the polypeptide probe can comprise a fragment of a protein encoded by a gene, or a fragment encoded by a sequence of a UTR region of a gene, wherein the gene is eIF4G1, 5'UTR BMI1, BRD2, RP3-323M22, SFRS14, or LOC388789.

In one embodiment, an antibody profiling panel comprises a plurality of polypeptide probes, wherein at least a subset of the polypeptide probes is a peptide sequence, or fragment thereof, as listed in Tables 1, 2, 3, or 4. In one embodiment, an antibody profiling panel comprises a plurality of polypeptide probes, wherein at least a subset of the polypeptide probes comprises a polypeptide sequence selected from SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof. In another embodiment, an antibody profiling panel comprises a plurality of polypeptide probes, wherein at least a subset of the polypeptide probes comprises a polypeptide sequence encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof. In yet another embodiment, the polypeptide probe comprises the full-length or a fragment of a protein that is encoded by SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

In another embodiment, an antibody profiling panel comprises a plurality of polypeptide probes, wherein at least a subset of the polypeptide probes comprises SEQ ID NO: 2, 5, 9, 11, 14, 56, 57, 58, 59, 60, 61, 62, 63, 64, 65, 66, 67, 68, 69, or a fragment thereof, or a fragment thereof. In another embodiment, an antibody profiling panel comprises a plurality of polypeptide probes, wherein at least a subset of the polypeptide probes is encoded by SEQ ID NO: 16, 19, 23, 25, 28, 70, 71, 72, 73, 74, 75, 76, 77, 78, 79, 80, 81, 82, 83, 84, or a fragment thereof.

In one embodiment, an antibody profiling panel comprises a plurality of polypeptide probes, wherein at least a subset of the polypeptide probes comprises SEQ ID NO: 1, 2, 3, 4, 5, 6, 7, 8, 9, 10, 11, 12, 13 or 14, or a fragment thereof. In another embodiment, an antibody profiling panel comprises a plurality of polypeptide probes, wherein at least a subset of the polypeptide probes is encoded by SEQ ID NO: 15, 16, 17, 18, 19, 20, 21, 22, 23, 24, 25, 26, 27, 28, 29, 30, 31, 32, 33, 34, 35, 36, 37, 38, 39, 40, 41, or a fragment thereof.

In one embodiment, an antibody profiling panel can also comprise one or more polypeptide probes of the protein PSA, or fragment of PSA, in combination with one or more of the polypeptide probes discussed herein.

In one embodiment, an antibody profiling panel can comprise polypeptide probes including a full-length protein or fragment of PSA and one or more polypeptide probes comprising SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof. In another embodiment, an antibody profiling panel can comprise polypeptide probes including a full-length protein or fragment of PSA and one or more polypeptide probes comprising a polypeptide sequence encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof. In yet another embodiment, the polypeptide probe comprises the full-length or a fragment of a protein that is encoded by SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

In another embodiment, an antibody profiling panel can comprise polypeptide probes including a full-length protein or fragment of PSA and a full-length protein encoded by a gene, fragment of a protein encoded by a gene, or a fragment encoded by a sequence of a UTR region of a gene, wherein the gene is CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, or Deaminase Domain.

In yet another embodiment, an antibody profiling panel can comprise a plurality of polypeptide probes, wherein the probes include a full-length protein or fragment of PSA and a full-length protein encoded by a gene, fragment of a protein encoded by a gene, or a fragment encoded by a sequence of a UTR region of a gene, wherein the gene is FAM53B, 5'UTR BMI1, RP3-323M22, or LOC388789.

In another embodiment, an antibody profiling panel can comprise polypeptide probes including a full-length protein or fragment of PSA and a full-length protein encoded by a gene, fragment of a protein encoded by a gene, or a fragment encoded by a sequence of a UTR region of a gene, wherein the gene is DCHS1, CEP164, KBTBD6, RPS19, RPL34, RNA binding protein 6, or Hemk1. In yet another embodiment, an antibody profiling panel can comprise a plurality of polypeptide probes, wherein the probes include a full-length protein or fragment of PSA and a full-length protein encoded by a gene, fragment of a protein encoded by a gene, or a fragment encoded by a sequence of a UTR region of a gene, wherein the gene is eIF4G1, 5'UTR BMI1, BRD2, RP3-323M22, SFRS14, or LOC388789.

In another embodiment, an autoantibody profiling panel can comprise a plurality of polypeptide probes, wherein the probes includes a full-length protein or fragment of PSA and one or probes comprising a peptide sequence, or fragment thereof, as listed in Tables 1, 2, 3 and 4. In one embodiment, an autoantibody profiling panel can comprise a plurality of polypeptide probes, wherein the probes includes a full-length protein or fragment of PSA and one or more probes comprising SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof. In another embodiment, an autoantibody profiling panel can comprise a plurality of polypeptide probes, wherein the probes includes a full-length protein or fragment of PSA and one or more probes comprising a polypeptide sequence encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof. In yet another embodiment, an autoantibody profiling panel can comprise a plurality of polypeptide probes, wherein the probes includes a full-length protein or fragment of PSA and one or more probes comprising the full-length or a fragment of a protein that is encoded by SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

In another embodiment, an autoantibody profiling panel can comprise a plurality of polypeptide probes, wherein the probes includes a full-length protein or fragment of PSA and one or more probes comprising SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or a fragment thereof.

In another embodiment, an autoantibody profiling panel can comprise a plurality of polypeptide probes, wherein the probes includes a full-length protein or fragment of PSA and one or more probes comprising SEQ ID NO: 2, 5, 9, 11, 14, 56, 57, 58, 59, 60, 61, 62, 63, 64, 65, 66, 67, 68, 69, or a fragment thereof, or a fragment thereof; or a polypeptide sequence encoded by a sequence selected from SEQ ID NOs. 16, 19, 23, 25, 28, 70, 71, 72, 73, 74, 75, 76, 77, 78, 79, 80, 81, 82, 83, 84, or a fragment thereof.

In one embodiment, a PSA polypeptide probe can be combined with any two or more of the polypeptide probes described herein, such as a polypeptide probe derived from a protein encoded by a gene, fragment of a protein encoded by a gene, or a fragment encoded by a sequence of a UTR region of a gene, wherein the gene is CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, Deaminase Domain, FAM53B, 5'UTR BMI1, RP3-323M22, or LOC388789.

In another embodiment, a PSA polypeptide probe can be combined with any two or more of the polypeptide probes described herein, such as a polypeptide probe derived from a protein encoded by a gene, fragment of a protein encoded by a gene, or a fragment encoded by a sequence of a UTR region of a gene, wherein the gene is DCHS1, CEP164, KBTBD6, RPS19, RPL34, RNA binding protein 6, Hemk1, eIF4G1, 5'UTR BMI1, BRD2, RP3-323M22, SFRS14, or LOC388789.

In yet another embodiment, a PSA polypeptide probe can be combined with at least 3, 4, 5, 6, 7, 8, 9, 10, 11, 12, 13 or 14 of polypeptide probes disclosed herein, such as listed in Tables 1, 2, 3, and 4. In one embodiment, a polypeptide probe comprises SEQ ID NO: 2, 5, 9, 11, 14, 56, 57, 58, 59, 60, 61, 62, 63, 64, 65, 66, 67, 68, 69, or a fragment thereof, or a fragment thereof. In one embodiment, a polypeptide probe comprises SEQ ID NO: 1, 2, 3, 4, 5, 6, 7, 8, 9, 10, 11, 12, 13 or 14, or a fragment thereof. In another embodiment, a polypeptide probe comprises SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof.

In another embodiment, a polypeptide probe comprises a polypeptide encoded by SEQ ID NO: 15, 16, 17, 18, 19, 20, 21, 22, 23, 24, 25, 26, 27, 28, 29, 30, 31, 32, 33, 34, 35, 36, 37, 38, 39, 40, 41, or a fragment thereof. In another embodiment, a polypeptide probe comprises a polypeptide encoded by SEQ ID NO: 16, 19, 23, 25, 28, 70, 71, 72, 73, 74, 75, 76, 77, 78, 79, 80, 81, 82, 83, 84, or a fragment thereof. In yet another embodiment a polypeptide probe comprises a polypeptide encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof.

In one embodiment, a polypeptide probe disclosed herein is attached to a substrate (e.g., glass slide chip or nanowell chip). A polypeptide probe can be directly or indirectly attached to the substrate. In one embodiment, a polypeptide probe is attached to a substrate via a phage. The substrate can be any physically separable solid to which a polypeptide probe can be directly or indirectly attached including, but not limited to, surfaces provided by microarrays and wells, particles such as beads, columns, optical fibers, wipes, glass and modified or functionalized glass, quartz, mica, diazotized membranes (paper or nylon), polyformaldehyde, cellulose, cellulose acetate, paper, ceramics, metals, metalloids, semiconductive materials, quantum dots, coated beads or particles, other chromatographic materials, magnetic particles; plastics (including acrylics, polystyrene, copolymers of styrene or other materials, polypropylene, polyethylene, polybutylene, polyurethanes, TEFLON™, etc.), polysaccharides, nylon or nitrocellulose, resins, silica or silica-based materials including silicon and modified silicon, carbon, metals, inorganic glasses, plastics, ceramics, conducting polymers (including polymers such as polypyrrole and polyindole); micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, or other fibrous or stranded polymers.

The polypeptide probe can bound to a planar surface or to a particle, such as a bead or microsphere. In one embodiment, the polypeptide probe is attached to a bead. The bead can be a polystyrene, brominated polystyrene, polyacrylic acid, polyacrylonitrile, polyacrylamide, polyacrolein, polydimethylsiloxane, polybutadiene, polyisoprene, polyurethane, polyvinyl acetate, polyvinylchloride, polyvinylpyridine, polyvinylbenzylchloride, polyvinyltoluene, polyvinylidene chloride, polydivinylbenzene, polyglycidylmethacrylate, polymethylmethacrylate, or copolymers, blends, composites, or combination thereof. The bead can have a diameter of between about 1 nm-1000 μm, 1 nm-500 μm, 5 nm-500 μm, or 10 nm-100 μm. In one embodiment, the bead has a diameter of between about 10 nm and 100 μm. In yet another embodiment, the bead has a diameter of less than about 1000 μm, 500 μm, 400 μm, 300 μm, 200 μm, or 100 μm.

In one embodiment, the bead is labeled or stained with more than one dye, such as at least 2, 3, 4, 5, 6, 7, 8, 9, or 10 different dyes. In one embodiment, the bead is labeled or stained with two dyes. In another embodiment, the two dyes are hydrophobic. In another embodiment, the two dyes are fluorescent dyes, such as squaric acid-based dyes. In yet another embodiment, the squaric acid-based dyes are selected from cyclobutenedione derivatives, symmetrical and unsymmetrical squaraines, substituted cephalosporin compounds, fluorinated squaraine compositions, alkylalkoxy squaraines, or squarylium compounds. In another embodiment, the squaric acid-based dyes are selected from a red fluorescent dye and an orange fluorescent dye, such as the red fluorescent dye comprising 1,3-bis(1,3-dihydro-1,3,3-trimethyl-2H-indol-2-ylidene)methyl]-2,4-dihydroxycyclobutenediylium, bis(inner salt) and the orange fluorescent dye comprising 2-(3,5-dimethylpyrrol-2-yl)-4-(3,5-dimethyl-2H-pyrrol-2-ylidene)-3-hydroxy-2-cyclobuten-1-one.

In one embodiment, the substrate is coated using passive or chemically-derivatized coatings with any number of materials, including polymers, such as dextrans, acrylamides, gelatins or agarose. Such coatings can facilitate the use of the array with a biological sample.

Cancer Screening

A presence of an immune response to a specific protein expressed in cancerous cells can be indicative of a presence of cancer. Accordingly, the present invention provides a method (e.g., diagnostic or screening method) for detecting a presence of an antibody, such as an autoantibody, to a tumor or tumor-associated antigen. In one embodiment, the presence of an antibody in cancerous but not cancerous cells is indicative of the presence of cancer. In one embodiment, the antibody is an antibody to a tumor antigen.

A method or composition disclosed herein can find utility in the diagnosis, screening, or characterization of a cancer. In one embodiment, a presence of an antibody, such as an autoantibody, to a specific protein can be indicative of a cancer. In another embodiment, detection of an antibody in a sample, such as an autoantibody, can be indicative of a specific stage or sub-type of the same cancer. The information obtained by detecting an antibody as described herein can be used to determine a prognosis or theranosis, wherein an appropriate course of treatment can be determined. In another embodiment, a subject with a specific antibody or stage of cancer can respond differently to a given treatment than individuals lacking the antibody. The information obtained from a method disclosed herein can thus provide for the personalization of diagnosis and treatment.

In one embodiment, a cancer is characterized by detecting the level or presence or absence of an antibody, such as an autoantibody, in a sample. The cancer can be, but is not limited to, breast cancer, ovarian cancer, lung cancer, colon cancer, hyperplastic polyp, adenoma, colorectal cancer, high grade dysplasia, low grade dysplasia, prostatic hyperplasia, prostate cancer, melanoma, pancreatic cancer, brain cancer (such as a glioblastoma), hematological malignancy, hepatocellular carcinoma, cervical cancer, endometrial cancer, head and neck cancer, esophageal cancer, gastrointestinal stromal tumor (GIST), renal cell carcinoma (RCC) or gastric cancer. The colorectal cancer can be CRC Dukes B or Dukes C-D. The hematological malignancy can be B-Cell Chronic Lymphocytic Leukemia, B-Cell Lymphoma-DLBCL, B-Cell Lymphoma-DLBCL-germinal center-like, B-Cell Lymphoma-DLBCL-activated B-cell-like, and Burkitt's lymphoma. The cancer can also be a premalignant condition, such as Barrett's Esophagus.

In one embodiment, a method for screening or characterizing a prostate cancer is provided. In one embodiment, the method can comprise detecting in a sample obtained from a subject a presence and/or level of one or more autoantibodies to one or more polypeptide probes comprising a polypeptide probe is a fragment of a protein encoded by a gene, or a fragment encoded by a sequence of a UTR region of a gene, wherein the gene is CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, Deaminase Domain, FAM53B, 5'UTR BMI1, RP3-323M22, or LOC388789. A polypeptide probe can also comprise a polypeptide sequence, or a fragment thereof, selected from Table 1, 2, 3 and 4, such as a polypeptide probe comprising polypeptide probe comprises SEQ ID NO: 1, 2, 3, 4, 5, 6, 7, 8, 9, 10, 11, 12, 13 or 14, or a fragment thereof, or a polypeptide probe comprising a polypeptide encoded by SEQ ID NO: 15, 16, 17, 18, 19, 20, 21, 22, 23, 24, 25, 26, 27, 28, 29, 30, 31, 32, 33, 34, 35, 36, 37, 38, 39, 40, 41, or a fragment thereof. A polypeptide probe can also comprise SEQ ID NO: 12, 5, 9, 11, 14, 56, 57, 58, 59, 60, 61, 62, 63, 64, 65, 66, 67, 68, 69, or a fragment thereof, or a fragment thereof, or a polypeptide encoded by SEQ ID NO: 16, 19, 23, 25, 28, 70, 71, 72, 73, 74, 75, 76, 77, 78, 79, 80, 81, 82, 83, 84, or a fragment thereof.

In one embodiment, the method can comprise detecting in a sample obtained from a subject a presence and/or level of one or more autoantibodies to one or more polypeptide probes comprising a polypeptide probe is a fragment of a protein encoded by a gene, or a fragment encoded by a sequence of a UTR region of a gene, wherein the gene is DCHS1, CEP164, KBTBD6, RPS19, RPL34, SFRS14, RNA binding protein 6, Hemk1, eIF4G1, 5'UTR BMI1, BRD2, RP3-323M22, SFRS14, or LOC388789. A polypeptide probe can also comprise a polypeptide sequence, or a fragment thereof, selected from Table 1 or Table 2, such as a polypeptide probe comprising SEQ ID NO: 1, 2, 3, 4, 5, 6, 7, 8, 9, 10, 11, 12, 13 or 14, or a fragment thereof, or a polypeptide probe encoded by SEQ ID NO: 15, 16, 17, 18, 19, 20, 21, 22, 23, 24, 25, 26, 27, 28, 29, 30, 31, 32, 33, 34, 35, 36, 37, 38, 39, 40, 41, or a fragment thereof.

In yet another embodiment, the method can comprise detecting in a sample obtained from a subject a presence and/or level of one or more autoantibodies to one or more polypeptide probes comprising SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof, or a fragment thereof; or polypeptide probe encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof; or polypeptide probe comprising full-length or a fragment of a protein that is encoded by SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

Depending on the results, a cancer (or absence of cancer) can be characterized. For example, in a sample from a subject a presence or level of DCHS1, CEP164 and/or RPS19 autoantibodies is detected, indicating a presence of prostate cancer in the subject. Alternately, a method further comprises detecting a presence or level of one or more autoantibodies to one or more polypeptide probe comprising a fragment of eIF4G1, 5'UTR BMI1, BRD2, RP3-323M22, SFRS14, or LOC388789. The fragment of a protein encoded by eIF4G1, 5'UTR BMI1, BRD2, RP3-323M22, SFRS14, or LOC388789 can comprise a polypeptide sequence selected from Table 2.

A method disclosed herein can comprise detecting a plurality of antibodies, such as through the detection of binding of one or more antibodies that bind to a plurality of polypeptide probes. In one embodiment, the antibodies are autoantibodies. In another embodiment, the antibodies are antibodies to foreign antigens. In one embodiment, the method comprises detecting in a sample one or more antibodies that binds to a panel of polypeptide probes, wherein the panel comprises 2-100 probes, 50-200 probes, 100-500 probes 200-750 probes, 200-1000 probes, 2-5,000 probes or 2-10,000 probes. In another embodiment, the panel of polypeptide probes comprises at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 polypeptide probes. In another embodiment, the panel comprises at least about 50, 100, 150, 200, 250, 500, 750, 1000, 5000, 10,000, 15,000, 20,000, 25,000, 30,000, 40,000, 50,000, 60,000, 70,000, 75,000, or 100,000 polypeptide probes. In one embodiment, the panels comprises a plurality of polypeptide probes, wherein a subset of the probes comprise fragments of the same full-length protein, such that autoantibodies to different epitopes bind to the different probes and indicate a presence of an immune response, or antibody, to the full-length protein.

A panel comprising multiple polypeptide probes allow for the simultaneous analysis of multiple markers correlating with carcinogenesis and/or metastasis. In one embodiment, a panel includes markers identified as correlating with cancerous tissue, metastatic cancer, localized cancer that is likely to metastasize, pre-cancerous tissue that is likely to become cancerous, pre-cancerous tissue that is not likely to become cancerous, or any combination thereof. Depending on the subject, a panel can be analyzed alone or in combination in order to provide a diagnosis, prognosis, or theranosis. One or more markers for inclusion on a panel can be selected by screening for their diagnostic, prognostic, or theranostic value.

Any of the proteins listed in Tables 1, 2, 3 or 4, or proteins encoded by the genes listed in Tables 1, 2, 3 or 4, in any combination, can be utilized to detect a presence of an antibody, such as an autoantibody, in a subject. In one embodiment, the protein is encoded SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

In one embodiment, detection of an autoantibody to a protein encoded by a gene, a fragment encoded by a sequence of a UTR region of a gene, or fragment of a protein encoded by a gene, wherein the gene is CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, Deaminase Domain, FAM53B, 5'UTR BMI1, RP3-323M22, or LOC388789, or any combination thereof, is indicative of a presence of prostate cancer in a subject. In another embodiment, any combination of two or more proteins (e.g., cancer markers) or fragments thereof is used to detect one or more autoantibodies (e.g., a panel consisting of one or more full-length or fragments of the polypeptides listed in Tables 1, 2, 3, and/or 4).

In another embodiment, detection of an autoantibody to a protein encoded by a gene, a fragment encoded by a sequence of a UTR region of a gene, or fragment of a protein encoded by a gene, wherein the gene is CEP164, KBTBD6, RPS19, RPL34, RNA binding protein 6, Hemk1, eIF4G1, 5'UTR BMI1, BRD2, RP3-323M22, SFRS14, LOC388789, or any combination thereof, is indicative of a presence of prostate cancer in a subject. In another embodiment, any combination of two or more proteins (e.g., cancer markers) or fragments thereof is used to detect one or more autoantibodies (e.g., a panel consisting of one or more full-length or fragments of the polypeptides listed in Tables 1 and 2).

In one embodiment, the method comprises detecting one or more antibodies that bind to at least 1, 2, 3, 4, 5, 6, 7, 8, 9, 10, 11, 12, 13, or 14 polypeptide probes, wherein the polypeptide probes are full-length or fragments of proteins encoded by the genes listed in Tables 1, 2, 3, and/or 4, or polypeptides encoded by the UTR sequence of the gene. In one embodiment, the antibody profiling panel comprises a plurality of polypeptide probes, wherein one or more polypeptide probes is a protein or fragment of a protein encoded by CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, Deaminase Domain, FAM53B, 5'UTR BMI1, RP3-323M22, or LOC388789, or any combination thereof. In another embodiment, the antibody profiling panel comprises a plurality of polypeptide probes, wherein one or more polypeptide probes is a protein or fragment of a protein encoded by DCHS1, CEP164, KBTBD6, RPS19, RPL34, RNA binding protein 6, Hemk1, eIF4G1, 5'UTR BMI1, BRD2, RP3-323M22, SFRS14, LOC388789, or any combination thereof.

The cancer can be characterized with increased accuracy, such as with increased specificity, sensitivity, or both. The sensitivity can be determined by: (number of true positives)/(number of true positives+number of false negatives), whereas the specificity can be determined by: (number of true negatives)/(number of true negatives+number of false positives).

In one embodiment, the cancer can be characterized (e.g., detected, prognosed, etc.) with at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% sensitivity. In another embodiment, the cancer can be characterized (e.g., detected, prognosed, etc.) with at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% specificity.

Specificity or sensitivity of detection can be altered by altering the polypeptide probe make-up of a panel. In one embodiment, sensitivity of a diagnostic, prognostic, or theranostic assay (e.g., an antibody detection assay, such as an autoantibody detection assay) can be increased by increasing the number of probes, increasing the diversity of probes (e.g, utilizing probes comprising distinct epitopes from the same and/or different markers), or tailoring the probes to a particular subject or cancer to be diagnosed/prognosed. Furthermore, the confidence level for determining the specificity, sensitivity, or both, may be with at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% confidence.

A method and system disclosed herein can also comprise detecting a plurality of antibodies, such as through the detection of antibodies binding to a plurality of polypeptide probes, and characterizing or screening for a cancer with increased or greater specificity as compared to a characterization based on detection of antibodies that bind to less than the plurality of polypeptide probes. In one embodiment, the antibodies are autoantibodies. In another embodiment, the antibodies are to foreign antigens.

Two or more polypeptide probes can be used to diagnose a particular cancer. For example, a cancer can be diagnosed by measuring the binding of autoantibodies to two polypeptide probe. The number of polypeptide useful for diagnosing a cancer includes, but is not limited to, 2, 3, 4, 5, 6, 7, 8, 9, 10, 11, 12, 13, 14, 15, 16, 17, 18, 19, and 20 polypeptide probes. In another embodiment, prostate cancer is diagnosed with 5 or more polypeptide probes. In one embodiment, prostate cancer is diagnosed with 5 polypeptide probes, which provides a diagnosis that has a higher sensitivity as compared to using less than the 5 polypeptide probes. In another embodiment, prostate cancer is diagnosed with 10 or more polypeptide probes. In another embodiment, a prostate cancer is diagnosed with 10 polypeptide probes, which provides a diagnosis that has a higher specificity as compared to using less than the 10 polypeptide probes.

Antibody Detection

The level, presence or absence of an antibody can be determined by detecting the binding of one or more autoantibodies to a polypeptide probe. Detection of an antibody can be either quantitative or qualitative. For quantitative assays, the amount of antibody detected can be compared to a control or reference to determine whether an antibody is overexpressed or underexpressed in a sample. For example, the control or reference can be a normal sample or a sample from a known disease state, such as a cancer sample.

Antibody binding to a polypeptide probe can be detected by techniques known in the art, such as, but not limited to, radioimmunoassay, ELISA (enzyme-linked immunosorbant assay), “sandwich” immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays. Any of the assays used can be quantitative or qualitative, as desired.

Detection of an antibody bound to a polypeptide probe can be detected using labeling technology. For example, one or more antibodies in a sample collected from a subject to be tested can be directly labeled (e.g., with a fluorescent or radioactive label) and exposed to a polypeptide probe or probe panel. Detection of a signal from the interaction can be achieved using methodology appropriate to the type of label used (e.g., fluorescent microscopy can be used to detect binding of a fluorescently labeled autoantibody to a polypeptide probe). In one embodiment, an autoantibody is detected by detecting binding of a labeled secondary antibody or other antibody-binding reagent which specifically binds to the antibody bound to the polypeptide probe (e.g., a “sandwich immunoassay”). Many methods are known in the art for detecting binding in an immunoassay and are within the scope of the present invention. In one embodiment, the immunoassay described in U.S. Pat. Nos. 5,599,677, 5,672,480, or both, each of which is herein incorporated by reference, is used.

In one embodiment, automation is utilized to detect binding of one or more autoantibodies to a polypeptide probe or probe panels. Methods for the automation of immunoassays include those described in U.S. Pat. Nos. 5,885,530, 4,981,785, 6,159,750, and 5,358,691, each of which is herein incorporated by reference. Analysis and/or presentation of results can also be automated. In one embodiment, a computer with software that analyzes raw data and generates a prognosis, diagnosis, or theranosis based on the level, presence or absence of antibody binding to one or more polypeptide probes is used. A computer-based analysis program can be used to translate the raw data generated by the detection assay (e.g., a presence, absence, or amount of antibody binding to one or more polypeptide probes) into data of predictive value for a clinician. The clinician can access the predictive data using any suitable means. In one embodiment, the data is transmitted over a network. In another embodiment, the data is accessible by a clinician.

Any method capable of receiving, processing, and transmitting the information to and from a laboratory conducting the assay, medical personnel, and a subject can be used. In one embodiment, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. In one embodiment, the sample comprises a tissue or other biological sample and the subject visits a medical center to have the sample obtained and sent to the profiling center. In another embodiment, a subject collects the sample themself (e.g., a buccal swab) and directly sends it to a profiling center. In another embodiment, the sample comprises previously determined biological information. The information can be directly sent to the profiling service by the subject (e.g., an information card containing the information may be scanned by a computer and the data transmitted to a computer of the profiling center using an electronic communication system). Upon being received by the profiling service, a sample can be processed and a profile produced (i.e., antibody level, presence or absence of antibody). A profile generated can be specific for the diagnostic, prognostic, or theranostic information desired for a subject. In one embodiment, a sample from a subject is analyzed for a presence or expression level of one or more antibodies to one or more proteins encoded by a gene, fragment of one or more proteins encoded by a gene, or fragment encoded by aUTR region of a gene, wherein the gene is CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, Deaminase Domain, FAM53B, 5'UTR BMI1, RP3-323M22, or LOC388789. In one embodiment, the antibodies are autoantibodies. In another embodiment, a sample from a subject is analyzed for a presence or expression level of one or more antibodies to one or more proteins encoded by a gene, fragment of one or more proteins encoded by a gene, or fragment encoded by aUTR region of a gene, wherein the gene is DCHS1, CEP164, KBTBD6, RPS19, RPL34, RNA binding protein 6, Hemk1, eIF4G1, BMI1, BRD2, RP3-323M22, SFRS14, or LOC388789. In one embodiment, the antibodies are autoantibodies.

Profile data can be prepared in a format suitable for interpretation by a treating clinician. In one embodiment, rather than providing raw expression data, the prepared format represents a diagnosis, screening or risk assessment (e.g., likelihood of metastasis or PSA failure or the development of high prostate specific antigen levels in a patient following prostate cancer therapy (e.g., surgery)) for the subject, along with recommendations for particular treatment options. The data can be displayed to the clinician by any suitable method. In one embodiment, the profiling service generates a report that is printed for the clinician (e.g., at the point of care). In another embodiment, the report is displayed to the clinician on a computer monitor.

In one embodiment, the information is first analyzed at the point of care or at a regional facility. The raw data is then sent to a central processing facility for further analysis. In one embodiment, further analysis comprises converting the raw data to information useful for a clinician or subject, such as a patient. The central processing facility can provide the advantage of privacy (all data is stored in a central facility with uniform security protocols), speed, and uniformity of data analysis. The central processing facility can also control the fate of the data following treatment of a subject. In one embodiment, using an electronic communication system, the central facility provides data to the clinician, the subject, researchers, or any other individual. In one embodiment, a subject is able to directly access the data using the electronic communication system. In another embodiment, a subject chooses further intervention or counseling based on the result. In one embodiment, the data is used for research use. The data can be used to further optimize the inclusion or elimination of markers as useful indicators of a particular condition or stage of disease.

Antibody Test

The detection of one or more antibodies from a sample, such as described herein, can be used in conjunction with one or more other tests used for detecting or screening for cancer. The antibody detection can be used prior to, concurrent with, or subsequent to one or more other tests. In one embodiment, a genetic test for a mutation or expression level of one or more genes can be used in conjunction with determining the antibody profile of a subject.

Antibody detection can provide a non-invasive, inexpensive means for detecting or screening for a cancer. Thus, in one embodiment, the detection of a level, presence or absence of one or more antibodies can be used to determine whether a second sample or additional analysis of a sample from a subject is to be performed. In one embodiment, after detecting an expression level of one or more antibodies of sample obtained from subject to one or more polypeptide probes comprising a fragment of a protein encoded by, or a polypeptide encoded by a UTR sequence of, CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, Deaminase Domain, FAM53B, 5'UTR BMI1, RP3-323M22, or LOC388789, a biopsy can be recommended for the subject. In another embodiment, after detecting an expression level of one or more antibodies of sample obtained from subject to one or more polypeptide probes comprising a fragment of a protein encoded by, or a polypeptide encoded by a UTR sequence of, DCHS1, CEP164, KBTBD6, RPS19, RPL34, SFRS14, RNA binding protein 6, Hemk1, eIF4G1, 5'UTR BMI1, BRD2, RP3-323M22, SFRS14, or LOC388789, a biopsy can be recommended for the subject.

In another embodiment, an expression level for one or more antibodies from a subject can be detected, and based on the expression level of the one or more antibodies, the subject can be identified as suspected of having cancer. In one embodiment, the subject is characterized as having a high probability or likelihood of having cancer. Based on the detection or expression level of the one or more antibodies, a recommendation that a biopsy be obtained can be made for the subject. In another embodiment, if there is a lack of detection or expression of the one or more antibodies, further analysis is not recommended and a biopsy not be obtained. (see for example, FIG. 1, "Autoantibody Test I")

In another embodiment, prior to detecting one or more antibodies from a subject, the subject is suspected of having cancer. The subject can have had a genetic test for a mutation or gene expression analysis, image analysis (such as magnetic resonance imaging (MRI), positron emission tomography (PET) scan, computerized tomography (CT) scan, nuclear magnetic resonance (NMR)), or biopsy, and have inconclusive or uncertain results. Thus, prior to further analysis and treatment for a suspected cancer, the subject can seek further verification of their likelihood of having a cancer, or their diagnosis, prognosis, or theranosis of a cancer.

In one embodiment, an antibody profiling panel described herein can be used in conjunction with a separate test which determines a presence or level of PSA (e.g., a serum PSA test). In one embodiment, the panels is utilized to diagnose or prognose a presence of a cancer (e.g., prostate cancer) in a subject. In one embodiment, a subject is suspected of having prostate cancer based on their PSA level, age, or both. A subject can be male and over 30, 35, 40, 45, 50, 55, 60, 65, 70 or 75 years of age. In another embodiment, the subject is between 30-80, 40-75, 45-75, or 50-75 years of age. In another embodiment, the subject had a PSA blood test, digital rectal exam, or both. In yet another embodiment, the subject may have a PSA level of at least about 1.0, 1.5, 2.0, 2.5, or 4.0 ng/ml. The subject can have a PSA level of between about 1.0-15 ng/ml, 2.0-15 ng/ml, or 2.5-10 ng/ml.

In one embodiment, a biological sample from a subject, such as a subject with a PSA level greater than about 2.5 ng/ml, is contacted with one or more probes for an antibody, such as one or more probes for an autoantibody. Based on the expression level of the antibody, a biopsy for the subject can be recommended (see for example FIG. 1, "Autoantibody Test I"). The antibody test can comprise detecting one or more antibodies in a sample that bind to a polypeptide probe as described herein. In another embodiment, the antibody test is an autoantibody test.

In one embodiment, the antibody binds a polypeptide probe comprising SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof. In another embodiment, the antibody binds a polypeptide probe comprising a polypeptide sequence encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof. In yet another embodiment, the antibody binds a polypeptide probe comprising full-length or a fragment of a protein that is encoded by SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

In one embodiment, the antibody binds a polypeptide probe comprising a full-length or fragment of a protein encoded by, or a polypeptide encoded by a CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, Deaminase Domain, FAM53B, 5'UTR BMI1, RP3-323M22, or LOC388789. In one embodiment, a polypeptide probe comprises SEQ ID NO: 2, 5, 9, 11, 14, 56, 57, 58, 59, 60, 61, 62, 63, 64, 65, 66, 67, 68, 69, or a fragment thereof, or a fragment thereof. In another embodiment, a polypeptide probe comprises a polypeptide encoded by SEQ ID NO: 16, 19, 23, 25, 28, 70, 71, 72, 73, 74, 75, 76, 77, 78, 79, 80, 81, 82, 83, 84, or a fragment thereof.

In another embodiment, the antibody binds a polypeptide probe comprising a full-length or fragment of a protein encoded by, or a polypeptide encoded by a UTR of, DCHS1, CEP164, KBTBD6, RPS19, RPL34, RNA binding protein 6, Hemk1, eIF4G1, 5'UTR BMI1, BRD2, RP3-323M22, SFRS14, or LOC388789. In one embodiment, a polypeptide probe comprises SEQ ID NO: 1, 2, 3, 4, 5, 6, 7, 8, 9, 10, 11, 12, 13, 14, or a fragment thereof. In another embodiment, a polypeptide probe comprises a polypeptide encoded by SEQ ID NO: 15, 16, 17, 18, 19, 20, 21, 22, 23, 24, 25, 26, 27, 28, 29, 30, 31, 32, 33, 34, 35, 36, 37, 38, 39, 40, 41, or a fragment thereof.

If a biopsy is recommended and the biopsy is positive for a cancer such as prostate cancer, a biological sample obtained from the subject can be contacted with one or more probes for an antibody, which can be the same or different, as those used in deciding whether to obtain a biopsy. Based on the expression level of antibodies in the sample, a prognosis for the cancer can be provided. (see for example, FIG. 1, "Autoantibody Test II")

Thus, in one embodiment, a method of characterizing or screening for a cancer from a subject with a positive biopsy result is provided. In another embodiment, the subject has not yet provided a sample for detecting one or more antibodies. In yet another embodiment, the subject has provided an initial sample for detecting one or more antibodies and detection of the one or more antibodies is used in deciding whether a biopsy is obtained. Furthermore, in one embodiment, detection of one or more antibodies is used for a diagnosis, prognosis or theranosis of a cancer, such as prostate cancer. In one embodiment, the method comprises detecting an expression level for one or more antibodies, wherein the expression level of the one or more antibodies is indicative of the presence, absence, or stage of the cancer. In another embodiment, the indication is whether the cancer is aggressive or indolent.

In one embodiment, a cancer is classified based on the detection of one or more antibodies to one or more polypeptide probes disclosed herein. In one embodiment, the cancer is classified as aggressive or malignant. In another embodiment, the cancer is classified as indolent or benign. Furthermore, after classification, detection of one or more antibodies from a sample from the subject can be used to select a treatment or therapeutic for the cancer.

The present disclosure is not limited to the embodiments described above, but is capable of modification within the scope of the appended claims. Those skilled in the art will recognize, or be able to ascertain using no more than routine experimentation, many equivalents of the specific embodiments of the present disclosure described herein.

EXAMPLES

Example 1: Probe Selection

Construction of T7 Phage Display Prostate Cancer cDNA Library mRNA was isolated from total RNA following Novogen's Straight A's mRNA isolation protocol. Orient Expression cDNA synthesis and cloning system were used for the construction of T7 phage prostate cancer cDNA libraries.

To eliminate the 3' bias inherent in oilgo(dT)-primed libraries, two libraries were constructed using directional oligo(dT) primer and random primer in parallel. After amplification, these two libraries were combined in same amount of titer.

Enrichment of Cancer Specific T7 Phage Library.

Protein A/G agarose beads (Pierce Biotechnology, Rockford, Ill.) were used to purify IgGs from the serum of prostate cancer patients. To enhance the selection of epitopes binding to IgGs specifically associated with prostate cancer, a dual procedure was performed.

First, a pre-clearing step was used to remove nonspecific clones by pre-absorbing the phage epitope libraries onto purified IgGs from normal serum pool from 10 control men. Next, the pre-cleared phage libraries were selected onto the pool of IgGs purified from the serum of 6 localized prostate cancer patients. In essence protein-A/G agarose beads provide a purification of the serum of IgGs. Fifty µl protein-A/G agarose beads were placed into 1.5 ml eppendorf tube and washed two times with 1×PBS. Washed beads were blocked with 4% nonfat milk at 4° C. for 1 hr. The beads were then incubated at 4° C. with 15 µl of pooled control sera at 1:30 dilution with 4% nonfat milk. After at least 2 hrs of incubation, the beads were washed three times with 1×PBS and then incubated with phage library (~1010 phage particles) at 4° C. for at least 2 hrs. The mixture was centrifuged at 3000 rpm for 2 min. The beads with unspecifically bounded phage particles were discarded and the supernatant was collected for further immunoscreening.

Fifty µl fresh protein-A/G agarose beads were washed and blocked as same as above. The beads were then incubated at 4° C. for 3 hrs with 500 ml of PBS containing 15 ml patient sera pool at a 1:30 dilution. This amount of serum provides a three-fold molar excess of IgG to calculated number of protein-A/G binding capacity. The beads were washed three times with 1×PBS and then incubated with phage library supernatant from above allowed to react with the antibodies on the beads at 4° C. overnight. The mixture was centrifuged at 3000 rpm for 2 min and supernatant was discarded. The beads were then washed three times with 1×PBS.

To elute the bound phage 100 ml 1% SDS was used to strongly break up the antibody-antigen reaction without disrupting the T7 phage particles. The mixture of phage and elution buffer was incubated at room temperature for 10 min. The bound phages were removed from the beads by centrifugation at 8000 rpm for 8 min. Eluted phages were transferred to 10 ml BLT 5403 bacterial cells with OD600=0.6~0.8 for amplification. Four or five cycles of affinity selections and biopanning were carried out with amplification of phage particles after each biopanning.

High Throughput Epitope Detection Using Phage Microarrays.

Random phage colonies were picked up and amplified in 96-well plates. Fresh phage lysates were spotted onto on FAST™ nitrocellulose coated glass slides (Schleicher & Schuell, Keene, N.H.). Extra T7 empty phage spots were spotted in quadruplicate as negative reference for normalizing the signal value from different slides. The arrays were dried overnight at room temperature. Before processing with serum, the arrays were rinsed briefly in a 4% nonfat milk/PBS with 0.1% tween-20 to remove unbound phage, then transferred immediately to 4% nonfat milk/PBS as a blocking solution for 1 hr at room temperature. Without allowing the array to dry, 2 ml of PBS containing human serum and T7-tag antibody (Novagen) at a dilution of 1:500 and 1:5000 respectively was applied to the surface in a screw-top slide hybridization tube.

The arrays were incubated at room temperature for 1 hour, and then washed gently three times in PBS/0.1% Tween-20 solution 10 min each. All washes were performed at room temperature. After washing, the arrays were incubated with 2 ml of PBS containing Cy3-labeled goat anti-mouse antibody and Cy5-labeled goat anti-human antibody (Jackson ImmunoResearch) at a dilution of 1:5,000 for both for 1 hr in the dark. Three washes were performed using PBS/0.1% Tween-20 solution with 10 min each. The arrays were then dried using a stream of compressed air and scanned using 532 nm and 635 nm lasers (Axon Laboratories).

Building Predictor and Validation of Biomarker Profile.

The arrays were quantified using GenePix software (Axon Laboratories). Raw ratios of each array were subtracted by median of ratios of the negative control spots with the observation that the signal for negative T7 empty phage on each chip correlates very well with the signal intensity for whole array. Then Z-transformation was applied to clones so that the mean of each clone is zero across arrays and the standard deviation is 1. Due to the fact a presence of antibodies specific to cancer was tested, epitopes with high reactivity in controls and low reactivity in patients were not expected. A GA/KNN algorithm, a machine learning language, was employed to calibrate the system. Briefly, the data set was randomly separated into a training set and a test set. In the training set, genetic algorithm (GA) was used to select optimized solutions (a subset of clones here) which had good fitness. The fitness was assessed by its ability to classify the training samples using the k-nearest neighbor (KNN) analysis (k=3 here). The fitness score was defined as the number of correctly classified training samples divided by the total number of training samples. The fitness score was specified to be equal or greater than 0.95. After getting 4000 optimized solutions, clones were ranked by their frequency in the solutions and top genes were used to predict the test samples. This cycle of sample partition, solution searching, clone ranking and test sample prediction was repeated 10 times and high-ranked clones were selected as optimized classifier.

What is claimed is:

1. A kit, comprising:

a plurality of polypeptide probes, wherein said polypeptide probes comprise all of:

(i) amino acid sequence SEQ ID NO: 13 or an amino acid sequence encoded by nucleic acid sequence SEQ ID NO: 27, (ii) amino acid sequence SEQ ID NO: 132 or an amino acid sequence encoded by nucleic acid sequence SEQ ID NO: 162, (iii) amino acid sequence SEQ ID NO: 2 or an amino acid sequence encoded by nucleic acid sequence SEQ ID NO: 16, (iv) amino acid sequence SEQ ID NO: 141 or an amino acid sequence encoded by nucleic acid sequence SEQ ID NO: 171, (v) amino acid sequence SEQ ID NO: 129 or an amino acid sequence encoded by nucleic acid sequence SEQ ID NO: 159, (vi) amino acid sequence SEQ ID NO: 118 or an amino acid sequence encoded by nucleic acid sequence SEQ ID NO: 148, (vii) amino acid sequence SEQ ID NO: 122 or an amino acid sequence encoded by nucleic acid sequence SEQ ID NO: 152, and (viii) amino acid sequence SEQ ID NO: 130 or an amino acid sequence encoded by nucleic acid sequence SEQ ID NO: 160.

2. The kit of claim 1, wherein said kit further comprises one or more polypeptide probes comprising a polypeptide or epitope fragment of amino acid sequence SEQ ID NO: 5, 11, 12, 14, 56, 58, 60, 62, 64, 67, 69, 115, 116, 123 or 140.

3. The kit of claim 1, wherein said kit further comprises one or more polypeptide probes comprising a polypeptide or epitope fragment of amino acid sequence SEQ ID NO: 19, 25, 26, 28, 70, 73, 75, 77, 79, 82, 84, 145, 146, 153, or 170.

4. A kit, comprising:

a plurality of polypeptide probes attached to a substrate, wherein said polypeptide probes comprise all of:

(i) amino acid sequence SEQ ID NO: 13 or an amino acid sequence encoded by nucleic acid sequence SEQ ID NO: 27, (ii) amino acid sequence SEQ ID NO: 132 or an amino acid sequence encoded by nucleic acid sequence SEQ ID NO: 162, (iii) amino acid sequence SEQ ID NO: 2 or an amino acid sequence encoded by nucleic acid sequence SEQ ID NO: 16, (iv) amino acid sequence SEQ ID NO: 141 or an amino acid sequence encoded by nucleic acid sequence SEQ ID NO: 171, (v) amino acid sequence SEQ ID NO: 129 or an amino acid sequence encoded by nucleic acid sequence SEQ ID NO: 159, (vi) amino acid sequence SEQ ID NO: 118 or an amino acid sequence encoded by nucleic acid sequence SEQ ID NO: 148, (vii) amino acid sequence SEQ ID NO: 122 or an amino acid sequence encoded by nucleic acid sequence SEQ ID NO: 152, and (viii) amino acid sequence SEQ ID NO: 130 or an amino acid sequence encoded by nucleic acid sequence SEQ ID NO: 160.

5. The kit of claim 4, wherein said kit further comprises one or more polypeptide probes comprising a polypeptide or epitope fragment of amino acid sequence SEQ ID NO: 5, 11, 12, 14, 56, 58, 60, 62, 64, 67, 69, 115, 116, 123 or 140.

6. The kit of claim 4, wherein said kit further comprises one or more polypeptide probes comprising a polypeptide or epitope fragment of amino acid sequence SEQ ID NO: 19, 25, 26, 28, 70, 73, 75, 77, 79, 82, 84, 145, 146, 153, or 170.

7. The kit of claim 4, wherein said substrate is an array, bead, or particle.

* * * * *

SEQUENCE LISTING

```
<160> NUMBER OF SEQ ID NOS: 172

<210> SEQ ID NO 1
<211> LENGTH: 14
<212> TYPE: PRT
<213> ORGANISM: Artificial Sequence
<220> FEATURE:
<223> OTHER INFORMATION: Synthetic

<400> SEQUENCE: 1

Pro Gln Thr Thr Ala Pro Arg Arg Ala Arg Pro Arg Arg Ser
1               5                   10


<210> SEQ ID NO 2
<211> LENGTH: 25
<212> TYPE: PRT
<213> ORGANISM: Artificial Sequence
<220> FEATURE:
<223> OTHER INFORMATION: Synthetic

<400> SEQUENCE: 2

Pro Val Ser Ser Ser Gly Ser Tyr Ser Thr Pro Ile Arg Lys Ser Leu
1               5                   10                  15

Arg Arg Ala Ala Pro Pro Phe Arg Ala
            20                  25


<210> SEQ ID NO 3
<211> LENGTH: 7
<212> TYPE: PRT
<213> ORGANISM: Artificial Sequence
<220> FEATURE:
<223> OTHER INFORMATION: Synthetic

<400> SEQUENCE: 3

Ser Ser Phe Ser Pro Leu Asn
1               5


<210> SEQ ID NO 4
<211> LENGTH: 55
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: Xaa can be any naturally occurring amino acid
```

-continued

<400> SEQUENCE: 4

Ala Ala Arg Arg Pro His Asp Ala Trp Ser Tyr Cys Lys Arg Arg Glu
1               5                   10                  15

Pro Ala Gly Val Xaa Gln Ser Ser Gly Ser Leu Pro Gln Lys Val Arg
            20                  25                  30

Glu Ala Glu Ser Pro Arg Met Gly Gly Tyr Arg Gln Ala Gly Gln Ala
        35                  40                  45

Gln Arg Ala Cys Ser Leu Arg
    50                  55

<210> SEQ ID NO 5
<211> LENGTH: 64
<212> TYPE: PRT
<213> ORGANISM: Artificial Sequence
<220> FEATURE:
<223> OTHER INFORMATION: Synthetic

<400> SEQUENCE: 5

Gln Ala Arg Leu Phe Ile Phe Ile Thr Gln Lys Ser Phe Ile Phe Leu
1               5                   10                  15

Phe Ser Phe Leu Thr Leu Cys Leu Cys Leu Gln His Phe His Asn Asp
            20                  25                  30

Phe Leu Leu Leu Asp Lys Glu Ser Thr Leu Asp Pro Val Thr Asn Thr
        35                  40                  45

Phe Ser Thr His Gly Thr Lys Thr Leu Leu Leu Thr Ser Leu Phe Leu
    50                  55                  60

<210> SEQ ID NO 6
<211> LENGTH: 22
<212> TYPE: PRT
<213> ORGANISM: Artificial Sequence
<220> FEATURE:
<223> OTHER INFORMATION: Synthetic

<400> SEQUENCE: 6

Leu Arg Gly Ile Thr Lys Asn Asp Arg Asn Phe Asn Arg Lys Ile His
1               5                   10                  15

Leu Asn Trp Ile Ser Lys
            20

<210> SEQ ID NO 7
<211> LENGTH: 10
<212> TYPE: PRT
<213> ORGANISM: Artificial Sequence
<220> FEATURE:
<223> OTHER INFORMATION: Synthetic

<400> SEQUENCE: 7

Arg Gly Cys Cys Ala Gly Ile Arg Cys Thr
1               5                   10

<210> SEQ ID NO 8
<211> LENGTH: 118
<212> TYPE: PRT
<213> ORGANISM: Artificial Sequence
<220> FEATURE:
<223> OTHER INFORMATION: Synthetic

<400> SEQUENCE: 8

Ile Arg Asp Pro Asn Gln Gly Gly Lys Asp Ile Thr Glu Glu Ile Met
1               5                   10                  15

```
Ser Gly Ala Arg Thr Ala Ser Thr Pro Thr Pro Pro Gln Thr Gly Gly
            20                  25                  30

Gly Leu Glu Pro Gln Ala Asn Gly Glu Thr Pro Gln Val Ala Val Ile
        35                  40                  45

Val Arg Pro Asp Asp Arg Ser Gln Gly Ala Ile Ile Ala Asp Arg Pro
    50                  55                  60

Gly Leu Pro Gly Pro Glu His Ser Pro Ser Glu Ser Gln Pro Ser Ser
65                  70                  75                  80

Pro Ser Pro Thr Pro Ser Pro Ser Pro Val Leu Glu Pro Gly Ser Glu
                85                  90                  95

Pro Asn Leu Ala Val Leu Ser Ile Pro Gly Asp Thr Met Thr Thr Ile
            100                 105                 110

Gln Met Ser Val Glu Glu
        115


<210> SEQ ID NO 9
<211> LENGTH: 22
<212> TYPE: PRT
<213> ORGANISM: Artificial Sequence
<220> FEATURE:
<223> OTHER INFORMATION: Synthetic

<400> SEQUENCE: 9

Gly Gly Gly Arg Gly Ala Gly Gly Gly Arg Gly Ala Gly Ala Gly Gly
1               5                   10                  15

Gly Arg Pro Glu Ala Ala
            20


<210> SEQ ID NO 10
<211> LENGTH: 89
<212> TYPE: PRT
<213> ORGANISM: Artificial Sequence
<220> FEATURE:
<223> OTHER INFORMATION: Synthetic

<400> SEQUENCE: 10

Glu Ser Arg Pro Met Ser Tyr Asp Glu Lys Arg Gln Leu Ser Leu Asp
1               5                   10                  15

Ile Asn Lys Leu Pro Gly Glu Lys Leu Gly Arg Val Val His Ile Ile
            20                  25                  30

Gln Ala Arg Glu Pro Ser Leu Arg Asp Ser Asn Pro Glu Glu Ile Glu
        35                  40                  45

Ile Asp Phe Glu Thr Leu Lys Pro Ser Thr Leu Arg Glu Leu Glu Arg
    50                  55                  60

Tyr Val Leu Ser Cys Leu Arg Lys Lys Pro Arg Lys Pro Tyr Ser Thr
65                  70                  75                  80

Tyr Glu Met Arg Phe Ile Ser Trp Phe
                85


<210> SEQ ID NO 11
<211> LENGTH: 11
<212> TYPE: PRT
<213> ORGANISM: Artificial Sequence
<220> FEATURE:
<223> OTHER INFORMATION: Synthetic

<400> SEQUENCE: 11

Leu Val Ser Ile Leu Leu Thr Lys Thr Ile Tyr
1               5                   10
```

<210> SEQ ID NO 12
<211> LENGTH: 84
<212> TYPE: PRT
<213> ORGANISM: Artificial Sequence
<220> FEATURE:
<223> OTHER INFORMATION: Synthetic

<400> SEQUENCE: 12

```
Lys Ala Glu Cys Phe Lys Asn Leu Ile Val Lys Lys Gln Lys Ser Leu
1               5                   10                  15

Cys Ser Gly Phe Lys Glu His Leu Asn Glu Ala Ser Ile Leu Ala Gln
            20                  25                  30

Val Ser Val Ser Ser Ser Lys Arg Val Trp Lys Ser Trp Glu Asn Leu
        35                  40                  45

Ile Ser Ser Phe Met Val Trp Asn Pro Ala His Leu Ile Ile Ser Ile
    50                  55                  60

Pro Asn Leu Glu Lys Thr Ser Asp Leu Ser Met Met Ser Lys Leu Ala
65                  70                  75                  80

Ala Ala Leu Glu
```

<210> SEQ ID NO 13
<211> LENGTH: 92
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (41)..(41)
<223> OTHER INFORMATION: Xaa can be any naturally occurring amino acid

<400> SEQUENCE: 13

```
Gln Arg Ser Gly Arg Asp Asn Gly Asp Val Gly Ala Gly Ala Pro Phe
1               5                   10                  15

Arg Leu Ser Ser Thr Ser Gln Pro Arg Arg Ile Lys Pro Ile Ala Pro
            20                  25                  30

Pro Pro Arg Ala Pro Ser Pro Glu Xaa Gly Ala Gly Gly Gly Gly Gly
        35                  40                  45

Gly Arg Gly Gly Gly Gly Gly Gly Pro Gly Gly Gly Gly Val Gly Gly
    50                  55                  60

Arg Gly Gly Gly Gly Gly Gly Gly Gly Arg Gly Ala Gly Gly Gly Arg
65                  70                  75                  80

Gly Ala Gly Ala Gly Gly Gly Arg Pro Glu Ala Ala
                85                  90
```

<210> SEQ ID NO 14
<211> LENGTH: 77
<212> TYPE: PRT
<213> ORGANISM: Artificial Sequence
<220> FEATURE:
<223> OTHER INFORMATION: Synthetic

<400> SEQUENCE: 14

```
Pro Ala Ser Ala Ser Ile Leu Ala Gly Val Pro Met Tyr Arg Asn Glu
1               5                   10                  15

Phe Thr Ala Trp Tyr Arg Arg Met Ser Val Val Tyr Gly Ile Gly Thr
            20                  25                  30

Trp Ser Val Leu Gly Ser Leu Leu Tyr Tyr Ser Arg Thr Met Ala Lys
        35                  40                  45

Ser Ser Val Asp Gln Lys Asp Gly Ser Ala Ser Glu Val Pro Ser Glu
    50                  55                  60
```

Leu Ser Glu Arg Pro Ser Leu Arg Pro His Ser Ser Asn
65 70 75

<210> SEQ ID NO 15
<211> LENGTH: 221
<212> TYPE: DNA
<213> ORGANISM: Artificial Sequence
<220> FEATURE:
<223> OTHER INFORMATION: Synthetic

<400> SEQUENCE: 15
agctttcgct agagacgcct ccataagtca cttgcccgtt ggcccccacg atcggggtcg 60
gttgctcgca gggctgagca gagatgtgcc aggagggttg ttctcacgca agaggacgct 120
gtactcctgc tgctggaaag taggcgcctc gtcgttgacg tcagcgacac tgacggtcag 180
gacctgcgtg gccgagcgcg gcggggagcc gtggtctgag g 221

<210> SEQ ID NO 16
<211> LENGTH: 267
<212> TYPE: DNA
<213> ORGANISM: Artificial Sequence
<220> FEATURE:
<223> OTHER INFORMATION: Synthetic

<400> SEQUENCE: 16
tggaggagag gctgggctgc cccaagcccc tgctcagggc ctcagaagcc atacaccttc 60
actctgattg tgctcatcaa ggcccagcat gcaggaggct caaagtagct tttggcttgg 120
gtgttgacga gaagagaggt aacctggggt cattcttgac acgttccagc cacctccggt 180
tggcctcaat tatgccctga aaggtggtgc tgcccgcctc agggacttgc gaatgggagt 240
gctgtaggag ccggagctgc tcactgg 267

<210> SEQ ID NO 17
<211> LENGTH: 168
<212> TYPE: DNA
<213> ORGANISM: Artificial Sequence
<220> FEATURE:
<223> OTHER INFORMATION: Synthetic

<400> SEQUENCE: 17
gaattcgtca ttctcacctt tgaattaaag cttagactaa atagtaatat atcgtgggaa 60
ggattttggt tttgtgatat ttctgtgaat taaggaatag atgttaacca ttattttgta 120
gaaaagtgat ttgtatgtgg ttaattataa ataaaactgg taccagaa 168

<210> SEQ ID NO 18
<211> LENGTH: 481
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (421)..(421)
<223> OTHER INFORMATION: n is a, c, g, or t

<400> SEQUENCE: 18
tttattaacc cagcatggtt tgttctaatg cttcttgttg gcagctgcca cctgtccggc 60
gattctgtcc agatctcttt gtccctgagg tgtcagtttg cggccgccat cttggtcctt 120

```
ttccaccatt ttcagcccct ccagggcttg gaggacccgg cgggccacac tcttggagcc    180

tcggctgaag tggctgggca tgacgccgtt tctctgacgt cccccataga tcttggtcat    240

ggagccaacc ccagcgccac cccggaggta caggtgccgc gctgtgnaag cagctcgcgt    300

gtagaaccag ttctcatcgt agggagcaag ctctttgtgc ttggccagct tgacggtatc    360

cacccattcg gggactttca gcttcccgga ctttttgagg aaggctgcca gagctctgac    420

naactcctgc tggttcacgt cttttacagt aactccaggc atcgtgcggc ctccgcgctg    480

c                                                                    481


<210> SEQ ID NO 19
<211> LENGTH: 326
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (60)..(60)
<223> OTHER INFORMATION: n is a, c, g, or t

<400> SEQUENCE: 19

ttctcgagtg cggccgcagc ttgggtatgg agacatatca tataagtaat gctagggtcn     60

gtggtaggaa gttttttcat aggaggtgta tgagttggtc gtagcggaat cgggggtatg    120

ctgttcgaat tcataagaac agggaggtta gaagtagggt cttggttcca tgtgtgctaa    180

atgtgttcgt gacaggatca agcgtgcttt ccttatcgag gagcagaaaa tcgttgtgaa    240

agtgttgaag gcacaagcac agagtcagaa agctaaataa aaaaatgaaa ctttttttgag   300

taataaaaat gaaaagacgc gcttga                                        326


<210> SEQ ID NO 20
<211> LENGTH: 453
<212> TYPE: DNA
<213> ORGANISM: Artificial Sequence
<220> FEATURE:
<223> OTHER INFORMATION: Synthetic

<400> SEQUENCE: 20

ctctgagggg catcaccaaa aatgacagga atttcaacag gaagatacat ctgaattgga     60

tctcgaaata aggagtttgt gtaagagaaa aggaggacac aagcaaggag acacaaaaga    120

caatttgtcc aagagagtag tagtagaaac tgacaaaggt aaggctgctt ggtggccggg    180

tgcagtgact cacgcctgta atcccagcac tttgggaggc caaggcgggt ggatcacctg    240

aggtcaggag ttcgagacca ccctgaccaa caggtgaaac ccctctctac taaaaataca    300

aacattagcc catagtccca gctactgggg aggctgaggc aggagaatcg cttgaacctg    360

ggaggcggag gttgcagtga gccaagatcg tgccattgca ctccagcctg ggcgacagaa    420

tgagactgtc tcaaaacaaa aggaaaaaaa aaa                                 453


<210> SEQ ID NO 21
<211> LENGTH: 388
<212> TYPE: DNA
<213> ORGANISM: Artificial Sequence
<220> FEATURE:
<223> OTHER INFORMATION: Synthetic

<400> SEQUENCE: 21

cacttcttca agctccaaca caaatgctgc ctcctttagg atgcctgctc tgtgctctcc     60
```

-continued

```
ctgcctcccc tagcccatac ctctgctggc accttctgta ccatgccttc agaaaccttc    120

ttatccccct catctctggg gccccctgtg gatctggcat acccaagttc agtaaatgtc    180

tatcagtaag ctgatggtac atgcattttc tagaatagag ctgggacttc ccatgtggcc    240

cacatctgac ctggcagccc atgtattccg gtcattaggg atgggaagcc atgaggacct    300

ggccttctgc ccgacccagg cagccattca agttgagcaa tggccacttc gaagactcaa    360

gtgcacctga tccctgcgca acagccac                                       388


<210> SEQ ID NO 22
<211> LENGTH: 361
<212> TYPE: DNA
<213> ORGANISM: Artificial Sequence
<220> FEATURE:
<223> OTHER INFORMATION: Synthetic

<400> SEQUENCE: 22

ttcttctaca gacatttgta tagttgtcat agtgtcccca ggaatagaga ggactgcgag     60

attaggctca gaccccggtt ccaagactgg ggatggtgat ggggtcggag aaggcgacga    120

aggctgggat tctgaagggc tatgctctgg gccaggcagc cctggccggt cagcaatgat    180

tgctccctgt gaccggtcat ctggccggac aatgacagca acctggggcg tctccccatt    240

agcttgaggc tccagaccgc ctcccgtctg gggaggggtg ggtgtggagg cagtgcgggc    300

cccagacatg atctcctctg tgatatcctt tcctccttgg tttggatctc gaattcggat    360

c                                                                    361


<210> SEQ ID NO 23
<211> LENGTH: 499
<212> TYPE: DNA
<213> ORGANISM: Artificial Sequence
<220> FEATURE:
<223> OTHER INFORMATION: Synthetic

<400> SEQUENCE: 23

atcacaaata ggacaatact tgctggtctc caggtaacga acaatacacg ttttacagaa     60

ggaatgtaga cattctatta tggttgtggc atcaatgaag taccctccac aaagcacaca    120

catcaggtgg ggatttagct cagtgatctt gattctcgtt gttcgatgca tttctgcttg    180

ataaaaaatc ccggaaagag cagccggcgc gaggcgatcg aagcgggcgg aaaagacaat    240

gaaagttaaa agtcgttcag cagaaaatga atgcgagcca agcggccatc ttgaagcgag    300

ctgcagacgc cgctgtcaat gggcaaccag cgcggccccg agcagccgcg gccgccacgc    360

tcgtctcatg ccgcctccgg ccggcctcct cctgctccgg cgcctcggcc tcctccggcg    420

cctcggcctc ctcctcctcc gcctccgcct cgacctccaa cgcctcctcc tccggggcct    480

cctcctcctc ctcctcggc                                                 499


<210> SEQ ID NO 24
<211> LENGTH: 235
<212> TYPE: DNA
<213> ORGANISM: Artificial Sequence
<220> FEATURE:
<223> OTHER INFORMATION: Synthetic

<400> SEQUENCE: 24

tgtagggctt ccggggtttc ttacgtaggc aggaaaggac atagcgctca agctctctaa     60

gtgtggatgg cttgagtgtt tcaaaatcaa tctcaatctc ttctgggttt gaatcacgta    120

aagagggctc cctggcttgg attatatgca caactcggcc cagcttctcc ccaggtaatt    180
```

tgttgatgtc caggctcagc tgccgcttct catcgtaact catgggcctg ctctc 235

<210> SEQ ID NO 25
<211> LENGTH: 373
<212> TYPE: DNA
<213> ORGANISM: Artificial Sequence
<220> FEATURE:
<223> OTHER INFORMATION: Synthetic

<400> SEQUENCE: 25
ttactgttac ctgatcaatg acagagcctt ctgaggacat tccaagacag tatacagtcc 60
tgtggtctcc ttggaaatcc gtctagttaa catttcaagg gcaataccgt gttggttttg 120
actggatatt catataaact ttttaaagag ttgagtgata gagctaaccc ttatctgtaa 180
gttttgaatt tatattgttt catcccatgt acaaaaccat tttttcctac aaatagtttg 240
ggttttgttg ttgtttcttt tttttgtttt gtttttgttt tttttttttt tgcgttcgtg 300
gggttgtaaa agaaaagaaa gcagaatgtt ttatcatggt ttttgcttca gcggctttag 360
gacaaattaa aag 373

<210> SEQ ID NO 26
<211> LENGTH: 235
<212> TYPE: DNA
<213> ORGANISM: Artificial Sequence
<220> FEATURE:
<223> OTHER INFORMATION: Synthetic

<400> SEQUENCE: 26
aagcagagtg ctttaaaaat ttgatagtaa aaaagcaaaa atctctgtgc tctggtttta 60
aggaacattt gaatgaggca agcattttag cacaggtttc tgtttcaagt tcaaagagag 120
tctggaaaag ttgggaaaat ttaatatcat cttttatggt gtggaatcct gcccatttga 180
ttatttctat cccaaatctt gaaaaaacat cagacttatc tatgatgtca aagct 235

<210> SEQ ID NO 27
<211> LENGTH: 761
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (355)..(355)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t
<220> FEATURE:
<221> NAME/KEY: misc_feature
<222> LOCATION: (757)..(757)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t

<400> SEQUENCE: 27
aagcttatta tctcatcatc agttataatt ctcttatctt catctgcaac ctctcctcta 60
tcttcattag agccattggc agcatcagca gaaggatgag ctgcataaaa atcccttctt 120
ctcttcattt catttttgaa aagccctgga actaatttgt atacaatatc ttggagagtt 180
ttatctgacc ttatattcag tagtggtctg gtcttgtgaa cttggacatc acaaatagga 240

-continued

```
caatacttgc tggtctccag gtaacgaaca atacacgttt tacagaagga atgtagacat    300

tctattatgg ttgtggcatc aatgaagtac cctccacaaa gcacacacat caggngggga    360

tttagctcag tgatcttgat tctcgttgtt cgatgcattt ctgcttgata aaaaatcccg    420

gaaagagcag ccggcgcgag gcgatcgaag cgggcggaaa agacaatgaa agttaaaagt    480

cgttcagcag aaaatgaatg cgagccaagc ggccatcttg aagcgagctg cagacgccgc    540

tgtcaatggn caaccagcgc ggccccgagc agccgcggcc gccacgctcg tctcatgccg    600

cctccggccg gcctcctcct gctccggcgc ctcggcctcc tccggcgcct cggcctcctc    660

ctcctccgcc tccgcctcga cctccaacgc ctcctcctcc gcttgaattc ggatccccga    720

gcatcacacc tgactggaat acgaacagct ccacatncng t                         761
```

```
<210> SEQ ID NO 28
<211> LENGTH: 190
<212> TYPE: DNA
<213> ORGANISM: Artificial Sequence
<220> FEATURE:
<223> OTHER INFORMATION: Synthetic

<400> SEQUENCE: 28

ttgggcgttc agagagttca ctgggtactt cacttgctga gccatccttt tggtctactg     60

acgacttcgc cattgtccgg ctatagtaaa gcagtgagcc caacacagac caggtgccga    120

tcccgtagac caccgacatc cgccggtacc aggccgtgaa ctcatttcga tacatgggta    180

cgccagcgag                                                            190
```

```
<210> SEQ ID NO 29
<211> LENGTH: 9911
<212> TYPE: DNA
<213> ORGANISM: Homo sapiens

<400> SEQUENCE: 29

gcgatcgcca tgcagaagga gctgggcatt gtgccttcct gccctggcat gaagagcccc     60

aggccccacc tcctgctacc attgctgctg ctgctgctgc tgctgctggg ggctggggtg    120

ccaggtgcct ggggtcaggc tgggagcctg gacttgcaga ttgatgagga gcagccagcg    180

ggtacactga ttggcgacat cagtgcgggg cttccggcag gcacggcagc tcctctcatg    240

tacttcatct ctgcccaaga gggcagcggc gtgggcacag acctggccat tgacgaacac    300

agtggggtcg tccgtacagc ccgtgtcttg gaccgtgagc agcgggaccg ctaccgcttc    360

actgcagtca ctcctgatgg tgccaccgta gaagttacag tgcgagtggc tgacatcaac    420

gaccatgctc cagccttccc acaggctcgg gctgccctgc aggtacctga gcatacagct    480

tttggcaccc gctacccact ggagcctgct cgtgatgcag atgctgggcg tctgggaacc    540

cagggctatg cgctatctgg tgatggggct ggagagacct tccggctgga gacacgcccc    600

ggtccagatg ggactccagt acctgagctg gtagttactg ggggaactgga ccgagagaac    660

cgctcacact atatgctaca gctggaggcc tatgatggtg gttcaccccc ccggagggcc    720

caggccctgc tggacgtgac actgctggac atcaatgacc atgccccggc tttcaatcag    780

agccgctacc atgctgtggt gtctgagagc ctggcccctg gcagtcctgt cttgcaggtg    840

ttcgcatctg atgccgatgc tggtgtcaat ggggctgtga cttacgagat caaccggagg    900

cagagcgagg gtgatggacc cttctccatc gacgcacaca cggggctgct gcagttagag    960

cggccactgg actttgagca gcggcgggtc catgaactgg tggtgcaagc acgagatggt   1020

ggggctcacc ctgagctggg ctcggccttt gtgactgtgc atgtgcgaga tgccaatgac   1080
```

-continued

```
aatcagccct ccatgactgt catctttctc agtgcagatg gctcccccca agtgtctgag   1140
gccgccccac ctggacagct cgttgctcgc atctctgtgt cagacccaga tgatggtgac   1200
tttgcccatg tcaatgtgtc cctggaaggt ggagagggcc actttgccct aagcacccaa   1260
gacagcgtca tctatctggt gtgtgtggct cggcggctgg atcgagagga gagggatgcc   1320
tataacttga gggttacagc cacagactca ggctcacctc cactgcgggc tgaggctgcc   1380
tttgtgctgc acgtcactga tgtcaacgac aatgcacctg cctttgaccg ccagctctac   1440
cgacctgagc ccctgcctga ggttgcgctg cctggcagct ttgtagtgcg ggtgactgct   1500
cgggatcctg accaaggcac caatggtcag gtcacttata gcctagcccc tggcgcccac   1560
acccactggt tctccattga ccccacctca ggcattatca ctacggctgc ctcactggac   1620
tatgagttgg aacctcagcc acagctgatt gtggtggcca cagatggtgg cctgcccccct  1680
ctagcctcct ctgccacagt tagcgtggcc ctgcaagatg tgaatgataa tgagccccaa   1740
ttccagagga ctttctacaa tgcctcactg cctgagggca cccagcctgg aacttgcttc   1800
ctgcaggtga cagccacaga cgcggatagt ggcccatttg gcctcctctc ctattccttg   1860
ggtgctggac ttgggtcctc cggatctccc ccattccgca ttgatgccca tagcggtgat   1920
gtgtgcacaa cccggaccct ggaccgtgac caggggccct caagctttga cttcacagtg   1980
acagctgtgg atgggggagg cctcaagtcc atggtatatg tgaaggtgtt tctgtcagac   2040
gagaatgaca accctcctca gttttatcca cgggagtatg ctgccagtat aagtgcccag   2100
agtccaccag gcacagctgt gctgaggttg cgtgcccatg accctgacca gggatcccat   2160
gggcgactct cctaccatat cctggctggc aacagccccc cactttttac cttggatgag   2220
caatcagggc tgttgacagt agcctggccc ttggccagac gggccaattc tgtggtgcag   2280
ctggagatcg gggctgagga cggaggtggc ctacaggcag aacccagtgc ccgagtggac   2340
atcagcattg tgcctggaac ccccacacca cccatatttg agcaactaca gtatgttttt   2400
tctgtgccag aggatgtggc accaggcacc agtgtgggca tagtccaggc acacaaccca   2460
ccaggtcgct tggcacctgt gaccctttcc ctatcaggtg gggatccccg aggactcttc   2520
tccctagatg cggtatcagg actgttgcaa acacttcgcc ctctggaccg ggagctactg   2580
ggaccagtgt tggagctgga ggtgcgagca ggcagtggag tgcccccagc tttcgctgta   2640
gctcgggtgc gtgtgctgct ggatgatgtg aatgacaact cccctgcctt tcctgcacct   2700
gaagacacgg tattgctacc accaaacact gccccaggga ctcccatcta tacactgcgg   2760
gctcttgacc ccgactcagg tgttaacagt cgagtcacct ttaccctgct tgctgggggt   2820
ggtggagcct tcaccgtgga ccccaccaca ggccatgtac ggcttatgag gcctctgggg   2880
ccctcaggag ggccagccca tgagctggag ctggaggccc gggatggggg ctccccacca   2940
cgcaccagcc actttcgact acgggtggtg gtacaggatg tgggaacccg tgggctggct   3000
ccccgattca acagccctac ctaccgtgtg gacctgccct caggcaccac tgctggaact   3060
caggtcctgc aagtgcaggc ccaagcacca gatgggggcc ctatcaccta tcaccttgca   3120
gcagagggag caagtagccc ctttggcctg gagccacaga gtgggtggct atgggtgcgg   3180
gcagcactag accgtgaggc ccaggaattg tacatactga aggtaatggc agtgtctggg   3240
tccaaagctg agttggggca gcagacaggc acagccaccg tgagggtcag catcctcaac   3300
cagaatgaac acagtccccg cttgtctgag gatcccacct tcctggctgt ggctgagaac   3360
cagcccccag ggaccagcgt gggccgagtc tttgccactg accgagactc aggacccaat   3420
```

-continued

```
ggacgtctga cctacagcct gcaacagctg tctgaagaca gcaaggcctt ccgcatccac   3480
ccccagactg gagaagtgac cacactccaa accctggacc gtgagcagca gagcagctat   3540
cagctcctgg tgcaggtgca ggatggaggg agcccacccc gcagcaccac aggcactgtg   3600
catgttgcag tgcttgacct caacgacaac agccccacgt tcctgcaggc ttcaggagct   3660
gctggtgggg gcctccctat acaggtacca gaccgcgtgc ctccaggaac actggtgacg   3720
actctgcagg cgaaggatcc agatgagggg gagaatggga ccatcttgta cacgctaact   3780
ggtcctggct cagagctttt ctctctgcac cctcactcag gggagctgct cactgcagct   3840
cccctgatcc gagcagagcg gccccactat gtgctgacac tgagtgctca tgaccaaggc   3900
agccctcctc gaagtgccag cctccagctg ctggtgcagg tgcttccctc agctcgcttg   3960
gccgagccgc ccccagatct cgcagagcgg gacccagcgg caccagtgcc tgtcgtgctg   4020
acggtgacag cagctgaggg actgcggccc ggctctctgt tgggctcggt ggcagcgcca   4080
gagcccgcgg gtgtgggtgc actcacctac acactggtgg gcggtgccga tcccgagggc   4140
accttcgcgc tggatgcggc ctcagggcgc ttgtacctgg cgcggcccct ggacttcgaa   4200
gctggcccgc cgtggcgcgc gctcacggta cgcgctgagg ggccgggagg cgcgggcgcg   4260
cggctgctgc gagtgcaggt gcaagtgcag gacgagaatg agcatgcgcc cgcctttgcg   4320
cgcgacccgc tggcgctggc gctgccagag aacccggagc ccggcgcagc gctgtacact   4380
ttccgcgcgt cggacgccga cggcccgggc cccaatagcg acgtgcgcta ccgcctgctg   4440
cgccaggagc cgcccgtgcc ggcgcttcgc ctggacgcgc gcaccggggc gctcagcgct   4500
ccgcgcggcc tggaccgaga gaccactccc gcgctgctgc tgctggtgga agccaccgac   4560
cggcccgcca acgccagccg ccgtcgtgca gcgcgcgttt cagcgcgcgt cttcgtcacg   4620
gatgagaatg acaacgcgcc tgtcttcgcc tcgccgtcac gcgtgcgcct cccagaggac   4680
cagccgcctg ggcccgcggc cctgcacgtg gtagcccggg acccggatct gggcgaggct   4740
gcacgcgtgt cctatcggct ggcatctggc ggggacggcc acttccggct gcactcaagc   4800
actggagcgc tgtccgtggt gcggccgttg gaccgcgaac aacgagctga gcacgtactg   4860
acagtggtgg cctcagacca cggctccccg ccgcgctcgg ccacgcaggt cctgaccgtc   4920
agtgtcgctg acgtcaacga cgaggcgcct actttccagc agcaggagta cagcgtcctc   4980
ttgcgtgaga acaaccctcc tggcacatct ctgctcaccc tgcgagcaac cgaccccgac   5040
gtgggggcca acgggcaagt gacttatgga ggcgtctcta gcgaaagctt ttctctggat   5100
cctgacactg gtgttctcac gactcttcgg gccctggatc gagaggaaca ggaggagatc   5160
aacctgacag tgtatgccca ggacaggggc tcacctcctc agttaacgca tgtcactgtt   5220
cgagtggctg tggaggatga gaatgaccat gcaccaacct ttgggagtgc ccatctctct   5280
ctggaggtgc ctgagggcca ggacccccag acccttacca tgcttcgggc ctctgatcca   5340
gatgtgggag ccaatgggca gttgcagtac cgcatcctag atggggaccc atcaggagcc   5400
tttgtcctag accttgcttc tggagagttt ggcaccatgc ggccactaga cagagaagtg   5460
gagccagctt tccagctgag gatagaggcc cgggatggag gccagccagc tctcagtgcc   5520
acgctgcttt tgacagtgac agtgctggat gccaatgacc atgctccagc ctttcctgtg   5580
cctgcctact cggtggaggt gccggaggat gtgcctgcag ggaccctgct gctgcagcta   5640
caggctcatg accctgatgc tggagctaat ggccatgtga cctactacct gggcgccggt   5700
acagcaggag ccttcctgct ggagcccagc tctggagaac tgcgcacagc tgcagccttg   5760
gacagagaac agtgtcccag ctacaccttt tctgtgagtg cagtggatgg tgcagctgct   5820
```

-continued

```
gggcccctaa gcaccacagt gtctgtcacc atcacggtgc gcgatgtcaa tgaccatgca   5880
cccaccttcc ccaccagtcc tctgcgccta cgtctgcccc gcccaggccc cagcttcagt   5940
accccaaccc tggctctggc cacactgaga gctgaagatc gtgatgctgg tgccaatgct   6000
tccattctgt accggctggc aggcacacca cctcctggca ctactgtgga ctcttacact   6060
ggtgaaatcc gcgtggcccg ctctcctgta gctctaggcc cccgagatcg tgtcctcttc   6120
attgtggcca ctgatcttgg ccgtccagct cgctctgcca ctggtgtgat cattgttgga   6180
ctgcaggggg aagctgagcg tggaccccgc tttccccggg ctagcagtga ggctacgatt   6240
cgtgagaatg cgcccccagg gactcctatt gtctccccca gggccgtcca tgcaggaggc   6300
acaaatggac ccatcaccta cagcattctc agtgggaatg agaaagggac attctccatc   6360
cagcctagta caggtgccat cacagttcgc tcagcagagg ggctagactt cgaggtgagt   6420
ccacggctgc gactggtgct gcaggcagag agtggaggag cctttgcctt cactgtgctg   6480
accctgaccc tgcaagatgc caacgacaat gctccccgtt tcctgcggcc ccattatgtg   6540
gccttccttc ctgagtcccg gcccttggag gggcccctgc tgcaggtgga ggcggatgac   6600
ctggatcaag gctctggagg acagatttcc tacagtctgg ctgcatccca gccggcacgt   6660
ggattgttcc acgtagaccc aaccacaggc actatcacta ccacagccat cctggaccgt   6720
gagatctggg ctgaaacacg gttggtgctg atggccacag acagagggag cccagccctg   6780
gtgggctcag ctaccttgac ggtgatggtc atcgacacca atgacaatcg ccccaccatc   6840
ccccaaccct gggagctccg agtgtcagaa gatgcgttat tgggctcaga gattgcacag   6900
gtaacaggga atgatgtgga ctcaggaccc gtgctgtggt atgtgctaag cccatctggg   6960
ccccaggatc ccttcagtgt tggccgctat ggaggccgtg tctccctcac ggggcccctg   7020
gactttgagc agtgtgaccg ctaccagctg cagctgctgg cacatgatgg gcctcatgag   7080
ggccgtgcca acctcacagt gcttgtggag gatgtcaatg acaatgcacc tgccttctca   7140
cagagcctct accaggtaat gctgcttgag cacacacccc caggcagtgc cattctctcc   7200
gtctctgcca ctgatcggga ctcaggtgcc aacggtcaca tttcctacca cctggcttcc   7260
cctgccgatg gcttcagtgt tgaccccaac aatgggaccc tgttcacaat agtgggaaca   7320
gtggccttgg gccatgacgg gtcaggagca gtggatgtgg tgctggaagc acgagaccac   7380
ggggctccag gccgggcagc acgagccaca gtgcacgtgc agctgcagga ccagaacgac   7440
cacgccccga gcttcacatt gtcacactac cgtgtggctg tgactgaaga cctgccccct   7500
ggctccactc tgctcaccct ggaggctaca gatgctgatg gaagccgcag ccatgccgct   7560
gtggactaca gcatcatcag tggcaactgg ggccgagtct tccagctgga acccaggctg   7620
gctgaggctg gggagagtgc tggaccaggc ccccgggcac tgggctgcct ggtgttgctt   7680
gaacctctag actttgaaag cctgacacag tacaatctaa cagtggctgc agctgaccgt   7740
gggcagccac cccaaagctc agtcgtgcca gtcactgtca ctgtactaga tgtcaatgac   7800
aacccacctg tctttacccg agcatcctac cgtgtgacag tacctgagga cacacctgtt   7860
ggagctgagc tgctgcatgt agaggcctct gacgctgacc ctggccctca tggcctcgtg   7920
cgtttcactg tcagctcagg cgacccatca gggctctttg agctggatga gagctcaggc   7980
accttgcgac tggcccatgc cctggactgt gagacccagg ctcgacatca gcttgtagta   8040
caggctgctg accctgctgg tgcacacttt gctttggcac cagtgacaat tgaggtccag   8100
gatgtgaatg atcatggccc agccttccca ctgaacttac tcagcaccag cgtggccgag   8160
```

-continued aatcagcctc caggcactct cgtgaccact ctgcatgcaa tcgacgggga tgctggggct 8220
tttgggaggc tccgttacag cctgttggag gctgggccag gacctgaggg ccgtgaggca 8280
tttgcactga acagctcaac aggggagttg cgtgcgcgag tgccctttga ctatgagcac 8340
acagaaagct tccggctgct ggtgggtgct gctgatgctg ggaatctctc agcctctgtc 8400
actgtgtcgg tgctagtgac tggagaggat gagtatgacc ctgtatttct ggcaccagct 8460
ttccacttcc aagtgcccga aggtgcccgg cgtggccaca gcttgggtca cgtgcaggcc 8520
acagatgagg atgggggtgc cgatggcctg gttctgtatt cccttgccac ctcttccccc 8580
tattttggta ttaaccagac tacaggagcc ctgtacctgc gggtggacag tcgggcacca 8640
ggcagcggaa cagccacctc tgggggtggg ggccggaccc ggcgggaagc accacgggag 8700
ctgaggctgg aggtgatagc acgggggcct ctgcctggtt cccggagtgc cacagtgcct 8760
gtgaccgtgg atatcaccca caccgcactg ggcctggcac ctgacctcaa cctgctatta 8820
gtaggggccg tggcagcctc cttgggagtt gtggtggtgc ttgcactggc agccctggtc 8880
ctaggacttg ttcgggcccg tagccgcaag gctgaggcag cccctggccc aatgtcacag 8940
gcagcacccc tagccagtga ctcactgcag aaactgggcc gggagccacc tagtccacca 9000
ccctctgagc acctctatca ccagactctt cccagctatg gtgggccagg agctggagga 9060
ccctaccccc gtggtggctc cttggaccct tcacattcaa gtggccgagg atcagcagag 9120
gctgcagagg atgatgagat ccgcatgatc aatgagttcc cccgtgtggc cagtgtggcc 9180
tcctctctgg ctgcccgtgg ccctgactca ggcatccagc aggatgcaga tggtctgagt 9240
gacacatcct gcgaaccacc tgcccctgac acctggtata agggccgaaa ggcagggctg 9300
ctgctgccag gtgcaggagc cactctctac agagaggagg ggcccccagc cactgccaca 9360
gccttcctgg ggggctgtgg cctgagccct gcacccactg gggactatgg cttcccagca 9420
gatggcaagc catgtgtggc aggtgcgctg acagccattg tggccggcga ggaggagctc 9480
cgtggcagct ataactggga ctacctgctg agctggtgcc ctcagttcca accactggcc 9540
agtgtcttca cagagatcgc tcggctcaag gatgaagctc ggccatgtcc cccagctccc 9600
cgtatcgacc caccacccct catcactgcc gtggcccacc caggagccaa gtctgtgccc 9660
cccaagccag caaacacagc tgcagcccgg gccatcttcc caccagcttc tcaccgctcc 9720
cccatcagcc atgaaggctc cctgtcctca gctgccatgt cccccagctt ctcaccctct 9780
ctgtctcctc tggctgctcg ctcacccgtt gtctcaccat ttggggtggc ccagggtccc 9840
tcagcctcag cactcagcgc agagtctggc ctggagccac ctgatgacac ggagctgcac 9900
atcgtttaaa c 9911

<210> SEQ ID NO 30
<211> LENGTH: 5634
<212> TYPE: DNA
<213> ORGANISM: Homo sapiens

<400> SEQUENCE: 30
ttgcgcgctg cagggcaaca ccccggcgtc cctggaagct gggggagcgg gagaaataac 60
tttatttgga ctgagagctg gagaatgaga ataggacctg agagtatatt gggctaagga 120
ggagaggtgt ttgagcccag atgagtcatg gctggacgac ccctccgcat aggagatcag 180
ctggttctgg aagaagatta tgatgagacc tacattccta gtgagcaaga aattcttgaa 240
tttgcccggg agattggtat tgatcccatc aaggaaccag aactgatgtg gctggcgcga 300
gagggcatcg tggccccact gcctggagag tggaaaccat gccaggacat cacaggtgac 360

-continued

```
atttactatt tcaacttcgc caacgggcag tctatgtggg accatccatg tgacgaacac    420
tatcggagct tggtgatcca agagcgggca aagctgtcaa cttctggggc cattaagaag    480
aagaaaaaaa aaaaggaaaa gaaagacaag aaggacagag acccccccaa aagttcgctg    540
gccttgggtt cctcattagc cccagttcat gttcctcttg ggggcctggc tcctttacga    600
ggtcttgtgg ataccccacc ctctgctctt cgtggatctc aaagcgtgag cctggggagc    660
tcagtggagt ctggacgtca gcttggagaa ctcatgctgc cttcacaggg tctcaagacc    720
tctgcttata caaagggtct cttgggctcc atatatgagg acaagactgc tctcagcctc    780
ttgggtttag gagaagaaac caatgaggag gatgaggagg aaagtgacaa ccagagtgtc    840
cacagctcaa gtgagcctct taggaaccta cacctggaca ttggggcact ggggggtgac    900
tttgagtatg aggagtctct gagaacaagc cagccagagg agaagaagga tgtttctctg    960
gattcagatg ctgccggtcc ccctactccc tgcaagccct ccagcccagg tgcagacagc   1020
agtctgagca gtgctgttgg caaagggcga cagggaagtg gagcaagacc tggtcttcca   1080
gaaaaagagg aaaatgagaa gagtgaacct aagatttgca ggaatctggt gacccccaag   1140
gcagacccta caggcagtga gcctgccaaa gcctctgaaa aggaagcacc agaggacaca   1200
gtagatgcag gagaggaggg ttccaggagg gaagaggcag ccaaggagcc aaagaagaag   1260
gcttctgctc tggaagaggg cagttcagac gccagccaag aactggaaat tagtgaacac   1320
atgaaggaac cacagctctc agactccata gcttctgacc ccaagtcctt ccatggcctg   1380
gacttcggtt ttcgcagccg gatctcggag cacctgctgg atgttgatgt gctttcccca   1440
gtcctgggtg gagcttgtcg gcaggcccag caaccactgg gaatagaaga caaggatgac   1500
agccagtcca gccaagatga gctgcagagc aagcagtcca aaggcctgga ggagaggtta   1560
tctcctccac ttccacacga ggagcgggcc cagagtcccc ctcgcagcct ggccactgaa   1620
gaagagcctc cccagggccc cgaggggcag cccgagtgga aggaggcaga ggagcttggg   1680
gaggactctg cagccagcct cagcctgcag ctgtccctcc agagggagca ggccccaagc   1740
ccacctgctg cctgtgagaa gggcaaggag cagcattccc aggccgagga gctgggccct   1800
gggcaggaag aggcagagga tcctgaggag aaggtggcgg tcagccccac cccgccagtc   1860
tctccagagg tgcgatccac agagcctgtg gctcccccag agcagctctc agaggctgca   1920
ctaaaggcca tggaagaggc agtggcccaa gtactcgagc aagaccagag gcacctgctg   1980
gaatccaagc aagagaagat gcagcaactg cgggagaagc tgtgccaaga ggaggaagag   2040
gagatcctcc ggcttcacca gcagaaagag caatctctca gttccttgag ggagcggctg   2100
cagaaagcca ttgaggagga ggaggcccgg atgagagagg aggaaagcca gaggctatcc   2160
tggctccgag ctcaggtcca gtccagcaca caagcagatg aggaccaaat cagggctgag   2220
caagaggctt ccctgcagaa actgagagaa gagttggagt ctcaacagaa ggctgagagg   2280
gccagcttgg aacagaaaaa taggcaaatg ctggagcagc tcaaggaaga gatagaggct   2340
tcggagaaga gcgagcaggc tgccctgaat gctgcaaagg agaaggctct gcagcagctg   2400
agggagcagc tggaagggga gaggaaagaa gctgtggcaa cgctggagaa ggagcacagt   2460
gctgagctgg agcggctctg ctcctcattg gaggccaagc accgggaggt ggtctccagc   2520
ctccagaaga agatacagga agctcaacag aaagaggagg cccagctgca gaagtgcctt   2580
gggcaagtgg agcacagagt tcaccagaag tcttatcacg tggctgggta tgagcacgag   2640
ctcagcagtc tcctgcgaga gaagcgccag gaagtggaag gggagcatga gaggaggttg   2700
```

-continued

```
gacaagatga aggaggagca ccagcaagtg atggctaagg ccagagagca gtatgaagct   2760
gaggagagga agcagcgggc tgagcttctg gggcacctga ccggagagct ggagcgcctg   2820
cagagggccc atgaacgaga actggagact gtgaggcagg agcaacacaa gcgtcttgag   2880
gacttgcggc gccggcacag ggagcaggaa aggaagctcc aggatttaga gttggacctt   2940
gaaaccagag ctaaagatgt caaggccaga ttggctctgc tggaggtcca ggaggagacc   3000
gcccggaggg agaagcagca gctgcttgat gtgcagaggc aggttgctct gaagagtgag   3060
gaagccacag ccacccatca gcagctggag gaggcacaga aggagcacac ccacctgttg   3120
cagtcaaacc agcagctccg agaaattctt gatgagctgc aggcccgcaa gctgaagctg   3180
gagtcccaag tggatctgct gcaggctcag agccagcaac tgcagaaaca cttcagcagc   3240
ctggaggctg aagctcaaaa gaagcagcac ctgttgagag aagtgacagt tgaggaaaat   3300
aatgcttccc cacattttga gccagatctc catattgagg acctgaggaa atcccttgga   3360
acaaaccaga ccaaagaggt gtcttcttct ctctcccaga gcaaggagga cttatacttg   3420
gacagcctgt cctcccacaa tgtctggcac ctcctctctg ctgagggggt agccctccgt   3480
agtgccaagg agttccttgt gcagcagaca cgctccatgc ggaggcggca gacagctctg   3540
aaagctgccc agcagcattg gcgccatgag ctggccagtg cgcaggaggt ggccaaagac   3600
ccaccaggca tcaaggccct ggaagatatg cgcaagaacc tggagaagga gaccaggcac   3660
ctggatgaga tgaagtcggc catgcggaaa ggccacaacc tgctgaagaa gaaagaggag   3720
aagctgaatc agttggagtc ctctctttgg gaagaggcct cagatgaggg cactctggga   3780
ggatccccca ccaagaaggc agtaaccttc gacctcagtg acatggacag cctgagcagt   3840
gaaagttctg aatctttttc cccgcctcac cgtgagtggt ggcggcagca gaggatcgac   3900
tcaaccccga gtctcacctc ccgcaagatc cacgggctta gccactccct ccggcagatc   3960
agcagccagc tgagcagtgt cctcagcatc ctggacagcc tcaaccctca gtcgccgccg   4020
ccgctcctcg cctccatgcc agcccagctc cctccccggg accctaagag cacccccacc   4080
cccacctact atggctccct ggccaggttc tcagccttat catctgctac acccacgtcc   4140
acccaatggg cctgggattc agggcagggg cccaggctcc cctcctctgt ggctcaaacg   4200
gtggacgact tcctgttgga gaagtggcgc aagtattttc catctggcat cccgctgctc   4260
agcaacagcc ccaccccgct ggagagcagg ctgggttaca tgtctgccag tgagcagctc   4320
cggctcctac agcactccca ttcgcaagtc cctgaggcgg gcagcaccac ctttcagggc   4380
ataattgagg ccaaccggag gtggctggaa cgtgtcaaga atgaccccag gttacctctc   4440
ttctcgtcaa cacccaagcc aaaagctact ttgagcctcc tgcagctggg ccttgatgag   4500
cacaacagag tgaaggtgta tcgcttctga ggccctgagc aggggcttgg ggcagcccag   4560
cctctcctcc acccagacca agtgcctgag gagctgcctg ccttcttcca tctgagaaag   4620
caccctcctt ccccctttga cttgcaggag ccaccaggga ccagggggtt gagtggaaca   4680
gtaaagccac acattctgtg actatataac ctatctcagg ctaaaatgtg tggactcgta   4740
cgagctcttg tcattgacat ggcaagctga tggcgtgcgg tggctgcggg gtatcagggc   4800
cgggagccct ttgggaggaa gggaggcgtt agaggagctg ccttcggagg ctcagggagt   4860
ccctttggag ctggttgttt ccttggccct gcagcgcact gctcggggct cccaaggagg   4920
ttgtgtgtat ggttcttaat tcatcaggac aaagaccccc agcatgtgtg taccctggga   4980
cccgatttct ctgggcccac atctatctcc aatacctcag cctcagatca gaccctttct   5040
tttttgtctt tcttctctta atttttaaat gcctcttttc ttgagcattc catctctctt   5100
```

-continued tttgaccctc tcaggactgg gcttagctgt ccagagccct gccggagggt gctgggggct 5160
gtccctctgc aggcactgtg ttttcctcag gggctgtcct cagaacaccc ctcctgctcc 5220
ctggggctcc tcagggagcc atttcagctg gagtctcagg tctcaaaaac aacttctcca 5280
ggaggccaaa aaaagactgg gttggcttct ggtcctcatg atggctttta tcctcctggg 5340
acactttggg tatattcatg ggcattgttt ccatctgtct tttctacctg tgccacccct 5400
gccctgattc cacggctgcc tcaggcaggc aggcaaggag ctaggccggt gcccggccct 5460
ggcagcaagg ggtctttgtg cagttggaga tgctgccgtt gtggcagagc gtcctgcagc 5520
cccgcttcca tcagcaggct ctggggtggg ggctttgcag gggatgctct ctgatgtttg 5580
ttccgttgtt taaataaaat gcacttattt ttgttttttt ttttgcaaaa aaaa 5634

<210> SEQ ID NO 31
<211> LENGTH: 5228
<212> TYPE: DNA
<213> ORGANISM: Homo sapiens

<400> SEQUENCE: 31
cattgtcgcc cacgctgcag tagcggcttc tgcggctcca agccagcggg tcctgtgaag 60
gcgagcagac gcggagaaag gacgcgggag tgagagaggg tgagtcagcc actgtctaaa 120
cgataacggg aggcggctct gcggggtagg gttgaattca gtaaatgggc tcgtgctgct 180
gtctcttcgg agacgctgct atcttagcgt cagcgaggga aggttgagga ggagccagag 240
ccgggtcctg cagcgtttct cgccatcagc gcccgtcgcc atctccacca tgcagtcccg 300
ggaagacgcc ccgcgctctc gccgcctagc cagtccccgt ggtgggaagc ggcccaagaa 360
gattcacaaa cccacagttt cggccttttt cacgggtcca gaggaattaa aggacacggc 420
ccattctgca gccctgctgg cacagctcaa gtccttctac gatgcgcggc tgctgtgtga 480
tgtgaccatc gaggtggtga cgcctggcag cgggcctggc acgggtcgcc tgttcccctg 540
caaccgcaat gtgctggccg cggcatgtcc ctacttcaag agcatgttca caggtggcat 600
gtacgagagc cagcaggcca gcgtgaccat gcacgatgtg gacgccgagt ccttcgaggt 660
gttggtcgac tactgctaca cgggtcgtgt gtctctcagt gaggccaacg tggagcgcct 720
gtacgcggcc tccgacatgc tacagctgga atatgtgcgg gaagcctgtg cctccttctt 780
agcccgacgt cttgacctga ccaactgcac cgccatcctc aagtttgcag atgcctttgg 840
ccatcgcaag ctgcgatccc aggcccagtc ctatatagct cagaacttca agcaactcag 900
ccacatgggt tcaattcggg aggagactct agcagatctg accctggccc agctgctggc 960
tgtcctgcgc ttggatagtc tggacgtgga gagtgagcag acagtgtgcc atgtggcagt 1020
gcagtggctg gaggctgctc ccaaagagcg gggtcccagt gctgcagaag tcttcaagtg 1080
cgtgcgctgg atgcacttca ctgaagaaga tcaggactac ttagaagggc tgctgaccaa 1140
gcccatcgtg aagaagtact gcctggacgt tattgaaggg gccctgcaga tgcgctatgg 1200
tgacctgttg tacaagtctc tggtgccagt gccaaacagc agcagcagca gtagcagcag 1260
caactctctt gtatctgcag cagaaaatcc accccagaga ctgggtatgt gtgccaagga 1320
gatggtgatc ttctttggac accccagaga tccctttctc tgctgtgatc catactcggg 1380
ggacctttac aaagtgccgt cacctttgac ctgtctggct cacactagga ctgtcaccac 1440
tctagctgtc tgtatctctc ctgaccatga catctatcta gctgctcagc ccaggacaga 1500
cctctgggtg tataaaccag ctcagaatag ttggcagcaa cttgcagatc gcttgctgtg 1560

-continued

```
tcgtgagggc atggatgtgg catatctcaa tggctatatc tacattttgg gggggcgaga   1620
ccctattact ggagttaagt tgaaggaagt ggaatgctac aatgttaaga gaaaccagtg   1680
ggcattggtg gctccactgc cccattcttt tttatccttt gacctaatgg taattcgaga   1740
ctatctctat gctctcaaca gtaagcgcat gttctgttat gatcctagcc acaatatgtg   1800
gctgaagtgc gtttctctga agcgcaatga ctttcaggaa gcctgcgtct tcaatgagga   1860
gatctattgt atctgtgata tcccagtcat gaaggtctac aacccagtta gggcagaatg   1920
gaggcaaatg aataatattc ccttggtctc agagaccaac aactacagaa ttatcaagca   1980
tggccaaaaa ttgttgctca tcacctctcg caccccacag tggaaaaaga accgggtgac   2040
tgtgtatgaa tatgatatta ggggagacca atggattaat ataggtacca cattaggcct   2100
cttgcagttt gattctaact ttttttgcct ctctgctcgt gtttatcctt cctgccttga   2160
acctggtcag agtttcctca ctgaagaaga agaaatacca agtgagtcta gcactgaatg   2220
ggacttaggt ggattcagtg agccagactc tgagtcagga agttcaagtt ctctttctga   2280
tgatgatttt tgggtgcgtg tagcgcctca gtgaaatgca caggatcaac agggtttgtt   2340
gtaactagat tgaaacacta agttgttttt actgttttgg aaaatatctt aaatatcctt   2400
tttgttccta aaggagagga aaagttgatt aacttctggt ttggtttaga aaaagtaatg   2460
tttgaaatac gaaggtaatt taatgttaca aattttaaca ctcaaatcaa ccttttaata   2520
attttctgtg ctaagggtcc agtatttatt tgattattta gtatgtttat gtttcatgac   2580
actaatttag tcttttgata cattttacat tctgtttact gccacaagca ctgtggcaat   2640
aacttttgaa ttttaatttt tataatagaa aaatgattag gaattgctag atagtgtttt   2700
gaaagcatat ctttttcttc agaacaatgt agacttccaa aatggttaac ctaaggggtc   2760
tttacaaaat gtgttataag ttaaacataa tttgggaagt tttacttttg ttttcttcta   2820
tgaagaaaaa aatgcaggct gggcgcggtg gctcacgcct gtaatcctag cactttggga   2880
ggccgaggca ggtggatcac ctgaggtcag ttcaagacca gcctggccaa catggtgaaa   2940
ccccgtctct actaaaaata caaaaattag ctgggcgtgg tggcatgcgc ctgtaatccc   3000
agctacccag gaggctgagg caggagaatt gctgaaaccc gggagtcaga ggctgcagag   3060
agccgagact gggccactgc actccagcct ggatgacaga gtgagactcc gtctcaaaaa   3120
aaaaaaaaaa aaaaaaagga aaaaaaaaaa agaaaaaaaa ccatatgtgt attagggtga   3180
ctgagtggtg acttcattta taataataca gagaatagct ataagctcat tgacagtaaa   3240
aacaacaaac caggattcta ctgtttgaaa agaagtttcg ttttaatttt ggaatttaga   3300
atgtgtattt gcaaagtcac caattttcat ctaaaaggtt atattctagt tgtgtcacca   3360
aatcatcaaa aaaccttaaa aaagaagtaa cttgctttgt aggtttgtat tgttgatcta   3420
aacctgatac atgcttcatt taatcaggaa taatcctttt ttttctgctg gacatgtata   3480
aatttcactg gattgtataa atttttatct attgccttaa acatttacat gattctcaat   3540
atgttttagc tgtacagttt tggtgttcat cttagaggat tcttcagcag aagtgatatt   3600
tctttactgt tttgtgaggt aatactgatt ttgaaaatat atataagcta aaaacagtat   3660
ttcgttgata tcagtagtca ttgtgttaac tataaagtca agtgccagca aagaacttta   3720
aaactgtaaa gctgtgtata gaactgtttt gtgtagcatg gaaatattct gtcagctttt   3780
taaagtcact aaatgttctt gattatcagc ttgaaggtat ttttgtatta caagttgaca   3840
gttgctgggt gtagtggctc atgcctgtaa tcctagcaac tcggggctga ggtgggagga   3900
ttgcttcagc ccaggagttt gagaccagcc tgggcaacat agcaaaaccc catctctaca   3960
```

aaaataaaaa atatgtctgg gcatggtggc ccaagtctga gtcccagtta cttgggagga 4020
tcacttgaat gtaggatcac ttgagtctag gagttcgggg ctgcagctat catctgcagc 4080
tataatcata gctcactgca gctatgatca tgtctcagca ctccagcttt ggcaacagaa 4140
cgagatccca tctcttagaa aaacaaagtt gatagttaaa gaacataagt ggatgatggc 4200
atttgaggcc actagtgaaa gtatgttttc tctaaaatat ttctctaata gtgatataaa 4260
tggctatttt attatgatgt ttgtatgtgt tttgtatttc tctgtaaacc atgctccagt 4320
ctttgttttt ctgttaccat aatgtaagag aaggtcctgg aacagagact aaatcccacg 4380
aaactgacat tgttaaacac actaaaacag aagtacttac ctcttgaaga tttaatatat 4440
aatggttgac atgatacatg tacatgatga atgaccagat gcttatggtc tacattttcc 4500
tttatcctgt tagtattacc ttccttaatc tttgttcatt aacatgctaa ttcctcttca 4560
gtgtttattt tctagtgaca gaatgctaac atttcttaca ccctggcaga agggagagaa 4620
atgtgttttg gggtgggtaa ctaaattttt gagtgaaata tcataagatg agaatggaaa 4680
gagggagaca caaagagtta taacaaaaaa acaatggttt ttttagccat ttgactggct 4740
ctttaaatag tctacaagac attcacgttt aacatcactt ttagtgaaat aaaatgtgcc 4800
atactagtat gtgcttcaaa agggcaaatg tgctttagtg ccctaaggct aaattttggt 4860
catttgacat cagagatgtt gtaagtattg cacttaatac gcacctattt ctcaatagtg 4920
ttattttttg gctagcattt tctttaccac tatcttgttg atagcttttt gttctctaag 4980
gttgaaacat gacagtgctt atctcaaaca gattacccat ctgcagaact aaggaaagca 5040
atttatgtat gaaagaaatt cttgaattcg tcattctcaa cctttgaatt aaagcttaga 5100
ctaaatagta atatatcgtg ggaaggattt tggttttgtg atatttctgt gaattaagga 5160
atagatgtta accattattt tgtagaaaag tgatttgtat gtggttaatt ataaataaaa 5220
ctggtacc 5228

<210> SEQ ID NO 32
<211> LENGTH: 872
<212> TYPE: DNA
<213> ORGANISM: Homo sapiens

<400> SEQUENCE: 32
gtactttcgc catcatagta ttctccacca ctgttccttc cagccacgaa cgacgcaaac 60
gaagccaagt tcccccagct ccgaacagga gctctctatc ctctctctat tacactccgg 120
gagaaggaaa cgcgggagga aacccaggcc tccacgcgcg accccttggc cctccccttt 180
acctctccac ccctcactag acaccctccc ctctaggcgg ggacgaactt tcgccctgag 240
agaggcggag cctcagcgtc taccctcgct ctcgcgagct ttcggaactc tcgcgagacc 300
ctacgcccga cttgtgcgcc cgggaaaccc cgtcgttccc tttcccctgg ctggcagcgc 360
ggaggccgca cgatgcctgg agttactgta aaagacgtga accagcagga gttcgtcaga 420
gctctggcag ccttcctcaa aaagtccggg aagctgaaag tccccgaatg ggtggatacc 480
gtcaagctgg ccaagcacaa agagcttgct ccctacgatg agaactggtt ctacacgcga 540
gctgcttcca cagcgcggca cctgtacctc cggggtggcg ctggggttgg ctccatgacc 600
aagatctatg gggacgtcaa gagaaacggc gtcatgccca gccacttcag ccgaggctcc 660
aagagtgtgg cccgccgggt cctccaagcc ctggaggggc tgaaaatggt ggaaaaggac 720
caagatggcg gccgcaaact gacacctcag ggacaaagag atctggacag aatcgccgga 780

```
caggtggcag ctgccaacaa gaagcattag aacaaaccat gctgggttaa taaattgcct    840

cattcgtaaa aaaaaaaaaa aaaaaaaaaa aa                                  872


<210> SEQ ID NO 33
<211> LENGTH: 1003
<212> TYPE: DNA
<213> ORGANISM: Homo sapiens

<400> SEQUENCE: 33

gtctgcaggt atggatgttg ttctcttttc cctgtcttta tttccttacc aatcggctgc     60

catccgagga gctgaggaag cctagagctc tcagaagcag tcctttgagc tggtgtaggg    120

gcactcagaa tggtccagcg tttgacatac cgacgtaggc tttcctacaa tacagcctct    180

aacaaaacta ggctgtcccg aacccctggt aatagaattg tttaccttta taccaagaag    240

gttgggaaag caccaaaatc tgcatgtggt gtgtgcccag gcagacttcg aggggttcgt    300

gctgtaagac ctaaagttct tatgagattg tccaaaacaa agaaacatgt cagcagggcc    360

tatggtggtt ccatgtgtgc taaatgtgtt cgtgacagga tcaagcgtgc tttccttatc    420

gaggagcaga aaatcgttgt gaaagtgttg aaggcacaag cacagagtca gaaagctaaa    480

taaaaaaatg aaactttttt gagtaataaa aatgaaaaga cgctgtccaa tagaaaaagt    540

tggtgtgctg gagctacctc acctcagctt gagagagcca gttgtgtgca tctctttcca    600

gttttgcatc cagtgacgtc tgcttggcat cttgagattg ttatggtgag agtatttaca    660

cctcagcaaa tgctgcaaaa tcctgttttc ccccagagag ctggaggtta aatactacca    720

gcacatccct agatactact caagttacag tatatgatca ctaatatagt atgctcttgg    780

taccaggagc tctgatatat atctggtaca tgtttgataa tgacttgatt gttattataa    840

gtacttatta atacttcgat tctgtaaaga gtttagggtt tgattttata aaatccaaaa    900

tgagcctttt attgaatcca gttctctatg tgaccagttc tctgtatgaa tggaagggaa    960

aagaattaaa aatcttgcaa aggggaaaaa aaaaaaaaaa aaa                     1003


<210> SEQ ID NO 34
<211> LENGTH: 5862
<212> TYPE: DNA
<213> ORGANISM: Homo sapiens

<400> SEQUENCE: 34

gcgtccgagg gagcgcgcga cgggccacgc acgtccgggc gtccagttcg gggcagcttc     60

tccggctggt gggtgggtgg ggcagccttt caggcagggt ggcaaccaac tatatctgag    120

gaccagagcc attttggggc accagagctt gtgacctctc catctccacc cagctgggtc    180

caggggccac tctcagcact cacctcagca gctgacatca taaagcagac ttgggaacct    240

ggaagcactc tggagaacct ttccctgaga catggagctt tggggccgaa tgctgtgggc    300

cctcctgtct ggcccaggga ggaggggaag tacccggggc tgggccttca gctcatggca    360

accccaacca cctctggctg ggttatccag tgccatagaa ctggtcagcc actggactgg    420

ggtctttgag aagaggggta tccctgaggc ccgggaatcc agtgagtaca tcgtggctca    480

tgtccttgga gccaaaacat ttcagagcct gaggccggca ctttggaccc agcccttgac    540

ctctcagcaa ctacagtgta tccgggagct gagtagccgt cgattgcaga ggatgccggt    600

gcagtacatc cttggagagt gggacttcca ggggctcagc ctaaggatgg tgcccccagt    660

gtttattcct cggccagaaa cagaggaact ggttgagtgg gtgctggaag aggtggccca    720

gaggtcccat gctgtgggat ccccaggcag ccccctcatt ctggaggtgg gctgcggatc    780
```

-continued

```
aggagccatc tccctcagcc tgctgagcca gctcccccag agccgagtca ttgctgtgga    840
taagcgggaa gctgctatct ctctgaccca tgagaatgct cagaggcttc ggttgcagga    900
caggatttgg atcatccacc tcgacatgac ctcagaaagg agctggacac acctgccctg    960
gggccccatg gacctgattg tcagcaaccc tccctacgtc ttccaccagg acatggagca   1020
gctggcccct gagatccgca gctatgaaga ccccgcggcc ctggatggtg gggaggaggg   1080
catggacatc attacccaca ttctggcctt ggcaccccgg ctcctgaaag actctggtag   1140
tatcttctta gaagtggacc caaggcaccc ggagcttgtc agcagctggc ttcagagccg   1200
gcctgacctg taccttaatc ttgtggctgt gcgcagggac ttctgtggga ggccccggtt   1260
cctgcatatc cggaggtctg ggccatagca tggctgccct gtggatgcct tgtcagtgcc   1320
gccagcctga ccagagggga ggtggatggc actttccaga gcccaggttc ttatggcatt   1380
tcccagggtt ctgtgatttc cccatgctct gcatttctag gatatttcta ggacacctgg   1440
attggctcca tcacatcaga gtggctgagg gcagttgctc tgtgttggtg aaattgctgt   1500
gggggtatcg gggatatgg ccagtaaagt attgagagac taacaaatgg tgacctaatg   1560
ttttgtccat gacttgcagg tcccctgacc cccttactcc caggtagcac tggggcaagg   1620
gtttccttct gccccagcag ggctggccgt cagtcccctg cttggtagtg gtgtgggggt   1680
gcagtgtgga ggaaggcacg tgagtcctca ctcctggcct tggataccat gggtcctggc   1740
atagagcagc tcactcccag ggattgatta gtcctccact gccctgggtg catgcgtaca   1800
caattccctg gccaagcctg gctcgagcac aggaagctca tctgcgtttt ggctcaagga   1860
tgactgcctg ctttctggag gggagggtct ggaggtcttt gctgcacagt tcctgggtcg   1920
cacatccacg ttcatttaac tgaaggcttg agccagtgag gggtgtttcc tttttatccc   1980
catagctttt agctaaaaca tccctcccga gttgaccccc tggggtttca aataacccat   2040
gtgtccctgg ttggggctgg ggagagtgag aagctgagat actgggcaca gggttgtggc   2100
ctccacccca gctctggtct gtgcagactc atggccacca ggaggcctgc agatccagcc   2160
ttcctgtcaa cagcgacagg aaatctctag gttggtgagt gctggtgatg tgagcctaca   2220
tcagggtggg tcctaagaaa catggcaaac caggctgtct cattccacta gactgccccc   2280
tgccaccctg gcacttccca gggcctggca gtatggtctg atgggcagta tggtccaata   2340
ggcagcatcc tctgctgcag ctgggagagc tgagttccag ggctgtgtcc tgcagtggga   2400
ccttgggcaa ctcctttccc tatgagaagc tggctcttct gagtccaggg ccaacgccaa   2460
ctggcaacct ctttactctt agtcaagtgg aatgtgcatg ctggcatctg aatgtccatt   2520
cgccaggcat ggagagcaag agaaggtatg tactgcctga ggtcacatga cagtgaccaa   2580
gtggagacag taagttagat ccctcccttt ggggagccta tattgctgga gtcataccca   2640
gcctaagtgt tgccctgcac tatggctgga ggacacattt ggtagaggtc acactgcagc   2700
tcccagtgcc ccagtgtcct gccctgtgcc cagccccagc tgcatggact ctgagctgcc   2760
cctggcttcc tttaaggagg ctgctccaga aggaacctgg gtggggaggg cgaagggggt   2820
gcacaaccag ggcaaggctc cccacttcct tagtccccca tgctcacaga cctttgcctg   2880
ctaaggtcct caccagtatt gccctttctg tctttctcct tgtgcccttt ggctcttgct   2940
gtcttcagca gcatctcagg gtagctgccc tgacctcgga gcagtctgtc gcccccctac   3000
acctcagcca gtcctggctt ccctgatggt ctctccctcc tggcctcagg cccattcctg   3060
aggaagggcc ttggcgagct tgtggatgtt gcaccagaag agagtgcagt gttggagagt   3120
```

-continued

```
gacactgtcg gggcagctgg ggccacaagc aggagccggc ctcgggcaca actttctgcc   3180
cagaaaaatg tgcagcttga ctctgctgag gaaaaggtcc aagccaagag gactggcagg   3240
cggggcctca agcctgcagc cactggcttg attgggccct ggacgttgag cccagatgtt   3300
ggagccacac cagcctggat ttcaatccca gaatctgccc ctcaccagga tgtgaccttg   3360
ggcagatgac ttcacctcac tcagccttgg cttctaaggc tgagaaatgg gacttaatgc   3420
tttattttat aggatgcatg tgaggagccc atggaatgtg cctggcttgg cacattgtgg   3480
catttttcct tgccttcctc ggagggcaga cacagggagg aaggacccag tgccctcagg   3540
cgtccatctg atgcatggga ccaacataag gcaggcaggg atacaaggca gtctggaaag   3600
aagggaaggc aggagtttca gtcttgggct cttgactcct cactgttgtc tagagatgga   3660
gccagcaggc tggtagcctg gcagcctaca tctcccctca gcctctcctc actatggccc   3720
cagtgccttg aggcccaggc cagggcagcc agtggctcta gctcagggaa agccaggccc   3780
acctgcccta tcccctccct tgctcctgag gccaaagcca gagactcgaa cagcctcccc   3840
accaccacca gcatatgtca aggagcactt gcaggcagaa tgggaggagg acatggagct   3900
gatggagtcc aggctgtgca agcccctgag gtcttgagag atgtgcccac tgcccgtgca   3960
gcctccttca gccagagccc agagcataga caggagtgta ggagtccctg tttgatgtac   4020
tctgggagag taattctatc tcctcttctg atagttgggg aaactgaggc cttgtctcac   4080
agttggatgc ttttcccagt tgtcagtggg tttctccatg ggtctcatac agctgcctta   4140
ttgaaatagg ccccgaaccc cctaaatgca aaaaatactc ttttttgctc ctttaccccc   4200
acctggaccc tgggctattg gctgctccca atccttgccc caaacactta gctggctccc   4260
catgacttaa gtgtgttctc ttgtgtccta tggaatccag ttctgaagag gtgggggagg   4320
acaactgtgg gaaaagccct gggggcccct cccaaggccc catcagtgct ctgagtaggc   4380
tgtcatcaga acaaagggct ccactgctga caaggtttga gaactgctgg cttgaggtga   4440
gaacccccttt aacctctgcg ggacagcatg tctttcccta tccaccttcg attcttttct   4500
cttttttttc ttcattggct ccttcttagt ggattctctt ctctactgcc ctgggcttca   4560
gcctttgtgc agtactctcg atgccctgaa cacacacctt ccctttgccc aggcggtgca   4620
aacaatccac ttcttcaagc tccaacacaa atgctgcctc ctttaggatg cctgctctgt   4680
gctctccctg cctcccctag cccatacctc tgctggcacc ttctgtacca tgccttcaga   4740
aaccttctta tccccctcat ctctggggcc ccctgtggat ctggcatacc caagttcagt   4800
aaatgtctat cagtaagctg atggtacatg cattttctag aatagagctg ggacttccca   4860
tgtggcccac atctgacctg gcagcccatg tattccggtc attagggatg ggaagccatg   4920
aggacctggc cttctgcccg acccaggcag ccattcaagt tgagcaatgg ccacttcgaa   4980
gactcaagtg cacctgatcc ctgcgcaaca gccacaccag gagaacaggc tgtccttggc   5040
ggcagtagga gcaggcgcca ggtttcctgg agctcttggc ttcagccagc cccagccag    5100
agtcctggct aggacagtga cctgatctcc tcctcatgac cttctgccct ggacaagccc   5160
cctgaactgg atttgggact gtcaaagcaa ctctacccct gctctggtag gctgaacagt   5220
gaccccccaa aatggcagtg tcttaatcac ctaaacctta acatgtgact atattacctt   5280
cacatagcaa aatggacttt gcagatgtga ttaaggatct tgagatggaa ggagtatcct   5340
ggatttttca ggtaaactga gtataatcac aagggcctct gtaaaggagg caggagtgtc   5400
agagtgacgg aagaaaatgt atgtaacaat ggaagcagag gtcagagtga tgcaattgct   5460
ggaggaagag ccatgagccg aggaatgcag acagcctctt ctcctctggg gcctcaagaa   5520
```

```
gaatgcagtc ctgccaatac cttgatttta agccctgtga aactgatttc agattgctga   5580

cctccagaac agtaagatca taaatttgtg ttgttttcac atgtgtgaaa acacatgtgt   5640

gataatttgt tacagcagcc acgggaaacg aatatagatt gtggtgccca aattagagtg   5700

ctgctgtaac acacgcctac tgattgaagt ggctttggaa ttgcaacgtg gaaatgggca   5760

gaggctggaa gaattttgag agtcatgata aattgcctta accacctctc ttctgatagg   5820

tgatgtggcc aggggaactc ttcctcaacc ttcagaccta aa                      5862
```

<210> SEQ ID NO 35
<211> LENGTH: 5662
<212> TYPE: DNA
<213> ORGANISM: Homo sapiens

<400> SEQUENCE: 35

```
tcctcgacgg ccgccgcccg cctggccttt tagggcctga ctcccgccct tcctggccta     60

cactcctggg cggcggcagg cctagcttct ggcccagtgc gggttccccg gcggcaggcg    120

tatcctgtgt gcccctgggc caggcccgaa cccggtgtcc ccgggtgggg ggtggggacg    180

ccacggccga agcagctagc tccgttcgtg atccgggagc ctggtgccag cgagacctgg    240

aatttccggt ctggttggtc tggggccccg cggagccagg ttgataccct cacctcccaa    300

ccccaggccc tcggatgccc agaacctgta ggccgcaccg tggacttgtt cttaatcgag    360

ggggtgctgg ggggaccctg atgtggcacc aaatgaaatg aacaaagctc cacagtccac    420

aggcccccca cccgccccat cccccggact cccacagcca gcgtttcccc cggggcagac    480

agcgccggtg gtgttcagta cgccacaagc gacacaaatg aacacgcctt ctcagccccg    540

ccagcacttc taccctagcc gggcccagcc cccgagcagt gcagcctccc gagtgcagag    600

tgcagcccct gcccgccctg gcccagctgc ccatgtctac cctgctggat cccaagtaat    660

gatgatccct tcccagatct cctacccagc ctcccagggg gcctactaca tccctggaca    720

ggggcgttcc acatacgttg tcccgacaca gcagtaccct gtgcagccag gagccccagg    780

cttctatcca ggtgcaagcc ctacagaatt tgggacctac gctggcgcct actatccagc    840

ccaaggggtg cagcagtttc ccactggcgt ggcccccgcc ccagttttga tgaaccagcc    900

accccagatt gctcccaaga gggagcgtaa gacgatccga attcgagatc caaaccaagg    960

aggaaaggat atcacagagg agatcatgtc tggggcccgc actgcctcca cacccacccc   1020

tccccagacg ggaggcggtc tggagcctca agctaatggg gagacgcccc aggttgctgt   1080

cattgtccgg ccagatgacc ggtcacaggg agcaatcatt gctgaccggc cagggctgcc   1140

tggcccagag catagccctt cagaatccca gccttcgtcg ccttctccga ccccatcacc   1200

atccccagtc ttggaaccgg ggtctgagcc taatctcgca gtcctctcta ttcctgggga   1260

cactatgaca actatacaaa tgtctgtaga agaatcaacc cccatctccc gtgaaactgg   1320

ggagccatat cgcctctctc cagaacccac tcctctcgcc gaacccatac tggaagtaga   1380

agtgacactt agcaaaccgg ttccagaatc tgagttttct tccagtcctc tccaggctcc   1440

cacccctttg gcatctcaca cagtggaaat tcatgagcct aatggcatgg tcccatctga   1500

agatctggaa ccagaggtgg agtcaagccc agagcttgct cctcccccag cttgcccctc   1560

cgaatcccct gtgcccattg ctccaactgc ccaacctgag gaactgctca acggagcccc   1620

ctcgccacca gctgtggact taagcccagt cagtgagcca gaggagcagg ccaaggaggt   1680

gacagcatca atggcgcccc ccaccatccc ctctgctact ccagctacgg ctccttcagc   1740
```

-continued

```
tacttcccca gctcaggagg aggaaatgga agaagaagaa gaagaggaag aaggagaagc   1800
aggagaagca ggagaagctg agagtgagaa aggaggagag gaactgctcc ccccagagag   1860
taccccctatt ccagccaact tgtctcagaa tttggaggca gcagcagcca ctcaagtggc   1920
agtatctgtg ccaaagagga gacggaaaat taaggagcta aataagaagg aggctgttgg   1980
agaccttctg gatgccttca aggaggcgaa cccggcagta ccagaggtgg aaaatcagcc   2040
tcctgcaggc agcaatccag gcccagagtc tgagggcagt ggtgtgcccc cacgtcctga   2100
ggaagcagat gagacctggg actcaaagga agacaaaatt cacaatgctg agaacatcca   2160
gcccggggaa cagaagtatg aatataagtc agatcagtgg aagcctctaa acctagagga   2220
gaaaaaacgt tacgaccgtg agttcctgct tggttttcag ttcatctttg ccagtatgca   2280
gaagccagag ggattgccac atatcagtga cgtggtgctg gacaaggcca ataaaacacc   2340
actgcggcca ctggatccca ctagactaca aggcataaat tgtggcccag acttcactcc   2400
atcctttgcc aaccttggcc ggacaaccct tagcacccgt gggcccccaa ggggtgggcc   2460
aggtggggag ctgccccgtg ggccggctgg cctgggaccc cggcgctctc agcagggacc   2520
ccgaaaagaa ccacgcaaga tcattgccac agtgttaatg accgaagata taaaactgaa   2580
caaagcagag aaagcctgga aacccagcag caagcggacg gcggctgata aggatcgagg   2640
ggaagaagat gctgatggca gcaaaaccca ggacctattc cgcagggtgc gctccatcct   2700
gaataaactg acaccccaga tgttccagca gctgatgaag caagtgacgc agctggccat   2760
cgacaccgag gaacgcctca aaggggtcat tgacctcatt tttgagaagg ccatttcaga   2820
gcccaacttc tctgtggcct atgccaacat gtgccgctgc ctcatggcgc tgaaagtgcc   2880
cactacggaa aagccaacag tgactgtgaa cttccgaaag ctgttgttga atcgatgtca   2940
gaaggagttt gagaaagaca aagatgatga tgaggttttt gagaagaagc aaaaagagat   3000
ggatgaagct gctacggcag aggaacgagg acgcctgaag gaagagctgg aagaggctcg   3060
ggacatagcc cggcggcgct ctttagggaa tatcaagttt attggagagt tgttcaaact   3120
gaagatgtta acagaggcaa taatgcatga ctgtgtggtc aaactgctta agaaccatga   3180
tgaagagtcc cttgagtgcc tttgtcgtct gctcaccacc attggcaaag acctggactt   3240
tgaaaaagcc aagccccgaa tggatcagta tttcaaccag atggaaaaaa tcattaaaga   3300
aaagaagacg tcatcccgca tccgctttat gctgcaggac gtgctggatc tgcgagggag   3360
caattgggtg ccacgccgag gggatcaggg tcccaagacc attgaccaga tccataagga   3420
ggctgagatg gaagaacatc gagagcacat caaagtgcag cagctcatgg ccaagggcag   3480
tgacaagcgt cggggcggtc ctccaggccc tcccatcagc cgtggacttc cccttgtgga   3540
tgatggtggc tggaacacag ttcccatcag caaaggtagc cgccccattg acacctcacg   3600
actcaccaag atcaccaagc ctggctccat cgattctaac aaccagctct ttgcacctgg   3660
agggcgactg agctggggca agggcagcag cggaggctca ggagccaagc cctcagacgc   3720
agcatcagaa gctgctcgcc cagctactag tactttgaat cgcttctcag cccttcaaca   3780
agcggtaccc acagaaagca cagataatag acgtgtggtg cagaggagta gcttgagccg   3840
agaacgaggc gagaaagctg gagaccgagg agaccgccta gagcggagtg aacggggagg   3900
ggaccgtggg gaccggcttg atcgtgcgcg gacacctgct accaagcgga gcttcagcaa   3960
ggaagtggag gagcggagta gagaacggcc ctcccagcct gaggggctgc gcaaggcagc   4020
tagcctcacg gaggatcggg accgtgggcg ggatgccgtg aagcgagaag ctgccctacc   4080
cccagtgagc cccctgaagg cggctctctc tgaggaggag ttagagaaga aatccaaggc   4140
```

```
tatcattgag gaatatctcc atctcaatga catgaaagag gcagtccagt gcgtgcagga   4200
gctggcctca ccctccttgc tcttcatctt tgtacggcat ggtgtcgagt ctacgctgga   4260
gcgcagtgcc attgctcgtg agcatatggg gcagctgctg caccagctgc tctgtgctgg   4320
gcatctgtct actgctcagt actaccaagg gttgtatgaa atcttggaat tggctgagga   4380
catggaaatt gacatccccc acgtgtggct ctacctagcg gaactggtaa cacccattct   4440
gcaggaaggt ggggtgccca tgggggagct gttcagggag attacaaagc ctctgagacc   4500
gttgggcaaa gctgcttccc tgttgctgga gatcctgggc ctcctgtgca aaagcatggg   4560
tcctaaaaag gtggggacgc tgtggcgaga agccgggctt agctggaagg aatttctacc   4620
tgaaggccag gacattggtg cattcgtcgc tgaacagaag gtggagtata ccctgggaga   4680
ggagtcggaa gcccctggcc agagggcact cccctccgag gagctgaaca ggcagctgga   4740
gaagctgctg aaggagggca gcagtaacca gcgggtgttc gactggatag aggccaacct   4800
gagtgagcag cagatagtat ccaacacgtt agttcgagcc ctcatgacgg ctgtctgcta   4860
ttctgcaatt atttttgaga ctcccctccg agtggacgtt gcagtgctga aagcgcgagc   4920
gaagctgctg cagaaatacc tgtgtgacga gcagaaggag ctacaggcgc tctacgccct   4980
ccaggccctt gtagtgacct tagaacagcc tcccaacctg ctgcggatgt tctttgacgc   5040
actgtatgac gaggacgtgg tgaaggagga tgccttctac agttgggaga gtagcaagga   5100
ccccgctgag cagcagggca agggtgtggc ccttaaatct gtcacagcct tcttcaagtg   5160
gctccgtgaa gcagaggagg agtctgacca caactgaggg ctggtggggc cggggacctg   5220
gagccccatg gacacacaga tggcccggct agccgcctgg actgcagggg ggcggcagca   5280
gcggcggtgg cagtgggtgc ctgtagtgtg atgtgtctga actaataaag tggctgaaga   5340
ggcaggatgg cttggggctg cctgggcccc cctccaggat gccgccaggt gtccctctcc   5400
tcccccctggg gcacagagat atattatata taaagtcttg aaatttggtg tgtcttgggg   5460
tggggagggg caccaacgcc tgcccctggg gtcctttttt ttattttctg aaaatcactc   5520
tcgggactgc cgtcctcgct gctgggggca tatgccccag cccctgtacc acccctgctg   5580
ttgcctgggc agggggaagg gggggcacgg tgcctgtaat tattaaacat gaattcaatt   5640
aagctcaaaa aaaaaaaaaa aa                                            5662
```

<210> SEQ ID NO 36
<211> LENGTH: 3251
<212> TYPE: DNA
<213> ORGANISM: Homo sapiens

<400> SEQUENCE: 36

```
cagcaactat gaaataatcg tagtatgaga ggcagagatc ggggcgagac aatggggatg     60
tgggcgcggg agccccgttc cggcttagca gcacctccca gccccgcaga ataaaaccga    120
tcgcgccccc tccgcgcgcg ccctccccg agtgcggagc gggaggaggc ggcggcggcc    180
gaggaggagg aggaggaggc cccggaggag gaggcgttgg aggtcgaggc ggaggcggag    240
gaggaggagg ccgaggcgcc ggaggaggcc gaggcgccgg agcaggagga ggccggccgg    300
aggcggcatg agacgagcgt ggcggccgcg gctgctcggg gccgcgctgg ttgcccattg    360
acagcggcgt ctgcagctcg cttcaagatg gccgcttggc tcgcattcat tttctgctga    420
acgactttta actttcattg tcttttccgc ccgcttcgat cgcctcgcgc cggctgctct    480
ttccgggatt ttttatcaag cagaaatgca tcgaacaacg agaatcaaga tcactgagct    540
```

-continued

```
aaatccccac ctgatgtgtg tgctttgtgg agggtacttc attgatgcca caaccataat    600
agaatgtcta cattccttct gtaaaacgtg tattgttcgt tacctggaga ccagcaagta    660
ttgtcctatt tgtgatgtcc aagttcacaa gaccagacca ctactgaata taaggtcaga    720
taaaactctc caagatattg tatacaaatt agttccaggg cttttcaaaa atgaaatgaa    780
gagaagaagg gatttttatg cagctcatcc ttctgctgat gctgccaatg gctctaatga    840
agatagagga gaggttgcag atgaagataa gagaattata actgatgatg agataataag    900
cttatccatt gaattctttg accagaacag attggatcgg aaagtaaaca aagacaaaga    960
gaaatctaag gaggaggtga atgataaaag atacttacga tgcccagcag caatgactgt   1020
gatgcactta agaaagtttc tcagaagtaa aatggacata cctaatactt tccagattga   1080
tgtcatgtat gaggaggaac ctttaaagga ttattataca ctaatggata ttgcctacat   1140
ttatacctgg agaaggaatg gtccacttcc attgaaatac agagttcgac ctacttgtaa   1200
aagaatgaag atcagtcacc agagagatgg actgacaaat gctggagaac tggaaagtga   1260
ctctgggagt gacaaggcca acagcccagc aggaggtatt ccctccacct cttcttgttt   1320
gcctagcccc agtactccag tgcagtctcc tcatccacag tttcctcaca tttccagtac   1380
tatgaatgga accagcaaca gccccagcgg taaccaccaa tcttcttttg ccaatagacc   1440
tcgaaaatca tcagtaaatg ggtcatcagc aacttcttct ggttgatacc tgagactgtt   1500
aaggaaaaaa attttaaacc cctgatttat atagatatct tcatgccatt acagctttct   1560
agatgctaat acatgtgact atcgtccaat ttgctttctt ttgtagtgac attaaatttg   1620
gctataaaag atggactaca tgtgatactc ctatggacgt taattgaaaa gaaagattgt   1680
tgttataaag aattggtttc ttggaaagca ggcaagactt tttctctgtg ttaggaaaga   1740
tgggaaatgg tttctgtaac cattgtttgg atttggaagt actctgcagt ggacataagc   1800
attgggccat agtttgttaa tctcaactaa cgcctacatt acattctcct tgatcgttct   1860
tgttattacg ctgttttgtg aacctgtaga aaacaagtgc tttttatctt gaaattcaac   1920
caacggaaag aatatgcata gaataatgca ttctatgtag ccatgtcact gtgaataacg   1980
atttcttgca tatttagcca ttttgattcc tgtttgattt atacttctct gttgctacgc   2040
aaaaccgatc aaagaaaagt gaacttcagt tttacaatct gtatgcctaa aagcgggtac   2100
taccgtttat tttactgact tgtttaaatg attcgctttt gtaagaatca gatggcatta   2160
tgcttgttgt acaatgccat attggtatat gacataacag gaaacagtat tgtatgatat   2220
atttataaat gctataaaga aatattgtgt ttcatgcatt cagaaatgat tgttaaaatt   2280
ctcccaactg gttcgacctt tgcagatacc cataacctat gttgagcctt gcttaccagc   2340
aaagaatatt tttaatgtgg atatctaatt ctaaagtctg ttccattaga agcaattggc   2400
acatctttct atactttata tacttttctc cagtaataca tgtttacttt aaaaattgtt   2460
gcagtgaaga aaaaccttta actgagaaat atggaaaccg tcttaatttt ccattggcta   2520
tgatggaatt aatattgtat tttaaaaatg catattgatc actataattc taaaacaatt   2580
ttttaaataa accagcaggt tgctaaaaga aggcatttta tctaaagtta ttttaatagg   2640
tggtatagca gtaattttaa atttaagagt tgcttttaca gttaacaatg gaatatgcct   2700
tctctgctat gtctgaaaat agaagctatt tattatgagc ttctacaggt atttttaaat   2760
agagcaagca tgttgaattt aaaatatgaa taacccccacc caacaatttt cagtttattt   2820
tttgctttgg tcgaacttgg tgtgtgttca tcacccatca gttatttgtg agggtgttta   2880
ttctatatga atattgtttc atgtttgtat gggaaaattg tagctaaaca tttcattgtc   2940
```

cccagtctgc aaaagaagca caattctatt gctttgtctt gcttatagtc attaaatcat 3000
tacttttaca tatattgctg ttacttctgc tttctttaaa aatatagtaa aggatgtttt 3060
atgaagtcac aagatacata tatttttatt ttgacctaaa tttgtacagt cccattgtaa 3120
gtgttgtttc taattataga tgtaaaatga aatttcattt gtaattggaa aaaatccaat 3180
aaaaaggata ttcatttaga aaaaaaaaaa aaaaaaaaaa aaaaaaaaaa aaaaaaaaaa 3240
aaaaaaaaaa a 3251

<210> SEQ ID NO 37
<211> LENGTH: 36230
<212> TYPE: DNA
<213> ORGANISM: Homo sapiens

<400> SEQUENCE: 37
accatatcct cctacactct gagcaatctc acggggtaga ccgcaggtta acacctctca 60
gactccttga aaaatagctg gtgacgggtc agtgcccaga gctcacctgc ctttcgccaa 120
actctaaaca cccctgtgtg tttcccctac tataccctgt tccctggggg caggtccctg 180
cattatgaag ccactaggaa aatgagataa agctttccta cttttcttcc cctgaaaaga 240
cagattttgt tttttatttt ttgagaatac caagtaagat tttatttttt atttatttta 300
aattatttta acctttgttt taggttcaag ggtacacatg caggtttgtt atataggtaa 360
attgtgtgtc atcgggattt ggcgtaaaaa tttatttcat cacccaggta ataagtatag 420
tatctgatag gtagtgtttt gatcctctcc ctcctcccat cctccaccct caagtagggc 480
ccagtgtcta ttattccctt ttttgtgtcc atgtgtactc aatgtttagc tcccacttat 540
aaaagtgaga acatgcagta tttcattttc tgctcctgtg ttagtttgcc taggataaca 600
gcccccagct ccatccatga tgctgcaaaa gacgtgatct cgtccttttt tgtctgtgga 660
gtattccatg gtgtatatgt accacatttt ctttatacag tctactgttg gtgggcattt 720
aggctgattc catgtctttg ctattatgaa tactgctgca gtgagcattc atgtgcatgt 780
gtccttatgg tagaacaatg tatactcctt tgggtatatg cctaataatg ggattcctgg 840
gacgaatggt agctctgttt taaggttctt gagaaattgc caaactgctt tcctcaatgg 900
ctgaactaat ttatgttccc accagcagtg tataagcctt ccgttttctc tgcaacctct 960
ccaacatttg ttattttttg actttttaat aatagccatt ctgactggtg tgagacggta 1020
tctcattatg attttgattt gcatttttct aatcattagt aatgttgaac attgtttcat 1080
atgcttcttg gtcacgtgtg tgtcttgaaa aggcagattt tatgtatttg cgtatttatt 1140
tttttcacag gttttttttt tgaaagtctc actctgtcgc ctaggctgga gtacagtggg 1200
ataatctcgg ctcactgcaa tcttcgcctc ctgggttcaa atgactctca tgcctcagcc 1260
acttgagtag ctggggttac agtcatgtgc caccactcct ggttagtttt tgtctttttt 1320
ttttttttgg tagagacagg gtttcatcat gttggccagg ctgttcttga actcctgacc 1380
tcaagtgatc cacccacctc agcctcctaa agtgctagga ttacaggcat gagccatcgt 1440
gcctggcctg aaaaagcaga ttttaaacgg caattcattc ttctatccca ttgtgaacta 1500
tacagttgat ggattttcca tcactaactt gaaactctaa attggcttcc ttctgctccc 1560
cagtaggttt cagggctgcc tcttcacatc ttagtttctg agaactcttg gattttatta 1620
aatagtgagc taaacaaaac aggattgtgg aaggggcccc ttgacaccac acttacctgc 1680
cctccctcaa agtccctgat ctcaggaaaa tctaacacct atgaagaaaa tggggataaa 1740

-continued

```
aaatgcatac aaagattatt accaaaaacg aaagattcgt tgtgtaacta attgagatta   1800
actgaagctc tgccatagct cccagccact gcccccactc accttgctta tatactctaa   1860
ctctgctaac gaactgtcaa gtgtgttgga atgggcagaa tatggggtgg ggagtgcata   1920
atctgtagag cttctacaga tacagtgcta ggtaggtcct ttctataata tctcatctca   1980
tcttaaaaga cttgttggcc gggcatggtg gctcacgctt gtaatcccag cactttggga   2040
ggctgaggaa ggcatatcac ctgaggtcag gagtttgaga ccagcctggc aaacatggtg   2100
aaaccccgtc tctacaaaaa atacaaaaat tagctgggtg tggtggcgcg tgcctgtaat   2160
cccagctact ctggaggctg aggcaggaga atcgattgaa cctgggaggt ggaggttgca   2220
gtgagccgag atcgtgccac tgcactccag cctgggtgac agaatgagac tgtctcaaaa   2280
aaaaaaaaaa aaaaaaaaaa cttgttaatt gtcctcattt cccaggttgg aaaacaggtc   2340
caaagattca cacccaaggt ctaaaggctg taactcctct tcttatacag ctgttacaca   2400
tgcacgtgtg tacacacaca cacacataca cactctcttg agcatgccca cacactcact   2460
acatcttgga actgggatgg ctcaaataaa gggagttagt gaggcctccg ctgagaaaga   2520
gagaaagaga agagtcacaa tccataaccc aattcaccca agtcttatct ttcctgtcct   2580
cagagttcct tctgctctga gaaccaccgt cccttccact ttctcttttg acaagtttca   2640
aaactgaatt ttcccccaca cccccccaat acatttcccc ctcacattcc tccccatcct   2700
gcccaggtaa gctgttagcc taaccttata ggaaccaagt cctgggatcc ttttcaatgt   2760
ctacaaagcc tagccctggc aagggagcac tggctgtgtg gtcctgtgcc agcactgaac   2820
atggccctag ccagtaacag tggggctgaa tgtagttccc tcttatgtct agatctctgc   2880
tccggcagtc aaaggagatg tgaaaccttc tgtgaggcca caacaggaaa tggtaggaga   2940
ggatttcact tctctattaa ttcaaacact gagggagctt tttagaataa agaaggacag   3000
aaaacccaga cacctgtgct cagcagtgtt ttccttcctc tcctcctccc aacccttcca   3060
tttttacaga tatagctctg tctttccacc tctagccaat tcaaaataac atttcagttg   3120
ctctgtccat tgttacttat ttgttaatta ttgatatagc accgggaccg aagaggtatg   3180
gagccccaac caggttccca catgttgcct ttcttttatt gcctctacac aaccacccaa   3240
agagtgagtc ctctcctttc ccattgcctc tgcccttagc ctgaccacca catgcctgca   3300
gtaaactagt cccagggttt gtgtgcaaag cattactggg aaaatacaga gtgagaagat   3360
atggattctg cccccatatc gctttgcttg tacgtcaatt ggggagtgag aacaaacact   3420
ttaaatagtt tatattaaag taagtaagca ataaggccag tggtcttaaa agagaagaga   3480
gaaatcacca tggacatggt agacagggag tactctcagt cgagagggcc tggaatgagc   3540
cttgaatact gggctggatt tgtgttggag aggaggaagg cagttggcat tgtaggtctg   3600
gtgtatagct ccacaagctt gacaatgctg tgaggtgcca tcagggagga ggtgtcctac   3660
gagagcctgg gttagctaaa acaaagacaa gctacaataa cgtcactggc actgcacgtt   3720
ggaggaagtc acaaatgtga tttcttgttt ttttctgaga gtatggccat aataataaat   3780
ctcttctagg cacttcctaa agttgctcca tgtcagttcg caggttcttg gggcagacgg   3840
ttttaactga agtctccatt ttataaacac aaaattgctc aaccagttaa tcacgcctca   3900
tagcataaga ccacattcgt gacttcagtg tcttttcaaa actacacaca cctacatcct   3960
gccaagatta tattacttgc ccaatctgtc caatccccac cccacccctg ccatctaccc   4020
cttacctcac ctccgcccac acacacaccc tcctaccctg tcaggattca ctgctctaga   4080
ccctgacctt tggattatag tttctgtagt cagttcacca tccttccaac ctacagtcaa   4140
```

-continued

```
attatttgaa ctactaggga tagtctatct gatttgccac aactattttt cctttttttaa   4200
ttttatttt tgccaccaca actattgaag aatgctatct tcatcttacc cacgagaaaa   4260
tggaggcaga gggaggttaa gtggttgccc agatttaccc agatactaag taataaaacc   4320
attacttgaa ctcaggattt attactttaa atcctgtatt gccaataatc aattggaaaa   4380
taactgaaaa ttgcctacta tttataataa caataaaaac catagcatat ttatgaatta   4440
acatatcaaa tataagaatt ttaagaaaaa agaaaacttt attgaagtgc acaaagacct   4500
gagaggtgta gagatatacc atattcatgg ataggccatg ctaacataat gacaacctct   4560
ccccacatct ctaacctaaa tgctacccca attaaagtaa cagtaggatt tcaggagaat   4620
ttaacaaact gattatagaa tgtacatgga aataaagtcc aagagtatct tagaatattt   4680
tgataaagaa aaggaaaata aatttttttgg gaaggtggtg aaggaatgga gactagttct   4740
actaaatagt aacacatatt aaaaagccaa aataatcaaa caatatgata ctgattagta   4800
atgagagaaa agcaaattaa aacaacaaaa taccactcta cacccaccat gttgccaaca   4860
tttgaaagtc aaataattac aagcattagt gagcataaag ggaaatgtga actatcttgc   4920
tttgttgatg ggagtgtaaa ctgtttatga tccctgaatt atagaaatta taaactagtt   4980
gggcgaaaaa attaacatag gaaataaagc ggcatatccc aatccttagg ttgagtgctt   5040
taagtcttgg aagatttcaa taaagagaaa ttaggggcag gttcatggaa taagttgaac   5100
tggagttgga cctatggagt gggttaagac aggaacaaga tgagcagaat aaagaaagca   5160
ttcttgtgag aggaaagagc ctgggcaaat gccctaaacc aaaatcagat ataatacctc   5220
aaggaagagt gaggaaaaaa gatttattca agaatagcat tcctgctggg aatagtgagt   5280
aatattttttt attagaaaag gggcaccaga ctagagagga tactgagtgc ttctagagta   5340
cttaagtaac agtatcatag aaggtttcat cagagagcat ctaatctaag cccatcattt   5400
tacagatgaa gactttgagg cccagagagg ggaagtgact tgtctaaagt cacacagcat   5460
aataaagcac ttttaagtct tgcctgacag gaaatatcta gataagttgg aaaacagaga   5520
gacagagaaa ttaggaagaa ctagaaagca ccacatctag aattactaac atgagaataa   5580
aaagaaaaac atctaaaatg gagaaaatac aatacttgaa gctagtattg aggtatattt   5640
cagaaaagag aaagaagtct acgaggcaac taagttctcc tctgaagatc aagaccaata   5700
atgataaggt taggttattc agcacatttt ctatgtgcca aacactattt taagcattct   5760
gtaggtatta acttatttaa gcttcacagc atgaggatat gctgccttat ttcctatatt   5820
aacttttttca ctcaactagt tcataatttc tgtaattcgg gcatcataaa cagtttacat   5880
tcccaccaac agaccaagat attacagttc acattttcct ttatcctcgc taatacttat   5940
ttgactttca aatgttggca acatggtggg tgtagagtgg taagggggac accattgtta   6000
tcatcatcct tttacagaaa atgacaccaa agcacaagtt aagtaacttg cccaagggct   6060
cacagctaaa cgctgacagt tacgattgaa tccccagcag tcaggttcca gagcccatgc   6120
ttcttaaccg gtacacatga tgctgttaga aatgagatgg ttcagagaca gtgcaacttc   6180
tcttagggag aatttaatat tttcttttag attagactct agtacaatgc caagaacaga   6240
aactccctca ccaaataatt gccctctcaa ctttattgcc accctgtcat ccaaagcaac   6300
tcccagaccc taaggaatgc aagaaagaaa gcatatgcaa agcaatttac caccagtggt   6360
catgtgctgc cacctttcgt tatcttccca ggacagcacc tgtgcagttc tccttggaca   6420
gttcactcag gccaaggaac agattgtcag gaaagacatg tgaattcttt gcccttccag   6480
```

-continued

```
gctgttttca cttcatgtta ggggcttcat gatactgttt tcccagaact gacataactg   6540
attggtatag cacttgggag cttattcttc ccatccctga gcttctgttt ctcagttacg   6600
gtgagggttg aagggagtta tatgttcctc agggcagcct atacgagaca taaacatttt   6660
cacaaacagt aaaatacaca acacacacac acacgcacaa aacacacaag cagcttcctt   6720
aaccatttg taagcagatt attagaaaat aactctgcct tcgtttctca catattttgc    6780
acaaaccgat agatggaaaa acatcatgta ccgccaagac cagggaataa gagctcagct   6840
ggcaaattag gggttttccc tatttccctc cctaacgagg tcaagctgtg ttcaggttaa   6900
ggcatgctga atttgaaacg acaacccact caagttgaga tatccagaaa caaataccat   6960
gagttaagaa agaagccaca ctgatataaa gaaatgagat ttattgcctt gtggggggaa   7020
gggatgtggt tgtgataggc aggccactct gggatccctg ggatgcaagc ccagggacag   7080
cagagtcccc aggtgggaaa tctacacaca caccccaggg atgtcccaga gacttcttct   7140
accctaagag gagatcctgg gcaggatgtg agaaatctga gcatcctctg tttggatggc   7200
cgaagctgct ggcatcaaac tctggtctgg aagaatcagt ctggggggaga gacagggatg  7260
gaggaaaggc atcaggggat ccatcctcct cctccttctc ctcctcctcc tcccccacaa   7320
aggccttgct cgccctgcct gcaccacacc ctgcagaagt tgatctctcc ttgttcccaa   7380
atcatctcca agcacccttc ctacagcacc ccatgattcc ttttttcact caaagcaatt   7440
cttgtgaccc ataactgtgt gtgtgtaact gggtccccaa ctgggaagat gtgcccccat   7500
ggtgctggat acaggccccc acacccaagg gcctgaggat cgctatatgt ccccccatgc   7560
cacaaaataa tcctgacaca tgcacgcatg caccactgta tctggctccc acaggctcac   7620
ccgccccctc cagatgacat accacctgag caaggcttcc ggaagtagat gatgagaaca   7680
atgcccacga tgatgcccag cacacccagg ccaaaggcca cgccacacag cacattctcc   7740
agcagatctg agggcagtgc gttccggggt actggaggaa atgagtggct cagcctgggg   7800
acctagttag ggagcctccc acccagggaa atgacgtggg tgtctgggat gacatgggag   7860
actgggatgg gcttagggta ggaatggact aaacaaggta ccagtggaga aagaagcctc   7920
ctcccatgga tctatccctt tttgccccca aaaggaccag aattccaggg agaaagcctc   7980
accccaatag gcaattgctg tgtagcggtc aatttcgtga gtcacaatgc aggagaaaat   8040
gtcagaaggt tctggtgtga agtttaagta agaaaaggcc tggaagctga gtccatcgac   8100
agctgagaca aaagtaggcc caaatccttc cacagggacg gaatgatgct gccagttcac   8160
tgtcagcatg ggtgggaaga gattactgac aaaacagacc aaagtgttgg gcttgccaaa   8220
ctccaggggc ttcagcgtga acacttcagc gataggaaac cctggtgggg ggattgaagt   8280
gtagggggaa aaagagacta gtttagatgg tatctctgtg tttggagggg ccatggcata   8340
tggaggggag ggcagagaag aacacagtgg gtcaggcttt gggagacaga gatgagcgag   8400
gagctgggct ctgaagggag gtcttcttcc aggcaaggac tgcagctaga cgtagaagca   8460
gagccagatc caggctactc tggacccctc caccatgact tccttcagca cttcctgtct   8520
agagctcaca ttgatgtcta accatgcact gtcttctcac taagacatag tcacgtcatc   8580
agatatttcc actcttccca tccatcttgc tgggcatagt agcacaagtg ttaatattca   8640
gtaggtatca gttggtacct gttgaattca tcacattcaa tacatagttc tgaatgccta   8700
ctacatgcta ggtacttcgg cccaccaaaa gaacacaggg tgcagaccaa ggctggtgga   8760
aaaattaagg tgatgaagag aaccagaaag tatttgagat ggggagctgg tatcaagggg   8820
aattattcag tgtacagatc aatgaggtta atgcagccct cctcccttca ctccccagaa   8880
```

-continued

```
aactcctgac ctctggacac cgggattttc ccatcaagtt ttggccctat ttgctggatc   8940
atccactcgc agaactcttt gtcaaataaa atggcaggag catctccctg ttcctgagcc   9000
cagtcagcaa attcgggcag gcgaggcacc cgagtgttct gggaaaagtc gaagaagaaa   9060
agctggtcct cgtcgtaggc ctcagagagt cccacactgg gactcccatc ctggcagtac   9120
actgtgtgca ggaatgtgtg gttttgcagg tcatctggcc acattggagt aggagctgca   9180
aaggacacag ggtgaggttc agggaggtgg gagccttctc ctccaactta aaaaacagca   9240
aggtggggct aggcgcagtg gctcatgcct gtaatcccag cactttggga ggccaaggtg   9300
ggtggatcat gaggtcagga gtttgagacc agcctggcca gcatggtgaa actccatctc   9360
tactaaaaat acaaaaaagt agctgggcat gttggcatgc gcctgtagct actcgggagg   9420
ctgagggagg agaattgctt gaaccaggga ggcagaggtt gccgggagct aagattaagc   9480
cactgcactc cagcctgggt gacagagtga gactctgtct caaaacaaaa caacaaaaac   9540
aagcaaggcc tgcttaagga gcgtgggctg aggtgagacc ctttcctgtg tctgttattt   9600
agactccccc tcccaaaggg ggtgaagaac aaattatggc atctctccaa gcttcccctg   9660
cctataaaaa ggccagttgg caaaagtaaa gagttctact ttctaaagtg acagattcag   9720
gccaggcatg gtggctcatg cctgtaatcc cagcactttg ggaggctgag gcaggcagat   9780
tgcttgagcc caggagttca agaccaacct gggcaacaca gcgagaccgt ctctacaaaa   9840
aatacaaaaa cttagccagg tgtggtggca aacacctgtg gtctcagcta ctctggaggc   9900
tgaggcagga ggattgcttg tgcctaggaa gttggggctg cagtgagcca tgattgtgcc   9960
actggactcc agcccaggtg acagaatgag cccgtctcaa aaaatatata tataaaggcc  10020
gggcgcggtg gctcaagctt gtaatcccag cactttggga ggccaaggcg ggtggatcac  10080
ctgaggtcag gagtttgaga ccagcctggc aaacataatg aaaccccatc tctactaaaa  10140
atacaaaaat cagctgggtg tggtggcatg cgcctgtaat cccagctact tgggaggctg  10200
aggcaggaga gtctcttgaa ccccagaggc aggggttgca gggagccgag atcacgtcac  10260
tgcactctag cctgggtgac agagcgagat gccgtgtcaa aaaaaataaa ttaaatcaaa  10320
taaaaaattt aaaaatgtat atatataaaa taaagtgaca gattcagagt cactgttcat  10380
tgtgtgtttg ggggctgcac aaagacacct agccaaagaa gcaagtgaaa gcctgcattc  10440
tgctcaccat gccatacatc ctggcatagg gctgtatcct cccaaagggg attcctttgt  10500
ctaattcata ccaggccact gtattgacta gagaaggcca tggatgggtt tctcactctt  10560
agaagggaaa gaggaggaat ggctacagcc tccccaagcc atagatggga ctgcctccca  10620
ctatccccag acacaaatgg taaattggaa aacctgtatc cagacatttc ttcagccact  10680
tcattggcac caagcgtctc tcaaaatgtc ttctgttcct taacctacca ggcctcccaa  10740
agacagcaat gggagaagtg accccataac tgcataaaat aatccctctt ctttgaagct  10800
cttggcagga atcgctcagc cagcaggaaa cctttaaccc aataccccaga aaaacagaca  10860
tttggaggaa gagggatctt ccagattatt cttccattct gccccatcct ctacagagaa  10920
ggaaactaag acacttttca agaatcacaa gataagttaa tgatagaaag cagagtagaa  10980
tcttgagtgg aggagtgaaa ataacattca ctttgttcaa atcccagctc taccactttc  11040
caatggtgtg aacttgcaca aataactctg agtctcattt tcttcatttg taaaatggag  11100
agaacaatct ccgcttcaag agattgtctt aaatggaaca tgcaaagcat cactgatatc  11160
gtttaccaac cacacatagc agctgtcttt ccccactccc ctgttgtttc cactgcctca  11220
```

-continued

```
taagacttcc caccactcac aaagcacagc gcttttcctc acaaagctga gtgggctccc  11280
taggttcagg atggaagtaa ataggagtac catcttacct tcagggacgg cccaggagtg  11340
gggtagcagc cacagaagtg gtaacatctg tagcagcgca gctccttggt tctgttcatg  11400
acccatacct tcttgccaca cagtaggtag gagctaccaa cccagccaac ccagcttccc  11460
caactccctc cccgagaggg tggccttaga tcatgttttg ccagatcatt tccaataggt  11520
gcccttgtca ttttgtctaa accaatcaga gaagcgtagg gtttaacatc atcagtcact  11580
ggggagacgc ctggggccag taacctcctg aagacttggc tgtttgacca gggcagagta  11640
tggcatgtaa ctgggctggg aagcccagtg gaggaatgtt gcttcctggt ggagttccct  11700
ctttggtttc aagctgtcag cctcagtctg taagcgacca gctggctctt cagagcagtg  11760
ccacctcctg gcagaatgct gcaatgggga accgcatctt ccccaagtaa acccccaggg  11820
ctcttcggac cctgccttct cctccctcct ggctcttcct ctttctcaaa aaaacttatt  11880
ctccttcagg cattagctct aattcatttg gcagacatat attgaaaata caagaaattc  11940
tgggtgttgg gcccagggct agaaatacaa agatgaatag gcatagtctg ccttcaaaga  12000
gcttagagtc tagtgctggg ggagggggcc aagggataat tacacaacaa tgtaatgtat  12060
tcaaataaga atgtgccaag tgttttggaa gtcgcagtaa ttttatgagg atgcggaata  12120
ggaggaacat aatcaggcag gctcctaaga cttgaaggaa aaacaatttg gccagcagaa  12180
catgaaggaa gagaaaaaca cgccagggca aagggtaggc agaagtacaa agatcacagg  12240
catccagagg tcctctttgg agaccctgtg tactagttga tatgaatgtt gtgaaggtcg  12300
cttgggtgtt cctgtataat aggaggtaat ggggggtaga aggatgttgt gataagctac  12360
aaattcgggc aagggccaga tcacgtgggc cctgctacgc cacaaggagg agcttgcttt  12420
tacttagcag atgatagaga tattaaaact ggggaatgac aatcatttta gcattttgga  12480
aaaaatgttc tgattgatat ttcaaacaat gaactggagc ttttaaagaa ttgaggcaaa  12540
actgctgggc aagagtctat agcataccaa gatgaacagt tgcacatata cacaccactc  12600
ctgtagcaat acagcaataa tttaaatgac agataataag agcctgaatt aagtcataat  12660
tagaggaggc agaggagata gaatatcaag ataattagga agtagaatct aaagggtttg  12720
gctactgatt agctgtggga gtgggaaggt ggaggagtca aagatatctc agatttccag  12780
catgggtggc tgggtgggtg gtcagggatg gactgaattg aagcagaaaa gaatgccatg  12840
ggagcaggtt tacagagaga aagagcttga ttttgtacat gttgaatttg aaatgccagt  12900
ggaacagcca gctgaaactg catgggagcg cagtgaggcg tgtgggtatg gaccccaggt  12960
atggtctgaa gaccctgatt tgagagtcat cagcacaaat gtcgaagcag aggccatgaa  13020
taagatcacc caagtaaact gtgcagaagg agtgggaagt gaaacaagga caaaagcatg  13080
catgggctca aaccccaaac ctcataccag ttatccagga tccagtcagg agcatttaac  13140
tactttatgt gcttcagact gaaagaattt aatatagaga attggttaca aaggtgttaa  13200
aagggcaaga agtacaaaaa aaaaaaaaaa ggagagtcct agaaatgtac attttaaaaa  13260
aagattgcta tctggaaatc agaagctgcc atcatccctg agctggaatc tgtaaatcta  13320
ctcattgcct tgtgagagac actgtcatag tcagttccaa tctactagaa aggtgccacc  13380
tccttcaagg ctagaatcct tgagaaggta cttctgctca ggaggctgga gtcctgagtc  13440
tcccattctt cctgctgcta cagctacagc caatagctac cagctattgc cagccaccgc  13500
cactgtttag aggctgaagc aggatgcttc tcagtttctc ttgccttctg atctcccatc  13560
agtgcctcct actggcagaa tcaaaaagga agccagatgt ccaggaaggc tgggaaatac  13620
```

acacctggct gactcctaag ctaagcagtt caaaacacag tagaggaggg tgtgtgtgtc 13680
actgagacaa agataataac gagtacactg aaataccctg gtttgtaaga atctggtggc 13740
acgaggacca tccagagcac taagaaaaga ccaaggtaga agcagatcag agaaataaaa 13800
aagaggtgtg ccatgaagga gggcaaggtc agcattttta aatgctactc aaaagtcaag 13860
aaaggattga aaagtgtcct tagatttggt gattatgaga tggctgacaa atttattgag 13920
agcagtttca gtgttgtagt gggagtcaac tccagattgt ggtgggctga gaagtaagtg 13980
ggaggtgagg aagaaactgt cagtgtacat gcttcaagtt tgttagacaa aagaaagaga 14040
aagacagaag gggtggggga agaggcagtg agaaagctct aatgtggcaa tcaagtaatc 14100
tgagaaatta atatatgtga atattgtcca acagtgtttc tgaggctttc aaaattcata 14160
ccttccacct tttttttttt tttttttaag acaaagtttc ccctgttgcc cagactggag 14220
tgcagtggct acttacaggt gcaatcataa ctcactccag tcttgaaccc ccgagttcaa 14280
gcgatcctcc cgcctcagta gctggggact ataggcacat gccactgtgc ctggcttcat 14340
atcctctttt gataaacaag taatagcagc agtaatagcc aaaaacaaaa acaactctat 14400
gacctcctag atattctgga acagcaatgt gtatatatgt gtgtgtgtct gtgtggtgga 14460
ggcagggtgc cagggaagga ctagggtttg gaaatcatgg taaccctcca gaaaacaaaa 14520
gaacatttcc cagtatccca acatttatgc actaacccat cagcggttct ggcagtgggg 14580
agattcaggc ccctggacag tagaaaagaa gtttatgaga ctaccagtgg ggagacatat 14640
gggacacagc cacctagagt cctaaaccag gggttagcaa actttttctg taaagggcca 14700
gatggcaaat attttagaca ttgtgggcta tcagatctct gtcatgagta ctcaactgtg 14760
gcacgaaagc ctccatgcac aatatgtaaa tgaaggagag tggctgtgtt cctagtttcc 14820
tcctagcttt tcctcccact tcttgagcat ctccttctca gtctccttca tagactcctt 14880
cctttcagct actctttaaa tactggtgtt ccctggagtt tttgtcctca accctctttt 14940
tatttatgga cactaaaatt caaatttcat gtaattttca tgtgtcacga aatattcttc 15000
atttgctttt tttttcccta accatttaaa aatgtgaaga ccattcttag cttttaggcc 15060
atttaaaaac aggtggtagg caagattgtg ctcacagccc atagtgtgct gaatgatgct 15120
ctacacgtgg tcagaattgg tacgaaagcc ccaaattaaa cccacccttc aaagaggaac 15180
ctcagtcccc ttattattgg attggcaatc agttaacaaa cactttgtgc cagttacacc 15240
agtctatttg gaaggagatc tggggaagaa caggagaaac tagactgggt ggaagggcat 15300
aggaataggt acagcagaca ctgcaatttc tctgggtgag aggaacaagg cagaggggtc 15360
caagttctcc atagggagca cagtgtagac aagaccaagg tgaggacaaa cataaccatc 15420
cctcaccaag actgtggtga ggggtggtta actccattct ccccttctat aatctcagtt 15480
taaatggtaa caagttcaaa cacttataac tactcttccc tccatgtaat ccttccccac 15540
caggacctcc caactacctc catcataagt atctcaggaa tagtctctca tcagtttgga 15600
aagtaataat tgtgggcaag agatgagcaa ggcagccagt tctgctttgc agtagttcac 15660
tgtctacttt gtcattagct atgaatgcct ctgaaaataa tggcacagca ccggtaaatc 15720
caggaggctc tggctttcta acactcagct ctgccatccc tttctagcat ttaaaaatgg 15780
actctatttg gccaggcgca gtgattcacg cctgtaatcc cagcactttg ggaggccgag 15840
gggggtggat cacgaggtca ggagatcaag gccatcctgg ttaatggtaa aatcccatct 15900
ctactaaaaa tacaaaaaaa aaaaaaaatt agccaggcgt gatggcgggt gcctgtaatc 15960

-continued

```
caagctactc aggaggctga ggcaggagaa tcacttgaat tcgggaggtg gaggttgcag  16020
tgagctgaga tcgtgccatt gcactccagc ctgggtgaca gagcaagact ccatctcaaa  16080
aaataaataa ataaatatat aaaaaggact ctattttttt tcccctagca gagtcagatt  16140
tcttggaaaa gtcatgggca actgtggccc cgctcccatt cttaccattt aatcttttaa  16200
ctctcaacaa tgcaattgtt caccaatact tttgtgttgc caaatcaaat gaactagtct  16260
ctgcaacatc tgacactgtt ggccataccc tatctcctaa attggtcaaa tttctggcat  16320
ccctgatggc actctctcct agttttccct cctacttttc tggcgtcccc ttttcagtcc  16380
ctttgggact cctttctttc agcaaccctt taagtattgg tgttccctgg agttttgtcc  16440
tcaaccttta ctcttcttag actatacact tgccctggat ggtcctctca tttactccca  16500
catgccttct gttaccaccc atttgctaat gtcttccaag cttacctctt cagctcagat  16560
cttgctctga gttccacact acccatatct gaaccacttc tggtcaaatc cacttggatg  16620
ctatgcaata gcagtttttt gtttttgttt ttttttaaa tatggaacgc ttcatgaatt  16680
tgcatgttct taaactgtat tcttcacaat agcgttcctc aagaaataaa aaaagtaagt  16740
ttgatgatag caatcattta tttttgaatt tatttccaca tagacataat gcaacatcaa  16800
acacatttat ataatatttt ttattatgta acaatttatt atatttaata agtctattta  16860
ttgcaagcaa tagaaaccaa ttctggctaa cttacatttt aaaaatgagg atttattgga  16920
aagatactga tctaactcat gaaatgaaag taatagttga ataagctagc ctcaggtaga  16980
atagccacag ggaccttaga agcaggggtt gagttgccat taatatgctc acctgcaaag  17040
gcctcctgcc tctttatctt tcaagttttg ctttgctggg agagcctctc tcactggctc  17100
agcttgtatt aggtgtgtac cactggattc attggttgtg gccaggtaca gtattacctc  17160
tatggattag agctattcct agagaaggga gaatcatatg aaaagtaacc acctcaatac  17220
agctattttc aacatatggc atctcagaca attgtatgag atcatctgag gcataaacat  17280
aaggttaaat ctgtgtatta atgctcaaac agcatttcct aactactcag gtgacatatg  17340
tcatctgctt gatgatctct ggtcggtcac ttgtcttatc acatattcaa attacattta  17400
tcatgtgatt caatattgat ttattaattt aaaattatat attccacgaa tttcctttga  17460
atctctgact aaaaaggttt ttttaatttt actttgaaaa gctccaagca cacacagaag  17520
agaagaatct aataaactcc aatgtactct catgaatgtc aacaattttc aacatttaac  17580
attcttccat tcttgtttca tctattgttc tgcatttttt ggagtatttt aaacaaattc  17640
tgtcattaca tttcaccagt aaatactttt aggcatatct ataatagata ataacctttc  17700
ccttaacata actataatgc catcaccaca accaacaaaa ttaaaaatta cttaacttca  17760
tttgacccaa tctgttcatt tctcctagtt atctcaaaaa tgtgtaagag aatgaagttt  17820
taaatgaaaa gcagtgtctt ataattttca aaccgtgcca ttagtttaaa aaaattggtg  17880
agttttctat tttatgtttc ataagctatt gatggttcaa taatgaattc taattaggta  17940
ttccataggc aaataaagtt agcaattgtt actctgaatg tatctccatc tcaagattac  18000
aagagtacac tcatcacttt cccttcccaa tatattccaa ctcctctctt atatttaaga  18060
cttcagtgaa taacaagatg tccacccgag ctacaaatgt gggtcatcgt tgatgacccc  18120
atcttcctca aaccttccca ttcaattgtc ctaacaattc tacctttcta atagctcttg  18180
aatcttcctt tcttttcctt ccattcctac tggtccaggc cttcaatggt tggttttcac  18240
tgattattgc aactttcttt ataattggtc tctctctctc caatcttatt attttccaca  18300
gtgctgccag aaggatattt ttattatgct tagttgatca tattatactt ctgcatgaaa  18360
```

-continued

```
accttccatg attgttaatg atctactttc cttgtcatga cccataatga cctgaagtct  18420
acttacctac ttctatatgt cttttcaggt gaaatctcac tcctctcagg aagccttcct  18480
tgaacccaga gttgagatta atagcctctt cagtacgttt ccaaagcacc ctgtgttggc  18540
cattatcact gttttaattg tattattctc ttccatttat atgtctgttt catagtcacc  18600
tcatctctac tgcaaggtcc ttaggggagg gtgtactata tatatatata tctccaccaa  18660
gaggcccact aagtgacctt tcactcgatg aacaaatggg ctaccagtct ctgaaggtgc  18720
tgaactgaga atggaagagc cttcaggtat tagatgatga tggattgtcc cttctaacag  18780
atgtttcaaa ggtaaatctt atcaggttta tctataagcc attctttttt tttttttttt  18840
gagatggagt ttcactctgt tgccaaggct ggagtgcagt ggtacggtgt ccgctcactg  18900
caacctccac ctcccaggtt caagtgattc tcctgcctca gcctctggag tatctgggac  18960
tacgggcacg tgccaccata cccggctaat tttttttttt tttttttgta tttttagtag  19020
agatggggtt tcactgtgtt agccaggata atcttgatct cctgacctcg tgatccacct  19080
ggctcggcct ccctaagtgc tttgattaca ggcatgagca accacaccca gtctctatga  19140
gccattttac acctccacag ccttccctat atactctact acccttccaa ttccattcta  19200
ggcccttccc aagctccttg ccaactacca ttttcttcct actccctgcc acctcctgtt  19260
tcagagagca aacctagcca tccagctccc acatttactc ttatttctac ctcagtacat  19320
ttctccatac ccatattcat cctcccttt agtgacatta ctatgatgca gcaatcctta  19380
caactactct acaaggttat aatttattat ccccattata taaacaagaa aactgggact  19440
cagaaaggtt catttattta gcaaatattt attggccacc ttctgtgtct agcagtatgc  19500
tctgtatcag atacctgcca tcatcacact taaagtctaa tgaaaataaa gagacattaa  19560
acaagaaaac atacaaattt ataaactaaa aggtccacac acacacacac acaaaatctc  19620
ttagaattga taaattcagt acagttgcag gatacaaaat tatcatataa aaattaatgg  19680
tgcttctgga tacaaacagt aaactagtgg gaaaagaaat caaagaaagt aatcccattt  19740
acaatagcta caacccctcc ccccaccaaa aaaacaaaat agaataccta gaataaacca  19800
aggaggtgaa agatctctac aaggaaaact atgagacact gaggaaaaaa actgaagagg  19860
tcacaaaaaa atagaaagac atcctatgtc ttcggaagaa ttcgtatcgt gaaaatgact  19920
gtactaccaa aagcaatcta cagatttgtt gcaattccta tcaaaataca aagatattcc  19980
ttgcagaaac agaaaaaaca aacctaaaat taatatggaa ccacagaaaa cacaaatagt  20040
caaggtaatt ctgaacaaaa agaacaaagc tgtagacatc ataccaccca acttcaaaat  20100
atactacaaa gctacagtaa ctaaaagagc acggtactgg cataaaaaca gatacacaga  20160
ccaatagaac cgaataaagg acccagaaat aatagatcca catcttaaca gccaactgat  20220
tttcaacaaa ggtaccaaga tattcaatgg gaaaaggaca cactcttcat taaatggtgc  20280
tgggaacact gaataacaat atgcagaaaa atacaactac acccccatct ctcatcaaat  20340
acaaaaatta aatcaaaatg gattaaaaac ttaaatgtaa gacctgaaac tataaaagtt  20400
actgtaagaa aatactgggg aaatgctcaa gactttgagc aaacattttt tggtttaaga  20460
cttcaaaagg agaggcaatg aaagcaaaaa tacacaaatg ggattacatc aagctaaaag  20520
gcttctgcca cagcaaagga aacaatcaac agagtgaaga gacaaccttc agaatgggaa  20580
aaaatatgtg caaactatcc atctgataag ggattaataa ccagaatata taaggaactc  20640
aaactcaaca gcaaaaatcc tccaaataat cccatttgaa aatgggcaaa tgatctgaat  20700
```

-continued

```
agacatttct caaaagacat acaaatggcc aacaggcata tgaaaaaatt ctcaacgtta  20760
ctaaccatca gggatatgca aatcaaaacc acaatgagat atcatctgaa tctaattaaa  20820
atggctatta tcaaaaagac acagataaga gatactggtg aggatgcaaa gaaaggggaa  20880
tgctcatata ctgatggtag aaatgtaaat taacatagcc actatggaaa acagcataaa  20940
ggttcctcaa acaactaaaa atagatctac tagatgattc agcaatccca ctgctgggta  21000
tatatccaaa agaaaggaaa tcagtgtatc aaagagatgt gtacatgccc atgtttattt  21060
cagcactacc cacagtagcc aagacatgga atcaatctaa gtgtctatca agtgactgga  21120
taaagaaaat gtggtgtata tatatacaat ggatactagt cagccataaa aaagaatgaa  21180
atcctgtcat ttccagcaac atggatggaa ctggaagtca ttatgttaat gaaataagtc  21240
agacacagaa aaaaaaatat cacgttctca taagtgggag ctaaaaaagt tgatcttatg  21300
gaggtagagg gtagaatgat ggttaccaga gactgggaaa gggagggggt ggagggggga  21360
tgaagagaga ttcattaatg gttacaaaaa tatagttaaa ttgaaggaat aaattctata  21420
gtgtttgata gcacagctgg gtgactacag ttaacattaa tttactgtat attccaaaat  21480
agctagtaga tttgaagtgc tcccaacaga aggaaataat aaatgtttga ggtgatggat  21540
atcctaatta tcctgatttg atcattacac atcgtatgca tgtatcaaaa tatcatatgt  21600
accccataaa tatgtacaat tattatgtat caataaaaaa taaaaaaaaa caattcagaa  21660
gtccataaac ttggatggaa taaaaaaaag tcaactttat tttcaaaaaa ctctcactga  21720
aatctaattt tatgaatgta gaaaataaat ctttgtagta ccagccagca gctgtaacac  21780
tgtcatcaat agaaaacacc atcaattaat attttcatat cacattatag ttgttacaga  21840
catcttaaaa tatcacttac aattatggga gctgttaaac ttgccaaaaa atcatgcttt  21900
ttaatgtatt agtaaagaaa cactgtattg tattaataca gaaacacata ctactagatc  21960
atcacacgtt tctttgaata tagtagtgtc ccccacacag caccaaatgt gattatacag  22020
tttattccta tccatagata tacctatgat aaagtttaat ttataaattt gcacaggaag  22080
agattaacaa caaaatagga caattatatt gtaataaaag ttatgtgaat atggtccttc  22140
tgtctcatac acaaagtatc ttattgtact tattttcaga ccaggttgac cttgggtaac  22200
tgaaatcaca gaaattgaaa ctgcagttaa ggggggacca ctgtattttg ataactatag  22260
tttatatttt attttatgca tttacaaata ttatcagaca agatccaaag gcttcaccaa  22320
actgccaaaa aagctaatgg cacataaaaa gcttaaggag tcctgattta atcagtcatt  22380
caatgaacat gacatccttc ctggaaccat ctcctgttct agcttcctca cattatgttg  22440
ctctgcttct ccttgagatc ttccattggt tccacttcct attcttgctt cctgtatgaa  22500
gatgtaaccc aaagctcaat ccttcaccct aaattgtttt tatacccccct cttttacaaa  22560
cctcagctac cttcgtggct gattcaaaca tcacctcaaa ggtgactctc aaatctgctt  22620
ttcctaatct tttttctcta acttcaatct tggatcttaa actccctgct gtgcctagta  22680
aacagaataa tatgccaccc agagtcagct gggttcaaat cccagttctg ctacttacta  22740
aaggtgtgac attaggtaaa tattacctgc tatggtttga atctctcctc caaaactctt  22800
gttgaaaata attgccattt tgacagtttt aagaagtggg acctttaaga gttaattagg  22860
tcatgagggc tctgctctca tgaatggatt aatgctacta atgtaggtat gggttcccat  22920
ttaaaagggg acattctgag gccgggcaca gtggctcaca cctgtaatcc cagcactttg  22980
ggaggccgag gcaggtggat catgaggtca ggagatggag accatcctgg ctaacacggt  23040
gaaaccccgt ccctactaaa aatacaaaaa attagccagg cttggtggcg ggcacctgta  23100
```

-continued

```
gtcctagcta cttgggaggc tgaggcagga gaatggtgtg aacccgggag gaggagcttg  23160
cagtgagtca agattgcact actgcactcc agtctgggcg acagagcgag actccgcctc  23220
aaaacaaaca aacaaacaaa caaacaaagg gtacattctg gcctctattc tctctccatc  23280
tcatgtgctt gtttgccttt ctgccgtggg atgatgcagc acaaggctct caccagatgc  23340
caatgccatg ctcttggact tccaagcaac tggaactgag ccaaataaac tactgtttat  23400
aaattaccca gtctgtggta ttctgtgata gcatcagaaa acagactaag acgtcctttg  23460
cttctgttgt ttcatttgaa aactgagggt gataatatta gtattgactt tatagggtta  23520
taaggattaa aagagttact acatgtactc attgcagtac ctgacacatt ttaactactc  23580
aataaatgtt ttgtatcacc aatcacatct ccttccaacc ccgacatttt aatttgatgt  23640
ttattaacat ggacggtgcc agccactgga agacagagtt tctatctaac aacataattc  23700
tgatcaagtc attagtcaaa aaatttcagt ggttccccac tgattccaaa cttaacagca  23760
ctggaaacct tctataatgt gttctctaat ataaatttac ctcccatttt ctcttctcct  23820
gctctacttc ttgtagctta tgttctggcc agactggact agactactct ctgtgacaat  23880
aacctgtgct gttctatgtc tgtctttcct cacataattc taatgtctca ggtttgaagg  23940
caataatttt gtctatgatt attcccctat acatggcacc ccataaaaca tacacatttc  24000
aatcttacct aagtcacata cttacttaca catcaattca cctccatatt tgctcaattt  24060
gtgagaacct aatattggcc agatactgtg ctaggaccta gggatattaa aaaaaaaaaa  24120
aaagcaaagc aagaaaaaga atgcataatg gccctgctct caaaatcaag gtctagtact  24180
agagagaaac atgtaatcac ataaatgcca ttcactgtgg aaagtaaaat cataagggga  24240
agggacacca aagaatgagc agttagctca acttgaacag taacattaag cttttcagag  24300
atgttatttg ggcgtacata gattggggaa aagtctactc catatagaaa gtgcacatgt  24360
gtaaaacaca gaggcatgaa acaaaatgat gtgtctggga aacagttcaa tacagctgga  24420
atatagggcc caagaggaag tggttagaca tgaggctgga aagctaggca gactgttttg  24480
gcaaacatag gaatttggac tttatcacat agccaataag gaataacaca gagttttaaa  24540
aagagctatg gccagggcta tattttggaa agctctctcc tggcagtatt gtggcagagg  24600
cagagaggaa agtctaaagc agcactgtcc aacagaactt cttgtaatga ggccgcgcgc  24660
agtggctcac gcctgtaatc ccagcacttt gggaggctga ggcgggcgga tcacgaggtc  24720
aggaattcga gactaatttg gccaacatgg tgaaaccccg tgtctactaa aaatacagac  24780
actagccggg tgtggtggca ggcgcctgta atcccagcta ctcgggaggc tgaggcagaa  24840
ttgcttgaac ccgggaggca gaggttgcag taagccaaga ctgcgccact gcactccatc  24900
ctaggccaca gagcaagact ccgtatcagg gaaagaaaaa aacaacttct tgcaatgaca  24960
caaatgttca ataatctgtg ctttcccata tgacagccac tagtcacatg tggctattga  25020
gaacttaaaa tgtggctagt gtattgaggc actaaattta aaattgtatt aatttaaatc  25080
caaatagcca tgtgtctagc aaataattta ggagactgtt ggtatagctc aggtgataga  25140
attaggacag aagggtgagt tgatggatag ttaagaggca aaattatgag tctgtaaggg  25200
tgtgagaaaa ggaaatcaag aacaggctcc cagattacag actttgtggt taaacagcca  25260
ccattactca ggacaacaga agagaaagag caggtctaga gtgtatagtg atttcatcaa  25320
ttttgaacat actggtgtct gagagttatc ccagtgggaa tatttagtag aaagtttagc  25380
ttagagagct gtctgaacta aagattcaga cttcagaggc tttgagccat ggagtcagat  25440
```

-continued

```
tacctagaga agttgaacaa aattagaagc aaacaagaat cacagcaaat atcaacacat  25500
aaaaaggggc taaggaagaa aaatctactg agactggaga ggaacagtta cacaaatagg  25560
aaaagaaaca agtgagagtg gtatagaagt caagggtaga gagaatgtca ggaaggaaac  25620
atgatcaaat gtcgaatgcc tcagaggtca aataaagtga gaactgtaaa gtgcttcctg  25680
actttgccag ttaggaggtt cttggtgaca tctgccagaa aagttttggt ggtagcagcc  25740
tgacagaggt agcttgaaga gtggggatgg ggaaagagaa tgtgaccaag aattgagata  25800
gtaaggataa tttcaatttc aggtcttggc tgtgcaagga agccgagaga catgagtctc  25860
taagagggca cgatattgag agggttgtta tctttctgtc agcggggaaa ccaagagaaa  25920
agtttaaaaa ggtcaaaagg gggagaaggg aagacagctt ccgggtaaca gagaaggttg  25980
accaggtcaa tagtaaagga tttcctcaaa ccgaagggag gacctctagt gaaatgagaa  26040
aggaatacac aattgaccca gtttgcaggt gggaaatggg aagccagttc tgcaaattgg  26100
cctttctgtt ctgtgaagtg ccatctgtcg gtgaggagag attagggtct gcagcgtgaa  26160
aatctggacc atactctggg taatcaaggg agaggttatc ggctaatgac aaattaaagg  26220
cttacttttt agctggcaac tgaatcacca taacatttta tgttaccagt tccaaaattt  26280
tggggggaat tcactcaagc ttgggagagg agagatcata actttaagag tataagaggt  26340
ttaaacggtc cactacgaaa taaatagaga aggaaaagtt atcagctggt aaatatcgta  26400
gaaggtagag cggtccaggg actcacaggt ctcactaaag aaaagtctag cgtaggttca  26460
cggcacggag agattttaag gctgcctaag actaaagcca aatacgaagt ccacatctgc  26520
ggtccgcacc ttatctctcc gcgcggcagg cgcgacgagg gcgagaaact ccctctccag  26580
tggtcgcacc acacgacacc agggaagggg cccctctctc cagaccctca tatctccagg  26640
tccaggcccc attttcctcc gctgacagct cagcagcgtg cgcttccgct ggattcaggc  26700
caggaccagc gaagccgcac cttacaccca ccgaggagga aacaagcctg gccacccgag  26760
gctaccccgc taggccgcgg gtagtggggg agggggcgct gaggcaggag gtcagcaccc  26820
gggcgcgggc tcccgcccca cgaaatgcgc gcgctccaag ccccgccgcc ggagatgcgg  26880
ttccggtccg gacgcctgcg cactacggct ctccccgcag cctctggccc tccttccccc  26940
tcccccagtc agggcgcacc cttgcgcctg cgctgtgtgt gttcctggtc tgcggcagcc  27000
atgctgaact cgtatggaga ggcgagtggg ggggacagag tccaggactg cgggatagga  27060
agctggggat atggacaagc agcagcgtta tagcgctctg ggtttcggga cataggcctg  27120
ggccatgcgg ccccccttggc cccttggcgc gacccccagg aacgttcgga aagctggtcc  27180
tcgtggctgg gggaaaggcg gggggtgggg gggaagcggg cacgtgaccc cggtcagcca  27240
atctgggtgc tgctgacgtg gccgcgcggc cccgatgctc tccccacccc cccagcccgt  27300
tcgggaaggg aggggctggg ggctacgccc cctcccccag cacggcttcg ttttctgggg  27360
gggggttgac accccggatt acatacccccg taccaagccg agggcaactt tggaggcccc  27420
ctggaaggct ttaggatcca ggtgagaagg ggcccttgtg gggcggagat gtcagtcaag  27480
tgcttaacca atggtgggga gtccgggagg gggattcttg gggttcagga aagaatcctg  27540
agagtgggaa gatttgtcct tcaaaccttt tacagccaat gggagcgtgg agggggggcg  27600
agcgggagag ggccatgggg ggggagggga atggccagcc tcatgcctcc gtacccattg  27660
gagggcaaag gggttagggg gcggtgtggc ccccccctatt ccattcgtcc cctgggggta  27720
cagcagccgg gagccaggtg agaagggatc catcggcggc cgagggaggg gtgacctggc  27780
ggtgggctga ggagtggtgg ctgtggcccc tacccgtgga tgtgaatgct ttaggagttg  27840
```

-continued

```
gccacccatg ttgtgaactg aggttgttcc caggcgccaa cttcctttct ccccagagcc  27900
tctggaggga gcattgctgt gcgccctttg tgtccgcggt aggggagctc cagtcgtcac  27960
accgcaggct ggaggttacg cttcgagtcg cttaccgaat ttgtgtgcat tcacgtggac  28020
acggcctgtg gggccttttg cccctgtagg gtctttactg agcacgtgtc tactccaggc  28080
tggggtgctt acaagctgaa agcttgaggt ctgcttagga acagaaacca ggcccaaggt  28140
gggtgctggc agtagggggt ctagacagca tggtctgaga tgcgagggag gctcgggacc  28200
tggaatgatt tcacagctcc caaggtttcg ggtttctcca gggtggcctc ttccatcgcc  28260
tccctcatcc cctcccccag tcctgaacag ttctctcctt gtgtactgcg ggggagggaa  28320
cggaaaggag gaaagagtta ctttcccaaa ttactgagta gcagtagcct ccctggtgac  28380
tcatgtgggg gaagggagga tagaggatcg ggaggcagtg attttccgga atgcagggaa  28440
taaacgagag caatgtctgg ctgccctttt cctaaggcct agtattttct cagcctccta  28500
agtttttact ccatggccgg ccccctgatg ggcctctgtc ctggcctgca gagccccggt  28560
ggagaaaagc agatttggga ggttgggccg ctagggggag gggaaaaggc ctctgcaaag  28620
ttgctgtgtc attgccctcc atgctgcagc cacccaaacg gggccgcttg tacttttggg  28680
ggccagggcc tgatccctgg ctgggggaag gggactctgc tctcctgacg ctcattttcc  28740
cccgccctcc cggggtttgc cctactcggg gggtcagaag acaggagatt ggcggccatt  28800
ttagacgcag taaccgaggt tggagttgaa gggctactgc agaggaggga gggtggcgtg  28860
gttgcagctc aaggacctag gcccttacga gcccttcccg ggcgaggggg aatcttaccg  28920
tatatttgtt cacctacgtt gattattttt cccagatacg tacacaagtt tgttttctcc  28980
ctggtagcga agaaagggga aacgggggag gggacgcccc accaaagccc aggttttctc  29040
gggtggggga gatcctttca ctctcttgta agggggcggg gacggcccca gagatgctct  29100
ggagatcctg actctgggct ctggttgatt cacagagtct gcacccttat ttagataacc  29160
aagttaggag gaagacttaa gagtaagttg gggggagggg gcgaaactga gctcccaaaa  29220
tggctcctgc ccctcctcgg aggcggacgg ccggggggag gggaggaggg gaggaggggg  29280
agggctagtc tgagccgcag ccgccgcctc ctccgctcgc cctcctccct ggcgctgacc  29340
gatggaccag ccgctccgtg gggaggactc cggaccctgg tgggggggcg ggggggttct  29400
ttcgcccccg tggcggaggg cccctgagag gcggatacgg gtgtgccttt gggggtgatg  29460
tggcgtgtgg ggggaaaggt ccgagctcgc ctggaggggg agggtttttc ccttaagtca  29520
tccctcccag gacttgcttt ttctgctctg agccggacgc cggaatggag tttgaggaag  29580
aggtgaggtg tgttgcattg tatagggtag atggatgcgt ttggagattt taatcccact  29640
tttagggttg ccgaggattt ttcgaacgag cagaaatgta ttggtaactg taggtgtgag  29700
tggggaggga ttagaaaggt gcttggacgt gcaaatttgg gagacgtatt ttagcttttg  29760
tggtctttgg gactaaacag tagtaaataa tgttttgctc gtctttccat cgtttggctt  29820
gagggaggga gtggagtatt ataagactct ggcaacactg ttttagactg tggggcatgg  29880
gaacgttaga tcccctcatc gccgttctga agcccgtagc tgttcgccat agaggagcag  29940
gccgcggctt ctaagatggc gtctttttcc tcgtttcaga ttcttcgctg ctgctgcctt  30000
accgccgaga accaccaccc gccaggcgtc ttgcggccac acccctggcg ggttcaggca  30060
ggctacgccc acgcgacccc tcccgtttcc ctgctttggc caatggagga gctacgaatg  30120
gcacgacctg ctcgagcttg gcagtctcca gttgggctgt gcatggaagc ttgggaagac  30180
```

-continued

```
tttgttggaa ggggaggcgg ggagagagtg ctggaggctc tggggcgatg gcttccgcac  30240
ctcttccaac caccctcttt ccctggagtc ggcggaccac agctcagcca attggcttgg  30300
agatgtggcg ggttgccact tccctgtggg tctctgcggc actcttctgc ctggtgactg  30360
acaccttgga aatgaagttt atgacgtcat cgttgcggct ggccaataga aaaagctccc  30420
gcggagaggt gttccttccc cttcgactca gcttcttcac ccgcgtgagc gagcgcgcgc  30480
gcgcggaggg ggtggggaaa atctcaagca gggtggcgcg catgagcggc gaagctcctc  30540
ctccccgcct atatataaag ggctggcgcg gggctcggcg gcgccatttc gtgctggagt  30600
ggagcagcct ctagaacgag ctggaggatt ctgcctaccg atacagagcc ttcgagtcgt  30660
ccggggccgc cattacaatc cacctccatc cgcttggaaa tggccttcgt cccggcctat  30720
gactggtccc agcgggcagt acagaccccc tagaagcccc tggagctccc ctttttcggg  30780
ccccgcccaa tcctcggagt ctgtccaccc cctctactcc gccctcaaga ggatttcaaa  30840
gatggaggcg gcggctccct aaaccacttt tcgtgttcat ccgcctccat ccgagatcga  30900
aacgggacct cgtcggcccc gtaggggccc gacaagaaga gggaatccct gcagaccaac  30960
agcgggctat attgacgacg gtgtctgaga tcggggaccg tcttttgaag agtcagtccc  31020
tccttagttg cccgcctcag ctgaggccgc cgccattttc ttgctgtccg ccgtctgcag  31080
agcgcgccaa gctgcccgga gctctccgag aggccccaaa gagactgctt tcgtgccggc  31140
caggcagggg gtttgtcgcc tggaggccca agaggaacgg cctcccccca acttagcggg  31200
ttatgctgga ccgggcggtg aggggaaccg aggccacccg gactttccgc ggctgagggc  31260
agcgccggtt ccttgcggtc aagatgctgc aaaacgtgac tccccacaat aagtacgttt  31320
ccgcgagccg cgtgtgggaa ggggatgttg cagggcggcg gcacaggggt gtggggcgcc  31380
gtgttgggag tactgagcgg ccccggcgcg ctgctgttgc ggcgcagctg tcgactcggt  31440
cgcgcggagg gaattgagcg acggttttgg aacggtggtg gcggctcggc tactgctcgt  31500
ggaggggaat acaggttgtc aatttatacg ctattaatgc cgccgtggcc cagtcttaac  31560
cgagtcaggc agagctagtt tgacggtgga gtggagtgag gttgaacagc aggtttggcg  31620
tttggtgggt ctggtatcta gcggcggtct gttagccttt tagggggat tcacggacac  31680
ctctagcgcc ctgtagggtt gccatggtga cggagcgctt aagggactgg caacggggat  31740
tcccagagaa gggtaaaggg atcactctcc cgtgtgtgca ggttcctaat gcccagggca  31800
tgtcattaaa tcttttgctt tctttgggtg ggtgggttgt gtgtggtgtt tgttggtgca  31860
gggattgttt tttcctaaca ttaaaagttt gattcagggc aggagggtag agctaaggtt  31920
cctagttcag ctctgcgatg taaacaatga gattcccata tgatgtttta attcttaggt  31980
ggtaggaaag actgatcgga ggagcaccag agggactgta aatgaaccac tgttagcgtt  32040
tggtgtccgg agttggtgct acagggggaa ctggtagtgg aatcgtgttg tgtagtgggt  32100
gggtggaagg gggctatcac ttggtgacct tgactgtttt gtacggcttt ttgacttcct  32160
tggagtgagg agactctgat ttggtgcgaa taattttgag ggcctggaag ttacgggctg  32220
tgaagtctga caaattcttc cttgtctgaa tttgttttta agttgatatg gttcttcctc  32280
tgggtttcta gtctatgttc tgttgtggcg tgaactaccc agaccttgtg gaagatggtg  32340
ctctctcttc tatctaggtg gattattctg tgtcttatca gcattttatg gaatttttta  32400
tagccataat ttgttctttt cctccttacc ggcgctcaac caccatggca accaccaaac  32460
ccctagtgag gaggaagctt ggggtttgag tttcttaact ccacccattt tgcttaatcc  32520
ccatccccat agggctgtag ttctgagatg tcgtgccttg tcagaaacaa tttgggagtt  32580
```

```
ttttaaaata tgaaaaagaa cagatagagc ctatcagact taagaaggtg ggatctagat  32640
agtatactaa aaatattaat aaaaggaagg cggggccagc aataaaagct ccacagattg  32700
tttggatatt gtttctgctt aagaagcact tggcataagc ttaaccacct cactagggcc  32760
agcacctgga ttcatcagac tattgtgcag atgcactttt tcctcatttg gacgatattg  32820
ccctaatttt gttcccatct ttacaggctc cctggggaag ggaatgcagg gttgctgggg  32880
ctgggcccag aagcagcagc accagggaaa aggattcgaa aaccctctct cttgtatgag  32940
ggctttgaga gccccacaat ggcttcggtg cctgctttgc aacttacccc tgccaaccca  33000
ccacccccgg aggtgtccaa tcccaaaaag ccaggacgag ttaccaacca gctgcaatac  33060
ctacacaagg tagtgatgaa ggctctgtgg aaacatcagt tcgcatggcc attccggcag  33120
cctgtggatg ctgtcaaact gggtctaccg gtgagtagag acattggagc cggggaggtg  33180
tgggatgagc aagaatgcgt gtgaatgggg gtggtctgcc tagtgtagat gctgcggccc  33240
ctagggagtt cccatttctc ccctgtaggg cagttagcta ccagatttct gggtatcttg  33300
gtcctttgtg attgatccga ccgcttgctg taactatctt ggcatctttc cttgtgccct  33360
ccatgtgtcc ttccttaact tttgtgccct ggctccattt tacagattcc cacctcgggt  33420
tgggagagga ccacggtggc caaaattctt agcttcttcc tttccctcat gcagcccatg  33480
gatagccagc cccagaggta atgtcacagg atgggaagtt tccagagtgg gtgggaggtg  33540
ggtggttaga gaaaggcagc aggggcctcc ctgtggatgt caagaatctt ttttatttat  33600
ttatttattt tgtcccacag tttaattggg gccgcagttt aactgttcct ttgatgcata  33660
gggggtgtgt gtgtgtgtgt gtgtgtgtgt gagagtcggg gatcggtagt ctccctataa  33720
gcatttattt ttctgtggtt ctgacctaac atttctttat ttaggattat cacaaaatta  33780
taaaacagcc tatggacatg ggtactatta agaggagact tgaaaacaat tattattggg  33840
ctgcttcaga gtgtatgcaa gattttaata ccatgttcac caactgttac atttacaaca  33900
aggtgagttt ttctgtgtgt tcatttagta ggtggggaga aacagtaatt tctattattg  33960
ctggatatgt tgtctacata aagtttaaat cctttgctac tgaaggtgtt atccaggtag  34020
ggtagtcgga gtcttaaaaa cctgactcta gatggtacta ttgaacacag tgatgtgact  34080
tcagagctct agttgaaggt tatttagaac acttcatact tgggggtggt ggtcctgttt  34140
cttagaaatc accagagacc tgagtagacc agggatctgt tttcttgtca gctctcaagt  34200
tttttcttct ttcgaatttt gggagacagt taggagaaag tggaaattag tagtggcctg  34260
gagtagaaat tttctttaag atttgatgac aagatgactg gtgggggtat ggtaatggcc  34320
tagggcctga atgcctctga gaaagatggt gtgtatctat cttctgttgg catttttttaa  34380
ctttctttat tgctgtctgt gttctcatag cccactgatg atattgtcct aatggcacaa  34440
acgctggaaa agatattcct acagaaggtt gcatcaatgc cacaagaaga acaagagctg  34500
gtagtgacca tccctaagaa cagccacaag aagggggcca agttggcagg taggaagagt  34560
gggagttttg caaatggaca acttaaagat ggggaagaga atcaaactac actttttttcc  34620
ttttttctag cgctccaggg cagtgttacc agtgcccatc aggtgcctgc cgtctcttct  34680
gtgtcacaca cagccctgta tactcctcca cctgagatac ctaccactgt cttcaacatt  34740
ccccacccat cagtcatttc ctctccactt ctcaagtcct tgcactctgc tggacccccg  34800
ctccttgctg ttactgcagc tcctccagcc cagccccttg ccaaggtatg atctgtggat  34860
ttcctctggg cagcagggag gcaaggtctt taagtaaagt gggcttggag tgacaggttc  34920
```

cctatcttgt ttctttctgc agaaaaaagg cgtaaagcgg aaagcagata ctaccacccc 34980
tacacctaca gccatcttgg ctcctggttc tccagctagc cctcctggga gtcttgagcc 35040
taaggcagca cggcttcccc ctatgcgtag agagagtggt cgccccatca agcccccacg 35100
caaagacttg cctgactctc agcaacaaca ccagagctct aagaaaggaa agctttcaga 35160
acagttaaaa cattgcaatg gcattttgaa ggagttactc tctaagaagc atgctgccta 35220
tgcttggcct ttctataaac cagtggatgc ttctgcactt ggcctgcatg actaccatga 35280
catcattaag caccccatgg acctcagcac tgtcaaggta cccactgcat ggggcagatg 35340
ggatgctcaa gcagtgatgg gagcctaggt gcaaaacaat aagtctcctt atgtgggcac 35400
acagcagtct ttggttcttg gcattttact tttataaaat aatagtggaa cagaaggtct 35460
ggtgttttga gaatttgtat ttcttggagt ttgaaacagt agggtggggt ttctttgtct 35520
tgagaaaaat actgtctata attaagtact aatgtggcag tgttgggtta aggaagttat 35580
agggtggaaa gacaggcata ggccacctct ctgtcactta gaaatgattt ctttttctag 35640
acataaatat ttcttcaacc cacccaaatt cctttgactt caaacttgaa ccccagggca 35700
cagatcctta aggtcatccc cactgtgctc tcaagagagg gctcttcttg tggtgtctgg 35760
ggttggcagg gaaaggtgag tcttcctgcc tgtgcagctt ctgatgctgc ctccttctgc 35820
agcggaagat ggagaaccgt gattaccggg atgcacagga gtttgctgct gatgtacggc 35880
ttatgttctc caactgctat aagtacaatc ccccagatca cgatgttgtg gcaatggcac 35940
gaaagctaca ggtgagtgga aaggttggag tttgaaaaat aaatggtatg gggagttatt 36000
ttgtcatgtg tgctgcatag cctcaacgtg agggtctcac tgttctgtac agttgtaaat 36060
tggagctata tcacttggtg gctgggtatg tagggcactg tttatcagca tagttttgag 36120
tttgtgcctc tttctaggat gtatttgagt tccgttatgc caagatgcca gatgaaccac 36180
tagaaccagg gcctttacca gtctctactg ccatgccccc tggcttggcc 36230

<210> SEQ ID NO 38
<211> LENGTH: 2732
<212> TYPE: DNA
<213> ORGANISM: Homo sapiens

<400> SEQUENCE: 38
ctttcgcctc agtctcgagc tctcgctggc cttcgggtgt acgtgctccg ggatcttcag 60
cacccgcggc cgccatcgcc gtcgcttggc ttcttctgga ctcatctgcg ccacttgtcc 120
gcttcacact ccgccgccat catggtgaag ctcgcgaagg caggtaaaaa tcaaggtgac 180
cccaagaaaa tggctcctcc tccaaaggag gtagaagaag atagtgaaga tgaggaaatg 240
tcagaagatg aagaagatga tagcagtgga gaagaggtcg tcatacctca gaagaaaggc 300
aagaaggctg ctgcaacctc agcaaagaag gtggtcgttt ccccaacaaa aaaggttgca 360
gttgccacac cagccaagaa agcagctgtc actccaggca aaaaggcagc agcaacacct 420
gccaagaaga cagttacacc agccaaagca gttaccacac ctggcaagaa gggagccaca 480
ccaggcaaag cattggtagc aactcctggt aagaagggtg ctgccatccc agccaagggg 540
gcaaagaatg gcaagaatgc caagaaggaa gacagtgatg aagaggagga tgatgacagt 600
gaggaggatg aggaggatga cgaggacgag gatgaggatg aagatgaaat tgaaccagca 660
gcgatgaaag cagcagctgc tgcccctgcc tcagaggatg aggacgatga ggatgacgaa 720
gatgatgagg atgacgatga cgatgaggaa gatgactctg aagaagaagc tatggagact 780
acaccagcca aaggaaagaa agctgcaaaa gttgttcctg tgaaagccaa gaacgtggct 840

-continued gaggatgaag atgaagaaga ggatgatgag gacgaggatg acgacgacga cgaagatgat 900
gaagatgatg atgatgaaga tgatgaggag gaggaagaag aggaggagga agagcctgtc 960
aaagaagcac ctggaaaacg aaagaaggaa atggccaaac agaaagcagc tcctgaagcc 1020
aagaaacaga aagtggaagg cacagaaccg actacggctt tcaatctctt tgttggaaac 1080
ctaaacttta acaaatctgc tcctgaatta aaaactggta tcagcgatgt ttttgctaaa 1140
aatgatcttg ctgttgtgga tgtcagaatt ggtatgacta ggaaatttgg ttatgtggat 1200
tttgaatctg ctgaagacct ggagaaagcg ttggaactca ctggtttgaa agtctttggc 1260
aatgaaatta aactagagaa accaaaagga aaagacagta agaaagagcg agatgcgaga 1320
acacttttgg ctaaaaatct cccttacaaa gtcactcagg atgaattgaa agaagtgttt 1380
gaagatgctg cggagatcag attagtcagc aaggatggga aaagtaaagg gattgcttat 1440
attgaattta agacagaagc tgatgcagag aaaacctttg aagaaaagca gggaacagag 1500
atcgatgggc gatctatttc cctgtactat actggagaga aaggtcaaaa tcaagactat 1560
agaggtggaa agaatagcac ttggagtggt gaatcaaaaa ctctggtttt aagcaacctc 1620
tcctacagtg caacagaaga aactcttcag gaagtatttg agaaagcaac ttttatcaaa 1680
gtaccccaga accaaaatgg caaatctaaa gggtatgcat ttatagagtt tgcttcattc 1740
gaagacgcta aagaagcttt aaattcctgt aataaaaggg aaattgaggg cagagcaatc 1800
aggctggagt tgcaaggacc caggggatca cctaatgcca gaagccagcc atccaaaact 1860
ctgtttgtca aaggcctgtc tgaggatacc actgaagaga cattaaagga gtcatttgac 1920
ggctccgttc gggcaaggat agttactgac cgggaaactg ggtcctccaa agggtttggt 1980
tttgtagact tcaacagtga ggaggatgcc aaagctgcca aggaggccat ggaagacggt 2040
gaaattgatg gaaataaagt taccttggac tgggccaaac ctaagggtga aggtggcttc 2100
gggggtcgtg gtggaggcag aggcggcttt ggaggacgag gtggtggtag aggaggccga 2160
ggaggatttg gtggcagagg ccggggaggc tttggagggc gaggaggctt ccgaggaggc 2220
agaggaggag gaggtgacca caagccacaa ggaaagaaga cgaagtttga atagcttctg 2280
tccctctgct ttccctttc catttgaaag aaaggactct ggggtttta ctgttacctg 2340 atcaatgaca gagccttctg aggacattcc aagacagtat acagtcctgt ggtctccttg 2400
gaaatccgtc tagttaacat ttcaagggca ataccgtgtt ggttttgact ggatattcat 2460
ataaactttt taaagagttg agtgatagag ctaaccctta tctgtaagtt ttgaatttat 2520
attgtttcat cccatgtaca aaaccatttt ttcctacaaa tagtttgggt tttgttgttg 2580
tttctttttt ttgttttgtt tttgtttttt tttttttgc gttcgtgggg ttgtaaaaga 2640
aaagaaagca gaatgtttta tcatggtttt tgcttcagcg gctttaggac aaattaaaag 2700
tcaactctgg tgccagaaaa aaaaaaaaaa aa 2732

<210> SEQ ID NO 39
<211> LENGTH: 4768
<212> TYPE: DNA
<213> ORGANISM: Homo sapiens

<400> SEQUENCE: 39
ggcggcttgc gcctgcgcgg cgcggcgctg cggagaccgt tggttcattt gcatgtcccc 60
gcctcgcgcg gcggcggcgg cgggtgagga gcctgaggcg gcggcggggg tggctccgcg 120
cgcggtggtc tcgggggcaa aataacatgg cagccagacg aattacacag gagacttttg 180

-continued

```
atgctgtatt acaagaaaaa gccaaacgat atcacatgga tgccagtggt gaggctgtaa    240
gcgaaactct tcagtttaaa gctcaagatc tcttaagggc agtcccaaga tccagagcag    300
agatgtatga tgacgtccac agcgatggca gatactccct cagtggatct gtagctcact    360
ctagagatgc cggaagagaa ggcctgagaa gtgacgtatt tccagggcct tccttcagat    420
caagcaaccc ttccatcagt gatgacagct actttcgcaa agaatgtggc cgggatctgg    480
aattttctca ctctgattct cgggaccagg tcattggcca ccggaaattg gggcatttcc    540
gttctcagga ctggaaattt gcgctccgtg gttcttggga acaagacttt ggccatccag    600
tttctcaaga gtcctcttgg tcacaggagt atagttttgg tccctctgca gttttggggg    660
actttggatc ttccaggctg attgagaaag agtgtttgga gaaggagagt cgggattatg    720
acgtggacca tcctggggag gctgactctg tgcttagggg cggcagtcaa gtccaggcca    780
gaggtcgagc tctaaacatc gttgaccagg aaggttccct cctaggaaag gggggagactc    840
agggcctgct cacagctaag gggggtgttg ggaaacttgt cacattgaga aatgtgagca    900
caaaaaaaat acccaccgtg aatcgtatta ctcccaaaac tcagggcact aaccaaatcc    960
agaaaaacac tccaagtcct gatgtgaccc tggggacaaa cccagggaca gaagatatcc   1020
agttccccat tcagaagatc cctctggggc tggatctgaa gaatcttcgg ctccccagaa   1080
gaaagatgag ctttgacatc atagataagt ctgatgtttt ttcaagattt gggatagaaa   1140
taatcaaatg ggcaggattc cacaccataa aagatgatat taaattttcc caacttttcc   1200
agactctctt tgaacttgaa acagaaacct gtgctaaaat gcttgcctca ttcaaatgtt   1260
ccttaaaacc agagcacaga gatttttgct tttttactat caaattttta aagcactctg   1320
ctttgaaaac acccagagtt gataatgagt ttttaaacat gcttttagac aaaggtgctg   1380
tgaagaccaa aaattgcttt tttgaaatca taaagccttt tgacaagtac ataatgagac   1440
ttcaagaccg gcttctgaag agtgtcacac ctttgcttat ggcctgcaat gcctacgagc   1500
taagtgtcaa gatgaagacc ctcagtaacc ccctggactt ggctcttgcc ctagaaacca   1560
ccaactctct ctgccggaag tctttggccc ttttgggaca gacattttcc ttggcctctt   1620
ctttccggca ggagaaaatc ttagaagctg tcggcctgca agatatagct ccctcacctg   1680
ctgcgtttcc aaacttcgaa gactccactt tgtttgggcg agagtacata gaccacctga   1740
aggcctggct agtcagcagc ggatgtcccc tccaggttaa gaaagccgaa ccagagccga   1800
tgcgagagga ggagaaaatg attcctccta cgaaacctga aattcaggcc aaggctccaa   1860
gtagtctgag tgatgctgtc ccccagcgag cagatcacag ggtagtgggc accatcgacc   1920
agcttgtgaa acgtgtcatc gaaggcagcc tgtctcccaa agagagaact cttctcaaag   1980
aggaccctgc ttactggttt ttgtctgatg aaaatagtct ggagtataaa tattacaagc   2040
tgaagttggc agaaatgcag cggatgagcg agaacttgcg aggagccgac cagaagccga   2100
cctcagcaga ctgtgcagtg agggccatgc tgtactcccg ggctgtccgc aacctcaaga   2160
agaaactcct tccgtggcag cggcgggggc tcctccgtgc tcaagggctc cggggctgga   2220
aggcgaggag agcgaccacc gggacccaga ccctcctatc ctcaggcacc aggctgaaac   2280
accacggccg gcaggctcca ggcctctcac aggcaaaacc atccctgcca gacagaaatg   2340
atgctgccaa ggactgcccg ccagacccag ttggaccttc tcctcaggac cccagcttag   2400
aagcctcagg cccatccccc aagccagcag gagtggacat ctctgaagca cctcagacct   2460
cttctccctg cccatctgct gacattgaca tgaagacaat ggagactgca gagaaactgg   2520
ctagatttgt tgctcaggtg ggaccagaga tcgaacaatt cagcatagaa aacagcaccg   2580
```

-continued

```
ataaccctga cctgtggttt ctacatgacc aaaatagttc tgctttcaaa ttctatcgaa   2640
agaaagtgtt tgaactatgt ccatcaattt gtttcacgtc atctccgcac aaccttcaca   2700
ctggtggtgg tgacaccacg ggttctcagg agagccccgt ggacctcatg gaaggggaag   2760
cagagtttga agacgagccc cctccgcggg aggctgagct ggagagccca gaggtgatgc   2820
ctgaggagga ggacgaggac gatgaggatg ggggagagga ggcccccgct cctggagggg   2880
cgggcaagtc tgagggcagc accccctgccg acggccttcc cggcgaggct gccgaggacg   2940
acctggctgg agcacctgcc ttgtcacagg cctcctcagg tacctgcttc cctcggaaga   3000
ggatcagcag caagtcattg aaggttggca tgattccagc tcccaagaga gtgtgtctca   3060
tccaggagcc aaaagtccat gaaccagttc gaattgccta tgacaggcct cggggtcgtc   3120
ccatgtccaa aaagaagaaa cccaaggact tggacttcgc ccagcagaag ctgaccgata   3180
agaacctggg cttccagatg ctgcagaaga tgggctggaa ggagggccat ggcctgggct   3240
ccctcggaaa gggcatcagg gagccggtca gcgtgggaac cccctcggaa ggggaagggt   3300
tgggtgctga cgggcaggag cacaaagaag acacattcga tgtgttccga cagaggatga   3360
tgcagatgta cagacacaag cgggccaaca aatagatcaa aaccactgat gtgaaagata   3420
agccttgaag cagcaattgc ccttaaaaca tcatccctgc cctggatcgg cctggagcca   3480
gtgcccaagt acggtttggt gtgtacatga aaacaaacgt ctctgcagtc tctggggcgg   3540
aggtttcgct ggcttttctt tctctcaaag aaaaaaaacat gcaccatttt caatgtgctt   3600
ttgcctctcc tctctgttca catgctttta gcagcaagtc ccctccaaat ctgtcttggt   3660
tccccttcag aaggtggcgc tgcccccgaa aggcacctca gcctgtgagt gctgaggaac   3720
cagctcctct ggctgatttt ccagttggac tggccattgc tctccagaag tgctctgtta   3780
gcaaacgtga tgtggaaacg atcacagatg gtgttttctc gttgttcgcc agaatttata   3840
cgggggagac aaattcccgg taattaccaa gtctgcactc gggtaccaaa gctctgaagc   3900
tctctgaaca gttgccatac ttgagttgat gaatgtgtta ttcatggtgt ctcatctcat   3960
caatgcatct tgagagactt aatgaaattt tagcaacagt atagaatagc tctatcgggt   4020
ggggagtaat cattaaacag atgaaatcgg ccccagattt acatgtctct ttagaatcca   4080
cagtgtaagc aaactacagt tacaaaggga tgggggttgt aaaccctctg agactctgca   4140
cttttcgcac gtatggcatc gtcaagtgct gtcttattac agcctttgta aggagaggca   4200
ggctcctcct ggggtgggct ctgcagctgc tctatttcca ggcatgtgat cgcccccgct   4260
ctccagattc cccagcactc tgctgcgtgt aactccactc aattctccac tcatccttcc   4320
ttgtgaagca ggatcgttga agttttaagt atgggcaaaa atctggaaaa cttaggatcc   4380
ctctgacacc ccaggattag gggacacagc agtggctagg gcatcagcca cagaactgag   4440
cgggaaatgc cacttgtatt ggctgtaaag aaatcctggc tttgggccag gcacagtggc   4500
tcaagcctgt aatcccagca ctttaggagg ttgaggcgga tggatcacct gaggtcagga   4560
gtttgagacc agcctggcca acatggtgta accccgtctc tactaaaaat acaaaaaaat   4620
tagccaggcg tggtagcggg cacctgtaat cccagctact caggaggctg aggcaggaga   4680
atcacttgaa ccggggaggc agaggttgca gtgagctgag atcatgccac tccactccag   4740
cctgggcgac agagcaagac tccatctc                                      4768
```

<210> SEQ ID NO 40
<211> LENGTH: 395
<212> TYPE: DNA

<213> ORGANISM: Homo sapiens

<400> SEQUENCE: 40
ctgcgagaat cgaggcactc gctggcgtac ccatgtatcg aaatgagttc acggcctggt 60
accggcggat gtcggtggtc tacgggatcg gcacctggtc tgtgttgggc tcactgcttt 120
actatagccg gacaatggcg aagtcgtcag tagaccaaaa ggatggctca gcaagtgaag 180
tacccagtga actctctgaa cgcccaaaag gattttatgt ggaaacagtt gtcacatata 240
aagaagattt tgttccaaat acagaaaaga tcctcaacta ttggaaatca tggactggtg 300
gccctggtac agaaccatga ctggctgctg aattctgaaa accaggactt ggttcaacat 360
ttaaatttga tagttgccct gattcccatt ttggt 395

<210> SEQ ID NO 41
<211> LENGTH: 137091
<212> TYPE: DNA
<213> ORGANISM: Homo sapiens

<400> SEQUENCE: 41
cgcggcgctg ggtcggtggc ggaggctgag gagaaggagg agcgggccgt ggaggcttcg 60
ccgcctaggt aagggcccgg gactggaggg gaggcgtgcc agagcctgcc agggaatagc 120
cagcagacag gcccgctcta gacatcgcag gcccgcgcag cctgaaagct gtggcttcag 180
tgtcgcgggg cggctgcggc ctcgctcggg aagaagacca agcaacggtg agatgaggga 240
ggcgccgccc gtggcaggaa cgcccggaa ccgtcgcggg cctggggcgg ggcccggcgc 300
ggcagtagat taccggtccc gccgcggagc ggccagctgt gaggctgggg ccggcgcgtg 360
gttgcggctc tgtgctccta ctcttcggag ctgtaagcgg gctgttcttg cggttttcct 420
gtttcagatc caattctgtg gcatcactag gaagggagct cttgtgctta gcacgtagcc 480
tcgtcctcag acttggacag acacaaggga ggctccgctg gaccggaggg cacaagagct 540
ccgagcccgg tcgtcggggc ggtagaacct ggaagcggga gagtggtctg gtgggttctg 600
cgcccgttag gcaatgaagg agaaggatgt tttatcgtat tcacgcttta gattccatta 660
gcggtgtaaa tagatgtttt tctctttatt ttagaattga cgttaggcga atgggttcaa 720
ctttgggaat gccttttttt tttttttttt tttgaaggaa gggccctgtt tcgtagggta 780
cataaaccgt gagcgtaatt gtattttttg catattccag gtttgcttgt gaaggtcaga 840
gtagccggat ttaagtgaag gagttcagta gacatgcaga catggtcacc tggttcattt 900
tctgaaccct ggattgtgcc ctcggcttgc tagtttccac cttcctattg agaaatgcca 960
ccagcgtgaa tgatttaaat atgtcaccat tactgaattt gtgaggtctc taacgagagg 1020
tgtcaagagc tggtgcgtga tggtaggact ggcagtgaag aaagtaacta aataatatgt 1080
taccattttg gtgaaacaca aaagttgaat ttgaaccttg tctcagaaac tagcatctaa 1140
ctagatacct aacctgcagg acaggtccca ggtctctctg gatagttgta gcacctttcc 1200
ttatagaatt ctattaccag gccgagcctg gtggctcaca cctgtaatcc cagcactttg 1260
ggaggctgag gtggggagtt cgagaccagc ctgactaaca tggagaaacc gcgtctctac 1320
taaaagtaca aaattagccg ggcatggtgg cacatgcctg taatcccagc tacttgggag 1380
gctgaggcag gagaatcgct tgaacctggg aggcggaggt tgcggtgagc tgagattgct 1440
ccattgcact ccagcctggg ccacaagagt gaaactctgt ctcaaaaaaa aaaaaaaaaa 1500
aaaaaaaaaa aaacccgcaa aactcaacaa aaaccaacat agtagaggca gcgtttcgcc 1560
ttatgcccag ctaatttttt gtattttttt agtagaggcg gagtttcgct atgttggcca 1620

-continued

```
ggctggtctt gaactactga cctcaggtga tccacctgcc ttggcctccc aaagtgctgg   1680
gattacaggc gtgagccacc gtgcccggcc ctgttatagt atttctaaaa caaattgtga   1740
gcctgggcaa catcgcaaaa ccctgtctct acaaaaaata caaaaaaaaa aaattagcca   1800
ggcgtggtgg catgctcctg ttagccctaa ctactcagga ggctgagatg gaaaaatcgc   1860
ttgagccggg gaggtagagg ttgtagtaag gggagatagt gccactgcac tccaacctgg   1920
gccacagaac aagactgtct caaaaaaaaa aaaatcaatt aaataaattg tggtaaatat   1980
atatttttat gtatgtttat gtatatttta acaaaatttg ctctttaaac cattgttaag   2040
tatacaattc agccaggcac ggtggctcac gcctgtaatc ccagcacttt gggacgccga   2100
ggtgggcgga tcacgaggtc aggagatcga gaccatcctg gctaacacgg tgaaacccca   2160
tctctactaa aaatacaaaa aatgagccgt gcgtggtggt gggcgcctgt agtcccaggt   2220
actcaggagg ctgaggcagg agaatggtgt gaacccgaga ggcggagctt gcagtgagcc   2280
gagattgcgc cactgcactc cagcctgggc aacagagcga gactccgaga ctccatctca   2340
aaaaaaaaaa aaaaaagtat acaattcaat ggtattaatt acattcacaa tgtagtacaa   2400
gcaataccac tatttctgaa actttagtat ctcaaacaga aactctgtaa ccagggaggg   2460
catggtggct cacgcctgta atcccagcac tttgggaggt caacgtgggc agatcacttg   2520
agttcaggag ttcaagaaca gcctggccaa catggtgaaa ccccgtatct actaaaaata   2580
caaaaattag ccatgcatgg tggcatgcat ctgtaacacc agctactaag gaggcagagg   2640
ttgcagtgag ctgaggtcat gccattgcac ttcagcctgg gctgcacagc cagactccat   2700
ctcaaaaaaa aagaaaaaaa gaaactgtaa ccattaaaca agttaacttc ccatttcctc   2760
ctcttaatct ctaatctact ttgtgtctgt ctgtgagtgt gcttgttcta ggtactgcaa   2820
atactaaatg gaatcataca gtattgtcct tttttgtgtc tggtttattt cacttagtgt   2880
aatggtttca aggttgatcc atgttgtact gtgtatcaga atttcattcc tttttaaggc   2940
ttaatccgtt gtgtgtgtac actacatttt gtttattaat tcatttgtag cagacacttg   3000
ggttgcttct gccttttgac tattgtaaat aatgatgctg tgatcattgg tgtacaaata   3060
tctctttgag tccctgcttt gaattctttt gggtatatac ccagaaggga aattgctata   3120
tggtaattat tattattatt aattatttta tttatttttt tttgagacag ggtcttgctc   3180
tgttgcccag gctggagttc agtggcacag tcatggctca ctgcagcctc gaactcgagc   3240
tcaagcagtc atcccgcctc agcttcctga gtagctggga ctacaggcat gggctgccac   3300
aaccagctaa ttttttgtt taatttttat tttttgtgat gaagtcttgc cttgttgtct   3360
agggtggtct cgaactcctg agttcaagtg atcctcctgt cttggcctcc cgaagtgctg   3420
gcattacagg catgagccac cacatctggc ccataatttt tttattttaa ttttttgtg   3480
gagacagggt ctccctatgt tgcctatgct ggtctcaaac tcctggcctc aagccatttt   3540
ccctccttgg cctctcaagg tactggtatt acaggcatga gccactgcac ccagttgata   3600
cttggttatt atatgtttag ctttttgagg acccaccata ctgttttcct caatggctgc   3660
atcgttttac attcccacca gtaatacaca agggttccaa ttttcccaca tcctccccaa   3720
cacttatttt ctgtttttcc ttttttgata aatttgtgtg tgtatatgtg gtttttttatt   3780
tgtgtgtttt gatgatagcc accctaatgg gtgtgaagtg gtatctcgtt gtgttttctt   3840
ggtttttgct tgtttgtacc tttttaccca tttttaagtg tgctacttag tagtagtaag   3900
tacattcttc tttttgtgca accataataa aaatccagct tcagaacttt tttcatcttc   3960
```

-continued

```
ccaaactgag tttctgtacc cattgaatag taactcccta ttctctcctc ccctgacaat   4020
caccattctg ctttctgtct ctatgaattt gactactcta ggtatctcat gtaagtggaa   4080
tcatataata tttgatcttt tgtgtatggc ttattttact tagcataata tcttcaggat   4140
tcatccatct tgtagtatgt atcagaattt tattcctttt taaggctgag taatattcca   4200
ttatacatat ataccacatt ttgtttatcc atttatctat tgatggacat ttgggttgtt   4260
tccacctttt tgctcttgtg aatataatgg tgctatgaat atcagtgtac aaatatcttt   4320
ttttttttt tttttgtgag acagtatcgc tcttgtcacc caggctggag tgcagtggcg   4380
cgaccttggc tcactgcaac ctctgcctcc tgggttcaag gcattctcct gcctcagcct   4440
cccgagtagc tgggattaca gatgtgcgcc accatgccta gctaattttt ttatttttag   4500
tagagaagga gtttcgccat gttgggcagg ctggtcttga acttctgacc tcaggtgatc   4560
aacctgcctc ggcctcccaa agtggtggaa ttacaggtgt cagccaccgc gcccagccac   4620
aaatatcaag tctttacttt catttctttt gggaatatat atactcagaa atggaatcga   4680
caattgacag agcaaatggt aattctatgt gtaatttttt tttaaatttt tttttttgag   4740
acggattctt gctctgtcgc ccaggctgga gtgcagtggc gtgatctcgg ctcactccaa   4800
gctccgcctc ctgggttctt gccattctcc tgcctcagcc tcccgagtag ctgggactac   4860
agcatccgcc accacgcccg gctaattttt tgtattttta gtagagacgg ggtttcaccg   4920
tgttagccag gatagtctcc atctcctgac ctcatgatct gcccgccttg gcctcccaaa   4980
gtgctgggat tacaggcgtg agccaccgcg cccggccaat tttttttttt ttttttttta   5040
gacagggtct tgctctgttg tccaggctgg agtgcagtgg tgcagtcaca gttctctgca   5100
gccctgacct tctcagttca agctatcctc tcacctcacc ctcttaagta gctgagacta   5160
caggtgcatg ccaccatgcc taactaattt ttttattttt ttgtagctgt gggatttcgc   5220
taggttgccc aggctttatg tatcattttt tgaggaactg ccttactgtt ttccacactg   5280
gttgcaccat tttacattct gttagcagtg tacaaaggtt ttgttataga ctgaattgtg   5340
tccccctgaa aattcacgtg ttgaagccct aagccccagt gtgactgtat ttggaaatag   5400
gacctttaca gagaaattaa aaagttagaa gatatcataa ggggctgggc gcgggtggct   5460
catgcctgta atcccagcac tttgggaggc tgaggcaggc ggatcacaag gtcaggagat   5520
cgagaccatc ctggccaaca cggtgaaacc ccgtctctac taaaaataca aaacattaac   5580
cgggcgtggc ggcatgcacc tgtagtccca gctgctgggg aggctggggc aggagaatgg   5640
cgtgaacccg ggaggcacag cttgcagtga gccaaaatcg cgccactgca ctccagcctg   5700
ggcgacagag cgagactcca tctcaaaaaa aaaaaaaaaa aaaaaaaaag aagatataag   5760
gatgagacct taatccagca ggactgctgt cttcgtaaga aaaggactgg ataccaggag   5820
tgcgtgtaca gagagaaaaa gctgcatgag gacagaggta gaagggggct gcctgcaagc   5880
caaggagaga gacctcacct aaaacaaacc ttgctgacac cttgatcttg gactcccagc   5940
ctccagagct gtgagaataa tttctgtggc ttaagccttc cactccatgg tattttgtta   6000
tggcagtcct agcatactgt gtaatatagg tttcaattca gtttctctgc atcctccaca   6060
tcctggccaa cacttgttat tttctttctt tttttttttt ggagacagat tctcgctctg   6120
tcacgcaggc tggagtgcag tggcacaatc ttggctcact gcaacctcca cctcccgggt   6180
tcaagcgatt ctcctgcctc agcctcccga gtaactggga ttacaggcag ccgccaccgt   6240
gcccagctaa tttttgcatt ttagttgaga tggtgtttct ccatgttggc caggctggtc   6300
ttgaactcct gacgtcaggt gacccgccag ccttggcctc ccaaagtgtt gggattataa   6360
```

-continued

```
gcatgagcca ccgcgcctgg cattttcttt ttttttgaga cagagtctca ctctgttgcc   6420
caggccggag tgaagtggca tgatctcggc tcactgcaac ctctgcctcc cagattgaag   6480
caattcttgt gcctcagcct cccgggtagc tgggattaca ggcgtgtgcc accacgcctg   6540
gctaattttt gtattttagt agagacaggg tttcaccata ttagccaggc tggtcttgaa   6600
ctcctgacct caagtgatct gtccaccttg gcctcccaag gtgctgggat tacaggtgtg   6660
agccatctca cccggcctat tttctgtttc gttttttttt ttttcattag tagctatcct   6720
agtggatgtg aagtggtatc ttattgtggt ttctgatttg catttccctg atgataagtg   6780
atgttgagcg tctgttcatg ttcttattgg ctatttgcat attctctttt ggagaagtat   6840
ctattcatgt cttttgttga ccattttaaa atggggtttt tcatcctggc taacacggtg   6900
aaaccctgtc tctactaaaa atacaaaaaa aaaaaaaaaa aaaaattagc cgggcgcagt   6960
ggcaggcgcc tgtagtccca gctactcggg aggctgaggc agaaggatgg tgtgaacctg   7020
ggaggcagag ctcgcagtga gcagagattg agccactgca ctccagcctg ggcgacagag   7080
cgagactccg tctcaaaaaa aaaaaggggg gggggggggg ttttgagctg ggtgtgcagg   7140
tgcacacctg tattcccagc tgctcaggag gctgaggtag gtggatctct tgagcccagg   7200
tgtttgaggg tgcagtgagc tgtgattgca ccactggact ctaccctggg tgacagagtg   7260
gcccagtctc taaaaataaa ataaaattag gtttttgtct gtgttgttga gttttaggag   7320
tcctttatac actctagata ttaattcctt gtcagatatt tgacttacaa atattttctc   7380
tctgtggttg tctttatact ctgttgatag tgtcttttga tgcacagagg ttttcatttt   7440
gatgaagtcc aatttatctt cttttttaa aatctgtgcc tcatctgcaa atattaccaa    7500
tcgaaagtca tgaaattttt cccctaagat tttatagttt tagcgcttac gtttgggtct   7560
ttgatccaat ttgagttaat tttttatata tttttgttgt gtaagagtcc cactttattg   7620
ttatgcatgt ggatattcag ttttcggagt accattttcc atttgggaaa aagattgtac   7680
tttccccatt ggatggtctt gacacctttg ttgaaaatca gttgactaaa gttcaagact   7740
agccttgcca acatggcaat atcccgtctg tactaaaaat accacaatta gctgggcatg   7800
gtggtgcctg gctgtaatcc cagctactcg ggaggctgag gcaggagaat cgcttgaact   7860
gggaggtgga ggctgcagtg agctgagatt gcgccactgc cctccagcct gggcgacaga   7920
gcgagacatg agaatctgtc ttaaaaaaaa aagaaaattg accatatatg tgaggattta   7980
tttctggtct ctccattcag ttgattggtc tttatgtcta tctttatgtc cttactgcac   8040
tgttgtgatg gctgtagcta aatggtacac ttaaaaatgg ttaaaatagg ccaggcacgg   8100
tggctcacgc ctataatctt agcactttag gaggctgagg tgggcagatt gcctgtgctc   8160
aggggttcga gaccagccta ggcaacatag tgaaaccccg attttactaa aatacaaaaa   8220
ttagctgggt gtggtgtgtg cctgtaattc cagctactca ggaggctaag gcacaagaat   8280
tgcttgaggc ctggtgctgt ggctcacgcc tgtaatccca gcactttggg aggccgaggc   8340
aggtcaagag atcgagacca tcctggccaa tgtcatgaaa cctagtctct actaaaaata   8400
caaaaaatta gctgggtgtg gtggcgcgca cctagtccca gctacttggg aggctgaggc   8460
aggaggatca cttgaaccca ggaggtggag gttgcagtga gccaagattg cgccactgca   8520
ctctagattg gcagcagagt gagactctgt ctcaaaaaag aaaaaaaaaa aaaagaattg   8580
cttgaaccca ggaggtagag gttgcagtga gctgagattg caccctgcac tccagcctgg   8640
gcaacagagt gagactattt acatacccaa ttttttttt ttttttttt tgggatggtg    8700
```

-continued

```
tcttgcactg tcgcccaggc tggagtgctg tggcgtgatc ttggctcact gcaacctctg   8760
cctcctgggt tcaagcaatt ctcctgcctc aggctctcaa gtagctgggt tacaggtacc   8820
tgccaccacg cctggctaat ttcttgtatt tttagtagag atggagtttc actatattgg   8880
ccaggctggt ctcaaatttc tgaccttgtg atccgctggc ctcagcctcc caaagtgctg   8940
ggactacagg tgtgagccac cacgcctggt catacccaaa tattttacca taattataca   9000
agaatttatt atttttattt ttttcttttt aaattcttta atcttcttca tttgttaatg   9060
ctttgctgaa tcataaaaaa ttatgaaata aaaagaatag gtcttgttga ttcttctttt   9120
tacttacctc cccctactta ccccctctta ctttatcaaa gaaaacactt catttgaaac   9180
ttaacggaag tacattctcc cagagaggaa aatccttcag gacaacattt tttttgttt   9240
gcttgttttt tttgagacgg agtctcactc tgtccccgag gctggagtgc agtggtgtga   9300
tcgcagctca ttgcaacctc tgcctcccgg gttcaagcga ttctcctgcc tcagcctccc   9360
gagtagctgg gactacaggc gcctgtcacc atgccctgct aatttctgta tttttagtag   9420
aaacagttgg ccaggatggt ttcaatctta tgactttgtg atctgaccac tttggcctcc   9480
caaagtgctg ggaatacagg cgtgagccac agtgctcagc caattttttg tatttttagt   9540
ggagaaaagg tttcaccgtc tttgccagga tggtcttgat ctcctgacct cgtgatccgc   9600
ccgcctccca aagtgctggg attacaggcc tgagctacca cgcccagcct ttttattttt   9660
ttattttatt tattttattc tcagccttct gggtaactgg gactacaggt gtataccacc   9720
acgctcagct aatttatgta tttttagtag aaatggggtt tcgccatatt ggccaggctg   9780
gttttgaatt cctggtctca agtgatctgc ctgcctccgc ctcctaaagt gctgagatta   9840
caggcatgag ccactggccc agactacact taaaattttc aaatcgagat attttggggg   9900
gcaagggtgc ttctagcagc cactaattcc agttcttgag tgcatattaa agttgctact   9960
gtttaaaagc ttgtagttgg atccagggag tgggtaggcg gtcagagtaa cccttgcttc  10020
ttggtgtctc cttgatgctc ttagctgaat gtcctgtgta gcccacaaca tttactttgg  10080
gaaaaaatta agagtgttta aagcaggatc aagctgctgc ataccacagc taaaactact  10140
agaataagac ccctggttct gtttcattgt tttttggagc taaagtcatg attaagaagg  10200
atggcctggg atattggtac tgtgctgcta gaggtgcaat tcctggttct ttgcaagata  10260
gaccagagtg aaagcatttg ttaggaatgt ttttattaat caagagtgaa aggcaaggcc  10320
aggcgtggtg actcaggctt gtaatcccag cactttggga ggccaaggtg tgggatcatt  10380
tgaggtcagg agttcaagac cagcctggcc aacatggtga aaccccgtct ctactaaaaa  10440
tacaaaaatt ggctgggtgt ggtggtgcat gcctgtaatc ccagctactc gggagactga  10500
ggcaggagaa tcgcttgaat ccgggagacg gaggttgcag taagctgaga tcatgtcact  10560
gtggtacagt ctgggtgaca gagggagact gtttcaaaaa aaaaaaacag aaagaatgaa  10620
aggcaaaaca ttaaaaatag aattaccatg tgatctaaca attttacttc tggatatata  10680
tccaaaataa ttgaaaacaa agaaaaagaa aaacagagtc tcgatgagat atttgtaccc  10740
atgttcataa cagcgttatt cacattagct aaaatgtgga agcaacccaa ctattcattg  10800
atggatgaat agataaggaa aatgtggtat gtacatataa ctgaaaaatt attcagtgtt  10860
aggaaggaag gtaattctga catatgctac aacatggatg aaccttgagg atattatgct  10920
aagtgaaata agccagtcat gtaaaagaca aataccatat aatttcactt agacactttg  10980
agtagtgaaa atcatagaaa cagaaaatag ttgtcaggga tggtgtgagg gatgaatcag  11040
cagttactat ttctttttgt ttgtttgttt tttgagatgg ggtcttgctc tgttgcccag  11100
```

-continued

```
gctggagtac agtggtgtga tcttggctca ctgcaacctc tgcctcccag gcacaagcca  11160
tcttcccacc tcagcgtcct cagtagctgg gactacagat gtgttccacc ttgtccggct  11220
gatttgtgtg tgtgtatatg tgtgtgtgtg tgtggagaca aggttttgcc atgttgccca  11280
ggctggtctc gaactcctga gctcaagcat caagcaatct accttttca gctttccaaa  11340
gtgctggcat tacagacaag ggccactgtg cctggccttt actatatttt attttattta  11400
ttatttattt atttatttat ttatgtattt tgagatgaag tctcactctg ttgcccaggc  11460
tggagtgcag tggcacgatc ttggctcact gcatcctctg cctcccaagt tcaagtgatt  11520
ctcctgcctc agcctccagt tattattatt attattatta tttttttgtt gttctgtttt  11580
tttgaggtgg agtctcgccc tgtcgcccag gctggagtgc agtggcacaa actcggctca  11640
ctgcaacctc catctcccag gttcaagtga ttcttctgcc tcaacctccc aagtagctgg  11700
gaatacaggt gcccgccacc acgcctggct aatttttgta tttttagtag agacggggtt  11760
tcaccacatt ggtcaggctg gtcttgatct cctgatcttg tggtccacct gcctcggcct  11820
cccaaagtgc tgggattata ggtgtgagcc cccatgccct gccttgttat tattattatt  11880
tttatttttt tgtctgagac ggagtcttgc tctgtcaccc aggctagaat gcagtggcac  11940
gatcttggct tagtacaacc tctgcctccc gagttcaagt gattctcctg cctcagcctc  12000
ccgagtatat aggactacag gtgtgtgcca ccatggctaa tttttgtatt tttagtagag  12060
atggggtttc accatgttgg tcaggatggt ctagatctct tgacctcgtg atctacccgc  12120
cttggcctcc caaagtgctg ggattacagg catgagccac tgcgcctggc cccagttttt  12180
gtatttttaa tagagacagg gttttggcat gttggccagg ctggtctcag actcctgacc  12240
tcaagtgatc tgcccacttc agccttctga agtgctggga ttaaagacat gagcactgtg  12300
cccagccact tttactatat tttaaattag gttacttatc ctttgttttt tttttttttt  12360
gagacgaagt tttgctcttg ttgcccaggc tggtgtgcaa tggtgcatct cgactcaacg  12420
caacctctgt ctcccgggtt caagtgattc tcctgcctca gcctcccgag tagctgggat  12480
tacaggcatg catcaccacg ccagctaatt ttgtattttt agtagagaca gggtttctcc  12540
atgttggtca ggctggtctc aaactcccga cctcaggtga tccacctgcc ttggcctccc  12600
aaagtgttgg gattacaggc gtgtgccact gctcctggct tatttttctt tttgttactg  12660
agttgaaatc attttttata tattttagat acaagtcact taccaaatat gtaatttgca  12720
caaattttct cccattctgt gggatgtctt ttcatttaaa ccaaaaaatt gtagagatgg  12780
gggttttgct gtgttgccca ggttggtctt gaactcctgg tcttaagtga tcctctgacc  12840
ttggcctcaa aaagtgctgc gattataggc atgagccaat gtgcgcagct taccttttct  12900
tcttttcttt ttttttgagg cagggtcttg ctctgttgcc caggctggag tgcagtggtg  12960
caatcatggc ttactgcagg ctgaaactcc catgctcaag tgatcctccc actttagcct  13020
cctaggtaac tgggacctta ggggcgtgcc atcacacctt gctaattttt tttttttttt  13080
gagatggagt cttgccctgt cgcccaggtt ggagtgcagt ggagcgatct tggctcactg  13140
caaattccac ctcccggatt caagtgattc tcctccctca gcctcctgag tagctgggac  13200
tacaggcgtg tgccaccacg cccagctaat ttttgtattc tgagtagaga cgggatttca  13260
ccacattggc caggctggtc tcgatctctt gacctcgtga tctgcccgcc ttggcctccc  13320
aaagtgctgg gattacaggt gtgagtgtga gccaccgaac ctggcctttt tttttttttt  13380
tgagaccgtc tctgtcaccc aggctggagt gcagtaacat gacacaatct ccgctcactg  13440
```

-continued

```
caacctctgc cttctgggtt caagtgatcc ttctgccaca gcctcctgag tagctgggat  13500
tgcaggcatg tgctaccacg cctggctaat ttttgtattt ttagtagaga cggggtttca  13560
ccatgttggc ctacctggtc ttgaattcct gacctcagat gatctgcccg catcagcctc  13620
ccaaagtgct ggggttacaa gcgtgagcca ccacgcctag ctggacctga ctaattaaaa  13680
aaaaaatttt gtaggctggg cagggtggct cacacctgta atcccagtac tttgagaggt  13740
ggaggcgggg taatcgcctg aatcaggagt ttgagaccag cccgggcaac ataacgaaac  13800
cctaggtcta ccagaaatac acaaaaaaat tagccgagca tggtagtgca catttgtagt  13860
cccagctact caggaggctg aggtgggagg atggctggag ccagggaagc agtggttaca  13920
gtgagccgag aatgtgccac tgcactcccg cttgggtgac agagtgagat aaggtctcag  13980
aaaaaaaaaa aaaatttata ggccgggcgc aatggctcac gcctgtaatc ccagcacttt  14040
gggaggacca ggcgggcgga tcacaaggtc aggagatcga gaccaccctg gccaacatgg  14100
tgaaaccccg tctccactaa aaaaatacaa aaattagctg ggcgtggtgg cacgtgcctg  14160
tagtcccagc tacttggcag gctgaggcag aagaattgct tgaaccctgg aggcggaggt  14220
tgcagtgagc cgagattgca ccattgcact ccagcctggg cgacagagcg agactccatc  14280
tcaaaaaaaa aaaaaaaaaa aatttgtgaa gacaaggtct caatatttgc ccaggatggt  14340
ctgaaacttc tgggctcaag ccatccttct gcctcagcct cccaaagtat tggaattaca  14400
ggtgtgagcc actgtgtctg gcctatttat agactcttaa ttctgtttcc ttggtctgta  14460
tgtctatact atgtcagtgc cacactgtct tgattactgt agctttgtgg tgagttttgg  14520
aattgggaag tgtcagtcct ctaactttgt tgtatatatt cttttctgtt ttgcacagat  14580
atcaggttac aaatattttg cacacttttt tttttttttg aaatggagtc ttactctgtc  14640
acccaggctg gagtgcagtg gcgcgatctc agcccactgc aagctccgcc tcccaggttc  14700
acaccattct cctgcctcag cctccccagc agctgggact gcaggcgcac actgccatgc  14760
ccagctaatt tttttgtatt ttaagtagag acagggtttc actgtgttag ccaggatggc  14820
ctcgatctcc tgacctcgtg atccgcctgc ctaggcctcc caaagtgctg ggattacagg  14880
cgtgagccac cgcacccggc cttgcacatg tttttaaaac ttaatacata atagcttatc  14940
ctgtatcaat taacatagct actttattta ttcttagggc cgcatagtat tttttttttct  15000
ttcttttttt tttttttttt tttttttgag actgagtctc gctctgttgc ccaggctgga  15060
gtgcagtggt gtgatcttgg cttaagcaac ctctgcctcc tgggatcaag cctcgggatc  15120
ctcctacctc aacctctgca gtatttggga ctacagacac ctgctaccac acccagttaa  15180
ttttcgtatt tttttgtaga gatagggtct ctattgatgt gcatttaggc tttataatat  15240
ttatatatat attttttgaa acaaagtttt gctcttgttg cccaggctgg agtgcagtgg  15300
catgatcttg gctcactgca accttcgcct cccaggttca agtgattctc ctgccttaga  15360
ctcccgagta gctgggatta cagtttttaa aaaatgtatc ctaggctggg cgcagtggct  15420
cacgcctgta atcccagccc tttgggaggc tgaggcgggt ggatcacctg aggtttggag  15480
tttgagacca gcctggccaa catggtgaaa cctcgtctgt actaaaaata caaaaaattag  15540
ctgggtgtac tggcgggcac ctgtaatctc agcttcttgg gaggctgaga caggagaatc  15600
tcttgaactt gagaggcggt ggttgcagtg agccattgca ctccagcctg ggtgtcaagc  15660
aaaactctgt ctctctctct ctctgtgtct ctctctctct ctctgtgtgt gtgtgtgtgt  15720
gtgtgtgtat atgtatatat attctgccaa tattttgtga ttagagagtt taaagtattt  15780
acatttaaag taattactga taaggacttt tgccattttg ctactacttt tatgtttagc  15840
```

-continued tgattttttt ttttttggta gtgaaaaaaa attttttttt tttgagagca tgagactgtt 15900
gcctaggctt tggtgagcaa aatagtgcag tgccacaatc tcagctcact gcaactttgg 15960
gctcaagtga tcctcctgtc ccagtctcct gagtagctgg tagtataggt gtgccaccac 16020
catgcctggc taatttttgt atttttttgta gagatagggt tttgccatgt tgcccaggct 16080
ggtctcaaac tgggttcaaa caatctacct gccttagcct tccaaagtgt tgggattaca 16140
ggcattagcc actttctgcc ccctcccccg cttttttttt tttttttttt tttttgagac 16200
ggagtttcac tcttgttgcc caggctggag tgcagtggca tgatttcagc tcactgcaac 16260
ctccgcctcc cgggttcagg cattttcctg cctctgcctc ccaagtagct gggattacag 16320
gcttgccacc atgcctggct aattttgtat ttttaataga gatggggttt ctctatgttg 16380
gtcaggctgg tctcgaactc ctgacctcag gtgatcctcc tgccttggct tcccaaagtg 16440
ctgggattat aggcgtaagc catcacgcct ggcccacgct ttattttttt atttttattt 16500
tttattattt atttatttat tttttgagac ggagtttcgt tcttgttgcc caggctggag 16560
tgcaatggca taatctcagc tcaccgcagc ctccgcctcc tgggttcaag tgattctcct 16620
gcctcagcct cctgagtagc tgaatttaca ggcatgcgcc accatgccca gctaattttg 16680
tatttttagt agagacgggg tttctccatg ttggtcaggc tggtctcgaa ctccagacct 16740
caggtgatcc tcccgcctcg gcctcccaaa gtgctgggat tacaggcgta agccaccagg 16800
cctggcctgc tttttttaatt ttttatttat tttttctttt taagagggag ggtcttgctg 16860
tgttgtccag attggagaac agtgatgaga tcatagctca ctgcagactt ggattcctgg 16920
actcaagcaa tcctcccgct tcattctttg caagtaactg gaagtgcaga catgtgccac 16980
ctgccttttt tgttttttaa atttttcata gagatggggt cttgctatat tgcctaggct 17040
ggtctcaaac tcctggcctc aagcaatcgg cttcctgaag tgctgggatt acagatgtta 17100
gccactggcc tgttgtgaaa atgttttgac tttcttctca ttttctttct ttcttttttt 17160 tttttttga agtagagaga gtctcactat atggccaatg gtggtttcaa acccctgagc 17220
ccaaggaatc ctcctgcctc agcctcccag tgcttgtcgt gctaggacaa caagcatgag 17280
ccactgtgcc tagcccccttc tcattttctt tttctttcta gtgcataagc aggcaacctt 17340
attttcttat gtgtatattc taaagatatg ttctttgcag ttaccatggg aattacactt 17400
aacatctcac agttataatc taatttgaat ttatactaac ttaagttcca tagtatacaa 17460
atctctgctc ctatccagct cctttctctt ccctttttctg ttaagtcatg gattacatct 17520
ttgtaaatcg tatctcagga acctagatta ataatttttt atgcatctgt cttttagatc 17580
acattgaaag tgaaaagtag gagttacaaa gcaaaattgc aataatgcta gtttttacag 17640
ttgcccctgt atttgccttt accagagatc tttctttctt tttttttttt ttgggatgga 17700
gtctcgctct ttcgcccagg ctggagtgca atggcgcaat ctcagctgac tgtaacctct 17760
gcctcccggg ttcaaaagat tttcttgcct caggctcctg agtagctggg actgtagttg 17820
tacgccacca cacgtggctg atttttgtat ttttagtaga gatggggttt tgccatgttg 17880
gccaggctgg tcttgaactc ctgacctcag gtgtgagcca ccgcacctgg ccgagatctt 17940
tatttcttca catggcttca cgtctagctt ttaaaaattc attctgggcc gggcgcagtg 18000
gctcacgcct gtaatcccga cactttggga ggctaaggcg ggcggatcac gaggtcagga 18060
gatcgagacc atcctggtta acacagtgaa accccgtctc tactaaaaac acaaaaggcc 18120
gggtgcggtg gctcacgcct gtaatcccag cactttggga ggctgaggtg ggtggatcac 18180

-continued gaggtcagga gatcgagacc atcctggcta acatggtgaa accccgtctc cactaaaaat 18240
acaaaaaaca aaacaaaaca aaaaaaacta ttagctggca ttgcggtggg cacctgtagt 18300
cccagctact cgggaggctg aggcaggaga atggcgtcaa cccaggaggc ggagcttgca 18360
gtgagccaag atcacgccac tgcactccag cctgggagac agcaagactc tgtctcaaaa 18420
acaaaaaaca aaaaaccaca aaaattagcc gggcgtggtg gcgggcgcct gtagtcccag 18480
ttactcggga agctgaggca ggagaatggc atgaacccag gaggtggagc ttgcagtgag 18540
ccgagatcgc tcaactgcat tccagccttg gcaacagagc gagactccat ttcaaaaaaa 18600
aaaaaaattc attctgaaga attccttttt tttttttttt ttttgtaaaa atggagtctc 18660
actctgttgc cctggctgga gtgctgagtg ccatggcatg atctcagctc actgcaacca 18720
acccccactc caagttgaag cgatactcct gcctcagcct cctgactagc tgggattagg 18780
ggtgcctgct actgcacctg gctaattttt gtatttttag tagagacggg tttcaccatc 18840
ttggccaggc tggtgtcgaa ctcctgacct cgtgaccaac ccacttcggc ctcccaaagt 18900
gctgggatta caggcgtgag ccactgtgcc cggactgaag aattcccttt tagcatttct 18960
tacaaggtct gtatagtggt aatgagcctc cctcagcttt tgtttatctg agaatgtctt 19020
gattttttc cttttttttt ttttttttg agatggagtc tcgctctgtc gcccaggctg 19080
gagtgcagtg gcgtgatctc agctcactgc aagctccgcc tcctgggttc acaccattct 19140
cctgcctcag cctcgtgagt agctgggact acaggtgccc gccaccacgc ctggctaatt 19200
ttttttttt tttttgtatt tttagtagag acggggtttc actgtgttag ccaggatggt 19260
ctcaatctcc tgaccttgtg atccgcccgc ctcggcctcc caaagtgctg ggattacagg 19320
tgtgagccgc ctcgcccggc caatgttttt ccctattttt tgaaagacag tgttgccatt 19380
tacagaattc ttggttggca atttatattt agggtttttt tttttttttt tgagacagag 19440
tcttgctctg ttgcccaggc tggagtgcag tggtgtgacc tcggctcact gcaacctccg 19500
cctccagggt tcaagtcatt ctcctgcctc agcctcccaa gtagctggga ctacaggtgc 19560
ccgccactac gcctggctaa ttttttgtat ttttagtaga gacggggtgt caccatgttg 19620
gccaggctgg tctcgaactc ctgacctcaa gtgatccaca cgcctcagcc tcccaaagtg 19680
cagggattac agacatgagc ccccacgccc ggcctaggtc ttgtatgatc atacattttg 19740
ccttggcatt catatggctt tctaaatttc accatataca tgttgctttg gaatgtccta 19800
atttgccaaa gagtttcacc tcaacttctg tgggcatcta tctgtaatct cttgccccaa 19860
gtgcctgtta gtctgtagtc tgctttgcag ctttcattag caatacctgc tgctttctct 19920
gcctgagttt tgtattaggt tgaaatagaa acatgcacct tatgtctgtc cttcaaatac 19980
ccccgcagac agggtagaac agatatgtac gataatttgc aaataaggtc tgctttgctc 20040
tttgagggag ggagctggga attgggcttc tactgcttta agacaaaaaa cactgccatg 20100
ctggagaggg ggtagggcaa ggttgagtaa aacaccacag aactttcctt ctgttttgaa 20160
gatggctttt tcttcattgg atatttgctt gtaaaccttt gactcttttc taaaactgtc 20220
aaatttggtt cagacagtta ctacttgttt ttctgatgtt tctatgaagg aatgagacct 20280
tgaaacttcc tagtctgcca ttttgatgac ctatgggctg tctttgtact ctcttgatag 20340
tgtcctttga tacacagaag tttttaattt tggtgaagtc cctttatcta ctttttcttt 20400
taaagttcct tgtgctgtag gggtcatatt taagaaatca ttgccaaatc caaggtcatg 20460
aagatttgcc tctttttcag tagctataac aaaggtcctg gaaataactt cttatcttga 20520
cttgagttac atgtctgtct tcaaagcaat gactgtggtg agggtaatag attattccga 20580
ttgctcatgc tggatggtgt ccgatcaggt ctgagacagt ggggttgata ctacagtgct 20640
gtttccaaaa aggaagggct agtgagcgct agaaaaatca gtaaatactt acttcatgta 20700
gtaaatgtga agcattcata gcacattgaa aagtttatgg tgcccagagt acctttttt 20760
ttttttttt ttgagacagc ctcactctgt ttcctgaact ggaatgcagt ggtgcgatct 20820
tggctcactg cagcctcaac ctcctgggtt caagcgatcc tcccccactt cagccttcca 20880
agaagctgag actacacata gtcatcatgc ctgactaatt tttgtatata tattttttaa 20940
gatggagtct cgctctgtca cccaggctgg agtgcagtgg catgatcttg gctgactgta 21000
gcctccgcct cccggtttca agcgtttctc ctgcctcagc ctcctgcata gctgggatta 21060
caggtgcctg ccaccacacc tggctaattt ttgtattttt agtagagatg agatttcacc 21120
atgttgccta ggctggtctc gaactcctga cctcaggtga tccacctgcc tagcctccca 21180
aagttctggt aatttttgta ttttttgtag agatggcatt ttgctatgtt gcccaggctg 21240
gtctcaaact ccttggctca agcggtctgc ctgccttggc ctcccaaagt gttgaggtta 21300
caggtatgag ccaccgtgcc cgaccccaga gtacacattt taattaaaaa cttatttttc 21360
tggccgggca cggtggctca cgcctgtaat cccagcactt tgggaggccg aggtgggtgg 21420
atcacaatgt taggagttcg agaccagcct ggccaatatg gtgaaacccc atctctacta 21480
aaaatacaaa aattagccgg gcatggtgac gcgtgcctgt agtcccagct actcgggagg 21540
ctgaggcaga agaatcgctc gaaccgggga ggcagaggtt gtggtgggct gagatagtgc 21600
cactggactc cagcctgggc gacagagaga gattctgtct ttaaaaaaaa aaaaaaagta 21660
tttttcttat tataaattta atatgtaagt gatgtaagtg tttgaaagtg acttccagct 21720
ggatgcggtg gctcatgcct gtaatcctag cactttggga ggccgaggcg ggcggactgc 21780
ttgagctcag gagtttgaga ccagcctggg taacacagtg aaaacccgtc tctactaaaa 21840
tacaaaaaaa ttagctgggc ggccggcgtg cgcctgtagt tctagctact tgggaggctg 21900
aggcaggaga attgcttgaa cccggaggtt gcagtgggct gagatcgtgc ctttgcactt 21960
cagcctgggc aacaaagcaa gactccatct cttaaaaaaa aaaaaaaaaa agaaggccgg 22020
gtgcagtggc tcacgcctgt aatctcacac tttgggaggc ctaggtgggc ggatcatgag 22080
gtcaggagat ctagaccaca gtaaaccccg tctctactaa aaatacaaaa aattagctag 22140
gcgtggtggc gggcgcctgt agtcctagct actcgggagg ctgaggcagg agaattgctt 22200
gaacccggag gttgcaatgg gctgagatca tgcctttgca ctccagcctg ggcgacagag 22260
cgagactcca tctcaaaaaa aaaaaagaaa agaaagaaaa gaaagacctt caaaattatt 22320
gctgctgatg tggtccctca taaaccaagc agtgggaaac tggtttagct tttagttcac 22380
attctaaagt actaattttt gtggtttatt ttgtacaggt actgctataa ccagaatttg 22440
gtagaaaaag gatttacttg ttggggccct cttgataaaa agagatgtgg ggggattctc 22500
gacctgctaa cagaactgga ccttttcggt aagttctcaa atttgaatat tgaaattgcc 22560
agtattttaa ttataaatgt gtaacatttt cgcctactat aaatgaagat attttctctg 22620
tggagaaata gtttctgatt ttttaaaaat agaaatttgg ctgggcgcgg tggctcacgc 22680
ctgtaatccc agcactttgg gaggctgagg cgggcagatc atgaggtcag gagatcgaga 22740
ccatcctggc tatcacggtg aaaccccgtc tctactaaaa aatacaaaaa aaactagccg 22800
ggcgtggtgg cggctgcctg tagtcccagc tactcgggag gctgaagcag gagaatggtg 22860
tgaacctggg aggcggagct tgcagtgagc cgagatcgtg ccactgcact ccagcttggg 22920

-continued

```
cgacagagga agactctgtc tcaaaaacaa aaacaaaaaa aaaaaaagaa aaaaaaagaa  22980
aaatagaaac tcaatttgga aaataatttc gaaaatgatt gtgagcctga atacccagca  23040
tgccaaatgt tttgtcacat agcattttaa aattttattt atttgtttgt tttttgagac  23100
aagtctctct ctgtctccca ggctggagtg cagtggtgcg atcttgactt actgcaacat  23160
ccgcctcccg tgttcaagtg attctcctgc ctcagccttc tgagtagctg ggattacagg  23220
cgcgtgccac tatgcctggc taatttcatt attttaatat taaaaaatac ccaaatattt  23280
tatttctttt tgtctcttag cgaaggaata catatttggc tagtaaggaa agctagcaaa  23340
atttacataa atgtttataa aagttgtatt gagttcacta atttatgtct agaattcaga  23400
gctgtgcctt gtctgtggca tgttgacgca gtttgctaag ccacctctca attttagggg  23460
ttacttggta ccaagaagag tggagaaagt ggtagcattt agttgtaaat agattgtatt  23520
ttaaatttgt agggaattaa tttttttata gctagtatca tacacactgt attttaacta  23580
gtatttaaac atttttcgta ttgtgtttac aattaatgag atgctatatg aatgtgactt  23640
ttttggtttt acttggtaca tagcaaataa atctgacctt taaatgtatg cattcataag  23700
tattgttgct ccagttgaaa cttctattaa ctagtacatt ttcctttttt tacctttttt  23760
caaaatggag tctcactctg ttgcccatgc tggagtgcag ggtatgatc tcagctcact  23820
gcagcctttg cctcctaggt tcaagtgatt ctcctccctt agcctcctga gtagctggga  23880
ctacaggtgt atgccaccat gcctggctaa ttattgtatt ttttttttta gtagagatgg  23940
cgtttcacca tgttggccag gctgatctca aactcctgac ctcaagtgat ccacctacct  24000
cagcctccca aagtgctggg actataagtg tgagccaccg cacctgccat ttggattggc  24060
aatctgcaag attttattac ttaaatgcaa cagatgttct cattcattgt tctgaagctt  24120
ggagttccaa tgaaaaattt aggtggagaa ctgagtttag aaaatccata taatgtttag  24180
taaaactagt atttcataaa tgctgaatga cagagattgg tctttaaatt aaaacaacag  24240
tgtgatgttg ggtatttttt ttctttcaaa atactaagga ttagatcagt ggtcagcaaa  24300
ctacagctga tagcctgttt ttgtaaataa agttttactg gaaaacagcc actcttactc  24360
atttgcagat tgtgtatggc tgctttcatg ctatgatggc agagttgaat agttgtaaca  24420
gagattgtat aacccacaaa atccgatatg tttacgaact ggctcttcat ggaaaaagtt  24480
tcctgacctc tcatctagat caatggggtt gtacgttacc atttaaaaat atttaggttg  24540
taatctatcc tcttattact tgtatttatg ggtaactatt ttgtaagtaa ggctgtttcg  24600
tatagaatta acgtggttta ggtaagcatt cagaaatgtt aggttaattt agctttattg  24660
tctaactttt ttcaaattta gaacatttgt ctttgactcg tttaaactta tttaaaatta  24720
tattttccca ccttaatttt agtttaaatg taagtcatta tatgctgttt tttaacatct  24780
ttgactagga gggagacagt tttgggaac taatttgaac caaaacagat ataggaaaat  24840
gattttgtta catttccttt gaacttttct tttaaaattt gtttttattt ggttgaaaat  24900
aattttcata actactgata ttttatatta gtagaatggt ttcttgattc gtctgtataa  24960
aatacaaatc taagaaccct gctacagtaa gttactctaa atctatttga tcttaattta  25020
gaagagtaag ataatcttta ggccatgttg gatgtgttct ggtcagaaaa catgtagatt  25080
tcatacctca gtcctcatcc catgagtgtc tgatgaagct taaatcttcc tgcaagaaag  25140
acttgaatga ttttaaacat gagagacact gtatttagtg gtaacatctt aattttagtg  25200
ttaaattgta ttgcctaaga agaacatcta gggcgggcgt ggcggctcac gcctgtaatc  25260
ccagcacttt gggaggccga ggcgggtgga tcacgaggtc aggagatcaa gaccatcctg  25320
```

```
gctaacacgg tgaaaccccg cctctacaaa aaatacaaaa aaattagctg ggcgtggtag  25380
cgggcgcctg tagtcccagc cccttgggaa gctgaggcag gagaatggcg tgaacccggg  25440
aggcggagct tgcagtgagc caatatcgcg ccactgcact ccagcctggg cgacagagcg  25500
agactccgtc tcaaaaaaaa aaaaaagaag aacatctaaa cttgctcctc ttatgatgaa  25560
ccacatagac ataactagtg ttaatggggg tcagtggaag tcatcatgtt ctgaaaatcc  25620
attaaatgta catcattcta gtgtttaggt taatgctgtt aaattcctgt tactttaaga  25680
aagggttggc cgggcatggt ggctcacgcc tgtaacccta accttgggga gacagagatg  25740
ggtggctcac ctgaggtcaa gagttcaaga ccagcctggg cagcatggta aaaccccatc  25800
tctgctaaaa ataaaaaaat tagctgggca tggtggcgca tgcctgtaat cccagctact  25860
ctggaggctg aggcatgaga attgcttgaa cccaggaggc agaggctgca gtgaaccgag  25920
atcatgccat tgcactccag cctgggcaac agagcgagac tccgtctcaa aaaaaaagaa  25980
aaagagaaag aaaaggtttg gcattgcaac tatttctctt gaactgagtg acccagaatc  26040
agttgtcctt tgaattttag tatagtagca tagtctgagc tcagaagggc cttatgatag  26100
accctgtatg ttctgggagg caagaattga gttggtatta atatcttaat gcttttgttt  26160
tactgctgaa taacagatga cccttcaggt cttttcatgt tttcctttt catgtctccc  26220
tgcctaggat cctaggtgcc taattgccta cttaaactag tttagggaat cttggactga  26280
agccaaaaca tgtaaaatgc cctgaaggtt aggcaaaggg aagaagttgg gtagtatgaa  26340
agattaggtc acatcttgtt tatctcttga gttctataaa ttgagaatgt aaatttaata  26400
ctatgtctat ttttaaaatg tattttattg ccatgaaaaa gtagcatgag acattggaat  26460
atggaatatc agcttcttca tttgggtcat ggggatcatg cttgaagacc taatgctctc  26520
tctaggtcta tctcagcatt gagcccctgg atgctgttgc gtggcttaga tgacttatac  26580
atgctttgtg gcatgattca tactaccttc taccttctgt gataccccttg ggtagttata  26640
ataggaccca ggttagagtg cttcttggtg gagccactgt agaactggga tttagatgca  26700
gccagggctg atgctcagct ggtgaacact ggtgtgcttg ttcctactgg tgatttacaa  26760
ccagtgtttc ttctttttgg gcctgcatcc attttgattg ggtggtgtcc atgctgtatc  26820
tgtaataaaa tatttttgaa tgttaccgct ggatgcagcg tgagaaagat acctcctgaa  26880
acttactgta agaaatttac agtgcattga tttttctgat atataggaat cgtcatgttg  26940
accttggaat tcttaagttc cctggctgta ggaaatggaa atttttgtag tatgtcacca  27000
ttgttagctt atttggtatt gcggattttc cctgttgcag gactgggtga aagcttttc  27060
tgcagcagtc atgttgaaaa ccttgtgttg actttcctcg tgttctgaaa tgggagcata  27120
aaagtttact ccgccacttc gtcttaaaat agcaaaactt tgctgttttc tgcagatcta  27180
ggaccttgtt acagaactct gccaaaaaaa aaatgtttac agaagaatgt gctgtgatta  27240
gagaagaata tgctggtgtg tagatttcaa actctctgga caatatgaat aacactgtct  27300
ttgtttctac agtgggagcc aagaagaaag gtttgctccc gggtggaaca gggattatcc  27360
tcctcctccc cttaagagtc atgctcaaga gagacactct ggcaactttc ctggcagaga  27420
ttcacttccc tttgatttcc aggggcattc ggggcctcct tttgcaaatg tagaggagca  27480
ttctttcagc tatggagcta gagacggacc gcatggtgac tatcgaggag gggagggacc  27540
tggacatgat ttcagggggg gagatttttc gtcttctgat ttccagagca gagattcatc  27600
acagttggac ttcaggggta gggacataca ttctggggat tttcgggata gagaaggacc  27660
```

-continued

```
acctatggac tatagggggtg gagatggtac ttctatggat tatagaggta gggaggcacc  27720
tcatatgaac tacagagaca gggatgctca cgctgttgac ttcagaggta gggatgctcc  27780
tccatctgac ttcaggggcc ggggcactta tgatttagat tttagaggcc gggatggatc  27840
ccatgcagat tttaggggaa gggatttatc agatttggat tttagggcca gagaacagtc  27900
ccgttctgat tttaggaata gagatgtatc tgatttggac tttagagaca aagacggaac  27960
acaagtagac tttagaggcc gaggttcagg tactactgat ctagacttta gggacaggga  28020
tacgccacat tcagatttca gaggtagaca ccgatctagg actgatcagg attttagggg  28080
cagagagatg ggatcttgta tggaatttaa agatagggag atgccccctg tggatccaaa  28140
tattttggat tacattcagc cctctacaca agatagagaa cattctggta tgaatgtgaa  28200
caggagagaa gaatccacac atgaccatac gatagaaagg cctgcttttg gcattcagaa  28260
gggagaattt gagcattcag aaacaagaga aggagaaaca caaggtgtag cctttgaaca  28320
tgagtctcca gcagactttc agaacagcca aagtccagtt caagaccaag ataagtcaca  28380
gctttctgga cgtgaagagc agagttcaga tgctggtctg tttaaagaag aaggcggtct  28440
ggactttctt gggcggcaag acaccgatta cagaagcatg gagtaccgtg atgtggatca  28500
taggctgcca ggaagccaga tgtttggcta tggccagagc aagtcttttc cagagggcaa  28560
aactgcccga gatgcccaac gggaccttca ggtatgttga tggggtggat tgcttttttt  28620
tttttttttt tttttttttt tgagacggag tctcgctctg ttgcccagcc tggagtgcag  28680
tggtgcgatc tctgctcatg caagctccgc ctcctgggtt catgccattc tcctgcctca  28740
gcctcctgag tagctgggac tgactacagg cgcccaccac cacgcctggt gtgagccacc  28800
gcgcccggcc tgcttttttt ttttttcttt aaataagact tttgtgaagg atgacattta  28860
tttatttatt tatttattta tttttgaaac ggagtcttgc tctgtcaccc aggctagagt  28920
gcagtgacat aatctcagct cactgcaacc tccgcctccc agggtcaagc aattttcctg  28980
cctcaacctc ctgagtagca gggattgcag gcatgtgcca ccatgcccag ttaatttttg  29040
tatttttagt gcagatgggg tttcaccatg ttggccaggc tggtctcgaa ctcctgacct  29100
cgtgatccgc ccacctcggc ctcccaaagt gctggaatta caggcatgag ccaccgtgcc  29160
tggccagttt tttttttttt ttttcatttt atttttatct ttgcataacc attagaaagc  29220
aaaatttgta ttcaggagtg gaatgtagga atgtaaatct ctagagaaaa ggtcctcagc  29280
tcagatcata tatatgtgtg tgtgtgtgta tatatatata tgaatatata tgtatatata  29340
tgaatatata tttatatata tatatttctt ttttctttta ttcttttctt cctgcttcac  29400
tttccatttg tgtatatatg tgtgtgtata tatgaaggaa ctatatatat atatatttga  29460
gacacggtct tgctctgtca ctcgggctga agtgcggtgg tgtaattatg gctccttgca  29520
gccttgacct cccaggctca agcgatcctc ccacctcagc cttctgagta gctggaacta  29580
cagatgtgcg ccagccacta tgcctggcta gttttttttt ttttcctttg agaatgagtc  29640
ttgctctgtc gctcaggctg aagtgcagtt gtgcgatctc agctcactgc aacctctacc  29700
tcctgggttc aaggggttcc cccgcctcag ccttccagga agctgggact acaggtatat  29760
ttcaccattc ctagttagtt gtgttttttt ttttcttttt tgagatggag cctcaccgtg  29820
ttgcctaggc tggagtgcag tggcacgatc ttggctcaca gcaacctccg cctcccgtgt  29880
tcaagcagtc ttcctgcctc agcctcctga gtagttggga ctgtagttgt gcaccaccaa  29940
atctgactaa tttttgtatt ttttgtagag atgaagttta ggcatgttac ctaggctggg  30000
ctggaacccc tgatctcaaa tgatccaccc ttctcagctt cccaaagagc tgggatttca  30060
```

```
ggcatgcacc accatgcctg gccagcaatt tttgtatttt tttgtagaca gaaggttgca  30120
acatatttcc caggctggtt tcaaattcct gggttcaagc agtcccccca ccttagcttc  30180
ccaaagtgct gggattacag caatgagcca ctgcccctac ccttttgatg tgtgtttatt  30240
cattattttg ttttatgatg ctgatttaca tgccttggga taatttagtt tgaaagtata  30300
tgtctttggg agttgactct tgcaactctc gcttagttag acctgtgatt gtttagggat  30360
cattttctta tttaaattca ttgagagaat acttaggagt ctccctagtt gtgaagagct  30420
gatattaatg ttgcaactat cctcttgcag ctaacgtaat taacttaaat gttaaacttc  30480
ttgaatatat gatttaagca aggagggtta tatttgtaat tttacaatga aggtattctc  30540
ttttaaagta gatttggctg ggtacagtgg cctatgcttg taatttcagt gctttaggag  30600
gctgaggtgg gaggatcact tgaggccagg aacttgagac cagtgtggtg caacctcagg  30660
agagaatgtg agggtgggga agaaaaataa ggccaggcac agtggctcat gcctgtaatc  30720
ccaacacttt gggaggcaaa ggtgggcaga tcatttgagg tcaggatttc aagaccagcc  30780
tggtcaacat ggtgaaaccc catctctact aaaaataaca aaaattaggc caggcgtggt  30840
ggttcttgcc tgtaatccca acactttggg aagctgaggc aggtggatca tttgaggtcg  30900
tgggtttgag accagcctga ccaacacgga gaaaccccat ttctactaaa aatacaaaat  30960
tagctgggcg tagtgatgca tgtgtgtaat cccagctact cgggaggctg aggcaggaga  31020
atcccttgaa cctgggaggc agaggttgcg gggaggcaga ggttgcacta ttacactcca  31080
gcctgggcag caagagcgaa actccatctg aaaaaaaaaa aaaaaacgaa aaccaaaacc  31140
agccaggtgt ggaggtgggc gcctgtaatc ccaactactt gggaggctga ggcaggagaa  31200
ttgcttgaac ctgggggcg gaggctgcag tgggctgaga ttgtgccact gcactccagc  31260
ctgggcgaca gagcgacact ctgtctcaaa aaaaaaaaga cattatctag tcatcttctc  31320
tcaccagagg tatgaagtac tgctagttta cagcccattc tccagctctc agaccaggga  31380
aatttttctt ttttttgag acgggggtct cgctctgtca cccaggctgg agtgcagtgg  31440
cacaatcttg gctcactgaa acctctgcct cccaggttca agtgattctt ccgcctcagc  31500
ctcctgagta gctgggacca caggcgtgca cagcacagtt ggctaatttt tgtattttta  31560
gtagagacgg ttttaccatg ttggctaggc tgagaaaatt actgttttga gactatgtta  31620
gtgtgtcttt ctggttatta aagtcttact cagtcttgtc tctcgtaatg ttttgcttta  31680
ctttgaagac tctttcagtg agacttggtc ttagcacatt tacattctta tgatttgaag  31740
tcacattctg gcactcagaa caatagagaa aattgtaatt ttttatatct tcacgtgaca  31800
tgtcattatc atttttgatc ctgagtggct aaatttcatg ttgatttgtg ttttgtgcag  31860
taaagtatat ttgtgaaata atttttcatt ctcaatttaa ggatcaagat tataggaccg  31920
gcccaagtga ggagaaaccc agcaggctta ttcgattaag tggggtacct gaagatgcca  31980
caaaagaaga ggtaaggcat gtcttctctc ctgtttctct gtgtcaatta aaaattaaaa  32040
aaacctttta atttgaaaaa ttgtagattc acaagaaggt gcaaagaaat gcacagagaa  32100
gtcttgtgta ttttttccc atcttccctc agtgttaata ttttgcacaa ctgtggtata  32160
gtatctaaac caggaaattg accctggtat aatacataaa gtttattcag atttcaccat  32220
ttatacatgc actcactgag gtgaggttaa aaaaaattat gacaaatgat tgctctcttt  32280
agacctgatc acatccttta gagcatatta tttctggagt atgtacataa ggatgcagtt  32340
tatttacaat agtaaaaact agaaactgcc taactgccct gtatcaaagg attggctgac  32400
```

-continued taaattaagt ctgaacttat ggcagtgctc gctctgtgcc aggcattgtg tgatacttac 32460
aagcattagt tcatttaatt atcacatatt taatataatc actctaaata ttaagcatta 32520
ctgtatgtaa ttgttctaga tactgagtga cacagcagtg tatattatca agtcactgcc 32580
tccatggata atgaaaaagc aagcaaaagg attacacaat tttagtcagc aaataaatac 32640
tctgaagaaa actaaagtac aggcggggca tggtagctcg gcctgtaact cggagacaga 32700
gtcttgcttt gtcgcccagg ctggagtgtg tggcgcgacc ttggtgcact gcaacctcca 32760
cctccccagt tcaagcagtt ctcctgccgc agcctcccga gtagctggga ctacaggcac 32820
acaccaccac gcccagctaa tttttgtact tttagtagag acggagtttc accacattgg 32880
tcaggctggt cttgaactcc tgacctcagg ttatctccct gcttctgcct cccaaagtac 32940
tgccattaca ggcatgagcc accaagccca gcccattttt gattttttg aggcagcgtc 33000 tcactttgtt gcccaggctg gagtgcagtg gcacaatcac ggctcactgc agcttctacc 33060
tcttgggctc aatcgatcct accacctcag cctcctgagt agctgggacc acgggcatgc 33120
atgctaatgg ggctgttttt tgtattgtgt agttagggag acatcactga ggaagaggca 33180
ttcgagccca ggcttgaatg ccgtgagaga acagtttata tgaatatggg gaaatgaact 33240
gcccaggcag ttcatgctga ggaagtgctg tggccctgga ctgtaatgaa cccagtacat 33300
cattttatat ttaacacatg agaaactgga cactaaaagg ttacacagca agtgagcaga 33360
gagcttggaa tgcacacagt atgatttcag agcttaagcc tttgaaggtt atgctcttct 33420
gcttttcttt tttttttttt ttttttgaga cagagtctca ctctgtcacc caggctggag 33480
tgcagtggcg cgatctcggc tcactgcaac ctctgccgcc agggttcaag agattctcct 33540
gcctcagcct cccaagtagc tgggattaca agcacctgcc actgcaccca gctgattttt 33600
gtatttttag tagagatggg gtttcaccat cttggtcagg ctgatcttga actcctgacc 33660
tcaagtgatc cacccgcctc ggcctctcaa agtgctgaga ttacacgcat gagccaccgc 33720
gcccagcatt ttgtttgttt gtttgtttgt ttgtttttga gacagagtct tgctctgtca 33780
cccaggctgg agtgcagtgg cacaatcttg ggtcactgca acctccgcct ctcgggttca 33840
aatggttctc ctgcctcagc ctcctgagta gctgggacta caggcatgtg ccaccacgcc 33900
cggctaagtt tttgtatttt tagtagagac ggggtttcac cgtgttagct aggatggtct 33960
cgatcccctg acgtcatgat ccgcctgtct cggcctccca aagtgctagg attacagatg 34020
tgagccaccg cttctggccc tgcttttcct atgtacctga gaatttttaa atatttattt 34080
atttattttt gagacagggt actccagact ggagtgcaat ggcccaatca aggctcacta 34140
cagcctcaaa ctcctgggct caaactatcc tcccgagtag ctgggattat aggtgtgagc 34200
cagtactcct ggctaatttt tttttttttt ttgagatgga gtctcgctct gttgcccagg 34260
ctggaatgca gtggtgcgat cttggctcac tgcaagctcc ttctcccggg ttcacgccat 34320
tcttctgcct cagcctccca agtagctggg actacaggtg cccgccacca cgcctggcta 34380
atttcttgta ttttttagta gaaacggggt tttaccgtgt tagccaggat ggtctcaatc 34440
tcctgacctt gtgatctgcc cacctcggcc tcccaaagtg ctgggattac aggcgtgagc 34500
caccgtgccc ggccaatttt tttttttttt tttttttttt tttttaaag atagtgtctc 34560 gctctgttgc ccaggctgga gtgcagtgtc atgatctcag ctcactgcag cctcagcctt 34620
ccaggttcaa gtgattctcc tgcctcagcc ttccaagtag ctgggattac aggtgtgtgc 34680
caccacacca ggctaatttt tgtattttta gtagaaatgg ggtttcacca tgttagccag 34740
gctggtctcg aactcctgac ctcaggttat ccacccgcct tggattccca aagtgctggg 34800

-continued attacatgtg tgagccacca cgcccggtct ctcctggcta attaagaatt tttttttttt 34860
ttttagagat agggtctcac tatgttgccc aggcttgtct caaacatgtg gctttaagca 34920
atcctctcac cttggcctcc caaagtgctg ggattatagg caggagccac tgcatcccac 34980
caatttttga ataattatgt tctactcatt caatatgtga atgccttgag tgttcatagt 35040
ttaactttgc ttttccaaag taatcatggc tttaaattat gtatgataaa aactgttagg 35100
gaaaatctga tattcagtgt ttgattatga tttgtatcat ttgtataaat gccatatttt 35160
tgcagattct taatgctttt cggactcctg atggcatgcc tgtaaagaac ttgcagttga 35220
aggagtataa cacaggtgag tttcttgact tgcatatggc cttgggttag gaagggtctt 35280
tgtcagatct ctgcatcatg tgctacttaa aatttgtttc aagaaaccac aattaaaatt 35340
tccagaagcc tcccgttggt gcctccaaat aacaaccagc tttagtttta gctgtggttc 35400
tttgtggatg tttgtccaca catgggtgat gaggatgcat gttccagttc ttctgaatgc 35460
ctgtgatata tagagtgttg cagcaattgc cttgaatata ttttatataa ttattaaact 35520
tgctatgcat gttcttcatg gtggtggaat gtttatgctt gagcctaata ggatttaata 35580
agcttgttgt atgtaaaatt ttacattcat tgcttcagta aaatttatga cttcccagag 35640
aaattgtaca aattagtggt ttaattttca gttttgcttt gagaatggag tcctgttaca 35700
gttattttgt tgaaatccat gaatagaccc agaagagctt tccctttgac atctgttctg 35760
tggtctgaat ggtagattaa acttttcaga atatcctcct agttgtattt cacagtacca 35820
atttcagtca tttcctttaa atcttactac agtaaaagta ggcaaaggtg aaatgccaag 35880
aactcaaggt tttgaccaa tatttttaga actatgtata ataataagtt tatttattta 35940
aaaataaagg taatctttag gtgacctatt ttgcagaatt ttaaatggaa gggaatagag 36000
catgagtctt cacagaactt agaatttcag taattcagtt aaagacatct tcaagtaaga 36060
acatgtcata ttttgaggat ataatttact attagcagtt tatcatggga taaaaatttt 36120
gcattaacta gataacttct tcagaatgct tctgcagagg aaaattatcc acaaaataaa 36180
ttttggtgct tgaaagaata tggtgttaag ttcagaaata atttgttctg taatttgaga 36240
acaagctcag aagtattatt tctcagagag ccaattattt atttgtttta aaaacatcaa 36300
ccctgaattt gtggaagcat gagtaagagt agatatatta ttattcttgg tatctcactt 36360
atgttggtta tatttatttt ttgcatatgc cttatacatg ctttctttgg gaactcaagg 36420
tagaatttac aggctggaga tgctttttaa ctctcaggat aataacctca gtctggtttc 36480
atgaactgtg ctttcattaa gtattgatat gtttaggaaa ggagatgtct taatatttaa 36540
atagcagttc aaactccagt ttctttagta ttcattgact ttctaattgt caaatttgtc 36600
aggacagtaa aaattgtatt aacatatagt gtctagagag gaagttctta aatttgccga 36660
ttgtggtagc tgttagaatt ggcagactga agacattgat acacatggga aatcattcag 36720
ggcagtgctt aaaaataaaa cgaaaaatac ctttcagcaa atacaatctt ttcttggcat 36780
tctgttaagt tgtgtttttt atttttgttt tttagtgaaa gaattggatt gctagtttca 36840
tgttatttat attacatctc tatgtgacaa ataggatgaa cttttgacaa tatcagccag 36900
atcatgttac tcccatgtct aaaaccctct tagggccttc atcttcactt ggaagaaatt 36960
cccagcttct tcttttgtct tacaaaccca tgcgtgagct gacccttggc tgtttgatct 37020
cattcagtac tgccctccac ctaccctatt ttgctgtagc cacactgagc ttttctcttg 37080
tctttgacca atacaaactt ctttctgtgt cagggtcttt gcactactct tctctctgat 37140

-continued

```
ctttacttgt cttctggggt ttagttcttg gcttcagttt cacgtctctg aggccttgtg  37200
tcactctcaa atctaaaatc atcgggcagt tgttttccat catatccttg tttggatcta  37260
tcactgattg gatatttcta tcactggtat ttttcagttg gatctatcac tgatctatca  37320
ctggtcactg attggattga atctgtcagt ggtattggat ctatcactga tatttttctc  37380
cgtggttttg tgtatcttat ttctctcact agagaggaat gtcagcagga gccttattcc  37440
ttcttgtttc caccagtgct tgacactcgg taggttccct atatgcatgg aatagattat  37500
tatttatggt gtatgtgaag agcagctgtg atttcccctc aggtgaggaa cataaaaggg  37560
tagtgtaggt ttcacagcag tgcagcttag gtcttacata tctgttgaag aatatgtctt  37620
ggaacaatca gatgttctaa gaactatagt gtttactgtt aaaagatcat atgtggtagt  37680
caggcatggt gttgcacacc tgtagtccta gctacttggg agtctgagat gggagaattt  37740
tttgagcctg agaatttgag atcagcctga gcaacatagc aagaccttgt ctcttaaaaa  37800
gaaaaagaaa aaaaaatgtg aatcttagta gtaacagtga cttaaaaatt tttttttata  37860
agagaaaggg tcttactctg ttgcccaggt tggagtgcat tggtacgatc atagcttact  37920
gtaacctcaa acccctcggc tcaagtgatc cttctgtctc aacctccaga gtatttggga  37980
ctacaggtgc gtaccaccat ggcaggctaa tttttaaact ttttgtagag gcgcggtctc  38040
actatgtttc ccaggctggt cttgaactcc tgggttcaag tgattctcct gcctcatcct  38100
cccacagtgc tgggattaca gatgtgaacc agtatgcaca gacaaaaagg tgacattcat  38160
aggtgaaaac tggtaataaa tattttaggc tgagtgatga cctgcagaga ccatgcagga  38220
tggatattgc tcataagagg ggaattgtgg agtacagtct gtcctgttag ttgatgtaat  38280
ggagggctga tctataacac aggagagaag attaacgcct cttcgttgac tctagtaatg  38340
tattagtgta atttttgtct cctctagagc tgtataagta cagggtcaca attttatcta  38400
gaacctgtga ggttaaatga gcttatgaat ttttcaagtt atagaaatgt agtttacata  38460
gatcatatgg gaattatatc tcccagggga atgtgtactc agacataata cttacgctgc  38520
aaaattatta atattctcac taacaggagt aaataaagtc tcacagtata ggccaggatt  38580
tgcctcaaaa tgagtttgtt gaattttacc aaaaaacttg acatttatgg gatttttggaa  38640
ttgtagataa gagattttgg acctatatat gttgtgtata tttgaatttt tcatttgcca  38700
tttacaaata cattataacc ccatgaattg taaattatct tgaattatat gattatttct  38760
ggaaaaagta ccaggagtaa aatgtctttt ggtgactaga caaactctag tatatatata  38820
aaatggaata cttctcagca atgaagaaga aactactcat gcacctaaca acatggatga  38880
atctcaatgg caatatgctg agtgaaagaa actagactca taaggatata tacactacca  38940
taaggaggaa tgaaatactg atgtatgcta caagttggat gaaccttgaa aacattataa  39000
aagaagccag acacaaaaga ccaaatattg tgcaattcag tttatatgaa atatctagag  39060
aaggcacacc cgtagagata gaaagcagat tggtggttgc caggggctaa gcgggaatgg  39120
ggaacgactc cctaatggtt atggtacttc ttttgggctg atagaagtgt tctggaacta  39180
ggtagtagtg atggttgcat gacattgtga atgtacttaa tgctcctgaa ttgtacactt  39240
taaaatgatg cattttattt gatgtgtatt tgcttacttt gttttttttt ttttttttg  39300
agatgaaatc ttgctcccgt tgtgtaggca ggagtgcagt ggcatgacct cggctcactg  39360
caacctccat ctcccgggtt caaacgattc tccttcctca gcctcccaag taactgggat  39420
tacaggtgtg tgccaccaca cctggctaat tttttgtatt tttagtagag acggggtttc  39480
gccatgttgg ccaggctggt cttgaactcc cgacctcagg ttatctacct gcctgggcct  39540
```

-continued cccaaagagc tagcattaca ggagtgagcc actgtgccca gccagcttac aatttttaa 39600 aaaggctaca tactatatgt gtatgtgtga tttcacttat gtgacattct ggaagggaca 39660 aaatttagg gattggaaat agtggtggcc agggtattgg gggaggagtt aactataaag 39720
cggaagcatg agggaatttt tgggtataat ggaattgttc tatatcttga ttgtggtgat 39780
gatgtatcaa tgttaaattc cccgagttga taactactgt ggttatgtta gagaacatct 39840
tttttctttt cttttttttt ttaaacggag tctcgtttgg tcacccaagc tggagcgtaa 39900
tggcgcgatc tcagcttact gcaacctctg cctcctggat tcaagcaatt ctgcctgcct 39960
taacttcctg agtagctggg attacaggcg cctgccccta ctcctagcta atttttgtat 40020 ttttttagt agcgacaggg ttgcgccatg ttgaccaggc tggtcttgaa cacctgacct 40080
caggtgatct gcccaccttg gcctcccaaa gtgctggaat tacagacgtg agccaccatg 40140
cccggctgag agtatcttta ttcttagaaa atacataatg aagtttttag aagtaaagta 40200
ctgtgatgta tgcagctttc tctcatggtt tcgaaaataa tacttgctat aaatggagaa 40260
ggaaggaaga gagtattgat aaagtagatg gatcacaatg ttattaatag ttgaatctgg 40320
ggccacacgc ggtggctcac gcctgtaatc ccagcacttt gggaggccaa ggcaggtaga 40380
tcatctgagg tcaggagttt gagaccagcc tggccaacat ggcgaacgaa acctgtctac 40440
taaaaaatac aaaaattagc cgggcgtggt ggcgggtgcc tgtaatccca gctactcggg 40500
aggctaaggc aggagaatca cttgaactcg ggaggcggag gttgcagtga gccaagatca 40560
cgccattgca ctccagcctg ggcgacagag caagaattca tcttaaaaaa aaaaaaaaaa 40620
aaagttgaac ctgggtaaag catatatgaa tcttttccct gtactattat tattgcaatt 40680
tttttgtaac ttggaaatta tttccaataa aaagttgaaa aactgacaaa actgatttat 40740
tttattttat tttttatttt tttgagacgg agtcttgcac tgtcaccagt gctggagtgc 40800
agtggcgcga tatcggctca ctgcaacctc cgcctcctgg gttcaagcga ttctcctgcc 40860
tcagccatcg gagtagctgg gattataggc gcctgccacc atgcccagct aatttttgt 40920 atttttagt agagacgggg tttcaccatg ttggccagcc tggtctcaaa ctgacctcat 40980
gattcgtcca cctctgcctc ccaaagtgct gggattacag gcatgagcca ctgcgtccgg 41040
cctatatttt atctttaaat gatcagcaga aaccttgtaa gctgaagact gcaatcaaca 41100
gcttatgtca agtaaactat agagcagtgg ttctcagagt ggatcctgga ccatcatcat 41160
ctctttaccc cttgggaact tgttggaatc caaattctta agccccatcc taaacctact 41220
gaatcagaaa ctctggggtg gggcccagta gcctgtgctt ttaagaagtc ctccagatat 41280
ttttaatgta ccctgaggac cactggcagt agataaagtg tttgtttaga ttctttattc 41340
tagaactttt gtatagttta aaagtgactt aataataagc aagtggacct tttgtaagta 41400
gacaaagcta atgcttatgt gctttaggag ccagtgctga tcacatgcct tgcctaccta 41460
atatcagttc tcctgctctg catagcagga gaaggagctg gagtagtgtt ggtactatct 41520
tatgacttta gttatatgta actaaggaca tataacttag ttgttttttc tgtttatata 41580
tagtatactt cctccagaga tcttggaatg gttgtagatc ttctcattca cacagtgttt 41640
ctgtgacata tgaatgcagg cagaattgct tttgattttt aggtttgttt gcatactacg 41700
tagtatataa gcttgctgtg atattttttcc aaaagggatt tatatcattt aagcaaaaat 41760
gatacagctt ctggattatg tttcctaata aggctcaaac atagaaagta attatagtaa 41820
ctgaagtgct acagaattac tttagtactg gtttattaac taatgtcaca aagttagagg 41880

-continued attactaagg tggtgttagt aggaagaagc aatatcttgc tttagcccgt cagtgttcat 41940
gtggtgaatg gacagtctct gtattcttgg gaaggaaaat tcttcttgga aagtgagtat 42000
ttgcaatgac taggtcagtc acttggtctg ttgcctggca ttttgggtct actgaaagtg 42060
acgttgtagc aaaggccctg taccttctgc atttcttttc ttttcttttt tttttttttt 42120
tttttttttt tttggtagaa acaaggtctt gctttgttgc ccaggctgcc cttgacctcc 42180
tgtcaagcag tcctcccacc ttagcttcct gagtagctgg gactacaggc gtgtgccacc 42240
atgcctggtt aatgtaaatt tgtttggttt ttttgagaca gagtttcact cttgttgccc 42300
aggttggagt gcagtgacgt gatctcagct cactacagtc tctgcctcct gggttcaagc 42360
gattctcctg cctcagtctc ccaagtagct gggcttacag gcacccgcca ccacgcccag 42420
ctaatttttt gtattttttt agtagagacg gggtttcatc atgttggcca ggctggtctt 42480
gaactcccga gctcaggtga tccacccacc tcggcctccc aaagtgctgg gattacaggt 42540
gtgagccacc gtgtctggcc tatttttaaa ttttttttga gacagagtct ctctcagtca 42600
cccaggctgg agtgcagtgg tgcaatctca gctcactgca gtctctgcct cctgagttca 42660
attctcctgc ctcagcctcc ctagtagctg ggattacagg cctgccatcg tgcccagcta 42720
atttttgtat ttttagtaga gacagggttt caccatgttg gccaggctgg tttcaatctc 42780
ctgacttcaa gcaatccacc tgcctcggcc tcccaaagtg ctgggattac aggcatgaac 42840
caccacgcct ggcctaaatt tttttttgt agagacaggg tctcacgctg ttgctcaggc 42900
tggtcttaca ctccaaggct caagcaatcc tcctgccttg gactcccaaa atgctgagat 42960
tacaagtgta agacactgag gccagctgcc ctttacattt cttaagggta acaggctcat 43020
gtcctttcat tattcacaat ttaaatattt tgagtcttta cttctgtgtc aatataacag 43080
aagtaacttc cttacgaaga aaattccaga gggaatcttt caatgtaggg atagaaatcc 43140
attgtgaaac tcgagaattg acactgatga tataaaacat gcacagtagc cgagtgtggt 43200
gatgtgtgcg tgtagtctta gctactcaac agtccgagac atgagctcag gagtttgtga 43260
ccagcatggg caatatagtg agactctgtc tcaaaaaaag gaaaaaaaaa agtgcatagt 43320
ttatggtatc ccaactggag gagctaaaga cagaatagct taacatcatt tagaaaaaaa 43380
attataattg aaaagtgcaa atacacattt tgcagtgttt ttggcattta caaaatatgt 43440
aaacactttt agtttcttag ggaaaagatg acgataggct gattgaaaaa tatcattttt 43500
acttgtcaca tctctaaaac agcagaagtt cttgttttta accaggagtc ctatcaggtt 43560
tgatacaacc ttcggggagg atgtggcagt tgaaatttaa ggaaacttag tttccttaag 43620
gtggctgagc ttaaaaaatc aaaatgttta ggaaggcagg agacactaat agggctgggc 43680
tagtcttgtg gaggcagtgg atggacgctt tggctggcct agggaagaat ctgtgattca 43740
gtgctgcagg gatcaggtga tcctggtgag agaggtcctg gaacaagggt taatttggtc 43800
atttttggaa tgacctggga tttggcttat ttattttatt tttaaaattt cccgctgggc 43860
acagtggctc aaacctgtaa ttccagcact ttggaacgcc aaggccagtg gatcactcga 43920
gctcaggagt tcgagaccac cctgggcaac atggtgaaac tctatctctc caaaaaaaat 43980
acaaaaaaaa ttagctggat gtggtggtgc atgcttgtag tcccagctac ttaggaggct 44040
aaagcaggaa gatcacttga gctagggagg tgagggtgga ggttgcagtg agccaagatc 44100
atgccactgc actccagcat gggcaacaga gagagacctt gtctcaaaaa aataaaatgg 44160
tgaatgtaaa ataaaatggt agctcacgcc tataatcctg gtactttggg aggccgagat 44220
gggtggatca cttgaggcca ggagttacag accagcctgg tcaatatggc aaaactccca 44280
tctctactaa aaatacaaaa actagctggg ctggtggtgt atgcctataa tcccagttac 44340
tcaggaggct gaggcagagg tcacagtgag ctgagatcac accactgcac tccaggctgg 44400
atgacagagt gagaccctgt ctaacgtgac atcacatcac atcacatcac atcacatcgc 44460
atcgcatcgc atcgcatcgc atcgcatcgc atcgcatcgc atcgcattgc atcacatcac 44520
atcacaacat aacataaatt ttcaaggcag aaatcttgta gtcagcctta ctgtttgttg 44580
acaaggacac ggccctgagc acagaaatct cggcagttga taaagccaag aagaaggata 44640
ctaattaaag aaattttcag attttgcatc ttctggcatc tcagctaaat agctctgagg 44700
aggaggatgc cacttaccag ttttgagaca caggcaggtt atattatttt cctgaaaacc 44760
atttagctga gatggaattt gcctctctga ggttggggaa ggtgtttgaa ctctgtttac 44820
agccctctgt cagttccact gccttgctga gttccctcac ccttctttag atagaattgc 44880
tgttggcttc tatagtcctc acttacctct tttgccaaat gctcaggtag ccttggctga 44940
gtcttccagg tttgataagg ctgtatgggg cttcctatgc cttttggtag ttagaagtca 45000
ctgaagaggt acttctgcta cagtgacaag aagaaaaggg cattactcag cttgtatagt 45060
gcaagggctg cttgactccc agcttcagtc taggcagggg aatttattta tacaattacc 45120
ttaaatgagc accagataga ggccatctat aaaaactgtt tacaggattt aaaaatacgt 45180
tgacattggc ttcttccttt aactttctgc ttgcaacaga acatctgatg cgacctatgc 45240
tgctcactgt ttctaggtta cattctctac ccttgcagtg taaattaatt tttgcctggt 45300
tccatgtttc ttgcttaggt tatctcttag gtcttttgtc tgatttaaat ataagccttc 45360
ttaggactag atagtggtga tggttgcact actttgtcaa tataccactg aattgtatgt 45420
attcactctt ttaagaatga gtttattttt atttttattt ttattttgag atagagcctc 45480
actctgtcgc ccaggctgga gtgcagtggc gtgatctcag ctcactgcaa cctccacctc 45540
ccgggttcac gccattctcc tgcctcagcc tcccgagtag ctgggactac aggcgcctgc 45600
caccacgccc ggctaatttt ttgtattttt agcagagacg gggtttcact gtgttagcca 45660
ggatggtctc gatctcctga ccttgtgatc cgcccacctc ggcctcccaa agtgctgggt 45720
ttacaggcgt gagccaccat gcctggcctt aagaatgagt tgattgttct tagtctcagt 45780
tgagtacatt gtgttatgta tagaaaatgt tatattttca tttttaaaaa ttattattat 45840
tattttgaga tggggtctca ctttgtcacc caggctggag tgcagtggca cggtcttggt 45900
tcactggcaa cctccacctc ccaggtacaa gtgattcttc tgcatcagcc tcctgaatag 45960
cgggaattac aggcgcctgc caccaagcct aagtaatttt tgtatttttt tttttagta 46020
gagacggggt ttcaccatgt tagccaggct gatcttaaac tcctgacctc aagtgatcca 46080
ttcgtctcag actcccaaag tgctgggatt acagatgtga gccattgcgc ccagcccatt 46140
ttaaaaaatt aaactggcct ggtgcggtgg ctcacgcgtg tgatcccagc actttgggag 46200
gccgaggcaa gcggatcatg aggtcaggag attgagacca tcctggctaa catggtgaaa 46260
ccccatctgt actaaaaaat acaaaaaatt agccgggcat ggtggcgggc tcctgtagtc 46320
ccagctaatt gggaggctga gacaggagaa tggcatgaac ccgggaggca gagcttgcag 46380
tgagccgaga tagcgccaat gcactccagc ctgggcaaca gagcaagact ccgtctcaaa 46440
aaaaaaaaaa aacaaaacaa aaaaaaacca aaacattaaa ccatactctc taactgtgaa 46500
gaagttgtga tttattcttt agtgttacct gccattcttt ttgtctcttt ctctctcttc 46560
tcttctcctc tcttctcttc tctcttcttc cctcccttcc cctcccctcc cctccccttc 46620

-continued

```
tcttttcttc tcttctcttt tcttttcttt cagagttttg ctctgttgcc caggatggag  46680
tgcattggca tgctcacggc tcactgcagt gtcaacctcc caggttcaag ctgtcctcct  46740
acctcaccct ccctagtagc tgggactata gacatgcacc accatgccta attattttgt  46800
attttttgta gagacgaggt tttgccatgt tgcccaggct ggtcttgaac tcctgagctc  46860
aagtgagcta cctgcctcag cctcccaaaa tgctgtgatt acaggtgtga gccttatttt  46920
attatttttt tttgggacag agtctctctc tgtcctccag gctggagtgc agtggcacga  46980
tcttggctca ctgcaacctc tgcttctcgg gttcaagcaa ttctcctgcc tcagcctccc  47040
aagtagcctc ccaaagtgct gggattacag gcatgagcca ccatgccagg cctctgatgc  47100
atatattttt taaaaatagt attttccacc ttacagtgta tttaagagtt tgtaaatttc  47160
ctttttgtt ttctttttgg aacagtgttg ctctgttgcc caggctggag tgcagtgaca  47220
tgatcttggc tcattgcaac ctccacctcc cagattcaag tgattctcct gcctcagctt  47280
cccgagtagc tgggattaca ggtgcccgcc actacgccca gctaaatttt ttgtaatttt  47340
agtagagaca ggtttcacca tgttggccag gcaggtcttg atctcctgac ctcaagtgat  47400
ccgcccacct cgacctccca aagtcctggg attacggaca taagatactg tgcctggctg  47460
agtttgtaaa tttctttctt tcttttttct tttttttttg agacagagtc ttactctgtc  47520
acctgggcta gaatgcaata atgcgatctc tgctcactgc aacctctgcc tcctgggttc  47580
aaacaattcc cctgcctcag cctcctgagt agctgggatt acagccgcct gccactatgc  47640
ccagctaatt tttgtatttt ttgtagagat ggggttttgc cgtgtaggcc aggctggtct  47700
agaactcctg acttcaggtg atccacccac cttggcctcc caagcgtggg gattacaggt  47760
atgagccacc acgcccggtc atcaaagata atgtttttaa tgatcaggag cactttgaga  47820
tgtttagaac aatctgaaac ctgatttcca agccatctca aaatatactt tggtaatcaa  47880
gacagggaaa tgatggtgtt atatcatttg tgggactcaa ctgattttgt tgagtattga  47940
ttttgctgtg ggattccttg ttctcttggt tgtgttgggc ctactgcttt ttaaaaaagt  48000
attttgagac agggtcttac tctgttgctc aggctggagt gtagtggcgc agtctcttgt  48060
ctctgcaacc tcaatctcct gggctcaagg gatcctccca cctcagcctc ccaagtagct  48120
gggaccacag gtacccacca tcacacctgg ctaatttttg tattttttgt agacatgggg  48180
gtcactgtct tgcccaggca ggtcttgaac tcctaagctc aaacaaccgt cctgccttgc  48240
cctcccaaat tgctggaatt acaggtgtga gccagtgcgc ctggccttct tttttttttt  48300
taaccactat tttttagaac tagatttggc ctggaaagag aaaaaagata ttcctcgact  48360
tgatctatat attttatggt tcattcattt gctttagagg tagaaggagc aggaaaaagt  48420
acaacaaaac aaaatcttac ctttggtgtt taatttgaat gcccacagat gcttttgcat  48480
ttattagtag tgagttttca taattatcaa atatgtagta gaaaaatctg gctgtgcatg  48540
gtggctaatg cctgtaaatc cctatatgct gggaggctga ggcaggtgga ttttctgagc  48600
tcaggagttc aagaccagcc tgggcaacat ggcaaaaccc catctctgcc aaaaataagc  48660
tgggtgtggt ggcacacgcc tgtggtacca ggtactccgg aggctgagct gagaagattg  48720
tggaggtttc agtgagccaa gattgcacca ctgcactcca acctgggtga cagagtgaga  48780
ctccatctca aaaaaaagaa aaaaaaatct ccttgtccag gagctgtgtt gagtgggctg  48840
tggactagca ggaattcata gctctggtga aagatgacta gataatgtca tttttttttt  48900
aaaagtccct gaatgattgt gacagggtag gaaaatcatc acatagcaaa atcttcatta  48960
gattttccct aatgacttat caactgggtt tgtgcaccaa acgaaacaac ttcctgcctt  49020
```

tgtttgtctg aaagtcaaag aaaatattat tcaggtatat tatattgtac tccatgctac 49080
agaagtttct ggcagcaata taggttatat gccaatcggt taaataatat ttgtgggcca 49140
ggcccggtgg ctcatgcctg taatgccagc actttgggag gccgaggcgg gtggatcact 49200
tgaggtcagg agttcaagac cagccagggc aacatggtga aaccccatct ctactaataa 49260
aacaaaaatt agcctagtgt ggtggcacac gcctgtaatc ccagctactc aggaggctga 49320
ggtaggagaa tcgcttgaac ccggaaggtg gaggttgcag ctgagattgt gccattgcac 49380
tctagcctgg ggccacaaga gtgaaactgt ctcaaaataa ataaataaat aaataaaata 49440
ataataatat ttgtgtaagt acagggatat gtttcttcaa ctccaaagta tgagttaatg 49500
tgcatatgcc aactctagaa ataaagtatt aagtcaaaac tcccaagaaa atttccccaa 49560
aaagttgcta acagacgtta ttttatttta tttatttatt ttgatacaga gtctctccca 49620
ctgtcaccca ggctggagtg gtgcagtggc atcatctcga ttcactgtag cctccgcctc 49680
ccagattcaa gccattctcg tgcctcagcc tcccttgtag ctgggattac agttgcccac 49740
caccacgcct ggctgatttt tgtattttta gtagagatga ggtttcacca tgttggccac 49800
gctggtctcg aactcctgac ctcaagtgat ctgcccgcct tggcttccca aagtgctggg 49860
attacagttg tgagccactg cacctggcct ttaattttaa tttctaaaac tatggagtaa 49920
tactacattg agggaacaga attttctatt ccttcatttg tattattatt aaatacagtc 49980
atgcattgca taatgacagg aatacatttt gagaaatgga tcaagtgatt ttttcattgt 50040
gtaaacatca tagggtatat ttacacaaac tagatgttat agcctactat acagctaggc 50100
tatattgtat agcctgttac tcttcggcca caaaactgta cagtgtgtta ctgtattgaa 50160
caccataggc aattgagaca caacggcatt tgtgtatcta aatatagaaa aggtaatgca 50220
ttgtgccacc aaatcaacaa cagctatgat gtcactgggt gataggaatt tttcagtgcc 50280
attataatct tatggaacca ttgtttcata tgcatgcagt ttgctgttga tcaaaatgta 50340
gttaagcagc acatggctgt aattaaaaca ctattgtttg ttataataga aaataaaatt 50400
tttcttttta gcctctgtat taataaagag cactagaaag tactttgttt atcagataat 50460
gaatatgttt gacagatgta catacgtatt tatcaaatga atcttttttt gtgggggaaa 50520
ccttaactaa gaataggcct gtgttttaaa atggctgcct ggaggacaag tgctataagg 50580
aaatttcagt ggtatttgct tgacctggca ttaagtgggg ggaaaaacaa gccccaggtg 50640
aattgataga tggatgtctg aacatgttca ggaatgatgt tttgaacaat gtttgcctcc 50700
tgtgtcatgt aggcagagag atgataaaag tttttttccc ctcttgatac caggtaattc 50760
tgataccgac taccagaagt tagcttcaga ctccgcaggt tgaagggctt tgtcccataa 50820
gaccattctt acttcagaca ccaattgcaa tgatcagtta tcaggtccca aggttaccta 50880
cacttatgtc tgatttggct acaaaattgg aggttcccac agtctacccc ttcagatttg 50940
ataactttct aatatggctg caaaaaactc agagaaatac ttatgtttat cagtttttta 51000
taaaggatac aattagccag atgaggagat agatagggca aagtccagga gggtcctgag 51060
tgttgagtgt aggagtctct gtcctgtgga atatgccacc gtcccagcat gtagatgtat 51120
tcaccaatca ggaagctctc tgagcccttt tgtgtagttg tttttatgga ggtctcatta 51180
tgtaggcagg attgattaaa tcattgacag tgggtgattt gctcaagccc ctctcccctc 51240
atcagaagtt ggtgggtggt actgaaagtt ctgaacttct ggtcaaggct ttgtctttct 51300
aggtagccct catcctgaag ctatctaggg gctttccaag agttgtctta ttagaacaaa 51360

```
gaacactcct atcaccctta tcactcagga aattccaagg gttttaggag ctgtatgcca  51420
ggaacctggg acagaccaag tatctttctg tgataccaca gaatgggacc ccaaaagcca  51480
gctccagctg gtgtctagtg cctttagttg ggcactggat atcggttaca gggcataagt  51540
ggcccagtgg ggttgccgtt taacccatct ctgctgtatt aacctcatgt accttagctc  51600
atggctaggt cgtttcaagt ctcacctaat gtcagttgtt tcatccttct ctggatgcat  51660
gttcacttct ggaataggtg aatatctggg ccactatgtt tgctgtcatc ctgagcaaac  51720
ttccagctta gaaaccagct ttatggaatc atcccagagc ctttatttta ttttatttta  51780
ttttatttta tttatttatt tatttatttt ttgaggcaga gtcttgctct gtagcccagg  51840
ctgaaatgca gtggcaaagt catggctcac tgcagcttca acctcccagg ctcaagcaat  51900
ccttccgttt cagcctccca agtagctgag attacaggtg tgtaccacga cacctggctg  51960
atttaaaacc ttttgtagag atagtgtccc agtgtgtttg cccaggctgg tctcagactc  52020
ctggggttaa gcgatcctct tgcctcagcc tcccaaaatg ttgggattac gggcgtgagc  52080
cactgaactt ggtcccagag ccttttagaa cagtgttgag ttgcccttta tttgcaccag  52140
ggctaaggca gtagaaaaaa aatgtttatg ggccatgttt ttcttcctag tcaaaataaa  52200
aatagccatg taatctatgg aggcagcaga tatgttgtta gtatacacta gaagtcagga  52260
aattcgtact gcctttcagc tgctaaagta ctgggacata tttgagaagc agtaatgcag  52320
aggcagctgt ctgatctttg atctctgata atgcttattt cattgcatcc ctgaaaccac  52380
cctgcaaagg atttatcatc tttgctgctt tgcatatgga atagcatagg cccagagaga  52440
cgtagcttga ctgcaatcac atggtgagtt agttgtagct tctgcaaatg tacagaacta  52500
agaagctact tttcttgtgt gttattctag tgatgatggt cattataatt gatgtacctg  52560
atattatgct aggtttaggg atacagaaat gaaagaagat cacagtccct catctgggac  52620
ctctgttttt ttggtgtcac ctctctgcat agacagttct gcagtattga tgctgctgtt  52680
ctggttgatc cttctgtcat gcctgcacca tcttttctgc cagactgaag tgttcttgct  52740
tggggaaaag cagatttgca aaggttctct tttcctgat tgttgctttg cagattgagt  52800
atatttgttt gtttgttttt aagtgaacaa aagttgaatg agattgatta ctggctcttt  52860
aaagaataat tactcccccct tttgacttat gtagcatctt gaggtgatct atgaccgttt  52920
gtacttgtca tgacttccat tagattaaac tctggggcaa agacgttgct cttcattgtg  52980
ctcatatgac accattactg ccagtggaat tgaaataaat tgagtaaggg cgagtgtttc  53040
ctaacaaatg ttatcctggg cctgaggaac catcatcaag atggagtggc cctgcgatta  53100
attttggact taaagcaaaa aacaaacaaa tttttttctt taaataacca gttggcacag  53160
atacagaata aaataagata gatccacgtg tagtttttga aaatttaggt caggtggctc  53220
actcctataa tcccagcact ttgggaggcc aaggcgtgtg gataactcga ggttaggagt  53280
ttaagaccag tctggccatc atgatgaaac cccatctcta ctaaaagtac aaaaattagc  53340
tgggcatggt ggcgcatgcc tgtaaaccta gctactcagg aggctaaggc aggagaattg  53400
cttgaacctg gtaggcggta gttgcaatga gccgagattg cgccactgca ctccagcctg  53460
ggtgacagag tgagactctg tctcaaaaga aaaaaaaatt taagaaataa tcatcagtgt  53520
atatcttcct tttttcattt ttctttaaaa aaaaaaacaa cccttgtatg catagctgaa  53580
ggagaaataa ttgaaagtgt ttataagatt tcaaggtgat gggctggaca cagttgctca  53640
tgcctaataa tctgcacgcc tgtaatccca gctattcggg agcctgaggc aggagaatca  53700
cttgaaccca ggaggcagag gttgcagtgg gccgagatag tgccattgca ctctagcctg  53760
```

ggcgacaaag gtgaaactcc atctcaaata aaaaaaaaga tttcaaggtg atgggtttca 53820
tgtggaccaa ttttatcctt ccctgatgat aatttgacat atgagtcaga tattttccta 53880
attttcgtaa ttcgagtggg attgtgtgtt tgtttgtttg ttttgagaca gggtctcact 53940
ctgttgttca ggctggagtg cagtaggcca gtcatggctc actgtagcct tggcttctca 54000
ggctcaagtg agcctcccac ctcagcctct taagtagctg ggactatagg tgcgtgctcc 54060
cacacctggc taattttttc tgtttttttt tgtagagaca aggtctcatt atattgccga 54120
ggctgggact cctgagctca agtaatcctc ctaccttggt ctcctaaagt gctgggatta 54180
tatccacgag ccaccacacc cagcctcgca tgagatttta acagagcaaa gtacctgttg 54240
gaaatcttgc gcacaaagcc tcctttattc tgttattccc actgacagga attcagatac 54300
ctggatcaat tctgtttcgg ttttgctaaa atctctaact tgatatttta cttttctaaa 54360
aacctgtatt atcaatgaaa tggaattagg aaaacaggac ctatagaagt taagacctct 54420
tcaatctatt gatgtttcat ggtgcctttt atattcaaaa tgctttgttc tcacaaaaat 54480
aatacttttt gtttggagaa aaaggctgtg gggtgtgtgt gtgtgtgtgt gtgtgtgttt 54540
tcctctcaaa gatagcagta aaataaactc cttctgacaa aggcttctta aaagaaagga 54600
gaaaaaaaaa ccttcctgct aattgtgttc tttaaaatcc tgattccccg ttttactttc 54660
tggatgtgta ttctgggctt tttcaatgtc aaccaatact ctcttgatgg gaaattcagc 54720
tggatttggg tatgttcatt gggttttcct agaacagttt gaagatccat ctcatttacc 54780
taaacaaata ttccttataa ttattatgaa aattgggcct gttatagact aataattgac 54840
ttaaaccata cagggttatg tttgtcagta tctcgtgagt cagcttttct aggggcagag 54900
attgaagagt tagttctgag attgaatact atttatcagg gttttgtttt gtgtacctta 54960
ttctcctgta accacctggt tggcttttat catagataca tttttgggaa acaggcaacc 55020
acatggttaa tgaagataga gaagacgtga aatttgttac ctttatagat tttttcccct 55080
tgccctgttc tcattcttct catttgccta aaaaaaaata taaggaggcc gggtgcggtg 55140
gctcacgcct gtaatcccag cactgaggca ggcagatcac ctgagctcag gagttcgaga 55200
ccagcctggc caacgtggcg aaactccgtc tctactgaaa atacaaaaat tagccgggcg 55260
tggtagtccc agctactgca ggtacctgag gcaggagaat tgcttgagcc tgagaggcag 55320
aggttgcaat gagccgagat tgtgtgccat tgcattccag cctgggtgac aaagcaagac 55380
tctgtctcaa aaaaaaaaaa aaaagtataa ggagtattca catttctatg agatctgtaa 55440
atttaggtta gaaaatttag ttaactgtgt tttgtaatag tcatataaat aagcacaaag 55500
accctccaga cttcttccca gcatgtgaca gtggaagaaa ggggtaataa agtagatttt 55560
tttgttactc tcattggtaa aaataagtct gtccatggga aggttaacac tgagtttacc 55620
atcttgatga ttccatatgg ttcctagcaa ttctaatctc aaagttggtt ggcagaatgt 55680
ttaggtcttt gggtagaata tcttctgtgc cttttctgtg aattgtaaaa ttacatttgg 55740
gaaataaaga aaaaaatccc tgattatccc actatagcaa tacaaccact gtaaacattt 55800
tggtatacag ttgtgttgca ttatatgcat tttctgattt ttgtatgtcc acctgtgctt 55860
atttgaactg tatccccctc cccacttccc acaccctgtt ttctcactcc tggagtgagc 55920
atgggcagtg gggatgagac tcgcctgtgg cttcagtttg tctccttttc taagtttctc 55980
tgagtgggca ttcactgtgc tggctgtgat tctgttattt aaagcaatat attttcatac 56040
cttatggccc ttaaatgcaa gccaacctct tcatctggtg tcaaccaaag gaaaagtgat 56100
ctgttgcagc gctggaggaa aaactggcaa tgttggactt acctaaattg aaagatggta 56160
tgttgttctt caccttgggg tcttcaagta tgatttttga cagtgcatgg tttttatctt 56220
acatgctgac ttttgtctct aacccttgag ttagatgcaa tttaattcca gccctttttc 56280
cctatataca ttttacataa ttatccataa gggtatattc atttttaagg ctcttaaaat 56340
atactatatc aagtatcttt ccatattgct atacaatttt tgtagctgtc atttataata 56400
agacatttta gttttcgtct tttcagaaga attttgggag ctagtataat cagctcctta 56460
gaatgctttc taatttgcat actcaggtct actcacaata gttctgccat agatatttaa 56520
aatagaagca actgttatgc tgctaaattg aatatttctt aactaggctt atttcttaac 56580
aggggcatag atgtatgttt tcaggcatat gggacccttt ctgtaactag gcttctagag 56640
tttagaatta agattattta aattggtcta tgatcttatt gaagagtgag aggctagagt 56700
gtagtggtta aaaacatcaa cttgaatctg gactgcttgc atttaaagct cagtattggt 56760
acttacttgg ttactttgat cagtttacct atcctttctt tgccgccttc tacatggcta 56820
aaatcaggtt aataatattt acctcttaag atagtattgt gaatattaaa tcagtatata 56880
caaagtattt agaataaaat cttgaaccaa caagttttat gtaaatatta cttactttca 56940
taggctagtt tgctaattgc tgaaaatcct tatggcacaa ccatgagtct tgaacacaca 57000
gaataccttt tttttttta acgttttagg cagtatagtt aaaccttaaa tttctgttct 57060
tgtttgatag ctaaagtttc agtcagaata aatttagtgt tgggcttgtg aatataatat 57120
taaatctgaa gtatgttgtc aacatatagt attgcagggt tgatgtctag aaatgctata 57180
ttagatgctc ataatgtttt ctgtatcttt ttcttcccaa tgtctacttg tcctttagca 57240
aagtatgaac gttgtcatga atcttttctc tctgtccaca gattctgtgt gctcctctgg 57300
gccacagtag ttacttcttt aagcacagaa aggaaactta gggctttgcc agttttagta 57360
ttagttctct atgtttttca tccgggcagc tatggagagg gttgctttcc acacacctgg 57420
gtactccatt gatatgttct gtagaggtaa tcaacacact agagagtaca cctgtttgtt 57480
ccatggctaa ccctttctga ttgtagacat gcatttgagt gtttgcagtg gatatttggt 57540
gctaacaggt gtcttagttc cttctgttat tctgtaatgt ttcccaagaa tattcagagc 57600
tgtttataaa atgcagagtg atttatgtat taggtgttca atgagtttga tcaagaagat 57660
tcacttgaaa ggaattaact aacaaagcag tttccattgt taataggata tgcatgctgt 57720
ttctctaaag tatttttatt tcttcaaaga gttattaagc agaggagact gattttgtgg 57780
taagtttgga ggggttagtt ttaatccacg ttggtcaaaa ctaaaagtag attagaaaat 57840
ctatttctca tcctacagta gtgctgaggt ttctagtaga ttgtttttct tcttcctagt 57900
cattttctga aactcaaaac aagaatcaac ctataccatt gtaatgtttc acagttaact 57960
tggagtattt aacaagtcta aaatcaaagt ttattgttat tagtaaaaca ttttgaagcc 58020
attcatttca tgtgacaagg aatcttattt caccaaatgt ggtatgtttt taaacttata 58080
ctttctattg ttctagtttt gttgatcttt gatattgatg cagtgatatc agtttcctat 58140
tgttatatat actttgtggt caaaattatc atagggtttt gtgtttttct ttgcctgagt 58200
tttgcttctc atctgaacat cacatctttt tcttgcggtt ccatttacac agtgtgattc 58260
ctagagatga gcttctttat cctctgaggc agtggaggaa gcatggaagc cacttgggga 58320
gcactgcatt gacaagtgta tttttgtagt cacatggtgg cagtgtcagg gaaattatag 58380
gactggttag attctagttc agcaacctat aaatcccagg acttcccagt ctcgtgagtc 58440
atacaactct caggcctgtg ctgcaaatga cacttgctta ggagtaaggt gaagggtatt 58500

-continued

```
ttatagctct aatggtttgt acagttctta aacatgtatt gattgctaac aactgctgtc  58560
tttctcccag cttgccccac caccagtctt tgtgcataag cacaattttg gacatagtta  58620
tttgtactta tttatgcttt tacaccttct tccttttata aagattttag ctggtttatg  58680
acttgagttg aaacaaggaa aaaaagagga gacctgaaat ggtctgtccc ctgccaacca  58740
gaagcctcct gtggtatcca aacagaatag ttgcctcagt ctgtcagcac ttctgtcttt  58800
gaaggtggtt tctgcttgaa aagtggtgac tattagcata gcctggggat aattgctttt  58860
ttttcttctc tcgggatacc tttttttttt tttttttcca gatactttct tgctcttgtc  58920
gactttgttt ttccagaaga tttagcctgt ggttaaaatg tttcgggtcc ccacgtgaac  58980
tctctgtggg attacccaat tctggggtac cttcaccaga tcaccagtgc taaagagggc  59040
aaaggatctt cttggttaat agaaaaggct gttttggaat gaatctcaaa gtccagaaac  59100
atcgagactt ttcttcaata ctttttttcta tttggggtag caactttacc tagtgtaggg  59160
gagggagggg ttagttggga gggcttgtgt ttaaggggtt cagaaacagg ggatttaagt  59220
gtgtcttttg tgtttgcaag gcactaacac cactcccgtc tgtatttaaa tgctgtcccc  59280
aggttacgac tatggctatg tctgcgtgga gttttcactc ttggaagatg ccatcggatg  59340
catggaggcc aaccaggttg ctttatactt cggtcaaatg atgctggaag gatatatttt  59400
tttatatatg gggagggagg gtttcaaatg attttacttt ggaaaggtac aagaagtcta  59460
tctgtggagc atactgtatt ccaaccatcg gttgtgagga aaatctttaa aaaggctgga  59520
aagctttctc tacaaaactt aatgggcaca gagtgcattt taaaagctag agcccagttg  59580
cttttggact agattccaaa gacaatagtt ggaaaaaaaa aaaaaagaca catctggagt  59640
gtttcctttt ggagtgtgac tgagatggta atcctgatgc aaagaatgat ccttgattgt  59700
ctgtgacccc aaggatctgc ctagcacaga aattctaggt caatagttac acccagacct  59760
agggtgaaga cctctgatgg tgacttctgt ggcatcagat cctgcctgca ggggctactt  59820
ccaaaagaga gctatcaggg aagagagagg agtggattgt tggtgtctat tgcattcatc  59880
attgtttttt gccaattgga gttgcatact caagtccttg gctgcgtata gtcagagctg  59940
gtgaatcaga atctgtactc accttacgtt tgaactatct ggagttactc agcttgccac  60000
ctagattttt catctatgtc tttaatagaa ccctacctgg tagttttgag aggaattaat  60060
aaataggtag aatccttctt gttatggtgc ttccttgggg aaagttgttt tctttgggtt  60120
gtttcagttc ctccatctgt aaagtaggaa aagaaactta ggaatatagt ttgatgtgtt  60180
tttttttttct tttttttttt ttttaatgta cccactgcct atacttaaca gtgtgaatac  60240
agtgggccca gaatctttct ttctttcttt tttttttttt gagacggagt tttgctcttg  60300
ttgcccaggc tggattgcaa tggtgcgatc tcggctcact gctacctcca cctccctggt  60360
tcaagcgatt ctcctgtctc agccccctga gtagctggga ttacaggcat gcgccaccac  60420
gccggctaat tttgtatttt tagtagagat ggggtttctc catgttggtc aggctgctct  60480
cgaactccag acctcaggtg atctgcctgc ctcggcctcc caaagtcctg ggattacagg  60540
catgagccac cgtgcccagc caggcccaga atcttaaaag aaggctctgc cagagaagag  60600
tagttattag atgagaactc ttcttcttct gtagcctgat gctttgttca gctttgttta  60660
actcagtgtg gctcattata cgtacttttc tcttcttggc caagttctcc tcttatgggt  60720
atggagatga catgctctaa atgctttggg agcaagcact cattagagaa gacttttgat  60780
gtatccttat cttgttagta gtttaagctt gtcagatcct taaagaatga caggcttagg  60840
```

accatatccc ctagacttaa gaggattctc attgaccatt tgttcagtgt ccatcactga 60900
atcacttacc aaatacagtt gacactctgt atccacaggt tccacaccca tagattcaac 60960
caaatgctga ttggacatat tcaggaaaaa aatgcattaa cactgcaaca ataaaaaata 61020
atacaggcca ggagtggtgg cttactctgt aatcccaaca ttttgggagg cccgggtggg 61080
aggattgctt gaggccagga gtttgagacc agcctgggca acacagggag accccatctc 61140
tacaaaaaat aaaagtgaaa aaattagcca agtgtggtgg ctatcaactt gggaggctaa 61200
gatgagagga ttacttgagt ctggattgag actgcagtga gctgtgatca ctctgctgca 61260
ctctagcctg ggtgacagaa gtgagacccc gtctcaaaaa acaaaaaagt acagttaact 61320
atttatatag tctttattag gtattagata taagtaatct agagatggtt taaagtatgt 61380
tggaggatgt gtgtaggttg tatgcaaata ccatgtgatt ttatataagg gacttgagca 61440
tcctgagatt tttgtgtcct tgtgggtcct ggaaccaatc ccctgtggac accaagggac 61500
aactgtacta accatgtgtc agaaactgct acatgccaat tttggagaga agaaaaaagc 61560
ttccaatctg tgtgctttcg gtggatccta ttctgacagt ctgtccaatt ttgagaacac 61620
tcattaattc ataagcagtg aatgtgatta agtcgttcgc ctctgtgcta aatactcaat 61680
gtaatagctg atagctgagt gctataaaga aaatgaagca gggtattggg agaatgcatc 61740
atggtggcaa ttttagaggg gtggtcaggg aaacttcttg aggagtgaca tacatttaag 61800
ttgtgactct tggcgaataa tgtatccaga acacttacta tagtacctag cacttggtag 61860
catttgaatt aatttgaaat tcagtgtcct tctttctctc tcttaccctc ctccacatgt 61920
caagtaattt ccaattataa attttgtgtg tgtgtgtgag acggagtcca gccaggctgg 61980
agtgcagtgg cgtaatcttg gctcactgca acctccgcca cccgggttcc agagatcctc 62040
ctgtctcagc ctcccaggta gctgggacta cagatatgcg ccaccatgct tgggtaaatt 62100
ttttttcttt tttttttttt ttgagatgga gtctcgctct gttgcccagg ctggagtgcg 62160
gtggcacgat ctcagctcat tgcaacctct acctcctggg ttcaagtgat tctcctgcct 62220
cagcctccca aatagctggg attacaggtg cccgccacca cacctggcta atttttgtat 62280
ttttagtaga gatggggttt caccatgttt gccaggctgg tctggaactc ctgacctcag 62340
gtgatccgac tgccttggcc tcccaaagtg ctgggactgc aggcgtgagc caccatgtcc 62400
tgccaatttt tgtattatta gtagagatgg ggtttcacta tgttggccag gctggtcttg 62460
aactgcagac cttaggtgat ctgcccacct tggcctccca aagtgctggg atgacacgca 62520
cgagtcaccg tgcctggcct tcaattataa ttataagaaa ataaatttat ttttatatct 62580
gaagtttaat aaaactaatt ctttaaggaa atggatgtgg attaaactcc ttatgacata 62640
gtaaacaatc ttatgagaga cataagaatg tgagggaaga agtcctgtct cctcagggtg 62700
aataaagtaa atattttggg aggctgaggc gagcggatca tgaggtcagg agagcaagac 62760
catcctgacc aacaaggtga aaccccgtct ctactaaaat acaaaaaaat tagccaggtg 62820
tggtggcgca cgcctgtagt cccagctact tgggaggctg gggcaggata attgcttgaa 62880
cccaggaggt ggaggttgca gtgagccaag attgcaccac tgcactccag cctgctgaca 62940
gagcaagact ctgtctcaag aaaacaataa aattgaataa ataaataaat aaataaaata 63000
aatatttgtg gaagataaaa tgtgtttgta ggccgggcac tatggctcaa gcttataatc 63060
ccaccacttt gggagaccaa ggctggagga tcacttgagc ccaggagttt gaaatgagca 63120
tggggtaaat agtgagaccc tgtctaaatt taaaaaaaaa aaaaaaaaaa aaaaagtctt 63180
tgtctatcct ttcccccagt tttacttaca gaccaaattg gtatggattc tgagtcacca 63240

```
cgatctgctt ggcaactctt agtagagcct gagtgtgtgt gtgcctctga gaaggttact  63300
ccgaagtact ttgagttttt ttgtaactct ttgctattcc gactcttgat gtgaaatgtc  63360
ttttatttat cattggctgg tacttgtagg cctaggggat ggaaataaag gaattttctg  63420
ctagcttgct ttgtcaaata ttgttgggta tgtgtgcctt cgtgaagttg ctcaagatga  63480
taaccaaggt ccctctagcc ttttcctggt gcctagatca agctgttaaa cagtaggatg  63540
ctctgcagca gtactgagct ttgtggctgt ggtgaccgat cagggtatca cttaggcagc  63600
agctgtctat ctggagaaat aatttccaac aggtatgaag gtatgaatct gttagtctgt  63660
accatcacca tttctgtcta ggagaagggg gcagccagca agcactgtca ggcagagcct  63720
ttcgttccac ccttcctgca aagtgtattt ctagccctgt catatgccct tggctttctt  63780
tgttgtcaag tctctgggag attgagggta catattattt ccttctgctt tgtgtgccct  63840
tgcactggga cttggggagg ggagtaagaa gtattgtgtt aaaatgttaa tccctttcat  63900
tggttgccca gttgtgagta ctagccctct cagactgttg gcatttggta tgcagggatt  63960
agcattttat gttctcaagt atgctggtgt gatgcttatt gtctattatt tggccaaatt  64020
agtcactaaa gtgcccttat agaagataac tctgggagag gtatttattt ctctgaaatt  64080
tttattctcc tttcccttt cctttccttt cctttttctt tttctttttt tctttccttt  64140
ttctcccctc cccccctcc cctctcctct tattggagac aaggtctccc tctgtcacct  64200
acgctggagt gtagtggtac aatcatggct cactgcggcc tcgatctctt gtgccgaagt  64260
gatcctccca actcagttct ctttagtagc tggaactacc accaccacag ctggctattt  64320
tttttttttt ttttttgtag aggcagggtt ttgcaacatt ccccaggctg gtcttgaact  64380
cctggactca agcaatttac ctatctcggc ctcccaaagc actgggattc caggtgtgag  64440
ccactatgcc tggcctattt ttaaattttt attttttga gacttagggt tctgttctgt  64500
tgctcaggct ggagtacagt ggtacgatga gagctcattg cagctttgaa ctcctgggct  64560
taagcaatcc tctcacctca gccttctgag tagctggact acaggcacct gccaccatgt  64620
tcggctaatt aaaaaaataa caaactctgt tcgtaaagat ggggtcttgc tgtgttgctc  64680
aggctgctct tgaactcctt gcctcaagtg agcctcccac ctggacctgc caaattgctg  64740
ggattataag catgagccac tgcgcccagc cttactcacc tttttgtatg acactatcag  64800
tctttctaaa gtgcaaagaa aaagggttct gttatcatct gatgtgaaaa ttcctttaaa  64860
cattgacttt ttctggtgtg aggaatgaaa gctgtggaat acgtgaagtt ttatgaaata  64920
gtgttttttt gtgtgtgtgt caacaaaatt aagagagttt gggttattga agatacaaga  64980
gtgtttttga aggtatatat aggaaaccaa atctcaaatg tggtctgtcc ttgtgattaa  65040
aattagagca atagggaagc caggtgtgat ggctcacacc tgtaattcca gcacttttgc  65100
aggctgtgac aggaggatca cttgagccca ggagttgagt ccagcctggg taacatagca  65160
agacctcatc tctacaaaac attgttaaaa attagctggg tgtagtggca catgcctatt  65220
gtcccagcta tttggaaggc taaagtggga ggattgcttg agcctgggag gtcaaagcta  65280
cagtgagccg tgattgtgcc actgcactgc aacctgggcg acagagagat cctgcctcaa  65340
aaaaaaaaaa aaaagcaaca gagaaagctt atgtttttag tgatgagaat gctatttgtg  65400
aggccatgat ggaaaaaatt gaagaaccta gtttgttgga aacttaaatt ggtagtaaag  65460
acataatact atctgaaaca ctttagtact taaattgtgt gcattccaag caacaaaacc  65520
aataatctgt aggttgaagg ttgtagtgtt acctaaacaa ctatcacccc aaaaacactt  65580
```

-continued

```
cattgaggag tatccagcat cctagccaga gctcaactgt ataacttatg gctggaatca  65640
tgccattctt gctggaaact tcaatttcag tactttttcc ttatcaccct cagaagggta  65700
gtagtagaaa catggggaac tgcattctaa aatgagtgta taggttcata acctagctag  65760
aaaaaaaaat taaaacaatt aatgagtaca aaccaagggt tattgaagag tctcgctctc  65820
aagagagttg gggtattcaa gaaaattgaa agtgagttta aggatcgatg acttgattac  65880
acattttggc tatttatcca ctgattgaga cttttttttt tgagatggag tctcactggt  65940
tcgcccaggc tgtagcgcag gggtgcgatt tatccactga ttgagacttt tttttttttt  66000
tttttcagat ggagtctcgc tgtgtcgccc aggctgtagc acagaggtgc tcactgcaac  66060
ctccgcctcc tgggttcaag tgattctcct gccttagcct cccgagtaac tgggattaca  66120
agcatgtgcc accacgcctg gctaattttt gtattttcag tagaaatggg gtttcaccat  66180
gttggccagg ctggtcttga actcctcacc tcaggtgatc cgcccgcctc ggcctcccag  66240
agtgctggga ttacacatgt gagccactgt gcccagccca gtgattgaga ctcgactgga  66300
catgaagcag tataatgtag cagtataaca tagtattctg gaagcagact accgggggtt  66360
gcatttcggc tccatcactt tctaaggtgt acttgaacaa gtggcttaac ctctctgtgt  66420
tttaacgtac tctcacacac atctagggat taaataagtt aatgcatgta aggtgattag  66480
aactggggct ggtggccggg tgcggtggct catgcctgta atcctagcaa gttgggaggc  66540
caagacgggc ggatcacgag gtcaggagat ggagaccatc ctggctaaca tggtgaaacc  66600
ccgtctctac taaaaataca aaaaaattag ctgggcgtgg tggcgggcgc ctgtagtccc  66660
agctacttgg gaggctgagg caggagaatg gcgtgaactg ggaggcggag cttgcagtga  66720
gccgagatcg caccactgca ctccagcctg ggcgacagag tgagactcca tctcaaaaaa  66780
aaaaaaaaag aactggggct ggcacaaagt gaatgttgag tgcatctttg ttgttttcac  66840
acaacttctc atctgaaaca aagtcttaag ttacagcagc tctggtcttg gcttaatgga  66900
gtatatggca aaaagaggat ttggtggcag tgcctaggag gatttttttt tttcccatca  66960
acaatacttc tcatttagcc tgttgattga tacggattat caggggactc cttccagctt  67020
ccctagttgg agtttttttt tttttttttc ctttttttgag acagggtctc attctgtctc  67080
ctaggctgga gtgcagtggt gcgatctcgg ctcactgcaa cctccgtttt tggggctcaa  67140
gccactctca tgcctcagcc tcccaagtag ctgtggctac agacacgtgc ctggctaatt  67200
ttgtattttt gtagagacgg ggttttgcca tattgcccag gctgatctcg aactcctgag  67260
gtcaaagcga tctgcctacc tcagcctccc aaagtgctgg attacaggag tgagctacca  67320
tgtccggccc ttagtaggag tttctgctgc cttagccttc aagagagaat cttaaatttt  67380
cttttttttt tttgagacag agtctggctc tgtcgcccag gttggagtgc ggtggcgtga  67440
tctcggctca ctgcatgctc cgcctcccgg gttcacacca ttctctcgcc tcagcctcct  67500
gagtagctgg gactacaggc gcctgccacc acacccggct aattttttttg tatttttagt  67560
agagacgggg tttcaccatg ttagccagga tggtctcgat ctcctgacct cgtgatccac  67620
ccgcctcggc ctcccaaagt gctgggatta caggcgtgag ccacctctcc cggccataag  67680
aatcttaaat tttctaaaga gaaagagcag gagacagaca gtaccacatg gagtatgttt  67740
aggccatgta ggaaatctag cctgtggctt taaaaccgta agttctaaat tagctgggta  67800
tggtggtgca cacctgtagt cctagctact ctggaggctg aggtaggagg atcacttgtg  67860
cccaggagtt caaggttgca gtgagctgtg atggtgtcac cgcactccag cctgggcaac  67920
agaatgagat gctgtctctc aaagcaaaac accctaagct ctgataacca gcccattatt  67980
```

-continued

```
tgccacatct caggctcttt aattatgaga ggtgctctaa acgactcatt ttaattctct  68040
cgaatttgaa aaataaacat ttatcatttg gcagttttaa gggaaccttc tgatatgtgt  68100
cctacaatgg gtttataatt atttttgtca caaatcatgg tttatttcta tggattaaag  68160
tagtttagtt cttaatttgt tctaaattgg aaatatacct atatgtttta acctcgtgct  68220
tcagtgttgt cacatctcat tagttcaggg gtcgtacaaa ggcatagttc agttagccat  68280
cttgattata actttggttt atgaccttat gtatgttcag atggtatagg gttcgtagca  68340
cagaaagatt tagaattcca gcttcattac ctcctggctc ttttgtaact tttttttttt  68400
tttttttttt tttttgagac ggatcttgct ctgttgtcca agctggagtg cagtggtgtg  68460
atctgggctc aatgcaacct ccacctcccg ggttaaagcg attctcctgc cttggcctcc  68520
cgagtagctg ggattacggg catacaccac cacgcccagc taatgtttat tttagtagag  68580
atggggtttc accatgttgg ccaggctgga cttgaactcc tgacctcagg tgatccaccc  68640
accttggcct ttcaaagtgt tgggattata ggcgtgagcc accgtgcctg gcctctcttt  68700
tgtaacttct gaacctcagt tttctcatct gtaaaatgag aggatgatca taataccacc  68760
catagtgcag ttgtgaggtt agagtatgta gtatatgtaa agtgatcagc atgataactg  68820
gcatgtggta agtgctctgt agtaaagggt gattcataac actggactct gcttggttgt  68880
accaacttct cattttccct ggctccttat ccacctcttg ggattcagag ttggctgaaa  68940
gtggcaggca gtgctgcttt gggtggcagc ttgattttag acagccagtt cacatagtgc  69000
ttttgttcag gacctctcgg gatttctaga cagacagcaa gagagttggg ctaacacctg  69060
tcatgaagtg tctaaggaat gagtgcacaa gcattcaggc atgtgagggc agaagaccat  69120
gaccatacct gccttcctac agtaaacagc ctgttgtttc tgcaggtagc attgcaggta  69180
gttcttttat cagaaaattc ttgtaggctg caggtgacat tgagtgttat taggtatctt  69240
cttcattcaa gttgaacttg gaggttacag tatatcttta tgtccccctc tccacaggtg  69300
tttaagtgtt gtcattcatc ctctagtgca tagattatgt gtgcacattt cttgttaagg  69360
atattgatga actgatagtt tatctagaat aatgtttatt ttatatttta ttttattgag  69420
acagggtctt gctctatcac ccaagctgga gtgcagcggc atgatcatgg ctcactgcag  69480
cctcaacctc ctgggttcaa gccatcctcc ctacctcagc cttctgaata gttgggacta  69540
caggtgtgcg ccaccacacc tggctaattt tgagggggta gaggggaggt acagatgaga  69600
tctcactgtg ttgtccaggc tggccttttg ctcctggact caagcagtcc tgcctcagac  69660
tcacaaagtt ctggaattac agatgtgagc cactgtaccc agcctagaat aattattatt  69720
tatttttatt tttatttatt tattttttga gacagagttt tgctcttgtt acccaggctg  69780
gagtgcgatg gcacagtctt ggctcactgc aacctctgcc tcccgggttc cagtgattct  69840
cctgcctcag cctcccatgt agctggaatt acaggcacac caccacacct ggctaatttt  69900
tgtattttta gtagagacag ggtttcacca tgttggccag gctgctctcg aactcctgac  69960
ctcaggcaat ccacccgtct cggcctccca aagtgctggg attacaggcg tgagtgatgg  70020
cacccagcca gaataattag ttttaatctc acagggtgag atttgtgagg ttaattttgt  70080
atattaatga tgtatatatt accaaaatct gtggtcaagt gaaatttgtg cttaatcttt  70140
gcaaatgcta tttccaaagg aaaatatgta ggagaaaagg tggtgtatca caggatgtag  70200
agtagtggtt actgggcaca agggtggccg gggagtcggg gggtggcagg agaggataga  70260
gaatgataac tgattgatac agggtctctt ttttgggatg aggaaaatat tttagaatta  70320
```

-continued

```
aatagtgagg atggttgacc aagcttgtgc atgtactaaa agccattaaa ttgtatatac  70380
tttaaaacag tggattttat ggtatgtgaa ttttatctca attttaaaaa aagtctttaa  70440
atgtagtatg aaactttttt taaggccagg cagggtggct cacacctgta atcccagcac  70500
tttgggaggc tgaggcgggc agatcacctg aggtcaggag ttctagacta gcctggccaa  70560
catgatgaaa ccctgtctct accaaaaata cgaaaattag cccagcatgg tggtgtgttc  70620
ctgtagtccc agctactcgg gaggctgagg caggagaatt gcttgaactc aggaggcaga  70680
ggttgcagtg agctgagatt gtaccactgc actccagcct gggcgacaga gcaagactgt  70740
ctcaaaaaaa aaaaaaaaaa aaaaaaagtt tttttagggt tccagcacaa tgggaatgag  70800
tccagatcta aaataaagta cagattcatt taccaccctc caccctaccc caacccccca  70860
aaaagattgt ctatcagttt gtcaggaagt tagagtaaaa tggtcttaaa atgcatcaag  70920
agggctgggc acagtggctg atgcctgtag tttcagctac tcaggaggct gagataggag  70980
gatcacttga gcccaggaat tcgagtgagc catgattaga tcactgcact ctagcctgaa  71040
tgacagagca ataccttgtc tcttaaaaaa aaaaaggcat gaagaatttt tttgctaatg  71100
gtatctactt accacagagg aacatttaag ctaaacatct gaaagattat ggatggagtt  71160
ggtaacaggc tccatttgaa ctggttatgt agtttatgct cagtaaggtt gaacggactt  71220
tctgctttga gttattcaca gttaaaaata aaggactatt ttgaagtaga ccgaaaatga  71280
aaataacatt aagaaatcct tggactaatt tttaggggag attcctgtaa tcggatggtt  71340
tgtagttgtc aatgtagacc tttcctggtt tcctgaaatt gctaatcaaa gctcaaagcc  71400
atgggaaaag actggattgc agctagaatg tgtgctctcc acatatgtct ttcttagagg  71460
cctctttcaa gcagcattga cactatggct atcatctttg accctcttag tatacagaga  71520
gttgtaggtt ttcttttttt aagggggaaa acattattga cataaattat atatcataaa  71580
agtcactcat tttaactgta caattcaatg attttttagt aaatttacca agttgtaaca  71640
tttattatta taattagttt tacaacattt ttcttttctt tctttttttt tttttctttt  71700
tctttttttc tgggacacag gatcttgctc tgttgcccaa gctgagtgca gtggcatgac  71760
catggctcac tgcagcctcc acctcccggg ctcaagcaat tctcccacct caacctcctg  71820
agtagctgga actataagtt ggaaccatcg tgcccagcta atttttttatt ttttgtagag  71880
agaaggtctt gctatattgt ccaggttggt cttgaacttc taaactcaag caatccttcc  71940
tgcctcacct tcccaaagtg ctgggattac aggtgtgaac catcatgcct ggtctagaac  72000
attttcatta cctcaatcgg atccccgttt ggggatacat ttacattttt aatttttttaa  72060
tttttatttt ttttagagac gaggtctcaa tctattgcca aggtggtctt gaactcctgg  72120
tttcaagtga tcctcccacc ttggtttccc gaagtgctgg gattacaggc atgaaccacc  72180
atgcccagtc cattccaatt tttttttttct ttttttttga gatagagcct cactctgtcg  72240
cccaggctgg agtgcagtgg cgtgatctca gctcactgca acctccacct cccgggttca  72300
cgccattctc ctgcctcagc ctcccgagta gctgggacta caggtgcctg ccaccacgcc  72360
cggctaagtt tttgtatttg tagtagagac ggggtttcac cgtgttagcc aggatggtct  72420
caatctcctg accctgtgat ccgcccgtct cagcctccca aagtgctgag attacaggcg  72480
tgagccaccg tgcctggccc attccaattt tttacaaaag tgatttcaga cttataaaaa  72540
agctgcaaaa attcctgtgt tcttttcacc tagattctac cttttttttt tttttttttt  72600
ttgaggcgga gttttgctct tgtttcccag gctggagtgc aatggcgcaa tctcggctca  72660
ccacaacctc cccgtcccgg gttcaagcaa ttctcctgcc tcagcctccc aagtaattgg  72720
```

-continued gattacagcc atgcgccacc acgcctggct aattttatat tttttagtgg agaccaggtt 72780
cctccatgtt ggtcaggctg gtattgaact cccgacctca ggtgatctga ccacctgggc 72840
ctcctaaagt gctgggatta caggcgtgag ccaccgtgcc aggcccaccc agattcttct 72900
tagcacattt gaatgcagat tttgaatag ttatgatcta ttctcattga aaaagggaca 72960
tcatttgact tgacctccca ccagactctt cctttgaggt tggatggagg tgcttaatgg 73020
atgctgtgga tggtgtgtga atttccattg ggttgagtgg atgatgtatg tggaaggcga 73080
ttgggattta ctttgtcggt gtctccaaga ggtcccccac tgggctttgt caggtgctgg 73140
ggttggaggt caagaagtag ggcaacatct aaagcttcta ctcctgggca ctgtgaggtt 73200
tttataggtc ttttaaaaaa aacagtgaat aggccgaacg cggtggctca cacctgtaat 73260
cccagcactt tcagaggccg agggaggcgg atcacgaggt caagagatca agaccatcct 73320
ggcctcgtgg tgaaacccca tctctactaa aaatacaaaa attagctggg catggtggca 73380
catgtctgta gtcccagcta ctcgggaggc tggagcagga taatcgcttg aaccctggag 73440
gtggaggttg cagtgagccc agatttcacc actgcactcc agcctggcga cagcgaggct 73500
ctgtctcaaa aatatgttct tccatgagac agcgggcatt tggatgcctg atacaaaaag 73560
aggagggact atgtgctagt cagctttaga ctgagaagca gcagcaacca tggcaaaggg 73620
gaagcaaact ttcctgagtg gccttaataa tgttattcgt caggcagtgg ctcttaaaca 73680
ggggcttcaa gcagtgattt ttgacatgct cttctcctcc ccaaccactg gacatttggc 73740
aatgtctgga gacatttttg gttgtcacca ctgggagagg gtgctactgg tatctagtga 73800
atagagccag ggatgctgct aaacatccta cagtgcaaag ggcagctctc cacacaaaga 73860
atcatctggc ccaaaaatct ctattgctga ggttgaaaaa tactggtgta aggagacaag 73920
agttgtggtt agtcagaaag gatgacctgg cttgccgtgg attgtcttat aataatcagt 73980
tatctctttc cttgccttat tcctggtccc aacagagtga ggattggcaa gggggtttgg 74040
gaatatagtg ggaatgctgt gtagtgagag tgcaggcacg gcactccaga ctaccagtca 74100
cgagcttagc ctgtgtcctt ggggtaggag ctgtagaata agacctattt tgatatgtgg 74160
accagaataa gttctttaaa taatcaaagg taataaacat tcttaaaata tactatcact 74220
aaggtagtct gtcatccagc agaatgaggg agtagtcaga agattacaca tatttggcag 74280
caattactag aaaaaacaaa caagttgaga gttttcaaaa tagatgttac ttcatatttc 74340
agatagtttt ccagggaata ttgaaaatgc aagtgcagat tttcacatcc ttctttatac 74400
tgattaaaac atttgaatct attggatcat cttttcatta ggctttactt cacagggcca 74460
tctactggat cctgtatgct gatatagtta aggggactga cctcaaagta aaagatgcat 74520
atattttatc ttaatacaat atcactttgc tgtgaagggg agctgctgtg tatatagaat 74580
gctgtgtaat agtgattggg ctgttgggaa tcacattgga aatatcagta agcaactcat 74640
tttaactttt gttaacacag ttaagtgctg agcacctctt gtgtttgaag ctctgtgcta 74700
ggtaatatgt gttcattaat gaatgaaaaa acaatacaaa aattagccag gcatggtggc 74760
gtacacctgc agtcccagct actcaggagg ctgaggcaca agaattgctt gaacccagaa 74820
ggtggaggtt gcggtgagcc gagatcacgc cactgtactc cagcctggcc aacagagtga 74880
gactgtctca aaaaaaaaaa aaaaaaaaaa aaaagttttt tatttttaaa ttttttgttt 74940
tatttctttt ttactttttt ttcttttgag acagagtcac gctctgtcac ccaagctgga 75000
gtgcagtagc accatcttgg ctcactgcaa ccccccgcct gccaggttca agtggttgtc 75060
ctgcttcagc ctcccaagta gctgggacta caggtaccca ccaccacgcc cggctaattt 75120
ttgtattttt agcagaggcg gggtttcacc atattggcca ggctggtctc aaactcctga 75180
ccttatggtc tgcccgcctc agcctcccaa agtgctggga ttacaagcat gagccactgt 75240
gcctggcaaa atttttattt tattattatt attatttttt tttttttttt tgagatggag 75300
cctcgctctg ttgcccaggc tggagtgcag tggcgcgatc tcggatcact gcaagctccg 75360
cctcctgggt tcatgccatt ctcctgcctc agcctcctga gtagctggga ctacaggcgc 75420
gtgccaccac gcccggctaa tttttttgaat ttttttagta gaggcggggt ttcaccatgt 75480
tagccaggat ggtctccatc tcctgacctc gtgatccacc tgcctcagcc tcccaaagtg 75540
ctgggattac aggcgtgagc caccgctccc ggccaatttt tattttattt ttaattgata 75600
attgtacatg tttatggagt acccatgtta tgatacatgt gcacattgta gaataatttt 75660
taattgataa ttgtatacgt ttatggagta cccacgttat gatacatgtg tacattgtag 75720
aatgattgaa tcagactagt taacatatcc atcacctcat gtagttattt ctttgtagtg 75780
agaacattta aaatctcttt tagcaatttt gaaatagata caatacattg ttattaacta 75840
tagtcaccat gctgtgcaat agataactaa aacttcttcc tcctgtctga ctgaaacttt 75900
atactctttg actaacattc tcccgttctc ctccacccgc cttctccacc cacggcctct 75960
ggtaaaccac cattctgctc tctacttctg tctgaatatt tgattttttt agattgcaca 76020
tgtgagatca tgcagtattt gtctttctgt acctagttta taatacactt agctaagtgt 76080
ccttcatgtt tttccacatg tcgcaaatgg cagaatttcc ttcttttttta aggccaaata 76140
gtatttcatt gtgcttacat accacatttt cattatccat tcattcattg atgggcaatg 76200
gatgaatgga tatcatggct attgtgaata gtactgcagt gaacatggga atgcaggtat 76260
ctctcagaca taatgatttc agtttcattg gatatatact gtacccaaaa gtgggactgc 76320
tagatcatat ggtgattctc gttttagttt tttttttttt aagaacctcc atacagtttc 76380
caaaatatct gtactaattt acattcccac agtgtaaagg gttccctttt ctccatatcc 76440
tcactaacac ttgttaccgt tcatcttttt tatagtaacc atgctaacaa gtatgaggtg 76500
acatctcatt atggttttgt ttgtttgttt gagacagtgt cttgctgcat cacacaggct 76560
ggagttcagt ggcgtgatcc cagctcattt gcagccttaa cttcctgcac tcaagcagtc 76620
ctcccacctc agcctcccag gtagctggtg tgtcaccatg cctagcgttt tttttttttt 76680
tttttgaga cagagtctcg ctgtgttgcc caggctggag tgcagtggta tgacctcggc 76740
ttactgcaat ctctgcctcc cgggttcaag taattctcat gcctcagcct cctgagtagt 76800
tgagattaca ggcatgtgcc accacaccca gttaactttt gtatttttag tagagatgag 76860
gtttcattat gttgtccggg ctggtcttga actcctaggc tcaagtgatc ctcccacctt 76920
ggtttctgaa agtgctggga ttaccagcat gaaccactat gcccagctcc ttatggtttt 76980
aatttgtaat tctctgataa ttattgatgt tgaacatttt gtcatatatt ttttggcaat 77040
tttttttctt cttttaaaaa ttttgttttt agccataagg ccaggaatgc acgtatgtct 77100
tctttcaaga aatgtctggg ctgggcacag tggctcacgc ctgtaatccc aacactttgg 77160
gaggccgagg cgggtggatc acgaggtcag gagatcgaga ccatcctggc taacatggtg 77220
aaaccccgtt tctactaaaa atacaaaaaa attagctggg tgtggtggtg ggcgcctgaa 77280
gtcccagcta tgtgggaggc tgaggcagga gaatggcgtg aacccaggag gtggagcgtg 77340
cagtgagcca agatcgcgcc actgcactcc agcctgggcg acagagcaag actctgtctc 77400
aaaaaaaaaa aaaagaaaaa gaaaaaaaaa tgtctattca ggtcctttgc ccattttta 77460 atagggttat ttgttttcat tattgagtag tttgagttct ttgtacattt tggatattag 77520
ccctttatca gatggaagat ttgtaagtat tttctctcaa tctgtgcatt gtttcttcac 77580
tttgttaatt gtttccttgc tttgcagaag ctttttagtt tgacgcaatt ccatttgtct 77640
gtttttgctt ttgttgcctg gcctttgggg gtcatgcaca agaaatcatt gcctagacca 77700
gtgttgtgga gctttccaac tatagtttct tctagtagtt ttacaatttc tgttcttaca 77760
tgaagctatg aacagttcct gtatagttat ccctgccacc cttctcccaa cattacatac 77820
acagcctccc caactatcag catcctgcag tgtagtgtat atgttacaat cagtgaagca 77880
acattgatac atcattatca agggttcact ctgggtgttg taccttctat gggtttccac 77940
aaatgtatgt catatatcca ccattatagt atcatacaga atagtttcat tgccctagaa 78000
accctctttt ctccacctgt ttgttctttc ctcttgcaaa cccctgcaac cactgaactt 78060
tttattgtcc gtgtagtttt gccttttgca gaattttata tagttggaat tggacaatat 78120
gtagcctttt cagattggct tctttcattt agtagtacat ttctctatgt agtctcattc 78180
ctctatgtct ttttgtggtt tgatagctca tttcttttta gcactgaata atatcccatt 78240
gtatggatat atcacagttt attcattcac ctactaaatg acattttggt tgcttccatg 78300
ttttgacagt tacgaataaa gctgcaataa atatccatat gcatgttttt gtacggacat 78360
acgttttcaa ctagtttggg taaatacaag gggcatgatt actggatcgt atggtaggag 78420
tgtgtttttt tttttttttt tttttttttt ttttgacacg gagccttgct ctgtcaccag 78480
ctggagtgca gtggtgcgat ctcggttcat tgcaacctct gcctcccagg ttcaagtgat 78540
tcttctgcct cagcctccca agtagctggg actacaggtg catgaccatg cccagctaat 78600
tttttgtatt tttagtagag acagggtttc aacatgttgg ccaggatggt cttgatcttg 78660
tgacctcgtg attcgtccac ctcggcctcc caaagtgttg ggattacagg cgtaagccac 78720
tgcacccagc ctgtagagta tgtttaattt tgtaagaaac tgtcaaacag tttttccaaa 78780
gtagcgatta caatttgcat tgctaccagc aatgaattag agttctgttg ctctgtatcc 78840
ttgccagcat ttggatggta gccatttttta tttttattta tttatttttt ttttttgaga 78900
caaggtcttg ctctttcacc caggctggag tacagttgga cgatctcagc tcactgcagc 78960
ctccgcctcc caggttcaag ttattctcct gcctcagcgt tctgcatagc tgggattaca 79020
ggcacgcacc accacaccca gctaattttt gtatttttag tttcaccatg ttggctaaga 79080
tggtcttgaa ctcctgacct taggtgatct gccccgcctt ggcctcctga attgctggga 79140
ttacaggcat gagccaccat gcctggcctc ctttgggtat ttctattgga cagtcatgtc 79200
attcatgaat aaagacaatt ttatttcttc ctttctaatc catatacctt ttatgtcctt 79260
ttcttggctt attgcactag ctaggatttc tagtacaatg ctgaaaggag ctgtctttct 79320
cttcttttct ctcctttcct tgccttttcc ttttcttctt tttctttctt ttcttcctat 79380
agagataggg tctcgctatg ttgccaaaac tggtctccag ctcttgggcc caggtgatcc 79440
tcccacctca gcctcccaaa gtgctgggat tacaggtgtg agccaccaca cctagctgaa 79500
aaggagctgt tgagaataca tccttgtctt gttcctgatg ttagtgggaa gaaagcatct 79560
agtctctcac cataagtgtg atgttagcta taggtttatc aagttgagga ggttcccctc 79620
tgttcctagt ttgctgagag gttttttttt ttaaatcatg aaaggggatt ggatttttgt 79680
caaatgattt ttctgcatct attggtatgt tcatgttaat ttcttcttca gcatgtcgat 79740
gtgatggatt acattaattg attttttttt tttttttag atgcagggtc tcactctgtt 79800

-continued gcccaggcta gagtgcagtg gcacaatcac agctcactat aacctcaagt tcctcagctc 79860
aagcaacttt cccatctcag ctttccaagt agctaggact acaggcacat accaccatac 79920
ccatctagtt ttttaaaaca ttatttgtaa agatgaagtc tctctatttt gtccaggctg 79980
gtctggaact cctgggcggg ctcaagcagt cttcaccttg gcctcccaat ttgtttggat 80040
tacaggtgtg agccactatg cccagcctca tttttgttat tagtaatttg tatcttcttt 80100
ctttttttct tagactggtt aaatgtttat caattttatt gatcttttca aagaaccaac 80160
ttttggtttc actgatttat ctctattgat ttactgtttt caatttcatt gacttcagct 80220
ctaattttta ttattttctt ctgcttactt ttgatttaat ttgctctttt actggtttcc 80280
taaagtggaa gctcagatta ttgattttta gatttttctt ctcttttaat atatgcattc 80340
agtgctataa atttccctct cagcactgct ttttgtgtat cgcacaaatt ttgataagtt 80400
gtgtttttca ttatcgttta cagttgtgtg ttaatcccca tacagttaat gatggggata 80460
aattctgaga aatgcactct taggcaattt tgtctttgtg caaataccat ggagtgtaca 80520
tacacaaacc taaatggtat agcctgctac ccacctaggc tatatcattt agcctattgc 80580
tccttaactg caaacctgta caacttgtta ccatattgta tatgataggc agttgtgaca 80640
cagtagtatc taaagataga aacggtacag tgaaaataca gtatttcagt attttgggac 80700
caccatcata tatgcaagcc cattgttgac tgagatgtca ttatacagca tctgaccata 80760
attcggaata tttttaaatt cctcttgaga tttcttcttt agcttgtgtg ttatttagaa 80820
gtatgttttt aaatctccat atactttggg atttttacaa ctatattact gttactgact 80880
tctagtttaa ttctattgtg atctgagagc atatattatt ttttctgtca ttttaaactg 80940
gaaaaggtat gttttatggc ccataatgtg ctgcgtgagc ttgaagagaa tatgtagttc 81000
gctgttgctg gatgaaatag tctacaaatg ttgattagat tgctgctgtt attttgatgc 81060
gtatccttcc agatttttct atgcatgtat catctatctg tgtatctatc tgtaggatag 81120
gagagtcttg tacaaatggt tttataactc tttaacttca aatattgtgg acttacttcc 81180
ttgtcattaa atacatttaa ggctgggtgc agtggctcat acctgtaatc ctagcacttt 81240
gggaggccga aacaggcaga tcacctgagg tcaggagttt gagaccagcc tagccaacat 81300
gttgaaaccc cgtctctact aaaaatacaa aaattagctg ggtgtggtgg cacacgcctg 81360
taatcccagc tgctcaagag gctgaggcac gaaaatcggt tgaacccaag gaggcggagg 81420
ttgcggtgaa ccaagattgc gccagtgcac tccagcctgg gtgacagagc aaaactttgt 81480
ctctaaataa ataaataaac aaataaaata catacctatg tacatacata cattttaaga 81540
atcattttga tatattcatc tccatactga ggaatttaag tgcttttttt tttttttttt 81600
tttttttttt tttgagacag agtctcactt tgttgcccag gctggagtgt ggcggcacga 81660
tcttggctca ctgcaacctc tctacctcct gggttcagga aattctcctg cctagccggg 81720
tgagatttcc tctttagctt gtgtgttatt tagaagcatg tttttgtacc tatcgtagct 81780
tctctagaga agggaggtag gagaatcgct tgagcccggg aggtcaaggc tgcagtgact 81840
gacccatgac catgccactg cactgtagcc tgggtgacag agtgagcccc tgtctcaaaa 81900
aggaaaaaaa agaaatcagc atattttatg acttaataaa tgtattcaaa ttccatccag 81960
atatttccta atttattatt ttactaacag tgtttgagag cacttgtctc ccctgccttc 82020
caaccagtgt caagtgtatt ttaacaaaat acttgtattg ggtagtagta catggttggt 82080
tgttactctc taatcgcctg ttgtgtttga aatatttaat aattttttta atgttgctag 82140
tgtagtgaag aagataatga tttagttttt cttctttctt tttttttttt gagatggagt 82200

```
ttcacccttg ttgcccaggc tagagtgcaa tggtgcgatc tcagctcacc aaaacctctg  82260
cctcccgggt tcaagtgatt ctcctgcctc agcttcccga gtagctggga ttataggctc  82320
atgtcaccac gcctggctaa ttttgtattt ttagtagaga cagggtttct ccatgttggt  82380
caggctggtc gcgaactccc gatcttaggt gatctgccta ctttggcctc ccaaagtgct  82440
gggattacag gcgtgagcca ccgcacctga caaatgatgt agtttttctc ccttaggtta  82500
ttagtaggca gaatagtttt acatttgatt attagttatt catatttctt ttgtgacttg  82560
ttggttctta atatatctat tcagccaaaa atgaaaaata ggatatctta gcctgtctag  82620
tcttaaggta aatatatgtg ggatataagg gagtttgggg gctgggcgca gtgactcaca  82680
cctgtaatcc cagcacgttg ggaagctgag gtgggctgat cacttgagcc caggagttca  82740
agaccagcct gggcaatgta gcaaaacccc atctctacca aaagtacaaa aattagccag  82800
gtacagtggc acatacctgt attcccagct actagggagg ctgagatgga aggatagctt  82860
gagcccaaga ggttgaggct gcagtgagct ataagcatgc cccactacat tccagcctgg  82920
gtgacagagc gagaccctgt ctcaaaaaaa agattttttt gaaaagttga aaatgagtat  82980
attcgctgaa tacgagatga gttttcccaa gaatttatcc ctcagaatct ttcacgttct  83040
tcctcctcct tctcctcctc ctgctttctt cttcttcttt cttctttttc tgtttcttct  83100
tcttgctttt ataaagtctt agctcctgtg gagttttctc tcagttactt cttatttatt  83160
tatttgagac agagtttcac tcttgttgcc caggctggag tacagtggcg cgatctcggc  83220
tgactgcaac ctccgcctcc tgggttcaag ctattctcct gtttcagcat cccaagtagc  83280
tgggattaca ggtgcctgcc accacacctg actaatttct gttacttctt ttgagccaca  83340
aagtatttga aaaagatgca ttaagtagtg accgcagtcc gtgctagtat tgggtgctta  83400
cagaggtcta gtagaatacc gtgttttaaa aggaggtgaa tttaataatt gctgtgatta  83460
ctctggcatt atacgctcac aaataaaatg tttggtgatt tttttttttt ttttttttgg  83520
agacagattc ttgctctgtc acccaggctg tgcaatgatg tgatctcagc ttactgcaac  83580
ctccgagttc aagtgattct cgtgcctcag cctctcgagt agctgggatt acaggcaccc  83640
gccatcatgc ctggctaatt tttgtatttt tgtagagatg ggtttcacc atgttggcca  83700
ggctggtctt gaactcctga cttcaggtga tccacccatc tcagcctccc aaagtgctgg  83760
gattacaggt gtgagccact gctcccagcc gggtgtgata tttttaataa aacaagtatt  83820
caaattcact tacaggacca atgaaagaat cgtttgtcgt aattttatgc caaagggtac  83880
ttgtggctta agataaactt cccataatga cattatccac agattcaaaa agtagtttat  83940
cttaaacaac ttctgtgaca ttttaaaatg atgtggctta gaaaattgct aggttatcta  84000
aaatggctct attgatgatg taaatgtagc acatgaagag cttgaataaa atagactttt  84060
gaagtgtgca aatggaaaga acagtccttc taaataatta tttcccctcc cttttattga  84120
cgtatacata cagaaaagat atcatgtcgt aagtgtattg cttagtgaat tactccaaag  84180
ttggatatac ctggttaacc accacctgaa tgaaaaaaac agaacactgc ttcatatgga  84240
gaagcccctc ctgcccctcc tggtcattgt ccttttcatc cctcccacag gtagtcactg  84300
agttctaata ccacagagtc ttttgacttt cttttgagcc ttatgtaatt agaatcacaa  84360
aagatgtatt cttttgcctg acttttatac ttagtattgt ttttgaaatt catcttgtgt  84420
gtaactgcga tttgttcatt ttcattgctt agtgaattat tccaaagttg gatatacctg  84480
gttaaccacc acccgaatga aaaaaacagt ttttggccgg gcacgatggc tcacgcctgt  84540
```

-continued

```
tatcccagca ctttgggagg ctgaagcgtg cagattacga ggtcaggaga tcaagaccat  84600
cctggctaac acggtgaaac cccgtctcta ctaaaaatac aaaaaattag ctgggcgtgg  84660
tgacgggccc ctgtagtccc agctactcag gaggctgagg caggacacct gtaatcccag  84720
ctacttgaga tgctgaaaca ggagagtggc gtgaacttgg gagatggagc ttgcagtgag  84780
ccgagattgc gccactgcac tccagcctgg gcgacagagc aagactccgt ctcaaaaaac  84840
aaaaaacaaa aaacaagaaa acagttttcc agtctaagaa tgtattacaa tttattcaaa  84900
ttccactcta gatggactgt gggttttttt ttttccccca tttggagcta tggcaaatga  84960
tgtttttca aagttgttat ttctcagcca ggcgcggtgg ctcacgcctg taatcccagt  85020
actttgggag actgaggtgg gcagatcacc tgaggtcaga agcaagacca gcctggctaa  85080
catggcgaaa ccccgtcttt tctaaaaata caaaaattag ccaggtgtgg tgatgggcac  85140
ctgtaatccc agctacacag gaggctgagg caggataatc acttgaaccc aggaggtaga  85200
ggttgcagtg agctgagatc acaccactgc actccagcct gggtgacaga gcgagactct  85260
atctcaaaaa agaaaacaaa acaccacgga attgttattt ctcttggcga ataggtagat  85320
gcacttattc ctgttaatat atacctacct gtgaatgtgc ttgttggatt ttctatgtat  85380
cttctgtctg ccacctagaa atttaacctt ttatatatat acaactttaa tttttttttt  85440
ttttttttta agagacaggg tgtcactatg ttgcccaggc tggttgggaa ctcctggcct  85500
taagccgtcc tcctgcttca gtctcccaaa gtgttgggaa tataggcgtg agccactgtg  85560
ccccactgtt caagttttca ttgattgctg cctacatata gttgttcaac agctattgat  85620
tccccctgct ctgtatatat gtctcctagt gtaggtatca gggttacagc agtaattaag  85680
accacattat ttcattttat catttaaata tataagacta attgataaat taagtataga  85740
actttgacca acatggtgaa accccatctc tactagaaat acaaaaatta gctgggtgtg  85800
gtggcagacg cctgtaatcc cagctactca ggaggccgag gcagaactgc ttggagatgg  85860
aggttgcagt gaaccaatat cagaccacta tactccagct tggatgacag agggagactt  85920
tgtctctttt tttttttctt tttttttgag acggaatctc gccgtcttcc aggctggagt  85980
gcagtggcac gatctcggct cactgcagcc tccgcctccc gggttcaagc gattcttcta  86040
cctcagcctt ccgagtagct gggattacag gcacccacca ccatgcccgg ctaatttttg  86100
tatttttagt agacagggtt tcaccatgtt ggccaggctg gtctcaaacc cctgacctca  86160
agggatcaac ctgctttggt ctcccaaagt gctaggatta taggcgtgag ccactgtgcc  86220
cggccctttt tttttttttt ggagacagaa tttcgcccag ttgccagact ggagtgcagt  86280
ggcacgatct cagctcactg caacctctgc ttcatgggtt caagccattt tcctgcctca  86340
gcctcccaaa tagctgggac tacaggcatg caccaccacg tctggctaat tttttgtatt  86400
tttagtaaag ccagagtccc aaagtgctgg gactaggcag gcgtgaacca ccacgcctgg  86460
ccaagactct gtctctcaaa aaaaaaaaaa agaaaaaaaa atataggact ttgggaggcc  86520
gaggcaggca gatcacctga ggtcaaaagt ttgagaccag cctgactaac atggtgaatc  86580
cccatatcta ccaaaaaata caaaaattag gcaggtgtgg tggcgtgcac ctgtagtccc  86640
agctattggg gaagccgagg tgggagattg tacctgggag gcagtgagca gagatcgcac  86700
cactgcactc cagcctgggt gacagagtga gaccttgtct caccaaaaaa aaaaaaaaaa  86760
aaaaaatagc ataggtaggc atttgatgat ttgatgattt cattcgcatc cctaaaagtt  86820
tatttgttcc tgggtcgtca gatagctttt tggccatctt cctgttgaga aaattgatgt  86880
acccttctgg agtcctccaa ttttccatta taatatggta agtgggagct agagctttgg  86940
```

gtaagaattg ggatgtgata aggaggatga gttttgcagt ggtgtgcatg gttaggagga 87000
gaaaaagctg gaggcagagt gttcacttag aggcttgggg taggaggggt aggtttaagt 87060
ggtgctcatc tgggccagaa tagggcaaaa agggaagaat gaaataacca gatgtctttg 87120
ctttgtcagt agtcttgcag ccctgaaagc tttttttgtt gtgttatatt tgttgtaatt 87180
gaggtataat ccacataaca taaaacttac ctctttcaag tgtacaattt agtagttttt 87240
agtatattca taaaattgtg caactatcac cactgatacc agaacatttc tgggaacaaa 87300
aagaaactat atatccatta agagtcactc tccattttct cctacttcct tctctacccc 87360
cagtcatctg ctagtcggct ttctgtctct atagatttgc ctgctctgga tatttcatat 87420
aaatggaatc atataccata tggtcttttg tgactggctt cttttactta gcctaatgtt 87480
tttaaggttc atccatgtta tatgaatcag tacttaaatc atttataggg ttgaataata 87540
ttccatcata tggatatacc acattgtctt tatctgctca ttaattggta gacatttagg 87600
ttgtttccac ttttgtttat tatgaataat actattcaca ttcatgtaca aggttttgtg 87660
tggacacatt ttcagttctc ttcgatatat accaaagagc cacaatgcta aaacttccag 87720
ctttttacca gctatcccca gatgcgtagc ctagtaagcc ccatgttgga gtggtgtagt 87780
gttgaaaaca tggcatactc atacattaga taaccaggtt tcaattctgg tttggaagcc 87840
tttggatatt tgcattaccc atttgaattc tctcttgggc tgtgtttggt ttggggtttt 87900
gtacttgttt tttttttttt aactagatgt tttgaggcac ttggtactgt ggacatgtgt 87960
cagtcttaaa tatttgggtt ttgagcatat caagggcttg gtttgcagtt gacagttgaa 88020
tagcagtctt cttccttcca ttccttacag attctcctgt tcagagtcaa ccattgaata 88080
gcatatttat tgtttctgcc tgtgtgtctg ttagtgctca tatggtctag ttcctgagtt 88140
aagaagtata gggtagtggt catctttttt ctttgacttg attcctgcgt actgtgaatg 88200
cagagcaatg caggatatgt tgggttttct acaaacagag catcagccca gagacatgtt 88260
tgcatttgtt tctgtcaggt ttcctggctc aactggcacc ctttaaggcc agagaacgtt 88320
agtttaggca cttttcctag taaaatactt cttgtggctc ttcctgtgta cttggaataa 88380
aggaggcatt ccattgttag acatgcttgg gtagttcagg gtaatcttag agtcatgaga 88440
gatatgatat aaaggaataa ctagctaaac cagaaaaaat gcctgggtaa tgactagcaa 88500
ataggtggtc aacagatgtc ctcattagat tgaaaggtcc atgaaagcag ggactatttc 88560
ttttctttac tgcttaaaaa ggttagaact ggacctggca acatatgatg agctaaataa 88620
atacatattt gtgaattggg ttaacacata ttgcataaag tggttttggc tctgttttat 88680
tcttcataag ccctagtgat ctttttaatt tctgtaaaat gtggtcttga cccccccaac 88740
ccaagtgacc tccttatttg ctaggctctg atatttctgt taggtttcta ctgtattttc 88800
tgagatagca attagtagat actatttctc ctttgatgga gctagccata tattcttgtt 88860
tgttcatttt agctttcaaa tttctgtctg attcttgttc ttttactctg gaatgtagtg 88920
aatggaatga cttggaaggt acaaggtagg tcagtttagg ttgtctaggg ccttgcattt 88980
aaaagtttaa tttgatgaca tggtggatta caagaatgta acagtatcaa aatgatacta 89040
tcttcttgtg gtggtatgta gacttaaaaa gagaaactgc agagaaaagg gtcccttagg 89100
atgtagagca gcagttgata tgtgagaagt tgatgccttg cattagggat taggagtaga 89160
tgtggaagga agagatcagg tttgaaagag tttaaacaaa gaatctctag gatttgataa 89220
cactggatat cagaggggaa ggtacaagag agagggcaga atcaaaggcc actcagaggt 89280

-continued taaaggaatc ataccggttt ggcatggtgg ctcacgcctg tcatcccagc actttgggag 89340
gctgaggcgg gcagatcacg aggtcaggag ttcgagacca gcctagccaa tatggcgaaa 89400
ccccgtctct actaaaaata caaaaattag ctgggcgtgg tggcgtgtac ctgtaggccc 89460
agctactcag gagactgagg cagaagaatc acttgaaccc aggaggcaga ggttgcagtg 89520
agccgagatc gtgccactgc actccagcca gggcgacaga gcgagactct gtctcaaaaa 89580
ataataataa taataaataa ataaaggagt aattccaaca cttgggaggc cgaggcagga 89640
ggattgcttg agcccaggag ttcaagacca gcctgggcaa catagtaaaa cctcatcgct 89700
ataaaaattt tttaaaaaga aatttagcca ggcatggtgg tgtgcccctg tagttcccat 89760
tactagagag gttgaggtgg aaggatctct tgaacccaag aggtcgagag tacagtgagc 89820
catgatgcac cagggcactc cagcatgggc aacagagtga gactttggga ggccatggca 89880
gaaggattgc ttgagcccag gagttcgaga ccagcctggg caatgtagtg ggaccttgtc 89940
tctataaaaa ttttacaaat atatataaaa gctgggcatg ggggcacgtg cctgtagtcc 90000
cagtgactgg tgggtggggc gggggtgagg tgggagaatc acttgggccc aggaagtcga 90060
gattgcagtg agccatgatc atgccactgc tctctagcct gggtgacaga gtgagactct 90120
ttttgtctta aaaaaaaaaa aaaaaaaaaa aaaaaatggt tgtaccttga acagatacaa 90180
agcatgtaga agaggaaagc atttgggagg gagaataatt ggttggatac attaagtgtc 90240
aagtgacagt aggacctcta gaaatacaca aacagagctc cacaggtttt ttcattgtca 90300
tttcttatac cttttgttcc actacctact tttttcctac aactttctgt ttattttata 90360
gtttatgaat tttaagcaaa atacttcctt ctgcctctta ccagtaattt tcaaaagcgt 90420
ctgtattggt taggattaga tttggctggg aatgacagaa aactaaaaat aaaagcagtt 90480
taaacaagtt tatttctctc taatgcaaat gaagtttgag ctgtccaggc tttcttatgg 90540
tggtttggtc atgatcaggg acccaggttc tttcaaccat gtagccccat cttaacatgt 90600
gatttctatc ttattgttca agatggctat ttgagtgtca gttatcagtt ttatttagca 90660
accaatggga aggaaggggg atgaaaatgg gccctgtctt taaggatact tcctggacat 90720
agtgagtaga aggatggtta ccagagtatg ggaagggtag ttagggggct gggggaaagg 90780
tgggaatggt aaaggggtat aaaaaaggta gaatgagtaa gaccatcaga gaaatgcaaa 90840
tcaaaaccac aatgatatag gtggctcacg cctatatgta tctcacacca gttagaatag 90900
tgatcagtaa aaagccagga aacaacaggt gctggagagg atgtggagaa acaggaacac 90960
ttttacactg ttggtgggac tgtaaactag ttcagccatt gtggaagaca gtgtggcgat 91020
tcctcaagga tctagaacta gaaataccat ttgacccagc catcccatta ctgggtatat 91080
acccaaagga ttataaatca tgctgctata aagacacatg cacatgtatg tttattgcgg 91140
cactattcac aatagcaaag acttggaacc aatccaaatg tccatcaatg atagactgga 91200
ttaagaaaat gtggcacata tacaccatgg aatactatgc agcaataaaa aaggatgagt 91260
tcatgtcctt tgtagggaca tggatgaagc tgtaaaccat cattctgagc aaactatcta 91320
agggcagaaa accggacacc acatgttctc acttatacgt gggaattgaa caatgagaac 91380
acttggacac agagcgggga acatcacaca ctggggcctg tcgtggggtg ggggaggggg 91440
gagtgatagc attaggagat atacttaatg taaatgacga gttaatgggt gcagcacacc 91500
aacatggcac atgtatacat gtgtaacaaa cctgcacatt gtgcaccatg taccctagaa 91560
cttaaagtat aaaaaaaaag acctactatt tgataccaca atagggtgag tatagtcaat 91620
aatgacttaa ttgtacattt taaaataaca taaaaagaaa aaaataaaat aatgcagagt 91680

-continued

```
ataatttgat tggttgtaac tcaaaagata aatgcatgag gggatggata ctctattccc  91740
catgatatgc ttatttcaca ttgcatgcct gtatcaaaac atctcctgta ctccataaat  91800
aaatacacct actatgtatc cacaaaaatt tcttaaaaaa ggatactttt gagcgtttca  91860
agcattactt ctagttatgt tcagttgatc agaatttagt catagccaca cttcagcttc  91920
aaggagggct gcagaacgtc tttattttag gcagctatgt gcccagttaa aaagcagatt  91980
ttctcccaag gtaaagagag cagataggca ttaggagact actagtagtc ttttaatttt  92040
ccaggccggg cacggtggct cacacctgta atcccagcac tttgggaggt cgaggcaggc  92100
ggatcatgag atcaagagat ggagaccatc ctggccaaca tggtgaaacc ccatctctac  92160
taaaaaaaat acaaaaatta gctgggcgtg gtggtgcgtg cctgtagtcc aagctactca  92220
ggaggctgag gcaggagaat tggttgaacc caggaggtgg aggttgcagt gagcgaaggt  92280
cgtgccattg cgctccagcc tggcaacagg gcgagactcc atctcaaaaa aaaaaaaaaa  92340
aaagcaggga tttgctccca aggtaagaga gcaaatagac attgggagac tattagtagt  92400
ctcttaattt cccagaatga gaaccagatt ctttccggtt acagaactcg tttctccaaa  92460
cattaattat tcttataata attttaaaaa atactaaata tataattatc accagccaaa  92520
tgcttctttt aagaaataga gacagggggc cgggcacggt ggctcacgcc tataatccca  92580
gcactttggg aggccgaggc aggtggatca cctaaggtca gagttcgaga ctagcctggc  92640
caacatgggg aaaccctgtc tctactaaaa atacaaaatt agccgggcat ggtggtgcat  92700
gcctgtaatt ccagctattc gggaggctga ggcaggagaa ccgcttgaaa caaggaggca  92760
gaggttgcag tgagccgaga tcgtgccatt gcactccaac ctgggcaaca agagcaaaac  92820
tccatctcaa aaaaaaaaga aaaagaaata gagaagagac agggaagcca agctcatgcc  92880
tgtaatcaca gcacttcggg aggccaaggt gggcagatca cctgaggtca ggagtttgag  92940
accagcctgg ccaacatgga gaaacccagt ctctactaaa aatacaaaaa ttagctgggc  93000
atggtggtgc ataccggtaa tcccagctac tcaggaggct cagacaggag aagtgcttga  93060
acccgggagg cagaggttgc agtgagccaa gactgtgcca ctgcactcca gcctgggtga  93120
cagagtgaga ctctgtctcg aaaagaaaaa aaagaaaaag agacggggcc tcacatatgt  93180
acagtggtat gatccgtagt tcactataat cttgagctcc tgaaacctga tgctttaaaa  93240
caaaacagta caaaactact aaatttataa ttaaatatat aaataaaata taataaaaat  93300
gttcacttct gtttttatat tctttaaaat gacccatagg ctggtgatta gtaactaaag  93360
catatgctgt ggaacatcca gcactgatgt aagtatatga agtttgaatg ccaggtcagt  93420
agattcagaa gctaagttac tgtatggtaa agaccatgtt ttgcctgagc agctttggat  93480
atggtttttt cttttttttc tttttttgag atggagtctc gctctgtcac caggtggagt  93540
gcagtggcgt aatctcagct cactgcaagc tctgcctccc aggttcaagt aattctgcct  93600
cagcctcccg agtagctggg gctacaggtg cataccacca cgcccagcta atttttgtat  93660
ttttagtaga gatggggttt taccatgtag gccaggatgg tctcaatctc ccgacctcgt  93720
gatccccctg ccttggcctc ccaaagtggt aggattacag gactgagcca cagcacttgg  93780
ccggatatag tttttctatg tgtgtttttc ctaaacctta ttatacataa acatacaagg  93840
acagagatca aatgccccct gtctagaaac accatttctg ccaggcccat cttaataaga  93900
ctatgtcttc tttttatttg tttctatact tccttttttt tttttttttt tctgagacag  93960
ggtttcactc ttgttgccac cacactcagc taatttttgt gtttttagta gagacaaggt  94020
```

ttcatcatgt tagccaggct ggtctggaac tcctgacctg aagtgatccc cccacctcgg 94080
catcccgaag tgctgggatt acaagcgtga gccatcacgc tcagcctaga cttcttagtg 94140
tggtgtttca ttttcttttc tctggttccc atccagcttt gttcattgta catgctcacg 94200
gtgcacttta tatgacctgt tggcatattt tctcactctc tttttgtctc tcttcacttc 94260
cagcagtgtt aaataactct ttccattctg cagttttcct gataagaatt tcagatggtg 94320
gtggccaggt gcggtggctc acgcctgtaa tcccagcact ttgggaggcc aaggcggcag 94380
atcacttgag gtcaggagtt tgagaccagc ctggccaaca tggcgaaacc ccatctctac 94440
taaaaataca aaagctagcc gggtgtagta gcgcatgctt gtaatcccag ctactaggga 94500
ggctgagtca ggagaattgc ttgaacccgg gaggcggaag ttgcagtgag ccgagatcac 94560
aacactgcac tccagcctgg gcgacagagc gagactccgt ctccaaaaaa aaaggcaatg 94620
aataattgga caaggaacca aaacttttat tctgaaaaga gaaaattcca gtctatagca 94680
agggcagttt tccttctaag gaacagtact gatatatcat ggctaaagaa gcaggctcag 94740
cttctttgtc cctttcacta atttgctatg gcttctaaca taggctagga aaagaaaaaa 94800
atctgtttct ctttctcctc tcctctcctc tcctcttccc tctcctctcc tctcctctca 94860
tcttccctcc cctcccctcc cctctcctcc cctactcccc tctcctcccc tcccctctct 94920
ttatctgtct atctgctaag ggcagcaaat ctgtatccat acaggtctgc agcaacttca 94980
attcttgcct cctcagaaga aacaatttga ctgagggtca taaggcagaa ggagagacca 95040
aggcaagttt tacaacagga gagagtttat ttaaaagctt tagaacagga atgaaaggaa 95100
ggaaagtaca cttggaagag ggccaagcag gtgacctgaa agacaagtgc accaacacat 95160
agcctttcaa caggatagag agcagttaaa actgccctgg aaaagccaga cttacaggct 95220
actctgtata atagaaactt caggacaggg tgcggtggct cacacctgta atctcagcac 95280
tttgggaggc cgaggtgggc ggatcacgag gtcagaagat cgagaccatc ctggctaata 95340
cggtgaaacc ccgtctctac taaaaataca aaaaattagc cgggcatggt ggcgggtgcc 95400
tgtagtccca gctacttggg aggctgaggc aggagaatgg tgtgaacctg ggaagcggag 95460
cttgcagtga gctgagatca tgccattgca ctccagcctg gtcgacagag ccagactccg 95520
tctcaaaaaa aaataaataa aaaagaaact tcagcatgct tcctaatact gttcaaaggt 95580
ctcccttttt atgattttat ttaaaaaaat tttttttttt tgagacagag tctcactctg 95640
ttgcccaggc tggaacgcag tggcgtgatt tcggctcact gcaacctccc ctcccaggtt 95700
caagcaattc tcgtgcctca gcctcctgag tagctgggat tacaggtgcc caccaccatg 95760
tctggctaat ttttttgtat ttttaataga gacagggttt caccatcttg gccaggctag 95820
tcttgaactc cacaccttgt gatccaccca ccttggcctc ccaaagtgct gggattacag 95880
acgtgagcca ctgcgcccag ctcaattttt atatttttgg tacagaccag gtttcactat 95940
attggccagg ctgttctcaa actcctgacc tcagttgatt cgcccacctc agctcccaaa 96000
gtgctgggat tacaggcatg agccactgcg cccagcaggg tctccctttt taaacgtatt 96060
ttctttttat agcctacaaa ctacaagaga tgccttttaa taaactggat ggtatgtctt 96120
aacgtctgat ggagtttaaa ggcatccaag ggttacgtct gtgatagatt gccaaggcat 96180
acaggtctga tcaggagagt ttcttgatga ctagctatgg gctatgcctt tgtagcacat 96240
gatcccaact ccagcaggga tatagttagt gacatgctgg ctttgtcttc tccctaactc 96300
ctggattact acaaatttct tcttcgtgca ggaatcattc cctcactcta tacatatctg 96360
ctgttaaaaa aaaaaaagtt aagatattat agccattata ttgtagcagc catgatatta 96420

-continued

```
tagctcagta aatgctgctt tccaaatatt ggctaattta accatagcat gtcttcaatg  96480
ttagaagcca gccctcattt ttatcaaggg ctgaagtttg ataattcttt gtgttatttg  96540
cttgtgaaaa taagtagaac aaaaaggatt agggacctaa ccttgtatcc catgtatccc  96600
agtgaacctt ttctgactta aagcttcctt tcttttttt tggagatggg agtcttgctc  96660
tgtcgcgagg ctagagtgca gtggcgcgat cttggctcac tgcagcctcc gcctcctggg  96720
ttcaagtgat tctcctgcct cagcctccca agtaattggg actacaggct catgccacca  96780
tgcccagcta attttttttt taatttttag tagagacggg gcttcaccat gttggccagt  96840
atggtctcga tctcttgacc tcgtgatcca tccaccttgg cctcccaaaa agcttccatt  96900
cttagtcttg gtacttctaa gtggcattgg gtcaatagct ttctgcctaa gaagagaatt  96960
ggctgggcat gatggctaac acctgtaatt ccagcccttt gggaggctgt ggcaggagga  97020
tcatttgagc ccaggagttc aagaccagcc ggggcatcat aggaagaccc catgtctgca  97080
taaaataaaa taaattagcc agacttggtg acatgcacgt attgtcccag cttgtcagga  97140
agctgaggtg ggatgattgc ttgagctcag gagatcaagg ctacaatgag ctatgatcat  97200
acaacaccag tgcactctag cctgagtgac agagcaagac cctgtctcaa aaaaagcagg  97260
ggggcatagt cacctcccta aaatattagt tgaacagtat gtattcagaa gtccagaggc  97320
tctgtatttt attaatattt tcaaggcact atttctgcag aaatcaagtc agcaagactc  97380
tttgaggacg ttacaggcag aggggctaaa gataccttg aggaagctca agtacttggg  97440
tgggaggtga tagataaagg gtcagtagaa ataatgtctc tttttatttt ttttcccatt  97500
aaaaaatttt gttttaatag caatggagat ggggtctcac tgtgttccct gagctggtct  97560
ggtctcgagc tcctgggttc aagcagttct cccaccttga ccttctaaag tgtagggatt  97620
atagacatga gccaccatgc gtggcaaatt tcttttcttt cctttttttt tttttttttt  97680
tgagacagag ttttgctctt gttgcccagg ctggagtgtg gtggcacgat cttggttcac  97740
tgcaccctcc acctcccagg ttcaggtgat tctcttgcct cagcctcctg agtagctggg  97800
attacaggcg cccgccacca tgcccgggta atttttgtat ttttagtaga gatgggattt  97860
caccatgttg gccaggctgg tcttgaactc ctgacctcag gtgatccacc cgcctcagcc  97920
tcccaaagtg ctgggattac aggtgtgagc caccgctgcc ggttccaatg tctcttttgg  97980
atggtggatc ctgaagaata gctgctggtt ctttggggat gcctggggaa tactgtgcag  98040
gctttgtgat gggctcagca gtgaggcctg tacagtatct taggtcttgt gggcctcagt  98100
ctgctctctt ggctgttctc taccacctcc tgccattaag tttttaagaa aaaggaatag  98160
ttttattata ttctttggta aacaaagcaa attaagaagc tttatatttt ccacatttat  98220
ttaccaaact ccctatttgt ttttctctat agtgattcag tttagagacc tattcaatga  98280
agcatgcctt gatgttgaat ttagagtcta ctttttccag aagaaaagag ccagggagct  98340
ccaatagtag tcatctcaga atataaaagt gttatagaaa tgatgtaaat caggccgggt  98400
acaggggctc acgcctgtaa tcccagcact ttgggaggcc gaggcgggcg gatcatgagg  98460
tccggagatc gagaacatcc tggctaacag ggtgaaaccc cgtctctact aaaaatacaa  98520
aaaaaatcag ccaggtgtgg tggccggcac ctgtagtccc aactactcag gaggctgaga  98580
caggagaatg gcgtgaaccc aggaggaaga gcttgcagtg agccgagatc gcgccactgc  98640
actccagcct aggcaacaga gcaagactcc gtccccaaaa aaagaagaaa aagaagaaaa  98700
gaaatgatgt aaatcagctg cccttcactc tgtgttgagg tgggggatgt ccctaattgc  98760
```

-continued agtaggagag agcctctctt ttatctggga ctaaaagccc ttgccctaca tacctcataa 98820
ttattttagg gttaactgat tcaattgtca gaaaagaaca agctgtatct tgtttctgta 98880
catattctac tttgtgagta tttttatttc attgctatgt gattggaatc aactcaggaa 98940
agaggaaaaa aataagatag aggttataga attctgaatt ctgaagggaa ttctgagaat 99000
tatcagtaaa atatgtcaaa atgtgatatt ttacttccac caagaattag gccatatctt 99060
tgtgtgaaaa taaattatta ttatttattt atttattttg agatggagtc tcgctctttt 99120
cacccaggct ggagtgcaat cacacaatct cggctcgctg caacctccac ctcccaggtt 99180
caagcgatgc tcctgcctca gcctcccgag tagctgggat tagaagcgcc cattaccaca 99240
cccagctaat tttgtacttg tagtagagac agggtttcac catgttggcc aggctggtct 99300
cgaactcctg acctcaggtg atccaccccc cccccccca cccttggtct cccaaagtgc 99360
tgggattaca ggcatgggcc accgcaccca gcatacggaa ataaattatt aaccagagaa 99420
attttgacta aggtttttat aaatgttagg tgaaccattg ctctaaaaga tacaaaatta 99480
taacaagctg aaaagttttt taaaaatctg cattttagtg gttcagtttt tcagttgttc 99540
tgagtgctaa tagttggagt ttataaattg taagaagcaa tctacggaga ttctgtgatg 99600
aaggaatttg ttgaatgccc tgtctgcctc acagtctcag tctttatgat agagtcttgt 99660
cttctcacaa ggagagaaaa gatttgaggc tcttttgatt acttacttac ttgcttattt 99720
atatattttg cctctttgtt tttgccgcaa atacaaatgt aatggaacct tagaatagga 99780
gagacgtgtg gatcccctgg taggcactgt tctttctatg ttcctggagc caagttcatg 99840
gaattacctc caagactacg gatccctggt tttctttcat catgatagga ggcattttct 99900
agaacctgaa tcttacttta aaatgcatgt aagacctgca aggagtggta gtgaagtggg 99960
tggaatatat tcttagcacc agacaccttt aaaatattta agttctcggc cgggtgccct 100020
ggctcacgcc tgtaatccca acactttggg aggccgaggt gggcagctca cgaggtcagg 100080
agaccgagac catcctggct aacacggtga aaccccatct ctactaaaaa tacaaaaaat 100140
tagccaggcg tggtgatggg tgcctgtagt cccagctact cgggaggctg aggcaggaaa 100200
attgcatgaa cccgggaggc agagcttgca gtgagctgag atcgcaccac tgcactccag 100260
cctgggtgac agagcaaggc tccttctcaa aaaaaaaaaa aaaaaaaaaa aaaaatatat 100320
atatatatat atatatacac acacacacac acacacacac gtgtgtatat atatacacac 100380
acacatgcat atatatatac acacacatgt atatctatag atatatacat atatatgtgt 100440
atatttacat tttcttatgt cagggtctgg cttggagtgt attgtgttcc cagagcagaa 100500
ttcttttttt tttttttgag attgggtctt actttgtcac ccaggctgga atgcaatggc 100560
gtgagcttgg ctcactgcag cctcgacctc acaggttcaa gcaaccctcc cacctcagcc 100620
cctggagtag ttaggataac aggcgcacac taccattttg tattttttgt agaggcgggg 100680
ttttatcaca ttgcccaggc tggtctcgaa ctcctgagct caagcaatcc acctgccttg 100740
acctccccaa atgctggggt tacaggcgtg agccactgtg cccagccgca gagttcatct 100800
tgagaccctg acttctgcca gctctgatcc tagtgggtgg ggctctgggg ctcagtgaaa 100860
cagtcagccg ttttgcttca gagaacacaa ataagatttt ggcttgatgc tggttgttgc 100920
tggcgtcata tagtctaaaa cgtttgctgt caagaacatt ttagtaaaag tttttgttgt 100980
gctttcatct agtcaagaaa agataggaag tggcagctga cagggcagtg tcttcatgcc 101040
cctcaacctt acattggaca ctgaagtagg attgtgtttt cactggaagt cccagtgggg 101100
ccttatctcc tggatgctca aagtgcagct cagatcctgt tgggtaaaaa gtctagtcaa 101160
aatggaggac atggagaagg ccaacaggca gagctataga gctgacatag ggcattcttt 101220
gtacttccct tagccactgt actttctttc ttcctccatc tcctccttcc ctcttctatc 101280
tcattttggt ttggcctttg ggaatagtgg gttttaaaaa atatttgaac tataacatat 101340
ccttgtacca taaagaatga gcctgactgc tttacaaagg atttctataa aaagtaatct 101400
tttatactaa gagaaatgac acatctgttt taaacctgtt acttttcttc cccgggcttt 101460
gctctttctg caggtccgtt tgacatggtt cttgaaactc ctggtagcag ccatttacta 101520
gtagcactct ttatcttaga cacagcacct aaagcaattg taggtgtttt aagaacagaa 101580
agcccatctt aagcagacca gtttgaggga ttggcagtgc tgtcaagaaa caagggcttt 101640
gtggcagtct ctctaaaaac tccctatgag tccatttctt gcaaacttct ttagactcta 101700
ctgtatcttt tcatcagaag ctacctcttt gatgtgggaa gtgtcatgaa tggactgact 101760
ctctggaatt taaaaacaaa gacaatatgg caaaaagaaa acctgacttt tagtactgta 101820
tgtgttgcta attagctctg tattcttggg cagactactc catgtatccc agccatccat 101880
atgccctatt tgtaaggatc taatgagatg atattgtgaa gaatgccttt gtaaactgta 101940
aattgctttg tgaataaaga tactatctct gataaacagt accagttctc agccaccaat 102000
aacctgatac tcccatactg tgtttggaag aaacacaaaa caatgaagag taattgtgac 102060
ttttcaatgt gagttgtatt cacaaagctc atatactttt tccctgcctt ttgatactgt 102120
ttatcgcttt ctgtgttgta atgggaagat cacacagcaa tcatttctc agtacaaagt 102180 ataactacaa ctgagcttgc attgaagatc tttaacaaag atgcaaagct gctgtccaga 102240
aatgttttct ttccattttc tcttgtacct cccagtattt taagaatcct tgaggctggg 102300
caccataact cacgcctgta atctcaacac tttgggaagc tgaggcagga ggatcacttg 102360
ggcccaggag tttgagacca gcctgggcaa catagtgaga cccccatctc tacaaaaaaa 102420
tttaaaaatt agctgggcat ggtggtgtgc acctgtggtc tcagctactt agggaggctg 102480
aggtaggagg attgcttgag cctgggaggt caaggctgca gtcagtcatg attgcaccac 102540
tgtgctctat ctagcctcca acctgggcaa cagaagcgag accctgtctt ttttttaaaa 102600
aaaaaagact atccttgatg attggttttg agccaacgga atgggagcat atggtagagt 102660
ttcaacactc tgaccctagt ccttctgaca ggcagtcaca aaatgagatc atgaagtctc 102720
taagagcagc tgatgaaaaa ggaaatggga atgtagatgt tcaatcagca gccctccaga 102780
cccagagttt gctcctctgt ggtgtctcta ggtggagaat aaggacttga tttgccattc 102840
tggagtgcaa atatctagct ttttgcagct tcatattaag atttcttgaa atgtacttag 102900
taatatccat gtgtgacttt gccaagtgat ggctttgggc tggaaaggat tttagcaggt 102960
tttagtctaa tttaagccta atctaacact gctgagaaag gaggagatgt ctttggtttt 103020
actttctaat atatggtacc tcttagccgg gtgcagtggc tcatgcctgt aatcccagca 103080
cttcgggagg ccgaggcagg cgatcacttt aggccaggag ttcaagacca gcctggccaa 103140
catggtgaaa ccccatctct actaaaaata caaaaattat cccggtgtag tggcgcacac 103200
ctgtaatccc agctacttgg gaggcagaaa caggagaatc gcttgaacct gggaggcaga 103260
ggttgcagtg tgccaagatc atgccactgc atgccactcc agcctgggca acagagcaag 103320
accctgtctc aaaaaaaaaa aagagagatc tatctctctt ctttttatat acatatacat 103380
atacatacat acatacatat atgtatgtac acacatatat atatatggcc cctctttttt 103440
tatttgagtc ggaatctggc tctcttgcca ggctagagtg cagtggcatg atcttggctc 103500

-continued actgcaacct ctgacttcct ggttcaaacg gttctcctgc ctcagcctcc cgagtagctg 103560
ggattacaag catgtgccac cacacccagc tcacttttgt atttttagta gagacgggat 103620
ttcaccatgt tggcagggat ggtcttgatc tcctgacctt gtgatcctcc cacctcagcc 103680
tcccaaagtg ctgggattac aggcatgggc caccgtgccc agcctttttt tttttttttt 103740
taaagagacg gagtctcact ctgtcaccca ggctggagtg cagtggcgtg atcttggctc 103800
agtgcaacct ccacctcccg ggttctagca attctgcctc agtcttccga ctggctggga 103860
ctgcaggtgt atatcaccgc aaccagctaa tttttttgtat tttagtagag acagggtttc 103920
actgtgttgc ccaggctggt ctcgaactga gctcaggcag tccacccgcc tcggcctccc 103980
aaagtgctag gattacaggc gtgagccacc gtgcctggcc tatatggtac ctctttagga 104040
gccagacctg gttaatcaga cacatggctt tcatgactcc tttgcttgag tagcttaata 104100
actcaataaa tcaaaagatg aataaatatt ctaatgtgtg aagatactct aatagataat 104160
aggcaattaa gaatggacat ccacggctgg gcgctggggc tcatgcctgt aatcccagca 104220
ctttgggagg ctgaggcggg tggatcatga ggtcaggagg tagagcccat cctggccaac 104280
atggtgaaac cccatctctg ctaaaataca agctactcga gaggccgagg caggagaatt 104340
gctcgaactt gggaggcgga ggttgcagtg agccaaaatc gcatcactgc actccagcct 104400
ggcgacagag cgagactccg tctcaaaaaa aaaaaaaaag aatggacatc tactgaaggt 104460
gattgcatca tcctacccat tcattaatct aactccctac aggatacttt cctaggagac 104520
actgacaggt ctgttttctg aaatccagag aaaggcagca atggggaggg gtgcagtgta 104580
tgtatgtcat acctgtgctt ggtatatctg agttgcctgt gtatgatagc agctggggaa 104640
tcaaatcata gataaattgt tctcatacag gtttgtccta tgactaccta ttcttattaa 104700
acaattggct atattgaccc tttttggttt tggaaaaata ataataattt ttttaagaga 104760
gaaaaagaaa caattggcta cccttcaaca gtgatgttaa aaccatttca cattctttag 104820
cagtggtcac tgtcctatgt ctaactatgt gcaggttgag aaaaaggact gcccgagtta 104880
tagatgattc tgtgagaata agaaatcatt gcttttgtaa cacatgaggt aaaagtaatc 104940
tcaaagttga catgctgatg gggactcctg gcaaggggag ttccctgccc tcaacaaaag 105000
gtcatccaca gctactggaa catttttgtt gtctgagaag tataaagtgc cttagaaata 105060
cctgaatcca ttaatgcctc cagttggtga aatcagaatt tgcaggtgac tgaaattgac 105120
agtagtgcct tgttcttact cactgttcaa atgacaaccc acatgtttta tggattgggt 105180
atacagatgt atgctctaac agcagtatct ccctccagag ccactgtgta ccaagcacca 105240
ggtcctccag ggatagttgg ctctattcag tctttgattc attcaacaag agcttactaa 105300
gctccttttt ggtaccagat actctttgtt gctgaaaata aataaaaggc cagcaagatt 105360
aagtagactg tgagatctgg accagtaatt tgacaacaca aagtactgtc gtaaagatac 105420
agtttctgat gtgtagtgac cattccgtat gaaagcttag tctttcagga gattaaaatg 105480
ggtggtggaa tattcctacc tagcaagcaa gcaaggtgaa atgagtggct gtttgactcc 105540
cacctgctga tgctggtctt ttttggttcc tagggcttat aatgatcaac atttcttgag 105600
ccctcactat attctatgct aagctcttta catgtatgaa tttacttaat cttcacaacc 105660
accctaagaa ataggtactg ttgtccttac tttacagatg aggaaatgga agcacaaaga 105720
agttaaggac cttgctgaag gtcatggagt agaggcagga ttcaaattta gggaactcag 105780
cctacagtcc atgctcttaa agatgttata tcctgtctct gggcttagaa ggggttcatc 105840
ttaggccgga cacagtggct cacgtctgta atcccagcac tttgggaggc caaagcgggc 105900

-continued agatcacgag gtcaggagtt cgagaccagc ctgaccaaca tagtgaaacc ccatctctac 105960
taaaaataca aaaattagcc aggcatggtg gtgtgcgcct gtagtcccag ctactcggga 106020
ggctgaggca ggagaattgc ttgaacctgg gaggcggagg ttgtggtgag ccgagatcgt 106080
gccactgtac ttgagagtga gtgacagagc aagactctgt ctcaaaaaaa aaaaaaagac 106140
ggccaggcgc agtggcttac gcctgtaatc ccagcacttt gggaggccga ggtgggcgga 106200
ttacctaagg ttgggaattc gagaccagcc tgaccaacgt ggagaaaccc cgtctctact 106260
aaaaatacaa aattagccaa gcgtggtggc atatatctat aatcccagct actcgggagg 106320
ctgaggcagg agactcgctt gaacctggga ggcggaggtt gcagtgagcc gagatcacgc 106380
catagcactc cagcctgggc aacaagagcg aaactctgtc tcagggaaaa aaaaaaaaaa 106440
aaaaggaggg ggcgcttcat cttgactaac ttcctgcatt ggtggagctt gatagagtgg 106500
tccttcccag atccttccct gcatacagag cctgtctctt ttctgattgg tccctaaggc 106560
cagattacct gtccctaata ctgagcagaa gctggtgaat gaaacaggag atccctcagt 106620
caaaacaaaa ggaaaaagaa aaatgaaaca ggagatccct tctctacagc ccagatgtaa 106680
gtccagctgt gcccttcacc acctgggtga ccccacctct gtgaacatag gtcctcatct 106740
gtaaagtgta gataatgtta tttcatcgga tcatttaggg gattaaataa gataatgtac 106800
ttcgtggttt ctggctctta gtaagtgctt aataaatgtt agcgattttt attatcattg 106860
tccttagcct tgagaacaag ccagggaata gtgtctcaga ccagatgcta agacctaggt 106920
agatgggcaa ttttccttgg ttttgacaag acaataattt tatcctgtgt atttctcttg 106980 actttttga tgtgaaaagc agagaggtaa agcattattt gacagatgta tggattcaag 107040
caagaaactg aggtccaatt gcaaagaaat ggcttgtata actcagagcc ctgtctgagg 107100
aaacacagag gaccctagag ggcggagaat gaacacagcg caggggctag ttccagagtc 107160
gcattctcgg ttagttcact ttcaagtgtg ggtgagggtc ccttgtcagt aggcagagaa 107220 ttttttccc ctgcaccaac acatacctgc tgcctagtgt ttattaaaca aaactttatt 107280
ttaatgtgaa atagaattca tgacttgtcc aaaatggaga ggcaagggag ctctttaaca 107340
ggcttgttga gcccctttc ccacctgttc ctgtgccaga ctttcccaaa ggcttacttg 107400
ccaatggttg ctcctcagat ctcagggcta gctcactcta taggctccaa gccagagtga 107460
taccgccgcc gccgctgttg ctcccaccag ccaatcagtt tcctgctgta aggatgtaac 107520
ttgctgtgaa gctttcacct tcctcctttc ttcctgtctt caatgttgta tgtctttgtc 107580
ctggtgcttt tgccatacag ccagtgtttc aaagaaaatt ttcaggcact aaagttatag 107640
cccttactac ctttccaagg agatgtgaga tagctgtgga aaagaagagg gctcctctgc 107700
ctctgtgcag aaggaacagt ttacttcttg atagtgtgct agctcctgag ctaggtgggg 107760
gacttgctgg gattcaagag agtgcattac ctgacctctg gacaagtaga ctgggcatag 107820
cctgcccaag gacagcaccc taacctgcag gaaccaaggc cgaagactga tttcaccttc 107880
tcgtactccc ctttcctaag ctaaagcttg ctctgtaaca ctgccccagg tctgtggctt 107940
aaaacagcca tttcctttca ccagtgaatt aagctcactc tttataaaat gtttcagctt 108000
ggggattgga aaggctctct gtgcctttct gtctctgtct gtttctccaa gggttgatgt 108060
tgatggcttc tgtctttgtc tttacaggga actctaatga tccaggacaa agaagttacc 108120
ctggagtatg tatcaagcct ggatttttgg tactgcaaac gagtaagtac caagaatccc 108180
tttctttaga agtaagtatc tggaataaca gctcctccat atctctagga aggctgcctg 108240

-continued ctaacatgca ttcccaagga caaagctctt cttcctcagg tcacttcagt tgaacaggag 108300
gaggtcaaga caaggtcatt cataatttct ccttcccagc tgctacatgt ggccatagag 108360
agttctggac ctgcaattgg agacactttc ccaaggacat gtgccattat ttctatcagt 108420
tataaaaata acagttcctt gacatataat atcttctcac ctctcctggg ggtggtcata 108480
aaggaattct tggttggaaa agtaggtttg gagagactag ttctttggga gtcgtacatt 108540
ttttggatat tcttgggttt ccaagggtat agaacttcag acaccatggc attttacctc 108600
tattaaactc catattctct tagagtggga tatttaaaat tttaggctat actctttttt 108660
tttgaaacgg aatctcattc tgttgcccag gctagagtgc aatggcgtga tttccactca 108720
ctacaacctc tggctcctgg gttccagtga ttctgctgcc tcagcctccc gagtagctgg 108780
gattacaggc acttgccacc tcacctgcct gatttttgta tttttagtag agatggggtt 108840
tcaccatgtt ggccaggctg gtcttgaact ccgacctcaa gtgatccacc tgcctcagcc 108900
tcccaaagtg ctgggattat aggcatgagc caccgcgctg gcctgtttat ttatttattt 108960
atttattttg agacagagtc ttgctctgtc gcccaggctg gagtgcagtg gcgcgatctc 109020
agctcactac aacctctgcc acccgggttc aaacgattct cctgccccag cctcccgagt 109080
agctaggatt acagttgtgt gccaccatgc tcagctaatt tttttgtagt ttttagtaga 109140
gatggggttt caccatcttg gccaggctgg tcttgaactc ctgacctcat tatccaccca 109200
cctcggcctc ccaaagtatt gagattacag gcttgagcca cggcacccag ccggctatac 109260
tctttaaagg tccagtttga ttgcagtgag catgaaaata taatttgttt tcattgctac 109320
tacttagtat caaaaataat tatgaaaaat atataaagtt tctgagcccc gacacactaa 109380
aaatgttaca gtacttgaaa aaatttagta aagactttag cttgacattt gttagtctcg 109440
gtagaattga cattgtgtta gtctcggtag aatacaactt gaagagctat gattgttatt 109500
agccaaagta ctcatatttc atggatatac tcccttatgg tgtcatttta ggaagatatt 109560
tcgtttcctt ttattgagat aaaatacatg taacattaca tttgccattt taaccatttt 109620
gaagcattaa ttcagtgaca ttaagtacct tcacaatgtt gtgcagctat caacactact 109680
tcctagaact tctttttttt tttttttaa ataagagatg ggatctcact atgttgccca 109740
ggctggtctc acagtccctg gctcaagtca tcctctcacc tcaacctccc aaatagctgg 109800
gactataggt gccatcatgt ccaggttagt tccagaaatt ttttttttct gtcttttttt 109860
tgagacagga tctcactctt gtttctcaag ctggagtaca gtgatgtgat catggctcac 109920
tgtacccttg acctcctgtg ctcaagcgat cctctcacct tggcctcccg aagttctggg 109980
attacaggtg tgagctgcca tatctagcct cagatctttt ttaaaccctc aaaaggaaac 110040
ctcttatcat taatcagtaa cttcccactt cttcttcccc cagtccccag aaaccattaa 110100
tctttttctt atctccatgg atttgcctat tccggatatt tcatataaat ggaatcaaaa 110160
tatgtaaact tttctgttgg cctttcacct agcatgtttt cagagttcat gtatgttgca 110220
gtatttatca gtacctcatt tctttttgtg gctaaataat atgaatatat cacattttgt 110280
tcatccattc ctcaattgat ggacatttgg gttgtttcta ccctgacttt ggtgaataat 110340
agaacctttg tgtgctagtt tttgtttgaa cagctgtttt cagttatttg ggggtatgta 110400
tccaggagtg gaattgctga gtcatatggt aattttatat ttaactcttt gaggaaccat 110460
caaactgtat ttcttttatt ttattagcaa accttttcat agaccacagc tgtaccattt 110520
tatattccag caatatgtaa gggcttcatt tctccacctg cttgccaaca tttgttcttt 110580
tccctttatt tgataatagc catcctaatg ggtatgaaat aatatctcat tgtggttttg 110640
atttgcattt tcctaatgac tttgagggtt ttttttcatg tgtttgttgg ccatttgtat 110700
acctcctttg gagaaatgtt caaccaagtc ctctgccctt tggaattgat ttgcatgtat 110760
ttttgttgtt gagttataag agtactttat attttctgga tattaatccc ttatcagata 110820
tatgatttat aaatattttc tatgtgttat ctttcacttt cttgagagta tcctttctaa 110880
agaaaaaaaa agagagagag agagataagg tgtggctcat ggctgtaatc ccaacacttt 110940
gggaggctaa agtgggcaga tcacttgagc ccaggagttc gagaccagcc tgggcaacat 111000
ggcaaaaccc catctctaca aaaaatacaa aatttaactg ggtgtggtgg tgcatgccta 111060
tgatcgcggc tactaagcag gctgaggtgg gaggatcacc tgagcccagg aggtcgaggc 111120
atcagtgagc tatgatagtg ccactgtact tcagtactcc atcctgggtg acagagcaag 111180
accttgtctc aaaatttttt ttagctgggt gtggtggctc acgcctataa tcccagcact 111240
ttgggaggcc gaggcaggcg gatcatctga ggtcgggagt tggagatcag cctgaccaac 111300
atggagaaac cccatctcta ttaaaaatac aaagttagct gggcatggtg gcacatgcct 111360
gtaatcccag ctacttggga ggccgaggca ggagaatcac ttgaacctgg gaggcagagg 111420
ttgcggtgag ctgaaattgc actattgcac tccagcctgg acatcaagag tgaaactcca 111480
tctcaaaaac aaaaaagaaa aattttaagt ttattatgta cctattaaaa tttttttgta 111540
attaaaacaa atgctaatgg cggtattatt cataatagcc aaaaaatgga aataaccaaa 111600
atgtccattg gctgatggat ggatgaacaa gttggcatat ccatacaatg aaatgctatt 111660
tgacaatgaa aaggaatgaa gtactgatgc atgttacaac ctagatgaac cttgaaaata 111720
ctatgccaga cacagaagac catacattgc acaattccat gtccctaggg gtaagaatgg 111780
gggaggtaac tccactagat ttcttttggg gtgatgaaaa tgtttcagaa ttagattatg 111840
gtgatggttg cactatacat ttactaaaaa tcattgaatt gtacacataa aataggtaaa 111900
ctttatgggg tttgtttttg tttttaagag agagtcttgg tttgtcaccc aggctggatt 111960
gcagtggcac aatctcggct cacgacaacc tccacctccc aggttcaagt gattctcgtg 112020
cctcagcctc ccaagtagct gggattacag gcgtgtgcca ccatccccag ctaatttttg 112080
tatttttaat agagatgagg tttctccatg ttggctaggc tggtcttgaa ctcctggccc 112140
gaaatgatcc aacttcctcg gcctcccaaa gtactgggat tactggcatg agccatcatg 112200
ccaggcctgt tttatgctat ttaaattata cctactaagg ttaggatcct aactgccact 112260
cactaactga agtgtcacat actttattcg ttggcatgta tatactcagt tgtcccagca 112320
ccatttgttg aagagactat tctttcccca ttggcacttt ccccattgtt agaaatcagt 112380
tgaccataat ctataggttt attcctagat tctcagtttt attctgttga tctatatgtt 112440
tacaaatagc accagttacc acagcagctc tcctgtagta acaactctcc aatcccagta 112500
gcttaaaaca gcaagcatat tcttcactca cattacatgt cagggactat gggttgtttg 112560
ctacagttct gttccacgtg gcttctcatc ccaggaccca ggcggaagaa acagtctcaa 112620
tatggggcag tgtccctctg gctaagggag agagaggttc attcacgcaa gcagtggctc 112680
ctaaggcttc tcttagacct agtgtaggtc atgttcactc atgttttatt ggtgaaagca 112740
aggaaggcac atggccaagg ctgacaatgg agagaggaag tatactcacc ctgtgggaag 112800
gcataacagc catttggcag tgggcagggg tgtgtgtgtg tgtgtgtgtg tgtgtgtgtg 112860
tgtgtgtgtg tgtgtgtgtt tataatctgt ttatagggaa gggaacaatg aaataactga 112920
ctgtagtgat cttcctcaag tgagttaacc tctctaggcc tcagtttcct catctacaaa 112980
atgaggagat aagagtaccc atttcatgaa gtttattggg gttgtcagga tcaataagtg 113040
atgacatata cagtaggcca aatacatggt atgtactatt taagaattag ccggctgggc 113100
gcagtgactc acacctataa tcccagcaat ttgggaggcc gaggcgggca gatcacctga 113160
ggtcgggagt tcgagaccag cctgaccaac atggagaaac cctgcctcta ctaaaaatac 113220
aaaattagcc aggtgtagtg gcacatgcct gtaatcccgg ctactcggga ggctgaggca 113280
ggagaatcgc ttgaacccgg gaggtggagg ttgtggtaag ccgagatcat gccgttgcac 113340
tccagcctgg gcaacaagag tgaaactccg tctcaaaaga aaaaaaaaaa aagaattagc 113400
cactgctact attgttattg ttttctcctc aactccatct ggcagacctt tactcgccct 113460
ataaggccct cctcaaatac catcctcttt atagttctta ctcttttatt tcctgccaac 113520
caagtttctg cccccatggc atttggaagc tcagtggcaa aagttcaggg atttcggggt 113580
tgggcagtgt gcttgacttt ttgttcacat gttcagacaa aaataattac attcacatta 113640
aaaatgtctc ttaccttatt ctgggctagt gaatgttccc tttcaatgtc ttttagatag 113700
ctgccagaga cactatctgt atctcttcct cctaccttgt acctcattat cagtgtttga 113760
gaaaggagtt gataactgaa ttctcagttc tagccaaatg tgaatgggga tctcatagtc 113820
agttcaggcc caagttttgg gtgcagactg taaatggctt tgggacaata atattctata 113880
aaccatgtaa cagtagtttt ctaggcatat ttcctatagg aatctttatc cagggcaaag 113940
gcatttgggc tgcaccaaag tcccagatgc cttgttataa ggtagctctc aaacagtagc 114000
tcatcagatc ccatctgcca gctctaatca gtggggaata tcagattctt tttttaagct 114060
ttgaggggat ctgggatatg gcttgtttct ttcatttttg gggggtttca ctttgttaga 114120
tatacataag atttttaaaa atgttttcag tcaaattgat ttccttcttc cttacagtgt 114180
aaggcaaaca ttggtgggca ccgatcttcc tgttcattct gcaagaaccc aagagaaggt 114240
gagtggcgaa agtggtagca gtttttatct cgtgcattga gcaaaacaaa tttcatgttt 114300
tccttggctt tgaagaatta tcatccctaa atccaagttg atctacaaac cttttttttt 114360
ttttttgaga tggagtctcg ctgtgttgcc caggctggag tgcagtggca ccatcttggc 114420
tcactgcaac ctccagctcc caggttcaag cgattcccct gccctagcct cctgattagc 114480
tgggattcca ggcatgtgcc accacgccct gtagcccggc taattttttt gtatttttag 114540
tagagacggg gtttcaccat gttggtcagg ctggccttga actcctgacc ttgtgacccg 114600
acccaccttg gcctcccata gtgctgggat tacaggtgtg aatcactgca caaggcctgc 114660
aaacctttat ttatttattt atttttgaga cagagtctcg tactcaccca ggctggagtg 114720
cagtggcgca atctcggatc actgcaagct ccgcctccca ggttcacgct gttctcctgc 114780
ctcagcctct ctagtagctg ggactatagg cgcccaccac catgcccagc taattatttg 114840
tattttagta gagacggagt ttcaccgtgt tagccaggat ggtctcgatc tcctgacctc 114900
gtgatctgtc tgcctcagcc tcccaaagtg ctgcgattac aggcgtgaac caccacgacc 114960
ggcccaaacc tttcaaaagt gcaatttgag ctaggcatgg tggctaacgc ttgtaatccc 115020
agcactttgg gaggccaagg caggtggatc acctgtggtc aggagttcaa gaccagcctg 115080
accaacatgc cgaaaccctg tctctactaa aattacaaaa attagccaca ggtgtggtgg 115140
cacatgcttg gaatcccagc tccttgggag gctgagacac tagaatcgct tgaacccagg 115200
agtcagaggt tgcagtgagc tgagatctcg ccactgcact ccagcctagg caacagagtg 115260
agaaaaaaaa aattgcagtt tggtgcccaa cttaacgtaa cctgttagta aatgatttca 115320
gatcttattt tcaccagagg aaagagatag ggttgtgggc tcctaggcta aagtggctaa 115380

-continued gtgggcagct gagcagaggt cagtatattg ttatttggaa tacatttaag gattaaggat 115440
gttaggttga aaaagagtct ttatgacatc agtctgtgtg gcaaaccttt ctcccactcc 115500
tacttctttg aagttattgg gaatcatttg ctctattgtt ttctctttta cattctgtaa 115560
gcatttcagg attttcaaga gaaaaacatt tgttaaaata acagtaaaaa cataaatagg 115620
agaaaataat caggatgtgg ggaacatttt attattttag aggaataaaa ctaccagctt 115680
ctcaagcact tatctttaat gtaaatttct ttagagaaat ttcaggtagg caacttcgaa 115740
gagtcagaca catgcatcca taacaacagt cctgtagtca tcccttaagg aaagccacag 115800
catgaccata aaatatagtt cagtgcaggg attcaggtag ccttctgttt gttgcaaggt 115860
tagagtttaa tgtgcctaca aggagtttct taggtgggct tttgtcctct tgtggagatt 115920
ttactctggt gaagactgaa aggcaggtgt tctgaaaatc tttaggggaa ggctgtgtat 115980
gttctagaaa ccaaaccaaa atgtgggaag gaggatgaac aactgagatt tttgcttgtt 116040
aggtcacttc aggttaggca aagttgtgtt tttttccccc cacaagaaac acttttttttc 116100
aaagctattc cagcaaatga atagatagtt ttttgttttt tttctttttt tttttgagac 116160
ggagtcttgc tctgtcaccc aggctgaagt gcagtggcgc aatctcggct cactgcaagc 116220
tctgcctccc aggttcacgc cattctcctg cctcagcctc ccaagtagct gggattacag 116280
gcacccgcca ccgtgcccag ctaatttttt gtattttcag tagagacagg gtttcactgt 116340
gttagccagg atggtctcga tctcctgacc tcgtgatctg cccgcctcag tctcccaatg 116400
tgctgggatt acaggcgtga gccaccgctc ccggccatga atagatagtg tatgaaaacc 116460
actgggcacc ataccactaa gatgagacag ctttaatctg gaaacctgtc actgctatta 116520
tgtaatctct atattgctct catataatac ctctttttga gccacatgga ttccagtgaa 116580
ccctccaaga atgaattagt tacaagaatg tgcccctaat tataaaacaa actataaaga 116640
caaattatcc tgctgtagta ggacatttga aataaatcat ttatattttg aaggacgtct 116700
gcccattatg tttatttgca tataaaggag ctacgtgcag atagggtctg ttcctagctt 116760
cactggagga gggcctgtgg tcttacagga tatgagtagc tgtttgagca ctgtaacact 116820
ggaagaagca aggcttctag atgtgtgttt gggatatgtg tttctactaa accttaagta 116880
agggccatat cttcggtaat tttgtcccca gatgtgttgt tatcattgat tatgatagtc 116940
aggttcaagg tgtcatgaag gatttgttat atttaaatgt ttagtaggtg atatagagat 117000
ttcataagat tacatttttt aaatgcttgg atagtttctt ctgtgaacta tttcatgtcc 117060
tgtctcagct tcacttaaaa tattttgtca ggaactgtca gaggactttt tattagatat 117120
ttctgagata atattaaaag cattccaggc cgggcgtgtt tgctcacacc tgtaatccca 117180
gcactctggg aggccgaggc aagtggatca cctgaggtca ggagttcgag accagcctgg 117240
ccaacatggt gaaacctcgt ttctactaaa aatacaaaaa attacctggg cgtggtggtg 117300
ggcacctgtg atcccagcta ctctgaaggc tgaggcagga gaatcgcttg aacccgggag 117360
gcagaggttg cagtgagcca agatcatgcc attgcacttc agctgggcaa caagagcaaa 117420
actccgtctc aaaaaaaaaa aaaaaaaaaa aaggcattcc agtatgagta tttgctggca 117480
ggtaaggaga aattacagta gcagtgtttt ttcttttttt ttttttttga taaagctttc 117540
tagagattct ctttgtttct gttccactag tgacagaggc caagcaagaa ttaataacct 117600
accctcagcc tcagaaaaca tccataccag caccattgga aaaacagccc aaccagcccc 117660
taagaccagc tgataaggaa cctgaaccca ggaagaggga agaaggccaa gagtcacgct 117720
taggacatca aaagagagaa gcagaaaggt atctgcctcc ttctcgaagg gaagggccaa 117780
ctttccgaag agaccgagag agggagtcat ggtctggaga gacacgccag gatggagaga 117840
gcaaaagtaa gtagtttgtc agggcacata ccagactgtg atcatcacaa tggagcatag 117900
atggccaatg ttatgtccgg gagctatctg ctttccagta ccctgagaga tctgtgcatg 117960
acctgatgac agaggccatt gctgtctgtg gaccttcctg tactgcttaa aggaatctat 118020
gcccttcaaa tagtaaattg ctatatgaat gcagtaaggc atgattttag atttctaagt 118080
attggtgaag aaaagtatgc agtatttatt tgtttagcat ttttttacag aaccagcctt 118140
gctagtagca tctatagtaa aaaatgacag tcagattctt gggacttcaa aaatttatct 118200
ttctctccct tgtgttgccc ttctcccatt tatggttgat tcagctatca tgctaaagcg 118260
tatctatcgt tccacaccac ctgaggtgat agtggaagtg ctggagccct atgtccgcct 118320
tactactgcc aacgtccgta tcatcaagaa cagaacaggc cctatggggc atacctatgg 118380
ctttattgac ctcgactccc atgcggtgag tttcctccac cttggattgg cctagagaca 118440
gatggctaaa gaaccttcaa gaaggtttga ctgggggccg ggcctggtgg cttacgcctg 118500
taatcccagc actttgggag gccgaggtgg gtggatcacg aggtcaggaa atcaagacca 118560
tcctggctaa cacggtgaaa ccctgtctct actaaaaaat acagaaaaat tagctgggcg 118620
tggtggcagg cgcctgtagt cgcagctact cgggaggctg aggcaggaga atggcgtgaa 118680
ctccggaggc ggagcttgca gtgagccgag atcgcgccac tgcacttcag cctgggtgac 118740
agagcgagac tctgtctcaa aaaaaaaaaa aaaaaatttg agggacttct tgatcatttg 118800
aattcttgtg tgctacctga tatcataatc cctcttgctc tctcctttgg gtttattgtt 118860
cattcaggtc aggtgacagc cctcaaaagt taggatcccg tctggttttc taggttcatt 118920
tttttcttgt gtcatttact gtttccaact tactcgcttg tgaagaatct gagtactgaa 118980
tccttcatga ttttagtgaa ctttctgatt tattttgtcc agccacagat ggttttatat 119040
ttgatgataa aacatttcct ctttttcctc aaagtattta tagattcctg tggcttaaat 119100
ttttagttgc ggggcctttt tctatggaag taaggtgaag ataatgaaag tcattggtat 119160
ttcttagatt tttcatgctc aaaagtcaca agggactttg taaactgaat ctgattgatg 119220
ataattgcaa cctaaaagaa gaggatttga atttctgaag tttatgccag aactgacatc 119280
tattctgatt cctgttccaa tcagtccttc attaaaagtt gcctgtttct gccagtatgc 119340
tcttactgtt aaaattttga cagaatataa tgtagtaaat ttatcctctg agaaggaaaa 119400
tccacgttca cttctctttc aaaggagaat ttttctgtct ttgggttctg gcattttctg 119460
tctctgggtt caagtgtgtc tggttctata ggaagctctt cgtgtggtga agatcttaca 119520
gaaccttgat ccgccattta gcattgatgg gaagatggta gctgtaaacc tggccactgg 119580
aaaacgaagg taaggcagaa gggtgaggat ctcttgtgct gcccccactt gtgtttttga 119640
gaggaaactc cttttcctgg ctggaaaaac agtaaagcat gatgttttcc taacatggac 119700
tgcttcagat aggtgtttat tacagtttct ttctgaagcc tgacttgtcc tgactctcga 119760
attgttttct ttcttgaata atactaggta cttttgtcct ttccctttg actgtctggt 119820 atctttgggt cccaaatggc ctggcgtggt agcacatatc tctattccaa gctactaaag 119880
aggctgaggc gagatgggga gcgggttaca tgagcccagg agttctaggc catagtgtgc 119940
aatgaagatg cctgtgaata accactgtac tctaccctgg gcaacacagc aagaccctat 120000
ctcttaacaa aaaaatgatg gtacagtttt ggatgtgcag acacatgtca atacattctt 120060
gccccttgca atcctaggaa aatgctgtcc tggcttttcc ttcccctgac cttgtgcata 120120
tttccatagc actgggaaat ctaatttctc tttcctcctt cactcatctt gacccaggag 120180
tggtaacttg gaaatggcca tgtcagagaa acaggcttac caatatgggg catatcttgc 120240
tctagcaccc tccacttaat ggctgttttg ctccaccact tggctttgta agagtcttac 120300
tgctcattgg gcaggcgtgg tggctcacgc ctgtaatctc agcacctggg gaggccgagg 120360
cgggcagatc atgaggtcag gagattgaga tcatcctggc taacacggta aaaccccgtc 120420
tctactaaaa atacaaaaaa aaaaaaatta gctgggcgtg gtggtgggca cctgtagtcc 120480
cagctacttg ggaggctgag gcaggagaat ggtgtgaacc caggaggcgg agcttgcagt 120540
gagctgagat cacgccaccg cactccagcc tgggcgacag agcaagactc cgtctcaaaa 120600
aaaaaaaaaa aaaaaaaaag agtcttactg ctcattcttt caggagtgtc tggaccaccc 120660
aacctgcttg ctgtctaggt tggttccttt ccctgcaaaa tgaggaacag aggatttctc 120720
gataggaact gtaggattaa gtactcgtca aatgccactt ggtagcagcc ttaagaattg 120780
ttgtgttatc tgttgcagaa atgattctgg ggaccattct gaccacatgc attactatca 120840
ggtaggctgt aacaggtggg gagtgctcta ttaaaatcct caggtgacta taagggtgat 120900
cttgaatttt ctttagtggg tgactgttaa ggtgaatgac cattggatag ttctgtaatt 120960
ttaacttgcc tttctgtgat agggtaaaaa atatttccga gataggaggg gaggtggcag 121020
aaattcagac tggtcttcag atacaaatcg acaaggacaa cagtgtaagt aacctttgtt 121080
ttatttctgt tgctcttttt tgcttgactt gctactcatt acttgacatc tgtgtgatca 121140
cagttggcaa gatacactgt tgactgaggg tgctcatcca gagagaggca tctgtagatg 121200
cacctatttg tgttggtcac cctaattctt gggttcttga tgagtctcca gtaagggctt 121260
cattggacag agactaacat tggctctgat cttgttacct ttagcatcat ctgactgcta 121320
catatatgat tctgctactg gctactatta tgaccccttg gcaggaactt attatgaccc 121380
caatacccag gtgagtttgg ggcttttttt tttttttttt ttttttttacc tctgtcaatg 121440
attcttttga gaaaagcacc cataatttgc tacttgagga ttttattccc tggattctct 121500
ggatgctcat tgcatgaaaa gtggaaaagt ttagatctat ggaaacagaa ctgttgccta 121560
tatggaaaat cagtgccttg tggcaataca ggtaagaaca gtgttgctct tgaaaaagtg 121620
gacagtgggt ggtctgaatg tgtcctggtc cctggagtgg gtttttagat tgatgtggac 121680
tcttcttaga cttgtaagta aaaaagttgt ttcttcccct aaaagggaac tgtgcgcctt 121740
agacctggaa ttgctgggaa actgaaacat tctgtagact tacttgtttc caactgtatc 121800
gcagcaagaa gtctatgtgc cccaggatcc tggattacct gaggaagaag agatcaagga 121860
aaaaaaaccc accagtcaag gaaagtcaag tagcaagaag gaaatgtcta aaagagatgg 121920
caaggagaaa aaagacagag gagtgacgag ggtaagagga attgttaatt tgctgtcttt 121980
tgccacatag ttattaaaat gttggaggta cgaacagagg atatctatgt ttgcaagtgt 122040
aaagtaactt taaaaatact ctgtcagccg ggcgtggtgg ctaacgcctg taatcccagc 122100
actttgggag gccaaggcgg gcggatcatg aggtcaggag atcgagacca tcctggccaa 122160
catggtgaaa cccctgtctc tactaaaaat acaaaaatta gctgcgtgtg gtggtacacg 122220
cctgtagtcc cagctactca ggaggctgag gcaggagaat tgcttgaacc ctggaggcag 122280
aggttgcagt gagccgagat cgcgccacta cactccagcc tggcaacaga gcaagactct 122340
gtatcaaaaa aaaaaaaaaa acctctgtta atgagtattt ttacctggtg taggcaattc 122400
cctcacctct tatatcccaa ctctctcttt tacaaatggg aaaactatgg atggtagaac 122460
aaagtggccc agctcaaatc ccaacacctc agctccatac attttcactt ttctacattc 122520 ctttttttagt gtttgacttt atacacattt ctctagttgt aattatagca ggagatactg 122580
tttagtcact ttttatccta agtatttttt ccatgtttct atatactcta ttatttttaa 122640
tgcccacatg gtaaaaattc acggtataac tgtaccttca ttttcttcat ctctcctaca 122700
ttatttgtct tctctttcta atcttttctt tttcctttttt tttttttttt ttctgagaca 122760
aagtcttcct ctgtctccca ggttggagtg cagtggcatg atcatagctc acttctacgt 122820
caaacccatg ggcttaagca gtcctcccac ctcagcctcc caagtagcgg ggactacagg 122880
catgagccac catgaccagc taatttttgc tttttttgtag agacaggatc ttgctagatt 122940
gaccaggctg atctcgaact tctggcctca agtaagcttc ctgtctcagt ctcccaaagt 123000
gcttcagtta caggcaagac ccaccttgct cgcctctttc taatcttata ctgtcataat 123060
atataacatt tagcattttg tttcttcttt taaattactc cctatgacac attttcagaa 123120
tcagagatga tgaacatttt tacatctaat acaaaatcaa attattaggc agggtgcagt 123180
ggctcacacc tgtaatccca gcacgttggg aggccaagac aggtggatgc ctgagtttag 123240
gagtttgaca ccagcaacat ggtgaaactc catctctacc aaaaatacaa aaaaaattag 123300
cctactgtgg tgatgcatgc ctgtagtcca agctacttgg gagactgagt taagaggatc 123360
gcttgagccc aggagattgc agtgagctgt gattgcgcca ctgcactcca gcatggacaa 123420
cagagccaga cttgtctcaa aaaaaaaaaa aaaagaaaat ctgccgggca tggtggctca 123480
tgcctgtaat cccagcactt tgagaggcca aggcaggcgg attactttag gtcaggagtt 123540
tgagaccgcc tagccaatat ggtgaaaccc ccatctctac taaaaagaca aaaattagct 123600
ggacgtggtg gcgcaagcct gtagtcccag ctactcagga ggctgaggca ggagaatctc 123660
ttgaacctga gaggcagagg ttgcagtgag ccaagatcac acctaccttg atatcagtta 123720
tgcattagtg aaaatggatg aatttgcttg tgattcaatt cataacacct tttttttccct 123780 tttttttcttt ttgagacgga gccgctctgt cgcccaggct ggagtgcagt ggcgtgatct 123840
atctcggctc actgcaacct ccgccttcca ggctcaaggg attctcctgc ctcagcctcc 123900
tgagtagctg ggatatcagg cgctgccaca acgcccagct aatttttgta tttttagtag 123960
agacgcggtt tcaccatgtt ggtcaagctg gtctcgaact cctgaccttg tgatccgccc 124020
acctcagcct accaaagtgc tgggattaca ggcatgagcc actgcgccca gcctttttttt 124080 ccccttctaa cactgttagt tgtttagaga tacagaaaag aggagagaga gtgtgtgtgt 124140
gtgtttaaaa acttagagtc atactgattt aatatttgga ctctgcttca gccacttaat 124200
ctgtcaaact atattcccaa tcatttgtaa aattaagata gtaaagctta cataggagga 124260
tcatagtaaa gtctgaagaa gacaatgttt atatatacat gcctcatctg gtctgacata 124320
cagtaatcat gcaatatata ctaacgtttt attttatttt attttatttt ttgagacaga 124380
gtctctctct gtcacccagg ctggaatgga gtggcacgat ctcggctcac tgcaacctct 124440
gcctcccagg ttccagcagt tcttctacct cagcctccca agtagctggg attacaggcc 124500
aaaaccacca cacccagcta atttttgtat ttttactaga gacggggttt caccatgttg 124560
gccaggctgg agcacagtgg cacaatcttg gctcactgca agctccgcct ctcgggttca 124620
ttctcctgcc tcagcctccc tactaactgg gactacaggt gcccgccacc acgcccagct 124680
aattttttgt atttttagta gagatggagt ttcactgcat tagccagggt ggtctcgatc 124740
tcctgacgtt gtgatccacc tgccttgacc tcccagagtg ctgggattat aggcgtgagc 124800
caccgcaccc agcccagcct ttatcagtta ttatgagtga atatcatgtg agagttacct 124860
ctggtttgat cagtttcagg aaaatgccag tgaagggaag gcccctgcag aagacgtctt 124920
taagaagccc ctgcctccta ctgtgaagaa ggaagagagt ccccctccag taagaccaac 124980
attgatcccc tggacctagg gctggggctg ggatggttc cgagtagaag aggaagcgca 125040
aaggctgatg ccttcctctg gtgttggtct tttacctcac tatgtctccc gaataaggat 125100
tcccatttct tttgagtaca agcatgagat aaagttttct gtctgctaat gggggtatta 125160
ctggagaacc agaggcagtt atctggactc tttctctctg ccctgtgcca ttcttaccag 125220
acgagatgcc tagccctttt tatcatcttg ttcttgtcag ttctctaaat caccaaggaa 125280
acccgttttc tcagcctcaa tctttcctgc cttttggcat cacacaagaa tctcttagat 125340
atggagtgca tgcgtggtca ttttttata gtttctgcct gttcagagtg aatgatgcta 125400
atattggtgc ccattttta gatgccttca agcagtagtc tcaacctaat caccagtgat 125460
tctgattgaa tgcaggtata taacaatagt gaccatgcat tatttattta ttttgagtga 125520
tcatagacca atgattatgc atcattattt aacagttctt ataaggtacc cttttcctgc 125580
tccgcattat taattcagct cattgtggca tctgtcttaa ccatgctttg cctttacctt 125640
acatgtgagc tggatctgtc tacccaagtg cctattaatg cagttgcttt tagtttactt 125700
cctaaatcct ctttgctaga gtcttaatga aagtcatctt ttcttccctc catgagttac 125760
agtaatttgg aggtatttat ctcttcctct ttgtaatttg taacctttta ctattttcta 125820
tgtttatttt cctttctctt ccttctcctc acattctgtt gctagagtca cttctaaagg 125880
aatctttctt gtttattctt aatgaacaag gagcaaagcc aagctctggc catgttgctt 125940
tcatctggga aatgagcagc atggctagtg agtttatttt gaacccaatt caatgaaatg 126000
agatgcccat atcagaatat caaaaaaaat ggaccccaaa atataggttg aatttggtat 126060
tgatccctgg ccttctcctt ccagcctaaa gtggtaaacc cactgatcgg cctcttgggt 126120
gaatatggag gagacagtga ctatgaggag gaagaagagg aggaacagac ccctccccca 126180
cagccccgca cagcacagcc ccagaagcga gaggagcaaa ccaagaagga gaatgaagaa 126240
gacaaactca ctgactggaa taaactggct tgtctgcttt gcagaaggca gtttcccaat 126300
aaagaagttc tgatcaaaca ccagcagctg tcagacctgc acaaggtatt aggggaagga 126360
gctatgccct ttcaaactgt tgactcttgg ccgggctttg tggctcatgc ctgtaatcct 126420
agcactttgg gaggccgagg cgggtggatt gcctgggctc agaagtacaa gaccagtctg 126480
ggcaacatgg tgaaaccccc tttgtactaa aatacaaaaa attagccagg tgtggtgttg 126540
tgtgcctgta gtcccagcca ctcgggaggc tgaggcagga gaattgctag aacctgggag 126600
gcagaggttg cagtgagccg agatcgtgcc actgcactcc agcctgggta acagagcaag 126660
actccatctc ttaaaaaaca aaacaaaaca aaactgttga ctcatattat tgatggggat 126720
tatggggaat aaaaaagatt atttaggccg ggcctagtgg tttacacctg taatcccagc 126780
actttgggag gccaaggcac ctaggtagat cacttgagat caggagtttg agaccagctt 126840
ggccaacatg gtgaaactgt ctctactaaa aatacaaaaa ttacctggat gtggtggcgc 126900
atgcctgtaa tcccaactac ttgggaggtt gaggcaggag aatcgcttga acctgggagg 126960
caaaggttgc agtgaaccga gatcacacca ctgcactcca gcctgggtga cagaccaaga 127020
ctctatctca aaaaaaaaaa aaaaaaaaaa aaaaagccgc agcagcttat acaatccttc 127080
ctcagtgtat atcagcccca gttcctatca ttaaaacagt ccaattcaag aatgaattgc 127140
tctggattaa ggttatgcct accctcaaag aacttccatg tataggccga agccaagcat 127200
tatgactgtg gctagggtgc caaatatgga ggatgggtag gaagagaaag ggttgtggaa 127260
taggacatta cttgctgggt ttctcatctt agctgtgtca ttaacgttac agttggacct 127320
cagataagcc ccttttcttc tttggtcctt gtaacttcat ctgattctat ccagctctga 127380
cagtgtgcag ttttcaccat aggtgagtca aattctgcca tttcttcatg tagtgaatat 127440
tgttatgagc cacagcacaa catctatact tgggatgtta aaccgacata cattggtctt 127500
cccctgtagt attcccattt atatgaactg accaaggatc caaattatgg acaaataaag 127560
tccctaaatg gactcacatt ctcagagcaa tttgtttcac accccttctc tagtagatgt 127620
tgcaagagca ggtgatggaa ctagattcag actttctctg aatacagagc tcaaagtttt 127680
atttagctaa aagctgagaa gttctgcttt tggtaatagg tacactactt ttcccagcca 127740
tctctgtgga ggctttgcaa agataggact ctgaaaagct cctgataatc cctggaacag 127800
actacctccc atgtcctttg acctgaagtt gtgagttgtc agactgacac attgaaattt 127860
cacccatctg atgtaaatac taataaatgg ctaaagagat aaaaagtaat cgtcaggaaa 127920
gaggagccac aggtctggtg aattcacaaa ctgaactggt cataggacag tggaaagtag 127980
actgtagtac ttttcctttc cttaaggtcg tctgctacaa agaaccacca cttcatgtaa 128040
gagctgcttt ggactcctta agtttcatac atatgtctga gggcttgtgt agtagagcca 128100
tgcgtgagga atttgcaact ctcagagcag tctcttggaa ccctggggct cctttccatg 128160
tttctctggg ggctgaaaga gtgactcatg tctgggaatg gtatgtatgg cagagtatgt 128220
gggcatttgg ttttcttcac tggtgtgccc acatcctctg tcccatgatt ttcaacttag 128280
ataaagagat agatatttgt ttcccacatc ttggagataa gtaaaatgat attcctctta 128340
tgccatacca cataactaat ctgcatgaca agaccagtta gggattgttg gttgcaggat 128400
acagtgatca tttagtagat ctgatcaatc aaaagagcta caatccaaaa gcaactattg 128460
ggaaaggcct agaagcatct ctaggaccat tgtttcttag acctatactc atagaattgc 128520
ctctcttctc agcaaaacct ggaaatccac cggaagataa aacagtctga gcaggagcta 128580
gcctatctgg aaaggagaga acgagaggta aactttggtg acctattact cccttgacct 128640
cagctctttt tgctttctga tatagacttc ataggctgtg ctgatccctc cttataagaa 128700
gatggagaac aaaagcagcc tcaaaagata gtgcatacat ttgccaaatt atataataca 128760
atcaaaatag gtgcttttta ttatttgtaa gtttatactt caatgaagtt gatatctttt 128820
ttaaaaggtg gtgttagggt ctctaggtag ataacactcc tctttcctgc ttagctttta 128880
aattagttga gttaatgaac aagtgttgaa tagcgctgct gaaatagcat cttttactat 128940
taaaggctaa gctggaggaa gtagcttagt gtcagagtca aatggacttg ctacctcaac 129000
cacacagtta gggtgaatta cccagtcata ggcttcactg gcctctctca tgatggttaa 129060
gaacccacct atgggtcagg cacggtggct cacgcctata atcccagtac tttgggaggc 129120
tgagacgggc ggatcacttg agctcacaag tttgaaacca gcctgggcga catggcgaaa 129180
tcctatctct acaaaaaata taaaaattag gtggacatgg ggtgtgtgcc tgtagtccca 129240
gctacttgag aggctgaggg aggatcgcat gagctgggag gcagaggttg cagtgagctg 129300
agtttgtgcc actgcgctcc agcctgggtc atagagccag accttgtctc aaaaaaaaaa 129360
aaaaaaaagg aagccacctg tggagagcca ggcacagtgg cacatgcatg taatcccagc 129420
agtttaggag gctgaggtgg gagaattgct tgagcccaag agttccaggc tgcagtgagc 129480
tatgatcaca gccctgtact ccagcctggg tcacagagta agtccctgtc tcaaaaccaa 129540
acaaaagaat ccacctatgg aggactgtta gagatagtga attcacaaac tgaactggcc 129600
ataggacagt ggaaagtaga ttgtagtatt tttcctttcc ttagagttgt ctactacaaa 129660
gaaccacctc tccatgtaag agctgctttg gactccttaa gttttatatt atatgcccga 129720
gggcttgtat agtggagggc ttgtgtactt tcccctgctt ctcagaaggg gaaaagacag 129780
cggaaccaag cgtgccaact tattctttcc aaatgtttaa gttaggaagt cactgctttc 129840
tctagaagaa cgtgtaaagg agtgagagat tccaggagtt accaagtgag ctactttcac 129900
tttaaaagaa ataacaaggc cgggtgcggt ggctcacacc tgtaatccca gcactttggg 129960
aggccgaggc tggtggatca tgaggtcagg agttcgagac tagcctgact aacatagtga 130020
aaccccgtct ctactaaaaa tagaaaaatt agctgggcat tgtggcactc acctgtagtc 130080
ccagctactt gggaggctga ggcaggagaa tcgcttgaac ctgggaggcg gaggttgcag 130140
tgagctgaga tcacgccagt gtactccagc ctgggcaaca gagtgagact ctgtctcaag 130200
aaaaaaataa taataataac agcaatgggg tagaatttcc ccactcccca attccctcag 130260
gtggcaatct caggtctgct cttctgctta ccaacaggga aagtttaaag gaagaggaaa 130320
tgatcgcagg gaaaagctcc agtcttttga ctctccagaa aggaaacgga ttaagtactc 130380
cagggaaact gacaggtaag ccaggaactc ttcattcagc ctaggcctca agcctaatga 130440
taaaaccacc tcctccttca actgtactgc tgttttctgt ctcagggaga tgatattatg 130500
agtagattct gtctgaactg ctaaaacatg aggtctatgc cagccttttt actatctgtc 130560
tttatacggg gagtgtacat ggaaggttgg ctggcagctt cgccttccca aagccagggc 130620
tggagtagcc atgatcggga accctttctg tcttcatcag taatactgca ccctctttac 130680
gggcctgata agaatgtcac actcttgggc tttttctcta gggaacctcc attctcacac 130740
ataggtgcta aataaatggt tggctgctga tggagatgta tgatatctag cttcctatac 130800
ttgttttcag tcagctagtt cccaagttgt aagcccagag ttatatagaa tttgttgata 130860
acccactgtt tacaggtgtc aagtgcaaga aatactcagg tggacaagac atagattatc 130920
cttgactgaa cacagaatag acaagactta ggtgatggtg cgtctcatag ggcagacaca 130980
gaaatcagtg gggaagggaa gggcatttca gggaatttca tataccaggg atataagagc 131040
ttatgatgtg tttgaggagt tgcaaatagt ttgatggtcc tgaacactgc aggtatattg 131100
ttgagtgaca gtagataagc ctggtccaaa agatgcaggc cagttcatga agtttaaaca 131160
ccttgaacac cttgctaagg ctttatctta aaggcagtgg acggtcatgg aataatttta 131220
agcagggtat tgacttagct ttgcattttg gagagattac taatcatgtg gaagatgagt 131280
ttgtagagag actaatgcat tatgcaaatt ctatagtaat tcaagtgaaa gatcatgatt 131340
gcctgagtga aggtgatgag tctagaaagg agagtggcct ataatcccaa cacagagagg 131400
ctgaggaagg aggatctctt gagcctagga gttccaggcc agcctaggca acatagggag 131460
aagggagacc ctgcctctat ttaaaaaaag aaaagaaaag gagtgtggct tagagagagg 131520
tgtcagatct gccagtcttt gtgatcacct ggggaaaggg agaagtcact gatggtgttc 131580
aggtctctgg tctctggata gctaggagga gaagggacag taaagtcctt gaaaaggaaa 131640
aatgggggcc aggcgtggtg gcttacgcct gtaatcccag cactttggga ggccgaggcg 131700
ggtggatcac aaggtcagga gttcgagacc agcctggcca agatggtgaa accccttctc 131760
tactaaaaat ataacaatta gctgggcgct gtggcaggcg cctgtaatcc cagctactca 131820
ggaggctggg gcagaagaat cgctcaaacc tgggaggcag aggttgcagt gagctgagat 131880
catgccactg cactctagcc tgggtgacag agcaagactc tgtctcaaaa aaaaaaaaaa 131940

-continued

```
aaaaaaaaga aaaggaaagg aaaaatgggg ccaggtgtgg tggctcacac ctgtaatccc 132000
agcactttgg gaggctgagg caggtggatc acttaaggtc aggagttcga gaccagcctg 132060
gccaacatgg tgaaaccctg tctctaccaa aaatataaaa aaattagcca ggcgtggtgg 132120
tgggtacctg taatcccagc tactcgggag actggggcag gagaatcgct tgaacatggg 132180
aggtggaggt tgcagtgagc caagattgca ccactgtact ctagcctggg taatagagcg 132240
agactccaaa tcaaaaaaaa aaaagaaaag aaaagaaaag gaaaagtggg taacaagtgg 132300
atgcatgagc agaaggaaag ggagataatt gacagagcaa ggcccttgag gaggctggac 132360
aggttttggg gctctggcat tccagcttat ttgatccaac ccacaataag agaagtattt 132420
ttgtatcatg gcccaataat aaagtgtgtg tgtgcacaac tgaaaaagtt ttcatctaaa 132480
atactttctt accaggtaca gtgaaccctg atatttttat tcaagtctag tctctcttca 132540
tttttatgag ttgttacagt gggaccattt agtgtgacat tccattgggt cattctctgc 132600
aatttgaaat acagtggatt aggactaggt gaaggagtca gccatcagga ggaaggacac 132660
cttggccttg agtcttctgg gacaaggctt aggtggggtg cggaaagaga cccttcttta 132720
ttctcagcac cctttatacc acattctcct ggctcttctc ctttccagtc accttttctg 132780
ctcctcttcc ttttctggat aaatccaggt gttctctagg actcttctct cagtgcttct 132840
ttggtcttgc tgctctaccc tcttgacctg ggctttctaa ggtacccatg gcctcaacca 132900
ccaccacagt ctaacaagtc caaatctcct gtattattat ttcagagtag cagcatcata 132960
gcatcactgt ctacatggtc tgatccatcc tcctccttta tcccctgtgt ccaattagtg 133020
accaaatccc taattaagtc ttgccccctg tcttagtctg ttttatgata ccataactga 133080
ataccacaga ctgggtaatt tataatgaac agaaatttat ttggctcatg cttctggagg 133140
ctgggaggtc caagattgag gagctgcatc tggtgagggc cttcttgctg tgtcacctca 133200
tggtggaaag taaaagaaca agagagctta ggcaaaagag gggggttggga gaaagaaacc 133260
agactaatca ttttatcagg agaacccact cctgcaataa cagcattaat ccatttgtga 133320
gggcagagct ctcatgacct aatcacttcc tgaagtttca cctctcaata ctgttgcatt 133380
ggggattatg tttccaacat atgtactttg agggacacat ttaaaccaca gcatctccca 133440
ttctattcca cctccacact ggactcctac tcccagtctt tgctcccact gttcttcagt 133500
ccattctcta ccctgccacc aaaatgactt ttgtaaagag aaatctactc ttataacttg 133560
tctttttaca aaccgtatac cttgcctaca gggaggcctg agctccaact tttgccagaa 133620
ggatgaggtt cagagacatg atttagctta ataagttcaa ggttttttac agtctgaccc 133680
catgcagcct tttttttttt tccttttgtt ttgagacagt ctcattctgt cgcccaggct 133740
ggagtgcaat ggcacgatct tggctcactg caacctccgc ctcccaggtt caagcgattc 133800
tcctgcctca gcctccccag tagctgggac tatgggctaa tgtttgtatt tttagtagag 133860
aggggtttca cctgttggtc agggtggtct cgaactcctg acctcaggtg atccacccgc 133920
cttggcctcc caaagtgctg ggattacagg cgtgagtcac tgcacccggc caccaagcag 133980
ccttaccttt gtcagtttct actactactc tcttggacaa attgtctttt gtgtctcctt 134040
gcttgtgtcc tccttttctc ttacacaaac tccttatttc gagatccaat tcagatgtat 134100
cttcctgttg aaattcctgt catttttggt gatgcccctt cagagttttc gttccttcta 134160
ctgcatttct tttttttttt tgaaacagag tttcactctt gttgcccagg ctggagtgca 134220
atggcgcgat atcagctaac cacaacctcc acctcctggg ttcaagcgat tctcctgcct 134280
cagcctcccg agtagctagg attacaggca tgcgccacca cacccggcta attttgtatt 134340
```

tttagtagag acagggtttc tccatgttgg tcaggctggt cacgaactcc caacctcagg 134400
tgatctgccc acctcagcct cccaaagtga ttccttctac tgtatttcta tagcagacat 134460
ctactgttgc tacatccatg gttgagctct cttcaatgtt ctataagcat ctcttgacat 134520
aatgtttgag acctttcttg tgaacagggc catatcttag tagtctgtgt acccagcaac 134580
aaaacatagc tatcaggcac tcagaggtac tgttaaatat acttacttaa taagaggcag 134640
atatgaatca agaggacaga gattttatat taggcttata agcaggtctt catcaaaatg 134700
atggtgtcag gttgggcatg gtggctcatg cctgtaatcc agcactttgg gaggccaagg 134760
catgcggatt acctgaggtc aggagtttga gagcagcctg gccaacacag tgaaactctg 134820
tctctactga aaaaaaaaaa aattaaaaat tagccaggtg tggtggcggg cacctgcaat 134880
cccagctaat cgggaggctg aggcaggaga atcgcctgaa cccaggaggc agaggttgca 134940
gtaagctgag ttcgagccat tgcactccag cctgggcaaa aagagtgaaa ctccgtctca 135000
aaaaaaaaaa aaaaggaagt gatggtgtct gcttcttttg cagtgatcgt aaacttgttg 135060
ataaagaaga tatcgacact agcagcaaag gaggctgtgt ccaacaggct actggctgga 135120
ggaaagggac aggcctggga tatggccatc ctggattggc ttcatcagag gaggtaaaat 135180
ggtttccatc ttttgggggg tgacatgaac ctggaatgta attaactttc actttctggc 135240
ctagagtgat gtctttgcca ttttgctggg ctttctctac tgctgggata ggacatgaga 135300
gttgaacact ttagccttga atactgggtt atagcttggc aggctgggcc ctttgcagtt 135360
tggagttagg aagagaagga aggagttgga atggatttca tcatactttt acatggagta 135420
aatagtagag cagtatctga ggcagtttga gactgaagaa tcatttgggc aaaagaacca 135480
gggaatcagc aatgaaaggt acagaggcat ctctgagagg gactgtcagc ggaagtcttt 135540
ggtggctaaa atttaaggag catgttgttc tggttcccat gaaggacttt gcccctcata 135600
tttcaagagc ctctagaaaa ggtgataaga ggaaacatta cccattttgt gttggcttgc 135660
ttctcctctg aaaatgccaa ccataagaga ttggcttatt tctctcctac cgagtttctc 135720
atatctctgg tattaaagcc tgtatcttgc aatcatagca tcaccaccca ccttaattca 135780
tcttgggtat ttgtttaata atgaaagatt cttttctttt tttttttttg agacagagtc 135840
ttgctctgtc gcccaggctg gaatgcagtg gtgcgatctc agctcactgc aacctcctcc 135900
tcccaggttc aagcaattct cccaccccaa cctcctgagt agctgggatt acaggtgcat 135960
accaccatac ccagctaatt tttgtgtttt tagtagagac agagttttgc catgttggcc 136020
aggctggtct cgaactcctg gcctcaagtg atccgcccac ctcagcctcc caaagtgttg 136080
ggattacagg cgtgagccac tgtgcccggc caaaagattc tttaaaaaaa ttatcctgcc 136140
agggtccggg cgcagtggct tatgcttgta atcccagcac tttgggaggc cgaggtgggt 136200
ggatcacaag gtcaggagtt cgagaccagc ctgaccaata tgatgaaacc cctgtctcta 136260
ctaaaaatac aaaaattagc tgggtgcagt ggcgcgcgcc tgtaatcaca gctactcagg 136320
aggctgaggc agaagaatcg cttgtaccgg ggaggcagag gttgcagtga gccaagatct 136380
tgatcgtgcc actgcactcc agcctgggtg acagagcgag actctgtctc aaaaaaaaaa 136440
ttattctgcc aggtgtggtg gctcacatct gtaatcccaa cactttggga ggccaaggtg 136500
ggcggatcac ttgaggccag gagttcgaga ccagcctggc caacatggcg aaaccctgtc 136560
tctactaaaa atacaaaaat tagccgggcg tggtggcagg cgcctgtagt cccagctact 136620
cagaggctga ggcacaagaa ttgcttgaac cggggaggca gacttgcagt gagcccagat 136680

-continued cgcaccactg cactctagcc cgggcgacag agcatgactc catctaaaaa aaaaaaaaaa 136740
attatcctat atactgcttc ttactagtcc agaaatgcct gtggtcaaag accagcgctg 136800
aggctaatta atctataggg cccacttcat agtttgtctt tgttttacag gctgaaggcc 136860
ggatgagggg ccccagtgtt ggagcctcag gaagaaccag caaaagacag tccaacgaga 136920
cttaccgaga tgctgttcga agagtcatgt ttgctcgata taaagaactc gattaagaaa 136980
ggagacaagt tccatgggat acaacctccc tcttgttttg tttgtctctc cttttctttt 137040
gttactgttc ttgctgctag aacttttta aataaacttt ttttcaatgt g 137091

<210> SEQ ID NO 42
<211> LENGTH: 2604
<212> TYPE: DNA
<213> ORGANISM: Homo sapiens

<400> SEQUENCE: 42
ggggaggagc caaggggggcg agcaagctcg gtggctgggt gggttggggc gttccgcgcg 60
cccttcattg aagcggcggt ggccgggctg ggcgccggta gtggaaagcg acggcgcggc 120
tggaaaatgc cagtccattc ccgaggggat aagaaggaga ccaaccatca cgatgagatg 180
gaggtggact acgccgaaaa tgaggggagc agctccgagg acgaggacac tgagagctcg 240
tcggtctccg aggatggaga tagctcagaa atggatgatg aagactgtga aagaagaaga 300
atggaatgtt tggatgaaat gtccaatctt gaaaaacagt ttaccgatct caaagatcaa 360
ctttataaag aacgattaag tcaggtggat gcaaaactac aagaagtcat agctggaaaa 420
gcaccagaat acttggaacc gctggcaact ttacaggaaa atatgcaaat tcgtacaaag 480
gtagcaggaa tctatagaga gctctgctta gaatctgtaa agaacaaata tgaatgtgaa 540
attcaagctt ctcgccagca ttgtgagagc gaaaagctgt tgctatatga tacagtccag 600
agtgaactag aggagaagat aagaaggctt gaagaggata ggcacagcat tgatattacc 660
tcagagctgt ggaatgatga gcttcagtca agaaaaaaga ggaaggatcc tttcagtcct 720
gacaaaaaga agccagttgt tgtttcaggt ccatatatag tttatatgct acaagatctt 780
gatattcttg aagactggac aacaattagg aaggcaatgg ctacattggg gccacacaga 840
gtgaaaacgg aaccacctgt gaaactggaa aaacatctgc acagtgctag atctgaagag 900
ggaagactat attatgatgg tgaatggtat atacgtggac aaacaatatg tattgataaa 960
aaagatgaat gtcctacaag tgctgtaatt acaacaatta accatgatga agtttggttt 1020
aagaggcctg atggaagcaa atctaagctt tacatttcac agctacagaa aggaaaatat 1080
tcaattaaac attcataatc atgatttaag tgttatctaa atttacctta ttagtgttac 1140
caaatgtaag tgccatgaga gtaaaaaaat gtattcaata acttaatatt ctcactgaat 1200
catgagagaa tgtgtatttg taggtagtac tctaaataga tctcattgat atgttattaa 1260
aagaaacagt aataaaaatt ttatcacgat ccttacgttg atttgcctct taggtccgat 1320
gaccaatagg tattctgtat atggtagggg tttctttcta aacatttttc tttggtttta 1380
aaaaaagtta tgcaaatttg tcttatcttt agtaaactat gactacattt atctgcaatt 1440
tttaaaattt tccatatctt tgtcattcat tgtgtgtttg taaataaggc cgatagaatg 1500
tttcctataa atggtttgta ctagtacatt agtgttaaac cagaactgaa atttaaacat 1560
atatatatat gaggatgtat atatggcatc atcagcttat ttagaactga tggccatacc 1620
ttacaatctt gttttaccca aaattaagct attggggttg aaagctaaaa ggagcacttt 1680
tgtagaatag caacttttct tttcctcttt cttgattgta tggtggggtg gtgacctatt 1740

-continued tttacaaatt atacctaatg agtaaaatta gtgtaaagtg ataacatgct tctacctgta 1800
tttctagtga ccctttagcg gcaggtattt atacctggta tttatgatgc agtatataag 1860
tggtgaacaa taactgacag tattgtgctt gctgtacatg tctggtcttt tgaaacagat 1920
tttagtaagc attttccaga ggtaaaactg tgtccttatt ctaattttat tcctagggca 1980
aagtagacag ggattatttc cttgaatcta tttccaaatt aatatttttt tctttggtat 2040
ttctacactt taaggccatt tggtgcaatt tagaaagtgt tggcctccct tccgctagcc 2100
acattcaaaa ttaacttcca aaacctcagg aacagtacaa agaattgaaa ccctcaatat 2160
ggcagcacag ccggctgtag tgtatattta gggtacacca aatcaggtat tcctggtggt 2220
cttgtgcact ttaatttctg ttacaatgag ttaagaggat gaggaagaaa tctacttatt 2280
aacacttact gcagaaatgt ctgcattatt ccgtttgttt tcttattatt ttacctctcc 2340
aaacatcttc ctgtgcagat cactacttca tagttgccaa attttaaaac acttaactgc 2400
tgaaattcag tgtcagcaaa gtgatattac gttgttctgt ttctaattaa ccttagcaaa 2460
tgtacataat gtcaaaaccc aatagtattt gacagtactt atgtatacaa tgtttgataa 2520
gcatttttaa taagatttgt atttttaaat ttagtatata ataaaaagat gtgtttcagt 2580
gtgaaaaaaa aaaaaaaaaa aaaa 2604

<210> SEQ ID NO 43
<211> LENGTH: 3281
<212> TYPE: DNA
<213> ORGANISM: Homo sapiens

<400> SEQUENCE: 43
gcggtgcggg ccgggcgggt gcattcaggc caaggcgggg ccgccgggat gctcagggtt 60
ccggagccgc ggcccgggga ggcgaaagcg gagggggccg cgccgccgac cccgtccaag 120
ccgctcacgt ccttcctcat ccaggacatc ctgcgggacg gcgcgcagcg gcaaggcggc 180
cgcacgagca gccagagaca gcgcgacccg gagccggagc cagagccaga gccagaggga 240
ggacgcagcc gcgccggggc gcagaacgac cagctgagca ccgggccccg cgccgcgccg 300
gaggaggccg agacgctggc agagaccgag ccagaaaggc acttggggtc ttatctgttg 360
gactctgaaa acacttcagg cgcccttcca aggcttcccc aaacccctaa gcagccgcag 420
aagcgctccc gagctgcctt ctcccacact caggtgatcg agttggagag gaagttcagc 480
catcagaagt acctgtcggc ccctgaacgg gcccacctgg ccaagaacct caagctcacg 540
gagacccaag tgaagatatg gttccagaac agacgctata agactaagcg aaagcagctc 600
tcctcggagc tgggagactt ggagaagcac tcctctttgc cggccctgaa agaggaggcc 660
ttctcccggg cctccctggt ctccgtgtat aacagctatc cttactaccc atacctgtac 720
tgcgtgggca gctggagccc agctttttgg taatgccagc tcaggtgaca accattatga 780
tcaaaaactg ccttccccag ggtgtctcta tgaaaagcac aaggggccaa ggtcagggag 840
caagaggtgt gcacaccaaa gctattggag atttgcgtgg aaatctcaga ttcttcactg 900
gtgagacaat gaaacaacag agacagtgaa agttttaata cctaagtcat tcctccagtg 960
catactgtag gtcatttttt ttgcttctgg ctacctgttt gaaggggaga gagggaaaat 1020
caagtggtat tttccagcac tttgtatgat tttggatgag ttgtacaccc aaggattctg 1080
ttctgcaact ccatcctcct gtgtcactga atatcaactc tgaaagagca aacctaacag 1140
gagaaaggac aaccaggatg aggatgtcac caactgaatt aaacttaagt ccagaagcct 1200

-continued

```
cctgttggcc ttggaatatg gccaaggctc tctctgtccc tgtaaaagag aggggcaaat   1260
agagagtctc caagagaacg ccctcatgct cagcacatat ttgcatggga gggggagatg   1320
ggtgggagga gatgaaaata tcagcttttc ttattccttt ttattccttt taaaatggta   1380
tgccaactta agtatttaca gggtggccca aatagaacaa gatgcactcg ctgtgatttt   1440
aagacaagct gtataaacag aactccactg caagaggggg ggccgggcca ggagaatctc   1500
cgcttgtcca agacaggggc ctaaggaggg tctccacact gctgctaggg gctgttgcat   1560
tttttatta gtagaaagtg gaaaggcctc ttctcaactt ttttcccttg ggctggagaa   1620
tttagaatca gaagtttcct ggagttttca ggctatcata tatactgtat cctgaaaggc   1680
aacataattc ttccttccct ccttttaaaa ttttgtgttc ctttttgcag caattactca   1740
ctaaagggct tcattttagt ccagattttt agtctggctg cacctaactt atgcctcgct   1800
tatttagccc gagatctggt cttttttttt tttttttttt tttttttcc gtctccccaa   1860
agctttatct gtcttgactt tttaaaaaag tttgggggca gattctgaat tggctaaaag   1920
acatgcattt ttaaaactag caactcttat ttctttcctt taaaaataca tagcattaaa   1980
tcccaaatcc tatttaaaga cctgacagct tgagaaggtc actactgcat ttataggacc   2040
ttctggtggt tctgctgtta cgtttgaagt ctgacaatcc ttgagaatct ttgcatgcag   2100
aggaggtaag aggtattgga ttttcacaga ggaagaacac agcgcagaat gaagggccag   2160
gcttactgag ctgtccagtg gagggctcat gggtgggaca tggaaaagaa ggcagcctag   2220
gccctgggga gcccagtcca ctgagcaagc aagggactga gtgagccttt tgcaggaaaa   2280
ggctaagaaa aaggaaaacc attctaaaac acaacaagaa actgtccaaa tgctttggga   2340
actgtgttta ttgcctataa tgggtcccca aaatgggtaa cctagacttc agagagaatg   2400
agcagagagc aaaggagaaa tctggctgtc cttccatttt cattctgtta tctcaggtga   2460
gctggtagag gggagacatt agaaaaaaat gaaacaacaa aacaattact aatgaggtac   2520
gctgaggcct gggagtctct tgactccact acttaattcc gtttagtgag aaacctttca   2580
attttctttt attagaaggg ccagcttact gttggtggca aaattgccaa cataagttaa   2640
tagaaagttg gccaatttca ccccattttc tgtggtttgg gctccacatt gcaatgttca   2700
atgccacgtg ctgctgacac cgaccggagt actagccagc acaaaaggca gggtagcctg   2760
aattgctttc tgctctttac atttctttta aaataagcat ttagtgctca gtccctactg   2820
agtactcttt ctctcccctc ctctgaattt aattctttca acttgcaatt tgcaaggatt   2880
acacatttca ctgtgatgta tattgtgttg caaaaaaaaa aaaaaagtgt ctttgtttaa   2940
aattacttgg tttgtgaatc catcttgctt tttccccatt ggaactagtc attaacccat   3000
ctctgaactg gtagaaaaac atctgaagag ctagtctatc agcatctgac aggtgaattg   3060
gatggttctc agaaccattt cacccagaca gcctgtttct atcctgttta ataaattagt   3120
ttgggttctc tacatgcata acaaaccctg ctccaatctg tcacataaaa gtctgtgact   3180
tgaagtttag tcagcacccc caccaaactt tatttttcta tgtgtttttt gcaacatatg   3240
agtgttttga aaataaagta cccatgtctt tattagattt a                       3281
```

<210> SEQ ID NO 44
<211> LENGTH: 1155
<212> TYPE: DNA
<213> ORGANISM: Homo sapiens

<400> SEQUENCE: 44

```
cgcctgtctt ttccgtgcta cctgcagagg ggtccatacg gcgttgttct ggattcccgt     60
```

cgtaacttaa agggaaattt tcacaatgtc cggagccctt gatgtcctgc aaatgaagga 120
ggaggatgtc cttaagttcc ttgcagcagg aacccactta ggtggcacca atcttgactt 180
ccagatggaa cagtacatct ataaaaggaa aagtgatggc atctatatca taaatctcaa 240
gaggacctgg gagaagcttc tgctggcagc tcgtgcaatt gttgccattg aaaaccctgc 300
tgatgtcagt gttatatcct ccaggaatac tggccagagg gctgtgctga agtttgctgc 360
tgccactgga gccactccaa ttgctggccg cttcactcct ggaaccttca ctaaccagat 420
ccaggcagcc ttccgggagc cacggcttct tgtggttact gaccccaggg ctgaccacca 480
gcctctcacg gaggcatctt atgttaacct acctaccatt gcgctgtgta acacagattc 540
tcctctgcgc tatgtggaca ttgccatccc atgcaacaac aagggagctc actcagtggg 600
tttgatgtgg tggatgctgg ctcgggaagt tctgcgcatg cgtggcacca tttcccgtga 660
acacccatgg gaggtcatgc ctgatctgta cttctacaga gatcctgaag agattgaaaa 720
agaagagcag gctgctgctg agaaggcagt gaccaaggag gaatttcagg gtgaatggac 780
tgctcccgct cctgagttca ctgctactca gcctgaggtt gcagactggt ctgaaggtgt 840
acaggtgccc tctgtgccta ttcagcaatt ccctactgaa gactggagcg ctcagcctgc 900
cacggaagac tggtctgcag ctcccactgc tcaggccact gaatgggtag gagcaaccac 960
tgactggtct taagctgttc ttgcataggc tcttaagcag catggaaaaa tggttgatgg 1020
aaaataaaca tcagtttcta aaagttgtct tcatttagtt tgctttttac tccagatcag 1080
aatacctggg attgcatatc aaagcataat aataaataca tgtctcgaca tgagttgtac 1140
ttctaaaaaa aaaaa 1155

<210> SEQ ID NO 45
<211> LENGTH: 784
<212> TYPE: DNA
<213> ORGANISM: Homo sapiens

<400> SEQUENCE: 45
gcccacgcgc cagagtcgca gtgggcgggc ctacgtgctc cgcccgctgt gagcctgtcc 60
ggcccccgcc cgctccggag caacccgcga gcttacaccg gcttctctct gtcctcagcc 120
cgcgcgccgc catcgccgtc atgctgggcg ccgctctccg ccgctgcgct gtggccgcaa 180
ccacccgggc cgaccctcga ggcctcctgc actccgcccg gacccccggc cccgccgtgg 240
ctatccagtc agttcgctgc tattcccatg ggtcacagga gacagatgag gagtttgatg 300
ctcgctgggt aacatacttc aacaagccag atatagatgc ctgggaattg cgtaaaggga 360
taaacacact tgttacctat gatatggttc cagagcccaa aatcattgat gctgctttgc 420
gggcatgcag acggttaaat gattttgcta gtacagttcg tatcctagag gttgttaagg 480
acaaagcagg acctcataag gaaatctacc cctatgtcat ccaggaactt agaccaactt 540
taaatgaact gggaatctcc actccggagg aactgggcct tgacaaagtg taaaccgcat 600
ggatgggctt ccccaaggat ttattgacat tgctacttga gtgtgaacag ttacctggaa 660
atactgatga taacatatta ccttatttga acaagttttc ctttattgag taccaagcca 720
tgtaatggta acttggactt taataaaagg gaaatgagtt tgaactgaaa aaaaaaaaaa 780
aaaa 784

<210> SEQ ID NO 46
<211> LENGTH: 5740
<212> TYPE: DNA

<213> ORGANISM: Homo sapiens

<400> SEQUENCE: 46

```
cgccgccgcc gcacgccgcc tgcctcctgc acgccgccgc cgcgcctagc gcccgggccc     60
gcgacaccgc ccgctaagcg ccgggccgag ttcacgcagc cgcggtctgg cggctccgcg    120
gcggcggcgg gtgcgggcgg cctggccggt gccggttaaa gggacgagtt gcaaacactt    180
caggaagtga caagtcgatt tcctcctccc cgggagtcgc tcgtacaaag cgctcggcgc    240
cggcaggcga gcgtgcgcgc ggcggacgcg cggcgggcac cccggacgac ttggcgagcg    300
ctggcggtga cggcgcgggg tccgcgcccg gagcgccccg ccgcgcacag gagttgacca    360
catttggcca tttcccagaa gggccccacc ccaagggtga gtggccaatg gggagctgtt    420
tctgctgaca tcaattcccc aggaggtact caccccaagt ctgcccaagt gaagatggct    480
gatacccacc ctgggatgga gcccagcgcc tgaggccctt atcatggtga tggtcctaag    540
tgaaagcctc agcacccggg gagctgactc cattgcatgt gggaccttca gccgtgaact    600
gcacacgcca aagaagatga gtcaaggacc tacacttttc tcttgtggaa ttatggaaaa    660
tgacagatgg cgagacctgg acaggaaatg ccctcttcag attgaccaac cgagcaccag    720
catctgggaa tgcctgcctg aaaaggacag ctcactatgg caccgggagg cagtgaccgc    780
ctgcgctgtg accagtctga tcaaagacct cagcatcagc gaccacaacg ggaacccctc    840
agcacccccct agcaagcgcc agtgccgctc actgtccttc tccgatgaga tgtccagttg    900
ccggacatca tggaggccct tgggctccaa agtctggact cccgtggaaa agagacgctg    960
ctacagcggg ggcagcgtcc agcgctattc caacggcttc agcaccatgc agaggagttc   1020
cagcttcagc ctcccttccc gggccaacgt gctctcctca ccctgcgacc aggcaggact   1080
ccaccaccga tttggagggc agccctgcca aggggtgcca ggctcagccc cgtgtggaca   1140
ggcaggtgac acctggagcc ctgacctgca ccccgtggga ggaggccggc tggacctgca   1200
gcggtccctc tcttgctcac atgagcagtt ttcctttgtg gaatactgtc ctccctcagc   1260
caacagcaca cctgcctcaa caccagagct ggcgagacgc tccagcggcc tttcccgcag   1320
ccgctcccag ccgtgtgtcc ttaacgacaa gaaggtcggt gttaaaaggc ggcgccctga   1380
agaagtgcaa gagcagaggc cttctctaga ccttgccaag atggcacaga actgtcagac   1440
cttcagcagc ctcagctgcc tgagcgcagg gacagaggac tgcggtcccc agagcccctt   1500
cgcccgccac gtcagcaaca ccagggcctg gaccgccctg ctctcagcct ccggcccagg   1560
gggcaggacc cccgctggga ccccggtccc tgagcctctt ccccccttcct tcgacgacca   1620
cctcgcctgc caggaggacc tgtcctgtga ggagtcagac agctgcgccc tggacgagga   1680
ttgtggcagg agagcggagc cggctgcagc ctggcgggac cgcggggccc ctgggaacag   1740
cctctgctcc ctggacggcg agttggacat tgagcagata gagaagaact gagggggtgt   1800
gggcccaggc agggctgggg tgtgctggca tcgacagccc ccactctggg cactaggtgg   1860
gcccttgaag ggagcccaa ctcgtgggcc tgatgaaagc ttcctgagtg gtgtcgggtc    1920
ccagagaggg agcccacctg ctgcctgggg gagagcctgg cctggccgcg tcatacagcg   1980
ggtgtgtcag cctctcaccg gctccccgag cgtggcagcc accaggtcca cagaactact   2040
gcagcccaga ggacagcttt gaagtttgcg tcttttctgc ctctttccct gtgggatgtt   2100
gggcagtctc tgttgtcccc ggcagagctg ggcaccgctc tgtatccccc tggtggtggg   2160
ggctgtcagg gagggcctgg ggtgggggcc aggggccatc tgctatgtca gggcccttct   2220
tggcctcact caggttcact tctggggagt cggccccgca gcttctttca ctcagtttta   2280
```

ctccgtgcct tctctcccag gtctccctgc ttcaggcttg ggaaggttcg ggagatgctt 2340
ccttctgtaa caccagaacc atttggcctt aattccaatg tgagagacag aatccctggg 2400
gtgctggact ggccctccag agggtaagcc atgtccggag tctcgggccc aaggaacgat 2460
ttggagggtg cttgttaggg cctcccgtgt tgggtagaaa tttggtggat ctgttggctg 2520
aaaagacgga cttgcttgcc tctcctacag catggagagg ctgaccccat ggctctgcca 2580
ccgttggggc agggttagca gatggcagcc cttctctgtg gctgacaggt cactgagtga 2640
taagcatggt tggttccggt gagtgtaggg atggcacgat accagggcag cctcttgaaa 2700
acggcctcgg gagacgggag ctgcgagcag gtgggcagat gagggcccta tgcgcactca 2760
ggggtgaagg gcgtccgctg gccactctgc aggggcccct gcaggattcc aggcacctcc 2820
cgtttgtcct tgaggactgc tggctgtaac cagggcacat cacccacctc aagacaagcc 2880
cacgcccttg tcagcttagg gggagcccag tcctgagggc tgcatctctg ttgtaggccc 2940
agccaccggc acaaagctgg attcatgctc cctgccccta ccccaccctg gctcctcacc 3000
ctggggcatc cgaggagcct agccccctga gggtttgctc tcctctcaag gtttgtagct 3060
cctctccggc tgccttgcag acaccaccac atgggctctg ctctatggga atctggcttt 3120
tagcgaatgt ggcgtcttct gcaaacaata gcaattgggc tggcttagga gcaagtggct 3180
cattttccca taaggctaaa aataactggt gcgctccctt gtgttggctg acacgcgcgt 3240
tcaaagcact tttgtagtca ctttgctttt gctcgtcttc atggacgagt gaacgcctcg 3300
cttctgcagg ttgagtccag atgcttctca ccttctttct cctcaagaaa gatgcttttt 3360
gggaaacgtt gtttaaatct tattttttta ctacatcaaa aggatggtgg ttcaagttcc 3420
caatatgtgg gtggcacttc ttaaaaatca gctttaagga gctggcagaa agcccccagc 3480
cccacagccc tgagagatgg tgttgctagc tcaggtggct gacacatggg gtatgccggg 3540
cactgggcag gtcccagagc cggggaacca gctcacctct ggttgctgta gctcctgccg 3600
gaggcatgtc tacttgtgat cccggacagc cgaacccaag agctggtggc tctgagcaga 3660
cagagacatc ttggcctgtc cctgcctggg ggtcatggag accatgtctt cttagagcaa 3720
atgtggaggc ggccagggca gttgttgggt gaatgtggag agcacatggc catgtcttgc 3780
ccccggagta ccactgggcg tggggggtcc tggcaccaca tgcccggtgt ggccgagggc 3840
acacagcctc tatagcaggc cttcctgtgg aaggcagagg cagtgaggga ggtggacggt 3900
gccagctgag gctgaggcat gcagcagccc ccagctacct ttgcttaggg ctggggtggg 3960
aggcacatgg tgacaggtat atgtcgtggg actggggtgt gggtgacctg ccctcaaacc 4020
ttgcctgcca cctccccatt caggcctggt ggcaggaagg gacaagctgt ggagctggct 4080
gagtcacagc cacctcccca cctccccgca agctggtccc atcgaccagc aagcccagcc 4140
ccagggcgct tagggagaaa tgacccagcc tcctcagacc ccgcctgcct gtcctgtgcc 4200
caccacgcag cagtcagggg agaaaatggt ggctatccct tctgcttaga gaaagaaatg 4260
gcctttagct ggtttcatgt ttgtgttttg actggaggga gtagacccta tctataaggt 4320
gccaccccat catccaagct gccacactgc ccggagcagc ctgttcctgc actccaccct 4380
gctggcccca ggacttctga tctcagtcct ctgggaggga ggttcgccta ggaggtgccc 4440
cccacattgg tgtccccatg ggcagcaggc agacagctca cccccaccag catgatggcc 4500
ccagctgggg gcagtggcag gagccttact tttgtcacag ccttgcccac aaaccctgcc 4560
tctgagggga gactgaggaa gggcagagcc agaagcaagc cgtgccaggc catctgcctg 4620

-continued

```
ctcatggggt cctaaagcgc gggctaagcc tgcaggaaag ccggggcggt gggggggct   4680
tagtgccaca tgcaccccac tcattccaaa gccaccaaac tgccaggggc tgccgtccac   4740
ccgtggggcc caggggctgg ggccacagcc ttgccatttt cgttgccata ccctcttgcc   4800
ttactcgcgg tggaggccgg atttgcacgg gcagacgtgc acctgggccc gtggggagct   4860
tgttctgacc agacgtacag attttcattc tcagaaagcc ttacttttca accaaatttt   4920
tgtagccagt tttgtgaatt tgtacactga aagaaaattt aaataaaggg gaagtccaca   4980
ttaaaaagaa aacaaaacaa accctaacta acttccaaat gggtctcctg gtgcgggggc   5040
gtgagtggcc gtgccctggg tgtgctgcct gtctgagcaa gcttccctag ctgtggaacc   5100
ccgggccccc tgctgcgggc tctgccttgg tgtcatgcct gctgcacccc cgtttccact   5160
gacgtgccgt ctgtggctat gggggtggtc actggaatga cggtcactcc agacgtcagc   5220
cggcagggat gcagcaggct ggccgcgcac cggggctcgg gcaccctctg gccccacact   5280
ggcaatgatg ccacaccttg ccatgtccac gctgttggtc aaacccctct gtcatgcctc   5340
tttaaagaga aaagaagaga aagatttttt ttttttttaa tggcagaccg aagtggagat   5400
cttgtagcct agataggata gtctgacctt ctagcatagt ctttttggca aatgatttgt   5460
gttttcagtg tgtggggaag ctgtcctggg ggctggggcg acagatagca cataggctgt   5520
ttctggggct gcaggggctt ccctgagctg gatgttgtgg gtgttgccgt gcttcaggaa   5580
gtgtggcgac cagaaagcgt agacccgggg cccagggtct gcccgcccct gcagcctggc   5640
ctccccgcac aggctgtggc ttgcactcca gccgctctag tctctcagga atttgcttgt   5700
tacttgtact gtgtaaataa agcttcctgg ttcaataccc                         5740
```

<210> SEQ ID NO 47
<211> LENGTH: 1980
<212> TYPE: DNA
<213> ORGANISM: Homo sapiens

<400> SEQUENCE: 47

```
gcaatggaca agtcttggtt aaatgtgctt tggaggaact tcctgaaatg ggaagagga     60
tcatctgaaa atgagataga gatccacatc tgatttgtaa ttttgaacct aatagtttat   120
tatttatatt tgagagtatc ctaaatctgc tattagcagc caaaaatgaa tacaagaaag   180
tacaatcgtt atttaaaaga agcaagttat agttgacaaa gattaaaatg ttaaaagttg   240
tttgaagttt aggcaactga caataacaga acaacttatt aataacagta atgaagttaa   300
aaattataga gcatttgcta taacctaagt atgtccgttt aaacttcacc actttcttag   360
attaggaagc tgaccttcag ataagtaaaa ttatatcgga aaggtcctct taattcacag   420
tgccaaatcc agattttccc tgacttcccc aaatgccact tataagataa tttaattatt   480
attcatcccc tgatgactgc aggaaaacct ctgtgggtaa gtagagataa atgtgaagag   540
cagaagcaaa gaaaagagct agcagtagtg aatgttgaac ttcatgtgct aattggtgtg   600
tgtccatttc tgatacagcc actttgagac aagggctata tcatccatga attggatctt   660
aatgtccatt gctgtatttt tacttctcta gtttttaaga aatttaggct gtggttcaca   720
ttgtgtattc gaaagataga atacctcgct aactagacaa acaaaagctt tgttctaaaa   780
atgtactttc cttaaagcag aagtaacctg cagagaagca ggatgcctga agagagatgg   840
atctctgctt actgtgtctt tagaacagaa atagtggttt tcaacttcac aactctgcat   900
tgagccctcc tttcacatct tccctgtatc attgcagaat tgatctgaat aattctcatt   960
ttatcttaga caatttttg tgtggcttga aaaaataaat ttgcaataga ggtgaaatgg   1020
```

-continued aaaaaattat ccttcatttc ctactccaaa ctgaggataa acaattattc ttggaaattc 1080
caccatagaa ttgaattcat tgtacgtgtg aattgcacct tttaagcttt taaatgatgt 1140
ggcattttta tttagcagca ttccaaaagg gaccacgaaa taaatgagct ccctggtttt 1200
gcagcatttt ataattccaa tatgaaagtt ttagcattat tactaactga agaatcagaa 1260
aggaaattca tagactatca cttctgggtt ttcaagtatt tttaatccat gcaactcttc 1320
ctccaaactt tttcttcaac ttctcatgag aaagtcagca tataaagttc ttaaaagctg 1380
tgctcccctg accgaaatgg agatgagtac catggtggga gaatgcatct ttccccctcg 1440
agagtcctct agcacctgcg gtggtctctg gaagaactca gcagaactcc caagtgccaa 1500
ggaacacata ttacagaaca acggactgca gaaattcaga tagatgaaaa ctatagatca 1560
ttctaggtac tttgttccca gacttataat actcccaata gcttctctaa tgtatgatca 1620
agtggctgtc tgctgtaata ttttcagagc tataatgttt atatctaacc tcttatattt 1680
atgtccaaat cagctggtat attttggctt attctgagca gtagctgcta gatctatctt 1740
gtggtacaca ttaagcctat tccttcttcc acagttcttc ttgacattat gctacttaaa 1800
aagtcatccc ttatcaaaat caaatttcat tattttagtt atatcacatc caatatttaa 1860
ttgtgtaaac cactctttac tctagctatt cgtcctcaga attgcttctg ttataaatgc 1920
tctttttgaa cagacttcct agagtagaag agaaagctcc agatatgatc tgatgggggt 1980

<210> SEQ ID NO 48
<211> LENGTH: 5602
<212> TYPE: DNA
<213> ORGANISM: Homo sapiens

<400> SEQUENCE: 48
atggagccct ccagagcgct tctcggctgc ctagcgagcg ccgccgctgc cgccccgccg 60
ggggaggatg gagcaggggc cggggccgag gaggaggagg aggaggagga ggaggcggcg 120
gcggcggtgg gccccgggga gctgggctgc gacgcgccgc tgccctactg gacggccgtg 180
ttcgagtacg aggcggcggg cgaggacgag ctgaccctgc ggctgggcga cgtggtggag 240
gtgctgtcca aggactcgca ggtgtccggc gacgagggct ggtggaccgg gcagctgaac 300
cagcgggtgg gcatcttccc cagcaactac gtgaccccgc gcagcgcctt ctccagccgc 360
tgccagcccg gcggcgagga ccccagttgc tacccgccca ttcagttgtt agaaattgat 420
tttgcggagc tcaccttgga agagattatt ggcatcgggg gctttgggaa ggtctatcgt 480
gctttctgga taggggatga ggttgctgtg aaagcagctc gccacgaccc tgatgaggac 540
atcagccaga ccatagagaa tgttcgccaa gaggccaagc tcttcgccat gctgaagcac 600
cccaacatca ttgccctaag aggggtatgt ctgaaggagc ccaacctctg cttggtcatg 660
gagtttgctc gtggaggacc tttgaataga gtgttatctg ggaaaaggat tccccccagac 720 atcctggtga attgggctgt gcagattgcc agagggatga actacttaca tgatgaggca 780
attgttccca tcatccaccg cgaccttaag tccagcaaca tattgatcct ccagaaggtg 840
gagaatggag acctgagcaa caagattctg aagatcactg attttggcct ggctcgggaa 900
tggcaccgaa ccaccaagat gagtgcggca gggacgtatg cttggatggc acccgaagtc 960
atccgggcct ccatgttttc caaaggcagt gatgtgtgga gctatggggt gctactttgg 1020
gagttgctga ctggtgaggt gccctttcga ggcattgatg gcttagcagt cgcttatgga 1080
gtggccatga acaaactcgc ccttcctatt ccttctacgt gcccagaacc ttttgccaaa 1140

-continued

```
ctcatggaag actgctggaa tcctgatccc cactcacgac catctttcac gaatatcctg   1200
gaccagctaa ccaccataga ggagtctggt ttctttgaaa tgcccaagga ctccttccac   1260
tgcctgcagg acaactggaa acacgagatt caggagatgt ttgaccaact cagggccaaa   1320
gaaaaggaac ttcgcacctg ggaggaggag ctgacgcggg ctgcactgca gcagaagaac   1380
caggaggaac tgctgcggcg tcgggagcag gagctggccg agcgggagat tgacatcctg   1440
gaacgggagc tcaacatcat catccaccag ctgtgccagg agaagccccg ggtgaagaaa   1500
cgcaagggca agttcaggaa gagccggctg aagctcaagg atggcaaccg catcagcctc   1560
ccttctgatt tccagcacaa gttcacggtg caggcctccc ctaccatgga taaaaggaag   1620
agtcttatca acagccgctc cagtcctcct gcaagcccca ccatcattcc tcgccttcga   1680
gccatccagt tgacaccagg tgaaagcagc aaaacctggg gcaggagctc agtcgtccca   1740
aaggaggaag gggaggagga ggagaagagg gccccaaaga agaagggacg gacgtggggg   1800
ccagggacgc ttggtcagaa ggagcttgcc tcgggagatg aaggatcccc tcagagacgt   1860
gagaaagcta atggtttaag taccccatca gaatctccac atttccactt gggcctcaag   1920
tccctggtag atggatataa gcagtggtcg tccagtgccc ccaacctggt gaagggccca   1980
aggagtagcc cggccctgcc agggttcacc agccttatgg agatggcctt gctggcagcc   2040
agttgggtgg tgcccatcga cattgaagag gatgaggaca gtgaaggccc agggagtgga   2100
gagagtcgcc tacagcattc acccagccag tcctacctct gtatcccatt ccctcgtgga   2160
gaggatggcg atggcccctc cagtgatgga atccatgagg agcccacccc agtcaactcg   2220
gccacgagta cccctcagct gacgccaacc aacagcctca agcggggcgg tgcccaccac   2280
cgccgctgcg aggtggctct gctcggctgt ggggctgttc tggcagccac aggcctaggg   2340
tttgacttgc tggaagctgg caagtgccag ctgcttcccc tggaggagcc tgagccacca   2400
gcccgggagg agaagaaaag acgggagggt ctttttcaga ggtccagccg tcctcgtcgg   2460
agcaccagcc ccccatcccg aaagcttttc aagaaggagg agcccatgct gttgctagga   2520
gacccctctg cctccctgac gctgctctcc ctctcctcca tctccgagtg caactccaca   2580
cgctccctgc tgcgctccga cagcgatgaa attgtcgtgt atgagatgcc agtcagccca   2640
gtcgaggccc ctcccctgag tccatgtacc cacaaccccc tggtcaatgt ccgagtagag   2700
cgcttcaaac gagatcctaa ccaatctctg actcccaccc atgtcaccct caccaccccc   2760
tcgcagccca gcagtcaccg gcggactcct tctgatgggg cccttaagcc agagactctc   2820
ctagccagca ggagcccctc cagcaatggg ttgagcccca gtcctggagc aggaatgttg   2880
aaaaccccca gtcccagccg agacccaggt gaattccccc gtctccctga ccccaatgtg   2940
gtcttccccc caaccccaag gcgctggaac actcagcagg actctacctt ggagagaccc   3000
aagactctgg agtttctgcc tcggccgcgt ccttctgcca accggcaacg gctggaccct   3060
tggtggtttg tgtcccccag ccatgcccgc agcacctccc cagccaacag ctccagcaca   3120
gagacgccca gcaacctgga ctcctgcttt gctagcagta gcagcactgt agaggagcgg   3180
cctggacttc cagccctgct cccgttccag gcagggccgc tgcccccgac tgagcggacg   3240
ctcctggacc tggatgcaga ggggcagagt caggacagca ccgtgccgct gtgcagagcg   3300
gaactgaaca cacacaggcc tgccccttat gagatccagc aggagttctg gtcttagcac   3360
gaaaaggatt ggggcgggca agggggacag ccagcggaga tgaggggagc tggcgggcac   3420
agccctttct cagggttgga ccccctgaga tccagcccta cttcttgcac tgataatgca   3480
ctttgaagat ggaagggatg gaaacagggc cacttcagag ggtctcctgc cctgcagggc   3540
```

ctttctaccc gtgtccactg gaggggctgt ggccatcagc tctggctgtg taggggagga 3600
aggggtgcat gcatgtcccc caccctccac agtcttcctt gcctttagag tgaccctgca 3660
gagtcactca gccaaatctg tctgctgctc cctctcctca gccagttggg tgtgcgcaga 3720
gctgtcatag ggtccctttg tcagccccga gttcagcttc ccaaacacca gtgttggata 3780
ttctgtgatt gattttggtc ctcctccgct gtcccccaac acccaggaat gggaatctgg 3840
cttggttcga gataggagct tttctgtgtc ctaagccctt tcatgctagc aggaagactg 3900
aaagcaaggt ggcccagtgt ggggtcatag ggcttgatag acctggcact gcctatctgc 3960
acttccaggt gccccaccta tttatctgag cccacaggtg gaaaggggaa ctgcctcagt 4020
gagaacgggg ggacggggat gttaggaaaa atacagtaaa gttgcaatga agaggttcat 4080
gaagtatgtc cttgttcttt ttggaaactc tcggcaaagg gcaaaccagc aagtattgag 4140
ggtacccatc tagctacttg gggtcaggac ctcgtcagac caggttcgga tacaatcatc 4200
tgctcatccc aggaatagtt tcttggggga ctcactcact ggtgccagtt ctaagtcaga 4260
gacaaaattc cactgtctgt tccttttgct gtctgaactt tatgtgttac tcccttcctt 4320
tggtcttcac tctaatccct ggagtttgtg ggcttttggt tatgtttggt tagtagatat 4380
caccgcaatg ccctagaaca gctatgaagc agaataccat atggccacct ggacattggg 4440
acttgggaat tcactctcaa ctgggccatc catgttgtga tgcccttgaa gtaaaatgga 4500
gccagcagga gtaccttctg taaatgcatg tggcaaagtg ctatttatag ggtgcccagg 4560
gagccgctga tgtacaataa ccttgaggtc ccccatactg aaaactgacc aaggcctgtg 4620
cacaggtagc ccctcatgct gggctctgga ccatgagctg agtaggaagg atagcagagg 4680
ccaaccctga ccttcctgga agttgtttcc ttaacttgaa tgttgagctt cctctaaagc 4740
tttctcgtgt atgtcttctc catgccacta ctctgaggcc tcctgtgtta tgtgtgaaca 4800
gttgtcttta tgtgggaatg acgacttgat tgggagtaga gtctcaaggt cattcccctc 4860
ttccctcaag actctctgaa tgctgctcca ctgtcttttg tcttggaggt cactcagcag 4920
gttccttgca tttgctgcct ggatgtgcag ctggcaacag tgatgaattg gtcactgctc 4980
tttctctata actgggatag atgtcctgcc ttggggtcac taaaggggtg accttgttcc 5040
ttgctttatg agcccattag cactttggtt caaggggccc accaagtctt ggacgggaag 5100
gcgctactgg ttttattgcc caaggttttg ttattgcttc tcttctgtgt ccttctcttt 5160
gttcagtgaa gccaatatgt aagatactgt tttgtcccc attcccctac tcctgagcta 5220
ggaggaaaaa atgtgaatct taccagcagt tccagccaac caagtgattc ttcttcattc 5280
ttgatgggga gaagtacata caaagtttgt tctgacaggg cgcggtggct cacgcctgta 5340
atcccagcgc tttgggaggc agaggcaggt ggatcacctg aggtcgggag ttcgagacca 5400
gcctgaccaa catggagata tcctgtctct actaaaaata caaaaaaatt agccaggcat 5460
ggtggcacgt gcctgtaatc ccagctactc gcaaggctga ggcaggagaa tcgcttgaac 5520
ctgggaggcg gaggttgcag tgagccaaga ttgcgccatt gcactccagc ctgggcaaca 5580
agagagaaac tctgtctcaa aa 5602

<210> SEQ ID NO 49
<211> LENGTH: 824
<212> TYPE: DNA
<213> ORGANISM: Homo sapiens

<400> SEQUENCE: 49

```
ccgggccccg ccgcgccgcc tccttcccag ctcgcccgcc caggcctggc ctcctgcttt      60
tccatttgat tccctgcctc tttctattcg gactggaatg ccgggccagg ctccggggcg     120
cgccgctgcg gcagccgcac ctcgcaggtc ccccggccga ccccgacgcg gaagcggcgg     180
ccctcctcgc cgtcggggag ccagggagcc ggggacgatc agtcacataa ggcttagagg     240
atcaaggatc ctgcccagat gacttaccga aatgttacag attaagttgg tgtggtaacc     300
tgggctgagc actctgggag aggaagagaa gagagaagac aggaaacaac tgaactatga     360
ccaatcccag cacggaggcc cagaaaactt taagatttga gtattaatgt ctcaaggtca     420
ggagcaacct caaggctaaa actcagatct caggactcaa tttcacagaa gttccactat     480
aaaggcaata atctaaagct ttaaatgata tgaaaatttt gtaataagag ttcagtattt     540
ctgccaacat tggcgcatgg attgcaaagt tcacaggatt gaaaacacca tcgacataat     600
ggaaattgaa cagcatctga ttactgagtg ctatatcagc aagttaaaag gatcttttgc     660
ataccttta atggtatata tcctaaaact gaagtgttca atatagacat ccagattgaa      720
actcaggcag tgaattacat acacaacaaa tcagttgaac atggcagagc ttgtcagact     780
tatgaaagat taaatacatt ttacatttcc acaagtgtgg tatt                      824
```

<210> SEQ ID NO 50
<211> LENGTH: 7130
<212> TYPE: DNA
<213> ORGANISM: Homo sapiens

<400> SEQUENCE: 50

```
gaattccaca ttgtttgctg cacgttggat tttgaaatgc tagggaactt tgggagactc      60
atatttctgg gctagaggat ctgtggacca caagatcttt ttatgatgac agtagcaatg     120
tatctgtgga gctggattct gggttgggag tgcaaggaaa agaatgtact aaatgccaag     180
acatctattt caggagcatg aggaataaaa gttctagttt ctggtctcag agtggtgcag     240
ggatcaggga gtctcacaat ctcctgagtg ctggtgtctt agggcacact gggtcttgga     300
gtgcaaagga tctaggcacg tgaggctttg tatgaagaat cggggatcgt acccaccccc     360
tgtttctgtt tcatcctggg catgtctcct ctgcctttgt cccctagatg aagtctccat     420
gagctacaag ggcctggtgc atccagggtg atctagtaat tgcagaacag caagtgctag     480
ctctccctcc ccttccacag ctctgggtgt gggagggggt tgtccagcct ccagcagcat     540
ggggagggcc ttggtcagcc tctgggtgcc agcagggcag gggcggagtc ctggggaatg     600
aaggttttat agggctcctg ggggaggctc cccagcccca agcttaccac ctgcacccgg     660
agagctgtgt caccatgtgg gtcccggttg tcttcctcac cctgtccgtg acgtggattg     720
gtgagagggg ccatggttgg ggggatgcag gagagggagc cagccctgac tgtcaagctg     780
aggctctttc ccccccaacc cagcacccca gcccagacag ggagctgggc tcttttctgt     840
ctctcccagc cccacttcaa gcccataccc ccagcccctc catattgcaa cagtcctcac     900
tcccacacca ggtccccgct ccctcccact taccccagaa ctttctcccc attgcccagc     960
cagctccctg ctcccagctg ctttactaaa ggggaagttc ctgggcatct ccgtgtttct    1020
ctttgtgggg ctcaaaacct ccaaggacct ctctcaatgc cattggttcc ttggaccgta    1080
tcactggtcc atctcctgag cccctcaatc ctatcacagt ctactgactt ttcccattca    1140
gctgtgagtg tccaacccta tcccagagac cttgatgctt ggcctcccaa tcttgcccta    1200
ggatacccag atgccaacca gacacctcct tcttcctagc caggctatct ggcctgagac    1260
aacaaatggg tccctcagtc tggcaatggg actctgagaa ctcctcattc cctgactctt    1320
```

-continued

```
agccccagac tcttcattca gtggcccaca ttttccttag gaaaaacatg agcatcccca   1380
gccacaactg ccagctctct gattccccaa atctgcatcc ttttcaaaac ctaaaaacaa   1440
aaagaaaaac aaataaaaca aaaccaactc agaccagaac tgttttctca acctgggact   1500
tcctaaactt tccaaaacct tcctcttcca gcaactgaac ctggccataa ggcacttatc   1560
cctggttcct agcacccctt atcccctcag aatccacaac ttgtaccaag tttcccttct   1620
cccagtccaa gaccccaaat caccacaaag gacccaatcc ccagactcaa gatatggtct   1680
gggcgctgtc ttgtgtctcc taccctgatc cctgggttca actctgctcc cagagcatga   1740
agcctctcca ccagcaccag ccaccaacct gcaaacctag ggaagattga cagaattccc   1800
agcctttccc agctccccct gcccatgtcc caggactccc agccttggtt ctctgccccc   1860
gtgtcttttc aaacccacat cctaaatcca tctcctatcc gagtccccca gttcccccctg  1920
tcaaccctga ttcccctgat ctagcacccc ctctgcaggc gctgcgcccc tcatcctgtc   1980
tcggattgtg ggaggctggg agtgcgagaa gcattcccaa ccctggcagg tgcttgtggc   2040
ctctcgtggc agggcagtct gcggcggtgt tctggtgcac ccccagtggg tcctcacagc   2100
tgcccactgc atcaggaagt gagtaggggc ctggggtctg gggagcaggt gtctgtgtcc   2160
cagaggaata acagctgggc attttcccca ggataacctc taaggccagc cttgggactg   2220
ggggagagag ggaaagttct ggttcaggtc acatggggag gcagggttgg ggctggacca   2280
ccctccccat ggctgcctgg gtctccatct gtgtccctct atgtctcttt gtgtcgcttt   2340
cattatgtct cttggtaact ggcttcggtt gtgtctctcc gtgtgactat tttgttctct   2400
ctctccctct cttctctgtc ttcagtctcc atatctcccc ctctctctgt ccttctctgg   2460
tccctctcta gccagtgtgt ctcaccctgt atctctctgc caggctctgt ctctcggtct   2520
ctgtctcacc tgtgccttct ccctactgaa cacacgcacg ggatgggcct ggggggaccc   2580
tgagaaaagg aagggctttg gctgggcgcg gtggctcaca cctgtaatcc cagcactttg   2640
ggaggccaag gcaggtagat cacctgaggt caggagttcg agaccagcct ggccaactgg   2700
tgaaacccca tctctactaa aaatacaaaa aattagccag gcgtggtggc gcatgcctgt   2760
agtcccagct actcaggagg ctgagggagg agaattgctt gaacctggga ggttgaggtt   2820
gcagtgagcc gagaccgtgc cactgcactc cagcctgggt gacagagtga gactccgcct   2880
caaaaaaaaa aaaaaaaaaa aaaaaaaaaa agaaaagaaa agaaaagaaa aggaatcttt   2940
tatccctgat gtgtgtgggt atgagggtat gagagggccc ctctcactcc attccttctc   3000
caggacatcc ctccactctt gggagacaca gagaagggct ggttccagct ggagctggga   3060
ggggcaattg agggaggagg aaggagaagg gggaaggaaa acagggtatg ggggaaagga   3120
ccctggggag cgaagtggag gatacaacct tgggcctgca ggccaggcta cctacccact   3180
tggaaaccca cgccaaagcc gcatctacag ctgagccact ctgaggcctc ccctccccgg   3240
cggtccccac tcagctccaa agtctctctc cctttttctct cccacacttt atcatccccc  3300
ggattcctct ctacttggtt ctcattcttc ctttgacttc ctgcttccct ttctcattca   3360
tctgtttctc actttctgcc tggttttgtt cttctctctc tctttctctg gcccatgtct   3420
gtttctctat gtttctgtct tttctttctc atcctgtgta ttttcggctc accttgtttg   3480
tcactgttct cccctctgcc ctttcattct ctctgtcctt ttaccctctt cctttttccc   3540
ttggtttctc tcagtttctg tatctgccct tcaccctctc acactgctgt ttcccaactc   3600
gttgtctgta tttttggcct gaactgtgtc ttccccaacc ctgtgttttt ctcactgttt   3660
```

ctttttctct tttggagcct cctccttgct cctctgtccc ttctctcttt ccttatcatc 3720
ctcgctcctc attcctgcgt ctgcttcctc cccagcaaaa gcgtgatctt gctgggtcgg 3780
cacagcctgt ttcatcctga agacacaggc caggtatttc aggtcagcca cagcttccca 3840
cacccgctct acgatatgag cctcctgaag aatcgattcc tcaggccagg tgatgactcc 3900
agccacgacc tcatgctgct ccgcctgtca gagcctgccg agctcacgga tgctgtgaag 3960
gtcatggacc tgcccaccca ggagccagca ctggggacca cctgctacgc ctcaggctgg 4020
ggcagcattg aaccagagga gtgtacgcct gggccagatg gtgcagccgg gagcccagat 4080
gcctgggtct gagggaggag gggacaggac tcctgggtct gagggaggag ggccaaggaa 4140
ccaggtgggg tccagcccac aacagtgttt ttgcctggcc cgtagtcttg accccaaaga 4200
aacttcagtg tgtggacctc catgttattt ccaatgacgt gtgtgcgcaa gttcaccctc 4260
agaaggtgac caagttcatg ctgtgtgctg gacgctggac agggggcaaa agcacctgct 4320
cggtgagtca tccctactcc caagatcttg aggggaaagg tgagtgggga ccttaattct 4380
gggctggggt ctagaagcca acaaggcgtc tgcctcccct gctccccagc tgtagccatg 4440
ccacctcccc gtgtctcatc tcattccctc cttccctctt ctttgactcc ctcaaggcaa 4500
taggttattc ttacagcaca actcatctgt tcctgcgttc agcacacggt tactaggcac 4560
ctgctatgca cccagcactg ccctagagcc tgggacatag cagtgaacag acagagagca 4620
gcccctccct tctgtagccc ccaagccagt gaggggcaca ggcaggaaca gggaccacaa 4680
cacagaaaag ctggagggtg tcaggaggtg atcaggctct cggggaggga gaaggggtgg 4740
ggagtgtgac tgggaggaga catcctgcag aaggtgggag tgagcaaaca cctgccgcag 4800
gggaggggag ggccctgcgg cacctggggg agcagaggga acagcatctg gccaggcctg 4860
ggaggagggg cctagagggc gtcaggagca gagaggaggt tgcctggctg gagtgaagga 4920
tcggggcagg gtgcgagagg gaagaaagga cccctcctgc agggcctcac ctgggccaca 4980
ggaggacact gcttttcctc tgaggagtca ggaactgtgg atggtgctgg acagaagcag 5040
gacagggcct ggctcaggtg tccagaggct gccgctggcc tccctatggg atcagactgc 5100
agggagggag ggcagcaggg atgtggaggg agtgatgatg gggctgacct gggggtggct 5160
ccaggcattg tccccacctg ggcccttacc cagcctccct cacaggctcc tggccctcag 5220
tctctcccct ccactccatt ctccacctac ccacagtggg tcattctgat caccgaactg 5280
accatgccag ccctgccgat ggtcctccat ggctccctag tgccctggag aggaggtgtc 5340
tagtcagaga gtagtcctgg aaggtggcct ctgtgaggag ccacggggac agcatcctgc 5400
agatggtcct ggcccttgtc ccaccgacct gtctacaagg actgtcctcg tggaccctcc 5460
cctctgcaca ggagctggac cctgaagtcc cttccctacc ggccaggact ggagccccta 5520
cccctctgtt ggaatccctg cccaccttct tctggaagtc ggctctggag acatttctct 5580
cttcttccaa agctgggaac tgctatctgt tatctgcctg tccaggtctg aaagatagga 5640
ttgcccaggc agaaactggg actgacctat ctcactctct ccctgctttt acccttaggg 5700
tgattctggg ggcccacttg tctgtaatgg tgtgcttcaa ggtatcacgt catggggcag 5760
tgaaccatgt gccctgcccg aaaggccttc cctgtacacc aaggtggtgc attaccggaa 5820
gtggatcaag gacaccatcg tggccaaccc ctgagcaccc ctatcaactc cctattgtag 5880
taaacttgga accttggaaa tgaccaggcc aagactcaag cctccccagt tctactgacc 5940
tttgtcctta ggtgtgaggt ccagggttgc taggaaaaga aatcagcaga cacaggtgta 6000
gaccagagtg tttcttaaat ggtgtaattt tgtcctctct gtgtcctggg gaatactggc 6060
catgcctgga gacatatcac tcaatttctc tgaggacaca gataggatgg ggtgtctgtg 6120
ttatttgtgg gatacagaga tgaaagaggg gtgggatcca cactgagaga gtggagagtg 6180
acatgtgctg gacactgtcc atgaagcact gagcagaagc tggaggcaca acgcaccaga 6240
cactcacagc aaggatggag ctgaaaacat aacccactct gtcctggagg cactgggaag 6300
cctagagaag gctgtgagcc aaggagggag ggtcttcctt tggcatggga tggggatgaa 6360
gtaaggagag ggactggacc ccctggaagc tgattcacta tggggggagg tgtattgaag 6420
tcctccagac aaccctcaga tttgatgatt tcctagtaga actcacagaa ataaagagct 6480
cttatactgt ggtttattct ggtttgttac attgacagga gacacactga aatcagcaaa 6540
ggaaacaggc atctaagtgg ggatgtgaag aaaacaggga aaatctttca gttgttttct 6600
cccagtgggg tgttgtggac agcacttaaa tcacacagaa gtgatgtgtg accttgtgta 6660
tgaagtattt ccaactaagg aagctcacct gagccttagt gtccagagtt cttattgggg 6720
gtctgtagga taggcatggg gtactggaat agctgacctt aacttctcag acctgaggtt 6780
cccaagagtt caagcagata cagcatggcc tagagcctca gatgtacaaa aacaggcatt 6840
catcatgaat cgcactgtta gcatgaatca tctggcacgg cccaaggccc caggtatacc 6900
aaggcacttg ggccgaatgt tccaagggat taaatgtcat ctcccaggag ttattcaagg 6960
gtgagccctg tacttggaac gttcaggctt tgagcagtgc agggctgctg agtcaacctt 7020
ttactgtaca ggggggtgag ggaaagggag aagatgagga aaccgcctag ggatctggtt 7080
ctgtcttgtg gccgagtgga ccatggggct atcccaagaa ggaggaattc 7130

<210> SEQ ID NO 51
<211> LENGTH: 534
<212> TYPE: DNA
<213> ORGANISM: Homo sapiens

<400> SEQUENCE: 51
cgactttccc gatcgccagg caggagtttc tctcggtgac tactatcgct gtcatgtctg 60
gtcgtggcaa gcaaggaggc aaggcccgcg ccaaggccaa gtcgcgctcg tcccgcgctg 120
gccttcagtt cccggtaggg cgagtgcatc gcttgctgcg caaaggcaac tacgcggagc 180
gagtgggggc cggcgcgccc gtctacatgg ctgcggtcct cgagtatctg accgccgaga 240
tcctggagct ggcgggcaac gcggctcggg acaacaagaa gacgcgcatc atccctcgtc 300
acctccagct ggccatccgc aacgacgagg aactgaacaa gctgctgggc aaagtcacca 360
tcgcccaggg cggcgtcttg cctaacatcc aggccgtact gctccctaag aagacggaga 420
gtcaccacaa ggcaaagggc aagtgaggct gacgtccggc ccaagtgggc ccagcccggc 480
ccgcgtctcg aaggggcacc tgtgaactca aaaggctctt ttcagagcca ccca 534

<210> SEQ ID NO 52
<211> LENGTH: 1478
<212> TYPE: DNA
<213> ORGANISM: Homo sapiens

<400> SEQUENCE: 52
gggtcctcgg agctgctctg gctgcgcgcg gagcgggctc cggagggaag tcccgagaca 60
aagggaagcg ccgccgccgc cgccccgctc ggtcctccac ctgtccgcta cgctcgccgg 120
ggctgcggcc gcccgaggct gccctgagga tctgtgtttg gtgaaaagga gccaaattca 180
cctgcagggc aggcggctct agcagcttca gaagcctggt gccctggcga cactggacct 240

```
gccttggctt ctttgatccc aaccccaccc ccgatttctg ctctgctgac tggggaagtc    300
atcgtgccac ccagaacctg agtgcgggcc tctcagagct ccttcgtccg tgggtctgcc    360
ggggactggg ccttgtctcc ctaacgagtg ccagggactt tgaacatgtc ggggatcgcc    420
ctcagcagac tcgcccagga gaggaaagca tggaggaaag accacccatt tggtttcgtg    480
gctgtcccaa caaaaaatcc cgatggcacg atgaacctca tgaactggga gtgcgccatt    540
ccaggaaaga aagggactcc gtgggaagga ggcttgttta aactacggat gcttttcaaa    600
gatgattatc catcttcgcc accaaaatgt aaattcgaac caccattatt tcacccgaat    660
gtgtaccctt cggggacagt gtgcctgtcc atcttagagg aggacaagga ctggaggcca    720
gccatcacaa tcaaacagat cctattagga atacaggaac ttctaaatga accaaatatc    780
caagacccag ctcaagcaga ggcctacacg atttactgcc aaaacagagt ggagtacgag    840
aaaagggtcc gagcacaagc caagaagttt gcgccctcat aagcagcgac cttgtggcat    900
cgtcaaaagg aagggattgg tttggcaaga acttgtttac aacatttttg caaatctaaa    960
gttgctccat acaatgacta gtcacctggg ggggttgggc gggcgccatc ttccattgcc   1020
gccgcgggtg tgcggtctcg attcgctgaa ttgcccgttt ccatacaggg tctcttcctt   1080
cggtcttttg tatttttgat tgttatgtaa aactcgcttt tattttaata ttgatgtcag   1140
tatttcaact gctgtaaaat tataaacttt tatacttggg taagtccccc aggggcgagt   1200
tcctcgctct gggatgcagg catgcttctc accgtgcaga gctgcacttg gcctcagctg   1260
gctgtatgga aatgcaccct ccctcctgcc gctcctctct agaaccttct agaacctggg   1320
ctgtgctgct tttgagcctc agaccccagg tcagcatctc ggttctgcgc cacttccttt   1380
gtgtttatat ggcgttttgt ctgtgttgct gtttagagta aataaactgt ttatataaag   1440
gttttggttg cattattatc attgaaagtg agaggagg                           1478
```

<210> SEQ ID NO 53
<211> LENGTH: 3670
<212> TYPE: DNA
<213> ORGANISM: Homo sapiens

<400> SEQUENCE: 53

```
cgcagcaaac acatccgtag aaggcagcgc ggccgccgag aaccgcagcg ccgctcgccc     60
gccgcccccc accccgccgc cccgcccggc gaattgcgcc ccgcgcccct cccctcgcgc    120
ccccgagaca aagaggagag aaagtttgcg cggccgagcg gggcaggtga ggagggtgag    180
ccgcgcggga ggggcccgcc tcggccccgg ctcagccccc gcccgcgccc ccagcccgcc    240
gccgcgagca gcgcccggac cccccagcgg cggcccccgc ccgcccagcc ccccggcccg    300
ccatgggcgc cgcggcccgc accctgcggc tggcgctcgg cctcctgctg ctggcgacgc    360
tgcttcgccc ggccgacgcc tgcagctgct ccccggtgca cccgcaacag gcgttttgca    420
atgcagatgt agtgatcagg gccaaagcgg tcagtgagaa ggaagtggac tctggaaacg    480
acatttatgg caaccctatc aagaggatcc agtatgagat caagcagata aagatgttca    540
aagggcctga gaaggatata gagtttatct acacggcccc ctcctcggca gtgtgtgggg    600
tctcgctgga cgttggagga aagaaggaat atctcattgc aggaaaggcc gagggggacg    660
gcaagatgca catcaccctc tgtgacttca tcgtgccctg ggacaccctg agcaccaccc    720
agaagaagag cctgaaccac aggtaccaga tgggctgcga gtgcaagatc acgcgctgcc    780
ccatgatccc gtgctacatc tcctccccgg acgagtgcct ctggatggac tgggtcacag    840
agaagaacat caacgggcac caggccaagt tcttcgcctg catcaagaga agtgacggct    900
```

cctgtgcgtg gtaccgcggc gcggcgcccc ccaagcagga gtttctcgac atcgaggacc 960
cataagcagg cctccaacgc ccctgtggcc aactgcaaaa aaagcctcca agggtttcga 1020
ctggtccagc tctgacatcc cttcctggaa acagcatgaa taaaacactc atcccatggg 1080
tccaaattaa tatgattctg ctcccccctt ctccttttag acatggttgt gggtctggag 1140
ggagacgtgg gtccaaggtc ctcatcccat cctccctctg ccaggcacta tgtgtctggg 1200
gcttcgatcc ttgggtgcag gcagggctgg gacacgcggc ttccctccca gtccctgcct 1260
tggcaccgtc acagatgcca agcaggcagc acttagggat ctcccagctg ggttagggca 1320
gggcctggaa atgtgcattt tgcagaaact tttgagggtc gttgcaagac tgtgtagcag 1380
gcctaccagg tccctttcat cttgagaggg acatggccct tgttttctgc agcttccacg 1440
cctctgcact ccctgcccct ggcaagtgct cccatcgccc cggtgcccac catgagctcc 1500
cagcacctga ctccccccac atccaagggc agcctggaac cagtggctag ttcttgaagg 1560
agccccatca atcctattaa tcctcagaat tccagtggga gcctccctct gagccttgta 1620
gaaatgggag cgagaaaccc cagctgagct gcgttccagc ctcagctgag tctttttggt 1680
ctgcacccac ccccccaccc cccccccccc gcccacatgc tccccagctt gcaggaggaa 1740
tcggtgaggt cctgtcctga ggctgctgtc cggggccggt ggctgccctc aaggtccctt 1800
ccctagctgc tgcggttgcc attgcttctt gcctgttctg gcatcaggca cctggattga 1860
gttgcacagc tttgctttat ccgggcttgt gtgcagggcc cggctgggct ccccatctgc 1920
acatcctgag gacagaaaaa gctgggtctt gctgtgccct cccaggctta gtgttccctc 1980
cctcaaagac tgacagccat cgttctgcac ggggctttct gcatgtgacg ccagctaagc 2040
atagtaagaa gtccagccta ggaagggaag gattttggag gtaggtggct ttggtgacac 2100
actcacttct ttctcagcct ccaggacact atggcctgtt ttaagagaca tcttattttt 2160
ctaaaggtga attctcagat gataggtgaa cctgagttgc agatatacca acttctgctt 2220
gtatttctta aatgacaaag attacctagc taagaaactt cctagggaac tagggaacct 2280
atgtgttccc tcagtgtggt ttcctgaagc cagtgatatg gggggttagga taggaagaac 2340
tttctcggta atgataagga gaatctcttg tttcctccca cctgtgttgt aaagataaac 2400
tgacgatata caggcacatt atgtaaacat acacacgcaa tgaaaccgaa gcttggcggc 2460
ctgggcgtgg tcttgcaaaa tgcttccaaa gccaccttag cctgttctat tcagcggcaa 2520
ccccaaagca cctgttaaga ctcctgaccc ccaagtggca tgcagccccc atgcccaccg 2580
ggacctggtc agcacagatc ttgatgactt ccctttctag ggcagactgg gagggtatcc 2640
aggaatcggc ccctgcccca cgggcgtttt catgctgtac agtgacctaa agttggtaag 2700
atgtcataat ggaccagtcc atgtgatttc agtatataca actccaccag acccctccaa 2760
cccatataac accccacccc tgttcgcttc ctgtatggtg atatcatatg taacatttac 2820
tcctgtttct gctgattgtt tttttaatgt tttggtttgt ttttgacatc agctgtaatc 2880
attcctgtgc tgtgtttttt attacccttg gtaggtatta gacttgcact tttttaaaaa 2940
aaggtttctg catcgtggaa gcatttgacc cagagtggaa cgcgtggcct atgcaggtgg 3000
attccttcag gtctttcctt tggttctttg agcatctttg ctttcattcg tctcccgtct 3060
ttggttctcc agttcaaatt attgcaaagt aaaggatctt tgagtaggtt cggtctgaaa 3120
ggtgtggcct ttatatttga tccacacacg ttggtctttt aaccgtgctg agcagaaaac 3180
aaaacaggtt aagaagagcc gggtggcagc tgacagagga agccgctcaa ataccttcac 3240

```
aataaatagt ggcaatatat atatagttta agaaggctct ccatttggca tcgtttaatt   3300

tatatgttat gttctaagca cagctctctt ctcctatttt catcctgcaa gcaactcaaa   3360

atatttaaaa taaagtttac attgtagtta ttttcaaatc tttgcttgat aagtattaag   3420

aaatattgga cttgctgccg taatttaaag ctctgttgat tttgtttccg tttggatttt   3480

tgggggaggg gagcactgtg tttatgctgg aatatgaagt ctgagacctt ccggtgctgg   3540

gaacacacaa gagttgttga aagttgacaa gcagactgcg catgtctctg atgctttgta   3600

tcattcttga gcaatcgctc ggtccgtgga caataaacag tattatcaaa gagaaaaaaa   3660

aaaaaaaaaa                                                          3670


<210> SEQ ID NO 54
<211> LENGTH: 2428
<212> TYPE: DNA
<213> ORGANISM: Homo sapiens

<400> SEQUENCE: 54

cgtccagttt gagtctaggt tggagttgga accgtggaga tgcggaagga aaccccaccc     60

cccctagtgc ccccggcggc ccgggagtgg aatcttcccc caaatgcgcc cgcctgcatg    120

gaacggcagt tggaggctgc gcggtaccgg tccgatgggg cgcttctcct cggggcctcc    180

agcctgagtg ggcgctgctg ggccggctcc ctctggcttt ttaaggaccc ctgtgccgcc    240

cccaacgaag gcttctgctc cgccggagtc caaacggagg ctggagtggc tgacctcact    300

tgggttgggg agagaggtat tctagtggcc tccgattcag gtgctgttga attgtgggaa    360

ctagatgaga atgagacact tattgtcagc aagttctgca agtatgagca tgatgacatt    420

gtgtctacag tcagtgtctt gagctctggc acacaagctg tcagtggtag caaagacatc    480

tgcatcaagg tttgggacct tgctcagcag gtggtactga gttcataccg agctcatgct    540

gctcaggtca cttgtgttgc tgcctctcct cacaaggact ctgtgtttct ttcatgcagc    600

gaggacaata gaattttact ctgggatacc cgctgtccca agccagcatc acagattggc    660

tgcagtgcgc ctggctacct tcctacctcg ctggcttggc atcctcagca aagtgaagtc    720

tttgtctttg gtgatgagaa tgggacagtc tcccttgtgg acaccaagag tacaagctgt    780

gtcctgagct cagctgtaca ctcccagtgt gtcactgggc tggtgttctc cccacacagt    840

gttcccttcc tggcctctct cagtgaagac tgctcacttg ctgtgctgga ctcaagcctt    900

tctgagttgt ttagaagcca agcccacaga gactttgtga gagatgcgac ttggtccccg    960

ctcaatcact ccctgcttac cacagtgggc tgggaccatc aggtcgtcca ccacgttgtg   1020

cccacagaac ctctcccagc ccctggacct gcaagtgtta ctgagtagat tggatttaag   1080

acaaaaagca agtcccccat gagtgtccac ttctttgccc tgccctctca gcttgtgaga   1140

caacacagga gccttctata gtatgttgat atgctagatc tgtgccgtta ataggcatcg   1200

tctctcagcc tgagggaggc tggattctgg gttcctgtag tcacagggag gaaaagcttt   1260

cttaaaaatg gacatgtatg tgcgtgtgag tgtgtgtgta gatttatagt ttttggtagt   1320

ggcaggaata aaaaaaatcc atcctacatc ttccctaagc actgcctctc tctcaccccc   1380

caaaacaagt tgacgaaagg gttttatgta gctgtctatg aggaattggc cgtgtctggg   1440

tgggttatgg gatgtgggca tccctgggtt cttggaagca gctcttatgc tactcataga   1500

gatgggattg actttatttt tttatagtgc ttaattcacc attatgagaa atgcttccag   1560

tcacaaaaat gcagcccagc tcactctgag gaagaagcag gacttggtac ggttttacac   1620

aactccttac cattaaactg aatcagaaat ccattttctg gctgaataaa aagtttggct   1680
```

tgcctgtgta atgcccactc ccttccccct ggctccctag tgatgggaca tatatgagag 1740
agaagtgttt ttctatcata gacaccatag gggaaagttt ggggatgaag gagagcttaa 1800
aggtgtttca attaagttag aaaactgaca caggctgttg agaattcttt gccacttttc 1860
ccaccccaaa acagcatggg gcctgacatc ttctgccctg gtcccctttc tcttgatgtg 1920
gaaagtctga atgcagtatt tatagacttc taaggtttta aaatccagta tcaagaagaa 1980
aatcagaaat actggttggt gaaataaaga gtttaggcat tgttggcctg tctttttga 2040 agcatgtgtg ttatgtgtag ttagatatat ttcacttatg tgagtcatca tggtgttggt 2100
cttgtagccc attattttc ctgtgcttcc ccagcttccc aaagtagcta gttagaactt 2160
aaggtaaata tttattcttg ggttggtgga gtggatattg ccagttagga gtcatggatc 2220
aattactgat tatattgaaa gtaaatataa tcaattatgt acttttgagc tttgcaggtt 2280
caatttaggt aaaaatcaca ttatgaaact gggaaagtct gaaggaatat gggcaaaata 2340
tttctcagta aagcttccat gcttcaccct tgacatgatt acccttgagt aaaacatggg 2400
aatttgtaaa aaaaaaaaaa aaaaaaaa 2428

<210> SEQ ID NO 55
<211> LENGTH: 1980
<212> TYPE: DNA
<213> ORGANISM: Homo sapiens

<400> SEQUENCE: 55
ttcgattttg gtgctgtgaa aagaatagaa aagaaaaaga aaatgaagag gtaagctcat 60
agcagattct ctttgtatgg atttaaggga aggacattat ccacaacaga aaactgacca 120
tttggatttt cttgtttgta gaaggtcttt aacatttcca ctgcttcctc agcccgatat 180
ccagggatac actgatggaa tgagaaagtt gagaataaac ataggcctat gaaaatgtgt 240
gctgtatccc ataaaaacaa catatatata catgattatg taaacagatt tcagatgtta 300
ataaactttg gggatattag taacatgggt aaggaggtac acttccaaaa gatgtttgat 360
atatcatctt tttcattact cccaatcaac tgttattagg catcactccc aatcaactgt 420
tattcatcca ttaactatta tagaagttac cagctttgtg atcttgggtt aggcacttaa 480
actctccatg ccttatttat acaatgctgg caataatagc acttacttca ggggattttg 540
tgaggattaa gtgagataat acctgttaaa taccaggcac atcataagtg ctcattaagc 600
attagttatt tttatctgct cctatttact agtggtccat taagcattcc atgctataga 660
gctagggttg gcaaattata cttggtggac caaatctgtt ccatagctga gaactgtgag 720
ctaagaatgg tttttatatc ttaaaagctt tgttaaagaa aaaaaaagac taggtgacag 780
agatgtaagc ggctcacaaa gggtgaaata tttactagtt aaccctttgc agaaaaagtt 840
tatcaaccct tgctacagag gattttaaaa aataaaatac agcttgttct atctttagca 900
tctaactggg gaaaagaaat cataacatgt gaaagaataa ataagaaatt gtgctaacag 960
taaggagtgt tatatgaaat attacctgaa gaacatgaaa cttgaacttg ccttagagat 1020
agagaatatt taaagaggct aagcagagca tttcagggaa agggcaagaa gaagcctggg 1080
ttgtgtgtga ggaaatcagc tgacagagga ggagactatt aaggaagcat aaggaaagaa 1140
agacaaaaaa ttggggtaaa aatatgtacg gctttgaaag cttgtcagaa gagtttggac 1200
ttaaaaccaa gcacccttct gaagtgcatg aagtgacaca atgagcatct ggaaggaagg 1260
agccagaaag cataggcaca gaggacagga ggaccagcta ctgtgagatg ctgttcagaa 1320

```
cgaacctccc attctcctgt gtcttcagtc tgcccttgcc tgggcctccg acacctgcat   1380

aaaccttcgc cataacaaat aaccttccat ccaccctgtc ccgtcaaagg ctgacaccct   1440

gctcctgcct tcactcctca gtggcctcat cttcactggc ttgagttccc agcacttcac   1500

tgagtctgcc ctctcagaaa tccccaggtc cctactgacc aaaacacttg cctcctttca   1560

gattcctcaa ctctgcagtc ctggaggcaa ctggccacac ctgctctgtc tgaccgctct   1620

tgcctccctt ggcttctcag cattttacca tcctaaccac tgccagccag tcccgtcaca   1680

gctgccccct gcttcctgct gtgttaagtg ctggagctcc ccagaggtcc ccctccactc   1740

cactcgcaca ctcagagccc tctcctctta cgtgggatga gagcagtggt tctcaaccat   1800

tgctgctcag gagaaccagt tggaactctc tggaaacaca gcactgttgg ccccctgcct   1860

tctgattcag atggtctggg gcagggactg agcagagtca ggcacagaag cctccaggtg   1920

attctaacgg gcagtccggg atgagaactg ctgagttaca ggcctcgaag gaaactgcac   1980
```

<210> SEQ ID NO 56
<211> LENGTH: 55
<212> TYPE: PRT
<213> ORGANISM: Artificial Sequence
<220> FEATURE:
<223> OTHER INFORMATION: Synthetic

<400> SEQUENCE: 56

```
Ala Pro Arg Thr Arg Thr Leu Arg Ala Arg Arg Ser Pro Arg Met Glu
1               5                   10                  15

Ile Ala Gln Lys Trp Met Met Lys Thr Val Lys Glu Glu Glu Trp Asn
            20                  25                  30

Val Trp Met Lys Cys Pro Ile Leu Lys Asn Ser Leu Pro Ile Ser Lys
        35                  40                  45

Ile Asn Phe Ile Lys Asn Asp
    50                  55
```

<210> SEQ ID NO 57
<211> LENGTH: 18
<212> TYPE: PRT
<213> ORGANISM: Artificial Sequence
<220> FEATURE:
<223> OTHER INFORMATION: Synthetic

<400> SEQUENCE: 57

```
Gly Thr Asn Gln Arg Arg Glu Gly Lys Ser Ser Gly Ile Phe Gln His
1               5                   10                  15

Phe Val
```

<210> SEQ ID NO 58
<211> LENGTH: 47
<212> TYPE: PRT
<213> ORGANISM: Artificial Sequence
<220> FEATURE:
<223> OTHER INFORMATION: Synthetic

<400> SEQUENCE: 58

```
Gly Lys Trp Cys His Ala Cys Ala Glu Leu Pro Glu Pro Ala Ser Thr
1               5                   10                  15

Thr Ser Asn Pro Leu Ser Glu Leu Pro Cys Cys Cys Met Gly Trp Gln
            20                  25                  30

Cys Pro His Ser Ala Glu Glu Asn Leu Cys Tyr Thr Ala Gln Trp
        35                  40                  45
```

<210> SEQ ID NO 59
<211> LENGTH: 77
<212> TYPE: PRT
<213> ORGANISM: Artificial Sequence
<220> FEATURE:
<223> OTHER INFORMATION: Synthetic

<400> SEQUENCE: 59

```
Ile Asn Thr Leu Val Thr Tyr Asp Met Val Pro Glu Pro Lys Ile Ile
1               5                   10                  15

Asp Ala Ala Leu Arg Ala Cys Arg Arg Leu Asn Asp Phe Ala Ser Thr
            20                  25                  30

Val Arg Ile Leu Glu Val Val Lys Asp Lys Ala Gly Pro His Lys Glu
        35                  40                  45

Ile Tyr Pro Tyr Val Ile Gln Glu Leu Arg Pro Thr Leu Asn Glu Leu
    50                  55                  60

Gly Ile Ser Thr Pro Glu Glu Leu Gly Leu Asp Lys Val
65                  70                  75
```

<210> SEQ ID NO 60
<211> LENGTH: 39
<212> TYPE: PRT
<213> ORGANISM: Artificial Sequence
<220> FEATURE:
<223> OTHER INFORMATION: Synthetic

<400> SEQUENCE: 60

```
Glu Val His Ile Lys Lys Lys Thr Lys Gln Thr Leu Thr Asn Phe Gln
1               5                   10                  15

Met Gly Leu Leu Val Arg Gly Arg Glu Trp Pro Cys Pro Gly Cys Ala
            20                  25                  30

Ala Cys Leu Ser Lys Leu Pro
        35
```

<210> SEQ ID NO 61
<211> LENGTH: 22
<212> TYPE: PRT
<213> ORGANISM: Artificial Sequence
<220> FEATURE:
<223> OTHER INFORMATION: Synthetic

<400> SEQUENCE: 61

```
Asp His Ser Met Val Glu Phe Pro Arg Ile Ile Val Tyr Pro Gln Phe
1               5                   10                  15

Gly Val Gly Asn Glu Gly
            20
```

<210> SEQ ID NO 62
<211> LENGTH: 150
<212> TYPE: PRT
<213> ORGANISM: Artificial Sequence
<220> FEATURE:
<223> OTHER INFORMATION: Synthetic

<400> SEQUENCE: 62

```
Ser Ser Gly Ser Gly Glu Ser Arg Leu Gln His Ser Pro Ser Gln Ser
1               5                   10                  15

Tyr Leu Cys Ile Pro Phe Pro Arg Gly Glu Asp Gly Asp Gly Pro Ser
            20                  25                  30

Ser Asp Gly Ile His Glu Glu Pro Thr Pro Val Asn Ser Ala Thr Ser
        35                  40                  45

Thr Pro Gln Leu Thr Pro Thr Asn Ser Leu Lys Arg Gly Gly Ala His
```

```
    50                  55                  60

His Arg Arg Cys Glu Val Ala Leu Leu Gly Cys Gly Ala Val Leu Ala
65                  70                  75                  80

Ala Thr Gly Leu Gly Phe Asp Leu Leu Glu Ala Gly Lys Cys Gln Leu
                85                  90                  95

Leu Pro Leu Glu Glu Pro Glu Pro Pro Ala Arg Glu Glu Lys Lys Arg
            100                 105                 110

Arg Glu Gly Leu Phe Gln Arg Ser Ser Arg Pro Arg Arg Ser Thr Ser
        115                 120                 125

Pro Pro Ser Arg Lys Leu Phe Lys Lys Glu Glu His Gln Ala Cys Gly
    130                 135                 140

Arg Thr Arg Val Thr Ser
145                 150


<210> SEQ ID NO 63
<211> LENGTH: 30
<212> TYPE: PRT
<213> ORGANISM: Artificial Sequence
<220> FEATURE:
<223> OTHER INFORMATION: Synthetic

<400> SEQUENCE: 63

Gln Lys Leu Cys Gln Ala Lys Glu Lys Gly Met Cys Met Lys Lys Leu
1               5                   10                  15

Arg Met Leu Trp Glu Cys Gln Lys Leu Tyr Ser Leu Gly Phe
            20                  25                  30


<210> SEQ ID NO 64
<211> LENGTH: 16
<212> TYPE: PRT
<213> ORGANISM: Artificial Sequence
<220> FEATURE:
<223> OTHER INFORMATION: Synthetic

<400> SEQUENCE: 64

Ser Glu Gly Arg Thr Val Thr Asn Lys Val Ser Arg Lys Tyr Thr Gly
1               5                   10                  15


<210> SEQ ID NO 65
<211> LENGTH: 42
<212> TYPE: PRT
<213> ORGANISM: Artificial Sequence
<220> FEATURE:
<223> OTHER INFORMATION: Synthetic

<400> SEQUENCE: 65

Gln Arg Gly Ser Gly Gln Gln Glu Asp Ala His His Pro Ser Ser Pro
1               5                   10                  15

Pro Ala Gly His Pro Gln Arg Arg Gly Thr Glu Gln Ala Ala Gly Gln
            20                  25                  30

Ser His His Arg Pro Gly Arg Arg Leu Ala
        35                  40


<210> SEQ ID NO 66
<211> LENGTH: 44
<212> TYPE: PRT
<213> ORGANISM: Artificial Sequence
<220> FEATURE:
<223> OTHER INFORMATION: Synthetic

<400> SEQUENCE: 66

Ile Leu Tyr Pro Glu Thr Leu Leu Lys Leu Leu Ile Ser Leu Arg Arg
```

-continued

```
1               5                   10                  15

Phe Trp Ala Glu Met Met Glu Phe Ser Arg Tyr Thr Ile Met Ser Ser
            20                  25                  30

Glu Asn Arg Asp Asn Leu Thr Ser Ser Phe Pro Asn
        35                  40


<210> SEQ ID NO 67
<211> LENGTH: 25
<212> TYPE: PRT
<213> ORGANISM: Artificial Sequence
<220> FEATURE:
<223> OTHER INFORMATION: Synthetic

<400> SEQUENCE: 67

Cys Ser Lys His Ser Ser Leu Leu Leu Phe Ser Ser Cys Lys Gln Leu
1               5                   10                  15

Lys Ile Phe Lys Ile Lys Phe Thr Leu
            20                  25


<210> SEQ ID NO 68
<211> LENGTH: 36
<212> TYPE: PRT
<213> ORGANISM: Artificial Sequence
<220> FEATURE:
<223> OTHER INFORMATION: Synthetic

<400> SEQUENCE: 68

Asn Ser Leu Pro Leu Phe Pro Pro Gln Asn Ser Met Gly Pro Asp Ile
1               5                   10                  15

Phe Cys Pro Gly Pro Leu Ser Leu Asp Val Glu Ser Leu Asn Ala Val
            20                  25                  30

Phe Ile Asp Phe
        35


<210> SEQ ID NO 69
<211> LENGTH: 27
<212> TYPE: PRT
<213> ORGANISM: Artificial Sequence
<220> FEATURE:
<223> OTHER INFORMATION: Synthetic

<400> SEQUENCE: 69

Val Ser Gly Ser Gln Arg Val Lys Tyr Leu Leu Val Asn Pro Leu Gln
1               5                   10                  15

Lys Lys Phe Ile Asn Pro Cys Tyr Arg Gly Phe
            20                  25


<210> SEQ ID NO 70
<211> LENGTH: 343
<212> TYPE: DNA
<213> ORGANISM: Artificial Sequence
<220> FEATURE:
<223> OTHER INFORMATION: Synthetic

<400> SEQUENCE: 70

tcgtcgaggc tcctgctcct gtgactctcg agcagccaga ggctcctacc tctatcgagt     60

ctttacctac tacttctgac actttcttct tcttacctta caaacctact ttacaggtta    120

gaactttttg tcaaatggct agagtttcta gttgaaatat ttcttgctaa ttcagtccac    180

ctacgttttg atgttcttca gtatcgacct tttcgtggtc ttatgaacct tggcgaccgt    240

tgaaatgtcc ttttatacgt ttaagcatgt ttccatcgtc cttagatatc tctcgagacg    300
```

aatcttagac atttcttgtt tatacttaca ctttaagttc gaa 343

<210> SEQ ID NO 71
<211> LENGTH: 711
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t

<400> SEQUENCE: 71
ggaggtcgag gcggaggcgg aggaggagga ggccgaggcg ccggaggagg ccgaggcgcc 60
ggagcaggag gaggccggcc ggaggcggca tgagacgagc gtggcggccg cggctgctcg 120
gggccgcgct ggttgnccat tgacagcggc gtctgcagct cgcttcaaga tggccgcttg 180
gctcgcattc attttctgct gaacgacttt taactttcat tgtcttttcc gcccgcttcg 240
atcgcctcgc gccggctgct ctttccggga ttttttatca agcagaaatg catcgaacaa 300
cgagaatcaa gatcactgag ctaaatcccc ncctgatgtg tgtgctttgt ggagggtact 360
tcattgatgc cacaaccata atagaatgtc tacattcctt ctgtaaaacg tgtattgttc 420
gttacctgga gaccagcaag tattgtccta tttgtgatgt ccaagttcac aagaccagac 480
cactactgaa tataaggtca gataaaactc tccaagatat tgtatacaaa ttagttccag 540
ggcttttcaa aaatgaaatg aagagaagaa gggattttta tgcagctcat ccttctgctg 600
atgctgccaa tggctctaat gaagatagag gaggacggtt gcagatgaag ataagagaat 660
tataanctga tgatgagata ataaggcttg cggccgcact cgagaaacag t 711

<210> SEQ ID NO 72
<211> LENGTH: 126
<212> TYPE: DNA
<213> ORGANISM: Artificial Sequence
<220> FEATURE:
<223> OTHER INFORMATION: Synthetic

<400> SEQUENCE: 72
ggagagaggg aaaatcaagt ggtattttcc agcactttgt atgattttgg atgagttgta 60
cacccaagga ttctgttctg caactccatc ctcctgtgtc actgaatatc aactctgaaa 120
gagcaa 126

<210> SEQ ID NO 73
<211> LENGTH: 404
<212> TYPE: DNA
<213> ORGANISM: Artificial Sequence
<220> FEATURE:
<223> OTHER INFORMATION: Synthetic

<400> SEQUENCE: 73
cgggaaatgg tgccacgcat gcgcagaact tcccgagcca gcatccacca catcaaaccc 60
actgagtgag ctcccttgtt gttgcatggg atggcaatgt ccacatagcg cagaggagaa 120
tctgtgttac acagcgcaat ggtaggtagg ttaacataag atgcctccgt gagaggctgg 180
tggtcagccc tggggtcagt aaccacaaga agccgtggct cccggaaggc tgcctggatc 240
tggttagtga aggttccagg agtgaagcgg ccagcaattg gagtggctcc agtggcagca 300
gcaaacttca gcacagccct ctggccagta ttcctggagg atataacact gacatcagca 360
gggttttcaa tggcaacaat tgcacgagct gccagcagaa gctt 404

<210> SEQ ID NO 74
<211> LENGTH: 412
<212> TYPE: DNA
<213> ORGANISM: Artificial Sequence
<220> FEATURE:
<223> OTHER INFORMATION: Synthetic

<400> SEQUENCE: 74
gataaacaca cttgttacct atgatatggt tccagagccc aaaatcattg atgctgcttt 60
gcgggcatgc agacggttaa atgattttgc tagtacagtt cgtatcctag aggttgttaa 120
ggacaaagca ggacctcata aggaaatcta cccctatgtc atccaggaac ttagaccaac 180
tttaaatgaa ctgggaatct ccactccgga ggaactgggc cttgacaaag tgtaaaccgc 240
atggatgggc ttccccaagg atttattgac attgctactt gagtgtgaac agttacctgg 300
aaatactgat gataacatat taccttattt gaacaagttt tcctttattg agtaccaagc 360
catgtaatgg taacttggac tttaataaaa gggaaatgag tttgaactga aa 412

<210> SEQ ID NO 75
<211> LENGTH: 281
<212> TYPE: DNA
<213> ORGANISM: Artificial Sequence
<220> FEATURE:
<223> OTHER INFORMATION: Synthetic

<400> SEQUENCE: 75
gggaagtcca cattaaaaag aaaacaaaac aaaccctaac taacttccaa atgggtctcc 60
tggtgcgggg gcgtgagtgg ccgtgccctg ggtgtgctgc ctgtctgagc aagcttccct 120
agctgtggaa ccccgggccc cctgctgcgg gctctgcctt ggtgtcatgc ctgctgcacc 180
cccgtttcca ctgacgtgcc gtctgtggct atgggggtgg tcactggaat gacggtcact 240
ccagacgtca gccggcaggg atgcagcagg ctggccgcgc a 281

<210> SEQ ID NO 76
<211> LENGTH: 327
<212> TYPE: DNA
<213> ORGANISM: Artificial Sequence
<220> FEATURE:
<223> OTHER INFORMATION: Synthetic

<400> SEQUENCE: 76
attctatggt ggaatttcca agaataattg tttatcctca gtttggagta ggaaatgaag 60
gataattttt tccatttcac ctctattgca aatttatttt ttcaagccac acaaaaaatt 120
gtctaagata aaatgagaat tattcagatc aattctgcaa tgatacaggg aagatgtgaa 180
aggagggctc aatgcagagt tgtgaagttg aaaaccacta tttctgttct aaagacacag 240
taagcagaga tccatctctc ttcaggcatc ctgcttctct gcaggttact tctgctttaa 300
ggaaagtaca tttttagaac aaagctt 327

<210> SEQ ID NO 77
<211> LENGTH: 532
<212> TYPE: DNA

<213> ORGANISM: Artificial Sequence
<220> FEATURE:
<223> OTHER INFORMATION: Synthetic
<220> FEATURE:
<221> NAME/KEY: misc_feature
<222> LOCATION: (490)..(490)
<223> OTHER INFORMATION: n is a, c, g, or t
<220> FEATURE:
<221> NAME/KEY: misc_feature
<222> LOCATION: (493)..(493)
<223> OTHER INFORMATION: n is a, c, g, or t
<220> FEATURE:
<221> NAME/KEY: misc_feature
<222> LOCATION: (502)..(502)
<223> OTHER INFORMATION: n is a, c, g, or t
<220> FEATURE:
<221> NAME/KEY: misc_feature
<222> LOCATION: (513)..(514)
<223> OTHER INFORMATION: n is a, c, g, or t
<220> FEATURE:
<221> NAME/KEY: misc_feature
<222> LOCATION: (526)..(527)
<223> OTHER INFORMATION: n is a, c, g, or t
<220> FEATURE:
<221> NAME/KEY: misc_feature
<222> LOCATION: (529)..(529)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t

<400> SEQUENCE: 77
tcaagcggga gtggagagag tcgcctacag cattcaccca gccagtccta cctctgtatc 60
ccattccctc gtggagagga tggcgatggc ccctccagtg atggaatcca tgaggagccc 120
accccagtca actcggccac gagtacccct cagctgacgc caaccaacag cctcaagcgg 180
ggcggtgccc accaccgccg ctgcgaggtg gctctgctcg gctgtggggc tgttctggca 240
gccacaggcc tagggtttga cttgctggaa gctggcaagt gccagctgct tcccctggag 300
gagcctgagc caccagcccg ggaggagaag aaaagacggg agggtctttt tcagaggtcc 360
agccgtcctc gtcggagcac cagcccccca tcccgaaagc ttttcaagaa ggaggagcac 420
caagcttgcg gccgcactcg agtaactagt taaccccttg gggcctctaa acgggtcttg 480
agggggttan ctngttactc gngtgcggcc gcnngcttgg tgctcnncnt tn 532

<210> SEQ ID NO 78
<211> LENGTH: 358
<212> TYPE: DNA
<213> ORGANISM: Artificial Sequence
<220> FEATURE:
<223> OTHER INFORMATION: Synthetic

<400> SEQUENCE: 78
atcccagcac ggaggcccag aaaactttaa gatttgagta ttaatgtctc aaggtcagga 60
gcaacctcaa ggctaaaact cagatctcag gactcaattt cacagaagtt ccactataaa 120
ggcaataatc taaagcttta aatgatatga aaattttgta ataagagttc agtatttctg 180
ccaacattgg cgcatggatt gcaaagttca caggattgaa aacaccatcg acataatgga 240
aattgaacag catctgatta ctgagtgcta tatcagcaag ttaaaaggat cttttgcata 300
ccttttaatg gtatatatcc taaaactgaa gtgttcaata tagacatcca gattgaaa 358

<210> SEQ ID NO 79
<211> LENGTH: 439
<212> TYPE: DNA
<213> ORGANISM: Artificial Sequence
<220> FEATURE:
<223> OTHER INFORMATION: Synthetic

<400> SEQUENCE: 79
tgtgtgggta tgagggtatg agagggcccc tctcactcca ttccttctcc aggacatccc 60
tccactcttg ggagacacag agaagggctg gttccagctg gagctgggag gggcaattga 120
gggaggagga aggagaaggg ggaaggaaaa cagggtatgg gggaaaggac cctggggagc 180
gaagtggagg atacaacctt gggcctgcag gccaggctac ctacccactt ggaaacccac 240
gccaaagccg catctacagc tgagccactc tgaggcctcc cctccccggc ggtccccact 300
cagctccaaa gtctctctcc cttttctctc ccacactcta tcatccccg gattcctctc 360 tacttggttc tcattcttcc tttgacttcc tgatcctgtg tattttcggc tcaccttgat 420
ttgtcactgt tctcccctc 439

<210> SEQ ID NO 80
<211> LENGTH: 236
<212> TYPE: DNA
<213> ORGANISM: Artificial Sequence
<220> FEATURE:
<223> OTHER INFORMATION: Synthetic

<400> SEQUENCE: 80
acgcggctcg gggacaacaa gaagacgcgc atcatccctc gtcacctcca gctggccatc 60
cgcaacgacg aggaactgaa caagctgctg ggcaaagtca ccatcgccca gggcggcgtc 120
ttgcctaaca tccaggccgt actgctccct aagaagacgg agagtcacca caaggcaaag 180
ggcaagtgag gctgacgtcc ggcccaagtg ggcccagccc ggcccgcgtc tcgaag 236

<210> SEQ ID NO 81
<211> LENGTH: 380
<212> TYPE: DNA
<213> ORGANISM: Artificial Sequence
<220> FEATURE:
<223> OTHER INFORMATION: Synthetic

<400> SEQUENCE: 81
tgtggcatcg tcaaaaggaa gggattggtt tggcaagaac ttgtttacaa catttttgca 60
aatctaaagt tgctccatac aatgactagt cacctggggg ggttgggcgg gcgccatctt 120
ccattgccgc cgcgggtgtg cggtctcgat tcgctgaatt gcccgtttcc atacagggtc 180
tcttccttcg gtcttttgta tttttgattg ttatgtaaaa ctcgctttta ttttaatatt 240
gatgtcagta tttcaactgc tgtaaaatta taaactttta tacttgggta agtcccccag 300
gggcgagttc ctcgctctgg gatgcaggca tgcttctcac cgtgcagagc tgcacttggc 360
ctcagctggc tgtatggaaa 380

<210> SEQ ID NO 82
<211> LENGTH: 352
<212> TYPE: DNA
<213> ORGANISM: Artificial Sequence
<220> FEATURE:
<223> OTHER INFORMATION: Synthetic

<400> SEQUENCE: 82
atgttctaag cacagctctc ttctcctatt ttcatcctgc aagcaactca aaatatttaa 60
aataaagttt acattgtagt tattttcaaa tctttgcttg ataagtatta agaaatattg 120
gacttgctgc cgtaatttaa agctctgttg attttgtttc cgtttggatt tttgggggag 180

-continued gggagcactg tgtttatgct ggaatatgaa gtctgagacc ttcggtgctg ggaacacaca 240
agagttgttg aaagttgaca agcagactgc gcatgtctct gatgctttgt atcattcttg 300
agcaatcgct cggtccgtgg acaataaaca gtattatcaa agagaaaaaa aa 352

<210> SEQ ID NO 83
<211> LENGTH: 506
<212> TYPE: DNA
<213> ORGANISM: Artificial Sequence
<220> FEATURE:
<223> OTHER INFORMATION: Synthetic

<400> SEQUENCE: 83
gccacttttc ccaccccaaa acagcatggg gcctgacatc ttctgccctg gtcccctttc 60
tcttgatgtg gaaagtctga atgcagtatt tatagacttc taaggtttta aaatccagta 120
tcaagaagaa aatcagaaat actggttggt gaaataaaga gtttaggcat tgttggcctg 180 tctttttga agcatgtgtg ttatgtgtag ttagatatat ttcacttatg tgagtcatca 240
tggtgttggt cttgtagccc attatttttc ctgtgcttcc ccagcttccc aaagtagcta 300
gttagaactt aaggtaaata tttattcttg ggttggtgga gtggatattg ccagttagga 360
gtcatggatc aattactgat tatattgaaa gtaaatataa tcaattatgt acttttgagc 420
tttgcaggtt caatttaggt aaaaatcaca ttatgaaact gggaaagtct gaaggaatat 480
gggcaaaata tttctcagta aagctt 506

<210> SEQ ID NO 84
<211> LENGTH: 401
<212> TYPE: DNA
<213> ORGANISM: Artificial Sequence
<220> FEATURE:
<223> OTHER INFORMATION: Synthetic

<400> SEQUENCE: 84
gagatgtaag cggctcacaa agggtgaaat atttactagt taaccccctt gcagaaaaag 60
ttatcaaccc ttgctacaga ggattttaaa aaataaaata cagcttgttc tatctttagc 120
atctaactgg ggaaaagaat cataacatgt gaaagaataa ataagaaatt gtgctaacag 180
taaggagtgt tatatgaaat attacctgaa gaacatgaaa cttgaacttg ctagagatag 240
agaatattta aagaggctaa gcagagcatt tcagggaaag ggcaagaaga agcctgggtt 300
gtgtgtgagg aaatcagctg acagaggagg agactattaa ggaagcataa ggaaagaaag 360
acaaaaaatt ggggtaaaaa tatgtacggc tttgaaagct t 401

<210> SEQ ID NO 85
<211> LENGTH: 2407
<212> TYPE: DNA
<213> ORGANISM: Homo sapiens

<400> SEQUENCE: 85
gagcgccgca cctacaccag ccaacccaga tcccgaggtc cgacagcgcc cggcccagat 60
ccccacgcct gccaggagca agccgagagc cagccggccg gcgcactccg actccgagca 120
gtctctgtcc ttcgacccga gccccgcgcc ctttccggga cccctgcccc gcgggcagcg 180
ctgccaacct gccggccatg gagaccccgt cccagcggcg cgccacccgc agcggggcgc 240
aggccagctc cactccgctg tcgcccaccc gcatcacccg gctgcaggag aaggaggacc 300
tgcaggagct caatgatcgc ttggcggtct acatcgaccg tgtgcgctcg ctggaaacgg 360
agaacgcagg gctgcgcctt cgcatcaccg agtctgaaga ggtggtcagc cgcgaggtgt 420
ccggcatcaa ggccgcctac gaggccgagc tcggggatgc ccgcaagacc cttgactcag 480
tagccaagga gcgcgcccgc ctgcagctgg agctgagcaa agtgcgtgag gagtttaagg 540
agctgaaagc gcgcaatacc aagaaggagg gtgacctgat agctgctcag gctcggctga 600
aggacctgga ggctctgctg aactccaagg aggccgcact gagcactgct ctcagtgaga 660
agcgcacgct ggagggcgag ctgcatgatc tgcggggcca ggtggccaag cttgaggcag 720
ccctaggtga ggccaagaag caacttcagg atgagatgct gcggcgggtg gatgctgaga 780
acaggctgca gaccatgaag gaggaactgg acttccagaa gaacatctac agtgaggagc 840
tgcgtgagac caagcgccgt catgagaccc gactggtgga gattgacaat gggaagcagc 900
gtgagtttga gagccggctg gcggatgcgc tgcaggaact gcgggcccag catgaggacc 960
aggtggagca gtataagaag gagctggaga agacttattc tgccaagctg gacaatgcca 1020
ggcagtctgc tgagaggaac agcaacctgg tgggggctgc ccacgaggag ctgcagcagt 1080
cgcgcatccg catcgacagc ctctctgccc agctcagcca gctccagaag cagctggcag 1140
ccaaggaggc gaagcttcga gacctggagg actcactggc ccgtgagcgg gacaccagcc 1200
ggcggctgct ggcggaaaag gagcgggaga tggccgagat gcgggcaagg atgcagcagc 1260
agctggacga gtaccaggag cttctggaca tcaagctggc cctggacatg gagatccacg 1320
cctaccgcaa gctcttggag ggcgaggagg agaggctacg cctgtccccc agccctacct 1380
cgcagcgcag ccgtggccgt gcttcctctc actcatccca gacacagggt gggggcagcg 1440
tcaccaaaaa gcgcaaactg gagtccactg agagccgcag cagcttctca cagcacgcac 1500
gcactagcgg gcgcgtggcc gtggaggagg tggatgagga gggcaagttt gtccggctgc 1560
gcaacaagtc caatgaggac cagtccatgg gcaattggca gatcaagcgc cagaatggag 1620
atgatccctt gctgacttac cggttcccac caaagttcac cctgaaggct gggcaggtgg 1680
tgacgatctg ggctgcagga gctggggcca cccacagccc ccctaccgac ctggtgtgga 1740
aggcacagaa cacctggggc tgcgggaaca gcctgcgtac ggctctcatc aactccactg 1800
gggaagaagt ggccatgcgc aagctggtgc gctcagtgac tgtggttgag gacgacgagg 1860
atgaggatgg agatgacctg ctccatcacc accacggctc ccactgcagc agctcggggg 1920
accccgctga gtacaacctg cgctcgcgca ccgtgctgtg cgggacctgc gggcagcctg 1980
ccgacaaggc atctgccagc ggctcaggag cccaggtggg cggacccatc tcctctggct 2040
cttctgcctc cagtgtcacg gtcactcgca gctaccgcag tgtgggggc agtgggggtg 2100 gcagcttcgg ggacaatctg gtcacccgct cctacctcct gggcaactcc agcccccgaa 2160
cccagagccc ccagaactgc agcatcatgt aatctgggac ctgccaggca ggggtggggg 2220
tggaggcttc ctgcgtcctc ctcacctcat gcccaccccc tgccctgcac gtcatgggag 2280
ggggcttgaa gccaaagaaa aataaccctt tggttttttt cttctgtatt ttttttcta 2340 agagaagtta ttttctacag tggttttata ctgaaggaaa aacacaagca aaaaaaaaaa 2400
aaaaaaa 2407

<210> SEQ ID NO 86
<211> LENGTH: 567
<212> TYPE: DNA
<213> ORGANISM: Homo sapiens

<400> SEQUENCE: 86
gcgcagggtt tgaaacatgg cggacgacgt agaccagcaa caaactacca acactgtaga 60

```
ggagcccctg gatcttatca ggctcagcct agatgagcga atttatgtga aaatgagaaa    120
tgaccgagag cttcgaggca gattacatgc ttatgatcaa catttaaata tgatcttggg    180
agatgtggaa gaaactgtga ctactataga aattgatgaa gaaacatatg aagagatata    240
taaatcaacg aaacggaata ttccaatgct ctttgtccgg ggagatggcg ttgtcctggt    300
tgcccctcca ctgagagttg gctgaaacaa agaatttgtc ctgtatggaa aacgggagac    360
tttgtacagt ggcctctcta aaagtacaaa acattcataa gagaaacctg catacatttt    420
gatattaaga aataattccg gggattcttc cactcctgaa atgagttgat ttgcagataa    480
ctcacaactt cttaagctaa atggtatttt catttttctc aagctctcca ataaatatga    540
ccaccaagaa aaaaaaaaaa aaaaaaa                                        567
```

<210> SEQ ID NO 87
<211> LENGTH: 1980
<212> TYPE: DNA
<213> ORGANISM: Homo sapiens

<400> SEQUENCE: 87

```
tttaagggtg tacaagctct aattgttttt tttttttttt tgagatggag tttcactctg     60
tagcccaggc tggagtgcag tggcgcaatc gcggctcact gcaagctccg cctcctgggt    120
tcacaccatt ctcctgcctc agtctcccga gtagctggga ctacaggcgc tcgccaccac    180
gcccggctaa tttttttgta tttttagtag agacggggtt tcaccatgtt agccagggtg    240
gtctcgatct cctgaccttg tgatccgcct gcctcggcct cccaaagtgc tgggattaca    300
ggcgtgagtg actgcgccca gcctcacagg ctctaattct tgactaattt tcctgtacac    360
gtcacttgta attgaaaagc tgagtgtaag atcagccgac acacccagag ttttatttta    420
ttttatttat ttatttatgg tttttttttg agatggagtc tcactctgtc gcccaggcta    480
gagtgcagtg gcgccatctc ggcttactgc aagctccacc tcctgggttc acgccattct    540
cctacctcag tctcctgagt agctgggact acaggcgccc accaccacgc ctggctaatt    600
tttttgtatt tttagtagag acagggtttc accgtgttag gcaggatggt ctcgatctcc    660
tgacctcgtg attcgcccgc ctcggcctcc caaagcgctg ggattagaag cgtgagccac    720
cgcgcccgga ctattttatt tattttttg agatggagtt tcacttttgt tgcccaggat    780
tgagtgcagt gccccgatct tggctcacta caacctctgc ctcctgggtt caagcgactc    840
tcctgcctca gtgtcctgag tagctgggat tacaggcgtc tgccaccacg cccggctaat    900
tttgtatttt tagtagagaa caggtttcac tatgttggtc aggctggtct tgaactcctg    960
acctcagcgc atccagaatt ttagacgggg cccccagggt gaggtcttgg caccctccag   1020
tagagaagaa gggacatggg ccatacgtgg ggtgtccttt ctgggagcct tgcgtccctt   1080
acctgcctag ccagggattg cacctcacag cacgcagcca gcaggaacgg caccgtgatc   1140
tgatttcacc tgcgggccct gggccctggg ggtgtttgac aattggggca tatcacagtg   1200
tgagctagtc ccgtctcggg ggtttggagg ctccacgtgg ccgtggtaca ggagcaggca   1260
gttccatcct ctggcctgga tcaggctctg cacacggagg cctgtgggcc agatgactga   1320
caggagggga gttgggtgga acctcggcct gcctgatatc cagcaacaga gggcaagggc   1380
ggcagcacct ccagcatgac agtcccttcc aagcacgtca ggatgctccc ttgcctgtgc   1440
tggcagcttc ctaaacatgg ggactgggca tggtggcagg tttttgtcct tctgaaagag   1500
caattttgct gtgaggttac ttgctccttg agttcttgtc tgaggcccac ctggcggctg   1560
ctccgtgagg aacgaggtgg ccctgctgca gctcagcatc ccgccacgct cccaggagtg   1620
```

```
tgtgtttcct ggggggagcg gcccgggacc gtggctctgt ggtccattct gtggatgtcc   1680

acaaggcctg ggcgttctgt gggtttgggt ggcagtcccg tctgggcagc tcctgctggg   1740

ctgggtgtgg gtctcctgct ggtctgcccc cagctgcaca acgtgtcttg tgccttgccc   1800

tcttgtacct ctgcaggttt tggctacggg cctccacctc caccgccaga tcagtttgcc   1860

cctccggggg ttcctcctcc accagccact cccggggcag cacctctggc tttcccaccg   1920

cctccgtctc aggctgcccc ggacatgagc aagcccccga cagctcagcc agacttcccc   1980
```

<210> SEQ ID NO 88
<211> LENGTH: 4005
<212> TYPE: DNA
<213> ORGANISM: Homo sapiens

<400> SEQUENCE: 88

```
cggcagggtt ggaaaatgat ggaagaggcg gaggtggagg cgaccgagtg ctgagaggaa     60

cctgcggaat cggccgagat ggggtctggc gcgcgctttc cctcggggac ccttcgtgtc    120

cggtggttgc tgttgcttgg cctggtgggc ccagtcctcg gtgcggcgcg gccaggcttt    180

caacagacct cacatctttc ttcttatgaa attataactc cttggagatt aactagagaa    240

agaagagaag cccctaggcc ctattcaaaa caagtatctt atgttattca ggctgaagga    300

aaagagcata ttattcactt ggaaaggaac aaagaccttt tgcctgaaga ttttgtggtt    360

tatacttaca acaaggaagg gactttaatc actgaccatc ccaatataca gaatcattgt    420

cattatcggg gctatgtgga gggagttcat aattcatcca ttgctcttag cgactgtttt    480

ggactcagag gattgctgca tttagagaat gcgagttatg ggattgaacc cctgcagaac    540

agctctcatt ttgagcacat catttatcga atggatgatg tctacaaaga gcctctgaaa    600

tgtggagttt ccaacaagga tatagagaaa gaaactgcaa aggatgaaga ggaagagcct    660

cccagcatga ctcagctact tcgaagaaga agagctgtct tgccacagac ccggtatgtg    720

gagctgttca ttgtcgtaga caaggaaagg tatgacatga tgggaagaaa tcagactgct    780

gtgagagaag agatgattct cctggcaaac tacttggata gtatgtatat tatgttaaat    840

attcgaattg tgctagttgg actggagatt tggaccaatg gaaacctgat caacatagtt    900

gggggtgctg gtgatgtgct ggggaacttc gtgcagtggc gggaaaagtt tcttatcaca    960

cgtcggagac atgacagtgc acagctagtt ctaaagaaag gttttggtgg aactgcagga   1020

atggcatttg tgggaacagt gtgttcaagg agccacgcag gcgggattaa tgtgtttgga   1080

caaatcactg tggagacatt tgcttccatt gttgctcatg aattgggtca taatcttgga   1140

atgaatcacg atgatgggag agattgttcc tgtggagcaa agagctgcat catgaattca   1200

ggagcatcgg gttccagaaa ctttagcagt tgcagtgcag aggactttga gaagttaact   1260

ttaaataaag gaggaaactg ccttcttaat attccaaagc ctgatgaagc ctatagtgct   1320

ccctcctgtg gtaataagtt ggtggacgct ggggaagagt gtgactgtgg tactccaaag   1380

gaatgtgaat tggacccttg ctgcgaagga agtacctgta agcttaaatc atttgctgag   1440

tgtgcatatg gtgactgttg taaagactgt cggttccttc caggaggtac tttatgccga   1500

ggaaaaacca gtgagtgtga tgttccagag tactgcaatg gttcttctca gttctgtcag   1560

ccagatgttt ttattcagaa tggatatcct tgccagaata acaaagccta ttgctacaac   1620

ggcatgtgcc agtattatga tgctcaatgt caagtcatct ttggctcaaa agccaaggct   1680

gcccccaaag attgtttcat tgaagtgaat tctaaaggtg acagatttgg caattgtggt   1740
```

-continued

```
ttctctggca atgaatacaa gaagtgtgcc actgggaatg ctttgtgtgg aaagcttcag   1800
tgtgagaatg tacaagagat acctgtattt ggaattgtgc ctgctattat tcaaacgcct   1860
agtcgaggca ccaaatgttg gggtgtggat ttccagctag gatcagatgt tccagatcct   1920
gggatggtta acgaaggcac aaaatgtggt gctggaaaga tctgtagaaa cttccagtgt   1980
gtagatgctt ctgttctgaa ttatgactgt gatgttcaga aaaagtgtca tggacatggg   2040
aaatgaatac tgcattgagg gacggacttc tggtcttctt cttcctaatt gttcccctta   2100
ttgtctgtgc tatttttatc ttcatcaaga gggatcaact gtggagaagc tacttcagaa   2160
agaagagatc acaaacatat gagtcagatg gcaaaaatca agcaaaccct tctagacagc   2220
cggggagtgt tcctcgacat gtttctccag tgacacctcc cagagaagtt cctatatatg   2280
caaacagatt tgcagtacca acctatgcag ccaagcaacc tcagcagttc ccatcaaggc   2340
cacctccacc acaaccgaaa gtatcatctc agggaaactt aattcctgcc cgtcctgctc   2400
ctgcacctcc tttatatagt tccctcactt gattttttta accttctttt tgcaaatgtc   2460
ttcagggaac tgagctaata cttttttttt ttcttgatgt tttcttgaaa agcctttctg   2520
ttgcaactat gaatgaaaac aaaacaccac aaaacagact tcactaacac agaaaaacag   2580
aaactgagtg tgagagttgt gaaatacaag gaaatgcagt aaagccaggg aatttacaat   2640
aacatttccg tttccatcat tgaataagtc ttattcagtc atcggtgagg ttaatgcact   2700
aatcatggat tttttgaaca tgttattgca gtgattctca aattaactgt attggtgtaa   2760
gatttttgtc attaagtgtt taagtgttat tctgaatttt ctaccttagt tatcattaat   2820
gtagttcctc attgaacatg tgataatcta atacctgtga aaactgacta atcagctgcc   2880
aataatatct aatatttttc atcatgcacg aattaataat catcatactc tagaatcttg   2940
tctgtcactc actacatgaa taagcaaata ttgtcttcaa aagaatgcac aagaaccaca   3000
attaagatgt catattattt tgaaagtaca aaatatacta aaagagtgtg tgtgtattca   3060
cgcagttact cgcttccatt tttatgacct ttcaactata ggtaataact cttagagaaa   3120
ttaatttaat attagaattt ctattatgaa tcatgtgaaa gcatgacatt cgttcacaat   3180
agcactattt taaataaatt ataagcttta aggtacgaag tatttaatag atctaatcaa   3240
atatgttgat tcatggctat aataaagcag gagcaattat aaaatcttca atcaattgaa   3300
cttttacaaa accacttgag aatttcatga gcactttaaa atctgaactt tcaaagcttg   3360
ctattaaatc atttagaatg tttacattta ctaaggtgtg ctgggtcatg taaaatatta   3420
gacactaata ttttcataga aattaggctg gagaaagaag gaagaaatgg ttttcttaaa   3480
tacctacaaa aaagttactg tggtatctat gagttatcat cttagctgtg ttaaaaatga   3540
atttttacta tggcagatat ggtatggatc gtaaaatttt aagcactaaa aatttttttca   3600
taacctttca taataaagtt taataatagg tttattaact gaatttcatt agtttttttaa   3660
aagtgttttt ggtttgtgta tatatacata tacaaataca acatttacaa taaataaaat   3720
acttgaaatt ctcttttgtg tctcctagta gcttcctact caactattta taatctcatt   3780
aattaaaaag ttataatttt agataaaaat tctagtcaaa tttttacaga tattatctca   3840
ctaattttca gacttttgcc aaagtgtgca caatggcttt ttgttaataa agaacagatt   3900
agttttgaag aaggcaaaaa tttcagtttt ctgaagacag catgttattt taacaatcaa   3960
gtatacatat taaaaattgt gagcaatctc aaaaaaaaaa aaaaa                   4005
```

<210> SEQ ID NO 89
<211> LENGTH: 1278

<212> TYPE: DNA
<213> ORGANISM: Homo sapiens

<400> SEQUENCE: 89
ccattggcct gtagattcac ctcccctggg cagggcccca ggacccagga taatatctgt 60
gcctcctgcc cagaaccctc caagcagaca caatggtaag aatggtgcct gtcctgctgt 120
ctctgctgct gcttctgggt cctgctgtcc cccaggagaa ccaagatggt cgttactctc 180
tgacctatat ctacactggg ctgtccaagc atgttgaaga cgtccccgcg tttcaggccc 240
ttggctcact caatgacctc cagttcttta gatacaacag taaagacagg aagtctcagc 300
ccatgggact ctggagacag gtggaaggaa tggaggattg gaagcaggac agccaacttc 360
agaaggccag ggaggacatc tttatggaga ccctgaaaga catcgtggag tattacaacg 420
acagtaacgg gtctcacgta ttgcagggaa ggtttggttg tgagatcgag aataacagaa 480
gcagcggagc attctggaaa tattactatg atggaaagga ctacattgaa ttcaacaaag 540
aaatcccagc ctgggtcccc ttcgacccag cagcccagat aaccaagcag aagtgggagg 600
cagaaccagt ctacgtgcag cgggccaagg cttacctgga ggaggagtgc cctgcgactc 660
tgcggaaata cctgaaatac agcaaaaata tcctggaccg gcaagatcct ccctctgtgg 720
tggtcaccag ccaccaggcc ccaggagaaa agaagaaact gaagtgcctg gcctacgact 780
tctacccagg gaaaattgat gtgcactgga ctcgggccgg cgaggtgcag gagcctgagt 840
tacggggaga tgttcttcac aatggaaatg gcacttacca gtcctgggtg gtggtggcag 900
tgcccccgca ggacacagcc ccctactcct gccacgtgca gcacagcagc ctggcccagc 960
ccctcgtggt gccctgggag gccagctagg aagcaagggt tggaggcaat gtgggatctc 1020
agacccagta gctgcccttc ctgcctgatg tgggagctga accacagaaa tcacagtcaa 1080
tggatccaca aggcctgagg agcagtgtgg ggggacagac aggaggtgga tttggagacc 1140
gaagactggg atgcctgtct tgagtagact tggacccaaa aaatcatctc accttgagcc 1200
cacccccacc ccattgtcta atctgtagaa gctaataaat aatcatccct ccttgcctag 1260
cataaaaaaa aaaaaaaa 1278

<210> SEQ ID NO 90
<211> LENGTH: 1980
<212> TYPE: DNA
<213> ORGANISM: Homo sapiens

<400> SEQUENCE: 90
tcatttcaaa atttaggagt taatttatat ttttaattga atcagatttc ataggcatag 60
atattgtctg tcaatattca tatgtttata tagtggtaat ttattaaact tcttaatcca 120
gatgtattat tttagttatc tttttccac tctagtgtca tagtttaaac ttgttctttg 180
atgttgagta tttattataa caatagtttt ttttgcctgc actctacaat gtatatttcc 240
agatataatt tgtttatgta acttgttgac catttataat ggggaaaaaa gcttgctaaa 300
agttctcaag atagctagga aaatatcaat gagatatatc taaaagaaag ggagaggggt 360
ttggaagatt actgccactc tctttcctta tatatttctt aggacttctg aggtgctttt 420
atgcttcttg ttttgtgtaa agtatatata tatatatata tatatacaca cacacaaagt 480
atatataaac acaaagtata tatatacaca cacatataca caaagtatat atatatacac 540
acaaagtata tatatatgta cacaaaatat atatatatac acaaaagtac ttacaaggca 600
tgttcttacc tcaaaaagat gccaacttat ttatgagaaa tagatcctac tttatggaaa 660
agcaaaatag gaacatgaca ataaaccaat atgataaagc actgtcagag ttcaaaaaca 720
cctatgatac ctaaatgtac tcatgtagtt tggatcaacc agaaaggctg gtgacaagag 780
gtacagctta cttggtaact taaagaataa gaagggtttg aaagtgaaga gacggtgaga 840
atagctaaag aagaggaaaa cagcatagcc tacaagacag gagatgataa agtttagggg 900
ctatttagca aataataaat aaattgattt agaatagaag aaatcatgtg ttggaaaaga 960
ggcttgaaac aagttcggtg ttagagaaga gaatattaag aaacaagtgg gagataggac 1020
ttctaaatgc tgcactaagg atttcggatt tattctcatg gtaaaggaga gccagccaag 1080
gcttttctac aggagagagg tataatcaag cagcgtgaag ctgagtcagt agggggatca 1140
gtgagaatag gaagacatca gggttgggga agatgaaagc ttagtttaag catgagttaa 1200
ttctaccagg atgatggtaa ttgttatatt aagataggga tgaataagaa atatttcaaa 1260
ggtataaagg ataagcttgt tgactgactg aacttaagga acaaagtaaa aagcagagtc 1320
aaagtggcag aggctatagc cagggacaac gactacatat ccagcctttt ctatgtctcg 1380
gggtgaagat gcctttctta ttcactattt ctctcttcaa ctcctccaca ccaccatgca 1440
aaatcatagc ccatctatgc ttgacgtgcc tacatgtaga aacctgtgat gatctctcca 1500
gcgagaaagc aggtttaatc ccttgacagt ccttgactca tagtaagttc ttattttatt 1560
tttaagaccg gcatggatga cttttactta atatctgttc tttgccattt aatgctagag 1620
ctgatgatat tgagtggcca tttcacaata tgtacctgtt ctgtgttagg aacacttcta 1680
aaaggggctt ggaattatta atttatacaa aaacataaaa tttcatcttg aatctataaa 1740
cttgctttaa tacaatgagt aaaagtgatc attttagctt tggatctgaa tttcacttga 1800
aggcatgcac atgggattag gagttgggtg aataatcagg actggaaaag taaacctaga 1860
aattattgac atggataaag agttgttgat accctgtgag aaggaacttt gggaaatgtg 1920
gatggaggag gacagaaagg agcagagaat aaaagtatga aagctagccc tgtaggctca 1980

<210> SEQ ID NO 91
<211> LENGTH: 4319
<212> TYPE: DNA
<213> ORGANISM: Homo sapiens

<400> SEQUENCE: 91
ctctgagtca ccggaatcta ggtggggccg cccggagcgg cgtcctcggg agccgcctcc 60
ccgcggcctc ttcgcttttg tggcggcgcc cgcgctcgca ggccactctc tgctgtcgcc 120
cgtcccgcgc gctcctccga cccgctccgc tccgctccgc tcggccccgc gccgcccgtc 180
aacatgatcc gctgcggcct ggcctgcgag cgctgccgct ggatcctgcc cctgctccta 240
ctcagcgcca tcgccttcga catcatcgcg ctggccggcc gcggctggtt gcagtctagc 300
gaccacggcc agacgtcctc gctgtggtgg aaatgctccc aagagggcgg cggcagcggg 360
tcctacgagg agggctgtca gagcctcatg gagtacgcgt ggggtagagc agcggctgcc 420
atgctcttct gtggcttcat catcctggtg atctgtttca tcctctcctt cttcgccctc 480
tgtggacccc agatgcttgt cttcctgaga gtgattggag gtctccttgc cttggctgct 540
gtgttccaga tcatctccct ggtaatttac cccgtgaagt acacccagac cttcaccctt 600
catgccaacc ctgctgtcac ttacatctat aactgggcct acggctttgg gtgggcagcc 660
acgattatcc tgattggctg tgccttcttc ttctgctgcc tccccaacta cgaagatgac 720
cttctgggca atgccaagcc caggtacttc tacacatctg cctaacttgg gaatgaatgt 780
gggagaaaat cgctgctgct gagatggact ccagaagaag aaactgtttc tccaggcgac 840

-continued

```
tttgaaccca ttttttggca gtgttcatat tattaaacta gtcaaaaatg ctaaaataat    900
ttgggagaaa atatttttta agtagtgtta tagtttcatg tttatctttt attatgtttt    960
gtgaagttgt gtcttttcac taattaccta tactatgcca atatttcctt atatctatcc   1020
ataacattta tactacattt gtaagagaat atgcacgtga aacttaacac tttataaggt   1080
aaaaatgagg tttccaagat ttaataatct gatcaagttc ttgttatttc caaatagaat   1140
ggactcggtc tgttaagggc taaggagaag aggaagataa ggttaaaagt tgttaatgac   1200
caaacattct aaaagaaatg caaaaaaaaa gtttattttc aagccttcga actatttaag   1260
gaaagcaaaa tcatttccta aatgcatatc atttgtgaga atttctcatt aatatcctga   1320
atcattcatt ttagctaagg cttcatgttg actcgatatg tcatctagga aagtactatt   1380
tcatggtcca aacctgttgc catagttggt aaggctttcc tttaagtgtg aaatatttag   1440
atgaaatttt ctcttttaaa gttctttata gggttagggt gtgggaaaat gctatattaa   1500
taaatctgta gtgttttgtg tttatatgtt cagaaccaga gtagactgga ttgaaagatg   1560
gactgggtct aatttatcat gactgataga tctggttaag ttgtgtagta aagcattagg   1620
agggtcattc ttgtcacaaa agtgccacta aaacagcctc aggagaataa atgacttgct   1680
tttctaaatc tcaggtttat ctgggctcta tcatatagac aggcttctga tagtttgcaa   1740
ctgtaagcag aaacctacat atagttaaaa tcctggtctt tcttggtaaa cagattttaa   1800
atgtctgata taaaacatgc cacaggagaa ttcggggatt tgagtttctc tgaatagcat   1860
atatatgatg catcggatag gtcattatga tttttttacca tttcgactta cataatgaaa   1920
accaattcat tttaaatatc agattattat tttgtaagtt gtggaaaaag ctaattgtag   1980
ttttcattat gaagttttcc caataaacca ggtattctaa acttgtttcc agtttgtagt   2040
ttttccattt ttcaaatctg gggaaaggaa ttaaaaaaaa aatgggtaat aagaacatgg   2100
gatataatga aaagtggttt ttgtttgttt ttttgtttga agttttaagg gccttgctca   2160
ttttaggtgt ccaaaaccaa tttttgagtg gagattaatg aattctaata gtctattccc   2220
tgaacttttc ctcaatgaac aataccctag acacacatta aacaatttct ctgcagtgct   2280
atcaaccaga ggaaaatgga ctaagagatt tctggcaggt tcagacaccc gggggacatg   2340
tgtgcagtgt agctgaagcc tcctccttgt gctggggtcc ccttccattc aggtggtggg   2400
gtagcagtct ctctatttc ccccttgccct ccttcccatt ttatcatttg ttattttttt   2460
tcccaccata agtcatatgt tacttccact atggtgtatg tcattgtgag gatgggtgca   2520
gagaggctgg gtgggagaac ggaaatatat ctccctaggg ctactgttgg ccagctagtc   2580
cttggcagtg aatttttcta tgcttttcaa aatgcgaggt gaatgtttct catagagaaa   2640
tgtaatctgg gtgattatac caaaattgaa aagaaaaacc cacacaacta tgccgtggct   2700
ggtggagaat ttgaagtggt cattaaaaat gttaaaaatc ccatctttta aagtgatacc   2760
acagctcatt caagaagata ctggatatct agagattaag aaacgtggtc tcctgttaaa   2820
catgaaaatg actccgttta taagcttctc taccacatgc acttgtcttt gcatgatttc   2880
ccatccagcc ttcttcccct cctcaatcac acaataccttt aacggcgcac atttaggaaa   2940
aatgcaacct cctgggacca acgagcctga tataatagaa ccatgtcaac ctaaagtatt   3000
tatgacaaag ataaactctt attttgcaga aatggtctgc ttccttcagc cttgttctag   3060
tatagagatc tgccattcct tgttgatcca gattcaccaa gacagatacc tttatgtcat   3120
aacagaaggg aagttccaga ggattctgga gagtaatgaa gaattgggct gagaaaccac   3180
```

-continued ctgaaggcta acagtgcatt gcatgagatt tcccacagta aagctgaggt gctttttggt 3240
tcagtaatta aatattgagt tcccaccctt taaataagca gttctaggtt cctaagcaat 3300
tatttcactc tgtaagtagc cagacatgct aagtggcact tactgctgat tgtaacaaag 3360
aagtaatata tcaaggtctt tccatgttca cacaaggtag cttgtgtgta ataacttagc 3420
ttcaaaacca tagactgcag aactcacaag ttcaacagcc tttccttttt taaggaaatg 3480
aaaacaatgg aaaatatagt catcataact taattcggtt tatttttttt ttctgtaaac 3540
tccccctgaa agacattcct attaatacag taaatgtgaa cactgacttg tttttataag 3600
cacatctgaa agggcatatt tgagtctcat cccaactttg gtccttgcta tctgtgcagg 3660
cttgggcagg tcatctccct gctggtctca atatcctcac ctgtaaaatg attgtaaatg 3720
atccccctac cttcaagatt ctctgattga tagaattttt tctttaatta aaaaatttta 3780
aatattcctt gagttggaag cactgatcaa taagtggatt gcttagggag gttggaacga 3840
atagattcag tcccaacttc ctcttttaaa ttccctcttc ctcactcttc ctgcaacact 3900
tatttttaca gttgagtttt aaaaataagt aatatataaa ataatttctg tagtgtggtt 3960
tcagatttaa aaattcctgc agacaggctg ggcttgcaac cccatcagtc gatggtcaga 4020
gccctttgct ttttgagacc atttttaggt gagcttggct tgcctggata cagtgtgcag 4080
tgcattcttc ctgaattttg caattctggt atctgggtgt attttctagg tgtgtcaggg 4140
tgagtgtaat ccacctaggg tgtggaaaaa gccaagaaag ggaaattaaa agaggttcct 4200
atccagtcat gttaatgatc ttccacttgt actatcctgt gcttcgttgt taacctcgaa 4260
aacatacttt gttggctgca aaaataaaca aagggaaact caaaaaaaaa aaaaaaaaa 4319

<210> SEQ ID NO 92
<211> LENGTH: 1980
<212> TYPE: DNA
<213> ORGANISM: Homo sapiens

<400> SEQUENCE: 92
ggcaccgtgg gagtttgcag ctctggttgc tccaagagca caaatattaa tgtagcacag 60
atattaatat tattaattag cacagacatt aatgtagtca cagaaagaaa aagagatgaa 120
aaagagacag gttcttcact gcatgagagg ctccgtttgg gatctctcag aaatgtggaa 180
gcagaggcta cagcacaagc ctgggttatt gctagtagca agacagaaaa taaggcttgg 240
gtaagctgta gttatagtta caatggaaat gactggccca agagagtgct acagattaca 300
tagcagctac taagaaaaag gacaggcaga aggggtaggc aagacatgtt ctctggctgt 360
tgcagccacc aaaaagccag gatacaaagg cagggagtta tctgaactgc cttcctggag 420
ggtcatgcat ttaggatccg actcattgac tcttttcctt aattttgctc tgtacatttc 480
tctaagaggg ctaaccagtg tcaaggtttg ataatatctg aaatggtatt ctggtgccaa 540
agtatcatct cacaaattat ttagaaattg caaagagaaa atatatttta taatccagat 600
atctggcagt taaccacatg accaaattta gcatcactaa cagtaggaca actagatatt 660
atatacctct tgctgtgata tactatgaag tacacatcat caactatgaa gtattatttt 720
ttttttcttt gagatagggt catgctctgt cgcccaattt agagtgcagc gatgcaatca 780
tagctcactg cagctttgac ctcccagtct caagtgatcc tcccacctca gcctccctag 840
tagctgggac tacagatgtg ttccaccaca cctggctaat ttttatatat tttttgtagt 900
gatggggttt caccatgttg cacaggctgg tcttgaactc ctgggcttaa gcaatctgcc 960
tgaaagttct gggattatag gcatgagcca ctgtgtccag actatgaagt attcttgcca 1020
aaactgatca acctaaatct aatcaagctt ctgggccaga actgtccaat agcaatgtaa 1080
tgtcagctac atgtaattta aaattttcta gttgccacca aaagcacaga aaagaaaaaa 1140
tagataaatt gtgctacatc aagattaaat acttctttgc atcaaaggac ataatcaaca 1200
cagagaaaag gcaaaccact gaatgggaga aaatatttgc aaattgatat tcataatatg 1260
taaagaatct ttacaactca acacccacaa aataaaaaaa aagattaaaa aatggggaaa 1320
ggacttgaat agacatttct ccaaagaaga tgtacaactt gccaataagc acaagaaaag 1380
actaattatg agggaaatgc aaattaaaac cacaatgaga tcaaacacat tatgttggct 1440
atcataaaaa gaaagtgcca ggcgcaatga tcacagctac tcaacaggct gggtggaaga 1500
atcccttgag accaggagtt agaggctgca gtgtgttatg atcatgcctg tgaatagcca 1560
ctgcactcca acataggtaa catagcaagc cccatccata aaataaaata aaataaaata 1620
aaataaaggc aacaaaaaat aacaagtatt ggtaaggatg tggagaaatt ggaaccctcg 1680
tgcattgctg gtgggtgtgt aaaaaggtat ggctgctgtg aaaaatggga tggctattct 1740
tcaaaaaatt aaccacagaa ttactatatg atccagcaat cccacttctg catacacatc 1800
caaaagaagt ggactcaagg actcagacag atatttgtac ccccctgttc atagcagcat 1860
tatttacaat agccaaaaag tagaagcaac cacagattca tcaatgtatg aatggataaa 1920
caaaatgtgg catatacaca tagtgggata tcattcagct ttaaaaaggg aggaaattct 1980

<210> SEQ ID NO 93
<211> LENGTH: 784
<212> TYPE: DNA
<213> ORGANISM: Homo sapiens

<400> SEQUENCE: 93
gcccacgcgc cagagtcgca gtgggcgggc ctacgtgctc cgcccgctgt gagcctgtcc 60
ggcccccgcc cgctccggag caacccgcga gcttacaccg gcttctctct gtcctcagcc 120
cgcgcgccgc catcgccgtc atgctgggcg ccgctctccg ccgctgcgct gtggccgcaa 180
ccacccgggc cgaccctcga ggcctcctgc actccgcccg gacccccggc cccgccgtgg 240
ctatccagtc agttcgctgc tattcccatg ggtcacagga gacagatgag gagtttgatg 300
ctcgctgggt aacatacttc aacaagccag atatagatgc ctgggaattg cgtaaaggga 360
taaacacact tgttacctat gatatggttc cagagcccaa aatcattgat gctgctttgc 420
gggcatgcag acggttaaat gattttgcta gtacagttcg tatcctagag gttgttaagg 480
acaaagcagg acctcataag gaaatctacc cctatgtcat ccaggaactt agaccaactt 540
taaatgaact gggaatctcc actccggagg aactgggcct tgacaaagtg taaaccgcat 600
ggatgggctt ccccaaggat ttattgacat tgctacttga gtgtgaacag ttacctggaa 660
atactgatga taacatatta ccttatttga acaagttttc ctttattgag taccaagcca 720
tgtaatggta acttggactt taataaaagg gaaatgagtt tgaactgaaa aaaaaaaaaa 780
aaaa 784

<210> SEQ ID NO 94
<211> LENGTH: 1980
<212> TYPE: DNA
<213> ORGANISM: Homo sapiens

<400> SEQUENCE: 94
ttcacttctg agtcccagag gttacccaag gcacccctct gacatccggc ctgcttcttc 60
tcacatgaca aaaactagcc cccatctcaa tcatatacca aatctctccc tcactaaacg 120
taagccttct cctcactctc tcaatcttat ccatcatagc aggcagttga ggtggattaa 180
accaaaccca gctacgcaaa atcttagcat actcctcaat tacccacata ggatgaataa 240
tagcagttct accgtacaac cctaacataa ccattcttaa tttaactatt tatattatcc 300
taactactac cgcattccta ctactcaact taaactccag caccacgacc ctactactat 360
ctcgcacctg aaacaagcta acatgactaa cacccttaat tccatccacc ctcctctccc 420
taggaggcct gcccccgcta accggctttt tgcccaaatg ggccattatc gaagaattca 480
caaaaaacaa tagcctcatc atccccacca tcatagccac catcaccctc cttaacctct 540
acttctacct acgcctaatc tactccacct caatcacact actccccata tctaacaacg 600
taaaaataaa atgacagttt gaacatacaa aacccacccc attcctcccc acactcatca 660
cccttaccac gctactccta cctatctccc cttttatact aataatctta tagaaattta 720
ggttaaatac agaccaagag ccttcaaagc cctcagcaag ttgcaatact taatttctgt 780
aacagctaag gactgcaaaa ccccactctg catcaactga acgcaaatca gccactttaa 840
ttaagctaag cccttactag accaatggga cttaaaccca caaacactta gttaacagct 900
aagcacccta atcaactggc ttcaatctac ttctcccgcc gccgggaaaa aaggcgggag 960
aagccccggc aggtttgaag ctgcttcttc gaatttgcaa ttcaatatga aaatcacctc 1020
ggagctggta aaaagaggcc tagcccctgt ctttagattt acagtccaat gcttcactca 1080
gccattttac ctcaccccca ctgatgttcg ccgaccgttg actattctct acaaaccaca 1140
aagacattgg aacactatac ctattattcg gcgcatgagc tggagtccta ggcacagctc 1200
taagcctcct tattcgagcc gagctgggcc agccaggcaa ccttctaggt aacgaccaca 1260
tctacaacgt tatcgtcaca gcccatgcat ttgtaataat cttcttcata gtaataccca 1320
tcataatcgg aggctttggc aactgactag ttcccctaat aatcggtgcc cccgatatgg 1380
cgtttccccg cataaacaac ataagcttct gactcttacc tccctctctc ctactcctgc 1440
tcgcatctgc tatagtggag gccggagcag gaacaggttg aacagtctac cctcccttag 1500
cagggaacta ctcccaccct ggagcctccg tagacctaac catcttctcc ttacacctag 1560
caggtgtctc ctctatctta ggggccatca atttcatcac aacaattatc aatataaaac 1620
cccctgccat aacccaatac caaacgcccc tcttcgtctg atccgtccta atcacagcag 1680
tcctacttct cctatctctc ccagtcctag ctgctggcat cactatacta ctaacagacc 1740
gcaacctcaa caccaccttc ttcgaccccg ccggaggagg agaccccatt ctataccaac 1800
acctattctg atttttcggt caccctgaag tttatattct tatcctacca ggcttcggaa 1860
taatctccca tattgtaact tactactccg gaaaaaaaga accatttgga tacataggta 1920
tggtctgagc tatgatatca attggcttcc tagggtttat cgtgtgagca caccatatat 1980

<210> SEQ ID NO 95
<211> LENGTH: 7505
<212> TYPE: DNA
<213> ORGANISM: Homo sapiens

<400> SEQUENCE: 95
gagggcgggg cgggaaggcg gcgaggagcc gagctgggtg cggtgaggcg cgcagatcac 60
cgcggttcct gggcagggca cggaaggcta agcaaggctg acctgctgca gctcccgcct 120
cgtgcgctcg ccccacccgg ccgccgcccg agcgctcgag aaagtcctct cgggagaagc 180
agcgcctgtt cccggggcag atccaggttc aggtcctggc tataagtcac catggcacag 240

```
caagctgccg ataagtatct ctatgtggat aaaaacttca tcaacaatcc gctggcccag    300
gccgactggg ctgccaagaa gctggtatgg gtgccttccg acaagagtgg ctttgagcca    360
gccagcctca aggaggaggt gggcgaagag gccatcgtgg agctggtgga gaatgggaag    420
aaggtgaagg tgaacaagga tgacatccag aagatgaacc cgcccaagtt ctccaaggtg    480
gaggacatgg cagagctcac gtgcctcaac gaagcctcgg tgctgcacaa cctcaaggag    540
cgttactact cagggctcat ctacacctat tcaggcctgt tctgtgtggt catcaatcct    600
tacaagaacc tgcccatcta ctctgaagag attgtggaaa tgtacaaggg caagaagagg    660
cacgagatgc cccctcacat ctatgccatc acagacaccg cctacaggag tatgatgcaa    720
gaccgagaag atcaatccat cttgtgcact ggtgaatctg gagctggcaa gacggagaac    780
accaagaagg tcatccagta tctggcgtac gtggcgtcct cgcacaagag caagaaggac    840
cagggcgagc tggagcggca gctgctgcag gccaacccca tcctggaggc cttcgggaac    900
gccaagaccg tgaagaatga caactcctcc cgcttcggca aattcattcg catcaacttt    960
gatgtcaatg gctacattgt tggagccaac attgagactt atcttttgga gaaatctcgt   1020
gctatccgcc aagccaagga agaacggacc ttccacatct tctattatct cctgtctggg   1080
gctggagagc acctgaagac cgatctcctg ttggagccgt acaacaaata ccgcttcctg   1140
tccaatggac acgtcaccat ccccgggcag caggacaagg acatgttcca ggagaccatg   1200
gaggccatga ggattatggg catcccagaa gaggagcaaa tgggcctgct gcgggtcatc   1260
tcaggggttc ttcagctcgg caacatcgtc ttcaagaagg agcggaacac tgaccaggcg   1320
tccatgcccg acaacacagc tgcccaaaag gtgtcccatc tcttgggtat caatgtgacc   1380
gatttcacca gaggaatcct caccccgcgc atcaaggtgg gacgggatta cgtccagaag   1440
gcgcagacta aagagcaggc tgactttgcc atcgaggcct tggccaaggc gacctatgag   1500
cggatgttcc gctggctggt gctgcgcatc aacaaggctc tggacaagac caagaggcag   1560
ggcgcctcct tcatcgggat cctggacatt gccggcttcg agatctttga tctgaactcg   1620
tttgagcagc tgtgcatcaa ttacaccaat gagaagctgc agcagctctt caaccacacc   1680
atgttcatcc tggagcagga ggagtaccag cgcgagggca tcgagtggaa cttcatcgac   1740
tttggcctcg acctgcagcc ctgcatcgac ctcattgaga agccagcagg ccccccgggc   1800
attctggccc tgctggacga ggagtgctgg ttccccaaag ccaccgacaa gagcttcgtg   1860
gagaaggtga tgcaggagca gggcacccac cccaagttcc agaagcccaa gcagctgaag   1920
gacaaagctg atttctgcat tatccactat gccggcaagg tggattacaa agctgacgag   1980
tggctgatga agaacatgga tcccctgaat gacaacatcg ccacactgct ccaccagtcc   2040
tctgacaagt ttgtctcgga gctgtggaag gatgtggacc gcatcatcgg cctggaccag   2100
gtggccggca tgtcggagac cgcactgccc ggggccttca agacgcggaa gggcatgttc   2160
cgcactgtgg ggcagcttta caaggagcag ctggccaagc tgatggctac gctgaggaac   2220
acgaacccca actttgtccg ctgcatcatc cccaaccacg agaagaaggc cggcaagctg   2280
gacccgcatc tcgtgctgga ccagctgcgc tgcaacggtg ttctcgaggg catccgtatc   2340
tgccgccagg gcttccccaa cagggtggtc ttccaggagt ttcggcagag atatgagatc   2400
ctgactccaa actccattcc caagggtttc atggacggga agcaggcgtg cgtgctcatg   2460
ataaaagccc tggagctcga cagcaatctg taccgcattg gccagagcaa agtcttcttc   2520
cgtgccggtg tgctggccca cctggaggag gagcgagacc tgaagatcac cgacgtcatc   2580
```

-continued

```
atagggttcc aggcctgctg caggggctac ctggccagga aagcatttgc caagcggcag   2640
cagcagctta ccgccatgaa ggtcctccag cggaactgcg ctgcctacct gaagctgcgg   2700
aactggcagt ggtggcggct cttcaccaag gtcaagccgc tgctgcaggt gagccggcag   2760
gaggaggaga tgatggccaa ggaggaggag ctggtgaagg tcagagagaa gcagctggct   2820
gcggagaaca ggctcacgga gatggagacg ctgcagtctc agctcatggc agagaaattg   2880
cagctgcagg agcagctcca ggcagaaacc gagctgtgtg ccgaggctga ggagctccgg   2940
gcccgcctga ccgccaagaa gcaggaatta gaagagatct gccatgacct agaggccagg   3000
gtggaggagg aggaggagcg ctgccagcac ctgcaggcgg agaagaagaa gatgcagcag   3060
aacatccagg agcttgagga gcagctggag gaggaggaga gcgcccggca gaagctgcag   3120
ctggagaagg tgaccaccga ggcgaagctg aaaaagctgg aggaggagca gatcatcctg   3180
gaggaccaga actgcaagct ggccaaggaa aagaaactgc tggaagacag aatagctgag   3240
ttcaccacca acctcacaga agaggaggag aaatctaaga gcctcgccaa gctcaagaac   3300
aagcatgagg caatgatcac tgacttggaa gagcgcctcc gcagggagga gaagcagcga   3360
caggagctgg agaagacccg ccggaagctg gagggagact ccacagacct cagcgaccag   3420
atcgccgagc tccaggccca gatcgcggag ctcaagatgc agctggccaa gaaagaggag   3480
gagctccagg ccgccctggc cagagtggaa gaggaagctg cccagaagaa catggccctc   3540
aagaagatcc gggagctgga atctcagatc tctgaactcc aggaagacct ggagtctgag   3600
cgtgcttcca ggaataaagc tgagaagcag aaacgggacc ttggggaaga gctagaggct   3660
ctgaaaacag agttggagga cacgctggat tccacagctg cccagcagga gctcaggtca   3720
aaacgtgagc aggaggtgaa catcctgaag aagaccctgg aggaggaggc caagacccac   3780
gaggcccaga tccaggagat gaggcagaag cactcacagg ccgtggagga gctggcggag   3840
cagctggagc agacgaagcg ggtgaaagca aacctcgaga aggcaaagca gactctggag   3900
aacgagcggg gggagctggc caacgaggtg aaggtgctgc tgcagggcaa aggggactcg   3960
gagcacaagc gcaagaaagt ggaggcgcag ctgcaggagc tgcaggtcaa gttcaacgag   4020
ggagagcgcg tgcgcacaga gctggccgac aaggtcacca agctgcaggt ggagctggac   4080
aacgtgaccg ggcttctcag ccagtccgac agcaagtcca gcaagctcac caaggacttc   4140
tccgcgctgg agtcccagct gcaggacact caggagctgc tgcaggagga gaaccggcag   4200
aagctgagcc tgagcaccaa gctcaagcag gtggaggacg agaagaattc cttccgggag   4260
cagctggagg aggaggagga ggccaagcac aacctggaga agcagatcgc caccctccat   4320
gcccaggtgg ccgacatgaa aaagaagatg gaggacagtg tggggtgcct ggaaactgct   4380
gaggaggtga agaggaagct ccagaaggac ctggagggcc tgagccagcg gcacgaggag   4440
aaggtggccg cctacgacaa gctggagaag accaagacgc ggctgcagca ggagctggac   4500
gacctgctgg tggacctgga ccaccagcgc cagagcgcgt gcaacctgga gaagaagcag   4560
aagaagtttg accagctcct ggcggaggag aagaccatct ctgccaagta tgcagaggag   4620
cgcgaccggg ctgaggcgga ggcccgagag aaggagacca aggctctgtc gctggcccgg   4680
gccctggagg aagccatgga gcagaaggcg gagctggagc ggctcaacaa gcagttccgc   4740
acggagatgg aggaccttat gagctccaag gatgatgtgg gcaagagtgt ccacgagctg   4800
gagaagtcca agcgggccct agagcagcag gtggaggaga tgaagacgca gctggaagag   4860
ctggaggacg agctgcaggc caccgaagat gccaagctgc ggttggaggt caacctgcag   4920
gccatgaagg cccagttcga gcgggacctg cagggccggg acgagcagag cgaggagaag   4980
```

aagaagcagc tggtcagaca ggtgcgggag atggaggcag agctggagga cgagaggaag 5040
cagcgctcga tggcagtggc cgcccggaag aagctggaga tggacctgaa ggacctggag 5100
gcgcacatcg actcggccaa caagaaccgg gacgaagcca tcaaacagct gcggaagctg 5160
caggcccaga tgaaggactg catgcgcgag ctggatgaca cccgcgcctc tcgtgaggag 5220
atcctggccc aggccaaaga gaacgagaag aagctgaaga gcatggaggc cgagatgatc 5280
cagttgcagg aggaactggc agccgcggag cgtgccaagc gccaggccca gcaggagcgg 5340
gatgagctgg ctgacgagat cgccaacagc agcggcaaag gagccctggc gttagaggag 5400
aagcggcgtc tggaggcccg catcgcccag ctggaggagg agctggagga ggagcagggc 5460
aacacggagc tgatcaacga ccggctgaag aaggccaacc tgcagatcga ccagatcaac 5520
accgacctga acctggagcg cagccacgcc cagaagaacg agaatgctcg gcagcagctg 5580
gaacgccaga acaaggagct taaggtcaag ctgcaggaga tggagggcac tgtcaagtcc 5640
aagtacaagg cctccatcac cgccctcgag gccaagattg cacagctgga ggagcagctg 5700
gacaacgaga ccaaggagcg ccaggcagcc tgcaaacagg tgcgtcggac cgagaagaag 5760
ctgaaggatg tgctgctgca ggtggatgac gagcggagga acgccgagca gtacaaggac 5820
caggccgaca aggcatctac ccgcctgaag cagctcaagc ggcagctgga ggaggccgaa 5880
gaggaggccc agcgggccaa cgcctcccgc cggaaactgc agcgcgagct ggaggacgcc 5940
actgagacgg ccgatgccat gaaccgcgaa gtcagctccc taaagaacaa gctcaggcgc 6000
ggggacctgc cgtttgtcgt gccccgccga atggcccgga aaggcgccgg ggatggctcc 6060
gacgaagagg tagatggcaa agcggatggg gctgaggcca aacctgccga ataagcctct 6120
tctcctgcag cctgagatgg atggacagac agacaccaca gcctcccctt cccagacccc 6180
gcagcacgcc tctccccacc ttcttgggac tgctgtgaac atgcctcctc ctgccctccg 6240
ccccgtcccc ccatcccgtt tccctccagg tgttgttgag ggcatttggc ttcctctgct 6300
gcatcccctt ccagctccct cccctgctca gaatctgata ccaaagagac agggcccggg 6360
cccaggcaga gagcgaccag caggctcctc agccctctct tgccaaaaag cacaagatgt 6420
tgaggcgagc agggcaggcc cccggggagg ggccagagtt ttctatgaat ctatttttct 6480
tcagactgag gccttttggt agtcggagcc cccgcagtcg tcagcctccc tgacgtctgc 6540
caccagcgcc cccactcctc ctcctttctt tgctgtttgc aatcacacgt ggtgacctca 6600
cacacctctg ccccttgggc ctcccactcc catggctctg ggcggtccag aaggagcagg 6660
ccctgggcct ccacctctgt gcagggcaca gaaggctggg gtggggggag gagtggattc 6720
ctccccaccc tgtcccaggc agcgccactg tccgctgtct ccctcctgat tctaaaatgt 6780
ctcaagtgca atgcccccctc ccctccttta ccgaggacag cctgcctctg ccacagcaag 6840
gctgtcgggg tcaagctgga aaggccagca gccttccagt ggcttctccc aacactcttg 6900
gggaccaaat atatttaatg gttaagggac ttgtcccaag tctgacagcc agagcgttag 6960
aggggccagc ggccctccca ggcgatcttg tgtctactct aggactgggc ccgagggtgg 7020
tttacctgca ccgttgactc agtatagttt aaaaatctgc cacctgcaca ggtatttttg 7080
aaagcaaaat aaggttttct tttttcccct ttcttgtaat aaatgataaa attccgagtc 7140
tttctcactg cctttgttta gaagagagta gctcgtcctc actggtctac actggttgcc 7200
gaatttactt gtattcctaa ctgttttgta tatgctgcat tgagacttac ggcaagaagg 7260
catttttttt ttttaaagga aacaaactct caaatcatga agtgatataa aagctgcata 7320

-continued tgcctacaaa gctctgaatt caggtcccag ttgctgtcac aaaggagtga gtgaaactcc 7380 cacccctaccc cctttttat ataataaaag tgccttagca tgtgttgcag ctgtcaccac 7440
tacagtaagc tggtttacag atgttttcca ctgagcatca caataaagag aaccatgtgc 7500
tacga 7505

<210> SEQ ID NO 96
<211> LENGTH: 2487
<212> TYPE: DNA
<213> ORGANISM: Homo sapiens

<400> SEQUENCE: 96
gctattggta agactcgcgg gaaaagaaag ggtgagcgcg gctggaagcg cgcatgcgct 60
gtggctaatg ccgtaggctc cttcagggct gagccatccc gcgtgtcttg cgctcggtgg 120
aaatgcccag ccgagggacg cgaccagagg acagctctgt gctgatcccc accgacaatt 180
cgaccccaca caaggaggat ctaagcagca agattaaaga acaaaaaatt gtggtggatg 240
aactttctaa ccttaagaag aataggaaag tatataggca acaacagaac agcaatatat 300
tctttcttgc agaccgaaca gaaatgctgt ctgagagcaa gaatatattg gatgaactga 360
aaaaagaata ccaagaaata gaaaacttag acaagaccaa aatcaagaaa tagtcaacct 420
gatttcacat aacaatgtgt ggcatttgtt gttctgtaaa cttttctgct gagcatttca 480
gtcaagattt aaaagaggac ttactatata atcttaaaca gcggggaccc aatagtagta 540
aacaattgtt aaagtctgat gttaactacc agtgtttatt ttctgctcac gtcctacact 600
tgaggggtgt tttgactacc cagcctgtgg aagatgaaag aggcaatgtg tttctatgga 660
atggagaaat ttttagtgga ataaaggttg aagctgaaga gaatgacact caaattttgt 720
ttaattatct ttcctcctgt aagaatgaat ctgagatttt gtcactcttc tcagaagtac 780
aaggtccctg gtcatttata tattatcaag catctagtca ttatttatgg tttggtaggg 840 attttttgg tcgccgtagc ttgctttggc attttagtaa tttgggcaag agtttctgcc 900
tctcttcagt tggcacccaa acatctggat tggcaaatca gtggcaagaa gttccagcat 960
ctggactttt cagaattgat cttaagtcta ctgtcatttc cagatgcatt attttacaac 1020
tgtatccttg gaaatatatt tctagggaga atattattga agaaaatgtt aatagcctga 1080
gtcaaatttc agcagactta ccagcatttg tatcagtggt agcaaatgaa gccaaactgt 1140
atcttgaaaa acctgttgtt cctttaaata tgatgttgcc acaagctgca ttggagactc 1200
attgcagtaa tatttccaat gtgccaccta caagagagat acttcaagtc tttcttactg 1260
atgtacacat gaaggaagta attcagcagt tcattgatgt cctgagtgta gcagtcaaga 1320
aacgtgtctt gtgtttacct agggatgaaa acctgacagc aaatgaagtt ttgaaaacgt 1380
gtgataggaa agcaaatgtt gcaatcctgt tttctggggg cattgattcc atggttattg 1440
caacccttgc tgaccgtcat attcctttag atgaaccaat tgatcttctt aatgtagctt 1500
tcatagctga agaaaagacc atgccaacta cctttaacag agaagggaat aaacagaaaa 1560
ataaatgtga aataccttca gaagaattct ctaaagatgt tgctgctgct gctgctgaca 1620
gtcctaataa acatgtcagt gtaccagatc gaatcacagg aagggcggga ctaaaggaac 1680
tacaagctgt tagcccttcc cgaatttgga attttgttga aattaatgtt tctatggaag 1740
aactgcagaa attaagaaga actcgaatat gtcacttaat tcggccattg gatacagttt 1800
tggatgatag cattggctgt gcagtctggt ttgcttctag aggaattggt tggttagtgg 1860
cccaggaagg agtgaaatcc tatcagagca atgcaaaggt agttctcact ggaattggtg 1920

```
cagatgagca acttgcaggt tattctcgtc atcgtgtccg ctttcagtcg catgggctgg   1980
aaggattgaa taaggaaata atgatggaac tgggtcgaat ttcttctaga aatcttggtc   2040
gtgatgacag agttattggt gatcatggaa aagaagcaag atttcctttc ctggatgaaa   2100
atgttgtctc ctttctaaat tctctgccga tttgggaaaa agcaaacttg actttacccc   2160
gaggaattgg tgaaaaatta cttttacgcc ttgcagctgt ggaacttggt cttacagcct   2220
ctgctcttct gcccaaacgg gccatgcagt ttggatcaag aattgcaaaa atggaaaaaa   2280
ttaatgaaaa ggcatctgat aaatgtggac ggctccaaat catgtcctta gaaaatcttt   2340
ctattgaaaa ggagactaaa ttgtaatgtg attcacaatg taacaatata aaaataagtt   2400
tttatataat tatataaaag taagatactc tgctgcttta ctattgtata atatagtagt   2460
tttaaagttc aaaaaaaaaa aaaaaaa                                        2487
```

<210> SEQ ID NO 97
<211> LENGTH: 2032
<212> TYPE: DNA
<213> ORGANISM: Homo sapiens

<400> SEQUENCE: 97

```
ggaggactca ggccccgctg gccgcgggct cggtacccgg tgggtcggtg gagcgtctgt     60
tgggtccggg ccgccggctt cgccctcgcc atggcgccct ggctgcagct cctgtcgctg    120
ctggggctgc tcccgggcgc agtggccgcc cccgcccagc cccgagccgc cagctttcag    180
gcctgggggc cgccgtcccc ggagctgctg gcgcccaccc gcttcgcgct ggagatgttc    240
aaccgcggcc gggctgcggg gacgcgggcc gtgctgggcc ttgtgcgcgg ccgcgtccgc    300
cgggcgggtc aggggtcgct gtactccctg gaggccaccc tggaggagcc accctgcaac    360
gaccccatgg tgtgccggct ccccgtgtcc aagaaaaccc tgctctgcag cttccaagtc    420
ctggatgagc tcggaagaca cgtgctgctg cggaaggact gtggcccagt ggacaccaag    480
gttccaggtg ctggggagcc caagtcagcc ttcactcagg gctcagccat gatttcttct    540
ctgtcccaaa accatccaga caacagaaac gagactttca gctcagtcat ttccctgttg    600
aatgaggatc ccctgtccca ggacttgcct gtgaagatgg cttcaatctt caagaacttt    660
gtcattacct ataaccggac atatgagtca aaggaagaag cccggtggcg cctgtccgtc    720
tttgtcaata acatggtgcg agcacagaag atccaggccc tggaccgtgg cacagctcag    780
tatggagtca ccaagttcag tgatctcaca gaggaggagt tccgcactat ctacctgaat    840
actctcctga ggaaagagcc tggcaacaag atgaagcaag ccaagtctgt gggtgacctc    900
gccccacctg aatgggactg gaggagtaag gggctgtca caaaagtcaa agaccagggc    960
atgtgtggct cctgctgggc cttctcagtc acaggcaatg tggagggcca gtggtttctc   1020
aaccagggga ccctgctctc cctctctgaa caggagctct tggactgtga caagatggac   1080
aaggcctgca tgggcggctt gccctccaat gcctactcgg ccataaagaa tttgggaggg   1140
ctggagacag aggatgacta cagctaccag ggtcacatgc agtcctgcaa cttctcagca   1200
gagaaggcca aggtctacat caatgactcc gtggagctga gccagaacga gcagaagctg   1260
gcagcctggc tggccaagag aggcccaatc tccgtggcca tcaatgcctt tggcatgcag   1320
ttttaccgcc acgggatctc ccgccctctc cggcccctct gcagcccttg gctcattgac   1380
catgcggtgt tgcttgtggg ctacggcaac cgctctgacg ttcccttttg ggccatcaag   1440
aacagctggg gcactgactg gggtgagaag ggttactact acttgcatcg tgggtccggg   1500
```

-continued

```
gcctgtggcg tgaacaccat ggccagctcg gcggtggtgg actgaagagg ggcccccagc   1560
tcgggacctg gtgctgatca gagtggctgc tgccccagcc tgacatgtgt ccaggcccct   1620
ccccgggagg tacagctggc agagggaaag gcactgggta cctcagggtg agcagagggc   1680
actgggctgg ggcacagccc ctgcttccct gcaccccatt cccaccctga agttctgcac   1740
ctgcaccttt gttgaattgt ggtagcttag gaggatgtcg ggtgaagggg tggtatcttg   1800
gcagttgaag ctggggcaag aactctgggc ttgggtaatg agcaggaaga aaattttctg   1860
atcttaagcc cagctctgtt ctgcccccgc tttcctctgt ttgatactat aaattttctg   1920
gttcccttgg atttagggat agtgtccctc tccatgtcca ggaaacttgt aaccaccctt   1980
ttctaacagc aataaagagg tgtccttgtc ccgaaaaaaa aaaaaaaaaa aa           2032
```

<210> SEQ ID NO 98
<211> LENGTH: 1980
<212> TYPE: DNA
<213> ORGANISM: Homo sapiens

<400> SEQUENCE: 98

```
ttgagtaata gaaaataaat ctgggtcact tttttgtagc tgtaaatcca gccttagtaa     60
tcctgacctc cattaacata gctagtattt caaattccac tgtaacagtt gctctgactc    120
tttgggggct gggaggcaat ccaagtagcc agagaagcaa ttgtttcaca tgcttcaatc    180
ctgccactcc agaaaaaata taagggggac tagggcaaaa gaaaatctct tatttgtttt    240
ccatttctca tttctcgtat ctttattgct tctctctcat ccttaacctg tatctccctt    300
cagctgatgc ctgattacct tctaccatgt tcaacattat gatcagtcac ctactatgtg    360
ccaggaagtg tgcagtgtgt gaggatacca gaccctacct actgggagct tacagtctag    420
ctcaacaggc acatcattaa ataagcaatt gcagcaatta tattaagtgc tgggccaagg    480
gaggtaccag aagtcataag aatccctcct ctgaggggat agaagtgaag acttcagagg    540
ggaagtaatg attctggatg tgtaggactc agccaggtga agtgtaaaag taaggatgga    600
ggagagtgtt ctaaaagagg gaacaacata atcaaagttc tggacaggag agagatttga    660
catatttgag gaagtgaaaa ttttatctag aaacttgcaa tgagtaagta aacaccaggt    720
caagaggaac tgagagattg gcagacaatg gaaaaccatt gaaaaggatt aaactgggaa    780
gtgatatgtt ctcttttgca tttaaaaaga tcaccaatgg ggatatggag aatggtctgg    840
ataggtctta agactagagc caggaagaca tgttagaagg ctatcaattg accctaaaga    900
cactgcttca atccctttga tgacagtgag tttgctttcc ccagagatag cttattggac    960
ctcaggactg ctgtgagaaa cagaaaatgc tcctttacgt gttgcctgaa gttaggctca   1020
ccgatttggg gcatgttcta attctaccag ctaggaacac acagaatcgc ttgtcaaaca   1080
ttctgagtca gatatgtcct ccctatgtct tttctgagaa aggcatacag aaattcccag   1140
ctaaacatca ccagttccct catttgttcc tcagatgata tggtccattc aagttttgta   1200
atcatcatgg gggtagatgg agggtcccag tcctcacaac cattctggta atttactctt   1260
gaatttactg gttcacatgt atctattttg tagtgtggct cctgaaactg aaaaacctac   1320
cccaggtatt ctgtgaacag acagagtaga gagtctgtca ctgcccacgg agagatgatt   1380
aggcttccgg gaaaaggtga gaacactggc aaagttccgg aaggaggaac aatatccctt   1440
cttcccttct tcatgagtcg taccatccct tacttttggc tggtcacata accacccaaa   1500
ataagggcta cattttccag ccactctagc agctaggggt gacagagtga ctaagattta   1560
cctggaagta tcgtgtgtga cttctgggaa gggtccttaa agagaggggt agtcctggct   1620
```

gggtgcggtg gctcacgtct gtaatcccag cactttggga ggccgaggca ggcggatcac 1680
aaggtcagga gttcaagacc agcctggcca agatgctgaa accccatctc taataaaaat 1740
acaaaaaaat tagccgggca tgctggcggg cgcctgtaat cccagctact taggaggctg 1800
agatggagaa ttgcttgaac ttgggaggca gagtttgcag tgggccaaaa tggcgccact 1860
gcactccagc ctgggcaaca gagcaagcct ccgtctcaaa aaaaaaaaaa aaaaaaaaaa 1920
aagagagggg tagtccttgt tgctgttgct gcaggtattt tctccttctt cccagctgga 1980

<210> SEQ ID NO 99
<211> LENGTH: 1674
<212> TYPE: DNA
<213> ORGANISM: Homo sapiens

<400> SEQUENCE: 99
gcggccgccc gccgccgcgc tcctcctcct cctcctccag cgcccggcgg cccgctgcct 60
cctccgcccg acgccccgcg tcccccgccg cgccgccgcc gccaccctct gcgccccgcg 120
ccgccccccg gtcccgcccg ccatgcccgg cccggccgcg ggcagcaggg cccgggtcta 180
cgccgaggtg aacagtctga ggagccgcga gtactgggac tacgaggctc acgtcccgag 240
ctggggtaat caagatgatt accaactggt tcgaaaactt ggtcggggaa aatatagtga 300
agtatttgag gccattaata tcaccaacaa tgagagagtg gttgtaaaaa tcctgaagcc 360
agtgaagaaa aagaagataa aacgagaggt taagattctg gagaaccttc gtggtggaac 420
aaatatcatt aagctgattg acactgtaaa ggaccccgtg tcaaagacac cagctttggt 480
atttgaatat atcaataata cagattttaa gcaactctac cagatcctga cagactttga 540
tatccggttt tatatgtatg aactacttaa agctctggat tactgccaca gcaagggaat 600
catgcacagg gatgtgaaac ctcacaatgt catgatagat caccaacaga aaaagctgcg 660
actgatagat tggggtctgg cagaattcta tcatcctgct caggagtaca atgttcgtgt 720
agcctcaagg tacttcaagg gaccagagct cctcgtggac tatcagatgt atgattatag 780
cttggacatg tggagtttgg gctgtatgtt agcaagcatg atctttcgaa gggaaccatt 840
cttccatgga caggacaact atgaccagct tgttcgcatt gccaaggttc tgggtacaga 900
agaactgtat gggtatctga agaagtatca catagaccta gatccacact tcaacgatat 960
cctgggacaa cattcacgga aacgctggga aaactttatc catagtgaga acagacacct 1020
tgtcagccct gaggccctag atcttctgga caaacttctg cgatacgacc atcaacagag 1080
actgactgcc aaagaggcca tggagcaccc atacttctac cctgtggtga aggagcagtc 1140
ccagccttgt gcagacaatg ctgtgctttc cagtggtctc acggcagcac gatgaagact 1200
ggaaagcgac gggtctgttg cggttctccc acttttccat aagcagaaca agaaccaaat 1260
caaacgtctt aacgcgtata gagagatcac gttccgtgag cagacacaaa acggtggcag 1320
gtttggcgag cacgaactag accaagcgaa gggcagccca ccaccgtata tcaaacctca 1380
cttccgaatg taaaaggctc acttgccttt ggcttcctgt tgacttcttc ccgacccaga 1440
aagcatgggg aatgtgaagg gtatgcagaa tgttgttggt tactgttgct ccccgagccc 1500
ctcaactcgt cccgtggccg cctgtttttc cagcaaacca cgctaactag ctgaccacag 1560
actccacagt ggggggacgg gcgcagtatg tggcatggcg gcagttacat attattattt 1620
taaaagtata tattattgaa taaaaggttt taaaagaaaa aaaaaaaaaa aaaa 1674

<210> SEQ ID NO 100

<211> LENGTH: 1032
<212> TYPE: DNA
<213> ORGANISM: Homo sapiens

<400> SEQUENCE: 100

```
cccgcacccc ctgggattgt gggaaatgta gttttttgcc tccgtaaggg accaggcgga     60
gctgaggaac cgcgcgagga ctgggaccgt gattccacta accggaaacc gtcgcctttc    120
gggcccggcg gggcctgagc caatgcagaa tcgggggccg cgaggacgcc agcgggcgct    180
gtgcgtagga accgccgggt ggccgctgcc gatcggggcc gacttgggga cggaccggaa    240
gtgcccgagg gcggccgcag aacggtcaat ttgagccgcg tcgagctccc ctgggacctg    300
tggccgccgc ccacagacca tgctcctggg gcgcctgact tcccagctgt tgagggccgt    360
tccttgggca ggcggccgcc cgccttggcc cgtctctgga gtgctgggca gccgggtctg    420
cgggcccctt tacagcacat cgccggccgg cccaggtagg gcggcctctc tccctcgcaa    480
gggggcccag ctggagctgg aggagatgct ggtccccagg aagatgtccg tcagcccccct    540
ggagagctgg ctcacggccc gctgcttcct gcccagactg gataccggga ccgcagggac    600
tgtggctcca ccgcaatcct accagtgtcc gcccagccag ataggggaag gggccgagca    660
gggggatgaa ggcgtcgcgg atgcgcctca aattcagtgc aaaaacgtgc tgaagatccg    720
ccggcggaag atgaaccacc acaagtaccg gaagctggtg aagaagacgc ggttcctgcg    780
gaggaaggtc caggagggac gcctgagacg caagcagatc aagttcgaga aagacctgag    840
gcgcatctgg ctgaaggcgg ggctaaagga agcccccgaa ggctggcaga cccccaagat    900
ctacctgcgg ggcaaatgag tctggcgccg cccttcccgc ccgttgctgc tgtgatccgt    960
agtaataaat tctcagagga ctcagccttt aaaaaaaaaa aaaaaaaaaa aaaaaaaaaa   1020
aaaaaaaaaa aa                                                         1032
```

<210> SEQ ID NO 101
<211> LENGTH: 1980
<212> TYPE: DNA
<213> ORGANISM: Homo sapiens

<400> SEQUENCE: 101

```
aagaaataag cttattcaag acctgtagga ccaattttag caagaatcct gctaaatcaa     60
tttatgattt cccccccgct ccacaccctt gaaatctgat caccccttgat atatagctcc    120
tcatctccca cctttgatct gtaagtcctt ggcctgcctt tagcaagagt cctattaggt    180
cgggttagca agaatccccc tacacttgat gtctcctctt aataattttc ccctcttagt    240
gaattttcct ctcccctcac actctgccca ttggctataa atttccagct gtctttgctg    300
tattcagaat agagccctat ctctgcctcc tactgtaata ctctaatgca atatagtctt    360
caataaagct ttacttacca tctcaaccag catcagaata atttttcctt taacatatcc    420
aagcttggtc agaattaggg tgtacctaca cctacctgca ctattaatac tccgcacagc    480
agggagaaag gaactaccta ccaggtgtca tgggcatgga aggatgtgag gaacgctagc    540
actggccaaa tacagtggcc tcacaagcca tcttcacctt caggaaaatg aatattgagc    600
tgccacagac actctgctgc cctcttaatt taccattacc atgaatctac aggatgctct    660
gttccaaaca cccagtacat tcttatacat cttgtcctga tagatgcctg tgaggtaggc    720
agggctgaga attatgaatt gttgtctatc aggctgaagt gactttccaa aaattgaagt    780
tgacagcaat aaggtcaaga atcagctctg tgctgttttg acggagtgag tcattgcctc    840
cttgaatctg gcacatacca gccaactgtc aaggtttgtt cttccacatg gtctaactgc    900
```

```
taaatacaaa gtatactagg tttgtcagct tagggcatgt ttgcttccac tctgaaaaca    960
tttcagctgc cctaatatat tgctataaag aattctctta ttattactgt cttcctcctc   1020
atatttagct ctgtcttcca tcacttcaaa agaagcattt gtagcttccc catcctcttt   1080
ctttctagtt gactttgaag actatctata taagtatttc tggcataaaa ctgacaggta   1140
aatgacttca aagctaattt ccgccccccc ccaccccttg cccttttca gtctcaagat    1200
accatgtcag tcctctattc actctcaaaa atgatggctt aactgcacag tgccgttctg   1260
ggtcaattct taaatatact agaatatact agacatatct ggctcattta agtcattctt   1320
caccaatctt tcttcttatt tacctccttc ctcaacttgg aaattttgcc ttttcacaat   1380
atgtggatag ccatttctgc caagattgtg ccgacaagac tggttataaa tctacctact   1440
ttgtaaaagg ggaatatttt tgtaaccatt gcatatctct attaaaacat gaaagaaaca   1500
ctgaaggcca agtgttcaag tgacacgcag gaaaaaaaaa agctgatatt cagaaagcca   1560
agcatacaga gaaataatga gaggttaatg aagtgagttc tgaatcacaa gtgctgttca   1620
gaaaacaaaa aaagacatct gtgaaggctg accttggaac tagtcactgt tattcagtcc   1680
atatgtatgt atgtttttat taaaataact gttcaaagtt aactttcatc caagttaact   1740
tctgaagaaa taaaaaggca tcacgttaag gtttcaaaaa tttaaccatt ctacctttag   1800
caatggttag tccaccttat tttcacacat ttccatctta atgaaagcaa gtacattaaa   1860
ggatactcag aatagctgca aggcatacca caagatgtac cacaagatta gaaatttctt   1920
taaaagtaat taagatcggc cgagtgcagt ggctgactcc agcaatccca gcattttggg   1980
```

<210> SEQ ID NO 102
<211> LENGTH: 3939
<212> TYPE: DNA
<213> ORGANISM: Homo sapiens

<400> SEQUENCE: 102

```
ggtcggcctc tgctgcgcct gcgtggtcgg gaggggaagt gaggcggttt cctcggcgcc     60
ttttccggca gcggcggcgg cagaactggg aggaggagtt ggaggccgga gggagcccgc    120
gctcggggcg gcggctggag gcagcgcacc gagttcccgc gaggatccat gacctgacgg    180
ggccccggag ccgcgctgcc tctcgggtgt cctgggtcgg tggggagccc agtgctcgca    240
ggccggcggg cgggccggag ggctgcagtc tccctcgcgg tgagaggaag gcggaggagc    300
gggaaccgcg gcggcgctcg cgcggcgcct gcggggggaa gggcagttcc gggccgggcc    360
gcgcctcagc agggcggcgg ctcccagcgc agtctcaggg cccgggtggc ggcggcgact    420
ggagaaatca agttgtgcgg tcggtgatgc ccgagtgagc ggggggcctg ggcctctgcc    480
cttaggaggc aactcccacg caggccgcaa aggcgctctc gcggccgaga ggcttcgttt    540
cggtttcgcg gcggcggcgg cgttgttggc tgaggggacc cgggacacct gaatgccccc    600
ggccccggct cctccgacgc gatggggaag gtgctatcca aaatcttcgg gaacaaggaa    660
atgcggatcc tcatgttggg cctggacgcg gccggcaaga caacaatcct gtacaagttg    720
aagctgggcc agtcggtgac caccattccc actgtgggtt tcaacgtgga gacggtgact    780
tacaaaaatg tcaagttcaa cgtatgggat gtgggcggcc aggacaagat ccggccgctc    840
tggcggcatt actacactgg gacccaaggt ctcatcttcg tagtggactg cgccgaccgc    900
gaccgcatcg atgaggctcg ccaggagctg caccgcatta tcaatgaccg ggagatgagg    960
gacgccataa tcctcatctt cgccaacaag caggacctgc ccgatgccat gaaaccccac   1020
```

-continued

```
gagatccagg agaaactggg cctgacccgg attcgggaca ggaactggta tgtgcagccc   1080
tcctgtgcca cctcagggga cggactctat gaggggctca catggttaac ctctaactac   1140
aaatcttaat gagcattctc cacccatccc ctggaaggag agaaatcaaa aacccattca   1200
taggattatc gccaccatca cctctttcaa ttgccacttt ctcttctttt gaatttgaac   1260
tctggagtta ctgttctaca gtttggcggg gacggggctt gggggttttc tcttttgttt   1320
gtttcccttt ctttttcctt tttttttttt tttttttttt gttggctttg cgttaggatg   1380
ctctgatctg acatttgaca tgaacacaaa gttgctagat gctcttgttg acttccagca   1440
gatgggatgg gggaaacaca gcagttcttg gtaaagtcct ttgtaataat agtttgattt   1500
ttttatttcg agagaatctt tcattttcct atgtatgctt ttttcctttt ttgcccagtt   1560
tccttatcac ttgctgtaga tggcttattt tgcattcatg cagactatgt tgcaagtctg   1620
tttcatctag taaactgaaa attattgctt aatcaaactg ccgtttgtct tttatattta   1680
aggccttccc cccccttcct tatgagttct aacttagtaa tttcaaatgt gaccttttat   1740
atctaagacc agtatagtaa acttagccca cagtggcaaa taatgagtaa tattgtaata   1800
tgttccagtt gcacctcagt atgttaaaca ggtaatgtaa gaagttctct gaaatgtcag   1860
caagtaagtt ctgaaacaca tcatgcatga gtaggaataa aacccaagtt ccccataacg   1920
tagataactt aatgctgcat aaaaatatga aagtgtaacc catgaaggac actttttctt   1980
tccactgcaa agttagccac tttgctgttt ttcctctttt ttaaactttg aaaatagact   2040
ctttccagaa attggagcaa taatggtgtt accacacaca gattaaataa tttgtagata   2100
ttttaagtga cttttgggca aaactggaat gtatactttt accttgtttc aaacacctaa   2160
gaccagtaat ttaaaaatta ctaaaaggtt tactttgttc attaataaaa catttaacaa   2220
ttcaaattat atgcaccttt tacctagttg aaaaaaatac acattcctgt tttcacatta   2280
tagcaactga ttaagctgaa gctgtaagtc atttttttata gatgagtgat ccgcatctcc   2340
atcaattaga acactggaaa agatgtttta taaaagaggt atttaatttt gtttgtagga   2400
ttaactcatg caaataataa aaaagatatc ctgttggttc aatagtacac tgtctccttt   2460
aaggaaggaa gcgtgatgaa tgaatgatgt gtagacttga gggatgacta ttaaagggga   2520
cgtaggatga agagaaagaa cctacagatg acaatgaatg taaacttatt tttcttcatg   2580
tgtaagcagt gtgctcgctg gtgatatcca gatcctaaca agattacttg gttagctggt   2640
taggaccagt aactggattg cgaccactat gataatattt tgaaccaaat gttaatgctt   2700
gatgcagaat tgtaaagcag catctggttc ctatatagcc ttaaggatta attttagtga   2760
tcctcaagga attaaatagg gaatttcaga aatgtagact gcaaaggcag tatacaggaa   2820
aaggtggagt gggttttgtt tatgagggtg tctgaaaact aaaattgagc gggatatcat   2880
ggtatagttg gacagtattg gtccttcaca ctttggccat attgtataat ggagctttta   2940
ccaaagatgt atgagaagtg taagactata aaaaaatgaa ctattcaaag taaaactctt   3000
aacaaacatt ttacttaaag cagatgcaaa agggtattct catgtaggct cctgttggtg   3060
cagagggatt tttttgattt caggatacaa ctaaagtacg aagttctcag tttcacttta   3120
gtagaaagag ctctagaaat gaggctgata aacacatcta agaacactgg ttgctttcta   3180
aaatttccaa agctccacca taaatgtaat ttttagtgtt tcaaatgatt gcattttaaa   3240
gtatataaat atgggttatc caatatcaat gctatagtaa catcctgaaa caaaacaagc   3300
acaaaggtat aaatgcctaa actggaggaa acttgaaacc ctcatgttaa atcttaaatg   3360
tagtatttct aacttgtgaa gacagattgg taggcagcca ttttttttgtg tcttaaaata   3420
```

actgggggca tagttaaaat tttatacatc aagtgattgc tattattgaa tgttgcaggt 3480
gagatgtggt tatttttagt ttatttgaaa tgtttgactg gaaagggggg agggggaagc 3540
aaatatttga aatttggaaa accctaaacc ttttggtaag aaattgtaat tttcacttaa 3600
aattttcttt aaggatataa gaggtttata attgatgtag ttaaattgaa caataaccat 3660
tggtgactgg agcaggtaat tatagcctgc agaaaaaatt atctaagaat tttaaaaata 3720
agatcctgaa gttgtttaat tgcatccatt tctgtattta tgtgaattta taaactgcag 3780
taagttttga atgaggttaa tcttgtttaa tataagtaaa tgagtctgta gactgtgatc 3840
tccccaaact aaaaagtaca gtacttggaa ttgtgttctt tatggttgta gtgttggtaa 3900
agcactaata tgcagaaaat aaaggaatta cacagtgca 3939

<210> SEQ ID NO 103
<211> LENGTH: 1980
<212> TYPE: DNA
<213> ORGANISM: Homo sapiens

<400> SEQUENCE: 103
ttgtcactag aaggaggaag gaatgctgtg tggcaaggaa aggaattaat gtccacttga 60
gatggatttg agaaggatgt ctgcaagcag aaataaaggg ttaaagggtg cttacattaa 120
aaattttgat agctactgct ctcaaaattg tatcgcgatt tatattccca gtgccaacag 180
tgtttgaaga gtctggctct ccagagcctg tagacactgg atattgtcag tgttttaaat 240
ttcagcagat ctgatatcta aaaatggtat ctcactgttc taaactgttc tagtatggtg 300
ttctacgtga acaccctttc atgtgtttag ctggcctttg catttctttt tttttttttt 360
tgaactgcct atgcatatct tttggtcaaa attcaattga attgcccttt tttattgtta 420
gagctgctac aaacattact gaaaaggcaa ctcagttgtg tgtgtgtgta tgcacacaca 480
tatatattta taatacatat gttacttagg gtttgtacca gctctatgag ctccttgagg 540
gtggcacctt gctgtaatac agcctgacac ctaatacgaa gtagaaatca gtgattattt 600
atcacgcaaa taaagaaaca aataagtgaa cgaatgaatg agtcaatagt gttgactgcc 660
ttgtattgtc ctaggcccaa gagacagtga aatatccctg ttcttgtata cttttctgta 720
agtttctgga agtttctctg taaagcatct cagtaagctt ttctataggc tgtgagaaac 780
gcatgagtca ggctaatagg aggcatataa ttttgaattg cttttcagaa atggccttca 840
tattccttta cactcactca tcctgttgat aagagcagat ggcctactgc atgtgactca 900
gactcaaaca cacacctccg ctcccttgaa gtgccagccc tggagctttg ttgaggctcg 960
catctgccac gggagtcagc tagtacgttg cccagttcaa catccatcca ggatttcata 1020
ggaacttgag aatcattgtt tttggcttga atcctgggtt tgaggtttct tcgtgtagga 1080
atctgaaaaa aggatttgga aacgttgttg tctctaatcc caaagtatgt atctgggagg 1140
ctgccttcgc catcacccac ctaataactc aggctcccgg ggccatttcg ctcaagtgca 1200
ttcattcctt tggtagaatc aaaagaaact gatccaggtg acagagtacc tgggttctaa 1260
tcccagtttt gatgagcaag ttatttaccc cttacagccc cattttccct attctaaaat 1320
gatatggttg caactgacga tctccaagtc tccgtccaac tcaacaattc agagtggaat 1380
tctgaattct gctctgccac caacagcatg tcctcggagc tttgcctatt actcatgaga 1440
atgtcaacgt ctgggtaaat agatattttg ggtcagctc taaaaaaccc agaagtacgt 1500
attgtatgtt gattttggca cacggacaag cctgaacagg gctgtgtcaa gccttttacc 1560

-continued atgatagctg ccggaagaaa ggccaggcga agcagtctgg gtgagctgct tggaatgaag 1620
aggaccagcc cacatcccat ggcacagatg accttcagga gaagtggagg ggagcagcta 1680
atgtaaagaa atcattagca tctgtgttgg aaatggctta tgacactgtc tcaaagccac 1740
gttctcagac aacagggaaa gctgtaaata gatgcacaca gttatccaag catagcagag 1800
taaaactaaa ggaaagccaa attaaacagg ctcaaccaaa gttttgagtg aaagtgttga 1860
atattgctca tgccttcaga acgggaagct ctgtttagaa tactcacaat ggtgggtcct 1920
cttgaggtga ctacaggctg gtaggtcggt tctatcctcc ccctaggagc catctcagca 1980

<210> SEQ ID NO 104
<211> LENGTH: 1980
<212> TYPE: DNA
<213> ORGANISM: Homo sapiens

<400> SEQUENCE: 104
gttcaacttt aaatttgccc acagaaccct ctaaatcccc ttgtaaattt aactgttagt 60
ccaaagagga acagctcttt ggacactagg aaaaaaactt gtagagagag taaaaaattt 120
aacacccata gtaggcctaa aagcagccac caattaagaa agcgttcaag ctcaacaccc 180
actacctaaa aaatcccaaa catataactg aactcctcac acccaattgg accaatctat 240
caccctatag aagaactaat gttagtataa gtaacatgaa aacattctcc tccgcataag 300
cctgcgtcag attaaaacac tgaactgaca attaacagcc caatatctac aatcaaccaa 360
caagtcatta ttaccctcac tgtcaaccca acacaggcat gctcataagg aaaggttaaa 420
aaaagtaaaa ggaactcggc aaatcttacc ccgcctgttt accaaaaaca tcacctctag 480
catcaccagt attagaggca ccgcctgccc agtgacacat gtttaacggc cgcggtaccc 540
taaccgtgca aaggtagcat aatcacttgt tccttaaata gggacctgta tgaatggctc 600
cacgagggtt cagctgtctc ttacttttaa ccagtgaaat tgacctgccc gtgaagaggc 660
gggcatgaca cagcaagacg agaagaccct atggagcttt aatttattaa tgcaaacagt 720
acctaacaaa cccacaggtc ctaaactacc aaacctgcat taaaaatttc ggttggggcg 780
acctcggagc agaacccaac ctccgagcag tacatgctaa gacttcacca gtcaaagcga 840
actactatac tcaattgatc caataacttg accaacggaa caagttaccc tagggataac 900
agcgcaatcc tattctagag tccatatcaa caatagggtt tacgacctcg atgttggatc 960
aggacatccc gatggtgcag ccgctattaa aggttcgttt gttcaacgat taaagtccta 1020
cgtgatctga gttcagaccg gagtaatcca ggtcggtttc tatctacttc aaattcctcc 1080
ctgtacgaaa ggacaagaga aataaggcct acttcacaaa gcgccttccc ccgtaaatga 1140
tatcatctca acttagtatt atacccacac ccacccaaga acagggtttg ttaagatggc 1200
agagcccggt aatcgcataa aacttaaaac tttacagtca gaggttcaat tcctcttctt 1260
aacaacatac ccatggccaa cctcctactc ctcattgtac ccattctaat cgcaatggca 1320
ttcctaatgc ttaccgaacg aaaaattcta ggctatatac aactacgcaa aggccccaac 1380
gttgtaggcc cctacgggct actacaaccc ttcgctgacg ccataaaact cttcaccaaa 1440
gagcccctaa aacccgccac atctaccatc accctctaca tcaccgcccc gaccttagct 1500
ctcaccatcg ctcttctact atgaaccccc ctccccatac ccaacccccct ggtcaacctc 1560 aacctaggcc tcctatttat tctagccacc tctagcctag ccgtttactc aatcctctga 1620
tcagggtgag catcaaactc aaactacgcc ctgatcggcg cactgcgagc agtagcccaa 1680
acaatctcat atgaagtcac cctagccatc attctactat caacattact aataagtggc 1740

```
tcctttaacc tctccaccct tatcacaaca caagaacacc tctgattact cctgccatca   1800

tgacccttgg ccataatatg atttatctcc acactagcag agaccaaccg aaccccccttc   1860

gaccttgccg aaggggagtc cgaactagtc tcaggcttca acatcgaata cgccgcaggc   1920

cccttcgccc tattcttcat agccgaatac acaaacatta ttataataaa caccctcacc   1980


<210> SEQ ID NO 105
<211> LENGTH: 1980
<212> TYPE: DNA
<213> ORGANISM: Homo sapiens

<400> SEQUENCE: 105

ctggagaatc ccttgaaccc aggaggagga ggttgcagtg agcgatcctg ccacggcact     60

ccagcagggg tgacaagaat gaaactctat ttcaaaataa agaaaaaaaa gaaaaaaaaa    120

gaaaacccaa cctcaactag cttaagcaaa agcaaattta tgtggtgaaa gggtggatct    180

ggttttagaa tcagttacca agggctcaag aagtgtcaca gggactgatc cccccacccc    240

cccgtccccc atgtcgtgtc attctccagg tctttccttt tcattgccag gagctccagg    300

tttctaccct cagaactcca aggccattgg aaaacagagg gcagttttct tagttgccca    360

aggaaatgtt cccaaattgt atcaaaagcc cacctctagg ttaattattg tggctggagg    420

atgtaatcca ttcataggtc agggctggcc aggtgtagtg gctcatgcct gtaatcccag    480

cactttggga gactgagatg ggtgggtcac ttgaggtcag aagttcgaga ccagcctggc    540

caacaggatg aaaccccgtc tctactaaaa atacaaaaat tagccaggca tggtggcggg    600

cgcctgtaat cccagctgct cgggaggctg aggcaggaga atggattgaa cccaggaggt    660

ggaggttgca gtgagcagag atcacgccac tgcactcaag cccaggcaac gaagcgagac    720

tccttctcaa aaaaaaaaaa agagagaaac ataggctagg actaggcata tgccatgcct    780

tgtgacataa actggacatg gggaagggga gtgattcccc agtgttagtt agccttgctc    840

ttgtcactag aaggaggaag gaatgctgtg tggcaaggaa aggaattaat gtccacttga    900

gatggatttg agaaggatgt ctgcaagcag aaataaaggg ttaaagggtg cttacattaa    960

aaattttgat agctactgct ctcaaaattg tatcgcgatt tatattccca gtgccaacag   1020

tgtttgaaga gtctggctct ccagagcctg tagacactgg atattgtcag tgttttaaat   1080

ttcagcagat ctgatatcta aaaatggtat ctcactgttc taaactgttc tagtatggtg   1140

ttctacgtga acaccctttc atgtgtttag ctggcctttg catttctttt tttttttttt   1200

tgaactgcct atgcatatct tttggtcaaa attcaattga attgcccttt tttattgtta   1260

gagctgctac aaacattact gaaaaggcaa ctcagttgtg tgtgtgtgta tgcacacaca   1320

tatatattta taatacatat gttacttagg gtttgtacca gctctatgag ctccttgagg   1380

gtggcacctt gctgtaatac agcctgacac ctaatacgaa gtagaaatca gtgattattt   1440

atcacgcaaa taaagaaaca aataagtgaa cgaatgaatg agtcaatagt gttgactgcc   1500

ttgtattgtc ctaggcccaa gagacagtga aatatccctg ttcttgtata cttttctgta   1560

agtttctgga agtttctctg taaagcatct cagtaagctt ttctataggc tgtgagaaac   1620

gcatgagtca ggctaatagg aggcatataa ttttgaattg cttttcagaa atggccttca   1680

tattccttta cactcactca tcctgttgat aagagcagat ggcctactgc atgtgactca   1740

gactcaaaca cacacctccg ctcccttgaa gtgccagccc tggagctttg ttgaggctcg   1800

catctgccac gggagtcagc tagtacgttg cccagttcaa catccatcca ggatttcata   1860
```

-continued ggaacttgag aatcattgtt tttggcttga atcctgggtt tgaggtttct tcgtgtagga 1920
atctgaaaaa aggatttgga aacgttgttg tctctaatcc caaagtatgt atctgggagg 1980

<210> SEQ ID NO 106
<211> LENGTH: 1980
<212> TYPE: DNA
<213> ORGANISM: Homo sapiens

<400> SEQUENCE: 106
attcatctgt gttattggga aatgatgtga acttaatttc tctttccctt ctaaaacttt 60
gcttactgaa tggaaatgtt cctgagatct gtttatttgg ttctatattt atgtacctcc 120
cttttaaaat agagaataca tgttaatgtt tctttgatga ctcagtgtgt attatcggta 180
acagtccatt catgatgttg ccataccaca cagcataatt ttctatctgc ttctgattga 240
ttcttcattc tcccttgatc tcagtttgtc atttaataca tctaagtttt tcactcaaca 300
aatcaaatac tgatggagaa tctgctatac accaggcact gtgctgctag gagctgagga 360
ttgaacgggg agaaacagga agctccctgc tctcatagtg cttcttagtt ggggagaaaa 420
gacattcatg atataatcac ataaatacct atttttatat gtaaaaaatg ttgtcaaaga 480
aaagaacggg gtgatgggaa cagttggaag aggtgtaaaa actccagaga agctgtggct 540
cctagaaaga aggtaggttt taggactaga atggtgatag tgggccggaa gagagagagt 600
gcattcgaaa gacactgagg agattgcatc agtaggactt ggtgacacat tagatgcaga 660
ggaagaggga cagaaatgct tcaaggagga cttttaggca tctgtcttgg gtaactagat 720
gatgccaatg gctgagatgg ggaattcttg ggtagatgag gtttggtggg atggtgattg 780
ttataacttt gactttgaac gtgctgagtt caggtgacat tgtgataccc caaaggaggt 840
gcagagtagg tagctggaga cacaggcccg aagatgatga gaggtctggc ctagaaacat 900
ggatgcagga gtcatggatc catcaaggca ctgtgagttt ggatgagatc atctagcaga 960
acacttaagt ggagaagcaa agtggtctag agactaagcc atgaggaact ccaacactta 1020
gaggcgtaga aagcaggtag aaagggaaca cctgaagact taggaaggag gggccagaaa 1080
gggatgatgg cacccgaaga cagtggtgtt caggaagcca agggaggaag gtatttagac 1140
aggaggggga gagcagaatt ggcaaagctg tggagaaagt gagatgagaa ctcctattaa 1200
aaacacacaa ctggtccaat gacatgggat ggcatggaaa tcactgatga ccaagcagga 1260
gacaggggtg gaccgcaggg gaaaaagagc aagctgaagc cagctaagga atgtcctcgg 1320
gccatctcct agcggaggcg gtagagccgt ggttgaaggt acaggaagtg gactgttagg 1380
gcccaggttc cccttaacca tgagacctga agcaagttac tttatttctc tagggctcaa 1440
ttttctcacc tgtaaaacaa gagtaacagt gctcacctac taggttgctg tgaggttctt 1500
tttctttttc ttttttttt ggagacagag tctcactctg tcacccaggc tggagtgcag 1560
tggtgcaatc ttggctcact gcaatctcca cctcccgggt tccagctatt ctcctgcctt 1620
agcctcctga gtggctggga ctacaggcgc ctgccaccac aactggctaa tttttgtatt 1680
tttagtagag atggggtttc accacgttgg ccagcctgga ctcaaactcc tgacctcagg 1740
tgatctgcct gcttcagcct cccaaagtgc tgggattaca ggcgtgagcc accacacctg 1800
gccttctgtg aggttcttaa catgtaagcc acttagccca gtggctgact catagtagtt 1860
gctgaataaa tgctaatttt atattaacac cctcataacc cattaaatca atatttattg 1920
agcatccatc tgccaggcac tgtactagat gctgacaaag acacccccaa caacaaataa 1980

<210> SEQ ID NO 107
<211> LENGTH: 1980
<212> TYPE: DNA
<213> ORGANISM: Homo sapiens

<400> SEQUENCE: 107
tgagcctagg agtttgagat caccccaggc agtgtggcaa aaccgcatct ctacatgaaa 60
aatacaaaaa taagtcaggc atggcagcat gtgcctgtgg tcctggctac tagggaggct 120
gaggtgagag gatcaattga gcccaggagg tcaaggccac agtgagctga gattgcacca 180
ctgcactctg gcctggggga cagagtgaga ccctgtctca aaaaaaaaaa aaaaaaatag 240
tattgtatca atgttaattt cctggttttg ataatagtgc caaaggtata taaactgtta 300
aggcaagagc aagtggctga aggctataca ggaactctct gcactatttt tgcaacttct 360
ctgttatcct aaaattattt caaaataaaa agttaaaaaa aaagtgttta ggccgggcgc 420
ggtggctcac gcctataatc ccagcacttt gggaggccga ggcgggcgga tcacgaggtc 480
aggagatcaa gaccatcctg gctaacacag tgaaacccca tctctactaa agatacaaaa 540
aattagccgg gcgaggtagc gggcgcctgt agtcccagct acgtgggagg ctgaggcagg 600
agaatggcat gaaccccagg gggtggagcc tgcagtgagc cgagatcgtg ccactgcact 660
ccagcctggg tgaaagagcg agactccttc tcaaaaaaaa aaaaaaaaaa aaaaagtgtt 720
taatcttttt tccaaaagga gcacacagaa cagagagtac agtacaagtc ccttaagaat 780 ttgtttttc tcagactatt ttctcacttg tcatcaagaa tcagccttta gattattggc 840
agcattagtc ctctagtaca gtctgcttgt gggtgaccag atggagtaat gctgagcaca 900
gagactatga tggccgtgct aaggtaagag tattgataat gtaagcatac ttcctctatc 960
aacaataatt gttaacagct gcttcaagca cttgatatta ccactagttg ttaactgaat 1020
caagcatgtg ctccaagttc acattaatgt gaattgaaca gcattgtgta cgtacgagga 1080
gcttcatgca agtgttatac actgcactca caagtattat gatcttacta agcattagaa 1140
atactctgtg ttaaagaagc ttggtctagg ccaagcgtgg tggctcatgc ctataatctc 1200
agcactttgg gaggccaagg caggcagatc acatgaggcc aggaatttga gaccagcctg 1260
gccaacatgg tgaaacccca tctctactaa aaatacaaat attagccagg tatgatggcg 1320
catgcctata atcctaacta ctcaggaggc cgaagcagaa gaatcacttg aacctgggag 1380
gcggaggttg cagtgagcca agatcatgcc actgcactcc agcctgggtg acagagtgag 1440
actctgtctc aaaaaaaaaa aaaagaaaga aaagaaaaag aaacttggtc tagttatttt 1500
ccttcctctg gggaagtaac catttgggtg ggaatagttt tgttgttgat cccatcttgc 1560
tggtttggaa acaatgcact ggctccactt ttccactcat gggctttaag gccccccttga 1620 gtcccagtct ttctcctgac acatggctgt ctcctgacag tcccctctgc tttacattgt 1680
tctcagaggg tcctgggcca tcgtttgagc ttcattcttt caaatacact tccctctttc 1740
tctatcaagc caaggctccc ctcccccaga actctgcata ggcccttcag cctccatgaa 1800
tcccttagtg agtgagtaaa ctaccactgg attcagtcac tgcaaatgta ctttatttac 1860
cccttagcac tcttactaca tgtatgtgtt agggttcttc aaagaaacag aaccaatagg 1920
atacatagag atatataaga gaagatttat aatgggaatt ggctcatgtg attatggagg 1980

<210> SEQ ID NO 108
<211> LENGTH: 1063
<212> TYPE: DNA
<213> ORGANISM: Homo sapiens

<400> SEQUENCE: 108
agaatacgag gaggaagagg tggccatacc gttgaccgct cctccaacta accagtaagt 60
taagactgct gttcaggaat ttgggaagct ggccccagaa aagaagtgga aatgaagggg 120
tggtatcacg gaaaacttga cagaacgata gcagaagaac gcctcaggca ggcagggaag 180
tctggcagtt atcttataag agagagtgat cggaggccag ggtcctttgt actttcattt 240
cttagccaga tgaatgttgt caaccatttt aggattattg ctatgtgtgg agattactac 300
attggtggaa gacgtttttc ttcactgtca gacctaatag gttattacag tcatgtttct 360
tgtttgctta aaggagaaaa attactttac ccagttgcac caccagagcc agtagaagat 420
agaaggcgtg tacgagctat tctaccttac acaaaagtac cagacactga tgaaataagt 480
ttcttaaaag gagatatgtt cattgttcat aatgaattag aagatggatg gatgtgggtt 540
acaaatttaa gaacagatga acaaggcctt attgttgaag acctagtaga agaggtgggc 600
cgggaagaag atccacatga aggaaaaata tggttccatg ggaagatttc caaacaggaa 660
gcttataatt tactaatgac agttggtcaa gtctgcagtt ttcttgtgag gccctcagat 720
aatactcctg gcgattattc actttatttc cggaccaatg aaaatattca gcgatttaaa 780
atatgtccaa cgccaaacaa tcagtttatg atgggaggcc ggtattataa cagcattggg 840
gacatcatag atcactatcg aaaagaacag attgttgaag gatattatct taaggaacct 900
gtaccaatgc aggatcaaga acaagtactc aatgacacag tggatggcaa ggaaatctat 960
aataccatcc gtcgtaaaac aaaggatgcc ttttataaaa acattgttaa gaaaggttat 1020
cttctgaaag aggccaaaaa aaaaaaaaaa aaaaaaaaaa aaa 1063

<210> SEQ ID NO 109
<211> LENGTH: 2599
<212> TYPE: DNA
<213> ORGANISM: Homo sapiens

<400> SEQUENCE: 109
agctctctcg agtcactccg gcgcagtgtt gggactgtct gggtatcgga aagcaagcct 60
acgttgctca ctattacgta taatcctttt cttttcaaga tttttatttt agatgcctga 120
ggaagtgcac catggagagg aggaggtgga gacttttgcc tttcaggcag aaattgccca 180
actcatgtcc ctcatcatca ataccttcta ttccaacaag gagattttcc ttcgggagtt 240
gatctctaat gcttctgatg ccttggacaa gattcgctat gagagcctga cagacccttc 300
gaagttggac agtggtaaag agctgaaaat tgacatcatc cccaaccctc aggaacgtac 360
cctgactttg gtagacacag gcattggcat gaccaaagct gatctcataa ataatttggg 420
aaccattgcc aagtctggta ctaaagcatt catggaggct cttcaggctg gtgcagacat 480
ctccatgatt gggcagtttg gtgttggctt ttattctgcc tacttggtgg cagagaaagt 540
ggttgtgatc acaaagcaca acgatgatga acagtatgct tgggagtctt ctgctggagg 600
ttccttcact gtgcgtgctg accatggtga gcccattggc aggggtacca aagtgatcct 660
ccatcttaaa gaagatcaga cagagtacct agaagagagg cgggtcaaag aagtagtgaa 720
gaagcattct cagttcatag gctatcccat caccctttat ttggagaagg aacgagagaa 780
ggaaattagt gatgatgagg cagaggaaga gaaaggtgag aaagaagagg aagataaaga 840
tgatgaagaa aaacccaaga tcgaagatgt gggttcagat gaggaggatg acagcggtaa 900
ggataagaag aagaaaacta agaagatcaa agagaaatac attgatcagg aagaactaaa 960
caagaccaag cctatttgga ccagaaaccc tgatgacatc acccaagagg agtatggaga 1020
attctacaag agcctcacta atgactggga agaccacttg gcagtcaagc acttttctgt 1080
agaaggtcag ttggaattca gggcattgct atttattcct cgtcgggctc cctttgacct 1140
ttttgagaac aagaagaaaa agaacaacat caaactctat gtccgccgtg tgttcatcat 1200
ggacagctgt gatgagttga taccagagta tctcaatttt atccgtggtg tggttgactc 1260
tgaggatctg cccctgaaca tctcccgaga aatgctccag cagagcaaaa tcttgaaagt 1320
cattcgcaaa aacattgtta agaagtgcct tgagctcttc tctgagctgg cagaagacaa 1380
ggagaattac aagaaattct atgaggcatt ctctaaaaat ctcaagcttg gaatccacga 1440
agactccact aaccgccgcc gcctgtctga gctgctgcgc tatcatacct cccagtctgg 1500
agatgagatg acatctctgt cagagtatgt ttctcgcatg aaggagacac agaagtccat 1560
ctattacatc actggtgaga gcaaagagca ggtggccaac tcagcttttg tggagcgagt 1620
gcggaaacgg ggcttcgagg tggtatatat gaccgagccc attgacgagt actgtgtgca 1680
gcagctcaag gaatttgatg ggaagagcct ggtctcagtt accaaggagg gtctggagct 1740
gcctgaggat gaggaggaga agaagaagat ggaagagagc aaggcaaagt ttgagaacct 1800
ctgcaagctc atgaaagaaa tcttagataa gaaggttgag aaggtgacaa tctccaatag 1860
acttgtgtct tcaccttgct gcattgtgac cagcacctac ggctggacag ccaatatgga 1920
gcggatcatg aaagcccagg cacttcggga caactccacc atgggctata tgatggccaa 1980
aaagcacctg gagatcaacc ctgaccaccc cattgtggag acgctgcggc agaaggctga 2040
ggccgacaag aatgataagg cagttaagga cctggtggtg ctgctgtttg aaaccgccct 2100
gctatcttct ggcttttccc ttgaggatcc ccagacccac tccaaccgca tctatcgcat 2160
gatcaagcta ggtctaggta ttgatgaaga tgaagtggca gcagaggaac ccaatgctgc 2220
agttcctgat gagatccccc ctctcgaggg cgatgaggat gcgtctcgca tggaagaagt 2280
cgattaggtt aggagttcat agttggaaaa cttgtgccct tgtatagtgt ccccatgggc 2340
tcccactgca gcctcgagtg cccctgtccc acctggctcc ccctgctggt gtctagtgtt 2400
tttttccctc tcctgtcctt gtgttgaagg cagtaaacta agggtgtcaa gccccattcc 2460
ctctctactc ttgacagcag gattggatgt tgtgtattgt ggtttatttt attttcttca 2520
ttttgttctg aaattaaagt atgcaaaata aagaatatgc cgtttttata cgaaaaaaaa 2580
aaaaaaaaaa aaaaaaaaa 2599

<210> SEQ ID NO 110
<211> LENGTH: 829
<212> TYPE: DNA
<213> ORGANISM: Homo sapiens

<400> SEQUENCE: 110
cctcttttcc gtggcgcctc ggaggcgttc agctgcttca agatgaagct gaacatctcc 60
ttcccagcca ctggctgcca gaaactcatt gaagtggacg atgaacgcaa acttcgtact 120
ttctatgaga agcgtatggc cacagaagtt gctgctgacg ctctgggtga agaatggaag 180
ggttatgtgg tccgaatcag tggtgggaac gacaaacaag gtttccccat gaagcagggt 240
gtcttgaccc atggccgtgt ccgcctgcta ctgagtaagg ggcattcctg ttacagacca 300
aggagaactg gagaaagaaa gagaaaatca gttcgtggtt gcattgtgga tgcaaatctg 360
agcgttctca acttggttat tgtaaaaaaa ggagagaagg atattcctgg actgactgat 420
actacagtgc ctcgccgcct gggccccaaa agagctagca gaatccgcaa acttttcaat 480
ctctctaaag aagatgatgt ccgccagtat gttgtaagaa agcccttaaa taaagaaggt 540
aagaaaccta ggaccaaagc acccaagatt cagcgtcttg ttactccacg tgtcctgcag 600
cacaaacggc ggcgtattgc tctgaagaag cagcgtacca agaaaaataa agaagaggct 660
gcagaatatg ctaaactttt ggccaagaga atgaaggagg ctaaggagaa gcgccaggaa 720
caaattgcga agagacgcag actttcctct ctgcgagctt ctacttctaa gtctgaatcc 780
agtcagaaat aagatttttt gagtaacaaa taaataagat cagactctg 829

<210> SEQ ID NO 111
<211> LENGTH: 1980
<212> TYPE: DNA
<213> ORGANISM: Homo sapiens

<400> SEQUENCE: 111
ttgatcttcc tgcctcagcc ttccaagtag ctgggactta aaggcgtgag ccaccacacc 60
tgactaattt tcgtattttt tgtagagatg gggtttcgcc atgttgcccg ggctgttctc 120
gaactcctga gctcaagcaa tctgcccacc tcagcctccc aaagcgctgg gattacaggc 180
atgagccacc atcccagcca aaactataaa acttttagaa aagaacatag aagaaaatct 240
ttgggtcctg ggggcaaaga gctctgagac ttgacatcaa aagcatgccg cataatagga 300
aaatactaga ctttatttag gggttaagag tttagactct ggactctctc agccttggtt 360
tcactagtta gctctatcac taactacatt gggcattgaa aattcctctg ttgtcccacg 420
tggtgcatgg atgattgtag acgaggacac tgagatcctg aaggcagaag taatttctct 480
aagcaacgtt gttggttggt ggcagagtct gggttacaac ccctggtttc ctgattccga 540
gtccaagtga aatacttttg cccctgcagt agaccctgct acagaggata aaaaggcacg 600
tcataggcta ggagaaaaat tttgcctacc acatatgtaa ccaaggacta gcagctagga 660
catctgaaga attctcaaca ttcaacgggg tagaagaatg aacgattcaa tagaatatgg 720
gcaaaagaca tgaagaggca ttttaccaaa catagggtgc tatggtccga atgtttgcat 780
tctcctcaaa ttcctgtgtt gaaatcctaa cccccaaggt attggtatta ggaggcaggg 840
gccctgggaa gtgattaggt cataaaggtg gagtcctcat ggatgggatt agtgtcttta 900
taaaagagac ctttgccatg tgaggttaca gtgagaagac atctgtctat gaagaaagtg 960
ggccctcacc aaacacagtc tgctggcact ttgcacttca actccccagc ttccagaact 1020
gtaaggaata taagtctgtt gttggtaagc cacccggtct atgatatttt gttatagcag 1080
cccaaacaga ctaagacagg tgacaaataa acatgaaaag atgttcaaca tcattagcca 1140
ttagggaaat gcagattaaa accacagcga aatatcatga tacagttttc agcatggcta 1200
aactagaaaa tagtgacacc accaaatgcc gacaaggctg tggggaaact gggttgttca 1260
gacactgcca ctggggctgt agcgtactat agccactttc ataaacagtt tgtcagtttc 1320
ttaaaaaact aaacctgcaa ctaccatatg acccagcaat tacacccctg ggcacctacc 1380
caagagaaat gaaaactcaa cgtttgcgca aaaacctgtg taggaatgtt caagcagctt 1440
tattcataat atgcccaaac aggaaacaac tcagctgtcc ttcagtaggt aaatagttaa 1500
gcaaattgtc atacccctgt gtcatggagc actacctagc aataacaagg agcaaattat 1560
tgatacataa caatctggat gaatctccag agaattatgt tgaatgaaaa aagccagccc 1620
ctgaaggata catactgtat gatgccattt acataacatt cttgaaattc taaaattaca 1680
gagatgggga acagatttgt ggttaaagat ggagccgggt gggaagaaag taggtgtggc 1740
tataaacggg taacatgaag gatccttgtg gtgatggaaa tttctgtatt tttattgtat 1800
ccgtgtcagt atcctggttg tgatatggta atacagtttt gcaagatact acccttaggg 1860
gaaatgaggt aagacctggc atctctctgt attatttctt aattgcatgt gaatctacaa 1920
ttatttcaaa ataaaaagta tgattgaagt aactctcagg aagcttagcc tactgtggat 1980

<210> SEQ ID NO 112
<211> LENGTH: 79
<212> TYPE: PRT
<213> ORGANISM: Artificial Sequence
<220> FEATURE:
<223> OTHER INFORMATION: Synthetic

<400> SEQUENCE: 112

Ser Cys Gly Pro Ser Met Arg Thr Arg Trp Ser Ser Ile Arg Arg Ser
1               5                   10                  15

Trp Arg Arg Leu Ile Leu Pro Ser Trp Thr Met Pro Gly Ser Leu Leu
            20                  25                  30

Arg Gly Thr Ala Thr Trp Trp Gly Leu Pro Thr Arg Ser Cys Ser Ser
        35                  40                  45

Arg Ala Ser Ala Ser Thr Ala Ser Leu Pro Ser Ser Ala Ser Ser Arg
    50                  55                  60

Ser Ser Trp Gln Pro Arg Arg Arg Ser Leu Arg Pro His Ser Ser
65                  70                  75

<210> SEQ ID NO 113
<211> LENGTH: 12
<212> TYPE: PRT
<213> ORGANISM: Artificial Sequence
<220> FEATURE:
<223> OTHER INFORMATION: Synthetic

<400> SEQUENCE: 113

Met Arg Asn Asp Arg Ala Ala Ser Arg Gln Ile Thr
1               5                   10

<210> SEQ ID NO 114
<211> LENGTH: 76
<212> TYPE: PRT
<213> ORGANISM: Artificial Sequence
<220> FEATURE:
<223> OTHER INFORMATION: Synthetic

<400> SEQUENCE: 114

Leu Ala His Arg Pro Pro Cys Ala Glu Pro Asp Pro Gly Gln Arg Met
1               5                   10                  15

Glu Leu Pro Ala Pro Val Pro Arg Pro Arg Gly Ala Ser Lys Pro Arg
            20                  25                  30

Asp Gly Thr Ser Ser His Cys Asp Met Pro Asn Cys Gln His Pro Gln
        35                  40                  45

Gly Pro Gly Pro Ala Gly Glu Ile Arg Ser Arg Cys Arg Ser Cys Trp
    50                  55                  60

Leu Arg Ala Val Arg Cys Asn Pro Trp Leu Gly Arg
65                  70                  75

<210> SEQ ID NO 115
<211> LENGTH: 20
<212> TYPE: PRT
<213> ORGANISM: Artificial Sequence
<220> FEATURE:
<223> OTHER INFORMATION: Synthetic

<400> SEQUENCE: 115

Asn Ser Gly Ala Ser Gly Ser Arg Asn Phe Ser Ser Cys Ser Ala Glu
1               5                   10                  15

Asp Phe Glu Lys
            20

<210> SEQ ID NO 116
<211> LENGTH: 31
<212> TYPE: PRT
<213> ORGANISM: Artificial Sequence
<220> FEATURE:
<223> OTHER INFORMATION: Synthetic

<400> SEQUENCE: 116

Ser Ser Val Pro Pro Gln Asp Thr Ala Pro Tyr Ser Cys His Val Gln
1               5                   10                  15

His Ser Ser Leu Ala Gln Pro Leu Val Val Pro Trp Glu Ala Ser
            20                  25                  30

<210> SEQ ID NO 117
<211> LENGTH: 37
<212> TYPE: PRT
<213> ORGANISM: Artificial Sequence
<220> FEATURE:
<223> OTHER INFORMATION: Synthetic

<400> SEQUENCE: 117

Val Ala Val Ala Gln Gly Ser Gly Ala Leu Glu Ser Ser Lys Trp Pro
1               5                   10                  15

Leu Leu Asn Leu Asn Gly Cys Leu Gly Arg Ala Glu Gly Gln Val Leu
            20                  25                  30

Met Ala Ser His Pro
        35

<210> SEQ ID NO 118
<211> LENGTH: 11
<212> TYPE: PRT
<213> ORGANISM: Artificial Sequence
<220> FEATURE:
<223> OTHER INFORMATION: Synthetic

<400> SEQUENCE: 118

Ser Ala Phe Arg Gly Tyr Leu Ala Asn Asn Lys
1               5                   10

<210> SEQ ID NO 119
<211> LENGTH: 36
<212> TYPE: PRT
<213> ORGANISM: Artificial Sequence
<220> FEATURE:
<223> OTHER INFORMATION: Synthetic

<400> SEQUENCE: 119

Ser Leu Ala His Arg Pro Pro Cys Ala Glu Pro Asp Pro Gly Gln Arg
1               5                   10                  15

Met Glu Leu Pro Ala Pro Val Pro Arg Pro Arg Gly Ala Ser Lys Pro
            20                  25                  30

Pro Arg Arg Asp
        35

<210> SEQ ID NO 120
<211> LENGTH: 51
<212> TYPE: PRT
<213> ORGANISM: Artificial Sequence
<220> FEATURE:
<223> OTHER INFORMATION: Synthetic

<400> SEQUENCE: 120

Leu Phe Ile Phe Ile Thr Gln Lys Ser Phe Ile Phe Leu Phe Ser Phe
1 5 10 15

Leu Thr Leu Cys Leu Cys Leu Gln His Phe His Asn Asp Phe Leu Leu
20 25 30

Leu Asp Lys Glu Ser Thr Leu Asp Pro Val Thr Asn Thr Phe Ser Thr
35 40 45

His Gly Thr
50

<210> SEQ ID NO 121
<211> LENGTH: 10
<212> TYPE: PRT
<213> ORGANISM: Artificial Sequence
<220> FEATURE:
<223> OTHER INFORMATION: Synthetic

<400> SEQUENCE: 121

Pro Tyr Gln Ile Tyr Gln Val Met Ile Asn
1 5 10

<210> SEQ ID NO 122
<211> LENGTH: 19
<212> TYPE: PRT
<213> ORGANISM: Artificial Sequence
<220> FEATURE:
<223> OTHER INFORMATION: Synthetic

<400> SEQUENCE: 122

Val Ser Thr Phe Leu Ser Arg Val Gly Arg Val Ser Leu Leu Asn Phe
1 5 10 15

Leu Pro Phe

<210> SEQ ID NO 123
<211> LENGTH: 76
<212> TYPE: PRT
<213> ORGANISM: Artificial Sequence
<220> FEATURE:
<223> OTHER INFORMATION: Synthetic

<400> SEQUENCE: 123

Asn Thr Leu Val Thr Tyr Asp Met Val Pro Glu Pro Lys Ile Ile Asp
1 5 10 15

Ala Ala Leu Arg Ala Cys Arg Arg Leu Asn Asp Phe Ala Ser Thr Val
20 25 30

Arg Ile Leu Glu Val Val Lys Asp Lys Ala Gly Pro His Lys Glu Ile
35 40 45

Tyr Pro Tyr Val Ile Gln Glu Leu Arg Pro Thr Leu Asn Glu Leu Gly
50 55 60

Ile Ser Thr Pro Glu Glu Leu Gly Leu Asp Lys Val
65 70 75

<210> SEQ ID NO 124
<211> LENGTH: 61
<212> TYPE: PRT
<213> ORGANISM: Artificial Sequence
<220> FEATURE:
<223> OTHER INFORMATION: Synthetic

<400> SEQUENCE: 124

Pro Pro Ser His His Ile Pro Asn Leu Ser Leu Thr Lys Arg Lys Pro
1 5 10 15

Ser Pro His Ser Leu Asn Leu Ile His His Ser Arg Gln Leu Arg Trp
20 25 30

Ile Lys Pro Asn Pro Ala Thr Gln Asn Leu Ser Ile Leu Leu Asn Tyr
35 40 45

Pro His Arg Met Asn Asn Ser Ser Ser Thr Val Gln Pro
50 55 60

<210> SEQ ID NO 125
<211> LENGTH: 8
<212> TYPE: PRT
<213> ORGANISM: Artificial Sequence
<220> FEATURE:
<223> OTHER INFORMATION: Synthetic

<400> SEQUENCE: 125

Ser Ala Gly Ser Cys Ser Ser Ala
1 5

<210> SEQ ID NO 126
<211> LENGTH: 51
<212> TYPE: PRT
<213> ORGANISM: Artificial Sequence
<220> FEATURE:
<223> OTHER INFORMATION: Synthetic

<400> SEQUENCE: 126

Lys Leu Leu Phe Ala Leu Gln Leu Trp Asn Leu Val Leu Gln Pro Leu
1 5 10 15

Leu Phe Cys Pro Asn Gly Pro Cys Ser Leu Asp Gln Glu Leu Gln Lys
20 25 30

Trp Lys Lys Leu Met Lys Arg His Leu Ile Asn Val Asp Gly Ser Lys
35 40 45

Ser Cys Pro
50

<210> SEQ ID NO 127
<211> LENGTH: 131
<212> TYPE: PRT
<213> ORGANISM: Artificial Sequence
<220> FEATURE:
<223> OTHER INFORMATION: Synthetic

<400> SEQUENCE: 127

Glu Asp Asp Tyr Ser Tyr Gln Gly His Met Gln Ser Cys Asn Phe Ser
1 5 10 15

Ala Glu Lys Ala Lys Val Tyr Ile Asn Asp Ser Val Glu Leu Ser Gln
20 25 30

Asn Glu Gln Lys Leu Ala Ala Trp Leu Ala Lys Arg Gly Pro Ile Ser
35 40 45

Val Ala Ile Asn Ala Phe Gly Met Gln Phe Tyr Arg His Gly Ile Ser
50 55 60

Arg Pro Leu Arg Pro Leu Cys Ser Pro Trp Leu Ile Asp His Ala Val
65 70 75 80

Leu Leu Val Gly Tyr Gly Asn Arg Ser Asp Val Pro Phe Trp Ala Ile
85 90 95

Lys Asn Ser Trp Gly Thr Asp Trp Gly Glu Lys Gly Tyr Tyr Tyr Leu
100 105 110

```
His Arg Gly Ser Gly Ala Cys Gly Val Asn Thr Met Ala Ser Ser Ala
        115                 120                 125

Val Val Asp
    130


<210> SEQ ID NO 128
<211> LENGTH: 11
<212> TYPE: PRT
<213> ORGANISM: Artificial Sequence
<220> FEATURE:
<223> OTHER INFORMATION: Synthetic

<400> SEQUENCE: 128

Gly Thr Asn Gln Arg Gln Thr Met Glu Asn His
1               5                   10


<210> SEQ ID NO 129
<211> LENGTH: 115
<212> TYPE: PRT
<213> ORGANISM: Artificial Sequence
<220> FEATURE:
<223> OTHER INFORMATION: Synthetic

<400> SEQUENCE: 129

Ser Ser Cys Ser Glu Tyr Asn Val Arg Val Ala Ser Arg Tyr Phe Lys
1               5                   10                  15

Gly Pro Glu Leu Leu Val Asp Tyr Gln Met Tyr Asp Tyr Ser Leu Asp
            20                  25                  30

Met Trp Ser Leu Gly Cys Met Leu Ala Ser Met Ile Phe Arg Arg Glu
        35                  40                  45

Pro Phe Phe His Gly Gln Asp Asn Tyr Asp Gln Leu Val Arg Ile Ala
    50                  55                  60

Lys Val Leu Gly Thr Glu Glu Leu Tyr Gly Tyr Leu Lys Lys Tyr His
65                  70                  75                  80

Ile Asp Leu Asp Pro His Phe Asn Asp Ile Leu Gly Gln His Ser Arg
                85                  90                  95

Lys Arg Trp Glu Asn Leu Ser Ile Val Arg Thr Asp Thr Leu Ser Ala
            100                 105                 110

Leu Arg Pro
        115


<210> SEQ ID NO 130
<211> LENGTH: 89
<212> TYPE: PRT
<213> ORGANISM: Artificial Sequence
<220> FEATURE:
<223> OTHER INFORMATION: Synthetic

<400> SEQUENCE: 130

Ala Ala Arg Leu Gly Pro Ser Leu Glu Cys Trp Ala Ala Gly Ser Ala
1               5                   10                  15

Gly Pro Phe Thr Ala His Arg Arg Pro Ala Gln Val Gly Arg Pro Leu
            20                  25                  30

Ser Leu Ala Arg Gly Pro Ser Trp Ser Trp Arg Arg Cys Trp Ser Pro
        35                  40                  45

Gly Arg Cys Pro Ser Ala Pro Trp Arg Ala Gly Ser Arg Pro Ala Ala
    50                  55                  60

Ser Cys Pro Asp Trp Ile Pro Gly Pro Gln Gly Leu Trp Leu His Arg
65                  70                  75                  80

Asn Pro Thr Ser Val Arg Pro Ala Arg
```

85

<210> SEQ ID NO 131
<211> LENGTH: 11
<212> TYPE: PRT
<213> ORGANISM: Artificial Sequence
<220> FEATURE:
<223> OTHER INFORMATION: Synthetic

<400> SEQUENCE: 131

Gly Lys Glu Arg Glu Asn Ile Arg Thr Asn Thr
1 5 10

<210> SEQ ID NO 132
<211> LENGTH: 22
<212> TYPE: PRT
<213> ORGANISM: Artificial Sequence
<220> FEATURE:
<223> OTHER INFORMATION: Synthetic

<400> SEQUENCE: 132

Pro Lys Cys Arg Leu Gln Arg Gln Tyr Thr Gly Lys Gly Gly Val Gly
1 5 10 15

Phe Val Tyr Glu Gly Val
20

<210> SEQ ID NO 133
<211> LENGTH: 40
<212> TYPE: PRT
<213> ORGANISM: Artificial Sequence
<220> FEATURE:
<223> OTHER INFORMATION: Synthetic

<400> SEQUENCE: 133

Gln Thr Gln Thr His Thr Ser Ala Pro Leu Lys Cys Gln Pro Trp Ser
1 5 10 15

Phe Val Glu Ala Arg Ile Cys His Gly Ser Gln Leu Val Arg Cys Pro
20 25 30

Val Gln His Pro Ser Arg Ile Ser
35 40

<210> SEQ ID NO 134
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 134

Pro Arg Leu His Gln Xaa Lys Ala Asn Tyr Ile Tyr Ser Ile Asp Pro
1 5 10 15

Ile Thr

<210> SEQ ID NO 135
<211> LENGTH: 14
<212> TYPE: PRT
<213> ORGANISM: Artificial Sequence
<220> FEATURE:
<223> OTHER INFORMATION: Synthetic

<400> SEQUENCE: 135

Pro Gln Thr Thr Ala Pro Arg Arg Ala Arg Pro Arg Arg Ser
1 5 10

<210> SEQ ID NO 136
<211> LENGTH: 47
<212> TYPE: PRT
<213> ORGANISM: Artificial Sequence
<220> FEATURE:
<223> OTHER INFORMATION: Synthetic

<400> SEQUENCE: 136

Gly Thr Ile Ser Ile Val Cys Cys Trp Gly Cys Leu Cys Gln His Leu
1 5 10 15

Val Gln Cys Leu Ala Asp Gly Cys Ser Ile Asn Ile Asp Leu Met Gly
20 25 30

Tyr Glu Gly Val Asn Ile Lys Leu Ala Phe Ile Gln Gln Leu Leu
35 40 45

<210> SEQ ID NO 137
<211> LENGTH: 18
<212> TYPE: PRT
<213> ORGANISM: Artificial Sequence
<220> FEATURE:
<223> OTHER INFORMATION: Synthetic

<400> SEQUENCE: 137

Gly Met Ser His His Ala Trp Pro Arg Pro Ser Phe Phe Asn Thr Glu
1 5 10 15

Tyr Phe

<210> SEQ ID NO 138
<211> LENGTH: 160
<212> TYPE: PRT
<213> ORGANISM: Artificial Sequence
<220> FEATURE:
<223> OTHER INFORMATION: Synthetic

<400> SEQUENCE: 138

Asp Arg Arg Pro Gly Ser Phe Val Leu Ser Phe Leu Ser Gln Met Glu
1 5 10 15

Thr Asn Val Val Thr His Phe Arg Ile Ile Ala Met Glu Thr Cys Gly
20 25 30

Asp Tyr Tyr Ile Gly Gly Arg Arg Phe Ser Ser Leu Ser Asp Leu Ile
35 40 45

Gly Tyr Tyr Ser His Val Ser Cys Leu Leu Lys Gly Glu Lys Leu Leu
50 55 60

Tyr Pro Val Ala Pro Pro Glu Pro Val Glu Asp Arg Arg Arg Val Arg
65 70 75 80

Ala Ile Leu Pro Tyr Thr Lys Val Pro Asp Thr Asp Glu Ile Ser Phe
85 90 95

Leu Lys Gly Asp Met Glu Thr Phe Ile Val His Asn Glu Leu Glu Asp
100 105 110

Gly Trp Met Glu Thr Trp Val Thr Asn Leu Arg Thr Asp Glu Gln Gly
115 120 125

Leu Ile Val Glu Asp Leu Val Glu Glu Val Gly Arg Glu Glu Asp Pro
130 135 140

His Glu Gly Lys Ile Trp Phe His Gly Lys Ile Ser Lys Gln Glu Ala
145 150 155 160

<210> SEQ ID NO 139

<211> LENGTH: 88
<212> TYPE: PRT
<213> ORGANISM: Artificial Sequence
<220> FEATURE:
<223> OTHER INFORMATION: Synthetic

<400> SEQUENCE: 139

```
Tyr Phe Ala Tyr Leu Ile Ser Glu Gln Asn Glu Glu Asn Lys Ile Asn
1               5                   10                  15

His Asn Thr Gln His Pro Ile Leu Leu Ser Arg Val Arg Glu Gly Met
            20                  25                  30

Gly Leu Asp Thr Leu Ser Leu Leu Pro Ser Thr Gln Gly Gln Glu Arg
        35                  40                  45

Glu Lys Asn Thr Arg His Gln Gln Gly Glu Pro Gly Gly Thr Gly Ala
    50                  55                  60

Leu Glu Ala Ala Val Gly Ala His Gly Asp Thr Ile Gln Gly His Lys
65                  70                  75                  80

Phe Ser Asn Tyr Glu Leu Leu Thr
                85
```

<210> SEQ ID NO 140
<211> LENGTH: 152
<212> TYPE: PRT
<213> ORGANISM: Artificial Sequence
<220> FEATURE:
<223> OTHER INFORMATION: Synthetic

<400> SEQUENCE: 140

```
Cys Ile Val Asp Ala Asn Leu Ser Val Leu Asn Leu Val Ile Val Lys
1               5                   10                  15

Lys Gly Glu Lys Asp Ile Pro Gly Leu Thr Asp Thr Thr Val Pro Arg
            20                  25                  30

Arg Leu Gly Pro Lys Arg Ala Ser Arg Ile Arg Lys Leu Phe Asn Leu
        35                  40                  45

Ser Lys Glu Asp Asp Val Arg Gln Tyr Val Val Arg Lys Pro Leu Asn
    50                  55                  60

Lys Glu Gly Lys Lys Pro Arg Thr Lys Ala Pro Lys Ile Gln Arg Leu
65                  70                  75                  80

Val Thr Pro Arg Val Leu Gln His Lys Arg Arg Arg Ile Ala Leu Lys
                85                  90                  95

Lys Gln Arg Thr Lys Lys Asn Lys Glu Glu Ala Ala Glu Tyr Ala Lys
            100                 105                 110

Leu Leu Ala Lys Arg Met Glu Thr Lys Glu Ala Lys Glu Lys Arg Gln
        115                 120                 125

Glu Gln Ile Ala Lys Arg Arg Arg Leu Ser Ser Leu Arg Ala Ser Thr
    130                 135                 140

Ser Lys Ser Glu Ser Ser Gln Lys
145                 150
```

<210> SEQ ID NO 141
<211> LENGTH: 22
<212> TYPE: PRT
<213> ORGANISM: Artificial Sequence
<220> FEATURE:
<223> OTHER INFORMATION: Synthetic

<400> SEQUENCE: 141

```
Leu Ile Cys Ile Ser Leu Met Ala Asn Asp Val Glu His Leu Phe Met
1               5                   10                  15
```

Phe Ile Cys His Leu Ser
20

<210> SEQ ID NO 142
<211> LENGTH: 219
<212> TYPE: DNA
<213> ORGANISM: Artificial Sequence
<220> FEATURE:
<223> OTHER INFORMATION: Synthetic

<400> SEQUENCE: 142
aagcttcgcc tccttggctg ccagctgctt ctggagctgg ctgagctggg cagagaggct 60
gtcgatgcgg atgcgcgact gctgcagctc ctcgtgggca gcccccacca ggttgctgtt 120
cctctcagca gactgcctgg cattgtccag cttggcagaa taagtcttct ccagctcctt 180
cttatactgc tccacctggt cctcatgctg ggcccgcag 219

<210> SEQ ID NO 143
<211> LENGTH: 438
<212> TYPE: DNA
<213> ORGANISM: Artificial Sequence
<220> FEATURE:
<223> OTHER INFORMATION: Synthetic

<400> SEQUENCE: 143
aatgagaaat gaccgagcag cttcgaggca gattacatga cttatgatct acatttaaat 60
atgatcttgg gagatgtgga agaaactgtg actactatag aaattgatga agaaacatat 120
gaagagatat ataaatcaac gaaacggaat attccaatgc tctttgtccg gggagatggc 180
gttgtcctgg ttgcccctcc actgagagtt ggctgaaaca aagaatttgt cctgtatgga 240
aaacgggaga ctttgtacag tggcctctct aaaagtacaa aacattcata agagaaacct 300
gcatacattt tgatattaag aaataattcc ggggattctc cactcctgaa atgagttgat 360
ttgcagataa ctctacaact tcttaagcta aatggtattt tcatttttct caagctctcc 420
aataaatatg accaccaa 438

<210> SEQ ID NO 144
<211> LENGTH: 555
<212> TYPE: DNA
<213> ORGANISM: Artificial Sequence
<220> FEATURE:
<223> OTHER INFORMATION: Synthetic

<400> SEQUENCE: 144
ggagtttcac ttttgttgcc caggattgag tgcagtgccc cgatcttggc tcactacaac 60
ctctgcctcc tgggttcaag cgactctcct gcctcagtgt cctgagtagc tgggattaca 120
ggcgtctgcc accacgcccg gctaattttg tatttttagt agagaacagg tttcactatg 180
ttggtcaggc tggtcttgaa ctcctgacct cagcgcatcc agaattttag acggggcccc 240
cagggtgagg tcttggcacc ctccagtaga gaagaaggga catgggccat acgtggggtg 300
tcctttctgg gagccttgcg tcccttacct gcctagccag ggattgcacc tcacagcacg 360
cagccagcag gaacggcacc gtgatctgat ttcacctgcg ggccctgggc cctgggggtg 420
ttgacaattg ggcatatcac agtgtgagct agtcccgtct cggggtttgg aggctccacg 480
tggccgtggt acaggagcag gcagttccat cctctggcct ggatcaggct ctgcacacgg 540
aggcctgtgg gccag 555

<210> SEQ ID NO 145

<211> LENGTH: 306
<212> TYPE: DNA
<213> ORGANISM: Artificial Sequence
<220> FEATURE:
<223> OTHER INFORMATION: Synthetic

<400> SEQUENCE: 145
tcggcataaa gtacctcctg gaaggaaccg acagtcttta caacagtcac catatgcaca 60
ctcagcaaat gatttaagct tacaggtact tccttcgcag caagggtcca attcacattc 120
ctttggagta ccacagtcac actcttcccc agcgtccacc aacttattac cacaggaggg 180
agcactatag gcttcatcag gctttggaat attaagaagg cagtttcctc ctttatttaa 240
agttacttct caaagtcctc tgcactgcaa ctgctaaagt ttctggaacc cgatgctcct 300
gaattc 306

<210> SEQ ID NO 146
<211> LENGTH: 463
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (410)..(410)
<223> OTHER INFORMATION: n is a, c, g, or t
<220> FEATURE:
<221> NAME/KEY: misc_feature
<222> LOCATION: (413)..(413)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t
<220> FEATURE:
<221> NAME/KEY: misc_feature
<222> LOCATION: (433)..(434)
<223> OTHER INFORMATION: n is a, c, g, or t
<220> FEATURE:
<221> NAME/KEY: misc_feature
<222> LOCATION: (448)..(448)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (457)..(457)
<223> OTHER INFORMATION: n is a, c, g, or t
<220> FEATURE:
<221> NAME/KEY: misc_feature
<222> LOCATION: (459)..(460)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t

<400> SEQUENCE: 146
tcaagcgtgc ccccgcagga cacagccccc tactcctgcc acgtgcagca cagcagcctg 60
gcccagcccc tcgtggtgcc ctgggaggcc agctaggaag caagggttgg aggcaatgtg 120
ggatctcaga cccagtagct gcccttcctg cctgatgtgg gagctgaacc acagaaatca 180
cagtcaatgg atccacaagg cctgaggagc agtgtggggg gacagacagg aggtggattt 240
ggagaccgaa gactgggatg cctgtcttga gtagacttgg acccaaaaaa tcatctcacc 300
ttgagcccac ccccacccca ttgtctaatc tgtagaagcc ggaagcttgc ggccgcactc 360
gagtaactag ttaacccctt ggggcctcta aacgggtctt gaggggttan ctngttnctc 420
gngtgcggcc gcnngcttcc ggcttctncn gnttngncnn tgn 463

<210> SEQ ID NO 147
<211> LENGTH: 388
<212> TYPE: DNA
<213> ORGANISM: Artificial Sequence
<220> FEATURE:
<223> OTHER INFORMATION: Synthetic

<400> SEQUENCE: 147
gtggctgttg cgcagggatc aggtgcactt gagtcttcga agtggccatt gctcaacttg 60
aatggctgcc tgggtcgggc agaaggccag gtcctcatgg cttcccatcc ctaatgaccg 120
gaatacatgg gctgccaggt cagatgtggg ccacatggga agtcccagct ctattctaga 180
aaatgcatgt accatcagct tactgataga catttactga acttgggtat gccagatcca 240
cagggggccc cagagatgag ggggataaga aggtttctga aggcatggta cagaaggtgc 300
cagcagaggt atgggctagg ggaggcaggg agagcacaga gcaggcatcc taaaggaggc 360
agcatttgtg ttggagcttg aagaagtg 388

<210> SEQ ID NO 148
<211> LENGTH: 292
<212> TYPE: DNA
<213> ORGANISM: Artificial Sequence
<220> FEATURE:
<223> OTHER INFORMATION: Synthetic

<400> SEQUENCE: 148
taagctttca tcttccccaa ccctgatgtc ttcctattct cactgatccc cctactgact 60
cagcttcacg cttcttgatt atacctctct cctgtagaaa agccttggct ggctctcctt 120
taggatgaga ataaatccga aatccttagt gtagcattta gaagtcctat ctcccacttg 180
tttcttaata ttctcttctc taacaccgaa cttgtttcaa gcctcttttc caacacatga 240
tttcttctat tctaaatcaa tttatttatt atttgctaaa tagcccctaa ac 292

<210> SEQ ID NO 149
<211> LENGTH: 419
<212> TYPE: DNA
<213> ORGANISM: Artificial Sequence
<220> FEATURE:
<223> OTHER INFORMATION: Synthetic

<400> SEQUENCE: 149
ggctaatttt gtatttttag tagagaacag gtttcactat gttggtcagg ctggtcttga 60
actcctgacc tcagcgcatc cagaatttta gacggggccc ccagggtgag gtcttggcac 120
cctccagtag agaagaaggg acatgggcca tacgtggggt gtcctttctg ggagccttgc 180
gtcccttacc tgcctagcca gggattgcac ctcacagcac gcagccagca ggaacggcac 240
cgtgatctga tttcacctgc gggccctggg ccctgggggt gtttgacaat tggggcatat 300
cacagtgtga gctagtcccg tctcgggggt ttggaggctc cacgtggccg tggtacagga 360
gcaggcagtt ccatcctctg gcctggatca ggctctgcac acggaggcct gtgggccag 419

<210> SEQ ID NO 150
<211> LENGTH: 157
<212> TYPE: DNA
<213> ORGANISM: Artificial Sequence
<220> FEATURE:
<223> OTHER INFORMATION: Synthetic

<400> SEQUENCE: 150
gtcttttcat ttttattact caaaaaagtt tcattttttt atttagcttt ctgactctgt 60
gcttgtgcct tcaacacttt cacaacgatt ttctgctcct cgataaggaa agcacgcttg 120
atcctgtcac gaacacattt agcacacatg gaaccaa 157

<210> SEQ ID NO 151
<211> LENGTH: 397
<212> TYPE: DNA
<213> ORGANISM: Artificial Sequence
<220> FEATURE:
<223> OTHER INFORMATION: Synthetic

<400> SEQUENCE: 151
cttaccagat ctatcaggtc atgataaatt agacccagtc catctttcaa tccagtctac 60
tctggttctg aacatataaa cacaaaacac tacagattta ttaatatagc attttcccac 120
accctaaccc tataaagaac tttaaaagag aaaatttcat ctaaatattt cacacttaaa 180
ggaaagcctt accaactatg gcaacaggtt tggaccatga aatagtactt tcctagatga 240
catatcgagt caacatgaag ccttagctga aatgaatgat tcaggatatt aatgagaaat 300
tctcacaaat gatatgcatt taggaaatga ttttgctttc cttaaatagt tcgaaggctt 360
gaaaataaac tttttttttg catttctttt aaaagtt 397

<210> SEQ ID NO 152
<211> LENGTH: 644
<212> TYPE: DNA
<213> ORGANISM: Artificial Sequence
<220> FEATURE:
<223> OTHER INFORMATION: Synthetic

<400> SEQUENCE: 152
gtttccacat tcttgtcaag ggttggtagg gtcagtcttt taaatttctt gccattttag 60
tgactgtgca ttggtatttc attgtggttt atttgcatga tgactaatgc tcaacaccaa 120
ctaatcatgt tgagtatttt taatgtgctt atttgccact catatatctt ctttgatgaa 180
gtgtctcttc aaatattttg cccatttaaa aactgtattg attcttatta ttgaattgca 240
ataattcttt ctatccggat atatatcctt tgccagatat gtgtattaca aatgttttct 300
cctagccttc cacctcagcc tcccaagtag ctgggaatgc aggtgtgcac caccactcca 360
gggttttttg ttgttgttgt tgttgttttt ctgtagagac agggtcttgc catgctgccg 420
aggctgctct caaactcctg ggatcaagaa atcctcctgc ctcggcctcc caaagtgctg 480
acattacaag catgagccac tgtgcctggc taacttttca tcttttaaag tagtgtcttg 540
caaagaacaa cattttaatg aagtccattt atcaactttt tgattcattg tccatgcttt 600
ttgcataata agaaatcttt gcctgcctca aaattgcaaa gctt 644

<210> SEQ ID NO 153
<211> LENGTH: 263

<212> TYPE: DNA
<213> ORGANISM: Artificial Sequence
<220> FEATURE:
<223> OTHER INFORMATION: Synthetic

<400> SEQUENCE: 153
aacacacttg ttacctatga tatggttcca gagcccaaaa tcattgatgc tgctttgcgg 60
gcatgcagac ggttaaatga ttttgctagt acagttcgta tcctagaggt tgttaaggac 120
aaagcaggac ctcataagga aatctacccc tatgtcatcc aggaacttag accaacttta 180
aatgaactgg gaatctccac tccggaggaa ctgggccttg acaaagtgta accgcataat 240
aaaagggaaa tgagtttgaa ctg 263

<210> SEQ ID NO 154
<211> LENGTH: 236
<212> TYPE: DNA
<213> ORGANISM: Artificial Sequence
<220> FEATURE:
<223> OTHER INFORMATION: Synthetic

<400> SEQUENCE: 154
gcccccatct catcatatac caaatctctc cctcactaaa cgtaagcctt ctcctcactc 60
tctcaatctt atccatcata gcaggcagtt gaggtggatt aaaccaaacc cagctacgca 120
aaatcttagc atactcctca attacccaca taggatgaat aatagcagtt ctaccgtaca 180
accctaacat aaccattctt aatttaacta tttatattat cctaactact accgca 236

<210> SEQ ID NO 155
<211> LENGTH: 332
<212> TYPE: DNA
<213> ORGANISM: Artificial Sequence
<220> FEATURE:
<223> OTHER INFORMATION: Synthetic

<400> SEQUENCE: 155
gggttcgtgt tcctcagcgt agccatcagg cttggccagc tgctccttgt aaagctgccc 60
cacagtgcgg aacatgccct tccgcgtctt gaaggccccg ggcagtgcgg tctccgacat 120
gccggccacc tggtccaggc cgatgatgcg gtccacatcc ttccacagct ccgagacaaa 180
cttgtcagag gactggtgga gcagtgtggc gatgttgtca ttcaggggat ccatgttctt 240
catcagccac tcgtcagctt tgtaatccac cttgccggca tagtggataa tgcagaaatc 300
agctttgtcc ttcagctgct tgggcttctg ga 332

<210> SEQ ID NO 156
<211> LENGTH: 279
<212> TYPE: DNA
<213> ORGANISM: Artificial Sequence
<220> FEATURE:
<223> OTHER INFORMATION: Synthetic

<400> SEQUENCE: 156
aaattacttt tcgccttgca gctgtggaac ttggtcttac agcctctgct cttctgccca 60
aacgggccat gcagtttgga tcaagaattg caaaaatgga aaaaattaat gaaaaggcat 120
ctgataaatg tggacggctc caaatcatgt ccttagaaaa tctttctatt gaaaaggaga 180
ctaaattgta atgtgattca caatgtaaca atataaaaat aagtttttat ataattatat 240
aaaagtaaga tactctgctg ctttactatt gtataatat 279

<210> SEQ ID NO 157

<211> LENGTH: 877
<212> TYPE: DNA
<213> ORGANISM: Artificial Sequence
<220> FEATURE:
<223> OTHER INFORMATION: Synthetic

<400> SEQUENCE: 157

```
cagaggatga ctacagctac cagggtcaca tgcagtcctg caacttctca gcagagaagg     60
ccaaggtcta catcaatgac tccgtggagc tgagccagaa cgagcagaag ctggcagcct    120
ggctggccaa gagaggccca atctccgtgg ccatcaatgc ctttggcatg cagttttacc    180
gccacgggat ctcccgccct ctccggcccc tctgcagccc ttggctcatt gaccatgcgg    240
tgttgcttgt gggctacggc aaccgctctg acgttccctt ttgggccatc aagaacagct    300
ggggcactga ctggggtgag aagggttact actacttgca tcgcgggtcc ggggcctgtg    360
gcgtgaacac catggccagc tcggcggtgg tggactgaag aggggccccc agctcgggac    420
ctggtgctga tcagagtggc tgctgcccca gcctgacatg tgtccaggcc cctccccggg    480
aggtacagct ggcagaggga aaggcactgg tacctcaggg tgagcagagg gcactgggct    540
ggggcacagc ccctgcttcc ctgcacccca ttcccaccct gaagttctgc acctgcacct    600
ttgttgaatt gtggtagctt aggaggatgt cagggtgaag ggtggtatct tggcagttga    660
agctggggca agaactctgg gcttgggtaa tgagcaggaa gaaaattttc tgatcttaag    720
cccagctgtg ttctgccccc gctttcctct gtttgatact ataaattttc tggttccctt    780
ggatttaggg atagtgtccc cctccatgtc caggaaactt gtaaccaccc ttttctaaca    840
gcaataaaga gggtccttgt cccgaaaaaa aaaaaaa                              877
```

<210> SEQ ID NO 158
<211> LENGTH: 568
<212> TYPE: DNA
<213> ORGANISM: Artificial Sequence
<220> FEATURE:
<223> OTHER INFORMATION: Synthetic

<400> SEQUENCE: 158

```
ggcagacaat ggaaaaccat tgaaaaggat taaactggga agtgatatgt tctcttttgc     60
atttaaaaag atcaccaatg gggatatgga gaatggtctg gataggtctt aagactagag    120
ccaggaagac atgttagaag gctatcaatt gaccctaaag acactgcttc aatccctttg    180
atgacagtga gtttgctttc cccagagata gcttattgga cctcaggact gctgtgagaa    240
acagaaaatg ctcctttacg tgttgcctga agttaggctc accgatttgg ggcatgttct    300
aattctacca gctaggaaca cacagaatcg cttgtcaaac attctgagtc agatatgtcc    360
tccctatgtc ttttctgaga aaggcataca gaaattccca gctaaacatc accagttccc    420
tcatttgttc ctcagatgat atggtccatt caagttttgt aatcatcatg gggtagatg     480
gagggtccca gtcctcacaa ccattctggt aatttactct tgaatttact ggttcacatg    540
tatctatttt gtagtgtggc tccagaaa                                       568
```

<210> SEQ ID NO 159
<211> LENGTH: 522
<212> TYPE: DNA
<213> ORGANISM: Artificial Sequence
<220> FEATURE:
<223> OTHER INFORMATION: Synthetic

<400> SEQUENCE: 159

```
tcatcctgct cggagtacaa tgttcgtgta gcctcaaggt acttcaaggg accagagctc     60
```

ctcgtggact atcagatgta tgattatagc ttggacatgt ggagtttggg ctgtatgtta 120
gcaagcatga tctttcgaag ggaaccattc ttccatggac aggacaacta tgaccagctt 180
gttcgcattg ccaaggttct gggtacagaa gaactgtatg ggtatctgaa gaagtatcac 240
atagacctag atccacactt caacgatatc ctgggacaac attcacggaa acgctgggaa 300
aacttatcca tagtgagaac agacaccttg tcagccctga ggccctagat cttctggaca 360
aacttctgcg atacgaccat caacagagac tgactgccaa agaggccatg gagcacccat 420
acttctaccc tgtggtgaag gagcagtccc agccttgtgc agacaatgct gtgctttcca 480
gtggtctcac ggcagcacga tgaagactgg aaagcgacgg gt 522

<210> SEQ ID NO 160
<211> LENGTH: 363
<212> TYPE: DNA
<213> ORGANISM: Artificial Sequence
<220> FEATURE:
<223> OTHER INFORMATION: Synthetic

<400> SEQUENCE: 160
cggccgcccg ccttggcccg tctctggagt gctgggcagc cgggtctgcg ggccccttta 60
cagcacatcg ccggccggcc caggtagggc ggcctctctc cctcgcaagg gggcccagct 120
ggagctggag gagatgctgg tccccaggaa gatgtccgtc agccccctgg agagctggct 180
cacggcccgc tgcttcctgc ccagactgga taccgggacc gcagggactg tggctccacc 240
gcaatcctac cagtgtccgc ccagccagat aggggaaggg gccgagcagg gggatgaagg 300
cgtcgcggat gcgcctcaaa ttcagtgcaa aaacgtgctg aagatccgcc ggcggaagat 360
gaa 363

<210> SEQ ID NO 161
<211> LENGTH: 662
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (413)..(413)
<223> OTHER INFORMATION: n is a, c, g, or t

<400> SEQUENCE: 161
ggcagggaag ggagaacatt aggacaaata cctaatgcac gccaggccct antaatcgta 60
gatgatgggt tgatgggtgt agcaaaccac catggcacat gtatatctat gtaacaaacc 120
tgcacattct gtacatgtat cccagaactt caagtaaaat tttaaaaaat tcaaaaaaag 180
taataggaaa aggggaaaca tccacgtgag cagtccagtt tcccaatctg gaacttggag 240
ctgttcacct ggtgggtgtt tgtgactatt cagacacaga caacaaaggc tactccagat 300
tgaagtgcac tgcttacttt cagtgacctc atagaactac tcaacattgt ttttggtgat 360
tcctgtgcta tggtttgaat ggctccgctc caaaactcag gtgttgccaa tgngatggta 420
ttaagaagta gggcatttaa aaaacaacaa caggcctggc gcggtggccc acgcctgtaa 480
tcccagcact ttgggaggct aaggcgggcg gatcaccgga ggtcaggaat tcaaaaccag 540
cctggccaac atggcgaaac cctgtctcta ctaaaaatac aaaaattagc caggcatggt 600
tgcgggcgcc tgtaatcccg gctactcggg aggctgaggc aggggaatcc ttgaacccgg 660
ga 662

<210> SEQ ID NO 162
<211> LENGTH: 547
<212> TYPE: DNA
<213> ORGANISM: Artificial Sequence
<220> FEATURE:
<223> OTHER INFORMATION: Synthetic

<400> SEQUENCE: 162
gaaatgtaga ctgcaaaggc agtatacagg aaaaggtgga gtgggttttg tttatgaggg 60
tgtctgaaaa ctaaaattga gcgggatatc atggtatagt tggacagtat tggtccttca 120
cactttggcc atattgtata atggagcttt taccaaagat gtatgagaag tgtaagacta 180
taaaaaaatg aactattcaa agtaaaactc ttaacaaaca ttttacttaa agcagatgca 240
aaagggtatt ctcatgtagg ctcctgttgg tgcagaggga tttttttgat ttcaggatac 300
aactaaagta cgaagttctc agtttcactt tagtagaaag agctctagaa atgaggctga 360
taaacacatc taagaacact ggttgctttc taaaatttcc aaagctccac cataaatgta 420
atttttagtg tttcaaatga ttgcatttta aagtatataa atatgggtta tccaatatca 480
atgctatagt aacatcctga aacaaaacaa gcacaaaggt ataaatgcct aaactggagg 540
aagcttg 547

<210> SEQ ID NO 163
<211> LENGTH: 277
<212> TYPE: DNA
<213> ORGANISM: Artificial Sequence
<220> FEATURE:
<223> OTHER INFORMATION: Synthetic

<400> SEQUENCE: 163
ctcagactca aacacacacc tccgctccct tgaagtgcca gccctggagc tttgttgagg 60
ctcgcatctg ccacgggagt cagctagtac gttgcccagt tcaacatcca tccaggattt 120
cataggaact tgagaatcat tgtttttggc ttgaatcctg ggtttgaggt ttcttcgtgt 180
aggaatctga aaaaaggatt tggaaacgtt gttgtctcta atcccaaagt atgtatctgg 240
gaggctgcct tcgccatcac ccacctaata actcagg 277

<210> SEQ ID NO 164
<211> LENGTH: 337
<212> TYPE: DNA
<213> ORGANISM: Artificial Sequence
<220> FEATURE:
<223> OTHER INFORMATION: Synthetic

<400> SEQUENCE: 164
agacttcacc agtcaaagcg aactacatat actcaattga tccaataact tgaccaacgg 60
aacaagttac cctagggata acagcgcaat cctattctag agtccatatc aacaataggg 120
tttacgacct cgatgttgga tcaggacatc ccgatggtgc agccgctatt aaaggttcgt 180
ttgttcaacg attaaagtcc tacgtgatct gagttcagac cggagtaatc caggtcggtt 240
tctatctact tcaaattcct ccctgtacga aaggacaaga gaaataaggc ctacttcaca 300
aagcgccttc ccccgtaaat gatatcatct caagctt 337

<210> SEQ ID NO 165
<211> LENGTH: 276

<212> TYPE: DNA
<213> ORGANISM: Artificial Sequence
<220> FEATURE:
<223> OTHER INFORMATION: Synthetic

<400> SEQUENCE: 165
ctcgctcaaa cacacacctc cgctcccttg aagtgccagc cctggagctt tgttgaggct 60
cgcatctgcc acgggagtca gctagtacgt tgcccagttc aacatccatc caggatttca 120
taggaacttg agaatcattg tttttggctt gaatcctggg tttgaggttt cttcgtgtag 180
gaatctgaaa aaaggatttg gaaacgttgt tgtctctaat cccaaagtat gtatctggga 240
ggctgccttc gccatcaccc acctaataac tcaggc 276

<210> SEQ ID NO 166
<211> LENGTH: 717
<212> TYPE: DNA
<213> ORGANISM: Artificial Sequence
<220> FEATURE:
<223> OTHER INFORMATION: Synthetic

<400> SEQUENCE: 166
attgtttgtt gttgggggtg tctttgtcag catctagtac agtgcctggc agatggatgc 60
tcaataaata ttgatttaat gggttatgag ggtgttaata taaaattagc atttattcag 120
caactactat gagtcagcca ctgggctaag tggcttacat gttaagaacc tcacagaagc 180
caggtgtggt ggctcacgcc tgtaatccca gcactttggg aggctgaagc gggcagatca 240
cctgaggtca ggagtttgag tccaggctgg ccaacgtggt gaaaccccat ctctactaaa 300
aatacaaaaa ttagccagtt gtggtggcag gcgcctgtag tcccagccac tcaggaggct 360
aaggcaggag aatagctgga acccgggagg tggagattgc agtgagccaa gattgcacca 420
ctgcactcca gcctgggtga cagagtgaga ctctgtctcc aaaaaaaaaa gaaaaagaaa 480
aagaacctcc agcaacctag taggtgagcc cggttactct tgttttacag gtgagaaaat 540
tgagccctag agaaataaag taacttgctt caggtctcat ggttaagggg aacctgggcc 600
ctaacagtcc acttcctgta ccttcaacca cggttctacc gcctccgcta ggaaatggcc 660
cgaggacatt ccttagctgg cttcagcttg ctctttttcc cctgcggtcc accccctg 717

<210> SEQ ID NO 167
<211> LENGTH: 316
<212> TYPE: DNA
<213> ORGANISM: Artificial Sequence
<220> FEATURE:
<223> OTHER INFORMATION: Synthetic

<400> SEQUENCE: 167
agagggagta tagggctgtg cacagagact atgatggccg tgctaaggta agagtattga 60
taatgtaagc atacttcctc tatcaacaat aattgttaac agctgcttca agcacttgat 120
attaccacta gttgttaact gaatcaagca tgtgctccaa gttcacatta atgtgaattg 180
aacagcattg tgtacgtacg aggagcttca tgcaagtgtt atacactgca ctcacaagta 240
ttatgatctt actaagcatt agaaatactc tgtgttaaag aagcttggtc taggccaagc 300
gtggtggctc atgcct 316

<210> SEQ ID NO 168
<211> LENGTH: 457
<212> TYPE: DNA
<213> ORGANISM: Artificial Sequence
<220> FEATURE:

<223> OTHER INFORMATION: Synthetic

<400> SEQUENCE: 168
gatcggaggc cagggtcctt tgtactttca tttcttagcc agatgaatgt tgtcacccat 60
tttaggatta ttgctatgtg tggagattac tacattggtg gaagacgttt ttcttcactg 120
tcagacctaa taggttatta cagtcatgtt tcttgtttgc ttaaaggaga aaaattactt 180
tacccagttg caccaccaga gccagtagaa gatagaaggc gtgtacgagc tattctacct 240
tacacaaaag taccagacac tgatgaaata agtttcttaa aaggagatat gttcattgtt 300
cataatgaat tagaagatgg atggatgtgg gttacaaatt taagaacaga tgaacaaggc 360
cttattgttg aagacctagt agaagaggtg ggccgggaag aagatccaca tgaaggaaaa 420
atatggttcc atgggaagat ttccaaacag gaagctt 457

<210> SEQ ID NO 169
<211> LENGTH: 361
<212> TYPE: DNA
<213> ORGANISM: Artificial Sequence
<220> FEATURE:
<223> OTHER INFORMATION: Synthetic

<400> SEQUENCE: 169
tgaagtggca gcagaggaac ccaatgctgc agttcctgat gagatccccc ctctcgaggg 60
cgatgaggat gcgtctcgca tggaagaagt cgattaggtt aggagttcat agttggaaaa 120
cttgtgccct tgtatagtgt ccccatgggc tcccactgca gcctcgagtg cccctgtccc 180
acctggctcc ccctgctggt gtctagtgtt tttttccctc tcctgtcctt gtgttgaagg 240
cagtaaacta agggtgtcaa gccccattcc ctctctcact cttgacagca ggattggatg 300
ttgtgtattg tggtttattt tattttcttc attttgttct gaaattaagt atgcaaaata 360
a 361

<210> SEQ ID NO 170
<211> LENGTH: 487
<212> TYPE: DNA
<213> ORGANISM: Artificial Sequence
<220> FEATURE:
<223> OTHER INFORMATION: Synthetic

<400> SEQUENCE: 170
gttgcattgt ggatgcaaat ctgagcgttc tcaacttggt tattgtaaaa aaaggagaga 60
aggatattcc tggactgact gatactacag tgcctcgccg cctgggcccc aaaagagcta 120
gcagaatccg caaacttttc aatctctcta aagaagatga tgtccgccag tatgttgtaa 180
gaaagccctt aaataaagaa ggtaagaaac ctaggaccaa agcacccaag attcagcgtc 240
ttgttactcc acgtgtcctg cagcacaaac ggcggcgtat tgctctgaag aagcagcgta 300
ccaagaaaaa taaagaagag gctgcagaat atgctaaact tttggccaag agaatgaagg 360
aggctaagga gaagcgccag gaacaaattg cgaagagacg cagactttcc tctctgcgag 420
cttctacttc taagtctgaa tccagtcaga aataagattt tttgagtaac aaataaataa 480
gatcaga 487

<210> SEQ ID NO 171
<211> LENGTH: 319
<212> TYPE: DNA
<213> ORGANISM: Artificial Sequence
<220> FEATURE:
<223> OTHER INFORMATION: Synthetic -continued

```
<400> SEQUENCE: 171

cctgggcagt gattaggtca taaaggtgga gtcctcatgg atgggattag tgtctttata     60

aaagagacct ttgccatgtg aggttacagt gagaagacat ctgtctatga agaaagtggg    120

ccctcaccaa acacagtctg ctggcacttt gcacttcaac tccccagctt ccagaactgt    180

aaggaatata agtctgttgt tggtaagcca cccggtctat gatattttgt tatagcagcc    240

caaacagact aagacaggtg acaaataaac atgaaaagat gttcaacatc attagccatt    300

agggaaatgc agattaaaa                                                 319


<210> SEQ ID NO 172
<211> LENGTH: 30
<212> TYPE: PRT
<213> ORGANISM: Artificial Sequence
<220> FEATURE:
<223> OTHER INFORMATION: Synthetic

<400> SEQUENCE: 172

Gly Gly Arg Gly Gly Gly Gly Gly Gly Gly Gly Arg Gly Ala Gly Gly
1               5                   10                  15

Gly Arg Gly Ala Gly Ala Gly Gly Gly Arg Pro Glu Ala Ala
            20                  25                  30
```